US008642010B2

(12) United States Patent
Sato et al.

(10) Patent No.: US 8,642,010 B2
(45) Date of Patent: *Feb. 4, 2014

(54) KDR AND VEGF/KDR BINDING PEPTIDES AND THEIR USE IN DIAGNOSIS AND THERAPY

(75) Inventors: Aaron K. Sato, Richmond, CA (US); Daniel J. Sexton, Melrose, MA (US); Daniel T. Dransfield, Hanson, MA (US); Robert C. Ladner, Ijamsville, MD (US); Christophe Arbogast, Viuz-en-Sallaz (FR); Philippe Bussat, La Roche-sur-Foron (FR); Hong Fan, PuDong (CN); Sudha Khurana, San Jose, CA (US); Karen E. Linder, Kingston, NJ (US); Edmund R. Marinelli, Lawrenceville, NJ (US); Palaniappa Nanjappan, Princeton, NJ (US); Adrian D. Nunn, Lambertville, NJ (US); Radhakrishna K. Pillai, Cranbury, NJ (US); Sibylle Pochon, Troinex (CH); Feng Yan, Grand-Lancy (CH); Kondareddiar Ramalingam, Dayton, NJ (US); Ajay Shrivastava, Princeton, NJ (US); Bo Song, Princeton, NJ (US); Rolf E. Swenson, Princeton, NJ (US); Mathew A. Von Wronski, Moorestown, NJ (US)

(73) Assignees: Dyax Corp., Burlington, MA (US); Bracco Suisse SA, Manno (CH)

( * ) Notice: Subject to any disclaimer, the term of this patent is extended or adjusted under 35 U.S.C. 154(b) by 283 days.

This patent is subject to a terminal disclaimer.

(21) Appl. No.: 12/480,578

(22) Filed: Jun. 8, 2009

(65) Prior Publication Data

US 2010/0003195 A1    Jan. 7, 2010

Related U.S. Application Data

(63) Continuation of application No. 10/661,156, filed on Sep. 11, 2003, now abandoned, which is a continuation-in-part of application No. 10/382,082, filed on Mar. 3, 2003, now abandoned, and a continuation-in-part of application No. PCT/US03/06731, filed on Mar. 3, 2003.

(60) Provisional application No. 60/360,851, filed on Mar. 1, 2002, provisional application No. 60/440,411, filed on Jan. 15, 2003.

(51) Int. Cl.
*A61K 49/00* (2006.01)
*A61B 8/00* (2006.01)

(52) U.S. Cl.
USPC .......................... 424/9.1; 424/9.52; 530/300

(58) Field of Classification Search
None
See application file for complete search history.

(56) References Cited

U.S. PATENT DOCUMENTS

| | | |
|---|---|---|
| 2,913,451 A | 11/1959 | De La Mater et al. |
| 4,093,709 A | 6/1978 | Choi et al. |
| 4,131,648 A | 12/1978 | Choi et al. |
| 4,138,344 A | 2/1979 | Choi et al. |
| 4,180,646 A | 12/1979 | Choi et al. |
| 4,391,797 A | 7/1983 | Folkman et al. |
| 4,544,500 A | 10/1985 | Bittle et al. |
| 4,718,433 A | 1/1988 | Feinstein |
| 4,774,958 A | 10/1988 | Feinstein |
| 4,844,882 A | 7/1989 | Widder et al. |
| 4,899,755 A | 2/1990 | Lauffer et al. |
| 4,900,540 A | 2/1990 | Ryan et al. |
| 5,021,556 A | 6/1991 | Srinivasan |
| 5,075,099 A | 12/1991 | Srinivasan et al. |
| 5,118,797 A | 6/1992 | Jurisson et al. |
| 5,123,414 A | 6/1992 | Unger |
| 5,137,928 A | 8/1992 | Erbel et al. |
| 5,180,816 A | 1/1993 | Dean |
| 5,183,653 A | 2/1993 | Linder et al. |
| 5,223,409 A | 6/1993 | Ladner et al. |
| 5,230,882 A | 7/1993 | Unger |
| 5,271,928 A | 12/1993 | Schneider et al. |
| 5,316,921 A | 5/1994 | Godowski et al. |
| 5,364,613 A | 11/1994 | Sieving et al. |
| 5,367,080 A | 11/1994 | Toner et al. |
| 5,380,519 A | 1/1995 | Schneider et al. |
| 5,387,409 A | 2/1995 | Nunn et al. |

(Continued)

FOREIGN PATENT DOCUMENTS

| | | |
|---|---|---|
| AU | 2003213730 | 7/2003 |
| AU | 2003228276 | 9/2009 |

(Continued)

OTHER PUBLICATIONS

Adams, Insight into tyrosine phosphorylation in v-Fps using proton inventory techniques. Biochemistry. Aug. 20, 1996;35(33):10949-56.
Bax et al., The structure of phosphorylated GSK-3beta complexed with a peptide, FRATtide, that inhibits beta-catenin phosphorylation. Structure. Dec. 2001;9(12):1143-52.
Bikfalvi et al., Interaction of vasculotropin/vascular endothelial cell growth factor with human umbilical vein endothelial cells: binding, internalization, degradation, and biological effects. J Cell Physiol 149: 50-59, 1991.
Binetruy-Tournaire et al., Identification of a peptide blocking vascular endothelial growth factor (VEGF)-mediated angiogenesis. EMBO J. Apr. 3, 2000;19(7):1525-33.

(Continued)

*Primary Examiner* — Anand Desai
(74) *Attorney, Agent, or Firm* — Pearl Cohen Zedek Latzer Baratz LLP

(57) ABSTRACT

The present invention provides polypeptides, peptide dimer, and multimeric complexes comprising at least one binding moiety for KDR or VEGF/KDR complex, which have a variety of uses wherever treating, detecting, isolating or localizing angiogenesis is advantageous. Particularly disclosed are synthetic, isolated polypeptides capable of binding KDR or VEGF/KDR complex with high affinity (e.g., having a $K_D<1$ μM), and dimer and multimeric constructs comprising these polypeptides.

42 Claims, 118 Drawing Sheets

(56) References Cited

U.S. PATENT DOCUMENTS

| | | |
|---|---|---|
| 5,413,774 A | 5/1995 | Schneider et al. |
| 5,445,813 A | 8/1995 | Schneider et al. |
| 5,469,854 A | 11/1995 | Unger et al. |
| 5,474,756 A | 12/1995 | Tweedle et al. |
| 5,529,766 A | 6/1996 | Klaveness et al. |
| 5,531,980 A | 7/1996 | Schneider et al. |
| 5,536,490 A | 7/1996 | Klaveness et al. |
| 5,547,656 A | 8/1996 | Unger |
| 5,547,856 A | 8/1996 | Godowski et al. |
| 5,556,610 A | 9/1996 | Yan et al. |
| 5,556,939 A | 9/1996 | Flanagan et al. |
| 5,558,856 A | 9/1996 | Klaveness et al. |
| 5,558,857 A | 9/1996 | Klaveness et al. |
| 5,567,414 A | 10/1996 | Schneider et al. |
| 5,578,292 A | 11/1996 | Schneider et al. |
| 5,580,563 A | 12/1996 | Tam |
| 5,585,112 A | 12/1996 | Unger et al. |
| 5,597,549 A | 1/1997 | Schneider et al. |
| 5,607,661 A | 3/1997 | Berg et al. |
| 5,608,110 A | 3/1997 | Ramalingam et al. |
| 5,627,286 A | 5/1997 | Ramalingam et al. |
| 5,637,289 A | 6/1997 | Klaveness et al. |
| 5,643,553 A | 7/1997 | Schneider et al. |
| 5,656,254 A | 8/1997 | Ramalingam et al. |
| 5,658,551 A | 8/1997 | Schneider et al. |
| 5,662,885 A | 9/1997 | Pollak et al. |
| 5,665,329 A | 9/1997 | Ramalingam et al. |
| 5,670,133 A | 9/1997 | Zamora |
| 5,686,060 A | 11/1997 | Schneider et al. |
| 5,686,292 A | 11/1997 | Schwall et al. |
| 5,688,487 A | 11/1997 | Linder et al. |
| 5,707,624 A | 1/1998 | Nickoloff et al. |
| 5,711,933 A | 1/1998 | Bichon et al. |
| 5,720,934 A | 2/1998 | Dean et al. |
| 5,723,584 A | 3/1998 | Schatz |
| 5,759,515 A | 6/1998 | Rhodes et al. |
| 5,759,996 A | 6/1998 | Cheng et al. |
| 5,766,860 A | 6/1998 | Terman et al. |
| 5,769,080 A | 6/1998 | Matthijset al. |
| 5,770,421 A | 6/1998 | Morris et al. |
| 5,773,024 A | 6/1998 | Unger et al. |
| 5,773,412 A | 6/1998 | Cheng et al. |
| 5,780,006 A | 7/1998 | Pollak et al. |
| 5,798,091 A | 8/1998 | Trevino et al. |
| 5,840,275 A | 11/1998 | Bichon et al. |
| 5,846,518 A | 12/1998 | Yan et al. |
| 5,846,519 A | 12/1998 | Tweedle et al. |
| 5,849,261 A | 12/1998 | Dean et al. |
| 5,851,999 A | 12/1998 | Ulrich et al. |
| 5,855,866 A | 1/1999 | Thorpe et al. |
| 5,861,301 A | 1/1999 | Terman et al. |
| 5,863,520 A | 1/1999 | Bichon et al. |
| 5,871,959 A | 2/1999 | Rong et al. |
| 5,876,973 A | 3/1999 | Marchionni |
| 5,877,289 A | 3/1999 | Thorpe et al. |
| 5,879,658 A | 3/1999 | Dean et al. |
| 5,885,866 A | 3/1999 | Chen |
| 5,886,142 A | 3/1999 | Thakur et al. |
| 5,908,610 A | 6/1999 | Schneider et al. |
| 5,911,972 A | 6/1999 | Schneider et al. |
| 5,935,820 A | 8/1999 | Hu et al. |
| 5,942,385 A | 8/1999 | Hirth |
| 5,976,495 A | 11/1999 | Pollak et al. |
| 5,990,263 A | 11/1999 | Dugstad et al. |
| 6,025,331 A | 2/2000 | Moses et al. |
| 6,033,645 A | 3/2000 | Unger et al. |
| 6,040,157 A | 3/2000 | Hu et al. |
| 6,051,230 A | 4/2000 | Thorpe et al. |
| 6,057,428 A | 5/2000 | Keyt et al. |
| 6,071,495 A | 6/2000 | Unger et al. |
| 6,071,532 A | 6/2000 | Chaikof et al. |
| 6,093,382 A | 7/2000 | Wedeking et al. |
| 6,110,433 A | 8/2000 | Kleinsorgen et al. |
| 6,110,443 A | 8/2000 | Schneider et al. |
| 6,123,922 A | 9/2000 | Bichon et al. |
| 6,130,071 A | 10/2000 | Alitalo et al. |
| 6,136,293 A | 10/2000 | Schneider et al. |
| 6,143,274 A | 11/2000 | Tweedle et al. |
| 6,146,657 A | 11/2000 | Unger et al. |
| 6,165,458 A | 12/2000 | Foldvari et al. |
| 6,171,614 B1 | 1/2001 | Chaikof et al. |
| 6,183,725 B1 | 2/2001 | Yan et al. |
| 6,187,288 B1 | 2/2001 | Schneider et al. |
| 6,200,548 B1 | 3/2001 | Bichon et al. |
| 6,204,011 B1 | 3/2001 | Kendall et al. |
| 6,207,152 B1 | 3/2001 | Schwall et al. |
| 6,221,839 B1 | 4/2001 | Alitalo et al. |
| 6,231,834 B1 | 5/2001 | Unger et al. |
| 6,245,318 B1 | 6/2001 | Klibanov et al. |
| 6,245,530 B1 | 6/2001 | Alitalo et al. |
| 6,258,378 B1 | 7/2001 | Schneider et al. |
| 6,261,535 B1 | 7/2001 | Thorpe et al. |
| 6,261,537 B1 | 7/2001 | Klaveness et al. |
| 6,264,917 B1 | 7/2001 | Klaveness et al. |
| 6,274,166 B1 | 8/2001 | Sintov et al. |
| 6,312,661 B1 | 11/2001 | Reubi |
| 6,312,665 B1 | 11/2001 | Modi |
| 6,322,770 B1 | 11/2001 | Rajopadhye et al. |
| 6,331,289 B1 | 12/2001 | Klaveness et al. |
| 6,359,115 B1 | 3/2002 | Kendall et al. |
| 6,361,946 B1 | 3/2002 | Alitalo et al. |
| 6,403,088 B1 | 6/2002 | Alitalo et al. |
| 6,451,764 B1 | 9/2002 | Lee et al. |
| 6,521,211 B1 | 2/2003 | Unger et al. |
| 6,524,533 B1 | 2/2003 | Tyrrell |
| 6,528,039 B2 | 3/2003 | Unger |
| 6,537,520 B1 | 3/2003 | Rajopadhye et al. |
| 6,548,048 B1 | 4/2003 | Cuthbertson et al. |
| 6,548,663 B1 | 4/2003 | Cheesman et al. |
| 6,576,608 B1 | 6/2003 | Lee et al. |
| 6,610,269 B1 | 8/2003 | Klaveness et al. |
| 6,645,933 B1 | 11/2003 | Alitalo et al. |
| 6,680,047 B2 | 1/2004 | Klaveness et al. |
| 6,689,352 B2 | 2/2004 | Achen et al. |
| 6,710,165 B2 | 3/2004 | Lee et al. |
| 6,730,658 B1 | 5/2004 | Alitalo et al. |
| 6,733,755 B2 | 5/2004 | Tchistiakova et al. |
| 6,773,696 B2 | 8/2004 | Unger |
| 6,777,534 B1 | 8/2004 | Klagsbrun et al. |
| 6,800,273 B2 | 10/2004 | Rajopadhye et al. |
| 6,818,220 B1 | 11/2004 | Alitalo et al. |
| 6,841,367 B2 | 1/2005 | Kendall et al. |
| 6,841,382 B2 | 1/2005 | Kendall et al. |
| 6,875,741 B2 | 4/2005 | Pillutla et al. |
| 6,984,373 B2 | 1/2006 | Wescott et al. |
| 7,034,105 B2 | 4/2006 | Alitalo et al. |
| 7,078,015 B2 | 7/2006 | Unger |
| 7,199,100 B2 | 4/2007 | Betz et al. |
| 7,211,240 B2 | 5/2007 | Arbogast et al. |
| 7,261,876 B2 | 8/2007 | Arbogast et al. |
| 7,666,979 B2 | 2/2010 | Fan et al. |
| 7,794,693 B2 * | 9/2010 | Bussat et al. .................. 424/9.1 |
| 7,854,919 B2 | 12/2010 | Arbogast et al. |
| 7,910,088 B2 | 3/2011 | Arbogast et al. |
| 7,985,402 B2 | 7/2011 | Bussat et al. |
| 2001/0031485 A1 | 10/2001 | Backer et al. |
| 2001/0038842 A1 | 11/2001 | Achen et al. |
| 2002/0001566 A1 | 1/2002 | Rajopadhye et al. |
| 2002/0010137 A1 | 1/2002 | Ashkenazi et al. |
| 2002/0015680 A1 | 2/2002 | Harris |
| 2002/0037289 A1 | 3/2002 | Thorpe et al. |
| 2002/0058619 A1 | 5/2002 | Tchistiakova et al. |
| 2002/0065218 A1 | 5/2002 | Achen et al. |
| 2002/0068697 A1 | 6/2002 | Tournaire et al. |
| 2002/0086013 A1 | 7/2002 | King |
| 2002/0091082 A1 | 7/2002 | Aiello |
| 2002/0098187 A1 | 7/2002 | Ferrara et al. |
| 2002/0102215 A1 | 8/2002 | Klaveness et al. |
| 2002/0102217 A1 | 8/2002 | Klaveness et al. |
| 2002/0102260 A1 | 8/2002 | Achen et al. |
| 2002/0119149 A1 | 8/2002 | Jakobsen et al. |
| 2002/0136721 A1 | 9/2002 | Schwall et al. |
| 2002/0164667 A1 | 11/2002 | Alitalo et al. |
| 2003/0023046 A1 | 1/2003 | Ferrara et al. |

(56) References Cited

U.S. PATENT DOCUMENTS

| | | |
|---|---|---|
| 2003/0027246 A1 | 2/2003 | Pedyczak et al. |
| 2003/0055006 A1 | 3/2003 | Siemeister et al. |
| 2003/0082103 A1 | 5/2003 | Wartchow et al. |
| 2003/0091567 A1 | 5/2003 | Alitalo et al. |
| 2003/0124120 A1 | 7/2003 | Harris |
| 2003/0125493 A1 | 7/2003 | Harris et al. |
| 2003/0129223 A1 | 7/2003 | Wartchow et al. |
| 2003/0149262 A1 | 8/2003 | Cheesman et al. |
| 2003/0157025 A1 | 8/2003 | Unger et al. |
| 2003/0166523 A1 | 9/2003 | Achen et al. |
| 2003/0166873 A1 | 9/2003 | Lee et al. |
| 2003/0176674 A1 | 9/2003 | Rosen et al. |
| 2003/0180305 A1 | 9/2003 | Rajopadhye et al. |
| 2003/0180718 A1 | 9/2003 | Pillutla et al. |
| 2003/0195147 A1 | 10/2003 | Pillutla et al. |
| 2003/0236190 A1 | 12/2003 | Pillutla et al. |
| 2004/0009122 A1 | 1/2004 | Klaveness et al. |
| 2004/0018974 A1 | 1/2004 | Arbogast et al. |
| 2004/0023887 A1 | 2/2004 | Pillutla et al. |
| 2004/0033949 A1 | 2/2004 | Bunting et al. |
| 2004/0037820 A1 | 2/2004 | Alitalo et al. |
| 2004/0141922 A1 | 7/2004 | Klaveness et al. |
| 2004/0147448 A1 | 7/2004 | Alitalo et al. |
| 2004/0147449 A1 | 7/2004 | Siemeister et al. |
| 2004/0147726 A1 | 7/2004 | Alitalo et al. |
| 2004/0213790 A1 | 10/2004 | Lee et al. |
| 2004/0223911 A1 | 11/2004 | Bednarski et al. |
| 2004/0224398 A1 | 11/2004 | Anand-Apte |
| 2004/0248781 A1 | 12/2004 | Kerbel |
| 2004/0266694 A1 | 12/2004 | Tchistiakova et al. |
| 2005/0002865 A1 | 1/2005 | Klaveness et al. |
| 2005/0037967 A1 | 2/2005 | Rosenblum |
| 2005/0100963 A1 | 5/2005 | Sato et al. |
| 2005/0147555 A1 | 7/2005 | Fan et al. |
| 2005/0181995 A1 | 8/2005 | Kawai et al. |
| 2005/0214859 A1 | 9/2005 | Dransfield et al. |
| 2005/0250700 A1 | 11/2005 | Sato et al. |
| 2006/0003926 A1 | 1/2006 | Rajopadhye et al. |
| 2006/0008930 A1 | 1/2006 | Toyoda et al. |
| 2006/0063699 A1 | 3/2006 | Larsen |
| 2006/0078501 A1 | 4/2006 | Goertz et al. |
| 2006/0089307 A1 | 4/2006 | Kulseth |
| 2007/0172428 A1* | 7/2007 | Arbogast et al. ............. 424/9.52 |
| 2007/0243139 A1 | 10/2007 | Arbogast et al. |
| 2008/0152594 A1* | 6/2008 | Bussat et al. ................ 424/9.52 |

FOREIGN PATENT DOCUMENTS

| | | |
|---|---|---|
| CA | 2477935 | 10/2003 |
| EP | 0122624 | 10/1984 |
| EP | 0123235 | 10/1984 |
| EP | 0324938 | 7/1989 |
| EP | 0365467 | 4/1990 |
| EP | 0458745 | 11/1991 |
| EP | 0474833 | 3/1992 |
| EP | 0554213 | 8/1993 |
| EP | 0 580 726 B1 | 2/1994 |
| EP | 0580726 | 2/1994 |
| EP | 0619743 | 10/1994 |
| EP | 0 627 940 B1 | 12/1994 |
| EP | 0627940 | 12/1994 |
| EP | 0682530 | 11/1995 |
| EP | 0711127 | 5/1996 |
| EP | 0 711 127 B1 | 6/1996 |
| EP | 0744962 | 12/1996 |
| EP | 0 804 932 A2 | 11/1997 |
| EP | 0804932 | 11/1997 |
| EP | 0831932 | 4/1998 |
| EP | 0842273 | 5/1998 |
| EP | 0881915 | 12/1998 |
| EP | 0977600 | 2/2000 |
| EP | 1007101 | 6/2000 |
| EP | 1 064 376 | 1/2001 |
| EP | 1064376 | 1/2001 |
| EP | 1 081 913 A2 | 3/2001 |
| EP | 1081913 | 3/2001 |
| EP | 1 166 798 A1 | 1/2002 |
| EP | 1 166 799 A1 | 1/2002 |
| EP | 0 666 868 B1 | 4/2002 |
| EP | 0 536 350 B1 | 8/2002 |
| EP | 1 238 986 A2 | 9/2002 |
| EP | 1261370 | 12/2002 |
| EP | 1268760 | 1/2003 |
| EP | 1278771 | 1/2003 |
| EP | 1292335 | 3/2003 |
| EP | 1 306 095 A2 | 5/2003 |
| EP | 1306095 | 5/2003 |
| EP | 0 848 755 B1 | 6/2003 |
| EP | 03002373 | 8/2003 |
| EP | 1 432 433 | 6/2004 |
| EP | 1432433 | 6/2004 |
| EP | 1444991 | 8/2004 |
| EP | 1259248 | 12/2004 |
| EP | 1 519 193 A2 | 3/2005 |
| EP | 1519193 | 3/2005 |
| EP | 1 068 224 B1 | 5/2005 |
| EP | 1 574 518 A2 | 9/2005 |
| EP | 1574518 | 9/2005 |
| EP | 1 586 333 A2 | 10/2005 |
| EP | 1586333 | 10/2005 |
| JP | 94-41458 | 2/1994 |
| JP | 07300452 A2 | 11/1995 |
| JP | 11-506327 | 6/1999 |
| JP | A-11-507638 | 7/1999 |
| JP | 2002-330772 | 11/2002 |
| JP | 3398382 | 2/2003 |
| WO | WO 86/06605 | 11/1986 |
| WO | WO 91/03200 | 3/1991 |
| WO | WO 92/14748 | 9/1992 |
| WO | WO 93/13809 | 7/1993 |
| WO | WO 94/00144 | 1/1994 |
| WO | WO 94/10202 | 5/1994 |
| WO | WO 94/10202 A1 | 5/1994 |
| WO | WO 95/01187 | 1/1995 |
| WO | WO 95/03280 | 2/1995 |
| WO | WO 95/06633 | 3/1995 |
| WO | WO 95/21631 | 8/1995 |
| WO | WO 95/28179 | 10/1995 |
| WO | WO 95/28967 | 11/1995 |
| WO | WO 96/03427 | 2/1996 |
| WO | WO 96/15815 | 5/1996 |
| WO | WO 96/17628 | 6/1996 |
| WO | WO 96/23524 | 8/1996 |
| WO | WO 96/23525 | 8/1996 |
| WO | WO 96/23526 | 8/1996 |
| WO | WO 96/38557 | 12/1996 |
| WO | WO 96/40285 A1 | 12/1996 |
| WO | WO 97/05250 | 2/1997 |
| WO | WO 97/05250 A2 | 2/1997 |
| WO | WO 97/09427 | 3/1997 |
| WO | WO 97/09427 A1 | 3/1997 |
| WO | WO 97/17442 A1 | 5/1997 |
| WO | WO 97/18841 | 5/1997 |
| WO | WO 97/29783 | 8/1997 |
| WO | WO 97/36619 | 10/1997 |
| WO | WO 98/05364 | 2/1998 |
| WO | WO 98/16198 | 4/1998 |
| WO | WO 98/17324 | 4/1998 |
| WO | WO 98/18495 | 5/1998 |
| WO | WO 98/18495 A2 | 5/1998 |
| WO | WO 98/18496 | 5/1998 |
| WO | WO 98/18497 | 5/1998 |
| WO | WO 98/18498 A2 | 5/1998 |
| WO | WO 98/18500 | 5/1998 |
| WO | WO 98/18500 A2 | 5/1998 |
| WO | WO 98/18501 A2 | 5/1998 |
| WO | WO 98/28179 | 7/1998 |
| WO | WO 98/33917 | 8/1998 |
| WO | WO 98/33917 A1 | 8/1998 |
| WO | WO 98/46612 | 10/1998 |
| WO | WO 98/47538 | 10/1998 |
| WO | WO 98/47541 A1 | 10/1998 |
| WO | WO 98/52618 | 11/1998 |

(56) References Cited

FOREIGN PATENT DOCUMENTS

| | | |
|---|---|---|
| WO | WO 98/53051 | 11/1998 |
| WO | WO 98/53051 A1 | 11/1998 |
| WO | WO 98/53857 | 12/1998 |
| WO | WO 98/57666 | 12/1998 |
| WO | WO 98/58053 | 12/1998 |
| WO | WO 98/58053 A1 | 12/1998 |
| WO | WO 99/17809 | 4/1999 |
| WO | WO 99/29861 A1 | 6/1999 |
| WO | WO 99/40102 | 8/1999 |
| WO | WO 99/40102 A1 | 8/1999 |
| WO | WO 99/40947 A2 | 8/1999 |
| WO | WO 99/55383 | 11/1999 |
| WO | WO 99/55383 A2 | 11/1999 |
| WO | WO 99/58162 A | 11/1999 |
| WO | WO 99/58162 A2 | 11/1999 |
| WO | WO 99/64052 | 12/1999 |
| WO | WO 00/20027 | 4/2000 |
| WO | WO 00/20027 A2 | 4/2000 |
| WO | WO 00/27414 A2 | 5/2000 |
| WO | WO 00/44777 | 8/2000 |
| WO | WO 00/44777 A1 | 8/2000 |
| WO | WO 00/45856 A2 | 8/2000 |
| WO | WO 00/63380 | 10/2000 |
| WO | WO 00/63380 A1 | 10/2000 |
| WO | WO 00/75167 | 12/2000 |
| WO | WO 00/75167 A2 | 12/2000 |
| WO | WO 01/16135 | 3/2001 |
| WO | WO 01/42284 A2 | 6/2001 |
| WO | WO 01/52875 | 7/2001 |
| WO | WO 01/52875 A | 7/2001 |
| WO | WO 01/52875 A1 | 7/2001 |
| WO | WO 01/54723 A1 | 8/2001 |
| WO | WO 01/57067 | 8/2001 |
| WO | WO 01/57067 A1 | 8/2001 |
| WO | WO 01/62942 A2 | 8/2001 |
| WO | WO 01/64235 A1 | 9/2001 |
| WO | WO 01/70268 A1 | 9/2001 |
| WO | WO 01/70681 | 9/2001 |
| WO | WO 01/70945 A1 | 9/2001 |
| WO | WO 01/72829 | 10/2001 |
| WO | WO 01/72829 A2 | 10/2001 |
| WO | WO 01/79479 | 10/2001 |
| WO | WO 01/82870 A2 | 11/2001 |
| WO | WO 01/83693 A2 | 11/2001 |
| WO | WO 01/91805 A2 | 12/2001 |
| WO | WO 01/93836 | 12/2001 |
| WO | WO 01/93836 A2 | 12/2001 |
| WO | WO 01/97850 A2 | 12/2001 |
| WO | WO 01/97860 | 12/2001 |
| WO | WO 02/06789 | 1/2002 |
| WO | WO 02/07747 A1 | 1/2002 |
| WO | WO 02/16412 | 2/2002 |
| WO | WO 02/16412 A2 | 2/2002 |
| WO | WO 02/28895 A2 | 4/2002 |
| WO | WO 02/057299 A2 | 7/2002 |
| WO | WO 02/060950 A2 | 8/2002 |
| WO | WO 02/072011 | 9/2002 |
| WO | WO 02/072011 A2 | 9/2002 |
| WO | WO 02/083849 A2 | 10/2002 |
| WO | WO 02/092573 | 11/2002 |
| WO | WO 02/092573 A2 | 11/2002 |
| WO | WO 02/096367 | 12/2002 |
| WO | WO 02/096367 A2 | 12/2002 |
| WO | WO 03/000842 | 1/2003 |
| WO | WO 03/000844 | 1/2003 |
| WO | WO 03/018797 | 3/2003 |
| WO | WO 03/027246 | 4/2003 |
| WO | WO 03/028643 A2 | 4/2003 |
| WO | WO 03/035839 | 5/2003 |
| WO | WO 03/035839 A2 | 5/2003 |
| WO | WO 03/070747 | 8/2003 |
| WO | WO 03/070747 A2 | 8/2003 |
| WO | WO 03/074005 A2 | 9/2003 |
| WO | WO 03/080653 | 10/2003 |
| WO | WO 03/084574 | 10/2003 |
| WO | WO 03/084574 A1 | 10/2003 |
| WO | WO 03/094617 A2 | 11/2003 |
| WO | WO 03/103581 | 12/2003 |
| WO | WO 03/103581 A2 | 12/2003 |
| WO | WO 2004/001064 | 12/2003 |
| WO | WO 2004/001064 A2 | 12/2003 |
| WO | WO 2004/033949 | 4/2004 |
| WO | WO 2004/058802 | 7/2004 |
| WO | WO 2004/058802 A1 | 7/2004 |
| WO | WO 2004/058803 | 7/2004 |
| WO | WO 2004/058803 A2 | 7/2004 |
| WO | WO 2004/064595 | 8/2004 |
| WO | WO 2004/064595 A2 | 8/2004 |
| WO | WO 2004/065621 | 8/2004 |
| WO | WO 2004/065621 A1 | 8/2004 |
| WO | WO 2004/069284 | 8/2004 |
| WO | WO 2004/078778 | 9/2004 |
| WO | WO 2004/085617 | 10/2004 |
| WO | WO 2004/085617 A2 | 10/2004 |
| WO | WO 2004/108074 | 12/2004 |
| WO | WO 2004/108074 A2 | 12/2004 |
| WO | WO 2005/011722 | 2/2005 |
| WO | WO 2005/011722 A2 | 2/2005 |
| WO | WO 2005/016963 | 2/2005 |
| WO | WO 2005/016963 A2 | 2/2005 |
| WO | WO 2005/037862 | 4/2005 |
| WO | WO 2005/070472 | 8/2005 |
| WO | WO 2005/070472 A2 | 8/2005 |
| WO | WO 2005/072417 | 8/2005 |
| WO | WO 2005/072417 A2 | 8/2005 |
| WO | WO 2006/015385 | 2/2006 |
| WO | WO 2006/015385 A2 | 2/2006 |
| WO | WO 2007/067979 | 6/2007 |
| WO | WO 2007/067979 A2 | 6/2007 |

OTHER PUBLICATIONS

Cann et al., Partial activation of the insulin receptor kinase domain by juxtamembrane autophosphorylation. Biochemistry. Aug. 11, 1998;37(32):11289-300.
Chinol et al., Biodistribution in tumour-bearing mice of two 90Y-labelled biotins using three-step tumour targeting. Nucl Med Commun. Feb. 1997;18(2):176-82.
Cho et al., Purification and characterization of a soluble catalytic fragment of the human transmembrane leukocyte antigen related (LAR) protein tyrosine phosphatase from an Escherichia coli expression system. Biochemistry. Jun. 25, 1991;30(25):6210-6.
Fairbrother et al., Novel peptides selected to bind vascular endothelial growth factor target the receptor-binding site. Biochemistry 37(51): 17754-17764, 1998.
Fukumura et al., Tumor induction of VEGF promoter activity in stromal cells. Cell 94: 715-725, 1998.
Hanahan et al., Patterns and emerging mechanisms of the angiogenic switch during tumorigenesis. Cell 86: 353-364, 1996.
Harvath et al., Laminin peptides stimulate human neutrophil motility. J Immunol. Jun. 1, 1994;152(11):5447-56.
Hetian et al., A novel peptide isolated from a phage display library inhibits tumor growth and metastasis by blocking the binding of vascular endothelial growth factor to its kinase domain receptor. J Biol Chem. Nov. 8, 2002;277(45):43137-42. Epub Aug. 14, 2002.
Hsu et al., Autophosphorylation of the intracellular domain of the epidermal growth factor receptor results in different effects on its tyrosine kinase activity with various peptide substrates. Phosphorylation of peptides representing Tyr(P) sites of phospholipase C-gamma. J Biol Chem. Jan. 5, 1991;266(1):603-8.
Holmes et al., Site specific 1:1 opioid:albumin conjugate with in vitro activity and long in vivo duration. Bioconjug Chem 11: 439-444, 2000.
Iwamoto et al., YIGSR, a synthetic laminin pentapeptide, inhibits experimental metastasis formation. Science. Nov. 20, 1987;238(4830):1132-4.
Jia et al., Peptides encoded by exon 6 of VEGF inhibit endothelial cell biological responses and angiogenesis induced by VEGF. Biochem Biophys Res Commun. Apr. 27, 2001;283(1):164-73.
Kim et al., Inhibition of vascular endothelial growth factor-induced angiogenesis suppresses tumour growth in vivo. Nature 362: 841-844, 1993.

(56) References Cited

OTHER PUBLICATIONS

Kitagawa et al., Synthesis of two substance P analogs, [8-Tyr] and [5-Asn] Substance P[1]. Chem Pharm Bull. Mar. 13, 1978;28(9):2899-2903.

Lecouter et al., Identification of an angiogenic mitogen selective for endocrine gland endothelium. Nature. Aug. 30, 2001;412(6850):877-84.

Matsudaira et al., Sequence from picomole quantities of proteins electroblotted onto polyvinylidene difluoride membranes. J Biol Chem. Jul. 25, 1987;262(21):10035-8.

Neufeld G et al., Vascular endothelial growth factor (VEGF) and its receptors. FASEB J 13: Sep. 22, 1999.

Pepper et al., Angiogenesis: a paradigm for balanced extracellular proteolysis during cell migration and morphogenesis. Enzyme Protein. 1996;49(1-3):138-62.

Pritchard et al., A truncated v-abl-derived tyrosine-specific tyrosine kinase expressed in *Escherichia coli*. Biochem J. Jan. 15, 1989;257(2):321-9.

Risau et al., Mechanisms of angiogenesis. Nature 386: 671-674, 1997.

Roberts M et al., Chemistry for peptide and protein PEGylation. Adv Drug Deliv Rev. Jun. 17, 2002;54(4):459-76.

Sato et al., Development of mammalian serum albumin affinity purification media by peptide phage display. Biotechnol Prog. Mar.-Apr. 2002;18(2):182-92.

Schaffer et al., Assembly of high-affinity insulin receptor agonists and antagonists from peptide building blocks. Proc Natl Acad Sci U S A. Apr. 15, 2003;100(8):4435-9.

Schmitz et al., Catalytic specificity of phosphotyrosine kinases Blk, Lyn, c-Src and Syk as assessed by phage display. J Mol Biol. Aug. 2, 1996;260(5):664-77.

Shrivastava et al., A distinct strategy to generate high-affinity peptide binders to receptor tyrosine kinases. Protein Eng Des Sel. Sep. 2005;18(9):417-24.

Sleep et al., Saccharomyces cerevisiae strains that overexpress heterologous proteins. Biotechnology (N Y). Feb. 1991;9(2):183-7.

Soker et al., Inhibition of vascular endothelial growth factor (VEGF)-induced endothelial cell proliferation by a peptide corresponding to the exon 7-encoded domain of VEGF165. J Biol Chem. Dec. 12, 1997;272(50):31582-8.

Strawn et al., Flk-1 as a target for tumor growth inhibition. Cancer Res 56: 3540-3545, 1996.

Thomas et al., A peptide sequence on carcinoembryonic antigen binds to a 80kD protein on Kupffer cells. Biochem Biophys Res Commun 188: 671-677, 1992.

Veikkola et al., Regulation of angiogenesis via vascular endothelial growth factor receptors. Cancer Res 60: 203-212, 2000.

Wedegaertner et al., Effect of carboxyl terminal truncation on the tyrosine kinase activity of the epidermal growth factor receptor. Arch Biochem Biophys. Jan. 1992;292(1):273-80.

European Search Report issued on Aug. 12, 2009 for European Patent No. 08008365.2.

Haiyan Jia et al., "Peptides encoded by exon 6 of VEGF inhibit endothelial cell biological responses and angiogenesis induced by VEGF," Biochemical and Biophysical Research Communications 283(1): 164-173, 2001.

Melkko et al., Encoded self-assembling chemical libraries. Nat. Biotechnol. 22(5): 568-574, May 2004.

U.S. Appl. No. 60/360,851, Mar. 1, 2002, Sato et al.
U.S. Appl. No. 60/440,201, Jan. 15, 2003, Marinelli et al.
U.S. Appl. No. 60/440,441, Jan. 15, 2003, Sato et al.
U.S. Appl. No. 60/451,588, Mar. 3, 2003, Dransfield et al.
US5,171,298, Dec. 15, 1992, Walker et al., (Abandoned).

Adams, "Insight into Tyrosine Phosphorylation in v-Fps using Proton Inventory Techniques," Biochemistry. Aug. 20, 1996;35(33):10949-56.

Alberico et al., "Preparation and handling of peptides containing methionine and cysteine," Fmoc Solid Phase Peptide Synthesis—A Practical Approach (Chan, W. C. and White, P. D. Eds.) Oxford University Press, New York, N.Y. Chap. 4, pp. 87-114 (2000).

Alexander et al., "Intracranial black-blood MR angiography with high-resolution 3D fast spin echo," Magnetic Resonance in Medicine, 40(2): 298-310 (1998).

Allcock et al., "Polyphosphazenes: New Polymers with Inorganic Backbone Atoms" Science 193:1214-19 (1976).

Alon et al. "Streptavidin contains an RYD sequence which mimics the RGD receptor domain of fibronectin." Biochem. Biophys. Res. Commun. 170:1236-41 (1990).

Anderson et al., "Fiber Optic Immunochemical Sensor for Continuous, Reversible Measurement of Phenytoin," Clin. Chem. 34:7, pp. 1417-21 (1988).

Andreu et al., "Formation of Disulfide Bonds in Synthetic Peptides and Proteins," Peptide Synthesis Protocols (Pennington, M. W. and Dunn, B. M. Eds.) Humana Press, Totowa N.J. Chap. 7, pp. 91-169 (1994).

Andrieux et al. "Amino acid sequences in fibrinogen mediating its interaction with its platelet receptor, GPIIbIIIa." Journal of Biological Chemistry, 264(16):9258-8265 (1989).

Angeloni et al., The Mannich bases in polymer synthesis: 3. Reduction of poly(betaaminoketone)s to poly(gamma-aminoalcohol)s and their N-alkylation to poly(gamma-hydroxyquaternary ammonium salt)s, Polymer 23, pp. 1693-1697 (1982).

Ashraf, M. et al., "Solid phase synthesis of peptide dimers and trimers linked through an N-terminal lysine residue" Tetrahedron Letters 2003, 44, 9115-9119.

Backes et al., "Activation Method to Prepare a Highly Reactive Acylsulfonamide ""Safety-Catch" Linker for Solid-Phase Synthesis J. Am. Chem. Soc., 118(12):3055-56 (1996).

Bajusz, "Peptide related drug research," Journal of Peptide Science 9(6), 321-332 (2003).

Bardelli et al., "A Peptide representing the carboxyl-terminal tail of the met receptor inhibits kinase activity and invasive growth," J. Biol. Chem. Oct. 8, 1999; 274(41):29274-81.

Barlos et al., "Convergent Peptide Synthesis" In FMOC Solid Phase Peptide Synthesis. A Practical Approach, WC Chan, PD White(eds), Oxford University Press, 2000, 215-228.

Bax et al., "The Structure of Phosphorylated GSK-3beta Complexed with a Peptide, FRATtide. that Inhibits Beta-Catenin Phosphorylation" Structure. Dec. 2001;9 (12):1143-1152.

Ben-Yedidia, T. et al., "Design of peptide and polypeptide vaccines," Current Opinion in Biotechnology vol. 8, pp. 442-448 (1997).

Bikfalvi et al., "Interaction of vasculotopin/vascular endothelial cell growth factor with human umbilical vein endothelial cells: binding, internalization, degradation and biological effects," J. Cell Physiol, 149: 50-59, 1991.

Binetruy-Tournaire et al., "Identification of a peptide blocking vascular endothelial growth factor (VEGF)-mediated angiogenesis," EMBO J., Apr. 3, 2000, vol. 19, No. 7, pp. 1525-1533.

Blackwell et al., "Highly efficient synthesis of covalently cross-linked peptide helices by ring-closing metathesis," Angew. Chem. Int. Ed., 37(23):3281-3284 (1998).

Botti et al. "Cyclic Peptides from Linear Unprotected Peptide Precursors through Thiazolidine Formation" J. Am. Chem. Soc., 118:10018-10034 1996.

Cann et al., "Partial Activation of the Isulin Receptor Kinase Domain by Juxtamembrane Autophosphorylation." Biochemistry. Aug. 11, 1998;37(32):11289-300.

Carlsson et al., "Protein Thiolation and Reversible Protein-Protein Conjugation," Biochem. J., 173:723-737 (1978).

Chan et al. "New N- and O-arylations with phenylboronic acids and cupric acetate" Tetrahedron Letters 39:2933-36 (1998).

Chen et al. "Evaluation of an 111In-DOTA—Rhenium Cyclized α-MSH Analog: A Novel Cyclic-Peptide Analog with Improved Tumor-Targeting Properties" J Nucl Med Dec. 1, 2001 vol. 42 No. 12 1847-1855.

Chen, H. et al., "Interaction of dendrimers (artificial proteins) with biological hydroxyapatite crystals," Journal of Dental Research 82, 443-448 (2003).

Chinol, M. et al. "Biodistribution in Tumor-bearing Mice of Two 90Y-Labelled Biotins Using Three-step Tumor Targeting," Nuclear Medicine Communications, vol. 18, No. 2, Feb. 1997, pp. 176-182.

Cho et al., "Purification and Characterization of a Soluble Catalytic Fragment of the Human Transmembrane Leukocyte Antigen Related

(56) References Cited

OTHER PUBLICATIONS (LAR) Protein Tyrosine Phosphatase from an *Escherichia Coli* Expression System" Biochemistry 37(51):17754-17764 (1998).
Clark et al., "Covalent Capture and Stabilization of Cylindrical β-Sheet Peptide Assemblies" Chem. Eur. J., 5(2):782-792 (1999).
Clark et al., "Supramolecular Design by Covalent Capture. Design of a Peptide Cylinder via Hydrogen-Bond- Promoted Intermolecular Olefin Metathesis" J Am. Chem. Soc., 117(49):12364-12365 (1995).
Date et al., HGF/NK4 is a specific antagonist for pleiotrophic actions of hepatocyte growth factor. FEBS Lett. Dec. 22, 1997; 420(1): 1-6.
Davis, L.G. et al. "Basic Methods in Molecular Biology", Elsevier, New York, p. 364 (1986).
Dawson, P.E. et al., "Synthesis of Native Proteins by Chemical Ligation," Ann. Rev. Biochem. 69, 923-960 (2000).
De Villiers, et al., "Solubilization of poorly water soluble non-steroidal anti-inflammatory drugs at low pH with N-methylglucamine," S. Afr. Pharmazie, 55, 544-546 (2000).
Edelman et al., "Extracranial carotid arteries: evaluation with "black blood" MR angiography" Radiology, 177(1):45-50 (1990).
Evans et al. "Synthesis of Diary! Ethers through the Copper-Promoted Arylation of Phenols with Arylboronic Acids. An Expedient Synthesis of Thyroxine," Tetrahedron Lett 39:2937-2940 (1998).
Fairbrother et al., "Novel peptides selected to bind vascular endothelial growth factor target the receptor-binding site," Biochemistry 37(51): 17754-17764, 1998.
Falorni et al., "New 1,3,5-triazine derivatives as templates for the homogeneous phase synthesis of chemical libraries" Tetrahedron Lett., 39(41):7607-7610 (1998).
Fields, G.B. et al., "Principles and Practice of Solid Phase Synthesis" in Synthetic Peptides, a Users Guide, Grant, G.A. ed., W.H. Freeman Co. NY. 1992, Chap. 3 pp. 77-183.
Folkman et al., Cancer Medicine, 5th Edition (B.C. Decker Inc.; Ontario, Canada, 2000) pp. 132-152.
Fukumura et al., "Tumor induction of VEGF promoter activity in stromal cells," Cell 94: 715-725, 1998.
Futaki, "Creation of ion channel function using synthetic peptides," Journal of Synthetic Organic Chemistry, Japan, vol. 56, No. 28; 125-133 (1998).
Gestwicki, J. E. et al., "Influencing Receptor-Ligand Binding Mechanisms with Multivalent Ligand Architecture," J. Am. Chem. Soc. 124, 14922-14933 (2002).
Goodrich et al. "A Quantitative Study of Ramped Radio Frequency, Magnetization Transfer, and Slab Thickness in Three-Dimensional Time-of-Flight Magnetic Resonance Angiography in a Patient Population" Investigative Radiology, 31(61):323-32 (1996).
Goodwin et al., "Advances in pretargeting biotechnology," Biotechnology Advances 19(6), 435-450 (2001).
Hanahan et al., "Patterns and emerging mechanisms of the angiogenic switch during tumorigenesis," Cell 86: 353-364, 1996.
Hanessian et al., "Synthesis of a Versatile Peptidomimetic Scaffold" in Methods in Molecular Medicine, vol. 23: Peptidomimetics Protocols, W.M. Kazmierski Ed. (Humana Press Inc. Totowa, Nj 1999), Chapter 10, pp. 161-174.
Hart et al., "Cyclophilin Inhibition by a (Z)-Alkene cis-Proline Mimic" J. Org. Chem., 64:2998-2999 (1999).
Harvath et al., "Laminin peptides stimulate human neutrophil motility," J. Immunol. 1994 Jun. 1; 152(11):5447-56.
Heller, "Controlled Release of Biologically Active Compounds from Bioerodible Polymers," Biomaterials, 1:51-57 (1980).
Herynk et al., "Down-Regulation of c-Met Inhibits Growth in the Liver of Human Colorectal Carninoma Cells," Cancer Research 63, 2990-2996, Jun. 1, 2003.
Hetian et al., A Novel Peptide Isolated from a Phage Display Library Inhibits Tumor Growth and Metastasis by Blocking the Binding of Vascular Endothelial Growth Factor to its Kinase Domain Receptor. J Biol Chem. 2002 Nov 8;277(45):43137-42. Epub 2002 Aug 14.
Hillairet de Boisferon, M. et al., "Enhanced Targeting Specificity to Tumor Cells by Simultaneous Recognition of Two Antigens," Bioconjugate Chem. 11, 452-460 (2000).

Hiller et al. "Biotin binding to avidin. Oligosaccharide side chain not required for ligand association." Biochem J. 248:167-171 (1987).
Holmes et al., "Site specific 1:1 opioid: albumin conjugate with in vitro activity and long in vivo duration," Bioconjug Chem 11: 439-444, 2000.
Howie et al. "Synthetic peptides representing discontinuous CD4 binding epitopes of HOV-1 gp120 that induce T cell apoptosis and block cell death induced by gp120", FASEB J, 12(11):991-998 (1998).
Hsu et al., "Autophosphorylation of the Intracellular Domain of the of the epidermal growth Factor Receptor Results in Different Effects on its Tyrosine Kinase Activity with Various Peptide Substrates. Phosphorylation of Peptides Representing Tyr(P) Sites of Phospholipase C-gamma." J Biol Chem. 1991 jan 5;266(1):603-8.
Hunter et al. "Native Chemical Ligation of Hydrophobic Peptides in Lipid Bilayer Systems," Bioconjugate Chem. 15, 437-440. (2004).
Hutchinson, "Evanescent wave biosensors Real-time analysis of biomolecular interactions" Molec. Biotechnology 1995: 3: 47-54.
Inman, J. et al., "Synthesis of N.alpha.-(tert-butoxycarbonyl)-N.epsilon.-[N-(bromoacetyl)-.beta.-alanyl]-L-lysine: Its use in peptide synthesis for placing a bromoacetyl cross-linking function at any desired sequence position", Bioconjugate Chem, 2:458-463 1991.
Iwamoto et al., "YIGSR, a synthetic laminin pentapeptide, inhibits experimental metastasis formation," Science, 1987 Nov. 20; 238(4830):1132-4.
Jackson, D. C. et al., "Preparation and properties of totally synthetic immunogens," Vaccine 18, 355-361 (2000).
Jia et al., "Peptides encoded by exon 6 of VEGF inhibit endothelial cell biological responses and angiogenesis induced by VEGF," Biochem Biophys Res Commun. 2001 Apr. 27; 283(1):164-73.
Johnson et al. "Libraries of N-alkylaminoheterocycles from nucleophilic aromatic substitution with purification by solid supported liquid extraction" Tetrahedron Lett., 54(16):4097-4106 (1998).
Kihlberg, "Glycopeptide synthesis," In Fmoc Solid Phase Peptide Synthesis—A Practical Approach (Chan, W.C. And White, P.D. eds) Oxford University Press, New York, NY, Chap. 8, pp. 195-213 (2000).
et al., "Inhibition of vascular endothelial growth factor-induced angiogenesis suppresses tumor growth in vivo," Nature 362: 841-844, 1993.
Kitagawa et al., "Synthesis of Two Substance p. Analogs, [8-Tyr] and [5-Asn] Substance P," Chem. Pharm. Bull., 26(9): 2899-2903 (1978).
Knudsen, et al., "Potent Derivatives of Glucagon-like Peptide-1 with Pharmacokinetic Properties Suitable for Once Daily Administration," J. Med. Chem., 43:1664-1669 (2000).
Laemmli et al., "Cleavage of Structural Proteins during the Assembly of the Head of Bacteriophage T4" Nature, 227:680-685 (1970).
Lam et al. "New aryl/heteroaryl C☐n bond cross-coupling reactions via arylboronic acid/cupric acetate arylation" Tetrahedron Letters 39:2941-2944 (1998).
Lanza et al. "High-frequency ultrasonic detection of thrombi with a targeted contrast system" Ultrasound in Med. & Bio., 23(6):863-870 (1997).
Lecouter et al., "Identification of an angiogenic mitogen selective for endocrine gland endothelium," Nature, 2001 Aug. 30; 412(6850):877-84.
Liu et al. "99mTc-Labeled Small Peptides as Diagnostic Radiopharmaceuticals" Chem. Rev., 99 (9), pp. 2235-2268 (1999).
Liu, S. et al., "99mTc-Labeling of Hydrazinonicotiniamide-Conjugated Vitronection Receptor Antagonist Useful for Imaging Tumors," Bioconjugate Chem. 12, 624-629 (2001).
Loffet, A. Q. Peptides as drugs: is there a market? In: Peptides: The Wave of the Future, Proceedings of the Second International and the Seventeenth American Peptide Symposium, San Diego, CA United States, Jun. 9-14, 2001; Lebl, M., and Houghten, R. A. Eds.; American Peptide Society: San Diego, Calif. 2001; pp. 214-216.
Lu et al., "Acquired antagonistic activity of a bispecific diabody directed against two different epitopes on vascular endothelial growth factor receptor 2," J. Immunol. Methods, Nov. 11, 1999, vol. 230, No. 1-2, pp. 159-171.
Lu, D. et al. "Identification of the Residues in the Extracellular Region of KDR Important for Interaction with Vascular Endothelial

(56) References Cited

OTHER PUBLICATIONS

Growth Factor and Neutralizing Anti-KDR Antibodies", J. Biol. Chem., May 2000, vol. 275, No. 19, pp. 14321-14330.

Lucke, a. J. et al., "Designing supramolecular structures from models of cyclic peptide scaffolds with heterocyclic constraints," Journal of Molecular Graphics & Modelling 21(5), 341-355 (2003).

Malmborg et al. Selection of binders from phage displayed antibody libraries using the BlAcoreTM biosensor. J Immunol Methods 1996;198:51-7.

Mammen, M. et al., "Polyvalent interactions in biological systems: Implications for design and use of multivalent ligands and inhibitors," Angew. Chem. Int. Edn. Engl. 37, 2754-2794 (1998).

Matsudiara et al., "Sequence from picomole quantities of proteins electroblotted onto polyvinylidene difluoride membranes," J. Biol Chem 1987 Jul. 25; 262(21): 10035-8.

Mayer et al., "Peptides, Frontiers of Peptide Science," in Proceedings of the 15th American peptide Symposium, Tam and Kaumaya (Eds.), Jun. 14-19, 1995, Nashville, Tenn. (Klumer Academic Pub., Boston), pp. 291-292.

Melkko et al. "Encoded self-assembling chemical libraries" Nature Biotechnology, vol. 22, No. 5, May 2004, pp. 568-574.

Mellor, S.L. et al., "Synthesis of Modified Peptides" in Fmoc Solid Phase Synthesis: a Practical Approach, White and Chan (eds), Oxford University Press, New York, 2000, Chap 6: pp. 169-178.

Merkx, R. et al., "Chemoselective coupling of peptide fragments using the Staudinger ligation." Tetrahedron Lett. 44, 4515-4518 (2003).

Miller et al., "Application of Ring-Closing Metathesis to the Synthesis of Rigidified Amino Acids and Peptides," J. Am. Chem. Soc. 118(40):9606-9614 (1996).

Miller et al., "Synthesis of Conformationally Restricted Amino Acids and Peptides Employing Olefin Metathesis," J. Am. Chem. Soc. 117(21):5855-5856 (1995).

Muller, K. et al. "A dimeric bispecific miniantibody combines two specificities with avidity" FEBS Letters, vol. 432, No. 1-2, Jul. 31, 1998, pp. 45-49.

Mutter et al., "Evolution versus design: template-directed self-assembly of peptides to artificial proteins (TASP)," Chimia 54, 552-557 (2000).

Neri, D. et al. "High-affinity Antigen Binding by Chelating Recombinant Antibodies" Journal of Molecular Biology, vol. 246, No. 3, Feb. 24, 1995, pp. 367-373.

Neufeld et al., "Vascular endothelial growth factor (Vegf) and its receptors," Faseb J 13: 9-22, 1999.

O'Brien-Simpson, N. et al., "Polymerization of Unprotected Synthetic Peptides: a View toward Synthetic Peptide Vaccines," Journal of the American Chemical Society 119, 1183-1188 (1997).

Offer et al., "Extending Synthetic Access to Proteins with a Removable Acyl Transfer Auxiliary," J. Am. Chem. Soc. 124, 4642-4646 (2002).

Oldberg et al. "Identification of a bone sialoprotein receptor in osteosarcoma cells." Journal of Biological Chemistry, 263(36):19433-19436 (1988).

Parr et al., "Hepatocyte growth factor activators, inhibitors and antagonists and their implication in cancer intervention" Histol Histopathol. Jan. 2001;16(1):251-68. Review.

Pepper et al., "Angiogenesis: a paradigm for balanced extracellular proteolysis during cell migration and morphogenesis," Enzyme Protein. 49(1-3): 138-62. 1996.

Pernerstorfer et al. "Cyclisation/cleavage of macrocycles by ring-closing metathesis on solid support—conformational studies" Chem. Commun., 20:1949-50 (1997).

Pillai et al, "A Flexible Method for Preparation of Peptide Homo- and Heterodimers Functionalized with Affinity Probes, Chelating Ligands and Latent Conjugating Groups" Biopolymers (Peptide Science), vol. 84, 576-585 (2006).

Pillai et al, "A Flexible Method for Preparation of Peptide Homo- and Heterodimers Functionalized with Affinity Probes, Chelating Ligands and Latent Conjugating Groups", the Ernst Felder Laboratories, Bracco Research Usa, Inc., 305 College Road East, Princeton, New Jersey, 08540-6608, Jun. 29, 2005.

Pillai et al., "A Novel and Flexible Method for Preparation of Peptide Homo and Heterodimers Functionalized with Affinity Probes, Reporter Molecules and Chelating Ligands" Poster Presentation at the Third International and Twenty-Eight European Peptide Symposium, Prague, Czech Republic, Sep. 5-10, 2004.

Pillai et al., "A Novel and Flexible Method for Preparation of Peptide Homo- and Heterodimers Functionalized with Affinity Probes, Reporter Molecules and Chelating Ligands," from the Proceedings of the Peptides Third International and Twenty-Eight European Peptide Symposium, Sep. 5-10, 2004, Prague, Czech Republic, pp. 254-256.

Ploinsky et al. "Synthesis and conformational properties of the lanthionine-bridged opioid peptide [D-AlaL2,AlaL5]enkephalin as determined by NMR and computer simulations" Med.Chem 35:4185-4194 1992.

Plow et al., "Arginyl-glycyl-aspartic acid sequences and fibrinogen binding to platelet" Blood, 70(1):110-5 (1987).

Pritchard et al., "A Truncated V-abl-derived tyrosine-specific Tyrosine Kinase Expressed in Escherichia Coli" Biochem J. Jan. 15, 1989;257(2):321-9.

Ripka et al., Synthesis of novel cyclic protease inhibitors using Grubbs olefin metathesis, Med. Chem. Lett., 8(4):357-360 (1998).

Risau et al., "Mechanisms of angiogenesis," Nature 386:671-674, 1997.

Robert, Bruno et al., "Tumor targeting with newly designed biparatopic antibodies directed against two different epitopes of the cecinoembryonic antigen (CEA)" International Journal of Cancer, New York, NY, US, vol. 81, Apr. 12, 1999, pp. 285291.

Roberts et al., "Chemistry for peptide and protein PEGylation," Adv Drug Deliv Rev. Jun. 17, 2002; 54(4): 459-76.

Robey, et al., "Automated Synthesis of N-Bromoacetyl-Modified Peptides for the Preparation of Synthetic Peptide Polymers, Peptide-Protein Conjugates, and Cyclic Peptides", Anal. Biochem. 177: 373-377 (1989).

Rose, K. et al., "Stepwise Solid-Phase Synthesis of Polyamides as Linkers", J. Am. Chem. Soc., 1999, 121:7034-7038.

Rosebrough, S. F., "Two-step immunological approaches for imaging and therapy", Q.J. Nucl. Med., 40:234-251 (1996).

Rovero, P. et al., "Solid phase synthesis and dimerization of an azobenzene- containing peptide as photoisomerizable proteinase inhibitor" Letters in Peptide Science 1995, 2, 27-32.

Sadler, Kristen et al., "Peptide dendrimers: applications and synthesis," Reviews in Molecular Biotechnology 90(3-4), 195-229 (2002) (general review).

Sal-Man, N. et al., "Preassembly of membrane-active peptides is an important factor in their selectivity toward target cells," Biochemistry 41, 11921-11930 (2002).

Sato et al., "Development of mammalian serum albumin affinity purification media by peptide phage display," Biotechnol Prog. Mar.-Apr. 2002; 18(2):182-92.

Schaeper, U. et al., "Coupling of Gab1 to c-Met, Grb2 and Shp2 Mediates Biological Responses" The Journal of Cell Biology, vol. 149, No. 7, Jun. 26, 2000, pp. 1419-1432.

Schaffer et al., "Assembly of high-affinity insulin receptor agonists and antagonists from peptide building blocks," Proc Natl Acad Sci USA Apr. 15, 2003:100(8): 4435-9.

Schmitz et al."Catalytic specificity of phosphotyrosine kinases Blk, Lyn, c-Src and Syk as assess by phage display," J. Mol. Biol. Aug. 2, 1996; 260(5):664-77.

Schuck, P. "Reliable Determination of Binding Affinity and Kinetics Using Surface Plasmon Resonance Biosensors". Current Opinion in Biotechnology. vol. 8: 498-502 (1997).

Shrivastava et al., "A distinct strategy to generate high-affinity peptide binders to receptor tyrosine kinases," Protein Eng Des Sel. Sep. 2005; 18(9):417-24.

Sleep et al., "Saccharomyces cerevisiae strains that overexpress heterologous proteins," Biotechnology (NY) Feb. 1991; 9(2): 183-7.

Soker et al., "Inhibition of vascular endothelial growth factor (VEGF)-induced endothelial cell proliferation by a peptide corresponding to the exon 7-encoded domain of VEGF165," Journal of Biol Chem 272(50): 31582-31588 (1997).

(56) References Cited

OTHER PUBLICATIONS

Sole, N. A., et al. "Optimization of solid-phase synthesis of [Ala8]-Dynorphin" A. J. Org. Chem. 57, 5399-5403. (1992).
Souriau, C. et al. "Recombinant antibodies for cancer diagnosis and therapy." Expert Opin. Biol. Ther. 1(5), 845-855. (2001).
Stankova et al. "Library Generation through Successice Substitution of Trichlorotriazine" Mol. Diversity, 2(1/2):75-80 (1996).
Strawn et al., "Flk-1 as a target for tumor growth inhibition," Cancer Res 56: 3540-3545, 1996.
Tam, J. P. et al., "Antimicrobial Dendrimeric Peptides," European Journal of Biochemistry 269, 923-932 (2002).
Tam, J., "Vaccines 90. Modern approaches to new vaccines including prevention of AIDS," p. 21 (R. A. Lemer,et al. Eds., Cold Spring Harbor Lab., New York, 1990).
Tam, J.P., et al., "Tandem Ligation of Unprotected Peptides through Thiaprolyl and Cysteinyl Bonds in Water" J. Am. Chem. Soc. 123, 2487-2494 (2001).
Tamura, S. et al. "Expression and Function of c-Met, a Receptor for Hepatocyte Growth Factor, During T-Cell Development", Scand. J. Immunol. 1998, vol. 47, pp. 296-301.
Taub et al. "A monoclonal antibody against the platelet fibrinogen receptor contains a sequence that mimics a receptor recognition domain in fibrinogen." Journal of Biological Chemistry, 264(1):259-265 (1989).
Thomas et al., "A peptide sequence on carcinoembryonic antigen binds to a 80kD protein on Kupffer cells," Biochem Biophys Res Commun 188: 671-677, 1992.
Thumshirn, G. et al., "Multimeric cyclic RGD peptides as potential tools for tumor targeting: Solid-phase peptide synthesis and chemoselective oxime ligation," Chemistry—A European Journal 9(12), 2717-2725 (2003).
Tissot et al., "Characterizing the functionality of recombinant T-cell receptors in vitro: a pMHC tetramer based approach," J. Immunol. Methods 236(1-2): 147-165 (2000).
Todorovska et al., "Design and Application of Diabodies, Triabodies and Tetrabodies for Cancer Targeting," J. Immunol. Methods vol. 248, No. 1-2, pp. 47-66 (Feb. 1, 2001).
Tweedle et al., Magnetic Resonance Imaging (2nd ed.), vol. 1, Partain et al., eds. (W.B. Saunders Co., 1988), pp. 796-797.
Veikkola et al., "Regulation of angiogenesis via vascular endothelial growth factor receptors," Cancer Res 60: 203-212, 2000.
Veprek, P. and Jezek, J. (1999) Peptide and glycopeptide dendrimers. Part I. J. Pept. Sci. 5, 5-23.
Veprek, P. and Jezek, J. (1999) Peptide and glycopeptide dendrimers. Part II. J. Pept. Sci. 5, 203-220.
Wade, J.D. et al., "Use of thiazolidine-mediated ligation for site specific biotinylation of mouse EGF for biosensor immobilisation," Letters in Peptide Science, vol. 8(3-5), 211-220 (2002).
Wahl et al. "Analogues of oxytocin with an oxime bridge using chemo selectively addressable building blocks," Tetrahedron Lett. 37, 6861-6864 (1996).
Wedegaertner et al., "Effect of Carboxyl Terminal Truncation on the Tyrosine Kinase Activity of the Epidemal Growth Factor Receptor" Arch Biochem Boiphys. Jan. 1992; 292(1):27.3-80.
Wei, K. et al. "Quantification of Renal Blood Flow With Contrast-Enhanced Ultrasound" J. Am. Coll. Cardiol., vol. 37, No. 4., pp. 1135-1140 (2001).
Wilken, J. et al., "Chemical protein synthesis," Current Opinion in Biotechnology 9(4), 412-426 (1998).
Zuo, Z. et al., "An efficient route to the production of an IgG-like bispecific antibody" Protein Engineering, vol. 13, No. 5, pp. 361-367, 2000.
Final Office Action for U.S. Appl. No. 10/379,287, mailed Jan. 24, 2006.
Final Office Action for U.S. Appl. No. 10/661,032, mailed Feb. 8, 2006.
Final Office Action for U.S. Appl. No. 11/624,894, mailed Mar. 10, 2010.
Final Office Action for U.S. Appl. No. 11/688,968, mailed Apr. 15, 2010.
Final Office Action issued in U.S. Appl. No. 10/661,156 and mailed Jan. 7, 2009.
Final Office Action issued in U.S. Appl. No. 10/661,156 and mailed Jul. 26, 2007.
Final Office Action issued in U.S. Appl. No. 11/608,395, mailed Jun. 1, 2009.
Final Office Action issued in U.S. Appl. No. 11/954,130, mailed Dec. 23, 2010.
Notice of Allowance for U.S. Appl. No. 10/379,287, mailed May 10, 2006.
Notice of Allowance for U.S. Appl. No. 10/379,287, mailed Oct. 18, 2006.
Notice of Allowance for U.S. Appl. No. 10/661,032, mailed Dec. 21, 2006.
Notice of Allowance for U.S. Appl. No. 10/661,032, mailed May 25, 2006.
Notice of Allowance for U.S. Appl. No. 10/792,582, mailed Oct. 30, 2007.
Notice of Allowance for U.S. Appl. No. 10/916,155, mailed Oct. 29, 2009.
Notice of Allowance for U.S. Appl. No. 11/608,395, mailed Feb. 19, 2010.
Notice of Allowance for U.S. Appl. No. 11/624,894, mailed Jun. 23, 2010.
Notice of Allowance for U.S. Appl. No. 11/688,968, mailed Sep. 21, 2010.
Notice of Allowance for U.S. Appl. No. 11/954,130, mailed Mar. 16, 2011.
Notice of Allowance for U.S. Appl. No. 12/012,011, mailed Jun. 9, 2011.
Office Action for U.S. Appl. No. 10/379,287, mailed Jun. 28, 2005.
Office Action for U.S. Appl. No. 10/661,032, mailed Aug. 1, 2005.
Office Action for U.S. Appl. No. 10/792,582, mailed Mar. 8, 2007.
Office Action for U.S. Appl. No. 10/916,155, mailed Aug. 12, 2009.
Office Action for U.S. Appl. No. 10/916,155, mailed Dec. 13, 2007.
Office Action for U.S. Appl. No. 11/608,395, mailed Dec. 2, 2008.
Office Action for U.S. Appl. No. 11/624,894, mailed Oct. 2, 2009.
Office Action for U.S. Appl. No. 11/624,894, mailed Sep. 30, 2009.
Office Action for U.S. Appl. No. 11/688,968, mailed Aug. 27, 2010.
Office Action for U.S. Appl. No. 11/688,968, mailed Oct. 28, 2009.
Office Action for U.S. Appl. No. 12/888,736, mailed May 11, 2012.
Office Action issued in U.S. Appl. No. 10/661,156 and mailed Mar. 31, 2008.
Office Action issued in U.S. Appl. No. 10/661,156 and mailed Nov. 9, 2006.
Office Action issued in U.S. Appl. No. 11/954,130, mailed Sep. 2, 2010.
Office Action issued in U.S. Appl. No. 12/257,552, mailed Nov. 28, 2011.
Supplemental Notice of Allowance for U.S. Appl. No. 11/624,894, mailed Aug. 19, 2010.
Rodionov, Abrf Electronic Discussion Group (Jul. 28, 2000); Downloaded Jul. 1, 2012.
Kirpotin et al., "Sterically stabilized Anti-HER2 immunoliposomes: design and targeting to human breast cancer cells in vitro," Biochemistry 36: 66-75 (1997).
Final Office Action issued in U.S. Appl. No. 12/257,552, mailed Jul. 9, 2012.
Dubey, et al., "Liposomes Modified with Cyclic RGD Peptide for Tumor Targeting," Journal of Drug Targeting, Jun. 2004, vol. 12, No. 5, pp. 257-264.
Extended European Search Report issued for European Patent Application No. 10190163.5, dated Jun. 29, 2012.
Notification of Reasons for Rejection issued in Japanese Patent Application No. 2008-544663, date of delivery Nov. 15, 2012 and an English translation thereof.
Office Action issued in Korean Patent Application No. 10-2008-7016674, dated Jun. 13, 2013, and an English translation thereof.
Preliminary Rejection issued for Korean Patent Application No. 10-2013-7021393, dated Oct. 30, 2013.

\* cited by examiner

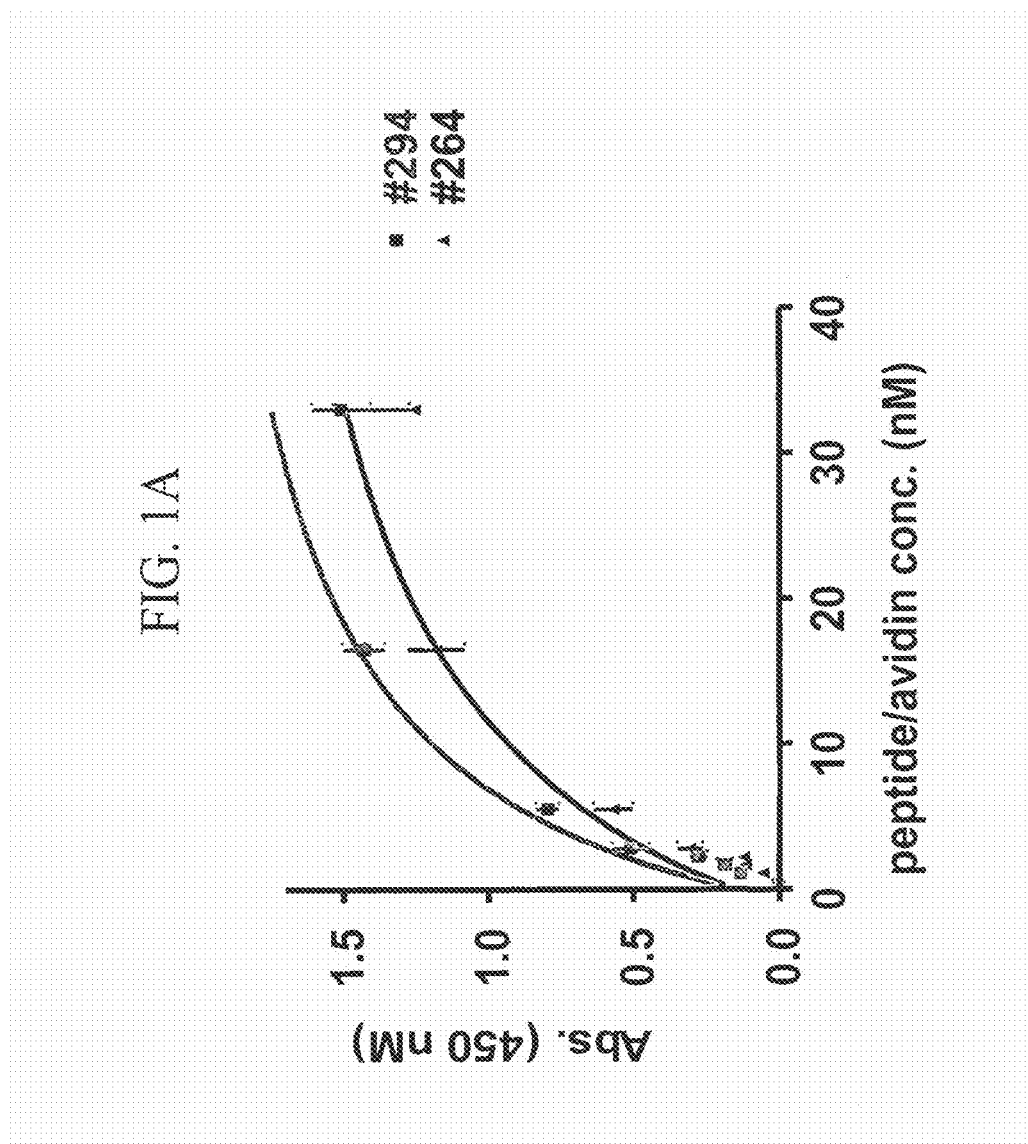

FIG. 3

(a) Ac-AGPKWCEEDWYYCMITGT-GGGK(Biotin-di(aminodioxaocta)-)-NH$_2$ (SEQ ID NO:264)
(b) Ac-AGPKWCEEDWYYCMITGT-GGGK(Biotin-)-NH$_2$ (SEQ ID NO:264)
(c) Ac-GDSRVCWEDSWGGEVCFRYDP-GGGK(Biotin-di(aminodioxaocta)-)-NH$_2$ (SEQ ID NO:294)
(d) Ac-GDSRVCWEDSWGGEVCFRYDP-GGGK-(Biotin-)-NH$_2$ (SEQ ID NO:294)

FIG. 8

| Sequence | SEQ ID NO: | $K_D$, B (μM) |
|---|---|---|
| GDSRVCWEDSWGGEVCFRYDPGGGK | 294 | 0.069 |
| VCWEDSWGGEVCFGGGK | 368 | 0.91 |
| GDSRVCWEDSWGGEVCFGGGK | 369 | 1.30 |
| VCWEDSWGGEVCFRYDPGGGK | 337 | 0.040 |
| SRVCWEDSWGGEVCFRYGGGK | 371 | 0.035 |
| GDSRVCWEDSWGGEVCFRYGGGK | 372 | 0.060 |

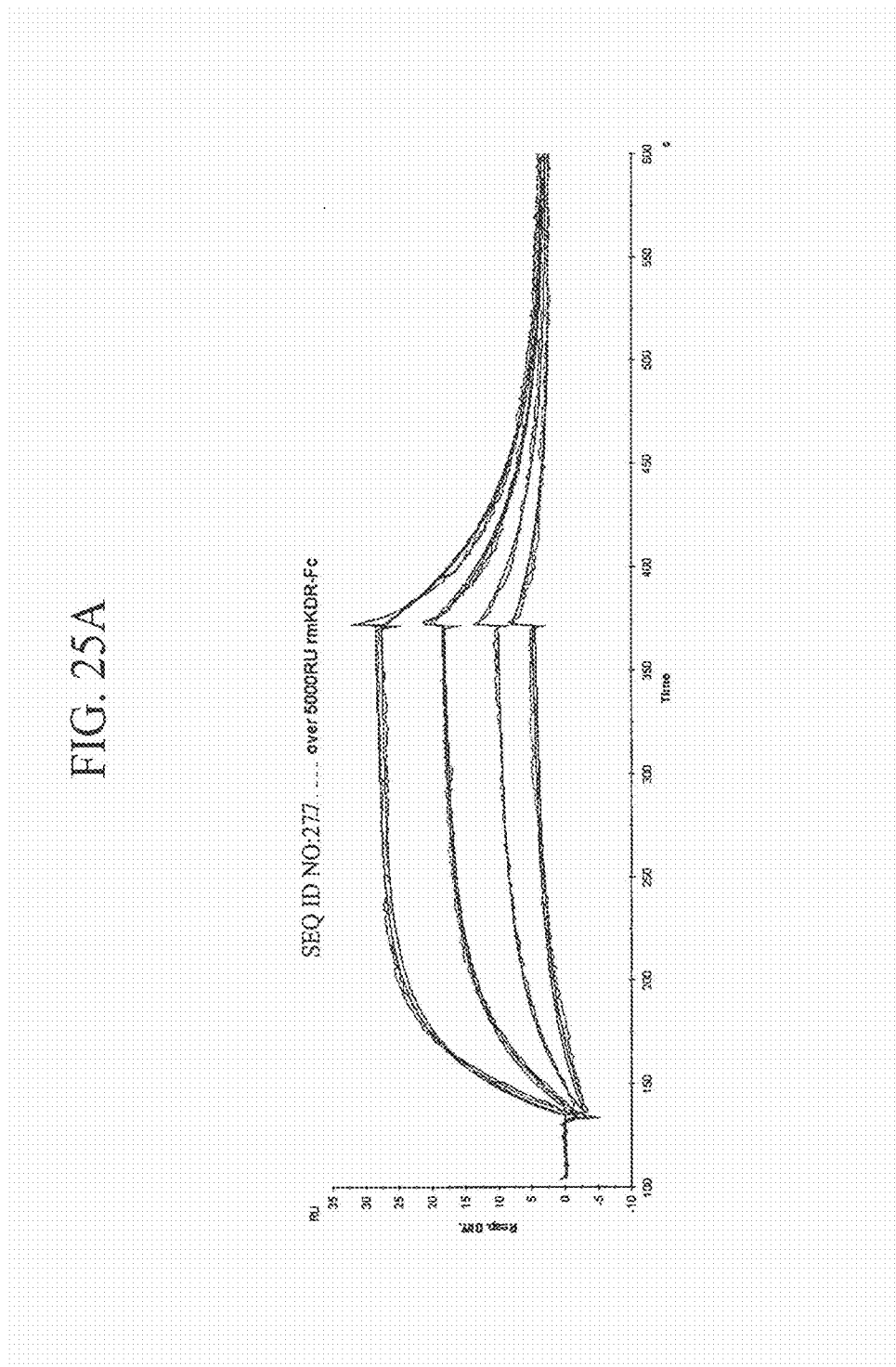

(20)

FIG. 34E
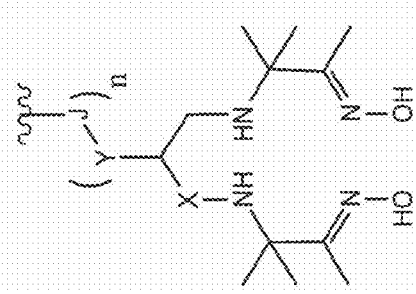
(24b)
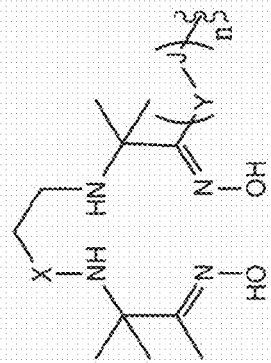
(24a)

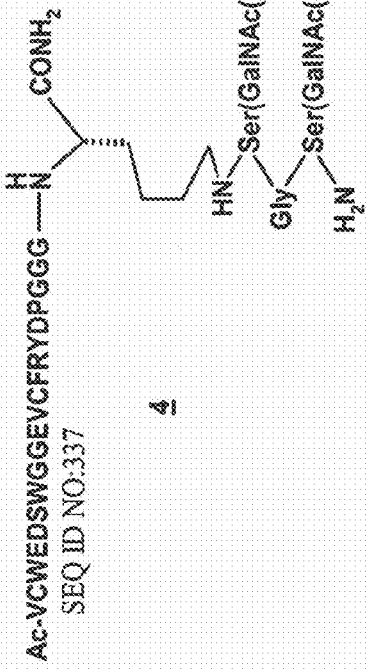
FIG. 69

| | | | |
|---|---|---|---|
| Explanation of Abbreviations: Other abbreviations: BOA = (S)-2-{Bis-[2-(bis-carboxymethyl-amino)-ethyl]-amino}-pentanedioic-4-oyl; Glut- = glutaryl or 1,5-pentanedi-oyl, SATA = S-acetyl-alpha-thioacetyl, GalNAc(Ac)3-alpha-D = O-Beta[2-acetamido-2-deoxy-3,4,6-tri-O-acetyl-alpha-D-galactopyranosyl]-L-serinyl, iV-Dde = 1-(4,4-dimethyl-2,6-dioxocyclohex-1-ylidene)-3-methylbutyl, 5CF = 5-carboxyfluoresceinyl; J = 3,6-dioxa-8-aminooctanoyl, Dpr = 2,3-diaminopropanoyl, Adca3 = (3β,5α,7α,12α)-3-amino-7,12-dihydroxycholan-24-oyl, PnAO6 = 4-{2-(2-Hydroxyimino-1,1-dimethyl-ethylamino)-1-{(2-hydroxyimino-1,1-dimethyl-ethylamino)-methyl]-ethylcarbamoyl}-butanoyl. | | | |

| Compound Sequence/Structure (Parent Sequence in red text) | Obtained? Y/N | SEQ ID NO | MS Data[f] |
|---|---|---|---|
| Ac-AGPTWCEDDWYYCWLFGTGGGK(Tc-Chelator)-NH₂ | | 277 | |
| Ac-AGPTWCEDDWYYCWLFGTGGGK(PnAO6-NH-(O=)C(CH₂)₃C(=O)-J)-NH₂ | Y | 277 | 1611.7 [M-2H]/2, 1074.4 [M-3H]/3[a] |
| Ac-AGPTWCEDDWYYCWLFGTGGGK-NH₂ | | 277 | |
| H₂N-JJK(ivDde)-AGPTWCEDDWYYCWLFGTGGG-NH₂ | Y | 277 | 1501.5 [M-2H]/2[a] |
| Ac-AGPTWCEDDWYYCWLFGTGGGK(BOA-K)-NH₂ | Y | 277 | 1561.9 [M-3H]/3[a] |
| NH₂-JJVCWEDDSWGGEVCFRYDPGGG-NH₂ | Y | 998 (337 - C term K) | 2505.4 [M-H], 1251.9 [M-2H]/2[a] |
| H₂N-JJAGPTWCEDDWYYCWLFGTGGGK(iV-Dde)-NH₂ | Y | 277 | 1501.5 [M-2H]/2, 1000.8 [M-3H]/3[a] |
| Ac-AGPTWCEDDWYYCWLFGTGGGK-NH₂ | Y | 277 | 1274.4 [M-2H]/2[a] |
| Ac-AGPTWCEDDWYYCWLFGTGGGK-NH₂ | Y | 277 | 1274.4 [M-2H]/2[a] |
| Ac-AGPTWCEDDWYYCWLFGTGGGK(5CF)-NH₂ | Y | 277 | 1453.5 [M-2H]/2, 968.7 [M-3H]/3[a] |
| Ac-AGPTWCEDDWYYCWLFATGGGK(Biotin-J)-NH₂ | Y | 379 | 1539.6 [M-2H]/2[a] |
| Ac-AQXXXXXXXXXXXXXXXXXGGGGGK(Biotin-J)-NH₂ | | 380 | |

Fig 79A

| Compound Sequence/Structure (Parent Sequence in red text) | Obtained ? Y/N | SEQ ID NO | MS Data[†] |
|---|---|---|---|
| Ac-AQPDNWKEFYESGWKYPSLYKPLGGGGGK(Biotin-JJ)-NH₂ | Y | 381 | 1878.9 [M+2H]/2ᵉ |
| Ac-AQQIEYVNDKWYWTGGYWNVPFGGGGGK(Biotin-JJ)-NH₂ | Y | 382 | 1866.6 [M-2H]/2ᵉ |
| Ac-AQDALEAPKRDWYYDWFLNHSPGGGGGK(Biotin-JJ)-NH₂ | Y | 383 | 1845.5 [M-2H]/2ᵉ |
| Ac-AQWYHDGLHNERKPPSHWIDNVGGGGGK(Biotin-JJ)-NH₂ | Y | 384 | 1833.7 [M-2H]/2ᵉ |
| Ac-AQDWYWQRERDKLREHYDDAFWGGGGGK(Biotin-JJ)-NH₂ | Y | 385 | 1990.6 [M-2H]/2ᵉ |
| Ac-AGPTWCEDDWYYCWLFGTGGGK-NH₂ | | 277 | |
| Ac-AAPTWCEDDWYYCWLFGTGGGK-NH₂ | Y | 386 | 2563.5 [M-H], 1281.8 [M-2H]/2ᵉ |
| Ac-AGATWCEDDWYYCWLFGTGGGK-NH₂ | Y | 387 | 2523.6 [M-H], 1261.5 [M-2H]/2ᵉ |
| Ac-AGPAWCEDDWYYCWLFGTGGGK-NH₂ | Y | 388 | 2519.6 [M-H], 1259.5 [M-2H]/2ᵉ |
| Ac-AGPTACEDDWYYCWLFGTGGGK-NH₂ | Y | 389 | 2434.6 [M-H], 1216.8 [M-2H]/2ᵉ |
| Ac-AGPTWCADDWYYCWLFGTGGGK-NH₂ | Y | 390 | 1244.9 [M-2H]/2e |
| Ac-AGPTWCEADWYYCWLFGTGGGK-NH₂ | Y | 391 | 2434.6 [M-H], 1216.6 [M-2H]/2ᵉ |
| Ac-AGPTWCEDAWYYCWLFGTGGGK-NH₂ | Y | 392 | 1252.7 [M-2H]/2ᵉ |
| Ac-AGPTWCEDDAYYCWLFGTGGGK-NH₂ | Y | 393 | 2434.3 [M-H], 1216.8 [M-2H]/2ᵉ |
| Ac-AGPTWCEDDWAYCWLFGTGGGK-NH₂ | Y | 394 | 2457.5 [M-H], 1239.0 [M-3H+Na], 1228.3 [M-2H]/2ᵉ |
| Ac-AGPTWCEDDWYACWLFGTGGGK-NH₂ | Y | 395 | 2456.6 [M-H], 1228.2 [M-2H]/2ᵉ |
| Ac-AGPTWCEDDWYYCALFGTGGGK-NH₂ | Y | 396 | 2505.4 [M-H], 1252.5 [M-2H]/2ᵉ |
| Ac-AGPTWCEDDWYYCWAFGTGGGK-NH₂ | Y | 397 | 1253.3 [M-2H]/2ᵉ |
| Ac-AGPTWCEDDWYYCWLAGTGGGK-NH₂ | Y | 398 | 1236.4 [M-2H]/2ᵉ |
| Ac-AGPTWCEDDWYYCWLFATGGGK-NH₂ | Y | 399 | 2564.6 [M-H], 1281.6 [M-2H]/2ᵉ |
| Ac-AGPTWCEDDWYYCWLFGAGGGK-NH₂ | Y | 400 | 2519.7 [M-H], 1259.6 [M-2H]/2ᵉ |
| Ac-AGPTWCEDDWYYCWLFGTGGGK-NH₂ | | 277 | |
| Ac-aGPTWCEDDWYYCWLFGTGGGK-NH₂ | Y | 277 | 2549.7 [M-H], 1274.7 [M-2]/2ᵉ |
| Ac-AaPTWCEDDWYYCWLFGTGGGK-NH₂ | Y | 401 | 2564.7 [M-H], 1292.7 [M-3H+Na]/2, 1281.2 [M-2H]/2ᵉ |
| Ac-AGaTWCEDDWYYCWLFGTGGGK-NH₂ | Y | 402 | 1261.4 [M-2H]/2ᵉ |
| Ac-AGPaWCEDDWYYCWLFGTGGGK-NH₂ | Y | 403 | 2519.2 [M-H], 1259.1 [M-2H]/2ᵉ |
| Ac-AGPTaCEDDWYYCWLFGTGGGK-NH₂ | Y | 404 | 2434.6 [M-H], 1217.1 [M-2H]/2ᵉ |
| Ac-AGPTWCaDDWYYCWLFGTGGGK-NH₂ | Y | 405 | 2490.8 [M-H], 1245.6 [M-2H]/2ᵉ |

Fig 79B

| Compound Sequence/Structure (Parent Sequence in red text) | Obtained? Y/N | SEQ ID NO | MS Data[1] |
|---|---|---|---|
| Ac-AGPTWCEaDWYYCWLFGTGGGK-NH₂ | Y | 406 | 2505.8 [M-H], 1252.1 [M-2H]/2ᵃ |
| Ac-AGPTWCEDaWYYCWLFGTGGGK-NH₂ | Y | 407 | 2506.0 [M-H], 1252.0 [M-2H]/2ᵃ |
| Ac-AGPTWCEDDaYYCWLFGTGGGK-NH₂ | Y | 408 | 2434.4 [M-H], 1217.1 [M-2H]/2ᵃ |
| Ac-AGPTWCEDDWaYCWLFGTGGGK-NH₂ | Y | 409 | 2456 [M-H], 1228.6 [M-2H]/2ᵃ |
| Ac-AGPTWCEDDWYaCWLFGTGGGK-NH₂ | Y | 410 | 2457.6 [M-H], 1228.5 [M-2H]/2ᵃ |
| Ac-AGPTWCEDDWYYCaLFGTGGGK-NH₂ | Y | 411 | 2434.8 [M-H], 1228.1 [M-3H+Na]/2, 1217.0 [M-2H]/2ᵃ |
| Ac-AGPTWCEDDWYYCWaFGTGGGK-NH₂ | Y | 412 | 2507.7 [M-H], 1264.1 [M-3H+Na]/2, 1253.6 [M-2H]/2ᵃ |
| Ac-AGPTWCEDDWYYCWLaGTGGGK-NH₂ | Y | 413 | 2473.6 [M-H], 1247.6 [M-3H+Na]/2, 1236.2 [M-2H]/2ᵃ |
| Ac-AGPTWCEDDWYYCWLFaTGGGK-NH₂ | Y | 414 | 2563.7 [M-H], 1709.3 (unassigned), 1292.7 [M-3H+Na]/2, 1281.9 [M-2H]/2ᵃ |
| Ac-AGPTWCEDDWYYCWLFGaGGGK-NH₂ | Y | 415 | 2519.0 [M-H], 1259.6 [M-2H]/2ᵃ |
| Ac-GDSRVCWEDSWGGEVCFRYDPGGGK-NH₂ | | 294 | |
| Ac-GDSRVCWEDaWGGEVCFRYDPGGGK-NH₂ | Y | 416 | 1401.9 [M-3H+Na], 1391.7 [M-2H]/2ᵃ |
| Ac-GDSRVCWEDSWaGEVCFRYDPGGGK-NH₂ | Y | 417 | 1664.4 [M-2H]/2ᵃ |
| Ac-GDSRVCWEDSWGaEVCFRYDPGGGK-NH₂ | Y | 418 | 1664.7 [M-2H]/2ᵃ |
| Ac-AGPTWCEDDWYYCWLFGTGGGK-NH₂ | | 277 | |
| Ac-AGjTWCEDDWYYCLFTGTGGGK-NH₂ | Y | 419 | 1267.9 [M-2H]/2ᵃ |
| Minimum Number of AA for DWYY Motif | | 420 | |
| Ac-GDWYYGGGK-NH₂ | Y | 421 | 1041.2 [M-H]ᵃ |
| Ac-EDDWYYGGGK-NH₂ | Y | 422 | 1228.3 [M-H], 612.8 [M-2H/2]ᵃ |
| Ac-AQDWYYAWLFTGGGGK-NH₂ | Y | 423 | 1859.7 [M-H], 986.4 [M-2H]/2ᵃ |
| Ac-AQDWYYAWL-NH₂ | Y | 424 | 1254.4 [M-H]ᵃ |
| Ac-AGPTWCEDDWYYCWLFGTGGGK-NH₂ | | 277 | |
| Ac-AGPTWCEDEWYYCWLFGTGGGK-NH₂ | Y | 425 | 1281.5 [M-2H/2], 853.6 [M-3H/3]ᵃ |
| Ac-AGPTWCEDDWWYCWLFGTGGGK-NH₂ | Y | 426 | 1285.4 [M-2H/2], 856.8 [M-3H/3]ᵃ |

Fig 79C

| Compound Sequence/Structure (Parent Sequence in red text) | Obtained? Y/N | SEQ ID NO | MS Data[†] |
|---|---|---|---|
| Ac-AGPTWCEDDWFYCWLFGTGGGK-NH2 | Y | 427 | 1265.8 [M-2H]/2[e] |
| Ac-AGPTWCEDDWYYCWLFGTGGGK-NH2 | | 277 | |
| Ac-AGPTWAEDDWYYAWLFGTGGGK-NH2 | Y | 428 | 2486.9 [M-H], 1243.6 [M-2H]/2[e] |
| Ac-AAPAWCAADWYYCWLFGTGGGK-NH2 | Y | 429 | 2432.7 [M-H], 1272.5 [M+TFA-2H]/2[e] |
| Ac-AGPTWCaDDWYYCWLFGTGGGK-NH2 | Y | 430 | 2192.6 [M-H], 1096.0 [M-2H]/2[e] |
| Ac-AGPTWCEDDWYYCWLFGTGGGK-NH2 | | 277 | |
| Ac-CEDDWYYCWLFGTGGGK-NH2 | Y | 431 | 2037.6 [M-H], 1018.4 [M-2H]/2, 520.8 [M-6H+2Na]/4[a] |
| Ac-WCEDDWYYCWLFGTGGGK-NH2 | Y | 432 | 2221.8 [M-H], 1111.6 [M-2H]/2, 740.7 [M-3H]/3[e] |
| Ac-WCAADWYYCWLF-NH2 | Y | 433 | 1663.5 [M-H][a] |
| Ac-WCEDDWYYCWLF-NH2 | Y | 434 | 1766.5 [M-H], 882.1 [M-2H]/2[e] |
| Ac-AGPTWCEDDWYYCWLFGTGGGK(Biotin-JJ)-NH2 | | 277 | |
| Ac-AGPTWCEDDWYYCWLFGTGGGKK(iV-Dde)-Adoa3-NH2 | Y | 373 | 1665.2 [M-2H]/2[e] |
| Ac-GDSRVCWEDSWGGEVCFRYDPGGGK(Biotin-JJ)-NH2 | | 294 | |
| Ac-VCWEDSWGGEVCFRYDPGGGK(Biotin-JJ)-NH2 | Y | 337 | 1449.3 [M-2H]/2, 965.8 [M-3H]/3[e] |
| Ac-VCWEDSWGGEVCFRYGGGK(Biotin-JJ)-NH2 | Y | 435 | 2689.4 [M-H], 1344.0 [M-2H]/2[e] |
| Ac-GDSRVCWEDSWGGEVCFRYDPGGGK-NH2 | | 294 | |
| Ac-GDSRVAWEDSWGGEVAFRYDPGGGK-NH2 | Y | 436 | 1368.4 [M-2H]/2[a] |
| Ac-VCWEDSWGGEVCFRYGGGK-NH2 | Y | 437 | 1085.8 [M-2H]/2[e] |
| Ac-VCWEDSWGGEVCFRYGGGK-NH2 | Y | 437 | 2172.0 [M-H], 1086.0 [M-2H]/2[e] |
| Ac-GDSRVCWEDaWGGEVCFRYDPGGGK-NH2 | Y | 438 | 1401.9 [M-3H+Na]/2, 1391.7 [M-2H]/2[e] |
| Ac-GDSRVCWEDiWGGEVCFRYDPGGGK-NH2 | Y | 439 | 1429.7 [M-2H]/2[a] |
| Ac-GDSRVCWEDkWGGEVCFRYDPGGGK-NH2 | Y | 440 | 1430.7 [M-3H+Na]/2, 1420.1 [M-2H]/2[e] |
| Ac-GDSRVCWEDSWGiEVCFRYDPGGGK-NH2 | Y | 441 | 1444.5 [M-2H]/2[a] |
| Ac-GDSRVCWEDSWGLEVCFRYDPGGGK-NH2 | Y | 442 | 1435.1 [M-2H]/2[e] |
| Ac-GDSRVCWEDSWGeEVCFRYDPGGGK-NH2 | Y | 443 | 1435.5 [M-2H]/2[a] |
| Sequences Binding to KDR-VEGF Complex | | | |
| Ac-AGPGPCKGYMPHQCWYMGTGGGK(SCF)-NH2 | Y | 321 | 1543.7 [M-2H]/2, 1028.8 [M-3H]/3, 771.3 [M-4H]/4, 617.0 [M-5H]/5[e] |

Fig 79D

| Compound Sequence/Structure (Parent Sequence in red text) | Obtained? Y/N | SEQ ID NO | MS Data† |
|---|---|---|---|
| Ac-AGPGPCKGYMPHQCWYMGTGGGK(Biotin-JJ)-NH₂ | Y | 321 | 2937.4 [M-H], 1468.2 [M-2]/2ᵃ |
| Ac-AGMPWCVEKDHWDCWWWGTGGGK(Biotin-JJ)-NH₂ | Y | 444 | 1622.5 [M-2H]/2ᵃ |
| Ac-AGYGPCKNMPPWMCWHEGTGGGK(5CF)-NH₂ | Y | 323 | 2860.1 [M-H], 1429.8 [M-2H]/2ᵃ |
| Ac-AGYGPCKNMPPWMCWHEGTGGGK(Biotin-JJ)-NH₂ | Y | 323 | 1058.6 [M-2H]/2ᵃ |
| Pathogenic Sequences | | | |
| Ac-GDQSWCEMRQDVGKWNCFSDDPGGGK(Biotin-JJ)-NH₂ | Y | 445 | 1537.5 [M-2H]/2ᵃ |
| Ac-GCKTKISKVKKKWNCYSNNKVTGGGK(Biotin-JJ)-NH₂ | Y | 446 | 1706.8 [M+2H]/2, 1138.6 [M+3H]/3, 854.0 [M+4H]/4, 683.7 [M+5H]/5, 569.8 [M+6H]/6, 488.5 [M+7H]/7ᵇ |
| Ac-KQFCEENWERGRNHYYCLTTLSGGGK(Biotin-JJ)-NH₂ | Y | 447 | 1817.5 [M+2H]/2, 1211.3 [M+3H]/3, 909.5 [M+4H]/4, 727.5 [M+5H]/5ᵇ |
| Ac-GDSRVCWEDWGGVVCRYRYDAGGGK(Biotin-JJ)-NH₂ | Y | 448 | 1675.2 [M+2H]/2, 1116.9 [M+3H]/3, 838.2 [M+4H]/4ᵇ |
| AGPTWCEDDWYYCWLFGTGGGK(Biotin-JJ)-NH₂ | | 277 | |
| Ac-AGPTWCEDDWYYCWLFGTGGGk(nSbGJJ)-NH₂ | Y | 277-nSbGJJ | 1621.5 [M-2H]/2ᵃ |
| AGPTWCEDDWYYCWLFGTGGGK-NH₂ | | 277 | |
| Dansyl-NH-AGPTWCEDDWYYCWLFGTGGGK(5CF)-NH₂ | Y | 277-5CF | 1549.1 [M-2H]/2ᵃ |
| Other KDR Compounds - Hangovers from Year 2001 such as DX-684 truncations etc. | | | |
| Ac-CEEDWYYCMITGTGGGK(Biotin-JJ)-NH₂ | Y | 449 | 1232.5 [M-2H]/2ᵃ |
| Ac-AGPKWCEEDWYYCMITaT-NH₂ | Y | 450 | 1509.6 [M-2H]/2ᵃ |
| Ac-AaPKWCEEDYYCMITGTGGGK-NH₂ | Y | 451 | 2504.2 [M-H], 1251.6 [M-2H]/2ᵃ |
| Ac-AaPKWCEEDYYCMITGTGGGK(Biotin-JJ)-NH₂ | Y | 451 | 1509.6 [M-2H]/2ᵃ |
| Ac-AGPDWCAADWYYCYITG-NH₂ | Y | 452 | 1992.5 [M-H], 995.8 [M-2H]/2ᵃ |
| Ac-AGPTWCEDDWYYCWLFGTGGGK-NH₂ | | 277 | |
| Ac-AGPTWEEDDWYYKWLFGTGGGK-NH₂ (6-13 lactam) | Y | 453 | 1291.9 [M-2H]/2ᵃ |
| Ac-AGPTWKEDDWYYEWLFGTGGGK-NH₂ (6-13 lactam) | Y | 454 | 1291.9 [M-2H]/2ᵃ |
| Ac-AGPTW-Dpr-EDDWYYDWLFGTGGGK-NH₂ (6-13 lactam) | Y | 455 | 1263.9 [M-2H]/2ᵃ |
| Ac-AGPTWDEDDWYY-Dpr-WLFGTGGGK-NH₂ (6-13 lactam) | Y | 456 | 1263.9 [M-2H]/2ᵃ |
| Ac-AGPTWDEDDWYYKWLFGTGGGK-NH₂ (6-13 lactam) | Y | 457 | 1285.1 [M-2H]/2ᵃ |
| Ac-AGPTWDEDDWYYKWLFGTGGGK-NH₂ | Y | 457 | 1294.1 [M-2H]/2ᵃ |
| Ac-AQDWYYDEILSMADQLRHAFLSGGGGK(Biotin-JJ)-NH₂ | Y/N | 356 | |

Fig 79E

| Compound Sequence/Structure (Parent Sequence in red text) | Obtained? Y/N | SEQ ID NO | MS Data† |
|---|---|---|---|
| Ac-AQDWYYDEILSMADQLR-NH₂ | Y | 458 | 2156.9 [M-H], 1077.9 [M-2H]/2ᵃ |
| Ac-DWYYDEILSMADQL-NH₂ | Y | 459 | 1800.5 [M-H], 900.2 [M-2H]/2ᵃ |
| Ac-AQDWYYDEILSMADQLRHAFLS-NH₂ | Y | 460 | 1355.2 [M-3H]/2ᵃ |
| Ac-AQDWYYGGGK-NH₂ | Y | 461 | 1183.3 [M-H]ᵃ |
| Ac-DWYYGGGK-NH₂ | Y | 462 | 984.2 [M-H]ᵃ |
| Ac-AQDWYYDEIL-NH₂ | Y | 463 | 1354.5 [M-H]ᵃ |
| Ac-AEWSYQDMIRLDYADLQLSHFAGGGGGK(Biotin-JJ)-NH₂ | Y | 464 | 1820.1 [M+2H]/2ᵇ |
| Ac-AQDWYYDEILSMADQLRHAFLSGGGGGK-NH₂ | Y | 356 | 1562.1 [M-2H]/2ᵃ |
| Ac-AQDWYYDEILSMADQLRHAFLSGGGGGK-NH₂ | Y | 356 | 1562.3 [M-2H]/2ᵃ |
| Ac-AQDWYYDEILSMADQLRHAFLSGGGGGK(iV-Ddc)-NH₂ | Y | 356 | 1729.7 [M-2H]/2, 1152.5 [M-3H]/3ᵃ |
| Ac-AQDWYYDEILSMADQLRHAFLSGGGGGK(SATA)-NH₂ | Y | 356-SATA | 1620.2 [M-2H]/2ᵃ |
| Ac-AEWSYQDMIRLDYADLQLSHFAGGGGGK(SATA)-NH₂ | Y | 464 | 1620.4 [M+2H]/2ᵇ |
| Various Parent Sequences | | | |
| Ac-AQDWYYDEILJGRGGRGGRGG-NH₂ | Y | 465 | 1185.0 [M+2H]/2, 790.8 [M+3H]/3ᵇ |
| Ac-EDDWYYJGRGGRGGRGG-NH₂ | Y | 466 | 972.3 [M+2H]/2, 648.0 [M+3H]/3ᵇ |
| Ac-GDWYYJGRGGRGGRGG-NH₂ | Y | 467 | 879.3 [M+2H]/2, 586.6 [M+3H]/3ᵇ |
| Ac-AQDWYYAWLFTJGRGGRGGRGG-NH₂ | Y | 468 | 1259.7 [M+2H]/2, 840.1 [M+3H]/3ᵇ |
| Ac-AQDWYYAWLJGRGGRGGRGG-NH₂ | Y | 469 | 1135.5 [M+2H]/2, 757.5 [M+3H]/3ᵇ |

Fig 79F

| Compound Sequence/Structure (Parent Sequence in red text) | Obtained? Y/N | SEQ ID NO | MS Data[f] |
|---|---|---|---|
| Ac-AQDWYYDEILJGRGGRGGRGGKK(IV-Dde)-NH$_2$ | Y | 470 | 1416.8 [M+2H]/2, 944.8 [M+3H]/3, 708.9 [M+4H]/4, 571.5 [M+4H+Na]/5[b] |
| Ac-GDSRVCWPDSWGGEVCFRYDP-NH$_2$ | Y | 471 | 1234.1 [M-2H]/2[a] |
| Ac-GDSRVCWEDSWGGVECFRYDP-NH$_2$ | Y | 472 | 1250.0 [M-2H]/2[a] |
| Ac-AQDWYYDEILJGRGGRGGRGGK(JJ)-NH$_2$ | Y | 473 | 930.23 [M+3H]/3, 697.9 [M+4H]/4, 558.5 [M+5H]/5[b] |
| Ac-AQDWYYDEILSMADQLRHAFLSGGGGGK(Biotin-JJ)-NH$_2$ | | 356 | |
| Ac-WYLDRQADPMYSAQAEDSLILHGGGGK(Biotin-JJ)-NH$_2$ | Y | 474 | 1820.5 [M-2H]/2, 1213.4 [M-3H]/3[a] |

Ac-VCWEDSWGGEVCFRYDPGGGK[K(iV-Dde)]-NH$_2$

SEQ ID NO:337    1

Compound B / DIEA / DMF

Ac-VCWEDSWGGEVCFRYDPGGGK[PnAO6-Glut-K(iV-Dde)]-NH$_2$

SEQ ID NO:337    2

1) 10% Hydrazine in DMF
2) HPLC Purification

Ac-VCWEDSWGGEVCFRYDPGGGK[PnAO6-Glut-K]-NH$_2$

SEQ ID NO:337    3

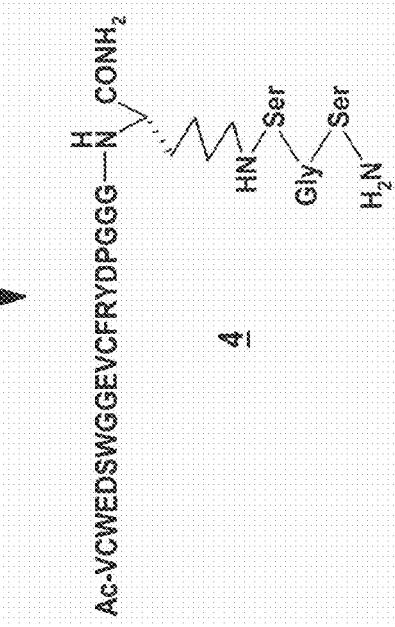
FIG. 88B

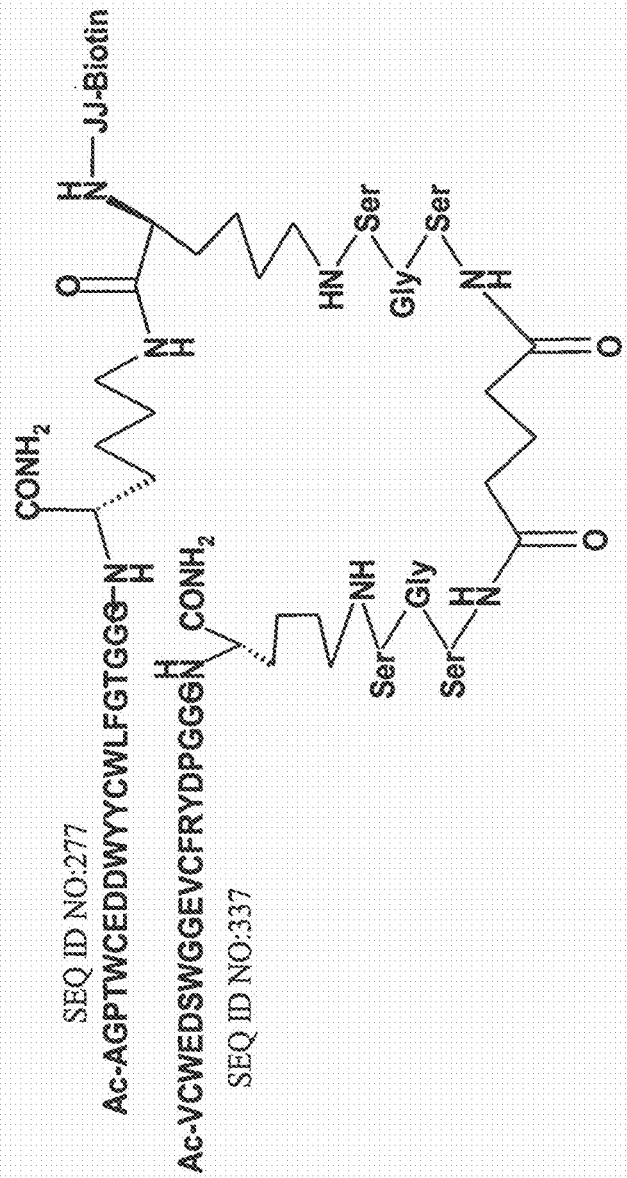

SEQUENCE LISTING

<160> NUMBER OF SEQ ID NOS: 617

<210> SEQ ID NO 1
<211> LENGTH: 19
<212> TYPE: PRT
<213> ORGANISM: Artificial Sequence
<220> FEATURE:
<223> OTHER INFORMATION: KDR or VEGF/KDR-Binding Consensus Sequence 5
<220> FEATURE:
<221> NAME/KEY: VARIANT
<222> LOCATION: (1)...(1)
<223> OTHER INFORMATION: Xaa = Arg, Glu, His, Ser or Trp
<220> FEATURE:
<221> NAME/KEY: VARIANT
<222> LOCATION: (2)...(2)
<223> OTHER INFORMATION: Xaa = Asn, Asp, Leu, Phe, Thr or Val
<220> FEATURE:
<221> NAME/KEY: VARIANT
<222> LOCATION: (3)...(3)
<223> OTHER INFORMATION: Xaa = Arg, Asp, Glu, His, Lys or Thr
<220> FEATURE:
<221> NAME/KEY: VARIANT
<222> LOCATION: (5)...(5)
<223> OTHER INFORMATION: Xaa = Asp, Glu, His or Thr
<220> FEATURE:
<221> NAME/KEY: VARIANT
<222> LOCATION: (6)...(6)
<223> OTHER INFORMATION: Xaa = Arg, His, Lys or Phe
<220> FEATURE:
<221> NAME/KEY: VARIANT
<222> LOCATION: (7)...(7)
<223> OTHER INFORMATION: Xaa = Gln, Ile, Lys, Tyr or Val -continued

```
<220> FEATURE:
<221> NAME/KEY: VARIANT
<222> LOCATION: (8)...(8)
<223> OTHER INFORMATION: Xaa = Gln, Ile, Leu, Met or Phe
<220> FEATURE:
<221> NAME/KEY: VARIANT
<222> LOCATION: (12)...(12)
<223> OTHER INFORMATION: Xaa = Asn, Asp, Gly, His or Tyr
<220> FEATURE:
<221> NAME/KEY: VARIANT
<222> LOCATION: (13)...(13)
<223> OTHER INFORMATION: Xaa = Gln, Gly, Ser or Thr
<220> FEATURE:
<221> NAME/KEY: VARIANT
<222> LOCATION: (14)...(14)
<223> OTHER INFORMATION: Xaa = Glu, Lys, Phe or Ser
<220> FEATURE:
<221> NAME/KEY: VARIANT
<222> LOCATION: (15)...(15)
<223> OTHER INFORMATION: Xaa = Glu, Ile, Ser or Val
<220> FEATURE:
<221> NAME/KEY: VARIANT
<222> LOCATION: (17)...(17)
<223> OTHER INFORMATION: Xaa = Glu, Gly, Lys, Phe, Ser or Val
<220> FEATURE:
<221> NAME/KEY: VARIANT
<222> LOCATION: (18)...(18)
<223> OTHER INFORMATION: Xaa = Arg, Asn, Ser or Tyr
<220> FEATURE:
<221> NAME/KEY: VARIANT
<222> LOCATION: (19)...(19)
<223> OTHER INFORMATION: Xaa = Asp, Gln, Glu, Gly, Met or Tyr

<400> SEQUENCE: 1

Xaa Xaa Xaa Cys Xaa Xaa Xaa Xaa Ser Gly Pro Xaa Xaa Xaa Xaa Cys
 1               5                  10                  15

Xaa Xaa Xaa

<210> SEQ ID NO 2
<211> LENGTH: 14
<212> TYPE: PRT
<213> ORGANISM: Artificial Sequence
<220> FEATURE:
<223> OTHER INFORMATION: KDR or VEGF/KDR-Binding Consensus Sequence 7
<220> FEATURE:
<221> NAME/KEY: VARIANT
<222> LOCATION: (5)...(5)
<223> OTHER INFORMATION: Xaa = Asp, Gln or His
<220> FEATURE:
<221> NAME/KEY: VARIANT
<222> LOCATION: (6)...(6)
<223> OTHER INFORMATION: Xaa = His or Tyr (preferably Tyr)
<220> FEATURE:
<221> NAME/KEY: VARIANT
<222> LOCATION: (7)...(7)
<223> OTHER INFORMATION: Xaa = Ile, His or Tyr
<220> FEATURE:
<221> NAME/KEY: VARIANT
<222> LOCATION: (9)...(9)
<223> OTHER INFORMATION: Xaa = Ile, Met or Val
<220> FEATURE:
<221> NAME/KEY: VARIANT
<222> LOCATION: (10)...(10)
<223> OTHER INFORMATION: Xaa = Gly or Tyr
<220> FEATURE:
<221> NAME/KEY: VARIANT
<222> LOCATION: (12)...(12)
<223> OTHER INFORMATION: Xaa = Asp, Lys or Pro
<220> FEATURE:
<221> NAME/KEY: VARIANT
<222> LOCATION: (13)...(13)
<223> OTHER INFORMATION: Xaa = Gln, Gly or Trp
<220> FEATURE:
<221> NAME/KEY: VARIANT
<222> LOCATION: (14)...(14)
<223> OTHER INFORMATION: Xaa = Phe, Ser or Thr
```

```
<400> SEQUENCE: 2

Trp Tyr Trp Cys Xaa Xaa Xaa Gly Xaa Xaa Cys Xaa Xaa Xaa
  1               5                   10

<210> SEQ ID NO 3
<211> LENGTH: 17
<212> TYPE: PRT
<213> ORGANISM: Artificial Sequence
<220> FEATURE:
<223> OTHER INFORMATION: KDR or VEGF/KDR-Binding Consensus Sequence 9
<220> FEATURE:
<221> NAME/KEY: VARIANT
<222> LOCATION: (1)...(1)
<223> OTHER INFORMATION: Xaa = Ser, Phe, Trp, Tyr or Gly
<220> FEATURE:
<221> NAME/KEY: VARIANT
<222> LOCATION: (2)...(2)
<223> OTHER INFORMATION: Xaa = Arg, Gly, Ser or Trp
<220> FEATURE:
<221> NAME/KEY: VARIANT
<222> LOCATION: (3)...(3)
<223> OTHER INFORMATION: Xaa = Ala, Glu, Ile or Val
<220> FEATURE:
<221> NAME/KEY: VARIANT
<222> LOCATION: (5)...(5)
<223> OTHER INFORMATION: Xaa = Ala, Phe or Trp
<220> FEATURE:
<221> NAME/KEY: VARIANT
<222> LOCATION: (6)...(6)
<223> OTHER INFORMATION: Xaa = Glu or Lys
<220> FEATURE:
<221> NAME/KEY: VARIANT
<222> LOCATION: (7)...(7)
<223> OTHER INFORMATION: Xaa = Asp, Ser, Trp or Tyr
<220> FEATURE:
<221> NAME/KEY: VARIANT
<222> LOCATION: (8)...(8)
<223> OTHER INFORMATION: Xaa = Phe, Pro or Ser
<220> FEATURE:
<221> NAME/KEY: VARIANT
<222> LOCATION: (12)...(12)
<223> OTHER INFORMATION: Xaa = Gln or Glu
<220> FEATURE:
<221> NAME/KEY: VARIANT
<222> LOCATION: (13)...(13)
<223> OTHER INFORMATION: Xaa = Ile, Phe or Val
<220> FEATURE:
<221> NAME/KEY: VARIANT
<222> LOCATION: (15)...(15)
<223> OTHER INFORMATION: Xaa = Gln, Ile, Leu, Phe or Tyr
<220> FEATURE:
<221> NAME/KEY: VARIANT
<222> LOCATION: (16)...(16)
<223> OTHER INFORMATION: Xaa = Arg, Gly or Pro
<220> FEATURE:
<221> NAME/KEY: VARIANT
<222> LOCATION: (17)...(17)
<223> OTHER INFORMATION: Xaa = Gln, His, Phe, Ser, Tyr or Val

<400> SEQUENCE: 3

Xaa Xaa Xaa Cys Xaa Xaa Xaa Xaa Trp Gly Gly Xaa Xaa Cys Xaa Xaa
  1               5                   10                  15

Xaa

<210> SEQ ID NO 4
<211> LENGTH: 18
<212> TYPE: PRT
<213> ORGANISM: Artificial Sequence
<220> FEATURE:
<223> OTHER INFORMATION: KDR or VEGF/KDR-Binding Consensus Sequence 10
<220> FEATURE:
<221> NAME/KEY: VARIANT
<222> LOCATION: (3)...(3)
<223> OTHER INFORMATION: Xaa = Gly or Trp
<220> FEATURE:
```

```
<221> NAME/KEY: VARIANT
<222> LOCATION: (5)...(5)
<223> OTHER INFORMATION: Xaa = His or Tyr
<220> FEATURE:
<221> NAME/KEY: VARIANT
<222> LOCATION: (7)...(7)
<223> OTHER INFORMATION: Xaa = His, Leu or Thr
<220> FEATURE:
<221> NAME/KEY: VARIANT
<222> LOCATION: (9)...(9)
<223> OTHER INFORMATION: Xaa = Asp or Leu
<220> FEATURE:
<221> NAME/KEY: VARIANT
<222> LOCATION: (11)...(11)
<223> OTHER INFORMATION: Xaa = Gly or Val
<220> FEATURE:
<221> NAME/KEY: VARIANT
<222> LOCATION: (12)...(12)
<223> OTHER INFORMATION: Xaa = Thr or Val
<220> FEATURE:
<221> NAME/KEY: VARIANT
<222> LOCATION: (13)...(13)
<223> OTHER INFORMATION: Xaa = Arg or Trp
<220> FEATURE:
<221> NAME/KEY: VARIANT
<222> LOCATION: (16)...(16)
<223> OTHER INFORMATION: Xaa = Ala or Val
<220> FEATURE:
<221> NAME/KEY: VARIANT
<222> LOCATION: (17)...(17)
<223> OTHER INFORMATION: Xaa = Asp or Pro
<220> FEATURE:
<221> NAME/KEY: VARIANT
<222> LOCATION: (18)...(18)
<223> OTHER INFORMATION: Xaa = Gly or Trp

<400> SEQUENCE: 4

Tyr Pro Xaa Cys Xaa Glu Xaa Ser Xaa Ser Xaa Xaa Xaa Phe Cys Xaa
 1               5                  10                  15

Xaa Xaa

<210> SEQ ID NO 5
<211> LENGTH: 18
<212> TYPE: PRT
<213> ORGANISM: Artificial Sequence
<220> FEATURE:
<223> OTHER INFORMATION: KDR or VEGF/KDR-Binding Consensus Sequence 11
<220> FEATURE:
<221> NAME/KEY: VARIANT
<222> LOCATION: (1)...(1)
<223> OTHER INFORMATION: Xaa = Asp, Gly, Pro or Ser
<220> FEATURE:
<221> NAME/KEY: VARIANT
<222> LOCATION: (2)...(2)
<223> OTHER INFORMATION: Xaa = Arg, Asn, Asp, Gly or Ser
<220> FEATURE:
<221> NAME/KEY: VARIANT
<222> LOCATION: (3)...(3)
<223> OTHER INFORMATION: Xaa = Gly, Thr, Trp or Tyr
<220> FEATURE:
<221> NAME/KEY: VARIANT
<222> LOCATION: (5)...(5)
<223> OTHER INFORMATION: Xaa = Glu, Met or Thr
<220> FEATURE:
<221> NAME/KEY: VARIANT
<222> LOCATION: (6)...(6)
<223> OTHER INFORMATION: Xaa = Ile, Leu, Met or Phe
<220> FEATURE:
<221> NAME/KEY: VARIANT
<222> LOCATION: (7)...(7)
<223> OTHER INFORMATION: Xaa = Arg, Asp, Glu, Met, Trp or Val
<220> FEATURE:
<221> NAME/KEY: VARIANT
<222> LOCATION: (8)...(8)
<223> OTHER INFORMATION: Xaa = Asn, Gln, Gly, Ser or Val
<220> FEATURE:
<221> NAME/KEY: VARIANT
```

```
<222> LOCATION: (9)...(9)
<223> OTHER INFORMATION: Xaa = Asp or Glu
<220> FEATURE:
<221> NAME/KEY: VARIANT
<222> LOCATION: (10)...(10)
<223> OTHER INFORMATION: Xaa = Lys, Ser, Thr or Val
<220> FEATURE:
<221> NAME/KEY: VARIANT
<222> LOCATION: (12)...(12)
<223> OTHER INFORMATION: Xaa = Arg, Gln, Lys or Trp
<220> FEATURE:
<221> NAME/KEY: VARIANT
<222> LOCATION: (14)...(14)
<223> OTHER INFORMATION: Xaa = Asn, Leu, Phe or Tyr
<220> FEATURE:
<221> NAME/KEY: VARIANT
<222> LOCATION: (16)...(16)
<223> OTHER INFORMATION: Xaa = Gly, Phe, Ser or Tyr
<220> FEATURE:
<221> NAME/KEY: VARIANT
<222> LOCATION: (17)...(17)
<223> OTHER INFORMATION: Xaa = Gly, Leu, Pro or Ser
<220> FEATURE:
<221> NAME/KEY: VARIANT
<222> LOCATION: (18)...(18)
<223> OTHER INFORMATION: Xaa = Ala, Asp, Pro, Ser, Trp or Tyr

<400> SEQUENCE: 5

Xaa Xaa Xaa Cys Xaa Xaa Xaa Xaa Xaa Xaa Gly Xaa Trp Xaa Cys Xaa
 1               5                  10                  15

Xaa Xaa

<210> SEQ ID NO 6
<211> LENGTH: 18
<212> TYPE: PRT
<213> ORGANISM: Artificial Sequence
<220> FEATURE:
<223> OTHER INFORMATION: KDR or VEGF/KDR-Binding Consensus Sequence 12
<220> FEATURE:
<221> NAME/KEY: VARIANT
<222> LOCATION: (3)...(3)
<223> OTHER INFORMATION: Xaa = Glu or Lys
<220> FEATURE:
<221> NAME/KEY: VARIANT
<222> LOCATION: (5)...(5)
<223> OTHER INFORMATION: Xaa = Glu or Gly
<220> FEATURE:
<221> NAME/KEY: VARIANT
<222> LOCATION: (6)...(6)
<223> OTHER INFORMATION: Xaa = Trp or Tyr
<220> FEATURE:
<221> NAME/KEY: VARIANT
<222> LOCATION: (7)...(7)
<223> OTHER INFORMATION: Xaa = Ser or Thr
<220> FEATURE:
<221> NAME/KEY: VARIANT
<222> LOCATION: (8)...(8)
<223> OTHER INFORMATION: Xaa = Asn or Gln
<220> FEATURE:
<221> NAME/KEY: VARIANT
<222> LOCATION: (9)...(9)
<223> OTHER INFORMATION: Xaa = Gly or Met
<220> FEATURE:
<221> NAME/KEY: VARIANT
<222> LOCATION: (10)...(10)
<223> OTHER INFORMATION: Xaa = Phe or Tyr
<220> FEATURE:
<221> NAME/KEY: VARIANT
<222> LOCATION: (11)...(11)
<223> OTHER INFORMATION: Xaa = Asp or Gln
<220> FEATURE:
<221> NAME/KEY: VARIANT
<222> LOCATION: (12)...(12)
<223> OTHER INFORMATION: Xaa = Lys or Tyr
<220> FEATURE:
<221> NAME/KEY: VARIANT
<222> LOCATION: (13)...(13)
```

```
<223> OTHER INFORMATION: Xaa = Glu or Thr
<220> FEATURE:
<221> NAME/KEY: VARIANT
<222> LOCATION: (14)...(14)
<223> OTHER INFORMATION: Xaa = Glu or Phe
<220> FEATURE:
<221> NAME/KEY: VARIANT
<222> LOCATION: (16)...(16)
<223> OTHER INFORMATION: Xaa = Ala or Val
<220> FEATURE:
<221> NAME/KEY: VARIANT
<222> LOCATION: (17)...(17)
<223> OTHER INFORMATION: Xaa = Arg or Tyr
<220> FEATURE:
<221> NAME/KEY: VARIANT
<222> LOCATION: (18)...(18)
<223> OTHER INFORMATION: Xaa = Leu or Pro

<400> SEQUENCE: 6

Asn Trp Xaa Cys Xaa Xaa Xaa Xaa Xaa Xaa Xaa Xaa Xaa Xaa Cys Xaa
 1               5                  10                 15

Xaa Xaa

<210> SEQ ID NO 7
<211> LENGTH: 10
<212> TYPE: PRT
<213> ORGANISM: Artificial Sequence
<220> FEATURE:
<223> OTHER INFORMATION: KDR or VEGF/KDR-Binding Consensus Sequence 14
<220> FEATURE:
<221> NAME/KEY: VARIANT
<222> LOCATION: (1)...(1)
<223> OTHER INFORMATION: Xaa = Asp, Gly or Ser
<220> FEATURE:
<221> NAME/KEY: VARIANT
<222> LOCATION: (2)...(2)
<223> OTHER INFORMATION: Xaa = Ile, Phe or Tyr
<220> FEATURE:
<221> NAME/KEY: VARIANT
<222> LOCATION: (3)...(3)
<223> OTHER INFORMATION: Xaa = Ala, Ser or Val
<220> FEATURE:
<221> NAME/KEY: VARIANT
<222> LOCATION: (7)...(7)
<223> OTHER INFORMATION: Xaa = Gln, Glu, Ile or Val
<220> FEATURE:
<221> NAME/KEY: VARIANT
<222> LOCATION: (8)...(8)
<223> OTHER INFORMATION: Xaa = Ala, Ile or Val
<220> FEATURE:
<221> NAME/KEY: VARIANT
<222> LOCATION: (9)...(9)
<223> OTHER INFORMATION: Xaa = Ala, Glu, Val or Thr

<400> SEQUENCE: 7

Xaa Xaa Xaa Tyr Trp Glu Xaa Xaa Xaa Leu
 1               5                  10

<210> SEQ ID NO 8
<211> LENGTH: 4
<212> TYPE: PRT
<213> ORGANISM: Artificial Sequence
<220> FEATURE:
<223> OTHER INFORMATION: KDR or VEGF/KDR Binding Polypeptide

<400> SEQUENCE: 8

Asp Trp Tyr Tyr
 1

<210> SEQ ID NO 9
<211> LENGTH: 6
<212> TYPE: PRT
<213> ORGANISM: Artificial Sequence
```

```
<220> FEATURE:
<223> OTHER INFORMATION: KDR or VEGF/KDR Binding Polypeptide

<400> SEQUENCE: 9

Glu Glu Asp Trp Tyr Tyr
1               5

<210> SEQ ID NO 10
<211> LENGTH: 16
<212> TYPE: PRT
<213> ORGANISM: Artificial Sequence
<220> FEATURE:
<223> OTHER INFORMATION: KDR or VEGF/KDR Binding Polypeptide

<400> SEQUENCE: 10

Asn Asn Ser Cys Trp Leu Ser Thr Thr Leu Gly Ser Cys Phe Phe Asp
1               5                   10                  15

<210> SEQ ID NO 11
<211> LENGTH: 16
<212> TYPE: PRT
<213> ORGANISM: Artificial Sequence
<220> FEATURE:
<223> OTHER INFORMATION: KDR or VEGF/KDR Binding Polypeptide

<400> SEQUENCE: 11

Asp His His Cys Tyr Leu His Asn Gly Gln Trp Ile Cys Tyr Pro Phe
1               5                   10                  15

<210> SEQ ID NO 12
<211> LENGTH: 16
<212> TYPE: PRT
<213> ORGANISM: Artificial Sequence
<220> FEATURE:
<223> OTHER INFORMATION: KDR or VEGF/KDR Binding Polypeptide

<400> SEQUENCE: 12

Asn Ser His Cys Tyr Ile Trp Asp Gly Met Trp Leu Cys Phe Pro Asp
1               5                   10                  15

<210> SEQ ID NO 13
<211> LENGTH: 13
<212> TYPE: PRT
<213> ORGANISM: Artificial Sequence
<220> FEATURE:
<223> OTHER INFORMATION: KDR-Binding Loop Consensus Sequence 19
<220> FEATURE:
<221> NAME/KEY: VARIANT
<222> LOCATION: (2)...(2)
<223> OTHER INFORMATION: Xaa = Asp, Glu, His or Thr
<220> FEATURE:
<221> NAME/KEY: VARIANT
<222> LOCATION: (3)...(3)
<223> OTHER INFORMATION: Xaa = Arg, His, Lys or Phe
<220> FEATURE:
<221> NAME/KEY: VARIANT
<222> LOCATION: (4)...(4)
<223> OTHER INFORMATION: Xaa = Gln, Ile, Lys, Tyr or Val
<220> FEATURE:
<221> NAME/KEY: VARIANT
<222> LOCATION: (5)...(5)
<223> OTHER INFORMATION: Xaa = Gln, Ile, Leu, Met or Phe
<220> FEATURE:
<221> NAME/KEY: VARIANT
<222> LOCATION: (9)...(9)
<223> OTHER INFORMATION: Xaa = Asn, Asp, Gly, His or Tyr
<220> FEATURE:
<221> NAME/KEY: VARIANT
<222> LOCATION: (10)...(10)
<223> OTHER INFORMATION: Xaa = Gln, Lys, Phe or Ser
<220> FEATURE:
<221> NAME/KEY: VARIANT
```

<222> LOCATION: (11)...(11)
<223> OTHER INFORMATION: Xaa = Glu, Lys, Phe or Ser
<220> FEATURE:
<221> NAME/KEY: VARIANT
<222> LOCATION: (12)...(12)
<223> OTHER INFORMATION: Xaa = Glu, Ile, Ser or Val

<400> SEQUENCE: 13

Cys Xaa Xaa Xaa Xaa Ser Gly Pro Xaa Xaa Xaa Xaa Cys
1 5 10

<210> SEQ ID NO 14
<211> LENGTH: 11
<212> TYPE: PRT
<213> ORGANISM: Artificial Sequence
<220> FEATURE:
<223> OTHER INFORMATION: KDR-Binding Loop Consensus Sequence 23
<220> FEATURE:
<221> NAME/KEY: VARIANT
<222> LOCATION: (2)...(2)
<223> OTHER INFORMATION: Xaa = Ala, Phe or Trp
<220> FEATURE:
<221> NAME/KEY: VARIANT
<222> LOCATION: (3)...(3)
<223> OTHER INFORMATION: Xaa = Glu or Lys
<220> FEATURE:
<221> NAME/KEY: VARIANT
<222> LOCATION: (4)...(4)
<223> OTHER INFORMATION: Xaa = Asp, Ser, Trp or Tyr
<220> FEATURE:
<221> NAME/KEY: VARIANT
<222> LOCATION: (5)...(5)
<223> OTHER INFORMATION: Xaa = Phe, Pro or Ser
<220> FEATURE:
<221> NAME/KEY: VARIANT
<222> LOCATION: (9)...(9)
<223> OTHER INFORMATION: Xaa = Gln or Glu
<220> FEATURE:
<221> NAME/KEY: VARIANT
<222> LOCATION: (10)...(10)
<223> OTHER INFORMATION: Xaa = Ile, Phe or Val

<400> SEQUENCE: 14

Cys Xaa Xaa Xaa Xaa Trp Gly Gly Xaa Xaa Cys
1 5 10

<210> SEQ ID NO 15
<211> LENGTH: 12
<212> TYPE: PRT
<213> ORGANISM: Artificial Sequence
<220> FEATURE:
<223> OTHER INFORMATION: KDR-Binding Loop Consensus Sequence 24
<220> FEATURE:
<221> NAME/KEY: VARIANT
<222> LOCATION: (2)...(2)
<223> OTHER INFORMATION: Xaa = His or Tyr
<220> FEATURE:
<221> NAME/KEY: VARIANT
<222> LOCATION: (4)...(4)
<223> OTHER INFORMATION: Xaa = Leu, His or Thr
<220> FEATURE:
<221> NAME/KEY: VARIANT
<222> LOCATION: (6)...(6)
<223> OTHER INFORMATION: Xaa = Asp or Leu
<220> FEATURE:
<221> NAME/KEY: VARIANT
<222> LOCATION: (8)...(8)
<223> OTHER INFORMATION: Xaa = Gly or Val
<220> FEATURE:
<221> NAME/KEY: VARIANT
<222> LOCATION: (9)...(9)
<223> OTHER INFORMATION: Xaa = Thr or Val
<220> FEATURE:
<221> NAME/KEY: VARIANT
<222> LOCATION: (10)...(10)
<223> OTHER INFORMATION: Xaa = Arg or Trp -continued

```
<400> SEQUENCE: 15

Cys Xaa Glu Xaa Ser Xaa Ser Xaa Xaa Xaa Phe Cys
1               5                   10

<210> SEQ ID NO 16
<211> LENGTH: 12
<212> TYPE: PRT
<213> ORGANISM: Artificial Sequence
<220> FEATURE:
<223> OTHER INFORMATION: KDR-Binding Loop Consensus Sequence 25
<220> FEATURE:
<221> NAME/KEY: VARIANT
<222> LOCATION: (2)...(2)
<223> OTHER INFORMATION: Xaa = Glu, Met or Thr
<220> FEATURE:
<221> NAME/KEY: VARIANT
<222> LOCATION: (3)...(3)
<223> OTHER INFORMATION: Xaa = Ile, Leu, Met or Phe
<220> FEATURE:
<221> NAME/KEY: VARIANT
<222> LOCATION: (4)...(4)
<223> OTHER INFORMATION: Xaa =Arg, Asp, Glu, Met, Trp or Val
<220> FEATURE:
<221> NAME/KEY: VARIANT
<222> LOCATION: (5)...(5)
<223> OTHER INFORMATION: Xaa = Asn, Gln, Gly, Ser or Val
<220> FEATURE:
<221> NAME/KEY: VARIANT
<222> LOCATION: (6)...(6)
<223> OTHER INFORMATION: Xaa = Glu or Asp
<220> FEATURE:
<221> NAME/KEY: VARIANT
<222> LOCATION: (7)...(7)
<223> OTHER INFORMATION: Xaa = Lys, Ser, Thr or Val
<220> FEATURE:
<221> NAME/KEY: VARIANT
<222> LOCATION: (9)...(9)
<223> OTHER INFORMATION: Xaa = Arg, Gln, Lys or Trp
<220> FEATURE:
<221> NAME/KEY: VARIANT
<222> LOCATION: (11)...(11)
<223> OTHER INFORMATION: Xaa = Asn, Leu, Phe or Tyr

<400> SEQUENCE: 16

Cys Xaa Xaa Xaa Xaa Xaa Xaa Gly Xaa Trp Xaa Cys
1               5                   10

<210> SEQ ID NO 17
<211> LENGTH: 13
<212> TYPE: PRT
<213> ORGANISM: Artificial Sequence
<220> FEATURE:
<223> OTHER INFORMATION: KDR-Binding Loop Consensus Sequence 29
<220> FEATURE:
<221> NAME/KEY: VARIANT
<222> LOCATION: (2)...(2)
<223> OTHER INFORMATION: Xaa = Asp, Glu, His or Thr
<220> FEATURE:
<221> NAME/KEY: VARIANT
<222> LOCATION: (3)...(3)
<223> OTHER INFORMATION: Xaa = Arg, His, Lys or Phe
<220> FEATURE:
<221> NAME/KEY: VARIANT
<222> LOCATION: (4)...(4)
<223> OTHER INFORMATION: Xaa = Gln, Ile, Lys, Tyr or Val
<220> FEATURE:
    221> VARIANT
<222> LOCATION: (5)...(5)
<223> OTHER INFORMATION: Xaa = Gln, Ile, Leu, Met or Phe
<220> FEATURE:
<221> NAME/KEY: VARIANT
<222> LOCATION: (9)...(9)
<223> OTHER INFORMATION: Xaa = Asn, Asp, Gly, His or Tyr
<220> FEATURE:
<221> NAME/KEY: VARIANT
```

```
<222> LOCATION: (10)...(10)
<223> OTHER INFORMATION: Xaa = Gln, Gly, Ser or Thr
<220> FEATURE:
<221> NAME/KEY: VARIANT
<222> LOCATION: (11)...(11)
<223> OTHER INFORMATION: Xaa = Glu, Lys, Phe or Ser
<220> FEATURE:
<221> NAME/KEY: VARIANT
<222> LOCATION: (12)...(12)
<223> OTHER INFORMATION: Xaa = Glu, Ile, Ser or Val

<400> SEQUENCE: 17

Cys Xaa Xaa Xaa Xaa Ser Gly Pro Xaa Xaa Xaa Xaa Cys
 1               5                   10

<210> SEQ ID NO 18
<211> LENGTH: 4
<212> TYPE: PRT
<213> ORGANISM: Artificial Sequence
<220> FEATURE:
<223> OTHER INFORMATION: C-Terminal Linker

<400> SEQUENCE: 18

Gly Gly Gly Lys
 1

<210> SEQ ID NO 19
<211> LENGTH: 19
<212> TYPE: PRT
<213> ORGANISM: Artificial Sequence
<220> FEATURE:
<223> OTHER INFORMATION: MTN13/I Template Sequence
<220> FEATURE:
<221> NAME/KEY: VARIANT
<222> LOCATION: (1)...(1)
<223> OTHER INFORMATION: Xaa = any amino acid except Cysteine (Cys)
<220> FEATURE:
<221> NAME/KEY: VARIANT
<222> LOCATION: (2)...(2)
<223> OTHER INFORMATION: Xaa = any amino acid except Cysteine (Cys)
<220> FEATURE:
<221> NAME/KEY: VARIANT
<222> LOCATION: (3)...(3)
<223> OTHER INFORMATION: Xaa = any amino acid except Cysteine (Cys)
<220> FEATURE:
<221> NAME/KEY: VARIANT
<222> LOCATION: (5)...(5)
<223> OTHER INFORMATION: Xaa = any amino acid except Cysteine (Cys)
<220> FEATURE:
<221> NAME/KEY: VARIANT
<222> LOCATION: (6)...(6)
<223> OTHER INFORMATION: Xaa = any amino acid except Cysteine (Cys)
<220> FEATURE:
<221> NAME/KEY: VARIANT
<222> LOCATION: (7)...(7)
<223> OTHER INFORMATION: Xaa = any amino acid except Cysteine (Cys)
<220> FEATURE:
<221> NAME/KEY: VARIANT
<222> LOCATION: (8)...(8)
<223> OTHER INFORMATION: Xaa = any amino acid except Cysteine (Cys)
<220> FEATURE:
<221> NAME/KEY: VARIANT
<222> LOCATION: (12)...(12)
<223> OTHER INFORMATION: Xaa = any amino acid except Cysteine (Cys)
<220> FEATURE:
<221> NAME/KEY: VARIANT
<222> LOCATION: (13)...(13)
<223> OTHER INFORMATION: Xaa = any amino acid except Cysteine (Cys)
<220> FEATURE:
<221> NAME/KEY: VARIANT
<222> LOCATION: (14)...(14)
<223> OTHER INFORMATION: Xaa = any amino acid except Cysteine (Cys)
<220> FEATURE:
<221> NAME/KEY: VARIANT
<222> LOCATION: (15)...(15)
<223> OTHER INFORMATION: Xaa = any amino acid except Cysteine (Cys)
```

```
<220> FEATURE:
<221> NAME/KEY: VARIANT
<222> LOCATION: (17)...(17)
<223> OTHER INFORMATION: Xaa = any amino acid except Cysteine (Cys)
<220> FEATURE:
<221> NAME/KEY: VARIANT
<222> LOCATION: (18)...(18)
<223> OTHER INFORMATION: Xaa = any amino acid except Cysteine (Cys)
<220> FEATURE:
<221> NAME/KEY: VARIANT
<222> LOCATION: (19)...(19)
<223> OTHER INFORMATION: Xaa = any amino acid except Cysteine (Cys)

<400> SEQUENCE: 19

Xaa Xaa Xaa Cys Xaa Xaa Xaa Xaa Ser Gly Pro Xaa Xaa Xaa Xaa Cys
1               5                   10                  15

Xaa Xaa Xaa

<210> SEQ ID NO 20
<211> LENGTH: 14
<212> TYPE: PRT
<213> ORGANISM: Artificial Sequence
<220> FEATURE:
<223> OTHER INFORMATION: Library Isolate

<400> SEQUENCE: 20

Asp Ser Trp Cys Ser Thr Glu Tyr Thr Tyr Cys Glu Met Ile
1               5                   10

<210> SEQ ID NO 21
<211> LENGTH: 14
<212> TYPE: PRT
<213> ORGANISM: Artificial Sequence
<220> FEATURE:
<223> OTHER INFORMATION: Library Isolate

<400> SEQUENCE: 21

Pro Lys Trp Cys Glu Glu Asp Trp Tyr Tyr Cys Met Ile Thr
1               5                   10

<210> SEQ ID NO 22
<211> LENGTH: 14
<212> TYPE: PRT
<213> ORGANISM: Artificial Sequence
<220> FEATURE:
<223> OTHER INFORMATION: Library Isolate

<400> SEQUENCE: 22

Ser Asp Trp Cys Arg Val Asp Trp Tyr Tyr Cys Trp Leu Met
1               5                   10

<210> SEQ ID NO 23
<211> LENGTH: 14
<212> TYPE: PRT
<213> ORGANISM: Artificial Sequence
<220> FEATURE:
<223> OTHER INFORMATION: Library Isolate

<400> SEQUENCE: 23

Ala Asn Trp Cys Glu Glu Asp Trp Tyr Tyr Cys Phe Ile Thr
1               5                   10

<210> SEQ ID NO 24
<211> LENGTH: 14
<212> TYPE: PRT
<213> ORGANISM: Artificial Sequence
<220> FEATURE:
<223> OTHER INFORMATION: Library Isolate
```

```
<400> SEQUENCE: 24

Ala Asn Trp Cys Glu Glu Asp Trp Tyr Tyr Cys Trp Ile Thr
1               5                   10

<210> SEQ ID NO 25
<211> LENGTH: 14
<212> TYPE: PRT
<213> ORGANISM: Artificial Sequence
<220> FEATURE:
<223> OTHER INFORMATION: Library Isolate

<400> SEQUENCE: 25

Pro Asp Trp Cys Glu Glu Asp Trp Tyr Tyr Cys Trp Ile Thr
1               5                   10

<210> SEQ ID NO 26
<211> LENGTH: 14
<212> TYPE: PRT
<213> ORGANISM: Artificial Sequence
<220> FEATURE:
<223> OTHER INFORMATION: Library Isolate

<400> SEQUENCE: 26

Ser Asn Trp Cys Glu Glu Asp Trp Tyr Tyr Cys Tyr Ile Thr
1               5                   10

<210> SEQ ID NO 27
<211> LENGTH: 14
<212> TYPE: PRT
<213> ORGANISM: Artificial Sequence
<220> FEATURE:
<223> OTHER INFORMATION: Library Isolate

<400> SEQUENCE: 27

Pro Asp Trp Cys Ala Ala Asp Trp Tyr Tyr Cys Tyr Ile Thr
1               5                   10

<210> SEQ ID NO 28
<211> LENGTH: 14
<212> TYPE: PRT
<213> ORGANISM: Artificial Sequence
<220> FEATURE:
<223> OTHER INFORMATION: Library Isolate

<400> SEQUENCE: 28

Pro Glu Trp Cys Glu Val Asp Trp Tyr Tyr Cys Trp Leu Leu
1               5                   10

<210> SEQ ID NO 29
<211> LENGTH: 14
<212> TYPE: PRT
<213> ORGANISM: Artificial Sequence
<220> FEATURE:
<223> OTHER INFORMATION: Library Isolate

<400> SEQUENCE: 29

Pro Thr Trp Cys Glu Asp Asp Trp Tyr Tyr Cys Trp Leu Phe
1               5                   10

<210> SEQ ID NO 30
<211> LENGTH: 14
<212> TYPE: PRT
<213> ORGANISM: Artificial Sequence
<220> FEATURE:
<223> OTHER INFORMATION: Library Isolate

<400> SEQUENCE: 30
```

-continued

```
Ser Lys Trp Cys Glu Gln Asp Trp Tyr Tyr Cys Trp Leu Leu
1               5                   10
```

<210> SEQ ID NO 31
<211> LENGTH: 14
<212> TYPE: PRT
<213> ORGANISM: Artificial Sequence
<220> FEATURE:
<223> OTHER INFORMATION: Library Isolate

<400> SEQUENCE: 31

```
Arg Asn Trp Cys Glu Glu Asp Trp Tyr Tyr Cys Phe Ile Thr
1               5                   10
```

<210> SEQ ID NO 32
<211> LENGTH: 14
<212> TYPE: PRT
<213> ORGANISM: Artificial Sequence
<220> FEATURE:
<223> OTHER INFORMATION: Library Isolate

<400> SEQUENCE: 32

```
Val Asn Trp Cys Glu Glu Asp Trp Tyr Tyr Cys Trp Ile Thr
1               5                   10
```

<210> SEQ ID NO 33
<211> LENGTH: 14
<212> TYPE: PRT
<213> ORGANISM: Artificial Sequence
<220> FEATURE:
<223> OTHER INFORMATION: Library Isolate

<400> SEQUENCE: 33

```
Ala Asn Trp Cys Glu Glu Asp Trp Tyr Tyr Cys Tyr Ile Thr
1               5                   10
```

<210> SEQ ID NO 34
<211> LENGTH: 14
<212> TYPE: PRT
<213> ORGANISM: Artificial Sequence
<220> FEATURE:
<223> OTHER INFORMATION: Library Isolate

<400> SEQUENCE: 34

```
Val Trp Glu Cys Ala Lys Thr Phe Pro Phe Cys His Trp Phe
1               5                   10
```

<210> SEQ ID NO 35
<211> LENGTH: 14
<212> TYPE: PRT
<213> ORGANISM: Artificial Sequence
<220> FEATURE:
<223> OTHER INFORMATION: Library Isolate

<400> SEQUENCE: 35

```
Val Thr Val Cys Tyr Glu Gly Thr Arg Ile Cys Glu Trp His
1               5                   10
```

<210> SEQ ID NO 36
<211> LENGTH: 14
<212> TYPE: PRT
<213> ORGANISM: Artificial Sequence
<220> FEATURE:
<223> OTHER INFORMATION: Library Isolate

<400> SEQUENCE: 36

```
Trp Val Glu Cys Arg Tyr Ser Thr Gly Leu Cys Ile Asn Tyr
1               5                   10
```

```
<210> SEQ ID NO 37
<211> LENGTH: 14
<212> TYPE: PRT
<213> ORGANISM: Artificial Sequence
<220> FEATURE:
<223> OTHER INFORMATION: Library Isolate

<400> SEQUENCE: 37

Trp Tyr Trp Cys Asp Tyr Tyr Gly Ile Gly Cys Lys Trp Thr
 1               5                  10

<210> SEQ ID NO 38
<211> LENGTH: 14
<212> TYPE: PRT
<213> ORGANISM: Artificial Sequence
<220> FEATURE:
<223> OTHER INFORMATION: Library Isolate

<400> SEQUENCE: 38

Trp Val Glu Cys Trp Trp Lys Ser Gly Gln Cys Tyr Glu Phe
 1               5                  10

<210> SEQ ID NO 39
<211> LENGTH: 14
<212> TYPE: PRT
<213> ORGANISM: Artificial Sequence
<220> FEATURE:
<223> OTHER INFORMATION: Library Isolate

<400> SEQUENCE: 39

Trp Ile Gln Cys Asp Met Glu Thr Gly Leu Cys Thr His Gly
 1               5                  10

<210> SEQ ID NO 40
<211> LENGTH: 14
<212> TYPE: PRT
<213> ORGANISM: Artificial Sequence
<220> FEATURE:
<223> OTHER INFORMATION: Library Isolate

<400> SEQUENCE: 40

Trp Val Glu Cys Phe Met Asp Thr Gly Ala Cys Tyr Thr Phe
 1               5                  10

<210> SEQ ID NO 41
<211> LENGTH: 14
<212> TYPE: PRT
<213> ORGANISM: Artificial Sequence
<220> FEATURE:
<223> OTHER INFORMATION: Library Isolate

<400> SEQUENCE: 41

Trp Leu Glu Cys Tyr Ala Glu Phe Gly His Cys Tyr Asn Phe
 1               5                  10

<210> SEQ ID NO 42
<211> LENGTH: 14
<212> TYPE: PRT
<213> ORGANISM: Artificial Sequence
<220> FEATURE:
<223> OTHER INFORMATION: Library Isolate

<400> SEQUENCE: 42

Trp Ile Glu Cys Asp Met Leu Thr Gly Met Cys Lys His Gly
 1               5                  10
```

```
<210> SEQ ID NO 43
<211> LENGTH: 14
<212> TYPE: PRT
<213> ORGANISM: Artificial Sequence
<220> FEATURE:
<223> OTHER INFORMATION: Library Isolate

<400> SEQUENCE: 43

Ser Val Glu Cys Phe Met Asp Thr Gly Ala Cys Tyr Thr Phe
1               5                   10

<210> SEQ ID NO 44
<211> LENGTH: 14
<212> TYPE: PRT
<213> ORGANISM: Artificial Sequence
<220> FEATURE:
<223> OTHER INFORMATION: Library Isolate

<400> SEQUENCE: 44

Trp Ile Gln Cys Asn Ser Ile Thr Gly His Cys Thr Ser Gly
1               5                   10

<210> SEQ ID NO 45
<211> LENGTH: 14
<212> TYPE: PRT
<213> ORGANISM: Artificial Sequence
<220> FEATURE:
<223> OTHER INFORMATION: Library Isolate

<400> SEQUENCE: 45

Trp Ile Glu Cys Tyr His Pro Asp Gly Ile Cys Tyr His Phe
1               5                   10

<210> SEQ ID NO 46
<211> LENGTH: 18
<212> TYPE: PRT
<213> ORGANISM: Artificial Sequence
<220> FEATURE:
<223> OTHER INFORMATION: Library Isolate

<400> SEQUENCE: 46

Gln Ala Trp Val Glu Cys Tyr Ala Glu Thr Gly Tyr Cys Trp Pro Arg
1               5                   10                  15

Ser Trp

<210> SEQ ID NO 47
<211> LENGTH: 18
<212> TYPE: PRT
<213> ORGANISM: Artificial Sequence
<220> FEATURE:
<223> OTHER INFORMATION: Library Isolate

<400> SEQUENCE: 47

Val Gly Trp Val Glu Cys Tyr Gln Ser Thr Gly Phe Cys Tyr His Ser
1               5                   10                  15

Arg Asp

<210> SEQ ID NO 48
<211> LENGTH: 18
<212> TYPE: PRT
<213> ORGANISM: Artificial Sequence
<220> FEATURE:
<223> OTHER INFORMATION: Library Isolate

<400> SEQUENCE: 48

Phe Thr Trp Val Glu Cys His Gln Ala Thr Gly Arg Cys Val Glu Trp
1               5                   10                  15
```

Thr Thr

<210> SEQ ID NO 49
<211> LENGTH: 18
<212> TYPE: PRT
<213> ORGANISM: Artificial Sequence
<220> FEATURE:
<223> OTHER INFORMATION: Library Isolate

<400> SEQUENCE: 49

Asp Trp Trp Val Glu Cys Arg Val Gly Thr Gly Leu Cys Tyr Arg Tyr
1               5                   10                  15

Asp Thr

<210> SEQ ID NO 50
<211> LENGTH: 18
<212> TYPE: PRT
<213> ORGANISM: Artificial Sequence
<220> FEATURE:
<223> OTHER INFORMATION: Library Isolate

<400> SEQUENCE: 50

Asp Ser Trp Val Glu Cys Asp Ala Gln Thr Gly Phe Cys Tyr Ser Phe
1               5                   10                  15

Leu Tyr

<210> SEQ ID NO 51
<211> LENGTH: 18
<212> TYPE: PRT
<213> ORGANISM: Artificial Sequence
<220> FEATURE:
<223> OTHER INFORMATION: Library Isolate

<400> SEQUENCE: 51

Gly Gly Trp Val Glu Cys Tyr Trp Ala Thr Gly Arg Cys Ile Glu Phe
1               5                   10                  15

Ala Gly

<210> SEQ ID NO 52
<211> LENGTH: 18
<212> TYPE: PRT
<213> ORGANISM: Artificial Sequence
<220> FEATURE:
<223> OTHER INFORMATION: Library Isolate

<400> SEQUENCE: 52

Glu Arg Trp Val Glu Cys Arg Ala Glu Thr Gly Phe Cys Tyr Thr Trp
1               5                   10                  15

Val Ser

<210> SEQ ID NO 53
<211> LENGTH: 18
<212> TYPE: PRT
<213> ORGANISM: Artificial Sequence
<220> FEATURE:
<223> OTHER INFORMATION: Library Isolate

<400> SEQUENCE: 53

Gly Gly Trp Val Glu Cys Arg Ala Glu Thr Gly His Cys Gln Glu Tyr
1               5                   10                  15

Arg Leu

<210> SEQ ID NO 54

```
<211> LENGTH: 18
<212> TYPE: PRT
<213> ORGANISM: Artificial Sequence
<220> FEATURE:
<223> OTHER INFORMATION: Library Isolate

<400> SEQUENCE: 54

Val Ala Trp Val Glu Cys Tyr Gln Thr Thr Gly Lys Cys Tyr Thr Phe
1               5                   10                  15
Arg Gly

<210> SEQ ID NO 55
<211> LENGTH: 18
<212> TYPE: PRT
<213> ORGANISM: Artificial Sequence
<220> FEATURE:
<223> OTHER INFORMATION: Library Isolate

<400> SEQUENCE: 55

Glu Gly Trp Val Glu Cys Phe Ala Asn Thr Gly Ala Cys Phe Thr Tyr
1               5                   10                  15
Pro Arg

<210> SEQ ID NO 56
<211> LENGTH: 14
<212> TYPE: PRT
<213> ORGANISM: Artificial Sequence
<220> FEATURE:
<223> OTHER INFORMATION: Library Isolate

<400> SEQUENCE: 56

Gly Val Glu Cys Tyr Lys His Ser Gly Met Cys Arg Ser Trp
1               5                   10

<210> SEQ ID NO 57
<211> LENGTH: 14
<212> TYPE: PRT
<213> ORGANISM: Artificial Sequence
<220> FEATURE:
<223> OTHER INFORMATION: Library Isolate

<400> SEQUENCE: 57

Gly Val Trp Cys Asp Met Val Thr Gly Trp Cys Tyr His Gly
1               5                   10

<210> SEQ ID NO 58
<211> LENGTH: 14
<212> TYPE: PRT
<213> ORGANISM: Artificial Sequence
<220> FEATURE:
<223> OTHER INFORMATION: Library Isolate

<400> SEQUENCE: 58

Trp Ile Glu Cys His Tyr Lys Thr Gly His Cys Ile His Ser
1               5                   10

<210> SEQ ID NO 59
<211> LENGTH: 14
<212> TYPE: PRT
<213> ORGANISM: Artificial Sequence
<220> FEATURE:
<223> OTHER INFORMATION: Library Isolate

<400> SEQUENCE: 59

Asp Phe Asn Cys Lys Met Ile Asp Gly Phe Cys Leu Leu Lys
1               5                   10
```

```
<210> SEQ ID NO 60
<211> LENGTH: 14
<212> TYPE: PRT
<213> ORGANISM: Artificial Sequence
<220> FEATURE:
<223> OTHER INFORMATION: Library Isolate

<400> SEQUENCE: 60

Trp Ile Gln Cys Asp Arg Lys Ala Gly Arg Cys Ser Arg Gly
 1               5                  10

<210> SEQ ID NO 61
<211> LENGTH: 14
<212> TYPE: PRT
<213> ORGANISM: Artificial Sequence
<220> FEATURE:
<223> OTHER INFORMATION: Library Isolate

<400> SEQUENCE: 61

Thr Ile Thr Cys Trp Met Asp Thr Gly His Cys Met His Glu
 1               5                  10

<210> SEQ ID NO 62
<211> LENGTH: 14
<212> TYPE: PRT
<213> ORGANISM: Artificial Sequence
<220> FEATURE:
<223> OTHER INFORMATION: Library Isolate

<400> SEQUENCE: 62

Gly Ile Asn Cys Tyr Pro Ala Thr Gly Lys Cys Gln Met Gly
 1               5                  10

<210> SEQ ID NO 63
<211> LENGTH: 14
<212> TYPE: PRT
<213> ORGANISM: Artificial Sequence
<220> FEATURE:
<223> OTHER INFORMATION: Library Isolate

<400> SEQUENCE: 63

Trp Thr Glu Cys His Tyr Ala Thr Gly Lys Cys His Ser Phe
 1               5                  10

<210> SEQ ID NO 64
<211> LENGTH: 14
<212> TYPE: PRT
<213> ORGANISM: Artificial Sequence
<220> FEATURE:
<223> OTHER INFORMATION: Library Isolate

<400> SEQUENCE: 64

Leu Asn Ile Cys Lys Glu Asp Trp Tyr Tyr Cys Phe Leu Leu
 1               5                  10

<210> SEQ ID NO 65
<211> LENGTH: 14
<212> TYPE: PRT
<213> ORGANISM: Artificial Sequence
<220> FEATURE:
<223> OTHER INFORMATION: Library Isolate

<400> SEQUENCE: 65

Gly Ile Thr Cys Tyr Ser Ala Thr Gly Lys Cys Gln Met Trp
 1               5                  10

<210> SEQ ID NO 66
```

```
<211> LENGTH: 14
<212> TYPE: PRT
<213> ORGANISM: Artificial Sequence
<220> FEATURE:
<223> OTHER INFORMATION: Library Isolate

<400> SEQUENCE: 66

Trp Val Gln Cys Ala Ser Asp Thr Gly Lys Cys Ile Met Gly
1               5                  10

<210> SEQ ID NO 67
<211> LENGTH: 14
<212> TYPE: PRT
<213> ORGANISM: Artificial Sequence
<220> FEATURE:
<223> OTHER INFORMATION: Library Isolate

<400> SEQUENCE: 67

Thr Gly Asn Cys Gln Glu Asp Trp Tyr Tyr Cys Trp Tyr Phe
1               5                  10

<210> SEQ ID NO 68
<211> LENGTH: 14
<212> TYPE: PRT
<213> ORGANISM: Artificial Sequence
<220> FEATURE:
<223> OTHER INFORMATION: Library Isolate

<400> SEQUENCE: 68

Lys Glu Leu Cys Glu Asp Asp Trp Tyr Tyr Cys Tyr Leu Met
1               5                  10

<210> SEQ ID NO 69
<211> LENGTH: 14
<212> TYPE: PRT
<213> ORGANISM: Artificial Sequence
<220> FEATURE:
<223> OTHER INFORMATION: Library Isolate

<400> SEQUENCE: 69

His Trp Glu Cys Tyr Ser Asp Thr Gly Lys Cys Trp Phe Phe
1               5                  10

<210> SEQ ID NO 70
<211> LENGTH: 14
<212> TYPE: PRT
<213> ORGANISM: Artificial Sequence
<220> FEATURE:
<223> OTHER INFORMATION: Library Isolate

<400> SEQUENCE: 70

Gly Ile Thr Cys Tyr Ser Asp Thr Gly Lys Cys Phe Ser Phe
1               5                  10

<210> SEQ ID NO 71
<211> LENGTH: 14
<212> TYPE: PRT
<213> ORGANISM: Artificial Sequence
<220> FEATURE:
<223> OTHER INFORMATION: Library Isolate

<400> SEQUENCE: 71

Ala Val Thr Cys Trp Ala Leu Thr Gly His Cys Val Glu Glu
1               5                  10

<210> SEQ ID NO 72
<211> LENGTH: 14
<212> TYPE: PRT
```

<213> ORGANISM: Artificial Sequence
<220> FEATURE:
<223> OTHER INFORMATION: Library Isolate

<400> SEQUENCE: 72

Tyr Val Asp Cys Tyr Tyr Asp Thr Gly Arg Cys Tyr His Gln
1               5                   10

<210> SEQ ID NO 73
<211> LENGTH: 13
<212> TYPE: PRT
<213> ORGANISM: Artificial Sequence
<220> FEATURE:
<223> OTHER INFORMATION: Library Isolate

<400> SEQUENCE: 73

Trp Tyr Trp Cys Gln Tyr His Gly Val Cys Pro Gln Ser
1               5                   10

<210> SEQ ID NO 74
<211> LENGTH: 14
<212> TYPE: PRT
<213> ORGANISM: Artificial Sequence
<220> FEATURE:
<223> OTHER INFORMATION: Library Isolate

<400> SEQUENCE: 74

Leu Val Met Cys Ile Ser Pro Glu Gly Tyr Cys Tyr Glu Ile
1               5                   10

<210> SEQ ID NO 75
<211> LENGTH: 14
<212> TYPE: PRT
<213> ORGANISM: Artificial Sequence
<220> FEATURE:
<223> OTHER INFORMATION: Library Isolate

<400> SEQUENCE: 75

Leu Ile Glu Cys Tyr Ala His Thr Gly Leu Cys Phe Asp Phe
1               5                   10

<210> SEQ ID NO 76
<211> LENGTH: 14
<212> TYPE: PRT
<213> ORGANISM: Artificial Sequence
<220> FEATURE:
<223> OTHER INFORMATION: Library Isolate

<400> SEQUENCE: 76

His Trp Trp Cys Ala Phe Gln Pro Gln Glu Cys Glu Tyr Trp
1               5                   10

<210> SEQ ID NO 77
<211> LENGTH: 14
<212> TYPE: PRT
<213> ORGANISM: Artificial Sequence
<220> FEATURE:
<223> OTHER INFORMATION: Library Isolate

<400> SEQUENCE: 77

His Tyr Glu Cys Trp Tyr Pro Glu Gly Lys Cys Tyr Phe Tyr
1               5                   10

<210> SEQ ID NO 78
<211> LENGTH: 14
<212> TYPE: PRT
<213> ORGANISM: Artificial Sequence
<220> FEATURE:

```
<223> OTHER INFORMATION: Library Isolate

<400> SEQUENCE: 78

Trp Tyr Trp Cys His His Ile Gly Met Tyr Cys Asp Gly Phe
 1               5                   10

<210> SEQ ID NO 79
<211> LENGTH: 14
<212> TYPE: PRT
<213> ORGANISM: Artificial Sequence
<220> FEATURE:
<223> OTHER INFORMATION: Library Isolate

<400> SEQUENCE: 79

Trp Glu Trp Cys Pro Ile Asp Ala Trp Glu Cys Ile Met Leu
 1               5                   10

<210> SEQ ID NO 80
<211> LENGTH: 14
<212> TYPE: PRT
<213> ORGANISM: Artificial Sequence
<220> FEATURE:
<223> OTHER INFORMATION: Library Isolate

<400> SEQUENCE: 80

Trp Leu Glu Cys Tyr Thr Glu Phe Gly His Cys Tyr Asn Phe
 1               5                   10

<210> SEQ ID NO 81
<211> LENGTH: 14
<212> TYPE: PRT
<213> ORGANISM: Artificial Sequence
<220> FEATURE:
<223> OTHER INFORMATION: Library Isolate

<400> SEQUENCE: 81

Trp Val Glu Cys Trp Trp Lys Tyr Gly Gln Cys Tyr Glu Phe
 1               5                   10

<210> SEQ ID NO 82
<211> LENGTH: 14
<212> TYPE: PRT
<213> ORGANISM: Artificial Sequence
<220> FEATURE:
<223> OTHER INFORMATION: Library Isolate

<400> SEQUENCE: 82

Pro Asn Thr Cys Glu Thr Phe Asp Leu Tyr Cys Trp Trp Ile
 1               5                   10

<210> SEQ ID NO 83
<211> LENGTH: 14
<212> TYPE: PRT
<213> ORGANISM: Artificial Sequence
<220> FEATURE:
<223> OTHER INFORMATION: Library Isolate

<400> SEQUENCE: 83

Trp Ile Ile Cys Asp Gly Asn Leu Gly Trp Cys Trp Glu Gly
 1               5                   10

<210> SEQ ID NO 84
<211> LENGTH: 14
<212> TYPE: PRT
<213> ORGANISM: Artificial Sequence
<220> FEATURE:
<223> OTHER INFORMATION: Library Isolate
```

```
<400> SEQUENCE: 84

Gly Glu Gln Cys Ser Asn Leu Ala Val Ala Cys Cys Ser Thr
1               5                   10

<210> SEQ ID NO 85
<211> LENGTH: 14
<212> TYPE: PRT
<213> ORGANISM: Artificial Sequence
<220> FEATURE:
<223> OTHER INFORMATION: Library Isolate

<400> SEQUENCE: 85

Trp Val Glu Cys Tyr Asp Pro Trp Gly Trp Cys Trp Glu Trp
1               5                   10

<210> SEQ ID NO 86
<211> LENGTH: 14
<212> TYPE: PRT
<213> ORGANISM: Artificial Sequence
<220> FEATURE:
<223> OTHER INFORMATION: Library Isolate

<400> SEQUENCE: 86

Trp Tyr Trp Cys Met His Tyr Gly Leu Gly Cys Pro Tyr Arg
1               5                   10

<210> SEQ ID NO 87
<211> LENGTH: 18
<212> TYPE: PRT
<213> ORGANISM: Artificial Sequence
<220> FEATURE:
<223> OTHER INFORMATION: Library Isolate

<400> SEQUENCE: 87

Tyr Pro Trp Cys His Glu Leu Ser Asp Ser Val Thr Arg Phe Cys Val
1               5                   10                  15

Pro Trp

<210> SEQ ID NO 88
<211> LENGTH: 17
<212> TYPE: PRT
<213> ORGANISM: Artificial Sequence
<220> FEATURE:
<223> OTHER INFORMATION: Library Isolate

<400> SEQUENCE: 88

Ser Arg Val Cys Trp Glu Asp Ser Trp Gly Gly Glu Val Cys Phe Arg
1               5                   10                  15

Tyr

<210> SEQ ID NO 89
<211> LENGTH: 17
<212> TYPE: PRT
<213> ORGANISM: Artificial Sequence
<220> FEATURE:
<223> OTHER INFORMATION: Library Isolate

<400> SEQUENCE: 89

Ser Arg Val Cys Trp Glu Tyr Ser Trp Gly Gly Glu Val Cys Tyr Arg
1               5                   10                  15

Val

<210> SEQ ID NO 90
<211> LENGTH: 17
<212> TYPE: PRT
```

<213> ORGANISM: Artificial Sequence
<220> FEATURE:
<223> OTHER INFORMATION: Library Isolate

<400> SEQUENCE: 90

Phe Gly Glu Cys Trp Glu Tyr Phe Trp Gly Gly Glu Phe Cys Leu Arg
1               5                   10                  15
Val

<210> SEQ ID NO 91
<211> LENGTH: 17
<212> TYPE: PRT
<213> ORGANISM: Artificial Sequence
<220> FEATURE:
<223> OTHER INFORMATION: Library Isolate

<400> SEQUENCE: 91

Trp Arg Ile Cys Trp Glu Ser Ser Trp Gly Gly Glu Val Cys Ile Gly
1               5                   10                  15
His

<210> SEQ ID NO 92
<211> LENGTH: 17
<212> TYPE: PRT
<213> ORGANISM: Artificial Sequence
<220> FEATURE:
<223> OTHER INFORMATION: Library Isolate

<400> SEQUENCE: 92

Tyr Gly Val Cys Trp Glu Tyr Ser Trp Gly Gly Glu Val Cys Leu Arg
1               5                   10                  15
Phe

<210> SEQ ID NO 93
<211> LENGTH: 17
<212> TYPE: PRT
<213> ORGANISM: Artificial Sequence
<220> FEATURE:
<223> OTHER INFORMATION: Library Isolate

<400> SEQUENCE: 93

Ser Ser Val Cys Phe Glu Tyr Ser Trp Gly Gly Glu Val Cys Phe Arg
1               5                   10                  15
Tyr

<210> SEQ ID NO 94
<211> LENGTH: 17
<212> TYPE: PRT
<213> ORGANISM: Artificial Sequence
<220> FEATURE:
<223> OTHER INFORMATION: Library Isolate

<400> SEQUENCE: 94

Ser Arg Val Cys Trp Glu Tyr Ser Trp Gly Gly Gln Ile Cys Leu Gly
1               5                   10                  15
Tyr

<210> SEQ ID NO 95
<211> LENGTH: 17
<212> TYPE: PRT
<213> ORGANISM: Artificial Sequence
<220> FEATURE:
<223> OTHER INFORMATION: Library Isolate

<400> SEQUENCE: 95

```
Phe Ser Val Cys Trp Glu Tyr Ser Trp Gly Gly Glu Val Cys Leu Arg
1               5                   10                  15

Gln

<210> SEQ ID NO 96
<211> LENGTH: 18
<212> TYPE: PRT
<213> ORGANISM: Artificial Sequence
<220> FEATURE:
<223> OTHER INFORMATION: Library Isolate

<400> SEQUENCE: 96

Asp His Met Cys Arg Ser Pro Asp Tyr Gln Asp His Val Phe Cys Met
1               5                   10                  15

Tyr Trp

<210> SEQ ID NO 97
<211> LENGTH: 18
<212> TYPE: PRT
<213> ORGANISM: Artificial Sequence
<220> FEATURE:
<223> OTHER INFORMATION: Library Isolate

<400> SEQUENCE: 97

Pro Pro Leu Cys Tyr Phe Val Gly Thr Gln Glu Trp His His Cys Asn
1               5                   10                  15

Pro Phe

<210> SEQ ID NO 98
<211> LENGTH: 18
<212> TYPE: PRT
<213> ORGANISM: Artificial Sequence
<220> FEATURE:
<223> OTHER INFORMATION: Library Isolate

<400> SEQUENCE: 98

Trp Trp Glu Cys Lys Arg Glu Glu Tyr Arg Asn Thr Thr Trp Cys Ala
1               5                   10                  15

Trp Ala

<210> SEQ ID NO 99
<211> LENGTH: 17
<212> TYPE: PRT
<213> ORGANISM: Artificial Sequence
<220> FEATURE:
<223> OTHER INFORMATION: Library Isolate

<400> SEQUENCE: 99

Asp Ser Tyr Cys Met Met Asn Glu Lys Gly Trp Trp Asn Cys Tyr Leu
1               5                   10                  15

Tyr

<210> SEQ ID NO 100
<211> LENGTH: 18
<212> TYPE: PRT
<213> ORGANISM: Artificial Sequence
<220> FEATURE:
<223> OTHER INFORMATION: Library Isolate

<400> SEQUENCE: 100

Pro Ala Gln Cys Trp Glu Ser Asn Tyr Gln Gly Ile Phe Phe Cys Asp
1               5                   10                  15

Asn Pro
```

-continued

<210> SEQ ID NO 101
<211> LENGTH: 18
<212> TYPE: PRT
<213> ORGANISM: Artificial Sequence
<220> FEATURE:
<223> OTHER INFORMATION: Library Isolate

<400> SEQUENCE: 101

Gly Ser Trp Cys Glu Met Arg Gln Asp Val Gly Lys Trp Asn Cys Phe
1               5                   10                  15

Ser Asp

<210> SEQ ID NO 102
<211> LENGTH: 17
<212> TYPE: PRT
<213> ORGANISM: Artificial Sequence
<220> FEATURE:
<223> OTHER INFORMATION: Library Isolate

<400> SEQUENCE: 102

Gly Trp Ala Cys Ala Lys Trp Pro Trp Gly Gly Glu Ile Cys Gln Pro
1               5                   10                  15

Ser

<210> SEQ ID NO 103
<211> LENGTH: 18
<212> TYPE: PRT
<213> ORGANISM: Artificial Sequence
<220> FEATURE:
<223> OTHER INFORMATION: Library Isolate

<400> SEQUENCE: 103

Ala Ser Thr Cys Val Phe His Asp His Pro Tyr Phe Pro Met Cys Gln
1               5                   10                  15

Asp Asn

<210> SEQ ID NO 104
<211> LENGTH: 18
<212> TYPE: PRT
<213> ORGANISM: Artificial Sequence
<220> FEATURE:
<223> OTHER INFORMATION: Library Isolate

<400> SEQUENCE: 104

Pro Asp Thr Cys Thr Met Trp Gly Asp Ser Gly Arg Trp Tyr Cys Phe
1               5                   10                  15

Pro Ala

<210> SEQ ID NO 105
<211> LENGTH: 18
<212> TYPE: PRT
<213> ORGANISM: Artificial Sequence
<220> FEATURE:
<223> OTHER INFORMATION: Library Isolate

<400> SEQUENCE: 105

Asn Trp Lys Cys Glu Tyr Thr Gln Gly Tyr Asp Tyr Thr Glu Cys Val
1               5                   10                  15

Tyr Leu

<210> SEQ ID NO 106
<211> LENGTH: 18
<212> TYPE: PRT

<213> ORGANISM: Artificial Sequence
<220> FEATURE:
<223> OTHER INFORMATION: Library Isolate

<400> SEQUENCE: 106

Asn Trp Glu Cys Gly Trp Ser Asn Met Phe Gln Lys Glu Phe Cys Ala
1               5                   10                  15

Arg Pro

<210> SEQ ID NO 107
<211> LENGTH: 18
<212> TYPE: PRT
<213> ORGANISM: Artificial Sequence
<220> FEATURE:
<223> OTHER INFORMATION: Library Isolate

<400> SEQUENCE: 107

Ser Gly Tyr Cys Glu Phe Glu Ser Asp Thr Gly Arg Trp Phe Cys Ser
1               5                   10                  15

Ser Trp

<210> SEQ ID NO 108
<211> LENGTH: 17
<212> TYPE: PRT
<213> ORGANISM: Artificial Sequence
<220> FEATURE:
<223> OTHER INFORMATION: Library Isolate

<400> SEQUENCE: 108

Gly Gly Trp Cys Gln Leu Val Asp His Ser Trp Trp Cys Gly Asp
1               5                   10                  15

Ser

<210> SEQ ID NO 109
<211> LENGTH: 18
<212> TYPE: PRT
<213> ORGANISM: Artificial Sequence
<220> FEATURE:
<223> OTHER INFORMATION: Library Isolate

<400> SEQUENCE: 109

Asp Asn Trp Cys Glu Ile Val Val Glu Lys Gly Gln Trp Phe Cys Tyr
1               5                   10                  15

Gly Ser

<210> SEQ ID NO 110
<211> LENGTH: 18
<212> TYPE: PRT
<213> ORGANISM: Artificial Sequence
<220> FEATURE:
<223> OTHER INFORMATION: Library Isolate

<400> SEQUENCE: 110

Tyr Pro Gly Cys Tyr Glu Thr Ser Leu Ser Gly Val Trp Phe Cys Ala
1               5                   10                  15

Asp Gly

<210> SEQ ID NO 111
<211> LENGTH: 16
<212> TYPE: PRT
<213> ORGANISM: Artificial Sequence
<220> FEATURE:
<223> OTHER INFORMATION: Library Isolate

<400> SEQUENCE: 111

Gly Trp Cys Gln Met Asp Ala Gln Gly Ile Trp Ser Cys Trp Ala Asp
1               5                   10                  15

<210> SEQ ID NO 112
<211> LENGTH: 18
<212> TYPE: PRT
<213> ORGANISM: Artificial Sequence
<220> FEATURE:
<223> OTHER INFORMATION: Library Isolate

<400> SEQUENCE: 112

Asp Arg Trp Cys Met Leu Asp Gln Glu Lys Gly Trp Trp Leu Cys Gly
1               5                   10                  15

Pro Pro

<210> SEQ ID NO 113
<211> LENGTH: 18
<212> TYPE: PRT
<213> ORGANISM: Artificial Sequence
<220> FEATURE:
<223> OTHER INFORMATION: Library Isolate

<400> SEQUENCE: 113

Asn Ser Glu Cys Gly Cys Pro Asn Met Leu His Lys Glu Phe Cys Ala
1               5                   10                  15

Arg His

<210> SEQ ID NO 114
<211> LENGTH: 18
<212> TYPE: PRT
<213> ORGANISM: Artificial Sequence
<220> FEATURE:
<223> OTHER INFORMATION: Library Isolate

<400> SEQUENCE: 114

Pro Phe Trp Cys Lys Phe Gln Gln Ser Lys Ala Met Phe Pro Cys Ser
1               5                   10                  15

Trp Phe

<210> SEQ ID NO 115
<211> LENGTH: 18
<212> TYPE: PRT
<213> ORGANISM: Artificial Sequence
<220> FEATURE:
<223> OTHER INFORMATION: Library Isolate

<400> SEQUENCE: 115

Tyr Pro Trp Cys His Glu His Ser Asp Ser Val Thr Arg Phe Cys Val
1               5                   10                  15

Pro Trp

<210> SEQ ID NO 116
<211> LENGTH: 17
<212> TYPE: PRT
<213> ORGANISM: Artificial Sequence
<220> FEATURE:
<223> OTHER INFORMATION: Library Isolate

<400> SEQUENCE: 116

Ser Asp Leu Cys Tyr Asn Gln Ser Gly Trp Trp Glu Leu Cys Tyr Phe
1               5                   10                  15

Asp

```
<210> SEQ ID NO 117
<211> LENGTH: 18
<212> TYPE: PRT
<213> ORGANISM: Artificial Sequence
<220> FEATURE:
<223> OTHER INFORMATION: Library Isolate

<400> SEQUENCE: 117

Leu Gly Tyr Cys Met Tyr Asp Tyr Glu Asn Arg Gly Trp Thr Cys Tyr
 1               5                  10                  15

Pro Pro

<210> SEQ ID NO 118
<211> LENGTH: 18
<212> TYPE: PRT
<213> ORGANISM: Artificial Sequence
<220> FEATURE:
<223> OTHER INFORMATION: Library Isolate

<400> SEQUENCE: 118

Tyr Tyr Gln Cys Gln Arg Tyr Trp Asp Gly Lys Thr Trp Trp Cys Glu
 1               5                  10                  15

Tyr Asn

<210> SEQ ID NO 119
<211> LENGTH: 18
<212> TYPE: PRT
<213> ORGANISM: Artificial Sequence
<220> FEATURE:
<223> OTHER INFORMATION: Library Isolate

<400> SEQUENCE: 119

Asp Ser Trp Cys Glu Leu Glu His Gln Ser Gly Ile Trp Arg Cys Asp
 1               5                  10                  15

Phe Trp

<210> SEQ ID NO 120
<211> LENGTH: 18
<212> TYPE: PRT
<213> ORGANISM: Artificial Sequence
<220> FEATURE:
<223> OTHER INFORMATION: Library Isolate

<400> SEQUENCE: 120

Asp Trp Ala Cys Asp Glu Tyr Trp Ser Ala Tyr Ser Val Leu Cys Lys
 1               5                  10                  15

His Pro

<210> SEQ ID NO 121
<211> LENGTH: 18
<212> TYPE: PRT
<213> ORGANISM: Artificial Sequence
<220> FEATURE:
<223> OTHER INFORMATION: Library Isolate

<400> SEQUENCE: 121

Leu Ser Leu Cys Tyr Asn Asp Met His Gly Trp Glu His Cys Gln
 1               5                  10                  15

Trp Tyr

<210> SEQ ID NO 122
<211> LENGTH: 18
<212> TYPE: PRT
<213> ORGANISM: Artificial Sequence
<220> FEATURE:
```

<223> OTHER INFORMATION: Library Isolate

<400> SEQUENCE: 122

Tyr Ser His Cys Ile Glu Thr Ser Met Glu Asn Ile Trp Phe Cys Asp
1               5                   10                  15

Phe Asp

<210> SEQ ID NO 123
<211> LENGTH: 18
<212> TYPE: PRT
<213> ORGANISM: Artificial Sequence
<220> FEATURE:
<223> OTHER INFORMATION: Library Isolate

<400> SEQUENCE: 123

Pro Pro Phe Cys Ile Tyr Gln Glu Pro Ser Gly Gln Trp Trp Cys Tyr
1               5                   10                  15

Asp His

<210> SEQ ID NO 124
<211> LENGTH: 18
<212> TYPE: PRT
<213> ORGANISM: Artificial Sequence
<220> FEATURE:
<223> OTHER INFORMATION: Library Isolate

<400> SEQUENCE: 124

Pro Gly Trp Cys Asp Phe Ser Pro Gln Leu Gly Gln Trp Met Cys Asp
1               5                   10                  15

Trp Phe

<210> SEQ ID NO 125
<211> LENGTH: 18
<212> TYPE: PRT
<213> ORGANISM: Artificial Sequence
<220> FEATURE:
<223> OTHER INFORMATION: Library Isolate

<400> SEQUENCE: 125

Leu Asp Asn Cys Ile Trp Asn Val Trp Lys Gly Val Gln Asp Cys Glu
1               5                   10                  15

Tyr Ser

<210> SEQ ID NO 126
<211> LENGTH: 18
<212> TYPE: PRT
<213> ORGANISM: Artificial Sequence
<220> FEATURE:
<223> OTHER INFORMATION: Library Isolate

<400> SEQUENCE: 126

Ala Gly Trp Cys Glu Tyr Val Ala Pro Gln Gly Ala Trp Arg Cys Phe
1               5                   10                  15

His Asn

<210> SEQ ID NO 127
<211> LENGTH: 18
<212> TYPE: PRT
<213> ORGANISM: Artificial Sequence
<220> FEATURE:
<223> OTHER INFORMATION: Library Isolate

<400> SEQUENCE: 127

Trp Asp Asp Cys Ile Trp His Met Trp Leu Lys Lys Lys Asp Cys Asn

```
                1               5                   10                  15
Ser Gly

<210> SEQ ID NO 128
<211> LENGTH: 18
<212> TYPE: PRT
<213> ORGANISM: Artificial Sequence
<220> FEATURE:
<223> OTHER INFORMATION: Library Isolate

<400> SEQUENCE: 128

Pro Gly His Cys Glu Tyr Ile Trp Ile Asp Glu Gln Pro Trp Cys Val
  1               5                   10                  15

Arg Leu

<210> SEQ ID NO 129
<211> LENGTH: 17
<212> TYPE: PRT
<213> ORGANISM: Artificial Sequence
<220> FEATURE:
<223> OTHER INFORMATION: Library Isolate

<400> SEQUENCE: 129

Tyr Ser Asp Cys Leu Phe Gln Leu Trp Lys Gly Ser Val Cys Pro Pro
  1               5                   10                  15

Ser

<210> SEQ ID NO 130
<211> LENGTH: 17
<212> TYPE: PRT
<213> ORGANISM: Artificial Sequence
<220> FEATURE:
<223> OTHER INFORMATION: Library Isolate

<400> SEQUENCE: 130

Tyr Phe Phe Cys Ser Phe Ala Asp Val Ala Tyr Glu Ser Cys His Pro
  1               5                   10                  15

Leu

<210> SEQ ID NO 131
<211> LENGTH: 18
<212> TYPE: PRT
<213> ORGANISM: Artificial Sequence
<220> FEATURE:
<223> OTHER INFORMATION: Library Isolate

<400> SEQUENCE: 131

Asn Tyr Met Cys Glu Ser Glu Asp His Thr Tyr Met Phe Pro Cys Trp
  1               5                   10                  15

Trp Tyr

<210> SEQ ID NO 132
<211> LENGTH: 18
<212> TYPE: PRT
<213> ORGANISM: Artificial Sequence
<220> FEATURE:
<223> OTHER INFORMATION: Library Isolate

<400> SEQUENCE: 132

Asp Ala Val Cys Tyr Asn Pro Trp Phe Lys Tyr Trp Glu Thr Cys Glu
  1               5                   10                  15

Tyr Asn
```

```
<210> SEQ ID NO 133
<211> LENGTH: 18
<212> TYPE: PRT
<213> ORGANISM: Artificial Sequence
<220> FEATURE:
<223> OTHER INFORMATION: Library Isolate

<400> SEQUENCE: 133

Asn Tyr Met Cys Glu Tyr Glu Asp His Thr Tyr Met Leu Thr Cys Glu
 1               5                  10                  15

Cys Asn

<210> SEQ ID NO 134
<211> LENGTH: 17
<212> TYPE: PRT
<213> ORGANISM: Artificial Sequence
<220> FEATURE:
<223> OTHER INFORMATION: Library Isolate

<400> SEQUENCE: 134

Trp Asp Asp Cys Ile Tyr Ser Met Trp Met Val His Thr Val Cys Asp
 1               5                  10                  15

Arg

<210> SEQ ID NO 135
<211> LENGTH: 18
<212> TYPE: PRT
<213> ORGANISM: Artificial Sequence
<220> FEATURE:
<223> OTHER INFORMATION: Library Isolate

<400> SEQUENCE: 135

Asn Trp Lys Cys Asp Ala His Gln Glu Gly Arg Ile His Ile Cys Trp
 1               5                  10                  15

Gly Tyr

<210> SEQ ID NO 136
<211> LENGTH: 18
<212> TYPE: PRT
<213> ORGANISM: Artificial Sequence
<220> FEATURE:
<223> OTHER INFORMATION: Library Isolate

<400> SEQUENCE: 136

Asn Gly Ser Cys Trp Tyr Asp Phe Gly Trp Glu Thr Glu Ile Cys Phe
 1               5                  10                  15

His Asn

<210> SEQ ID NO 137
<211> LENGTH: 20
<212> TYPE: PRT
<213> ORGANISM: Artificial Sequence
<220> FEATURE:
<223> OTHER INFORMATION: Library Isolate

<400> SEQUENCE: 137

Gln Val Gln Tyr Gln Phe Phe Leu Gly Thr Pro Arg Tyr Glu Gln Trp
 1               5                  10                  15

Asp Leu Asp Lys
             20

<210> SEQ ID NO 138
<211> LENGTH: 20
<212> TYPE: PRT
<213> ORGANISM: Artificial Sequence
```

```
<220> FEATURE:
<223> OTHER INFORMATION: Library Isolate

<400> SEQUENCE: 138

Glu Pro Glu Gly Tyr Ala Tyr Trp Glu Val Ile Thr Leu Tyr His Glu
 1               5                  10                  15

Glu Asp Gly Asp
         20

<210> SEQ ID NO 139
<211> LENGTH: 20
<212> TYPE: PRT
<213> ORGANISM: Artificial Sequence
<220> FEATURE:
<223> OTHER INFORMATION: Library Isolate

<400> SEQUENCE: 139

Trp Tyr Tyr Asp Trp Phe His Asn Gln Arg Lys Pro Pro Ser Asp Trp
 1               5                  10                  15

Ile Asp Asn Leu
         20

<210> SEQ ID NO 140
<211> LENGTH: 20
<212> TYPE: PRT
<213> ORGANISM: Artificial Sequence
<220> FEATURE:
<223> OTHER INFORMATION: Library Isolate

<400> SEQUENCE: 140

Ala Phe Pro Arg Phe Gly Gly Asp Asp Tyr Trp Ile Gln Gln Tyr Leu
 1               5                  10                  15

Arg Tyr Thr Asp
         20

<210> SEQ ID NO 141
<211> LENGTH: 20
<212> TYPE: PRT
<213> ORGANISM: Artificial Sequence
<220> FEATURE:
<223> OTHER INFORMATION: Library Isolate

<400> SEQUENCE: 141

Gly Asp Tyr Val Tyr Trp Glu Ile Ile Glu Leu Thr Gly Ala Thr Asp
 1               5                  10                  15

His Thr Pro Pro
         20

<210> SEQ ID NO 142
<211> LENGTH: 20
<212> TYPE: PRT
<213> ORGANISM: Artificial Sequence
<220> FEATURE:
<223> OTHER INFORMATION: Library Isolate

<400> SEQUENCE: 142

Arg Gly Asp Tyr Gln Glu Gln Tyr Trp His Gln Gln Leu Val Glu Gln
 1               5                  10                  15

Leu Lys Leu Leu
         20

<210> SEQ ID NO 143
<211> LENGTH: 18
<212> TYPE: PRT
<213> ORGANISM: Artificial Sequence
```

```
<220> FEATURE:
<223> OTHER INFORMATION: Library Isolate

<400> SEQUENCE: 143

Arg Ser Trp Tyr Leu Gly Pro Pro Tyr Glu Glu Trp Asp Pro Ile
1               5                   10                  15
Pro Asn

<210> SEQ ID NO 144
<211> LENGTH: 20
<212> TYPE: PRT
<213> ORGANISM: Artificial Sequence
<220> FEATURE:
<223> OTHER INFORMATION: Library Isolate

<400> SEQUENCE: 144

Pro Ser Asn Ser Trp Ala Ala Val Trp Glu Asp Asp Met Gln Arg Leu
1               5                   10                  15
Met Arg Gln His
            20

<210> SEQ ID NO 145
<211> LENGTH: 20
<212> TYPE: PRT
<213> ORGANISM: Artificial Sequence
<220> FEATURE:
<223> OTHER INFORMATION: Library Isolate

<400> SEQUENCE: 145

Pro Arg Leu Gly Asp Asp Phe Glu Glu Ala Pro Pro Leu Glu Trp Trp
1               5                   10                  15
Trp Ala His Phe
            20

<210> SEQ ID NO 146
<211> LENGTH: 20
<212> TYPE: PRT
<213> ORGANISM: Artificial Sequence
<220> FEATURE:
<223> OTHER INFORMATION: Library Isolate

<400> SEQUENCE: 146

Met Pro Pro Gly Phe Ser Tyr Trp Glu Gln Val Val Leu His Asp Asp
1               5                   10                  15
Ala Gln Val Leu
            20

<210> SEQ ID NO 147
<211> LENGTH: 20
<212> TYPE: PRT
<213> ORGANISM: Artificial Sequence
<220> FEATURE:
<223> OTHER INFORMATION: Library Isolate

<400> SEQUENCE: 147

Lys Lys Glu Asp Ala Gln Gln Trp Tyr Trp Thr Asp Tyr Val Pro Ser
1               5                   10                  15
Tyr Leu Tyr Arg
            20

<210> SEQ ID NO 148
<211> LENGTH: 20
<212> TYPE: PRT
<213> ORGANISM: Artificial Sequence
<220> FEATURE:
```

<223> OTHER INFORMATION: Library Isolate

<400> SEQUENCE: 148

Trp Val Thr Lys Gln Gln Phe Ile Asp Thr Tyr Gly Arg Lys Glu Trp
 1               5                  10                  15

Thr Ile Leu Phe
            20

<210> SEQ ID NO 149
<211> LENGTH: 20
<212> TYPE: PRT
<213> ORGANISM: Artificial Sequence
<220> FEATURE:
<223> OTHER INFORMATION: Library Isolate

<400> SEQUENCE: 149

Trp Leu Tyr Asp Tyr Trp Asp Arg Gln Gln Lys Ser Glu Glu Phe Lys
 1               5                  10                  15

Phe Trp Ser Gln
            20

<210> SEQ ID NO 150
<211> LENGTH: 20
<212> TYPE: PRT
<213> ORGANISM: Artificial Sequence
<220> FEATURE:
<223> OTHER INFORMATION: Library Isolate

<400> SEQUENCE: 150

Pro Val Thr Asp Trp Thr Pro His His Pro Lys Ala Pro Asp Val Trp
 1               5                  10                  15

Leu Phe Tyr Thr
            20

<210> SEQ ID NO 151
<211> LENGTH: 16
<212> TYPE: PRT
<213> ORGANISM: Artificial Sequence
<220> FEATURE:
<223> OTHER INFORMATION: Library Isolate

<400> SEQUENCE: 151

Glu Trp Tyr Trp Thr Glu His Val Gly Met Lys His Gly Phe Phe Val
 1               5                  10                  15

<210> SEQ ID NO 152
<211> LENGTH: 20
<212> TYPE: PRT
<213> ORGANISM: Artificial Sequence
<220> FEATURE:
<223> OTHER INFORMATION: Library Isolate

<400> SEQUENCE: 152

Asp Ala Leu Glu Ala Pro Lys Arg Asp Trp Tyr Tyr Asp Trp Phe Leu
 1               5                  10                  15

Asn His Ser Pro
            20

<210> SEQ ID NO 153
<211> LENGTH: 21
<212> TYPE: PRT
<213> ORGANISM: Artificial Sequence
<220> FEATURE:
<223> OTHER INFORMATION: Library Isolate

<400> SEQUENCE: 153

Pro Asp Asn Trp Lys Glu Phe Tyr Glu Ser Gly Trp Lys Tyr Pro Ser
1               5                   10                  15

Leu Tyr Lys Pro Leu
            20

<210> SEQ ID NO 154
<211> LENGTH: 20
<212> TYPE: PRT
<213> ORGANISM: Artificial Sequence
<220> FEATURE:
<223> OTHER INFORMATION: Library Isolate

<400> SEQUENCE: 154

Glu Trp Asp Ala Gln Tyr Trp His Asp Leu Arg Gln Gln Tyr Met Leu
1               5                   10                  15

Asp Tyr Ile Gln
            20

<210> SEQ ID NO 155
<211> LENGTH: 20
<212> TYPE: PRT
<213> ORGANISM: Artificial Sequence
<220> FEATURE:
<223> OTHER INFORMATION: Library Isolate

<400> SEQUENCE: 155

Ala Phe Glu Ile Glu Tyr Trp Asp Ser Val Arg Asn Lys Ile Trp Gln
1               5                   10                  15

His Phe Pro Asp
            20

<210> SEQ ID NO 156
<211> LENGTH: 20
<212> TYPE: PRT
<213> ORGANISM: Artificial Sequence
<220> FEATURE:
<223> OTHER INFORMATION: Library Isolate

<400> SEQUENCE: 156

Ala Phe Pro Arg Phe Gly Gly Asp Asp Tyr Trp Ile Gln Gln Tyr Leu
1               5                   10                  15

Arg Tyr Thr Phe
            20

<210> SEQ ID NO 157
<211> LENGTH: 19
<212> TYPE: PRT
<213> ORGANISM: Artificial Sequence
<220> FEATURE:
<223> OTHER INFORMATION: Library Isolate

<400> SEQUENCE: 157

Ala His Met Pro Pro Trp Arg Pro Val Ala Val Asp Ala Leu Phe Asp
1               5                   10                  15

Trp Val Glu

<210> SEQ ID NO 158
<211> LENGTH: 19
<212> TYPE: PRT
<213> ORGANISM: Artificial Sequence
<220> FEATURE:
<223> OTHER INFORMATION: Library Isolate

<400> SEQUENCE: 158

```
Ala His Met Pro Pro Trp Trp Pro Leu Ala Val Asp Ala Gln Glu Asp
1               5                   10                  15

Trp Phe Glu
```

<210> SEQ ID NO 159
<211> LENGTH: 19
<212> TYPE: PRT
<213> ORGANISM: Artificial Sequence
<220> FEATURE:
<223> OTHER INFORMATION: Library Isolate

<400> SEQUENCE: 159

```
Ala Gln Met Pro Pro Trp Trp Pro Leu Ala Val Asp Ala Leu Phe Asp
1               5                   10                  15

Trp Phe Glu
```

<210> SEQ ID NO 160
<211> LENGTH: 20
<212> TYPE: PRT
<213> ORGANISM: Artificial Sequence
<220> FEATURE:
<223> OTHER INFORMATION: Library Isolate

<400> SEQUENCE: 160

```
Ala Arg Met Gly Asp Asp Trp Glu Glu Ala Pro Pro His Glu Trp Gly
1               5                   10                  15

Trp Ala Asp Gly
            20
```

<210> SEQ ID NO 161
<211> LENGTH: 20
<212> TYPE: PRT
<213> ORGANISM: Artificial Sequence
<220> FEATURE:
<223> OTHER INFORMATION: Library Isolate

<400> SEQUENCE: 161

```
Asp Trp Tyr Trp Gln Arg Glu Arg Asp Lys Leu Arg Glu His Tyr Asp
1               5                   10                  15

Asp Ala Phe Trp
            20
```

<210> SEQ ID NO 162
<211> LENGTH: 19
<212> TYPE: PRT
<213> ORGANISM: Artificial Sequence
<220> FEATURE:
<223> OTHER INFORMATION: Library Isolate

<400> SEQUENCE: 162

```
Asp Trp Tyr Trp Arg Glu Trp Met Pro Met His Ala Gln Phe Leu Ala
1               5                   10                  15

Asp Asp Trp
```

<210> SEQ ID NO 163
<211> LENGTH: 20
<212> TYPE: PRT
<213> ORGANISM: Artificial Sequence
<220> FEATURE:
<223> OTHER INFORMATION: Library Isolate

<400> SEQUENCE: 163

```
Asp Trp Tyr Tyr Asp Glu Ile Leu Ser Met Ala Asp Gln Leu Arg His
1               5                   10                  15
```

```
Ala Phe Leu Ser
        20

<210> SEQ ID NO 164
<211> LENGTH: 20
<212> TYPE: PRT
<213> ORGANISM: Artificial Sequence
<220> FEATURE:
<223> OTHER INFORMATION: Library Isolate

<400> SEQUENCE: 164

Glu Glu Gln Gln Ala Leu Tyr Pro Gly Cys Glu Pro Ala Glu His Trp
1               5                   10                  15

Val Tyr Ala Gly
        20

<210> SEQ ID NO 165
<211> LENGTH: 16
<212> TYPE: PRT
<213> ORGANISM: Artificial Sequence
<220> FEATURE:
<223> OTHER INFORMATION: Library Isolate

<400> SEQUENCE: 165

Phe Asp Val Val Asn Trp Gly Asp Gly Ile Trp Tyr Ala Tyr Pro Ser
1               5                   10                  15

<210> SEQ ID NO 166
<211> LENGTH: 20
<212> TYPE: PRT
<213> ORGANISM: Artificial Sequence
<220> FEATURE:
<223> OTHER INFORMATION: Library Isolate

<400> SEQUENCE: 166

Phe Pro Ser Gln Met Trp Gln Gln Lys Val Ser His His Phe Phe Gln
1               5                   10                  15

His Lys Gly Tyr
        20

<210> SEQ ID NO 167
<211> LENGTH: 20
<212> TYPE: PRT
<213> ORGANISM: Artificial Sequence
<220> FEATURE:
<223> OTHER INFORMATION: Library Isolate

<400> SEQUENCE: 167

Gly Ser Asp His Val Arg Val Asp Asn Tyr Trp Trp Asn Gly Met Ala
1               5                   10                  15

Trp Glu Ile Phe
        20

<210> SEQ ID NO 168
<211> LENGTH: 20
<212> TYPE: PRT
<213> ORGANISM: Artificial Sequence
<220> FEATURE:
<223> OTHER INFORMATION: Library Isolate

<400> SEQUENCE: 168

Ile Ser Pro Trp Arg Glu Met Ser Gly Trp Gly Met Pro Trp Ile Thr
1               5                   10                  15

Ala Val Pro His
        20
```

```
<210> SEQ ID NO 169
<211> LENGTH: 21
<212> TYPE: PRT
<213> ORGANISM: Artificial Sequence
<220> FEATURE:
<223> OTHER INFORMATION: Library Isolate

<400> SEQUENCE: 169

Leu Glu Glu Val Phe Glu Asp Phe Gln Asp Phe Trp Tyr Thr Glu His
 1               5                  10                  15

Ile Ile Val Asp Arg
            20

<210> SEQ ID NO 170
<211> LENGTH: 20
<212> TYPE: PRT
<213> ORGANISM: Artificial Sequence
<220> FEATURE:
<223> OTHER INFORMATION: Library Isolate

<400> SEQUENCE: 170

Met Pro Pro Gly Phe Ser Tyr Trp Glu Gln Ala Ala Leu His Asp Asp
 1               5                  10                  15

Ala Gln Asp Leu
            20

<210> SEQ ID NO 171
<211> LENGTH: 20
<212> TYPE: PRT
<213> ORGANISM: Artificial Sequence
<220> FEATURE:
<223> OTHER INFORMATION: Library Isolate

<400> SEQUENCE: 171

Pro Glu Asp Ser Glu Ala Trp Tyr Trp Leu Asn Tyr Arg Pro Thr Met
 1               5                  10                  15

Phe His Gln Leu
            20

<210> SEQ ID NO 172
<211> LENGTH: 20
<212> TYPE: PRT
<213> ORGANISM: Artificial Sequence
<220> FEATURE:
<223> OTHER INFORMATION: Library Isolate

<400> SEQUENCE: 172

Gln Ile Glu Tyr Val Asn Asp Lys Trp Tyr Trp Thr Gly Gly Tyr Trp
 1               5                  10                  15

Asn Val Pro Phe
            20

<210> SEQ ID NO 173
<211> LENGTH: 20
<212> TYPE: PRT
<213> ORGANISM: Artificial Sequence
<220> FEATURE:
<223> OTHER INFORMATION: Library Isolate

<400> SEQUENCE: 173

Gln Val Gln Tyr Gln Phe Ile Leu Gly Thr Pro Arg Tyr Glu Gln Trp
 1               5                  10                  15

Asp Pro Asp Lys
            20
```

```
<210> SEQ ID NO 174
<211> LENGTH: 20
<212> TYPE: PRT
<213> ORGANISM: Artificial Sequence
<220> FEATURE:
<223> OTHER INFORMATION: Library Isolate

<400> SEQUENCE: 174

Arg Asp Glu Trp Gly Trp Thr Gly Val Pro Tyr Glu Gly Glu Met Gly
1               5                   10                  15

Tyr Gln Ile Ser
            20

<210> SEQ ID NO 175
<211> LENGTH: 20
<212> TYPE: PRT
<213> ORGANISM: Artificial Sequence
<220> FEATURE:
<223> OTHER INFORMATION: Library Isolate

<400> SEQUENCE: 175

Ser Thr Asn Gly Asp Ser Phe Val Tyr Trp Glu Glu Val Glu Leu Val
1               5                   10                  15

Asp His Pro Tyr
            20

<210> SEQ ID NO 176
<211> LENGTH: 19
<212> TYPE: PRT
<213> ORGANISM: Artificial Sequence
<220> FEATURE:
<223> OTHER INFORMATION: Library Isolate

<400> SEQUENCE: 176

Ser Tyr Glu Gln Trp Leu Pro Gln Tyr Trp Ala Gln Tyr Lys Ser Asn
1               5                   10                  15

Tyr Phe Leu

<210> SEQ ID NO 177
<211> LENGTH: 20
<212> TYPE: PRT
<213> ORGANISM: Artificial Sequence
<220> FEATURE:
<223> OTHER INFORMATION: Library Isolate

<400> SEQUENCE: 177

Thr Lys Trp Gly Pro Asn Pro Glu His Trp Gln Tyr Trp Tyr Ser His
1               5                   10                  15

Tyr Ala Ser Ser
            20

<210> SEQ ID NO 178
<211> LENGTH: 20
<212> TYPE: PRT
<213> ORGANISM: Artificial Sequence
<220> FEATURE:
<223> OTHER INFORMATION: Library Isolate

<400> SEQUENCE: 178

Val Ser Lys Gly Ser Ile Asp Val Gly Glu Gly Ile Ser Tyr Trp Glu
1               5                   10                  15

Ile Ile Glu Leu
            20
```

```
<210> SEQ ID NO 179
<211> LENGTH: 20
<212> TYPE: PRT
<213> ORGANISM: Artificial Sequence
<220> FEATURE:
<223> OTHER INFORMATION: Library Isolate

<400> SEQUENCE: 179

Trp Glu Ser Asp Tyr Trp Asp Gln Met Arg Gln Gln Leu Lys Thr Ala
1               5                   10                  15

Tyr Met Lys Val
            20

<210> SEQ ID NO 180
<211> LENGTH: 20
<212> TYPE: PRT
<213> ORGANISM: Artificial Sequence
<220> FEATURE:
<223> OTHER INFORMATION: Library Isolate

<400> SEQUENCE: 180

Trp Tyr His Asp Gly Leu His Asn Glu Arg Lys Pro Pro Ser His Trp
1               5                   10                  15

Ile Asp Asn Val
            20

<210> SEQ ID NO 181
<211> LENGTH: 20
<212> TYPE: PRT
<213> ORGANISM: Artificial Sequence
<220> FEATURE:
<223> OTHER INFORMATION: Library Isolate

<400> SEQUENCE: 181

Ala Pro Ala Trp Thr Phe Gly Thr Asn Trp Arg Ser Ile Gln Arg Val
1               5                   10                  15

Asp Ser Leu Thr
            20

<210> SEQ ID NO 182
<211> LENGTH: 20
<212> TYPE: PRT
<213> ORGANISM: Artificial Sequence
<220> FEATURE:
<223> OTHER INFORMATION: Library Isolate

<400> SEQUENCE: 182

Glu Gly Trp Phe Arg Asn Pro Gln Glu Ile Met Gly Phe Gly Asp Ser
1               5                   10                  15

Trp Asp Lys Pro
            20

<210> SEQ ID NO 183
<211> LENGTH: 20
<212> TYPE: PRT
<213> ORGANISM: Artificial Sequence
<220> FEATURE:
<223> OTHER INFORMATION: Library Isolate

<400> SEQUENCE: 183

Gly Trp Asp Leu Ser Val Asn Arg Asp Lys Arg Trp Phe Trp Pro Trp
1               5                   10                  15

Ser Ser Arg Glu
            20
```

```
<210> SEQ ID NO 184
<211> LENGTH: 20
<212> TYPE: PRT
<213> ORGANISM: Artificial Sequence
<220> FEATURE:
<223> OTHER INFORMATION: Library Isolate

<400> SEQUENCE: 184

Lys Ser Gly Val Asp Ala Val Gly Trp His Ile Pro Val Trp Leu Lys
1               5                   10                  15

Lys Tyr Trp Phe
            20

<210> SEQ ID NO 185
<211> LENGTH: 20
<212> TYPE: PRT
<213> ORGANISM: Artificial Sequence
<220> FEATURE:
<223> OTHER INFORMATION: Library Isolate

<400> SEQUENCE: 185

Gly Met Asp Leu Tyr Gln Tyr Trp Ala Ser Asp Asp Tyr Trp Gly Arg
1               5                   10                  15

His Gln Glu Leu
            20

<210> SEQ ID NO 186
<211> LENGTH: 17
<212> TYPE: PRT
<213> ORGANISM: Artificial Sequence
<220> FEATURE:
<223> OTHER INFORMATION: Library Isolate

<400> SEQUENCE: 186

Gly Val Asp Ile Trp His Tyr Trp Lys Ser Ser Thr Arg Tyr Phe His
1               5                   10                  15

Gln

<210> SEQ ID NO 187
<211> LENGTH: 13
<212> TYPE: PRT
<213> ORGANISM: Artificial Sequence
<220> FEATURE:
<223> OTHER INFORMATION: Library Isolate

<400> SEQUENCE: 187

Gly Val Glu Cys Asn His Met Gly Leu Cys Val Ser Trp
1               5                   10

<210> SEQ ID NO 188
<211> LENGTH: 13
<212> TYPE: PRT
<213> ORGANISM: Artificial Sequence
<220> FEATURE:
<223> OTHER INFORMATION: Library Isolate

<400> SEQUENCE: 188

Gly Ile Thr Cys Asp Glu Leu Gly Arg Cys Val His Trp
1               5                   10

<210> SEQ ID NO 189
<211> LENGTH: 13
<212> TYPE: PRT
<213> ORGANISM: Artificial Sequence
<220> FEATURE:
<223> OTHER INFORMATION: Library Isolate
```

```
<400> SEQUENCE: 189

Trp Ile Gln Cys Asn His Gln Gly Gln Cys Phe His Gly
 1               5                  10

<210> SEQ ID NO 190
<211> LENGTH: 13
<212> TYPE: PRT
<213> ORGANISM: Artificial Sequence
<220> FEATURE:
<223> OTHER INFORMATION: Library Isolate

<400> SEQUENCE: 190

Trp Ile Glu Cys Asn Lys Asp Gly Lys Cys Trp His Tyr
 1               5                  10

<210> SEQ ID NO 191
<211> LENGTH: 13
<212> TYPE: PRT
<213> ORGANISM: Artificial Sequence
<220> FEATURE:
<223> OTHER INFORMATION: Library Isolate

<400> SEQUENCE: 191

Trp Val Glu Cys Asn His Lys Gly Leu Cys Arg Glu Tyr
 1               5                  10

<210> SEQ ID NO 192
<211> LENGTH: 13
<212> TYPE: PRT
<213> ORGANISM: Artificial Sequence
<220> FEATURE:
<223> OTHER INFORMATION: Library Isolate

<400> SEQUENCE: 192

Trp Tyr Trp Cys Glu Phe Tyr Gly Val Cys Ser Glu Glu
 1               5                  10

<210> SEQ ID NO 193
<211> LENGTH: 15
<212> TYPE: PRT
<213> ORGANISM: Artificial Sequence
<220> FEATURE:
<223> OTHER INFORMATION: Library Isolate

<400> SEQUENCE: 193

Ile Asp Phe Cys Lys Gly Met Ala Pro Trp Leu Cys Ala Asp Met
 1               5                  10                  15

<210> SEQ ID NO 194
<211> LENGTH: 15
<212> TYPE: PRT
<213> ORGANISM: Artificial Sequence
<220> FEATURE:
<223> OTHER INFORMATION: Library Isolate

<400> SEQUENCE: 194

Pro Trp Thr Cys Trp Leu Glu Asp His Leu Ala Cys Ala Met Leu
 1               5                  10                  15

<210> SEQ ID NO 195
<211> LENGTH: 15
<212> TYPE: PRT
<213> ORGANISM: Artificial Sequence
<220> FEATURE:
<223> OTHER INFORMATION: Library Isolate

<400> SEQUENCE: 195
```

Asp Trp Gly Cys Ser Leu Gly Asn Trp Tyr Trp Cys Ser Thr Glu
1               5                   10                  15

<210> SEQ ID NO 196
<211> LENGTH: 15
<212> TYPE: PRT
<213> ORGANISM: Artificial Sequence
<220> FEATURE:
<223> OTHER INFORMATION: Library Isolate

<400> SEQUENCE: 196

Met Pro Trp Cys Ser Glu Val Thr Trp Gly Trp Cys Lys Leu Asn
1               5                   10                  15

<210> SEQ ID NO 197
<211> LENGTH: 15
<212> TYPE: PRT
<213> ORGANISM: Artificial Sequence
<220> FEATURE:
<223> OTHER INFORMATION: Library Isolate

<400> SEQUENCE: 197

Arg Gly Pro Cys Ser Gly Gln Pro Trp His Leu Cys Tyr Tyr Gln
1               5                   10                  15

<210> SEQ ID NO 198
<211> LENGTH: 15
<212> TYPE: PRT
<213> ORGANISM: Artificial Sequence
<220> FEATURE:
<223> OTHER INFORMATION: Library Isolate

<400> SEQUENCE: 198

Pro Trp Gly Cys Asp His Phe Gly Trp Ala Trp Cys Lys Gly Met
1               5                   10                  15

<210> SEQ ID NO 199
<211> LENGTH: 15
<212> TYPE: PRT
<213> ORGANISM: Artificial Sequence
<220> FEATURE:
<223> OTHER INFORMATION: Library Isolate

<400> SEQUENCE: 199

Met Pro Trp Cys Val Glu Lys Asp His Trp Asp Cys Trp Trp Trp
1               5                   10                  15

<210> SEQ ID NO 200
<211> LENGTH: 15
<212> TYPE: PRT
<213> ORGANISM: Artificial Sequence
<220> FEATURE:
<223> OTHER INFORMATION: Library Isolate

<400> SEQUENCE: 200

Pro Gly Pro Cys Lys Gly Tyr Met Pro His Gln Cys Trp Tyr Met
1               5                   10                  15

<210> SEQ ID NO 201
<211> LENGTH: 15
<212> TYPE: PRT
<213> ORGANISM: Artificial Sequence
<220> FEATURE:
<223> OTHER INFORMATION: Library Isolate

<400> SEQUENCE: 201

Tyr Gly Pro Cys Ala Glu Met Ser Pro Trp Leu Cys Trp Tyr Pro
1               5                   10                  15

```
<210> SEQ ID NO 202
<211> LENGTH: 15
<212> TYPE: PRT
<213> ORGANISM: Artificial Sequence
<220> FEATURE:
<223> OTHER INFORMATION: Library Isolate

<400> SEQUENCE: 202

Tyr Gly Pro Cys Lys Asn Met Pro Pro Trp Met Cys Trp His Glu
 1               5                  10                  15

<210> SEQ ID NO 203
<211> LENGTH: 15
<212> TYPE: PRT
<213> ORGANISM: Artificial Sequence
<220> FEATURE:
<223> OTHER INFORMATION: Library Isolate

<400> SEQUENCE: 203

Gly His Pro Cys Lys Gly Met Leu Pro His Thr Cys Trp Tyr Glu
 1               5                  10                  15

<210> SEQ ID NO 204
<211> LENGTH: 16
<212> TYPE: PRT
<213> ORGANISM: Artificial Sequence
<220> FEATURE:
<223> OTHER INFORMATION: Library Isolate

<400> SEQUENCE: 204

Asn Asn Ser Cys Trp Leu Ser Thr Thr Leu Gly Ser Cys Phe Phe Asp
 1               5                  10                  15

<210> SEQ ID NO 205
<211> LENGTH: 16
<212> TYPE: PRT
<213> ORGANISM: Artificial Sequence
<220> FEATURE:
<223> OTHER INFORMATION: Library Isolate

<400> SEQUENCE: 205

Asp His His Cys Tyr Leu His Asn Gly Gln Trp Ile Cys Tyr Pro Phe
 1               5                  10                  15

<210> SEQ ID NO 206
<211> LENGTH: 16
<212> TYPE: PRT
<213> ORGANISM: Artificial Sequence
<220> FEATURE:
<223> OTHER INFORMATION: Library Isolate

<400> SEQUENCE: 206

Asn Ser His Cys Tyr Ile Trp Asp Gly Met Trp Leu Cys Phe Pro Asp
 1               5                  10                  15

<210> SEQ ID NO 207
<211> LENGTH: 19
<212> TYPE: PRT
<213> ORGANISM: Artificial Sequence
<220> FEATURE:
<223> OTHER INFORMATION: Library Isolate

<400> SEQUENCE: 207

Ser Asn Lys Cys Asp His Tyr Gln Ser Gly Pro His Gly Lys Ile Cys
 1               5                  10                  15

Val Asn Tyr
```

<210> SEQ ID NO 208
<211> LENGTH: 19
<212> TYPE: PRT
<213> ORGANISM: Artificial Sequence
<220> FEATURE:
<223> OTHER INFORMATION: Library Isolate

<400> SEQUENCE: 208

Ser Asn Lys Cys Asp His Tyr Gln Ser Gly Pro Tyr Gly Glu Val Cys
1               5                   10                  15

Phe Asn Tyr

<210> SEQ ID NO 209
<211> LENGTH: 19
<212> TYPE: PRT
<213> ORGANISM: Artificial Sequence
<220> FEATURE:
<223> OTHER INFORMATION: Library Isolate

<400> SEQUENCE: 209

Arg Leu Asp Cys Asp Lys Val Phe Ser Gly Pro Tyr Gly Lys Val Cys
1               5                   10                  15

Val Ser Tyr

<210> SEQ ID NO 210
<211> LENGTH: 18
<212> TYPE: PRT
<213> ORGANISM: Artificial Sequence
<220> FEATURE:
<223> OTHER INFORMATION: Library Isolate

<400> SEQUENCE: 210

Arg Leu Asp Cys Asp Lys Val Phe Ser Gly Pro Asp Thr Ser Cys Gly
1               5                   10                  15

Ser Gln

<210> SEQ ID NO 211
<211> LENGTH: 19
<212> TYPE: PRT
<213> ORGANISM: Artificial Sequence
<220> FEATURE:
<223> OTHER INFORMATION: Library Isolate

<400> SEQUENCE: 211

Arg Leu Asp Cys Asp Lys Val Phe Ser Gly Pro His Gly Lys Ile Cys
1               5                   10                  15

Val Arg Tyr

<210> SEQ ID NO 212
<211> LENGTH: 19
<212> TYPE: PRT
<213> ORGANISM: Artificial Sequence
<220> FEATURE:
<223> OTHER INFORMATION: Library Isolate

<400> SEQUENCE: 212

Arg Leu Asp Cys Asp Lys Val Phe Ser Gly Pro His Gly Lys Ile Cys
1               5                   10                  15

Val Asn Tyr

<210> SEQ ID NO 213
<211> LENGTH: 19
<212> TYPE: PRT

```
<213> ORGANISM: Artificial Sequence
<220> FEATURE:
<223> OTHER INFORMATION: Library Isolate

<400> SEQUENCE: 213

Arg Val Asp Cys Asp Lys Val Ile Ser Gly Pro His Gly Lys Ile Cys
 1               5                  10                  15

Val Asn Tyr

<210> SEQ ID NO 214
<211> LENGTH: 19
<212> TYPE: PRT
<213> ORGANISM: Artificial Sequence
<220> FEATURE:
<223> OTHER INFORMATION: Library Isolate

<400> SEQUENCE: 214

Arg Thr Thr Cys His His Gln Ile Ser Gly Pro His Gly Lys Ile Cys
 1               5                  10                  15

Val Asn Tyr

<210> SEQ ID NO 215
<211> LENGTH: 19
<212> TYPE: PRT
<213> ORGANISM: Artificial Sequence
<220> FEATURE:
<223> OTHER INFORMATION: Library Isolate

<400> SEQUENCE: 215

Glu Phe His Cys His His Ile Met Ser Gly Pro His Gly Lys Ile Cys
 1               5                  10                  15

Val Asn Tyr

<210> SEQ ID NO 216
<211> LENGTH: 19
<212> TYPE: PRT
<213> ORGANISM: Artificial Sequence
<220> FEATURE:
<223> OTHER INFORMATION: Library Isolate

<400> SEQUENCE: 216

His Asn Arg Cys Asp Phe Lys Met Ser Gly Pro His Gly Lys Ile Cys
 1               5                  10                  15

Val Asn Tyr

<210> SEQ ID NO 217
<211> LENGTH: 19
<212> TYPE: PRT
<213> ORGANISM: Artificial Sequence
<220> FEATURE:
<223> OTHER INFORMATION: Library Isolate

<400> SEQUENCE: 217

Trp Gln Glu Cys Thr Lys Val Leu Ser Gly Pro Gly Thr Phe Glu Cys
 1               5                  10                  15

Ser Tyr Glu

<210> SEQ ID NO 218
<211> LENGTH: 19
<212> TYPE: PRT
<213> ORGANISM: Artificial Sequence
<220> FEATURE:
<223> OTHER INFORMATION: Library Isolate

<400> SEQUENCE: 218
```

```
Trp Gln Glu Cys Thr Lys Val Leu Ser Gly Pro Gly Gln Phe Ser Cys
1               5                   10                  15

Val Tyr Gly

<210> SEQ ID NO 219
<211> LENGTH: 19
<212> TYPE: PRT
<213> ORGANISM: Artificial Sequence
<220> FEATURE:
<223> OTHER INFORMATION: Library Isolate

<400> SEQUENCE: 219

Trp Gln Glu Cys Thr Lys Val Leu Ser Gly Pro Gly Gln Phe Glu Cys
1               5                   10                  15

Glu Tyr Met

<210> SEQ ID NO 220
<211> LENGTH: 19
<212> TYPE: PRT
<213> ORGANISM: Artificial Sequence
<220> FEATURE:
<223> OTHER INFORMATION: Library Isolate

<400> SEQUENCE: 220

Trp Gln Glu Cys Thr Lys Val Leu Ser Gly Pro Asn Ser Phe Glu Cys
1               5                   10                  15

Lys Tyr Asp

<210> SEQ ID NO 221
<211> LENGTH: 19
<212> TYPE: PRT
<213> ORGANISM: Artificial Sequence
<220> FEATURE:
<223> OTHER INFORMATION: Library Isolate

<400> SEQUENCE: 221

Trp Asp Arg Cys Glu Arg Gln Ile Ser Gly Pro Gly Gln Phe Ser Cys
1               5                   10                  15

Val Tyr Gly

<210> SEQ ID NO 222
<211> LENGTH: 19
<212> TYPE: PRT
<213> ORGANISM: Artificial Sequence
<220> FEATURE:
<223> OTHER INFORMATION: Library Isolate

<400> SEQUENCE: 222

Trp Gln Glu Cys Thr Lys Val Leu Ser Gly Pro Gly Gln Phe Leu Cys
1               5                   10                  15

Ser Tyr Gly

<210> SEQ ID NO 223
<211> LENGTH: 19
<212> TYPE: PRT
<213> ORGANISM: Artificial Sequence
<220> FEATURE:
<223> OTHER INFORMATION: Library Isolate

<400> SEQUENCE: 223

Arg Leu Asp Cys Asp Met Val Phe Ser Gly Pro His Gly Lys Ile Cys
1               5                   10                  15

Val Asn Tyr
```

```
<210> SEQ ID NO 224
<211> LENGTH: 18
<212> TYPE: PRT
<213> ORGANISM: Artificial Sequence
<220> FEATURE:
<223> OTHER INFORMATION: Library Isolate

<400> SEQUENCE: 224

Lys Arg Cys Asp Thr Thr His Ser Gly Pro His Gly Ile Val Cys Val
 1               5                  10                  15

Val Tyr

<210> SEQ ID NO 225
<211> LENGTH: 19
<212> TYPE: PRT
<213> ORGANISM: Artificial Sequence
<220> FEATURE:
<223> OTHER INFORMATION: Library Isolate

<400> SEQUENCE: 225

Ser Asn Lys Cys Asp His Tyr Gln Ser Gly Pro Tyr Gly Ala Val Cys
 1               5                  10                  15

Leu His Tyr

<210> SEQ ID NO 226
<211> LENGTH: 19
<212> TYPE: PRT
<213> ORGANISM: Artificial Sequence
<220> FEATURE:
<223> OTHER INFORMATION: Library Isolate

<400> SEQUENCE: 226

Ser Pro His Cys Gln Tyr Lys Ile Ser Gly Pro Phe Gly Pro Val Cys
 1               5                  10                  15

Val Asn Tyr

<210> SEQ ID NO 227
<211> LENGTH: 19
<212> TYPE: PRT
<213> ORGANISM: Artificial Sequence
<220> FEATURE:
<223> OTHER INFORMATION: Library Isolate

<400> SEQUENCE: 227

Ala His Gln Cys His His Trp Thr Ser Gly Pro Tyr Gly Glu Val Cys
 1               5                  10                  15

Phe Asn Tyr

<210> SEQ ID NO 228
<211> LENGTH: 19
<212> TYPE: PRT
<213> ORGANISM: Artificial Sequence
<220> FEATURE:
<223> OTHER INFORMATION: Library Isolate

<400> SEQUENCE: 228

Tyr Asp Lys Cys Ser Ser Arg Phe Ser Gly Pro Phe Gly Glu Ile Cys
 1               5                  10                  15

Val Asn Tyr

<210> SEQ ID NO 229
<211> LENGTH: 19
<212> TYPE: PRT
```

<213> ORGANISM: Artificial Sequence
<220> FEATURE:
<223> OTHER INFORMATION: Library Isolate

<400> SEQUENCE: 229

Met Gly Gly Cys Asp Phe Ser Phe Ser Gly Pro Phe Gly Gln Ile Cys
1               5                   10                  15

Gly Arg Tyr

<210> SEQ ID NO 230
<211> LENGTH: 19
<212> TYPE: PRT
<213> ORGANISM: Artificial Sequence
<220> FEATURE:
<223> OTHER INFORMATION: Library Isolate

<400> SEQUENCE: 230

Arg Thr Thr Cys His His Gln Ile Ser Gly Pro Phe Gly Asp Val Cys
1               5                   10                  15

Val Ser Tyr

<210> SEQ ID NO 231
<211> LENGTH: 19
<212> TYPE: PRT
<213> ORGANISM: Artificial Sequence
<220> FEATURE:
<223> OTHER INFORMATION: Library Isolate

<400> SEQUENCE: 231

Trp Tyr Arg Cys Asp Phe Asn Met Ser Gly Pro Asp Phe Thr Glu Cys
1               5                   10                  15

Leu Tyr Pro

<210> SEQ ID NO 232
<211> LENGTH: 19
<212> TYPE: PRT
<213> ORGANISM: Artificial Sequence
<220> FEATURE:
<223> OTHER INFORMATION: Library Isolate

<400> SEQUENCE: 232

Trp Met Gln Cys Asn Met Ser Ala Ser Gly Pro Lys Asp Met Tyr Cys
1               5                   10                  15

Glu Tyr Asp

<210> SEQ ID NO 233
<211> LENGTH: 19
<212> TYPE: PRT
<213> ORGANISM: Artificial Sequence
<220> FEATURE:
<223> OTHER INFORMATION: Library Isolate

<400> SEQUENCE: 233

Gly Ile Ser Cys Lys Trp Ile Trp Ser Gly Pro Asp Arg Trp Lys Cys
1               5                   10                  15

His His Phe

<210> SEQ ID NO 234
<211> LENGTH: 19
<212> TYPE: PRT
<213> ORGANISM: Artificial Sequence
<220> FEATURE:
<223> OTHER INFORMATION: Library Isolate

<400> SEQUENCE: 234

-continued

Trp Gln Val Cys Lys Pro Tyr Val Ser Gly Pro Ala Ala Phe Ser Cys
1               5                   10                  15

Lys Tyr Glu

<210> SEQ ID NO 235
<211> LENGTH: 19
<212> TYPE: PRT
<213> ORGANISM: Artificial Sequence
<220> FEATURE:
<223> OTHER INFORMATION: Library Isolate

<400> SEQUENCE: 235

Gly Trp Trp Cys Tyr Arg Asn Asp Ser Gly Pro Lys Pro Phe His Cys
1               5                   10                  15

Arg Ile Lys

<210> SEQ ID NO 236
<211> LENGTH: 19
<212> TYPE: PRT
<213> ORGANISM: Artificial Sequence
<220> FEATURE:
<223> OTHER INFORMATION: Library Isolate

<400> SEQUENCE: 236

Glu Gly Trp Cys Trp Phe Ile Asp Ser Gly Pro Trp Lys Thr Trp Cys
1               5                   10                  15

Glu Lys Gln

<210> SEQ ID NO 237
<211> LENGTH: 19
<212> TYPE: PRT
<213> ORGANISM: Artificial Sequence
<220> FEATURE:
<223> OTHER INFORMATION: Library Isolate

<400> SEQUENCE: 237

Phe Pro Lys Cys Lys Phe Asp Phe Ser Gly Pro Pro Trp Tyr Gln Cys
1               5                   10                  15

Asn Thr Lys

<210> SEQ ID NO 238
<211> LENGTH: 19
<212> TYPE: PRT
<213> ORGANISM: Artificial Sequence
<220> FEATURE:
<223> OTHER INFORMATION: Library Isolate

<400> SEQUENCE: 238

Arg Leu Asp Cys Asp Lys Val Phe Ser Gly Pro Tyr Gly Arg Val Cys
1               5                   10                  15

Val Lys Tyr

<210> SEQ ID NO 239
<211> LENGTH: 19
<212> TYPE: PRT
<213> ORGANISM: Artificial Sequence
<220> FEATURE:
<223> OTHER INFORMATION: Library Isolate

<400> SEQUENCE: 239

Arg Leu Asp Cys Asp Lys Val Phe Ser Gly Pro Tyr Gly Asn Val Cys
1               5                   10                  15

Val Asn Tyr

<210> SEQ ID NO 240
<211> LENGTH: 19
<212> TYPE: PRT
<213> ORGANISM: Artificial Sequence
<220> FEATURE:
<223> OTHER INFORMATION: Library Isolate

<400> SEQUENCE: 240

Arg Leu Asp Cys Asp Lys Val Phe Ser Gly Pro Ser Met Gly Thr Cys
 1               5                  10                  15

Lys Leu Gln

<210> SEQ ID NO 241
<211> LENGTH: 19
<212> TYPE: PRT
<213> ORGANISM: Artificial Sequence
<220> FEATURE:
<223> OTHER INFORMATION: Library Isolate

<400> SEQUENCE: 241

Arg Thr Thr Cys His His His Ile Ser Gly Pro His Gly Lys Ile Cys
 1               5                  10                  15

Val Asn Tyr

<210> SEQ ID NO 242
<211> LENGTH: 19
<212> TYPE: PRT
<213> ORGANISM: Artificial Sequence
<220> FEATURE:
<223> OTHER INFORMATION: Library Isolate

<400> SEQUENCE: 242

Gln Phe Gly Cys Glu His Ile Met Ser Gly Pro His Gly Lys Ile Cys
 1               5                  10                  15

Val Asn Tyr

<210> SEQ ID NO 243
<211> LENGTH: 19
<212> TYPE: PRT
<213> ORGANISM: Artificial Sequence
<220> FEATURE:
<223> OTHER INFORMATION: Library Isolate

<400> SEQUENCE: 243

Pro Val His Cys Ser His Thr Ile Ser Gly Pro His Gly Lys Ile Cys
 1               5                  10                  15

Val Asn Tyr

<210> SEQ ID NO 244
<211> LENGTH: 19
<212> TYPE: PRT
<213> ORGANISM: Artificial Sequence
<220> FEATURE:
<223> OTHER INFORMATION: Library Isolate

<400> SEQUENCE: 244

Ser Val Thr Cys His Phe Gln Met Ser Gly Pro His Gly Lys Ile Cys
 1               5                  10                  15

Val Asn Tyr

<210> SEQ ID NO 245
<211> LENGTH: 19
<212> TYPE: PRT

```
<213> ORGANISM: Artificial Sequence
<220> FEATURE:
<223> OTHER INFORMATION: Library Isolate

<400> SEQUENCE: 245

Pro Arg Gly Cys Gln His Met Ile Ser Gly Pro His Gly Lys Ile Cys
1               5                   10                  15

Val Asn Tyr

<210> SEQ ID NO 246
<211> LENGTH: 19
<212> TYPE: PRT
<213> ORGANISM: Artificial Sequence
<220> FEATURE:
<223> OTHER INFORMATION: Library Isolate

<400> SEQUENCE: 246

Arg Thr Thr Cys His His Gln Ile Ser Gly Pro His Gly Gln Ile Cys
1               5                   10                  15

Val Asn Tyr

<210> SEQ ID NO 247
<211> LENGTH: 19
<212> TYPE: PRT
<213> ORGANISM: Artificial Sequence
<220> FEATURE:
<223> OTHER INFORMATION: Library Isolate

<400> SEQUENCE: 247

Trp Thr Ile Cys His Met Glu Leu Ser Gly Pro His Gly Lys Ile Cys
1               5                   10                  15

Val Asn Tyr

<210> SEQ ID NO 248
<211> LENGTH: 19
<212> TYPE: PRT
<213> ORGANISM: Artificial Sequence
<220> FEATURE:
<223> OTHER INFORMATION: Library Isolate

<400> SEQUENCE: 248

Phe Ile Thr Cys Ala Leu Trp Leu Ser Gly Pro His Gly Lys Ile Cys
1               5                   10                  15

Val Asn Tyr

<210> SEQ ID NO 249
<211> LENGTH: 19
<212> TYPE: PRT
<213> ORGANISM: Artificial Sequence
<220> FEATURE:
<223> OTHER INFORMATION: Library Isolate

<400> SEQUENCE: 249

Met Gly Gly Cys Asp Phe Ser Phe Ser Gly Pro His Gly Lys Ile Cys
1               5                   10                  15

Val Asn Tyr

<210> SEQ ID NO 250
<211> LENGTH: 19
<212> TYPE: PRT
<213> ORGANISM: Artificial Sequence
<220> FEATURE:
<223> OTHER INFORMATION: Library Isolate

<400> SEQUENCE: 250
```

```
Lys Asp Trp Cys His Thr Thr Phe Ser Gly Pro His Gly Lys Ile Cys
1               5                   10                  15

Val Asn Tyr

<210> SEQ ID NO 251
<211> LENGTH: 19
<212> TYPE: PRT
<213> ORGANISM: Artificial Sequence
<220> FEATURE:
<223> OTHER INFORMATION: Library Isolate

<400> SEQUENCE: 251

Ala Trp Gly Cys Asp Asn Met Met Ser Gly Pro His Gly Lys Ile Cys
1               5                   10                  15

Val Asn Tyr

<210> SEQ ID NO 252
<211> LENGTH: 19
<212> TYPE: PRT
<213> ORGANISM: Artificial Sequence
<220> FEATURE:
<223> OTHER INFORMATION: Library Isolate

<400> SEQUENCE: 252

Ser Asn Lys Cys Asp His Ile Met Ser Gly Pro His Gly Lys Ile Cys
1               5                   10                  15

Val Asn Tyr

<210> SEQ ID NO 253
<211> LENGTH: 19
<212> TYPE: PRT
<213> ORGANISM: Artificial Sequence
<220> FEATURE:
<223> OTHER INFORMATION: Library Isolate

<400> SEQUENCE: 253

Ser Asn Lys Cys Asp His Tyr Gln Ser Gly Pro Phe Gly Asp Ile Cys
1               5                   10                  15

Val Met Tyr

<210> SEQ ID NO 254
<211> LENGTH: 19
<212> TYPE: PRT
<213> ORGANISM: Artificial Sequence
<220> FEATURE:
<223> OTHER INFORMATION: Library Isolate

<400> SEQUENCE: 254

Ser Asn Lys Cys Asp His Tyr Gln Ser Gly Pro Phe Gly Asp Val Cys
1               5                   10                  15

Val Ser Tyr

<210> SEQ ID NO 255
<211> LENGTH: 19
<212> TYPE: PRT
<213> ORGANISM: Artificial Sequence
<220> FEATURE:
<223> OTHER INFORMATION: Library Isolate

<400> SEQUENCE: 255

Ser Asn Lys Cys Asp His Tyr Gln Ser Gly Pro Phe Gly Asp Ile Cys
1               5                   10                  15

Val Ser Tyr
```

```
<210> SEQ ID NO 256
<211> LENGTH: 19
<212> TYPE: PRT
<213> ORGANISM: Artificial Sequence
<220> FEATURE:
<223> OTHER INFORMATION: Library Isolate

<400> SEQUENCE: 256

Arg Thr Thr Cys His His Gln Ile Ser Gly Pro Phe Gly Pro Val Cys
1               5                   10                  15

Val Asn Tyr

<210> SEQ ID NO 257
<211> LENGTH: 19
<212> TYPE: PRT
<213> ORGANISM: Artificial Sequence
<220> FEATURE:
<223> OTHER INFORMATION: Library Isolate

<400> SEQUENCE: 257

Arg Thr Thr Cys His His Gln Ile Ser Gly Pro Tyr Gly Asp Ile Cys
1               5                   10                  15

Val Lys Tyr

<210> SEQ ID NO 258
<211> LENGTH: 20
<212> TYPE: PRT
<213> ORGANISM: Artificial Sequence
<220> FEATURE:
<223> OTHER INFORMATION: Library Isolate

<400> SEQUENCE: 258

Pro His Gly Lys Ile Cys Val Asn Tyr Gly Ser Glu Ser Ala Asp Pro
1               5                   10                  15

Ser Tyr Ile Glu
            20

<210> SEQ ID NO 259
<211> LENGTH: 19
<212> TYPE: PRT
<213> ORGANISM: Artificial Sequence
<220> FEATURE:
<223> OTHER INFORMATION: Library Isolate

<400> SEQUENCE: 259

Arg Tyr Lys Cys Pro Arg Asp Leu Ser Gly Pro Pro Tyr Gly Pro Cys
1               5                   10                  15

Ser Pro Gln

<210> SEQ ID NO 260
<211> LENGTH: 14
<212> TYPE: PRT
<213> ORGANISM: Artificial Sequence
<220> FEATURE:
<223> OTHER INFORMATION: TN8 Secondary Library Template
<220> FEATURE:
<221> NAME/KEY: VARIANT
<222> LOCATION: (5)...(5)
<223> OTHER INFORMATION: Xaa = any amino acid
<220> FEATURE:
<221> NAME/KEY: VARIANT
<222> LOCATION: (6)...(6)
<223> OTHER INFORMATION: Xaa = any amino acid
<220> FEATURE:
<221> NAME/KEY: VARIANT
<222> LOCATION: (7)...(7)
```

```
<223> OTHER INFORMATION: Xaa = any amino acid
<220> FEATURE:
<221> NAME/KEY: VARIANT
<222> LOCATION: (10)...(10)
<223> OTHER INFORMATION: Xaa = any amino acid
<220> FEATURE:
<221> NAME/KEY: VARIANT
<222> LOCATION: (12)...(12)
<223> OTHER INFORMATION: Xaa = any amino acid
<220> FEATURE:
<221> NAME/KEY: VARIANT
<222> LOCATION: (13)...(13)
<223> OTHER INFORMATION: Xaa = any amino acid
<220> FEATURE:
<221> NAME/KEY: VARIANT
<222> LOCATION: (14)...(14)
<223> OTHER INFORMATION: Xaa = any amino acid

<400> SEQUENCE: 260

Trp Val Glu Cys Xaa Xaa Xaa Thr Gly Xaa Cys Xaa Xaa Xaa
 1               5                  10

<210> SEQ ID NO 261
<211> LENGTH: 18
<212> TYPE: PRT
<213> ORGANISM: Artificial Sequence
<220> FEATURE:
<223> OTHER INFORMATION: Secondary Library Template
<220> FEATURE:
<221> NAME/KEY: VARIANT
<222> LOCATION: (1)...(1)
<223> OTHER INFORMATION: Xaa = any amino acid
<220> FEATURE:
<221> NAME/KEY: VARIANT
<222> LOCATION: (2)...(2)
<223> OTHER INFORMATION: Xaa = any amino acid
<220> FEATURE:
<221> NAME/KEY: VARIANT
<222> LOCATION: (7)...(7)
<223> OTHER INFORMATION: Xaa = any amino acid
<220> FEATURE:
<221> NAME/KEY: VARIANT
<222> LOCATION: (8)...(8)
<223> OTHER INFORMATION: Xaa = any amino acid
<220> FEATURE:
<221> NAME/KEY: VARIANT
<222> LOCATION: (9)...(9)
<223> OTHER INFORMATION: Xaa = any amino acid
<220> FEATURE:
<221> NAME/KEY: VARIANT
<222> LOCATION: (12)...(12)
<223> OTHER INFORMATION: Xaa = any amino acid
<220> FEATURE:
<221> NAME/KEY: VARIANT
<222> LOCATION: (14)...(18)
<223> OTHER INFORMATION: Xaa = any amino acid

<400> SEQUENCE: 261

Xaa Xaa Trp Val Glu Cys Xaa Xaa Xaa Thr Gly Xaa Cys Xaa Xaa Xaa
 1               5                  10                  15

Xaa Xaa

<210> SEQ ID NO 262
<211> LENGTH: 4
<212> TYPE: PRT
<213> ORGANISM: Artificial Sequence
<220> FEATURE:
<223> OTHER INFORMATION: Library isolate

<400> SEQUENCE: 262

Gly Gly Gly Lys
 1
```

```
<210> SEQ ID NO 263
<211> LENGTH: 22
<212> TYPE: PRT
<213> ORGANISM: Artificial Sequence
<220> FEATURE:
<223> OTHER INFORMATION: Synthesized KDR-Binding Polypeptide

<400> SEQUENCE: 263

Ala Gly Asp Ser Trp Cys Ser Thr Glu Tyr Thr Tyr Cys Glu Met Ile
1               5                   10                  15

Gly Thr Gly Gly Gly Lys
            20

<210> SEQ ID NO 264
<211> LENGTH: 22
<212> TYPE: PRT
<213> ORGANISM: Artificial Sequence
<220> FEATURE:
<223> OTHER INFORMATION: Synthesized KDR-Binding Polypeptide

<400> SEQUENCE: 264

Ala Gly Pro Lys Trp Cys Glu Glu Asp Trp Tyr Tyr Cys Met Ile Thr
1               5                   10                  15

Gly Thr Gly Gly Gly Lys
            20

<210> SEQ ID NO 265
<211> LENGTH: 22
<212> TYPE: PRT
<213> ORGANISM: Artificial Sequence
<220> FEATURE:
<223> OTHER INFORMATION: Synthesized KDR-Binding Polypeptide

<400> SEQUENCE: 265

Ala Gly Val Trp Glu Cys Ala Lys Thr Phe Pro Phe Cys His Trp Phe
1               5                   10                  15

Gly Thr Gly Gly Gly Lys
            20

<210> SEQ ID NO 266
<211> LENGTH: 22
<212> TYPE: PRT
<213> ORGANISM: Artificial Sequence
<220> FEATURE:
<223> OTHER INFORMATION: Synthesized KDR-Binding Polypeptide

<400> SEQUENCE: 266

Ala Gly Trp Val Glu Cys Trp Trp Lys Ser Gly Gln Cys Tyr Glu Phe
1               5                   10                  15

Gly Thr Gly Gly Gly Lys
            20

<210> SEQ ID NO 267
<211> LENGTH: 22
<212> TYPE: PRT
<213> ORGANISM: Artificial Sequence
<220> FEATURE:
<223> OTHER INFORMATION: Synthesized KDR-Binding Polypeptide

<400> SEQUENCE: 267

Ala Gly Trp Leu Glu Cys Tyr Ala Glu Phe Gly His Cys Tyr Asn Phe
1               5                   10                  15

Gly Thr Gly Gly Gly Lys
            20
```

<210> SEQ ID NO 268
<211> LENGTH: 22
<212> TYPE: PRT
<213> ORGANISM: Artificial Sequence
<220> FEATURE:
<223> OTHER INFORMATION: Synthesized KDR-Binding Polypeptide

<400> SEQUENCE: 268

Ala Gly Trp Ile Gln Cys Asn Ser Ile Thr Gly His Cys Thr Ser Gly
1               5                   10                  15

Gly Thr Gly Gly Gly Lys
            20

<210> SEQ ID NO 269
<211> LENGTH: 22
<212> TYPE: PRT
<213> ORGANISM: Artificial Sequence
<220> FEATURE:
<223> OTHER INFORMATION: Synthesized KDR-Binding Polypeptide

<400> SEQUENCE: 269

Ala Gly Trp Ile Glu Cys Tyr His Pro Asp Gly Ile Cys Tyr His Phe
1               5                   10                  15

Gly Thr Gly Gly Gly Lys
            20

<210> SEQ ID NO 270
<211> LENGTH: 22
<212> TYPE: PRT
<213> ORGANISM: Artificial Sequence
<220> FEATURE:
<223> OTHER INFORMATION: Synthesized KDR-Binding Polypeptide

<400> SEQUENCE: 270

Ala Gly Ser Asp Trp Cys Arg Val Asp Trp Tyr Tyr Cys Trp Leu Met
1               5                   10                  15

Gly Thr Gly Gly Gly Lys
            20

<210> SEQ ID NO 271
<211> LENGTH: 22
<212> TYPE: PRT
<213> ORGANISM: Artificial Sequence
<220> FEATURE:
<223> OTHER INFORMATION: Synthesized KDR-Binding Polypeptide

<400> SEQUENCE: 271

Ala Gly Ala Asn Trp Cys Glu Glu Asp Trp Tyr Tyr Cys Phe Ile Thr
1               5                   10                  15

Gly Thr Gly Gly Gly Lys
            20

<210> SEQ ID NO 272
<211> LENGTH: 22
<212> TYPE: PRT
<213> ORGANISM: Artificial Sequence
<220> FEATURE:
<223> OTHER INFORMATION: Synthesized KDR-Binding Polypeptide

<400> SEQUENCE: 272

Ala Gly Ala Asn Trp Cys Glu Glu Asp Trp Tyr Tyr Cys Trp Ile Thr
1               5                   10                  15

Gly Thr Gly Gly Gly Lys
            20

```
<210> SEQ ID NO 273
<211> LENGTH: 22
<212> TYPE: PRT
<213> ORGANISM: Artificial Sequence
<220> FEATURE:
<223> OTHER INFORMATION: Synthesized KDR-Binding Polypeptide

<400> SEQUENCE: 273

Ala Gly Pro Asp Trp Cys Glu Glu Asp Trp Tyr Tyr Cys Trp Ile Thr
1               5                   10                  15

Gly Thr Gly Gly Gly Lys
            20

<210> SEQ ID NO 274
<211> LENGTH: 22
<212> TYPE: PRT
<213> ORGANISM: Artificial Sequence
<220> FEATURE:
<223> OTHER INFORMATION: Synthesized KDR-Binding Polypeptide

<400> SEQUENCE: 274

Ala Gly Ser Asn Trp Cys Glu Glu Asp Trp Tyr Tyr Cys Tyr Ile Thr
1               5                   10                  15

Gly Thr Gly Gly Gly Lys
            20

<210> SEQ ID NO 275
<211> LENGTH: 22
<212> TYPE: PRT
<213> ORGANISM: Artificial Sequence
<220> FEATURE:
<223> OTHER INFORMATION: Synthesized KDR-Binding Polypeptide

<400> SEQUENCE: 275

Ala Gly Pro Asp Trp Cys Ala Ala Asp Trp Tyr Tyr Cys Tyr Ile Thr
1               5                   10                  15

Gly Thr Gly Gly Gly Lys
            20

<210> SEQ ID NO 276
<211> LENGTH: 22
<212> TYPE: PRT
<213> ORGANISM: Artificial Sequence
<220> FEATURE:
<223> OTHER INFORMATION: Synthesized KDR-Binding Polypeptide

<400> SEQUENCE: 276

Ala Gly Pro Glu Trp Cys Glu Val Asp Trp Tyr Tyr Cys Trp Leu Leu
1               5                   10                  15

Gly Thr Gly Gly Gly Lys
            20

<210> SEQ ID NO 277
<211> LENGTH: 22
<212> TYPE: PRT
<213> ORGANISM: Artificial Sequence
<220> FEATURE:
<223> OTHER INFORMATION: Synthesized KDR-Binding Polypeptide

<400> SEQUENCE: 277

Ala Gly Pro Thr Trp Cys Glu Asp Asp Trp Tyr Tyr Cys Trp Leu Phe
1               5                   10                  15

Gly Thr Gly Gly Gly Lys
            20
```

-continued

```
<210> SEQ ID NO 278
<211> LENGTH: 22
<212> TYPE: PRT
<213> ORGANISM: Artificial Sequence
<220> FEATURE:
<223> OTHER INFORMATION: Synthesized KDR-Binding Polypeptide

<400> SEQUENCE: 278

Ala Gly Ser Lys Trp Cys Glu Gln Asp Trp Tyr Tyr Cys Trp Leu Leu
1               5                   10                  15

Gly Thr Gly Gly Gly Lys
            20

<210> SEQ ID NO 279
<211> LENGTH: 22
<212> TYPE: PRT
<213> ORGANISM: Artificial Sequence
<220> FEATURE:
<223> OTHER INFORMATION: Synthesized KDR-Binding Polypeptide

<400> SEQUENCE: 279

Ala Gly Arg Asn Trp Cys Glu Glu Asp Trp Tyr Tyr Cys Phe Ile Thr
1               5                   10                  15

Gly Thr Gly Gly Gly Lys
            20

<210> SEQ ID NO 280
<211> LENGTH: 22
<212> TYPE: PRT
<213> ORGANISM: Artificial Sequence
<220> FEATURE:
<223> OTHER INFORMATION: Synthesized KDR-Binding Polypeptide

<400> SEQUENCE: 280

Ala Gly Val Asn Trp Cys Glu Glu Asp Trp Tyr Tyr Cys Trp Ile Thr
1               5                   10                  15

Gly Thr Gly Gly Gly Lys
            20

<210> SEQ ID NO 281
<211> LENGTH: 22
<212> TYPE: PRT
<213> ORGANISM: Artificial Sequence
<220> FEATURE:
<223> OTHER INFORMATION: Synthesized KDR-Binding Polypeptide

<400> SEQUENCE: 281

Ala Gly Ala Asn Trp Cys Glu Glu Asp Trp Tyr Tyr Cys Tyr Ile Thr
1               5                   10                  15

Gly Thr Gly Gly Gly Lys
            20

<210> SEQ ID NO 282
<211> LENGTH: 26
<212> TYPE: PRT
<213> ORGANISM: Artificial Sequence
<220> FEATURE:
<223> OTHER INFORMATION: Synthesized KDR-Binding Polypeptide

<400> SEQUENCE: 282

Ala Gly Gln Ala Trp Val Glu Cys Tyr Ala Glu Thr Gly Tyr Cys Trp
1               5                   10                  15

Pro Arg Ser Trp Gly Thr Gly Gly Gly Lys
            20                  25
```

-continued

```
<210> SEQ ID NO 283
<211> LENGTH: 26
<212> TYPE: PRT
<213> ORGANISM: Artificial Sequence
<220> FEATURE:
<223> OTHER INFORMATION: Synthesized KDR-Binding Polypeptide

<400> SEQUENCE: 283

Ala Gly Gln Ala Trp Ile Glu Cys Tyr Ala Glu Asp Gly Tyr Cys Trp
1               5                   10                  15

Pro Arg Ser Trp Gly Thr Gly Gly Gly Lys
            20                  25

<210> SEQ ID NO 284
<211> LENGTH: 26
<212> TYPE: PRT
<213> ORGANISM: Artificial Sequence
<220> FEATURE:
<223> OTHER INFORMATION: Synthesized KDR-Binding Polypeptide

<400> SEQUENCE: 284

Ala Gly Val Gly Trp Val Glu Cys Tyr Gln Ser Thr Gly Phe Cys Tyr
1               5                   10                  15

His Ser Arg Asp Gly Thr Gly Gly Gly Lys
            20                  25

<210> SEQ ID NO 285
<211> LENGTH: 26
<212> TYPE: PRT
<213> ORGANISM: Artificial Sequence
<220> FEATURE:
<223> OTHER INFORMATION: Synthesized KDR-Binding Polypeptide

<400> SEQUENCE: 285

Ala Gly Phe Thr Trp Val Glu Cys His Gln Ala Thr Gly Arg Cys Val
1               5                   10                  15

Glu Trp Thr Thr Gly Thr Gly Gly Gly Lys
            20                  25

<210> SEQ ID NO 286
<211> LENGTH: 26
<212> TYPE: PRT
<213> ORGANISM: Artificial Sequence
<220> FEATURE:
<223> OTHER INFORMATION: Synthesized KDR-Binding Polypeptide

<400> SEQUENCE: 286

Ala Gly Asp Trp Trp Val Glu Cys Arg Val Gly Thr Gly Leu Cys Tyr
1               5                   10                  15

Arg Tyr Asp Thr Gly Thr Gly Gly Gly Lys
            20                  25

<210> SEQ ID NO 287
<211> LENGTH: 26
<212> TYPE: PRT
<213> ORGANISM: Artificial Sequence
<220> FEATURE:
<223> OTHER INFORMATION: Synthesized KDR-Binding Polypeptide

<400> SEQUENCE: 287

Ala Gly Asp Ser Trp Val Glu Cys Asp Ala Gln Thr Gly Phe Cys Tyr
1               5                   10                  15

Ser Phe Leu Tyr Gly Thr Gly Gly Gly Lys
            20                  25
```

```
<210> SEQ ID NO 288
<211> LENGTH: 26
<212> TYPE: PRT
<213> ORGANISM: Artificial Sequence
<220> FEATURE:
<223> OTHER INFORMATION: Synthesized KDR-Binding Polypeptide

<400> SEQUENCE: 288

Ala Gly Gly Gly Trp Val Glu Cys Tyr Trp Ala Thr Gly Arg Cys Ile
 1               5                  10                  15

Glu Phe Ala Gly Gly Thr Gly Gly Gly Lys
            20                  25

<210> SEQ ID NO 289
<211> LENGTH: 26
<212> TYPE: PRT
<213> ORGANISM: Artificial Sequence
<220> FEATURE:
<223> OTHER INFORMATION: Synthesized KDR-Binding Polypeptide

<400> SEQUENCE: 289

Ala Gly Glu Arg Trp Val Glu Cys Arg Ala Glu Thr Gly Phe Cys Tyr
 1               5                  10                  15

Thr Trp Val Ser Gly Thr Gly Gly Gly Lys
            20                  25

<210> SEQ ID NO 290
<211> LENGTH: 26
<212> TYPE: PRT
<213> ORGANISM: Artificial Sequence
<220> FEATURE:
<223> OTHER INFORMATION: Synthesized KDR-Binding Polypeptide

<400> SEQUENCE: 290

Ala Gly Gly Gly Trp Val Glu Cys Arg Ala Glu Thr Gly His Cys Gln
 1               5                  10                  15

Glu Tyr Arg Leu Gly Thr Gly Gly Gly Lys
            20                  25

<210> SEQ ID NO 291
<211> LENGTH: 26
<212> TYPE: PRT
<213> ORGANISM: Artificial Sequence
<220> FEATURE:
<223> OTHER INFORMATION: Synthesized KDR-Binding Polypeptide

<400> SEQUENCE: 291

Ala Gly Val Ala Trp Val Glu Cys Tyr Gln Thr Thr Gly Lys Cys Tyr
 1               5                  10                  15

Thr Phe Arg Gly Gly Thr Gly Gly Gly Lys
            20                  25

<210> SEQ ID NO 292
<211> LENGTH: 26
<212> TYPE: PRT
<213> ORGANISM: Artificial Sequence
<220> FEATURE:
<223> OTHER INFORMATION: Synthesized KDR-Binding Polypeptide

<400> SEQUENCE: 292

Ala Gly Glu Gly Trp Val Glu Cys Phe Ala Asn Thr Gly Ala Cys Phe
 1               5                  10                  15

Thr Tyr Pro Arg Gly Thr Gly Gly Gly Lys
            20                  25
```

<210> SEQ ID NO 293
<211> LENGTH: 26
<212> TYPE: PRT
<213> ORGANISM: Artificial Sequence
<220> FEATURE:
<223> OTHER INFORMATION: Synthesized KDR-Binding Polypeptide

<400> SEQUENCE: 293

Gly Asp Tyr Pro Trp Cys His Glu Leu Ser Asp Ser Val Thr Arg Phe
 1               5                  10                  15

Cys Val Pro Trp Asp Pro Gly Gly Gly Lys
            20                  25

<210> SEQ ID NO 294
<211> LENGTH: 25
<212> TYPE: PRT
<213> ORGANISM: Artificial Sequence
<220> FEATURE:
<223> OTHER INFORMATION: Synthesized KDR-Binding Polypeptide

<400> SEQUENCE: 294

Gly Asp Ser Arg Val Cys Trp Glu Asp Ser Trp Gly Gly Glu Val Cys
 1               5                  10                  15

Phe Arg Tyr Asp Pro Gly Gly Gly Lys
            20                  25

<210> SEQ ID NO 295
<211> LENGTH: 26
<212> TYPE: PRT
<213> ORGANISM: Artificial Sequence
<220> FEATURE:
<223> OTHER INFORMATION: Synthesized KDR-Binding Polypeptide

<400> SEQUENCE: 295

Gly Asp Asp His Met Cys Arg Ser Pro Asp Tyr Gln Asp His Val Phe
 1               5                  10                  15

Cys Met Tyr Trp Asp Pro Gly Gly Gly Lys
            20                  25

<210> SEQ ID NO 296
<211> LENGTH: 26
<212> TYPE: PRT
<213> ORGANISM: Artificial Sequence
<220> FEATURE:
<223> OTHER INFORMATION: Synthesized KDR-Binding Polypeptide

<400> SEQUENCE: 296

Gly Asp Pro Pro Leu Cys Tyr Phe Val Gly Thr Gln Glu Trp His His
 1               5                  10                  15

Cys Asn Pro Phe Asp Pro Gly Gly Gly Lys
            20                  25

<210> SEQ ID NO 297
<211> LENGTH: 25
<212> TYPE: PRT
<213> ORGANISM: Artificial Sequence
<220> FEATURE:
<223> OTHER INFORMATION: Synthesized KDR-Binding Polypeptide

<400> SEQUENCE: 297

Gly Asp Asp Ser Tyr Cys Met Met Asn Glu Lys Gly Trp Trp Asn Cys
 1               5                  10                  15

Tyr Leu Tyr Asp Pro Gly Gly Gly Lys
            20                  25

```
<210> SEQ ID NO 298
<211> LENGTH: 26
<212> TYPE: PRT
<213> ORGANISM: Artificial Sequence
<220> FEATURE:
<223> OTHER INFORMATION: Synthesized KDR-Binding Polypeptide

<400> SEQUENCE: 298

Gly Asp Pro Ala Gln Cys Trp Glu Ser Asn Tyr Gln Gly Ile Phe Phe
 1               5                  10                  15

Cys Asp Asn Pro Asp Pro Gly Gly Gly Lys
            20                  25

<210> SEQ ID NO 299
<211> LENGTH: 26
<212> TYPE: PRT
<213> ORGANISM: Artificial Sequence
<220> FEATURE:
<223> OTHER INFORMATION: Synthesized KDR-Binding Polypeptide

<400> SEQUENCE: 299

Gly Asp Gly Ser Trp Cys Glu Met Arg Gln Asp Val Gly Lys Trp Asn
 1               5                  10                  15

Cys Phe Ser Asp Asp Pro Gly Gly Gly Lys
            20                  25

<210> SEQ ID NO 300
<211> LENGTH: 25
<212> TYPE: PRT
<213> ORGANISM: Artificial Sequence
<220> FEATURE:
<223> OTHER INFORMATION: Synthesized KDR-Binding Polypeptide

<400> SEQUENCE: 300

Gly Asp Gly Trp Ala Cys Ala Lys Trp Pro Trp Gly Gly Glu Ile Cys
 1               5                  10                  15

Gln Pro Ser Asp Pro Gly Gly Gly Lys
            20                  25

<210> SEQ ID NO 301
<211> LENGTH: 26
<212> TYPE: PRT
<213> ORGANISM: Artificial Sequence
<220> FEATURE:
<223> OTHER INFORMATION: Synthesized KDR-Binding Polypeptide

<400> SEQUENCE: 301

Gly Asp Pro Asp Thr Cys Thr Met Trp Gly Asp Ser Gly Arg Trp Tyr
 1               5                  10                  15

Cys Phe Pro Ala Asp Pro Gly Gly Gly Lys
            20                  25

<210> SEQ ID NO 302
<211> LENGTH: 26
<212> TYPE: PRT
<213> ORGANISM: Artificial Sequence
<220> FEATURE:
<223> OTHER INFORMATION: Synthesized KDR-Binding Polypeptide

<400> SEQUENCE: 302

Gly Asp Asn Trp Lys Cys Glu Tyr Thr Gln Gly Tyr Asp Tyr Thr Glu
 1               5                  10                  15

Cys Val Tyr Leu Asp Pro Gly Gly Gly Lys
            20                  25
```

```
<210> SEQ ID NO 303
<211> LENGTH: 26
<212> TYPE: PRT
<213> ORGANISM: Artificial Sequence
<220> FEATURE:
<223> OTHER INFORMATION: Synthesized KDR-Binding Polypeptide

<400> SEQUENCE: 303

Gly Asp Asn Trp Glu Cys Gly Trp Ser Asn Met Phe Gln Lys Glu Phe
1               5                   10                  15

Cys Ala Arg Pro Asp Pro Gly Gly Gly Lys
            20                  25

<210> SEQ ID NO 304
<211> LENGTH: 25
<212> TYPE: PRT
<213> ORGANISM: Artificial Sequence
<220> FEATURE:
<223> OTHER INFORMATION: Synthesized KDR-Binding Polypeptide

<400> SEQUENCE: 304

Ala Gln Gln Val Gln Tyr Gln Phe Phe Leu Gly Thr Pro Arg Tyr Glu
1               5                   10                  15

Gln Trp Asp Leu Asp Lys Gly Gly Lys
            20                  25

<210> SEQ ID NO 305
<211> LENGTH: 25
<212> TYPE: PRT
<213> ORGANISM: Artificial Sequence
<220> FEATURE:
<223> OTHER INFORMATION: Synthesized KDR-Binding Polypeptide

<400> SEQUENCE: 305

Ala Gln Glu Pro Glu Gly Tyr Ala Tyr Trp Glu Val Ile Thr Leu Tyr
1               5                   10                  15

His Glu Glu Asp Gly Asp Gly Gly Lys
            20                  25

<210> SEQ ID NO 306
<211> LENGTH: 25
<212> TYPE: PRT
<213> ORGANISM: Artificial Sequence
<220> FEATURE:
<223> OTHER INFORMATION: Synthesized KDR-Binding Polypeptide

<400> SEQUENCE: 306

Ala Gln Ala Phe Pro Arg Phe Gly Gly Asp Asp Tyr Trp Ile Gln Gln
1               5                   10                  15

Tyr Leu Arg Tyr Thr Asp Gly Gly Lys
            20                  25

<210> SEQ ID NO 307
<211> LENGTH: 25
<212> TYPE: PRT
<213> ORGANISM: Artificial Sequence
<220> FEATURE:
<223> OTHER INFORMATION: Synthesized KDR-Binding Polypeptide

<400> SEQUENCE: 307

Ala Gln Gly Asp Tyr Val Tyr Trp Glu Ile Ile Glu Leu Thr Gly Ala
1               5                   10                  15

Thr Asp His Thr Pro Pro Gly Gly Lys
            20                  25
```

```
<210> SEQ ID NO 308
<211> LENGTH: 25
<212> TYPE: PRT
<213> ORGANISM: Artificial Sequence
<220> FEATURE:
<223> OTHER INFORMATION: Synthesized KDR-Binding Polypeptide

<400> SEQUENCE: 308

Ala Gln Arg Gly Asp Tyr Gln Glu Gln Tyr Trp His Gln Gln Leu Val
1               5                   10                  15

Glu Gln Leu Lys Leu Leu Gly Gly Lys
            20                  25

<210> SEQ ID NO 309
<211> LENGTH: 23
<212> TYPE: PRT
<213> ORGANISM: Artificial Sequence
<220> FEATURE:
<223> OTHER INFORMATION: Synthesized KDR-Binding Polypeptide

<400> SEQUENCE: 309

Ala Gln Arg Ser Trp Tyr Leu Gly Pro Pro Tyr Tyr Glu Glu Trp Asp
1               5                   10                  15

Pro Ile Pro Asn Gly Gly Lys
            20

<210> SEQ ID NO 310
<211> LENGTH: 26
<212> TYPE: PRT
<213> ORGANISM: Artificial Sequence
<220> FEATURE:
<223> OTHER INFORMATION: Synthesized KDR-Binding Polypeptide

<400> SEQUENCE: 310

Ala Gln Asp Trp Tyr Tyr Asp Glu Ile Leu Ser Met Ala Asp Gln Leu
1               5                   10                  15

Arg His Ala Phe Leu Ser Gly Gly Gly Lys
            20                  25

<210> SEQ ID NO 311
<211> LENGTH: 23
<212> TYPE: PRT
<213> ORGANISM: Artificial Sequence
<220> FEATURE:
<223> OTHER INFORMATION: Synthesized KDR-Binding Polypeptide

<400> SEQUENCE: 311

Ala Gly Ile Asp Phe Cys Lys Gly Met Ala Pro Trp Leu Cys Ala Asp
1               5                   10                  15

Met Gly Thr Gly Gly Gly Lys
            20

<210> SEQ ID NO 312
<211> LENGTH: 23
<212> TYPE: PRT
<213> ORGANISM: Artificial Sequence
<220> FEATURE:
<223> OTHER INFORMATION: Synthesized KDR-Binding Polypeptide

<400> SEQUENCE: 312

Ala Gly Pro Trp Thr Cys Trp Leu Glu Asp His Leu Ala Cys Ala Met
1               5                   10                  15

Leu Gly Thr Gly Gly Gly Lys
            20
```

```
<210> SEQ ID NO 313
<211> LENGTH: 23
<212> TYPE: PRT
<213> ORGANISM: Artificial Sequence
<220> FEATURE:
<223> OTHER INFORMATION: Synthesized KDR-Binding Polypeptide

<400> SEQUENCE: 313

Ala Gly Asp Trp Gly Cys Ser Leu Gly Asn Trp Tyr Trp Cys Ser Thr
 1               5                  10                  15

Glu Gly Thr Gly Gly Gly Lys
            20

<210> SEQ ID NO 314
<211> LENGTH: 24
<212> TYPE: PRT
<213> ORGANISM: Artificial Sequence
<220> FEATURE:
<223> OTHER INFORMATION: Synthesized KDR-Binding Polypeptide

<400> SEQUENCE: 314

Gly Ser Asp His His Cys Tyr Leu His Asn Gly Gln Trp Ile Cys Tyr
 1               5                  10                  15

Pro Phe Ala Pro Gly Gly Gly Lys
            20

<210> SEQ ID NO 315
<211> LENGTH: 24
<212> TYPE: PRT
<213> ORGANISM: Artificial Sequence
<220> FEATURE:
<223> OTHER INFORMATION: Synthesized KDR-Binding Polypeptide

<400> SEQUENCE: 315

Gly Ser Asn Ser His Cys Tyr Ile Trp Asp Gly Met Trp Leu Cys Phe
 1               5                  10                  15

Pro Asp Ala Pro Gly Gly Gly Lys
            20

<210> SEQ ID NO 316
<211> LENGTH: 27
<212> TYPE: PRT
<213> ORGANISM: Artificial Sequence
<220> FEATURE:
<223> OTHER INFORMATION: Synthesized KDR-Binding Polypeptide

<400> SEQUENCE: 316

Ser Gly Arg Leu Asp Cys Asp Lys Val Phe Ser Gly Pro Tyr Gly Lys
 1               5                  10                  15

Val Cys Val Ser Tyr Gly Ser Gly Gly Gly Lys
            20                  25

<210> SEQ ID NO 317
<211> LENGTH: 27
<212> TYPE: PRT
<213> ORGANISM: Artificial Sequence
<220> FEATURE:
<223> OTHER INFORMATION: Synthesized KDR-Binding Polypeptide

<400> SEQUENCE: 317

Ser Gly Arg Leu Asp Cys Asp Lys Val Phe Ser Gly Pro His Gly Lys
 1               5                  10                  15

Ile Cys Val Asn Tyr Gly Ser Gly Gly Gly Lys
            20                  25
```

```
<210> SEQ ID NO 318
<211> LENGTH: 27
<212> TYPE: PRT
<213> ORGANISM: Artificial Sequence
<220> FEATURE:
<223> OTHER INFORMATION: Synthesized KDR-Binding Polypeptide

<400> SEQUENCE: 318

Ser Gly Arg Thr Thr Cys His His Gln Ile Ser Gly Pro His Gly Lys
 1               5                  10                  15

Ile Cys Val Asn Tyr Gly Ser Gly Gly Gly Lys
                20                  25

<210> SEQ ID NO 319
<211> LENGTH: 27
<212> TYPE: PRT
<213> ORGANISM: Artificial Sequence
<220> FEATURE:
<223> OTHER INFORMATION: Synthesized KDR-Binding Polypeptide

<400> SEQUENCE: 319

Ser Gly Ala His Gln Cys His His Trp Thr Ser Gly Pro Tyr Gly Glu
 1               5                  10                  15

Val Cys Phe Asn Tyr Gly Ser Gly Gly Gly Lys
                20                  25

<210> SEQ ID NO 320
<211> LENGTH: 23
<212> TYPE: PRT
<213> ORGANISM: Artificial Sequence
<220> FEATURE:
<223> OTHER INFORMATION: KDR or KDR/VEGF Complex Binding Polypeptide

<400> SEQUENCE: 320

Ala Gly Met Pro Trp Cys Val Glu Lys Asp His Trp Asp Cys Trp Trp
 1               5                  10                  15

Trp Gly Thr Gly Gly Gly Lys
                20

<210> SEQ ID NO 321
<211> LENGTH: 23
<212> TYPE: PRT
<213> ORGANISM: Artificial Sequence
<220> FEATURE:
<223> OTHER INFORMATION: KDR or KDR/VEGF Complex Binding Polypeptide

<400> SEQUENCE: 321

Ala Gly Pro Gly Pro Cys Lys Gly Tyr Met Pro His Gln Cys Trp Tyr
 1               5                  10                  15

Met Gly Thr Gly Gly Gly Lys
                20

<210> SEQ ID NO 322
<211> LENGTH: 23
<212> TYPE: PRT
<213> ORGANISM: Artificial Sequence
<220> FEATURE:
<223> OTHER INFORMATION: KDR or KDR/VEGF Complex Binding Polypeptide

<400> SEQUENCE: 322

Ala Gly Tyr Gly Pro Cys Ala Glu Met Ser Pro Trp Leu Cys Trp Tyr
 1               5                  10                  15

Pro Gly Thr Gly Gly Gly Lys
                20
```

```
<210> SEQ ID NO 323
<211> LENGTH: 23
<212> TYPE: PRT
<213> ORGANISM: Artificial Sequence
<220> FEATURE:
<223> OTHER INFORMATION: KDR or KDR/VEGF Complex Binding Polypeptide

<400> SEQUENCE: 323

Ala Gly Tyr Gly Pro Cys Lys Asn Met Pro Pro Trp Met Cys Trp His
1               5                   10                  15

Glu Gly Thr Gly Gly Gly Lys
            20

<210> SEQ ID NO 324
<211> LENGTH: 23
<212> TYPE: PRT
<213> ORGANISM: Artificial Sequence
<220> FEATURE:
<223> OTHER INFORMATION: KDR or KDR/VEGF Complex Binding Polypeptide

<400> SEQUENCE: 324

Ala Gly Gly His Pro Cys Lys Gly Met Leu Pro His Thr Cys Trp Tyr
1               5                   10                  15

Glu Gly Thr Gly Gly Gly Lys
            20

<210> SEQ ID NO 325
<211> LENGTH: 28
<212> TYPE: PRT
<213> ORGANISM: Artificial Sequence
<220> FEATURE:
<223> OTHER INFORMATION: KDR or KDR/VEGF Complex Binding Polypeptide

<400> SEQUENCE: 325

Ala Gln Ala Pro Ala Trp Thr Phe Gly Thr Asn Trp Arg Ser Ile Gln
1               5                   10                  15

Arg Val Asp Ser Leu Thr Gly Gly Gly Gly Gly Lys
            20                  25

<210> SEQ ID NO 326
<211> LENGTH: 28
<212> TYPE: PRT
<213> ORGANISM: Artificial Sequence
<220> FEATURE:
<223> OTHER INFORMATION: KDR or KDR/VEGF Complex Binding Polypeptide

<400> SEQUENCE: 326

Ala Gln Glu Gly Trp Phe Arg Asn Pro Gln Glu Ile Met Gly Phe Gly
1               5                   10                  15

Asp Ser Trp Asp Lys Pro Gly Gly Gly Gly Lys
            20                  25

<210> SEQ ID NO 327
<211> LENGTH: 25
<212> TYPE: PRT
<213> ORGANISM: Artificial Sequence
<220> FEATURE:
<223> OTHER INFORMATION: Library isolate

<400> SEQUENCE: 327

Gly Asp Ser Ser Val Cys Phe Glu Tyr Ser Trp Gly Gly Glu Val Cys
1               5                   10                  15

Phe Arg Tyr Asp Pro Gly Gly Gly Lys
            20                  25
```

```
<210> SEQ ID NO 328
<211> LENGTH: 25
<212> TYPE: PRT
<213> ORGANISM: Artificial Sequence
<220> FEATURE:
<223> OTHER INFORMATION: Library isolate

<400> SEQUENCE: 328

Gly Asp Ser Arg Val Cys Trp Glu Tyr Ser Trp Gly Gly Gln Ile Cys
1               5                   10                  15

Leu Gly Tyr Asp Pro Gly Gly Gly Lys
            20                  25

<210> SEQ ID NO 329
<211> LENGTH: 22
<212> TYPE: PRT
<213> ORGANISM: Artificial Sequence
<220> FEATURE:
<223> OTHER INFORMATION: KDR or KDR/VEGF Complex Binding Polypeptide

<400> SEQUENCE: 329

Ala Gly Met Pro Trp Cys Val Glu Lys Asp His Trp Asp Cys Trp Trp
1               5                   10                  15

Gly Thr Gly Gly Gly Lys
            20

<210> SEQ ID NO 330
<211> LENGTH: 26
<212> TYPE: PRT
<213> ORGANISM: Artificial Sequence
<220> FEATURE:
<223> OTHER INFORMATION: KDR or KDR/VEGF Complex Binding Polypeptide

<400> SEQUENCE: 330

Ala Gln Glu Gly Trp Phe Arg Asn Pro Gln Glu Ile Met Gly Phe Gly
1               5                   10                  15

Asp Ser Trp Asp Lys Pro Gly Gly Gly Lys
            20                  25

<210> SEQ ID NO 331
<211> LENGTH: 26
<212> TYPE: PRT
<213> ORGANISM: Artificial Sequence
<220> FEATURE:
<223> OTHER INFORMATION: KDR or KDR/VEGF Complex Binding Polypeptide

<400> SEQUENCE: 331

Ala Gln Arg Gly Asp Tyr Gln Glu Gln Tyr Trp His Gln Gln Leu Val
1               5                   10                  15

Glu Gln Leu Lys Leu Leu Gly Gly Gly Lys
            20                  25

<210> SEQ ID NO 332
<211> LENGTH: 20
<212> TYPE: PRT
<213> ORGANISM: Artificial Sequence
<220> FEATURE:
<223> OTHER INFORMATION: KDR or KDR/VEGF Complex Binding Polypeptide

<400> SEQUENCE: 332

Ala Gly Trp Tyr Trp Cys Asp Tyr Tyr Gly Ile Gly Cys Lys Trp Thr
1               5                   10                  15

Gly Gly Gly Lys
            20
```

```
<210> SEQ ID NO 333
<211> LENGTH: 22
<212> TYPE: PRT
<213> ORGANISM: Artificial Sequence
<220> FEATURE:
<223> OTHER INFORMATION: KDR or KDR/VEGF Complex Binding Polypeptide

<400> SEQUENCE: 333

Ala Gly Trp Tyr Trp Cys Asp Tyr Tyr Gly Ile Gly Cys Lys Trp Thr
 1               5                  10                  15

Gly Thr Gly Gly Gly Lys
            20

<210> SEQ ID NO 334
<211> LENGTH: 26
<212> TYPE: PRT
<213> ORGANISM: Artificial Sequence
<220> FEATURE:
<223> OTHER INFORMATION: KDR or KDR/VEGF Complex Binding Polypeptide

<400> SEQUENCE: 334

Ala Gln Trp Tyr Tyr Asp Trp Phe His Asn Gln Arg Lys Pro Pro Ser
 1               5                  10                  15

Asp Trp Ile Asp Asn Leu Gly Gly Gly Lys
            20                  25

<210> SEQ ID NO 335
<211> LENGTH: 22
<212> TYPE: PRT
<213> ORGANISM: Artificial Sequence
<220> FEATURE:
<223> OTHER INFORMATION: KDR or KDR/VEGF Complex Binding Polypeptide

<400> SEQUENCE: 335

Ala Gly Pro Lys Trp Cys Glu Glu Asp Trp Tyr Tyr Cys Met Ile Thr
 1               5                  10                  15

Gly Thr Gly Gly Gly Lys
            20

<210> SEQ ID NO 336
<211> LENGTH: 19
<212> TYPE: PRT
<213> ORGANISM: Artificial Sequence
<220> FEATURE:
<223> OTHER INFORMATION: KDR or KDR/VEGF Complex Binding Polypeptide

<400> SEQUENCE: 336

Trp Gln Pro Cys Pro Trp Glu Ser Trp Thr Phe Cys Trp Asp Pro Gly
 1               5                  10                  15

Gly Gly Lys

<210> SEQ ID NO 337
<211> LENGTH: 21
<212> TYPE: PRT
<213> ORGANISM: Artificial Sequence
<220> FEATURE:
<223> OTHER INFORMATION: KDR or KDR/VEGF Complex Binding Polypeptide

<400> SEQUENCE: 337

Val Cys Trp Glu Asp Ser Trp Gly Gly Glu Val Cys Phe Arg Tyr Asp
 1               5                  10                  15

Pro Gly Gly Gly Lys
            20

<210> SEQ ID NO 338
```

```
<211> LENGTH: 19
<212> TYPE: PRT
<213> ORGANISM: Artificial Sequence
<220> FEATURE:
<223> OTHER INFORMATION: KDR or KDR/VEGF Complex Binding Polypeptide

<400> SEQUENCE: 338

Ala Gly Pro Thr Trp Cys Glu Asp Asp Trp Tyr Tyr Cys Trp Leu Phe
1               5                   10                  15

Gly Thr Lys

<210> SEQ ID NO 339
<211> LENGTH: 22
<212> TYPE: PRT
<213> ORGANISM: Artificial Sequence
<220> FEATURE:
<223> OTHER INFORMATION: KDR or KDR/VEGF Complex Binding Polypeptide

<400> SEQUENCE: 339

Ala Gly Pro Thr Trp Cys Glu Asp Asp Trp Tyr Tyr Cys Trp Leu Phe
1               5                   10                  15

Gly Thr Gly Gly Gly Lys
            20

<210> SEQ ID NO 340
<211> LENGTH: 27
<212> TYPE: PRT
<213> ORGANISM: Artificial Sequence
<220> FEATURE:
<223> OTHER INFORMATION: KDR or KDR/VEGF Complex Binding Polypeptide

<400> SEQUENCE: 340

Ala Gln Ala His Met Pro Pro Trp Arg Pro Val Ala Val Asp Ala Leu
1               5                   10                  15

Phe Asp Trp Val Glu Gly Gly Gly Gly Gly Lys
            20                  25

<210> SEQ ID NO 341
<211> LENGTH: 27
<212> TYPE: PRT
<213> ORGANISM: Artificial Sequence
<220> FEATURE:
<223> OTHER INFORMATION: KDR or KDR/VEGF Complex Binding Polypeptide

<400> SEQUENCE: 341

Ala Gln Ala His Met Pro Pro Trp Trp Pro Leu Ala Val Asp Ala Gln
1               5                   10                  15

Glu Asp Trp Phe Glu Gly Gly Gly Gly Gly Lys
            20                  25

<210> SEQ ID NO 342
<211> LENGTH: 27
<212> TYPE: PRT
<213> ORGANISM: Artificial Sequence
<220> FEATURE:
<223> OTHER INFORMATION: KDR or KDR/VEGF Complex Binding Polypeptide

<400> SEQUENCE: 342

Ala Gln Ala Gln Met Pro Pro Trp Trp Pro Leu Ala Val Asp Ala Leu
1               5                   10                  15

Phe Asp Trp Phe Glu Gly Gly Gly Gly Gly Lys
            20                  25

<210> SEQ ID NO 343
<211> LENGTH: 27
```

-continued

```
<212> TYPE: PRT
<213> ORGANISM: Artificial Sequence
<220> FEATURE:
<223> OTHER INFORMATION: KDR or KDR/VEGF Complex Binding Polypeptide

<400> SEQUENCE: 343

Ala Gln Asp Trp Tyr Trp Arg Glu Trp Met Pro Met His Ala Gln Phe
 1               5                  10                  15

Leu Ala Asp Asp Trp Gly Gly Gly Gly Gly Lys
            20                  25

<210> SEQ ID NO 344
<211> LENGTH: 28
<212> TYPE: PRT
<213> ORGANISM: Artificial Sequence
<220> FEATURE:
<223> OTHER INFORMATION: KDR or KDR/VEGF Complex Binding Polypeptide

<400> SEQUENCE: 344

Ala Gln Lys Lys Glu Asp Ala Gln Gln Trp Tyr Trp Thr Asp Tyr Val
 1               5                  10                  15

Pro Ser Tyr Leu Tyr Arg Gly Gly Gly Gly Gly Lys
            20                  25

<210> SEQ ID NO 345
<211> LENGTH: 28
<212> TYPE: PRT
<213> ORGANISM: Artificial Sequence
<220> FEATURE:
<223> OTHER INFORMATION: KDR or KDR/VEGF Complex Binding Polypeptide

<400> SEQUENCE: 345

Ala Gln Pro Val Thr Asp Trp Thr Pro His His Pro Lys Ala Pro Asp
 1               5                  10                  15

Val Trp Leu Phe Tyr Thr Gly Gly Gly Gly Gly Lys
            20                  25

<210> SEQ ID NO 346
<211> LENGTH: 28
<212> TYPE: PRT
<213> ORGANISM: Artificial Sequence
<220> FEATURE:
<223> OTHER INFORMATION: KDR or KDR/VEGF Complex Binding Polypeptide

<400> SEQUENCE: 346

Ala Gln Asp Ala Leu Glu Ala Pro Lys Arg Asp Trp Tyr Tyr Asp Trp
 1               5                  10                  15

Phe Leu Asn His Ser Pro Gly Gly Gly Gly Gly Lys
            20                  25

<210> SEQ ID NO 347
<211> LENGTH: 19
<212> TYPE: PRT
<213> ORGANISM: Artificial Sequence
<220> FEATURE:
<223> OTHER INFORMATION: KDR or KDR/VEGF Complex Binding Polypeptide

<400> SEQUENCE: 347

Lys Trp Cys Glu Glu Asp Trp Tyr Tyr Cys Met Ile Thr Gly Thr Gly
 1               5                  10                  15

Gly Gly Lys

<210> SEQ ID NO 348
<211> LENGTH: 19
<212> TYPE: PRT
```

<213> ORGANISM: Artificial Sequence
<220> FEATURE:
<223> OTHER INFORMATION: KDR or KDR/VEGF Complex Binding Polypeptide

<400> SEQUENCE: 348

Ala Gly Pro Lys Trp Cys Glu Glu Asp Trp Tyr Tyr Cys Met Ile Gly
1               5                   10                  15

Gly Gly Lys

<210> SEQ ID NO 349
<211> LENGTH: 16
<212> TYPE: PRT
<213> ORGANISM: Artificial Sequence
<220> FEATURE:
<223> OTHER INFORMATION: KDR or KDR/VEGF Complex Binding Polypeptide

<400> SEQUENCE: 349

Lys Trp Cys Glu Glu Asp Trp Tyr Tyr Cys Met Ile Gly Gly Gly Lys
1               5                   10                  15

<210> SEQ ID NO 350
<211> LENGTH: 29
<212> TYPE: PRT
<213> ORGANISM: Artificial Sequence
<220> FEATURE:
<223> OTHER INFORMATION: KDR or KDR/VEGF Complex Binding Polypeptide

<400> SEQUENCE: 350

Ala Gln Pro Asp Asn Trp Lys Glu Phe Tyr Glu Ser Gly Trp Lys Tyr
1               5                   10                  15

Pro Ser Leu Tyr Lys Pro Leu Gly Gly Gly Gly Lys
            20                  25

<210> SEQ ID NO 351
<211> LENGTH: 28
<212> TYPE: PRT
<213> ORGANISM: Artificial Sequence
<220> FEATURE:
<223> OTHER INFORMATION: KDR or KDR/VEGF Complex Binding Polypeptide

<400> SEQUENCE: 351

Ala Gln Met Pro Pro Gly Phe Ser Tyr Trp Glu Gln Val Val Leu His
1               5                   10                  15

Asp Asp Ala Gln Val Leu Gly Gly Gly Gly Gly Lys
            20                  25

<210> SEQ ID NO 352
<211> LENGTH: 27
<212> TYPE: PRT
<213> ORGANISM: Artificial Sequence
<220> FEATURE:
<223> OTHER INFORMATION: KDR or KDR/VEGF Complex Binding Polypeptide

<400> SEQUENCE: 352

Ala Gln Ala Arg Met Gly Asp Asp Trp Glu Glu Ala Pro Pro His Glu
1               5                   10                  15

Trp Gly Trp Ala Asp Gly Gly Gly Gly Lys
            20                  25

<210> SEQ ID NO 353
<211> LENGTH: 28
<212> TYPE: PRT
<213> ORGANISM: Artificial Sequence
<220> FEATURE:
<223> OTHER INFORMATION: KDR or KDR/VEGF Complex Binding Polypeptide

<400> SEQUENCE: 353

Ala Gln Pro Glu Asp Ser Glu Ala Trp Tyr Trp Leu Asn Tyr Arg Pro
1               5                   10                  15

Thr Met Phe His Gln Leu Gly Gly Gly Gly Gly Lys
            20                  25

<210> SEQ ID NO 354
<211> LENGTH: 27
<212> TYPE: PRT
<213> ORGANISM: Artificial Sequence
<220> FEATURE:
<223> OTHER INFORMATION: KDR or KDR/VEGF Complex Binding Polypeptide

<400> SEQUENCE: 354

Ala Gln Ser Thr Asn Gly Asp Ser Phe Val Tyr Trp Glu Glu Val Glu
1               5                   10                  15

Leu Val Asp His Pro Gly Gly Gly Gly Gly Lys
            20                  25

<210> SEQ ID NO 355
<211> LENGTH: 28
<212> TYPE: PRT
<213> ORGANISM: Artificial Sequence
<220> FEATURE:
<223> OTHER INFORMATION: KDR or KDR/VEGF Complex Binding Polypeptide

<400> SEQUENCE: 355

Ala Gln Trp Glu Ser Asp Tyr Trp Asp Gln Met Arg Gln Gln Leu Lys
1               5                   10                  15

Thr Ala Tyr Met Lys Val Gly Gly Gly Gly Gly Lys
            20                  25

<210> SEQ ID NO 356
<211> LENGTH: 28
<212> TYPE: PRT
<213> ORGANISM: Artificial Sequence
<220> FEATURE:
<223> OTHER INFORMATION: KDR or KDR/VEGF Complex Binding Polypeptide

<400> SEQUENCE: 356

Ala Gln Asp Trp Tyr Tyr Asp Glu Ile Leu Ser Met Ala Asp Gln Leu
1               5                   10                  15

Arg His Ala Phe Leu Ser Gly Gly Gly Gly Gly Lys
            20                  25

<210> SEQ ID NO 357
<211> LENGTH: 30
<212> TYPE: DNA
<213> ORGANISM: Artificial Sequence
<220> FEATURE:
<223> OTHER INFORMATION: Smart II Oligonucleotide

<400> SEQUENCE: 357
aagcagtggt aacaacgcag agtacgcggg                                    30

<210> SEQ ID NO 358
<211> LENGTH: 23
<212> TYPE: DNA
<213> ORGANISM: Artificial Sequence
<220> FEATURE:
<223> OTHER INFORMATION: Oligonucleotide for Cloning

<400> SEQUENCE: 358
gatggagagc aaggtgctgc tgg                                           23

```
<210> SEQ ID NO 359
<211> LENGTH: 23
<212> TYPE: DNA
<213> ORGANISM: Artificial Sequence
<220> FEATURE:
<223> OTHER INFORMATION: Oligonucleotide for Cloning

<400> SEQUENCE: 359
ccaagttcgt cttttcctgg gca                                              23

<210> SEQ ID NO 360
<211> LENGTH: 36
<212> TYPE: DNA
<213> ORGANISM: Artificial Sequence
<220> FEATURE:
<223> OTHER INFORMATION: Oligonucleotide for Cloning

<400> SEQUENCE: 360
tcccccggga tcattattct agtaggcacg gcggtg                                36

<210> SEQ ID NO 361
<211> LENGTH: 23
<212> TYPE: DNA
<213> ORGANISM: Artificial Sequence
<220> FEATURE:
<223> OTHER INFORMATION: Oligonucleotide for Cloning

<400> SEQUENCE: 361
caggaggaga gctcagtgtg gtc                                              23

<210> SEQ ID NO 362
<211> LENGTH: 41
<212> TYPE: DNA
<213> ORGANISM: Artificial Sequence
<220> FEATURE:
<223> OTHER INFORMATION: Oligonucleotide for Cloning

<400> SEQUENCE: 362
ataagaatgc ggccgcagga tggagagcaa ggtgctgctg g                          41

<210> SEQ ID NO 363
<211> LENGTH: 27
<212> TYPE: DNA
<213> ORGANISM: Artificial Sequence
<220> FEATURE:
<223> OTHER INFORMATION: Oligonucleotide for Cloning

<400> SEQUENCE: 363
ttccaagttc gtcttttcct gggcacc                                          27

<210> SEQ ID NO 364
<211> LENGTH: 27
<212> TYPE: DNA
<213> ORGANISM: Artificial Sequence
<220> FEATURE:
<223> OTHER INFORMATION: Oligonucleotide for Cloning

<400> SEQUENCE: 364
atcattattc tagtaggcac ggcggtg                                          27

<210> SEQ ID NO 365
<211> LENGTH: 41
<212> TYPE: DNA
<213> ORGANISM: Artificial Sequence
<220> FEATURE:
<223> OTHER INFORMATION: Oligonucleotide for Cloning
```

-continued

```
<400> SEQUENCE: 365
ataagaatgc ggccgcaaca ggaggagagc tcagtgtggt c                           41

<210> SEQ ID NO 366
<211> LENGTH: 26
<212> TYPE: PRT
<213> ORGANISM: Artificial Sequence
<220> FEATURE:
<223> OTHER INFORMATION: KDR-Binding Polypeptide

<400> SEQUENCE: 366

Gly Asp Trp Trp Glu Cys Lys Arg Glu Glu Tyr Arg Asn Thr Thr Trp
 1               5                  10                  15

Cys Ala Trp Ala Asp Pro Gly Gly Gly Lys
            20                  25

<210> SEQ ID NO 367
<211> LENGTH: 23
<212> TYPE: PRT
<213> ORGANISM: Artificial Sequence
<220> FEATURE:
<223> OTHER INFORMATION: KDR-Binding Polypeptide

<400> SEQUENCE: 367

Ala Gly Pro Gly Pro Cys Lys Gly Tyr Met Pro His Gln Cys Trp Tyr
 1               5                  10                  15

Met Gly Thr Gly Gly Gly Lys
            20

<210> SEQ ID NO 368
<211> LENGTH: 17
<212> TYPE: PRT
<213> ORGANISM: Artificial Sequence
<220> FEATURE:
<223> OTHER INFORMATION: KDR-Binding Polypeptide

<400> SEQUENCE: 368

Val Cys Trp Glu Asp Ser Trp Gly Gly Glu Val Cys Phe Gly Gly Gly
 1               5                  10                  15

Lys

<210> SEQ ID NO 369
<211> LENGTH: 21
<212> TYPE: PRT
<213> ORGANISM: Artificial Sequence
<220> FEATURE:
<223> OTHER INFORMATION: KDR-Binding Polypeptide

<400> SEQUENCE: 369

Gly Asp Ser Arg Val Cys Trp Glu Asp Ser Trp Gly Gly Glu Val Cys
 1               5                  10                  15

Phe Gly Gly Gly Lys
            20

<210> SEQ ID NO 370
<211> LENGTH: 20
<212> TYPE: PRT
<213> ORGANISM: Artificial Sequence
<220> FEATURE:
<223> OTHER INFORMATION: KDR-Binding Polypeptide

<400> SEQUENCE: 370

Val Cys Trp Glu Asp Ser Trp Gly Gly Glu Val Cys Phe Arg Tyr Asp
 1               5                  10                  15
```

```
Pro Gly Gly Gly
        20

<210> SEQ ID NO 371
<211> LENGTH: 22
<212> TYPE: PRT
<213> ORGANISM: Artificial Sequence
<220> FEATURE:
<223> OTHER INFORMATION: KDR-Binding Polypeptide

<400> SEQUENCE: 371

Ser Arg Val Cys Trp Glu Asp Ser Trp Gly Gly Glu Val Cys Phe Arg
1               5                   10                  15

Tyr Gly Gly Gly Gly Lys
        20

<210> SEQ ID NO 372
<211> LENGTH: 23
<212> TYPE: PRT
<213> ORGANISM: Artificial Sequence
<220> FEATURE:
<223> OTHER INFORMATION: KDR-Binding Polypeptide

<400> SEQUENCE: 372

Gly Asp Ser Arg Val Cys Trp Glu Asp Ser Trp Gly Gly Glu Val Cys
1               5                   10                  15

Phe Arg Tyr Gly Gly Gly Lys
        20

<210> SEQ ID NO 373
<211> LENGTH: 23
<212> TYPE: PRT
<213> ORGANISM: Artificial Sequence
<220> FEATURE:
<223> OTHER INFORMATION: KDR-Binding Polypeptide

<400> SEQUENCE: 373

Ala Gly Pro Thr Trp Cys Glu Asp Asp Trp Tyr Tyr Cys Trp Leu Phe
1               5                   10                  15

Gly Thr Gly Gly Gly Lys Lys
        20

<210> SEQ ID NO 374
<211> LENGTH: 21
<212> TYPE: PRT
<213> ORGANISM: Artificial Sequence
<220> FEATURE:
<223> OTHER INFORMATION: KDR-Binding Polypeptide

<400> SEQUENCE: 374

Gly Asp Ser Arg Val Cys Trp Glu Asp Ser Trp Gly Gly Glu Val Cys
1               5                   10                  15

Phe Arg Tyr Asp Pro
        20

<210> SEQ ID NO 375
<211> LENGTH: 18
<212> TYPE: PRT
<213> ORGANISM: Artificial Sequence
<220> FEATURE:
<223> OTHER INFORMATION: KDR-Binding Polypeptide

<400> SEQUENCE: 375

Ala Gly Asp Ser Trp Cys Ser Thr Glu Tyr Thr Tyr Cys Glu Met Ile
1               5                   10                  15
```

Gly Thr

<210> SEQ ID NO 376
<211> LENGTH: 24
<212> TYPE: PRT
<213> ORGANISM: Artificial Sequence
<220> FEATURE:
<223> OTHER INFORMATION: KDR-Binding Polypeptide

<400> SEQUENCE: 376

Ala Gln Asp Trp Tyr Tyr Asp Glu Ile Leu Ser Met Ala Asp Gln Leu
1               5                   10                  15

Arg His Ala Phe Leu Ser Gly Gly
            20

<210> SEQ ID NO 377
<211> LENGTH: 26
<212> TYPE: PRT
<213> ORGANISM: Artificial Sequence
<220> FEATURE:
<223> OTHER INFORMATION: Negative Control Polypeptide

<400> SEQUENCE: 377

Ala Glu Gly Thr Gly Asp Leu His Cys Tyr Phe Pro Trp Val Cys Ser
1               5                   10                  15

Leu Asp Pro Gly Pro Glu Gly Gly Gly Lys
            20                  25

<210> SEQ ID NO 378
<211> LENGTH: 22
<212> TYPE: PRT
<213> ORGANISM: Artificial Sequence
<220> FEATURE:
<223> OTHER INFORMATION: KDR-Binding Polypeptide

<400> SEQUENCE: 378

Ala Gly Pro Thr Trp Cys Glu Asp Asp Trp Tyr Tyr Cys Trp Leu Phe
1               5                   10                  15

Gly Thr Gly Gly Gly Lys
            20

<210> SEQ ID NO 379
<211> LENGTH: 22
<212> TYPE: PRT
<213> ORGANISM: Artificial Sequence
<220> FEATURE:
<223> OTHER INFORMATION: KDR-Binding Polypeptide

<400> SEQUENCE: 379

Ala Gly Pro Thr Trp Cys Glu Asp Asp Trp Tyr Tyr Cys Trp Leu Phe
1               5                   10                  15

Ala Thr Gly Gly Gly Lys
            20

<210> SEQ ID NO 380
<211> LENGTH: 26
<212> TYPE: PRT
<213> ORGANISM: Artificial Sequence
<220> FEATURE:
<223> OTHER INFORMATION: Vector Template
<220> FEATURE:
<221> NAME/KEY: VARIANT
<222> LOCATION: 3, 4, 5, 6, 7, 8, 9, 10, 11, 12, 13, 14, 15, 16, 17, 18,
      19, 20
<223> OTHER INFORMATION: Xaa = any amino acid

<400> SEQUENCE: 380

```
Ala Gln Xaa Xaa Xaa Xaa Xaa Xaa Xaa Xaa Xaa Xaa Xaa Xaa Xaa
1               5                   10                  15

Xaa Xaa Xaa Xaa Gly Gly Gly Gly Gly Lys
            20                  25

<210> SEQ ID NO 381
<211> LENGTH: 29
<212> TYPE: PRT
<213> ORGANISM: Artificial Sequence
<220> FEATURE:
<223> OTHER INFORMATION: Library Isolate

<400> SEQUENCE: 381

Ala Gln Pro Asp Asn Trp Lys Glu Phe Tyr Glu Ser Gly Trp Lys Tyr
1               5                   10                  15

Pro Ser Leu Tyr Lys Pro Leu Gly Gly Gly Gly Lys
            20                  25

<210> SEQ ID NO 382
<211> LENGTH: 28
<212> TYPE: PRT
<213> ORGANISM: Artificial Sequence
<220> FEATURE:
<223> OTHER INFORMATION: Library Isolate

<400> SEQUENCE: 382

Ala Gln Gln Ile Glu Tyr Val Asn Asp Lys Trp Tyr Trp Thr Gly Gly
1               5                   10                  15

Tyr Trp Asn Val Pro Phe Gly Gly Gly Gly Lys
            20                  25

<210> SEQ ID NO 383
<211> LENGTH: 28
<212> TYPE: PRT
<213> ORGANISM: Artificial Sequence
<220> FEATURE:
<223> OTHER INFORMATION: Library Isolate

<400> SEQUENCE: 383

Ala Gln Asp Ala Leu Glu Ala Pro Lys Arg Asp Trp Tyr Tyr Asp Trp
1               5                   10                  15

Phe Leu Asn His Ser Pro Gly Gly Gly Gly Lys
            20                  25

<210> SEQ ID NO 384
<211> LENGTH: 28
<212> TYPE: PRT
<213> ORGANISM: Artificial Sequence
<220> FEATURE:
<223> OTHER INFORMATION: Library Isolate

<400> SEQUENCE: 384

Ala Gln Trp Tyr His Asp Gly Leu His Asn Glu Arg Lys Pro Pro Ser
1               5                   10                  15

His Trp Ile Asp Asn Val Gly Gly Gly Gly Lys
            20                  25

<210> SEQ ID NO 385
<211> LENGTH: 28
<212> TYPE: PRT
<213> ORGANISM: Artificial Sequence
<220> FEATURE:
<223> OTHER INFORMATION: Library Isolate

<400> SEQUENCE: 385
```

Ala Gln Asp Trp Tyr Trp Gln Arg Glu Arg Asp Lys Leu Arg Glu His
1               5                   10                  15

Tyr Asp Asp Ala Phe Trp Gly Gly Gly Gly Lys
                20                  25

<210> SEQ ID NO 386
<211> LENGTH: 22
<212> TYPE: PRT
<213> ORGANISM: Artificial Sequence
<220> FEATURE:
<223> OTHER INFORMATION: Library Isolate

<400> SEQUENCE: 386

Ala Ala Pro Thr Trp Cys Glu Asp Asp Trp Tyr Tyr Cys Trp Leu Phe
1               5                   10                  15

Gly Thr Gly Gly Gly Lys
                20

<210> SEQ ID NO 387
<211> LENGTH: 22
<212> TYPE: PRT
<213> ORGANISM: Artificial Sequence
<220> FEATURE:
<223> OTHER INFORMATION: Library Isolate

<400> SEQUENCE: 387

Ala Gly Ala Thr Trp Cys Glu Asp Asp Trp Tyr Tyr Cys Trp Leu Phe
1               5                   10                  15

Gly Thr Gly Gly Gly Lys
                20

<210> SEQ ID NO 388
<211> LENGTH: 22
<212> TYPE: PRT
<213> ORGANISM: Artificial Sequence
<220> FEATURE:
<223> OTHER INFORMATION: Library Isolate

<400> SEQUENCE: 388

Ala Gly Pro Ala Trp Cys Glu Asp Asp Trp Tyr Tyr Cys Trp Leu Phe
1               5                   10                  15

Gly Thr Gly Gly Gly Lys
                20

<210> SEQ ID NO 389
<211> LENGTH: 22
<212> TYPE: PRT
<213> ORGANISM: Artificial Sequence
<220> FEATURE:
<223> OTHER INFORMATION: Library Isolate

<400> SEQUENCE: 389

Ala Gly Pro Thr Ala Cys Glu Asp Asp Trp Tyr Tyr Cys Trp Leu Phe
1               5                   10                  15

Gly Thr Gly Gly Gly Lys
                20

<210> SEQ ID NO 390
<211> LENGTH: 22
<212> TYPE: PRT
<213> ORGANISM: Artificial Sequence
<220> FEATURE:
<223> OTHER INFORMATION: Library Isolate

<400> SEQUENCE: 390

```
Ala Gly Pro Thr Trp Cys Ala Asp Asp Trp Tyr Tyr Cys Trp Leu Phe
1               5                   10                  15

Gly Thr Gly Gly Gly Lys
            20

<210> SEQ ID NO 391
<211> LENGTH: 22
<212> TYPE: PRT
<213> ORGANISM: Artificial Sequence
<220> FEATURE:
<223> OTHER INFORMATION: Library Isolate

<400> SEQUENCE: 391

Ala Gly Pro Thr Trp Cys Glu Ala Asp Trp Tyr Tyr Cys Trp Leu Phe
1               5                   10                  15

Gly Thr Gly Gly Gly Lys
            20

<210> SEQ ID NO 392
<211> LENGTH: 22
<212> TYPE: PRT
<213> ORGANISM: Artificial Sequence
<220> FEATURE:
<223> OTHER INFORMATION: Library Isolate

<400> SEQUENCE: 392

Ala Gly Pro Thr Trp Cys Glu Asp Ala Trp Tyr Tyr Cys Trp Leu Phe
1               5                   10                  15

Gly Thr Gly Gly Gly Lys
            20

<210> SEQ ID NO 393
<211> LENGTH: 22
<212> TYPE: PRT
<213> ORGANISM: Artificial Sequence
<220> FEATURE:
<223> OTHER INFORMATION: Library Isolate

<400> SEQUENCE: 393

Ala Gly Pro Thr Trp Cys Glu Asp Asp Ala Tyr Tyr Cys Trp Leu Phe
1               5                   10                  15

Gly Thr Gly Gly Gly Lys
            20

<210> SEQ ID NO 394
<211> LENGTH: 22
<212> TYPE: PRT
<213> ORGANISM: Artificial Sequence
<220> FEATURE:
<223> OTHER INFORMATION: Library Isolate

<400> SEQUENCE: 394

Ala Gly Pro Thr Trp Cys Glu Asp Asp Trp Ala Tyr Cys Trp Leu Phe
1               5                   10                  15

Gly Thr Gly Gly Gly Lys
            20

<210> SEQ ID NO 395
<211> LENGTH: 22
<212> TYPE: PRT
<213> ORGANISM: Artificial Sequence
<220> FEATURE:
<223> OTHER INFORMATION: Library Isolate

<400> SEQUENCE: 395
```

Ala Gly Pro Thr Trp Cys Glu Asp Asp Trp Tyr Ala Cys Trp Leu Phe
1               5                   10                  15

Gly Thr Gly Gly Gly Lys
            20

<210> SEQ ID NO 396
<211> LENGTH: 22
<212> TYPE: PRT
<213> ORGANISM: Artificial Sequence
<220> FEATURE:
<223> OTHER INFORMATION: Library Isolate

<400> SEQUENCE: 396

Ala Gly Pro Thr Trp Cys Glu Asp Asp Trp Tyr Tyr Cys Ala Leu Phe
1               5                   10                  15

Gly Thr Gly Gly Gly Lys
            20

<210> SEQ ID NO 397
<211> LENGTH: 22
<212> TYPE: PRT
<213> ORGANISM: Artificial Sequence
<220> FEATURE:
<223> OTHER INFORMATION: Library Isolate

<400> SEQUENCE: 397

Ala Gly Pro Thr Trp Cys Glu Asp Asp Trp Tyr Tyr Cys Trp Ala Phe
1               5                   10                  15

Gly Thr Gly Gly Gly Lys
            20

<210> SEQ ID NO 398
<211> LENGTH: 22
<212> TYPE: PRT
<213> ORGANISM: Artificial Sequence
<220> FEATURE:
<223> OTHER INFORMATION: Library Isolate

<400> SEQUENCE: 398

Ala Gly Pro Thr Trp Cys Glu Asp Asp Trp Tyr Tyr Cys Trp Leu Ala
1               5                   10                  15

Gly Thr Gly Gly Gly Lys
            20

<210> SEQ ID NO 399
<211> LENGTH: 22
<212> TYPE: PRT
<213> ORGANISM: Artificial Sequence
<220> FEATURE:
<223> OTHER INFORMATION: Library Isolate

<400> SEQUENCE: 399

Ala Gly Pro Thr Trp Cys Glu Asp Asp Trp Tyr Tyr Cys Trp Leu Phe
1               5                   10                  15

Ala Thr Gly Gly Gly Lys
            20

<210> SEQ ID NO 400
<211> LENGTH: 22
<212> TYPE: PRT
<213> ORGANISM: Artificial Sequence
<220> FEATURE:
<223> OTHER INFORMATION: Library Isolate

<400> SEQUENCE: 400

Ala Gly Pro Thr Trp Cys Glu Asp Asp Trp Tyr Tyr Cys Trp Leu Phe
1               5                   10                  15

Gly Ala Gly Gly Gly Lys
            20

<210> SEQ ID NO 401
<211> LENGTH: 22
<212> TYPE: PRT
<213> ORGANISM: Artificial Sequence
<220> FEATURE:
<223> OTHER INFORMATION: Library Isolate

<400> SEQUENCE: 401

Ala Ala Pro Thr Trp Cys Glu Asp Asp Trp Tyr Tyr Cys Trp Leu Phe
1               5                   10                  15

Gly Thr Gly Gly Gly Lys
            20

<210> SEQ ID NO 402
<211> LENGTH: 22
<212> TYPE: PRT
<213> ORGANISM: Artificial Sequence
<220> FEATURE:
<223> OTHER INFORMATION: Library Isolate

<400> SEQUENCE: 402

Ala Gly Ala Thr Trp Cys Glu Asp Asp Trp Tyr Tyr Cys Trp Leu Phe
1               5                   10                  15

Gly Thr Gly Gly Gly Lys
            20

<210> SEQ ID NO 403
<211> LENGTH: 22
<212> TYPE: PRT
<213> ORGANISM: Artificial Sequence
<220> FEATURE:
<223> OTHER INFORMATION: Library Isolate

<400> SEQUENCE: 403

Ala Gly Pro Ala Trp Cys Glu Asp Asp Trp Tyr Tyr Cys Trp Leu Phe
1               5                   10                  15

Gly Thr Gly Gly Gly Lys
            20

<210> SEQ ID NO 404
<211> LENGTH: 22
<212> TYPE: PRT
<213> ORGANISM: Artificial Sequence
<220> FEATURE:
<223> OTHER INFORMATION: Library Isolate

<400> SEQUENCE: 404

Ala Gly Pro Thr Ala Cys Glu Asp Asp Trp Tyr Tyr Cys Trp Leu Phe
1               5                   10                  15

Gly Thr Gly Gly Gly Lys
            20

<210> SEQ ID NO 405
<211> LENGTH: 22
<212> TYPE: PRT
<213> ORGANISM: Artificial Sequence
<220> FEATURE:
<223> OTHER INFORMATION: Library Isolate

<400> SEQUENCE: 405

-continued

Ala Gly Pro Thr Trp Cys Ala Asp Asp Trp Tyr Tyr Cys Trp Leu Phe
1               5                   10                  15

Gly Thr Gly Gly Gly Lys
            20

<210> SEQ ID NO 406
<211> LENGTH: 22
<212> TYPE: PRT
<213> ORGANISM: Artificial Sequence
<220> FEATURE:
<223> OTHER INFORMATION: Library Isolate

<400> SEQUENCE: 406

Ala Gly Pro Thr Trp Cys Glu Ala Asp Trp Tyr Tyr Cys Trp Leu Phe
1               5                   10                  15

Gly Thr Gly Gly Gly Lys
            20

<210> SEQ ID NO 407
<211> LENGTH: 22
<212> TYPE: PRT
<213> ORGANISM: Artificial Sequence
<220> FEATURE:
<223> OTHER INFORMATION: Library Isolate

<400> SEQUENCE: 407

Ala Gly Pro Thr Trp Cys Glu Asp Ala Trp Tyr Tyr Cys Trp Leu Phe
1               5                   10                  15

Gly Thr Gly Gly Gly Lys
            20

<210> SEQ ID NO 408
<211> LENGTH: 22
<212> TYPE: PRT
<213> ORGANISM: Artificial Sequence
<220> FEATURE:
<223> OTHER INFORMATION: Library Isolate

<400> SEQUENCE: 408

Ala Gly Pro Thr Trp Cys Glu Asp Asp Ala Tyr Tyr Cys Trp Leu Phe
1               5                   10                  15

Gly Thr Gly Gly Gly Lys
            20

<210> SEQ ID NO 409
<211> LENGTH: 22
<212> TYPE: PRT
<213> ORGANISM: Artificial Sequence
<220> FEATURE:
<223> OTHER INFORMATION: Library Isolate

<400> SEQUENCE: 409

Ala Gly Pro Thr Trp Cys Glu Asp Asp Trp Ala Tyr Cys Trp Leu Phe
1               5                   10                  15

Gly Thr Gly Gly Gly Lys
            20

<210> SEQ ID NO 410
<211> LENGTH: 22
<212> TYPE: PRT
<213> ORGANISM: Artificial Sequence
<220> FEATURE:
<223> OTHER INFORMATION: Library Isolate

<400> SEQUENCE: 410

Ala Gly Pro Thr Trp Cys Glu Asp Asp Trp Tyr Ala Cys Trp Leu Phe
1               5                   10                  15

Gly Thr Gly Gly Gly Lys
            20

<210> SEQ ID NO 411
<211> LENGTH: 22
<212> TYPE: PRT
<213> ORGANISM: Artificial Sequence
<220> FEATURE:
<223> OTHER INFORMATION: Library Isolate

<400> SEQUENCE: 411

Ala Gly Pro Thr Trp Cys Glu Asp Asp Trp Tyr Tyr Cys Ala Leu Phe
1               5                   10                  15

Gly Thr Gly Gly Gly Lys
            20

<210> SEQ ID NO 412
<211> LENGTH: 22
<212> TYPE: PRT
<213> ORGANISM: Artificial Sequence
<220> FEATURE:
<223> OTHER INFORMATION: Library Isolate

<400> SEQUENCE: 412

Ala Gly Pro Thr Trp Cys Glu Asp Asp Trp Tyr Tyr Cys Trp Ala Phe
1               5                   10                  15

Gly Thr Gly Gly Gly Lys
            20

<210> SEQ ID NO 413
<211> LENGTH: 22
<212> TYPE: PRT
<213> ORGANISM: Artificial Sequence
<220> FEATURE:
<223> OTHER INFORMATION: Library Isolate

<400> SEQUENCE: 413

Ala Gly Pro Thr Trp Cys Glu Asp Asp Trp Tyr Tyr Cys Trp Leu Ala
1               5                   10                  15

Gly Thr Gly Gly Gly Lys
            20

<210> SEQ ID NO 414
<211> LENGTH: 22
<212> TYPE: PRT
<213> ORGANISM: Artificial Sequence
<220> FEATURE:
<223> OTHER INFORMATION: Library Isolate

<400> SEQUENCE: 414

Ala Gly Pro Thr Trp Cys Glu Asp Asp Trp Tyr Tyr Cys Trp Leu Phe
1               5                   10                  15

Ala Thr Gly Gly Gly Lys
            20

<210> SEQ ID NO 415
<211> LENGTH: 22
<212> TYPE: PRT
<213> ORGANISM: Artificial Sequence
<220> FEATURE:
<223> OTHER INFORMATION: Library Isolate

<400> SEQUENCE: 415

```
Ala Gly Pro Thr Trp Cys Glu Asp Asp Trp Tyr Tyr Cys Trp Leu Phe
1               5                   10                  15

Gly Ala Gly Gly Gly Lys
            20
```

<210> SEQ ID NO 416
<211> LENGTH: 25
<212> TYPE: PRT
<213> ORGANISM: Artificial Sequence
<220> FEATURE:
<223> OTHER INFORMATION: Library Isolate

<400> SEQUENCE: 416

```
Gly Asp Ser Arg Val Cys Trp Glu Asp Ala Trp Gly Gly Glu Val Cys
1               5                   10                  15

Phe Arg Tyr Asp Pro Gly Gly Gly Lys
            20                  25
```

<210> SEQ ID NO 417
<211> LENGTH: 25
<212> TYPE: PRT
<213> ORGANISM: Artificial Sequence
<220> FEATURE:
<223> OTHER INFORMATION: Library Isolate

<400> SEQUENCE: 417

```
Gly Asp Ser Arg Val Cys Trp Glu Asp Ser Trp Ala Gly Glu Val Cys
1               5                   10                  15

Phe Arg Tyr Asp Pro Gly Gly Gly Lys
            20                  25
```

<210> SEQ ID NO 418
<211> LENGTH: 25
<212> TYPE: PRT
<213> ORGANISM: Artificial Sequence
<220> FEATURE:
<223> OTHER INFORMATION: Library Isolate

<400> SEQUENCE: 418

```
Gly Asp Ser Arg Val Cys Trp Glu Asp Ser Trp Gly Ala Glu Val Cys
1               5                   10                  15

Phe Arg Tyr Asp Pro Gly Gly Gly Lys
            20                  25
```

<210> SEQ ID NO 419
<211> LENGTH: 21
<212> TYPE: PRT
<213> ORGANISM: Artificial Sequence
<220> FEATURE:
<223> OTHER INFORMATION: Library Isolate

<400> SEQUENCE: 419

```
Ala Gly Thr Trp Cys Glu Asp Asp Trp Tyr Tyr Cys Leu Phe Thr Gly
1               5                   10                  15

Thr Gly Gly Gly Lys
            20
```

<210> SEQ ID NO 420
<211> LENGTH: 4
<212> TYPE: PRT
<213> ORGANISM: Artificial Sequence
<220> FEATURE:
<223> OTHER INFORMATION: Binding Motif

<400> SEQUENCE: 420

Asp Trp Tyr Tyr
1

<210> SEQ ID NO 421
<211> LENGTH: 9
<212> TYPE: PRT
<213> ORGANISM: Artificial Sequence
<220> FEATURE:
<223> OTHER INFORMATION: Library Isolate

<400> SEQUENCE: 421

Gly Asp Trp Tyr Tyr Gly Gly Gly Lys
1               5

<210> SEQ ID NO 422
<211> LENGTH: 10
<212> TYPE: PRT
<213> ORGANISM: Artificial Sequence
<220> FEATURE:
<223> OTHER INFORMATION: Library Isolate

<400> SEQUENCE: 422

Glu Asp Asp Trp Tyr Tyr Gly Gly Gly Lys
1               5                   10

<210> SEQ ID NO 423
<211> LENGTH: 16
<212> TYPE: PRT
<213> ORGANISM: Artificial Sequence
<220> FEATURE:
<223> OTHER INFORMATION: Library Isolate

<400> SEQUENCE: 423

Ala Gln Asp Trp Tyr Tyr Ala Trp Leu Phe Thr Gly Gly Gly Gly Lys
1               5                   10                  15

<210> SEQ ID NO 424
<211> LENGTH: 9
<212> TYPE: PRT
<213> ORGANISM: Artificial Sequence
<220> FEATURE:
<223> OTHER INFORMATION: Library Isolate

<400> SEQUENCE: 424

Ala Gln Asp Trp Tyr Tyr Ala Trp Leu
1               5

<210> SEQ ID NO 425
<211> LENGTH: 22
<212> TYPE: PRT
<213> ORGANISM: Artificial Sequence
<220> FEATURE:
<223> OTHER INFORMATION: Library Isolate

<400> SEQUENCE: 425

Ala Gly Pro Thr Trp Cys Glu Asp Glu Trp Tyr Tyr Cys Trp Leu Phe
1               5                   10                  15

Gly Thr Gly Gly Gly Lys
            20

<210> SEQ ID NO 426
<211> LENGTH: 22
<212> TYPE: PRT
<213> ORGANISM: Artificial Sequence
<220> FEATURE:
<223> OTHER INFORMATION: Library Isolate

<400> SEQUENCE: 426

Ala Gly Pro Thr Trp Cys Glu Asp Asp Trp Trp Tyr Cys Trp Leu Phe
1               5                   10                  15

Gly Thr Gly Gly Gly Lys
            20

<210> SEQ ID NO 427
<211> LENGTH: 22
<212> TYPE: PRT
<213> ORGANISM: Artificial Sequence
<220> FEATURE:
<223> OTHER INFORMATION: Library Isolate

<400> SEQUENCE: 427

Ala Gly Pro Thr Trp Cys Glu Asp Asp Trp Phe Tyr Cys Trp Leu Phe
1               5                   10                  15

Gly Thr Gly Gly Gly Lys
            20

<210> SEQ ID NO 428
<211> LENGTH: 22
<212> TYPE: PRT
<213> ORGANISM: Artificial Sequence
<220> FEATURE:
<223> OTHER INFORMATION: Library Isolate

<400> SEQUENCE: 428

Ala Gly Pro Thr Trp Ala Glu Asp Asp Trp Tyr Tyr Ala Trp Leu Phe
1               5                   10                  15

Gly Thr Gly Gly Gly Lys
            20

<210> SEQ ID NO 429
<211> LENGTH: 22
<212> TYPE: PRT
<213> ORGANISM: Artificial Sequence
<220> FEATURE:
<223> OTHER INFORMATION: Library Isolate

<400> SEQUENCE: 429

Ala Ala Pro Ala Trp Cys Ala Ala Asp Trp Tyr Tyr Cys Trp Leu Phe
1               5                   10                  15

Gly Thr Gly Gly Gly Lys
            20

<210> SEQ ID NO 430
<211> LENGTH: 22
<212> TYPE: PRT
<213> ORGANISM: Artificial Sequence
<220> FEATURE:
<223> OTHER INFORMATION: Library Isolate

<400> SEQUENCE: 430

Ala Gly Pro Thr Trp Cys Ala Asp Asp Trp Tyr Tyr Cys Trp Leu Phe
1               5                   10                  15

Gly Thr Gly Gly Gly Lys
            20

<210> SEQ ID NO 431
<211> LENGTH: 17
<212> TYPE: PRT
<213> ORGANISM: Artificial Sequence
<220> FEATURE:
<223> OTHER INFORMATION: Library Isolate

```
<400> SEQUENCE: 431

Cys Glu Asp Asp Trp Tyr Tyr Cys Trp Leu Phe Gly Thr Gly Gly
  1               5                  10                  15

Lys

<210> SEQ ID NO 432
<211> LENGTH: 18
<212> TYPE: PRT
<213> ORGANISM: Artificial Sequence
<220> FEATURE:
<223> OTHER INFORMATION: Library Isolate

<400> SEQUENCE: 432

Trp Cys Glu Asp Asp Trp Tyr Tyr Cys Trp Leu Phe Gly Thr Gly
  1               5                  10                  15

Gly Lys

<210> SEQ ID NO 433
<211> LENGTH: 12
<212> TYPE: PRT
<213> ORGANISM: Artificial Sequence
<220> FEATURE:
<223> OTHER INFORMATION: Library Isolate

<400> SEQUENCE: 433

Trp Cys Ala Ala Asp Trp Tyr Tyr Cys Trp Leu Phe
  1               5                  10

<210> SEQ ID NO 434
<211> LENGTH: 12
<212> TYPE: PRT
<213> ORGANISM: Artificial Sequence
<220> FEATURE:
<223> OTHER INFORMATION: Library Isolate

<400> SEQUENCE: 434

Trp Cys Glu Asp Asp Trp Tyr Tyr Cys Trp Leu Phe
  1               5                  10

<210> SEQ ID NO 435
<211> LENGTH: 19
<212> TYPE: PRT
<213> ORGANISM: Artificial Sequence
<220> FEATURE:
<223> OTHER INFORMATION: Library Isolate

<400> SEQUENCE: 435

Val Cys Trp Glu Asp Ser Trp Gly Gly Glu Val Cys Phe Arg Tyr Gly
  1               5                  10                  15

Gly Gly Lys

<210> SEQ ID NO 436
<211> LENGTH: 25
<212> TYPE: PRT
<213> ORGANISM: Artificial Sequence
<220> FEATURE:
<223> OTHER INFORMATION: Library Isolate

<400> SEQUENCE: 436

Gly Asp Ser Arg Val Ala Trp Glu Asp Ser Trp Gly Gly Glu Val Ala
  1               5                  10                  15

Phe Arg Tyr Asp Pro Gly Gly Gly Lys
                 20                  25
```

```
<210> SEQ ID NO 437
<211> LENGTH: 19
<212> TYPE: PRT
<213> ORGANISM: Artificial Sequence
<220> FEATURE:
<223> OTHER INFORMATION: Library Isolate

<400> SEQUENCE: 437

Val Cys Trp Glu Asp Ser Trp Gly Gly Glu Val Cys Phe Arg Tyr Gly
 1               5                  10                  15

Gly Gly Lys

<210> SEQ ID NO 438
<211> LENGTH: 25
<212> TYPE: PRT
<213> ORGANISM: Artificial Sequence
<220> FEATURE:
<223> OTHER INFORMATION: Library Isolate

<400> SEQUENCE: 438

Gly Asp Ser Arg Val Cys Trp Glu Asp Ala Trp Gly Gly Glu Val Cys
 1               5                  10                  15

Phe Arg Tyr Asp Pro Gly Gly Gly Lys
            20                  25

<210> SEQ ID NO 439
<211> LENGTH: 25
<212> TYPE: PRT
<213> ORGANISM: Artificial Sequence
<220> FEATURE:
<223> OTHER INFORMATION: Library Isolate

<400> SEQUENCE: 439

Gly Asp Ser Arg Val Cys Trp Glu Asp Phe Trp Gly Gly Glu Val Cys
 1               5                  10                  15

Phe Arg Tyr Asp Pro Gly Gly Gly Lys
            20                  25

<210> SEQ ID NO 440
<211> LENGTH: 25
<212> TYPE: PRT
<213> ORGANISM: Artificial Sequence
<220> FEATURE:
<223> OTHER INFORMATION: Library Isolate

<400> SEQUENCE: 440

Gly Asp Ser Arg Val Cys Trp Glu Asp Lys Trp Gly Gly Glu Val Cys
 1               5                  10                  15

Phe Arg Tyr Asp Pro Gly Gly Gly Lys
            20                  25

<210> SEQ ID NO 441
<211> LENGTH: 25
<212> TYPE: PRT
<213> ORGANISM: Artificial Sequence
<220> FEATURE:
<223> OTHER INFORMATION: Library Isolate

<400> SEQUENCE: 441

Gly Asp Ser Arg Val Cys Trp Glu Asp Ser Trp Gly Phe Glu Val Cys
 1               5                  10                  15

Phe Arg Tyr Asp Pro Gly Gly Gly Lys
            20                  25

<210> SEQ ID NO 442
```

```
<211> LENGTH: 25
<212> TYPE: PRT
<213> ORGANISM: Artificial Sequence
<220> FEATURE:
<223> OTHER INFORMATION: Library Isolate

<400> SEQUENCE: 442

Gly Asp Ser Arg Val Cys Trp Glu Asp Ser Trp Lys Glu Val Cys
 1               5                  10                  15

Phe Arg Tyr Asp Pro Gly Gly Gly Lys
             20                  25

<210> SEQ ID NO 443
<211> LENGTH: 25
<212> TYPE: PRT
<213> ORGANISM: Artificial Sequence
<220> FEATURE:
<223> OTHER INFORMATION: Library Isolate

<400> SEQUENCE: 443

Gly Asp Ser Arg Val Cys Trp Glu Asp Ser Trp Glu Glu Val Cys
 1               5                  10                  15

Phe Arg Tyr Asp Pro Gly Gly Gly Lys
             20                  25

<210> SEQ ID NO 444
<211> LENGTH: 23
<212> TYPE: PRT
<213> ORGANISM: Artificial Sequence
<220> FEATURE:
<223> OTHER INFORMATION: Library Isolate

<400> SEQUENCE: 444

Ala Gly Met Pro Trp Cys Val Glu Lys Asp His Trp Asp Cys Trp Trp
 1               5                  10                  15

Trp Gly Thr Gly Gly Gly Lys
             20

<210> SEQ ID NO 445
<211> LENGTH: 26
<212> TYPE: PRT
<213> ORGANISM: Artificial Sequence
<220> FEATURE:
<223> OTHER INFORMATION: Library Isolate

<400> SEQUENCE: 445

Gly Asp Gly Ser Trp Cys Glu Met Arg Gln Asp Val Gly Lys Trp Asn
 1               5                  10                  15

Cys Phe Ser Asp Asp Pro Gly Gly Gly Lys
             20                  25

<210> SEQ ID NO 446
<211> LENGTH: 26
<212> TYPE: PRT
<213> ORGANISM: Artificial Sequence
<220> FEATURE:
<223> OTHER INFORMATION: Library Isolate

<400> SEQUENCE: 446

Gly Cys Lys Thr Lys Ile Ser Lys Val Lys Lys Trp Asn Cys Tyr
 1               5                  10                  15

Ser Asn Asn Lys Val Thr Gly Gly Gly Lys
             20                  25

<210> SEQ ID NO 447
```

```
<211> LENGTH: 26
<212> TYPE: PRT
<213> ORGANISM: Artificial Sequence
<220> FEATURE:
<223> OTHER INFORMATION: Library Isolate

<400> SEQUENCE: 447

Lys Gln Phe Cys Glu Glu Asn Trp Glu Arg Gly Arg Asn His Tyr Tyr
1               5                   10                  15
Cys Leu Thr Thr Leu Ser Gly Gly Gly Lys
            20                  25

<210> SEQ ID NO 448
<211> LENGTH: 25
<212> TYPE: PRT
<213> ORGANISM: Artificial Sequence
<220> FEATURE:
<223> OTHER INFORMATION: Library Isolate

<400> SEQUENCE: 448

Gly Asp Ser Arg Val Cys Trp Glu Asp Trp Gly Gly Val Val Cys Arg
1               5                   10                  15
Tyr Arg Tyr Asp Ala Gly Gly Gly Lys
            20                  25

<210> SEQ ID NO 449
<211> LENGTH: 17
<212> TYPE: PRT
<213> ORGANISM: Artificial Sequence
<220> FEATURE:
<223> OTHER INFORMATION: Library Isolate

<400> SEQUENCE: 449

Cys Glu Glu Asp Trp Tyr Tyr Cys Met Ile Thr Gly Thr Gly Gly Gly
1               5                   10                  15
Lys

<210> SEQ ID NO 450
<211> LENGTH: 18
<212> TYPE: PRT
<213> ORGANISM: Artificial Sequence
<220> FEATURE:
<223> OTHER INFORMATION: Library Isolate

<400> SEQUENCE: 450

Ala Gly Pro Lys Trp Cys Glu Glu Asp Trp Tyr Tyr Cys Met Ile Thr
1               5                   10                  15
Ala Thr

<210> SEQ ID NO 451
<211> LENGTH: 21
<212> TYPE: PRT
<213> ORGANISM: Artificial Sequence
<220> FEATURE:
<223> OTHER INFORMATION: Library Isolate

<400> SEQUENCE: 451

Ala Ala Pro Lys Trp Cys Glu Glu Asp Tyr Tyr Cys Met Ile Thr Gly
1               5                   10                  15
Thr Gly Gly Gly Lys
            20

<210> SEQ ID NO 452
<211> LENGTH: 17
<212> TYPE: PRT
```

```
<213> ORGANISM: Artificial Sequence
<220> FEATURE:
<223> OTHER INFORMATION: Library Isolate

<400> SEQUENCE: 452

Ala Gly Pro Asp Trp Cys Ala Ala Asp Trp Tyr Tyr Cys Tyr Ile Thr
1               5                   10                  15

Gly

<210> SEQ ID NO 453
<211> LENGTH: 22
<212> TYPE: PRT
<213> ORGANISM: Artificial Sequence
<220> FEATURE:
<223> OTHER INFORMATION: Library Isolate

<400> SEQUENCE: 453

Ala Gly Pro Thr Trp Glu Glu Asp Asp Trp Tyr Tyr Lys Trp Leu Phe
1               5                   10                  15

Gly Thr Gly Gly Gly Lys
            20

<210> SEQ ID NO 454
<211> LENGTH: 22
<212> TYPE: PRT
<213> ORGANISM: Artificial Sequence
<220> FEATURE:
<223> OTHER INFORMATION: Library Isolate

<400> SEQUENCE: 454

Ala Gly Pro Thr Trp Lys Glu Asp Asp Trp Tyr Tyr Glu Trp Leu Phe
1               5                   10                  15

Gly Thr Gly Gly Gly Lys
            20

<210> SEQ ID NO 455
<211> LENGTH: 22
<212> TYPE: PRT
<213> ORGANISM: Artificial Sequence
<220> FEATURE:
<223> OTHER INFORMATION: Library Isolate
<220> FEATURE:
<221> NAME/KEY: Variant
<222> LOCATION: (6)...(6)
<223> OTHER INFORMATION: Xaa = Dpr

<400> SEQUENCE: 455

Ala Gly Pro Thr Trp Xaa Glu Asp Asp Trp Tyr Tyr Cys Trp Leu Phe
1               5                   10                  15

Gly Thr Gly Gly Gly Lys
            20

<210> SEQ ID NO 456
<211> LENGTH: 22
<212> TYPE: PRT
<213> ORGANISM: Artificial Sequence
<220> FEATURE:
<223> OTHER INFORMATION: Library Isolate
<220> FEATURE:
<221> NAME/KEY: variant
<222> LOCATION: (13)...(13)
<223> OTHER INFORMATION: Xaa = Dpr

<400> SEQUENCE: 456

Ala Gly Pro Thr Trp Asp Glu Asp Asp Trp Tyr Tyr Xaa Trp Leu Phe
1               5                   10                  15
```

-continued

Gly Thr Gly Gly Gly Lys
            20

<210> SEQ ID NO 457
<211> LENGTH: 22
<212> TYPE: PRT
<213> ORGANISM: Artificial Sequence
<220> FEATURE:
<223> OTHER INFORMATION: Library Isolate

<400> SEQUENCE: 457

Ala Gly Pro Thr Trp Asp Glu Asp Asp Trp Tyr Tyr Lys Trp Leu Phe
1               5                   10                  15

Gly Thr Gly Gly Gly Lys
            20

<210> SEQ ID NO 458
<211> LENGTH: 17
<212> TYPE: PRT
<213> ORGANISM: Artificial Sequence
<220> FEATURE:
<223> OTHER INFORMATION: Library Isolate

<400> SEQUENCE: 458

Ala Gln Asp Trp Tyr Tyr Asp Glu Ile Leu Ser Met Ala Asp Gln Leu
1               5                   10                  15

Arg

<210> SEQ ID NO 459
<211> LENGTH: 14
<212> TYPE: PRT
<213> ORGANISM: Artificial Sequence
<220> FEATURE:
<223> OTHER INFORMATION: Library Isolate

<400> SEQUENCE: 459

Asp Trp Tyr Tyr Asp Glu Ile Leu Ser Met Ala Asp Gln Leu
1               5                   10

<210> SEQ ID NO 460
<211> LENGTH: 22
<212> TYPE: PRT
<213> ORGANISM: Artificial Sequence
<220> FEATURE:
<223> OTHER INFORMATION: Library Isolate

<400> SEQUENCE: 460

Ala Gln Asp Trp Tyr Tyr Asp Glu Ile Leu Ser Met Ala Asp Gln Leu
1               5                   10                  15

Arg His Ala Phe Leu Ser
            20

<210> SEQ ID NO 461
<211> LENGTH: 10
<212> TYPE: PRT
<213> ORGANISM: Artificial Sequence
<220> FEATURE:
<223> OTHER INFORMATION: Library Isolate

<400> SEQUENCE: 461

Ala Gln Asp Trp Tyr Tyr Gly Gly Gly Lys
1               5                   10

<210> SEQ ID NO 462
<211> LENGTH: 8
<212> TYPE: PRT

```
<213> ORGANISM: Artificial Sequence
<220> FEATURE:
<223> OTHER INFORMATION: Library Isolate

<400> SEQUENCE: 462

Asp Trp Tyr Tyr Gly Gly Gly Lys
1               5

<210> SEQ ID NO 463
<211> LENGTH: 10
<212> TYPE: PRT
<213> ORGANISM: Artificial Sequence
<220> FEATURE:
<223> OTHER INFORMATION: Library Isolate

<400> SEQUENCE: 463

Ala Gln Asp Trp Tyr Tyr Asp Glu Ile Leu
1               5                   10

<210> SEQ ID NO 464
<211> LENGTH: 28
<212> TYPE: PRT
<213> ORGANISM: Artificial Sequence
<220> FEATURE:
<223> OTHER INFORMATION: Library Isolate

<400> SEQUENCE: 464

Ala Glu Trp Ser Tyr Gln Asp Met Ile Arg Leu Asp Tyr Ala Asp Leu
1               5                   10                  15

Gln Leu Ser His Phe Ala Gly Gly Gly Gly Lys
            20                  25

<210> SEQ ID NO 465
<211> LENGTH: 19
<212> TYPE: PRT
<213> ORGANISM: Artificial Sequence
<220> FEATURE:
<223> OTHER INFORMATION: Library Isolate

<400> SEQUENCE: 465

Ala Gln Asp Trp Tyr Tyr Asp Glu Ile Leu Gly Arg Gly Arg Gly Gly
1               5                   10                  15

Arg Gly Gly

<210> SEQ ID NO 466
<211> LENGTH: 16
<212> TYPE: PRT
<213> ORGANISM: Artificial Sequence
<220> FEATURE:
<223> OTHER INFORMATION: Library Isolate

<400> SEQUENCE: 466

Glu Asp Asp Trp Tyr Tyr Gly Arg Gly Gly Arg Gly Gly Arg Gly Gly
1               5                   10                  15

<210> SEQ ID NO 467
<211> LENGTH: 15
<212> TYPE: PRT
<213> ORGANISM: Artificial Sequence
<220> FEATURE:
<223> OTHER INFORMATION: Library Isolate

<400> SEQUENCE: 467

Gly Asp Trp Tyr Tyr Gly Arg Gly Gly Arg Gly Gly Arg Gly Gly
1               5                   10                  15
```

```
<210> SEQ ID NO 468
<211> LENGTH: 21
<212> TYPE: PRT
<213> ORGANISM: Artificial Sequence
<220> FEATURE:
<223> OTHER INFORMATION: Library Isolate

<400> SEQUENCE: 468

Ala Gln Asp Trp Tyr Tyr Ala Trp Leu Phe Thr Gly Arg Gly Gly Arg
1               5                   10                  15

Gly Gly Arg Gly Gly
            20

<210> SEQ ID NO 469
<211> LENGTH: 19
<212> TYPE: PRT
<213> ORGANISM: Artificial Sequence
<220> FEATURE:
<223> OTHER INFORMATION: Library Isolate

<400> SEQUENCE: 469

Ala Gln Asp Trp Tyr Tyr Ala Trp Leu Gly Arg Gly Gly Arg Gly Gly
1               5                   10                  15

Arg Gly Gly

<210> SEQ ID NO 470
<211> LENGTH: 22
<212> TYPE: PRT
<213> ORGANISM: Artificial Sequence
<220> FEATURE:
<223> OTHER INFORMATION: Library Isolate

<400> SEQUENCE: 470

Ala Gln Asp Trp Tyr Tyr Asp Glu Ile Leu Gly Arg Gly Gly Arg Gly
1               5                   10                  15

Gly Arg Gly Gly Lys Lys
            20

<210> SEQ ID NO 471
<211> LENGTH: 21
<212> TYPE: PRT
<213> ORGANISM: Artificial Sequence
<220> FEATURE:
<223> OTHER INFORMATION: Library Isolate

<400> SEQUENCE: 471

Gly Asp Ser Arg Val Cys Trp Pro Asp Ser Trp Gly Gly Glu Val Cys
1               5                   10                  15

Phe Arg Tyr Asp Pro
            20

<210> SEQ ID NO 472
<211> LENGTH: 21
<212> TYPE: PRT
<213> ORGANISM: Artificial Sequence
<220> FEATURE:
<223> OTHER INFORMATION: Library Isolate

<400> SEQUENCE: 472

Gly Asp Ser Arg Val Cys Trp Glu Asp Ser Trp Gly Gly Val Glu Cys
1               5                   10                  15

Phe Arg Tyr Asp Pro
            20

<210> SEQ ID NO 473
```

```
<211> LENGTH: 21
<212> TYPE: PRT
<213> ORGANISM: Artificial Sequence
<220> FEATURE:
<223> OTHER INFORMATION: Library Isolate

<400> SEQUENCE: 473

Ala Gln Asp Trp Tyr Tyr Asp Glu Ile Leu Gly Arg Gly Gly Arg Gly
1               5                   10                  15

Gly Arg Gly Gly Lys
        20

<210> SEQ ID NO 474
<211> LENGTH: 28
<212> TYPE: PRT
<213> ORGANISM: Artificial Sequence
<220> FEATURE:
<223> OTHER INFORMATION: Library Isolate

<400> SEQUENCE: 474

Trp Tyr Leu Asp Arg Gln Ala Asp Phe Met Tyr Ser Ala Gln Ala Glu
1               5                   10                  15

Asp Ser Leu Ile Leu His Gly Gly Gly Gly Gly Lys
        20                  25

<210> SEQ ID NO 475
<211> LENGTH: 25
<212> TYPE: PRT
<213> ORGANISM: Artificial Sequence
<220> FEATURE:
<223> OTHER INFORMATION: Library isolate

<400> SEQUENCE: 475

Val Cys Trp Glu Asp Ser Trp Glu Asp Ser Gly Gly Glu Val Cys
1               5                   10                  15

Phe Arg Tyr Asp Pro Gly Gly Gly Lys
        20                  25

<210> SEQ ID NO 476
<211> LENGTH: 22
<212> TYPE: PRT
<213> ORGANISM: Artificial Sequence
<220> FEATURE:
<223> OTHER INFORMATION: Library Isolate

<400> SEQUENCE: 476

Ala Gly Pro Thr Trp Cys Glu Asp Asp Trp Tyr Tyr Cys Trp Leu Phe
1               5                   10                  15

Gly Thr Gly Gly Gly Lys
        20

<210> SEQ ID NO 477
<211> LENGTH: 25
<212> TYPE: PRT
<213> ORGANISM: Artificial Sequence
<220> FEATURE:
<223> OTHER INFORMATION: Library Isolate

<400> SEQUENCE: 477

Gly Asp Ser Arg Val Cys Trp Glu Asp Ser Trp Gly Gly Glu Val Cys
1               5                   10                  15

Phe Arg Tyr Asp Pro Gly Gly Gly Lys
        20                  25

<210> SEQ ID NO 478
```

```
<211> LENGTH: 21
<212> TYPE: PRT
<213> ORGANISM: Artificial Sequence
<220> FEATURE:
<223> OTHER INFORMATION: Synthesized KDR-Binding Polypeptide

<400> SEQUENCE: 478

Ala Gln Asp Trp Tyr Tyr Asp Glu Ile Leu Gly Arg Gly Gly Arg Gly
 1               5                  10                  15

Gly Arg Gly Gly Lys
            20

<210> SEQ ID NO 479
<211> LENGTH: 22
<212> TYPE: PRT
<213> ORGANISM: Artificial Sequence
<220> FEATURE:
<223> OTHER INFORMATION: Library isolate

<400> SEQUENCE: 479

Ala Gly Pro Thr Trp Cys Asp Tyr Asp Trp Glu Tyr Cys Trp Leu Phe
 1               5                  10                  15

Thr Phe Gly Gly Gly Leu
            20

<210> SEQ ID NO 480
<211> LENGTH: 23
<212> TYPE: PRT
<213> ORGANISM: Artificial Sequence
<220> FEATURE:
<223> OTHER INFORMATION: Synthesized KDR-Binding Polypeptide

<400> SEQUENCE: 480

Ala Gly Pro Thr Trp Cys Glu Asp Asp Trp Tyr Tyr Cys Trp Leu Phe
 1               5                  10                  15

Gly Thr Gly Gly Gly Gly Lys
            20

<210> SEQ ID NO 481
<211> LENGTH: 21
<212> TYPE: PRT
<213> ORGANISM: Artificial Sequence
<220> FEATURE:
<223> OTHER INFORMATION: Synthesized KDR-Binding Polypeptide

<400> SEQUENCE: 481

Ala Gly Pro Thr Trp Cys Glu Asp Asp Trp Tyr Tyr Cys Trp Leu Phe
 1               5                  10                  15

Thr Gly Gly Gly Lys
            20

<210> SEQ ID NO 482
<211> LENGTH: 24
<212> TYPE: PRT
<213> ORGANISM: Artificial Sequence
<220> FEATURE:
<223> OTHER INFORMATION: Synthesized KDR-Binding Polypeptide

<400> SEQUENCE: 482

Gly Ser Pro Glu Met Cys Met Met Phe Pro Phe Leu Tyr Pro Cys Asn
 1               5                  10                  15

His His Ala Pro Gly Gly Gly Lys
            20

<210> SEQ ID NO 483
```

```
<211> LENGTH: 24
<212> TYPE: PRT
<213> ORGANISM: Artificial Sequence
<220> FEATURE:
<223> OTHER INFORMATION: Library isolate

<400> SEQUENCE: 483

Gly Ser Phe Phe Pro Cys Trp Arg Ile Asp Arg Phe Gly Tyr Cys His
 1               5                  10                  15

Ala Asn Ala Pro Gly Gly Gly Lys
            20

<210> SEQ ID NO 484
<211> LENGTH: 26
<212> TYPE: PRT
<213> ORGANISM: Artificial Sequence
<220> FEATURE:
<223> OTHER INFORMATION: Library isolate

<400> SEQUENCE: 484

Ala Gln Glu Trp Glu Arg Glu Tyr Phe Val Asp Gly Phe Trp Gly Ser
 1               5                  10                  15

Trp Phe Gly Ile Pro His Gly Gly Gly Lys
            20                  25

<210> SEQ ID NO 485
<211> LENGTH: 26
<212> TYPE: PRT
<213> ORGANISM: Artificial Sequence
<220> FEATURE:
<223> OTHER INFORMATION: Library isolate

<400> SEQUENCE: 485

Gly Asp Tyr Ser Glu Cys Phe Phe Glu Pro Asp Ser Phe Glu Val Lys
 1               5                  10                  15

Cys Tyr Asp Arg Asp Pro Gly Gly Gly Lys
            20                  25

<210> SEQ ID NO 486
<211> LENGTH: 26
<212> TYPE: PRT
<213> ORGANISM: Artificial Sequence
<220> FEATURE:
<223> OTHER INFORMATION: Synthesized KDR-Binding Polypeptide

<400> SEQUENCE: 486

Gly Asp Trp Trp Glu Cys Lys Arg Glu Glu Tyr Arg Asn Thr Thr Trp
 1               5                  10                  15

Cys Ala Trp Ala Asp Pro Gly Gly Gly Lys
            20                  25

<210> SEQ ID NO 487
<211> LENGTH: 25
<212> TYPE: PRT
<213> ORGANISM: Artificial Sequence
<220> FEATURE:
<223> OTHER INFORMATION: Synthesized KDR-Binding Polypeptide

<400> SEQUENCE: 487

Gly Asp Ser Ser Val Cys Phe Glu Tyr Ser Trp Gly Gly Glu Val Cys
 1               5                  10                  15

Phe Arg Tyr Asp Pro Gly Gly Gly Lys
            20                  25

<210> SEQ ID NO 488
```

```
<211> LENGTH: 25
<212> TYPE: PRT
<213> ORGANISM: Artificial Sequence
<220> FEATURE:
<223> OTHER INFORMATION: Synthesized KDR-Binding Polypeptide

<400> SEQUENCE: 488

Gly Asp Ser Arg Val Cys Trp Glu Tyr Ser Trp Gly Gln Ile Cys
1               5                  10                  15

Leu Gly Tyr Asp Pro Gly Gly Gly Lys
            20                  25

<210> SEQ ID NO 489
<211> LENGTH: 25
<212> TYPE: PRT
<213> ORGANISM: Artificial Sequence
<220> FEATURE:
<223> OTHER INFORMATION: Library Isolate

<400> SEQUENCE: 489

Gly Val Asp Phe Arg Cys Glu Trp Ser Asp Trp Gly Glu Val Gly Cys
1               5                  10                  15

Arg Ser Pro Asp Tyr Gly Gly Gly Lys
            20                  25

<210> SEQ ID NO 490
<211> LENGTH: 4
<212> TYPE: PRT
<213> ORGANISM: Artificial Sequence
<220> FEATURE:
<223> OTHER INFORMATION: Binding Motif

<400> SEQUENCE: 490

Ala Trp Tyr Tyr
1

<210> SEQ ID NO 491
<211> LENGTH: 15
<212> TYPE: PRT
<213> ORGANISM: Artificial Sequence
<220> FEATURE:
<223> OTHER INFORMATION: Polypeptide Linker

<400> SEQUENCE: 491

Gly Gly Ser Gly Gly Glu Gly Arg Pro Gly Glu Gly Gly Ser Gly
1               5                  10                  15

<210> SEQ ID NO 492
<211> LENGTH: 16
<212> TYPE: PRT
<213> ORGANISM: Artificial Sequence
<220> FEATURE:
<223> OTHER INFORMATION: Polypeptide Linker

<400> SEQUENCE: 492

Gly Ser Glu Ser Gly Gly Arg Pro Glu Gly Gly Ser Gly Glu Gly Gly
1               5                  10                  15

<210> SEQ ID NO 493
<211> LENGTH: 19
<212> TYPE: PRT
<213> ORGANISM: Artificial Sequence
<220> FEATURE:
<223> OTHER INFORMATION: KDR-Binding Polypeptide

<400> SEQUENCE: 493

Ala Gly Pro Thr Trp Cys Glu Asp Asp Trp Tyr Tyr Cys Trp Leu Phe
```

-continued

```
                1               5                   10                  15

Gly Thr Lys

<210> SEQ ID NO 494
<211> LENGTH: 22
<212> TYPE: PRT
<213> ORGANISM: Artificial Sequence
<220> FEATURE:
<223> OTHER INFORMATION: KDR-Binding Polypeptide

<400> SEQUENCE: 494

Val Cys Trp Glu Asp Ser Trp Gly Gly Glu Val Cys Phe Arg Tyr Asp
1               5                   10                  15

Pro Gly Gly Gly Lys Lys
            20

<210> SEQ ID NO 495
<211> LENGTH: 29
<212> TYPE: PRT
<213> ORGANISM: Artificial Sequence
<220> FEATURE:
<223> OTHER INFORMATION: KDR-Binding Polypeptide

<400> SEQUENCE: 495

Ala Gln Asp Trp Tyr Tyr Asp Glu Ile Leu Ser Met Ala Asp Gln Leu
1               5                   10                  15

Arg His Ala Phe Leu Ser Gly Gly Gly Gly Gly Lys Lys
            20                  25

<210> SEQ ID NO 496
<211> LENGTH: 21
<212> TYPE: PRT
<213> ORGANISM: Artificial Sequence
<220> FEATURE:
<223> OTHER INFORMATION: KDR-Binding Polypeptide

<400> SEQUENCE: 496

Ala Gln Asp Trp Tyr Tyr Glu Ile Leu Gly Arg Gly Gly Arg Gly Gly
1               5                   10                  15

Arg Gly Gly Lys Lys
            20

<210> SEQ ID NO 497
<211> LENGTH: 22
<212> TYPE: PRT
<213> ORGANISM: Artificial Sequence
<220> FEATURE:
<223> OTHER INFORMATION: KDR-Binding Polypeptide

<400> SEQUENCE: 497

Ala Pro Gly Thr Trp Cys Asp Tyr Asp Trp Glu Tyr Cys Trp Leu Gly
1               5                   10                  15

Thr Phe Gly Gly Gly Lys
            20

<210> SEQ ID NO 498
<211> LENGTH: 6
<212> TYPE: PRT
<213> ORGANISM: Artificial Sequence
<220> FEATURE:
<223> OTHER INFORMATION: Carcinoembryonic Antigen-Derived Peptide

<400> SEQUENCE: 498

Tyr Pro Glu Leu Pro Lys
1               5
```

<210> SEQ ID NO 499
<211> LENGTH: 13
<212> TYPE: PRT
<213> ORGANISM: Artificial Sequence
<220> FEATURE:
<223> OTHER INFORMATION: Carcinoembryonic Antigen-Derived Peptide

<400> SEQUENCE: 499

Arg Val Tyr Pro Glu Leu Pro Lys Pro Ser Gly Gly Gly
 1               5                  10

<210> SEQ ID NO 500
<211> LENGTH: 585
<212> TYPE: PRT
<213> ORGANISM: Artificial Sequence
<220> FEATURE:
<223> OTHER INFORMATION: Homo sapiens

<400> SEQUENCE: 500

Asp Ala His Lys Ser Glu Val Ala His Arg Phe Lys Asp Leu Gly Glu
 1               5                  10                  15

Glu Asn Phe Lys Ala Leu Val Leu Ile Ala Phe Ala Gln Tyr Leu Gln
             20                  25                  30

Gln Cys Pro Phe Glu Asp His Val Lys Leu Val Asn Glu Val Thr Glu
         35                  40                  45

Phe Ala Lys Thr Cys Val Ala Asp Glu Ser Ala Glu Asn Cys Asp Lys
     50                  55                  60

Ser Leu His Thr Leu Phe Gly Asp Lys Leu Cys Thr Val Ala Thr Leu
 65                  70                  75                  80

Arg Glu Thr Tyr Gly Glu Met Ala Asp Cys Cys Ala Lys Gln Glu Pro
                 85                  90                  95

Glu Arg Asn Glu Cys Phe Leu Gln His Lys Asp Asp Asn Pro Asn Leu
            100                 105                 110

Pro Arg Leu Val Arg Pro Glu Val Asp Val Met Cys Thr Ala Phe His
        115                 120                 125

Asp Asn Glu Glu Thr Phe Leu Lys Lys Tyr Leu Tyr Glu Ile Ala Arg
    130                 135                 140

Arg His Pro Tyr Phe Tyr Ala Pro Glu Leu Leu Phe Phe Ala Lys Arg
145                 150                 155                 160

Tyr Lys Ala Ala Phe Thr Glu Cys Cys Gln Ala Ala Asp Lys Ala Ala
                165                 170                 175

Cys Leu Leu Pro Lys Leu Asp Glu Leu Arg Asp Glu Gly Lys Ala Ser
            180                 185                 190

Ser Ala Lys Gln Arg Leu Lys Cys Ala Ser Leu Gln Lys Phe Gly Glu
        195                 200                 205

Arg Ala Phe Lys Ala Trp Ala Val Ala Arg Leu Ser Gln Arg Phe Pro
    210                 215                 220

Lys Ala Glu Phe Ala Glu Val Ser Lys Leu Val Thr Asp Leu Thr Lys
225                 230                 235                 240

Val His Thr Glu Cys Cys His Gly Asp Leu Leu Glu Cys Ala Asp Asp
                245                 250                 255

Arg Ala Asp Leu Ala Lys Tyr Ile Cys Glu Asn Gln Asp Ser Ile Ser
            260                 265                 270

Ser Lys Leu Lys Glu Cys Cys Glu Lys Pro Leu Leu Glu Lys Ser His
        275                 280                 285

Cys Ile Ala Glu Val Glu Asn Asp Glu Met Pro Ala Asp Leu Pro Ser
    290                 295                 300

Leu Ala Ala Asp Phe Val Glu Ser Lys Asp Val Cys Lys Asn Tyr Ala
305                 310                 315                 320

Glu Ala Lys Asp Val Phe Leu Gly Met Phe Leu Tyr Glu Tyr Ala Arg
                325                 330                 335

Arg His Pro Asp Tyr Ser Val Val Leu Leu Arg Leu Ala Lys Thr
            340                 345                 350

Tyr Lys Thr Thr Leu Glu Lys Cys Cys Ala Ala Ala Asp Pro His Glu
        355                 360                 365

Cys Tyr Ala Lys Val Phe Asp Glu Phe Lys Pro Leu Val Glu Glu Pro
    370                 375                 380

Gln Asn Leu Ile Lys Gln Asn Cys Glu Leu Phe Glu Gln Leu Gly Glu
385                 390                 395                 400

Tyr Lys Phe Gln Asn Ala Leu Leu Val Arg Tyr Thr Lys Lys Val Pro
                405                 410                 415

Gln Val Ser Thr Pro Thr Leu Val Glu Val Ser Arg Asn Leu Gly Lys
            420                 425                 430

Val Gly Ser Lys Cys Cys Lys His Pro Glu Ala Lys Arg Met Pro Cys
        435                 440                 445

Ala Glu Asp Tyr Leu Ser Val Val Leu Asn Gln Leu Cys Val Leu His
    450                 455                 460

Glu Lys Thr Pro Val Ser Asp Arg Val Thr Lys Cys Cys Thr Glu Ser
465                 470                 475                 480

Leu Val Asn Arg Arg Pro Cys Phe Ser Ala Leu Glu Val Asp Glu Thr
                485                 490                 495

Tyr Val Pro Lys Glu Phe Asn Ala Glu Thr Phe Thr Phe His Ala Asp
            500                 505                 510

Ile Cys Thr Leu Ser Glu Lys Glu Arg Gln Ile Lys Lys Gln Thr Ala
        515                 520                 525

Leu Val Glu Leu Val Lys His Lys Pro Lys Ala Thr Lys Glu Gln Leu
    530                 535                 540

Lys Ala Val Met Asp Asp Phe Ala Ala Phe Val Glu Lys Cys Cys Lys
545                 550                 555                 560

Ala Asp Asp Lys Glu Thr Cys Phe Ala Glu Glu Gly Lys Lys Leu Val
                565                 570                 575

Ala Ala Ser Arg Ala Ala Leu Gly Leu
            580                 585

<210> SEQ ID NO 501
<211> LENGTH: 690
<212> TYPE: PRT
<213> ORGANISM: Artificial Sequence
<220> FEATURE:
<223> OTHER INFORMATION: HSA-Linked Dimer

<400> SEQUENCE: 501

Ala Gly Asp Trp Trp Val Glu Cys Arg Val Gly Thr Gly Leu Cys Tyr
1               5                   10                  15

Arg Tyr Asp Thr Gly Thr Gly Gly Lys Pro Gly Gly Ser Gly Gly
            20                  25                  30

Glu Gly Gly Ser Gly Gly Glu Gly Gly Arg Pro Gly Gly Ser Glu Gly
        35                  40                  45

Gly Thr Gly Gly Asp Ala His Lys Ser Glu Val Ala His Arg Phe Lys
    50                  55                  60

Asp Leu Gly Glu Glu Asn Phe Lys Ala Leu Val Leu Ile Ala Phe Ala
65                  70                  75                  80

-continued

Gln Tyr Leu Gln Gln Cys Pro Phe Glu Asp His Val Lys Leu Val Asn
                85                  90                  95

Glu Val Thr Glu Phe Ala Lys Thr Cys Val Ala Asp Glu Ser Ala Glu
            100                 105                 110

Asn Cys Asp Lys Ser Leu His Thr Leu Phe Gly Asp Lys Leu Cys Thr
        115                 120                 125

Val Ala Thr Leu Arg Glu Thr Tyr Gly Glu Met Ala Asp Cys Cys Ala
    130                 135                 140

Lys Gln Glu Pro Glu Arg Asn Glu Cys Phe Leu Gln His Lys Asp Asp
145                 150                 155                 160

Asn Pro Asn Leu Pro Arg Leu Val Arg Pro Glu Val Asp Val Met Cys
            165                 170                 175

Thr Ala Phe His Asp Asn Glu Glu Thr Phe Leu Lys Lys Tyr Leu Tyr
        180                 185                 190

Glu Ile Ala Arg Arg His Pro Tyr Phe Tyr Ala Pro Glu Leu Leu Phe
    195                 200                 205

Phe Ala Lys Arg Tyr Lys Ala Ala Phe Thr Glu Cys Cys Gln Ala Ala
210                 215                 220

Asp Lys Ala Ala Cys Leu Leu Pro Lys Leu Asp Glu Leu Arg Asp Glu
225                 230                 235                 240

Gly Lys Ala Ser Ser Ala Lys Gln Arg Leu Lys Cys Ala Ser Leu Gln
            245                 250                 255

Lys Phe Gly Glu Arg Ala Phe Lys Ala Trp Ala Val Ala Arg Leu Ser
        260                 265                 270

Gln Arg Phe Pro Lys Ala Glu Phe Ala Glu Val Ser Lys Leu Val Thr
    275                 280                 285

Asp Leu Thr Lys Val His Thr Glu Cys Cys His Gly Asp Leu Leu Glu
290                 295                 300

Cys Ala Asp Asp Arg Ala Asp Leu Ala Lys Tyr Ile Cys Glu Asn Gln
305                 310                 315                 320

Asp Ser Ile Ser Ser Lys Leu Lys Glu Cys Cys Glu Lys Pro Leu Leu
            325                 330                 335

Glu Lys Ser His Cys Ile Ala Glu Val Glu Asn Asp Glu Met Pro Ala
        340                 345                 350

Asp Leu Pro Ser Leu Ala Ala Asp Phe Val Glu Ser Lys Asp Val Cys
    355                 360                 365

Lys Asn Tyr Ala Glu Ala Lys Asp Val Phe Leu Gly Met Phe Leu Tyr
370                 375                 380

Glu Tyr Ala Arg Arg His Pro Asp Tyr Ser Val Val Leu Leu Leu Arg
385                 390                 395                 400

Leu Ala Lys Thr Tyr Lys Thr Thr Leu Glu Lys Cys Cys Ala Ala Ala
            405                 410                 415

Asp Pro His Glu Cys Tyr Ala Lys Val Phe Asp Glu Phe Lys Pro Leu
        420                 425                 430

Val Glu Glu Pro Gln Asn Leu Ile Lys Gln Asn Cys Glu Leu Phe Glu
    435                 440                 445

Gln Leu Gly Glu Tyr Lys Phe Gln Asn Ala Leu Leu Val Arg Tyr Thr
450                 455                 460

Lys Lys Val Pro Gln Val Ser Thr Pro Thr Leu Val Glu Val Ser Arg
465                 470                 475                 480

Asn Leu Gly Lys Val Gly Ser Lys Cys Cys Lys His Pro Glu Ala Lys
            485                 490                 495

Arg Met Pro Cys Ala Glu Asp Tyr Leu Ser Val Val Leu Asn Gln Leu
        500                 505                 510

```
Cys Val Leu His Glu Lys Thr Pro Val Ser Asp Arg Val Thr Lys Cys
        515                 520                 525

Cys Thr Glu Ser Leu Val Asn Arg Arg Pro Cys Phe Ser Ala Leu Glu
        530                 535                 540

Val Asp Glu Thr Tyr Val Pro Lys Glu Phe Asn Ala Glu Thr Phe Thr
545                 550                 555                 560

Phe His Ala Asp Ile Cys Thr Leu Ser Glu Lys Glu Arg Gln Ile Lys
                565                 570                 575

Lys Gln Thr Ala Leu Val Glu Leu Val Lys His Lys Pro Lys Ala Thr
            580                 585                 590

Lys Glu Gln Leu Lys Ala Val Met Asp Asp Phe Ala Ala Phe Val Glu
        595                 600                 605

Lys Cys Cys Lys Ala Asp Asp Lys Glu Thr Cys Phe Ala Glu Glu Gly
        610                 615                 620

Lys Lys Leu Val Ala Ala Ser Arg Ala Ala Leu Gly Leu Gly Gly Ser
625                 630                 635                 640

Gly Gly Glu Gly Gly Ser Gly Gly Gly Ser Gly Pro Gly Glu
                645                 650                 655

Gly Gly Glu Gly Ser Gly Gly Arg Pro Gly Asp Ser Arg Val Cys Trp
                660                 665                 670

Glu Asp Ser Trp Gly Gly Glu Val Cys Phe Arg Tyr Asp Pro Gly Gly
            675                 680                 685

Gly Lys
    690

<210> SEQ ID NO 502
<211> LENGTH: 19
<212> TYPE: PRT
<213> ORGANISM: Artificial Sequence
<220> FEATURE:
<223> OTHER INFORMATION: Mature HSA

<400> SEQUENCE: 502

Trp Gln Pro Cys Pro Trp Glu Ser Trp Thr Phe Cys Trp Asp Pro Gly
1               5                   10                  15

Gly Gly Lys

<210> SEQ ID NO 503
<211> LENGTH: 5
<212> TYPE: PRT
<213> ORGANISM: Artificial Sequence
<220> FEATURE:
<223> OTHER INFORMATION: NP-1 Binding Peptide

<400> SEQUENCE: 503

Thr Lys Pro Pro Arg
1               5

<210> SEQ ID NO 504
<211> LENGTH: 21
<212> TYPE: PRT
<213> ORGANISM: Artificial Sequence
<220> FEATURE:
<223> OTHER INFORMATION: Library Isolate

<400> SEQUENCE: 504

Glu Arg Val Thr Thr Cys Trp Pro Gly Glu Tyr Gly Gly Val Glu Cys
1               5                   10                  15

Tyr Ser Val Ala Tyr
            20
```

<210> SEQ ID NO 505
<211> LENGTH: 21
<212> TYPE: PRT
<213> ORGANISM: Artificial Sequence
<220> FEATURE:
<223> OTHER INFORMATION: Library Isolate

<400> SEQUENCE: 505

Gly Ser Asn Met Val Cys Met Asp Asp Ser Tyr Gly Gly Thr Thr Cys
1               5                   10                  15

Tyr Ser Met Ala Pro
            20

<210> SEQ ID NO 506
<211> LENGTH: 21
<212> TYPE: PRT
<213> ORGANISM: Artificial Sequence
<220> FEATURE:
<223> OTHER INFORMATION: Library Isolate

<400> SEQUENCE: 506

Gly Ser Tyr Asn Gln Cys Tyr Gly Asp Tyr Trp Gly Gly Glu Thr Cys
1               5                   10                  15

Tyr Leu Ile Ala Pro
            20

<210> SEQ ID NO 507
<211> LENGTH: 21
<212> TYPE: PRT
<213> ORGANISM: Artificial Sequence
<220> FEATURE:
<223> OTHER INFORMATION: Library Isolate

<400> SEQUENCE: 507

Gly Ser Arg Val Asn Cys Gly Ala Glu Asp Gly Leu Ser Phe Leu Cys
1               5                   10                  15

Met Met Asp Ala Pro
            20

<210> SEQ ID NO 508
<211> LENGTH: 21
<212> TYPE: PRT
<213> ORGANISM: Artificial Sequence
<220> FEATURE:
<223> OTHER INFORMATION: Library Isolate

<400> SEQUENCE: 508

Gly Ser Ile Trp Asp Cys Gln Ile Ser Glu Tyr Gly Gly Glu Asp Cys
1               5                   10                  15

Tyr Leu Val Ala Pro
            20

<210> SEQ ID NO 509
<211> LENGTH: 21
<212> TYPE: PRT
<213> ORGANISM: Artificial Sequence
<220> FEATURE:
<223> OTHER INFORMATION: Library Isolate

<400> SEQUENCE: 509

Gly Ser Tyr Trp His Cys Met Asp Asp Phe Phe Gly Gly Glu Thr Cys
1               5                   10                  15

Phe Ala Thr Ala Pro
            20

-continued

```
<210> SEQ ID NO 510
<211> LENGTH: 21
<212> TYPE: PRT
<213> ORGANISM: Artificial Sequence
<220> FEATURE:
<223> OTHER INFORMATION: Library Isolate

<400> SEQUENCE: 510

Gly Ser Gly Glu Tyr Cys Phe Pro Ser Ile Tyr Gly Gly Glu Thr Cys
1               5                   10                  15

Tyr Ala His Ala Pro
            20

<210> SEQ ID NO 511
<211> LENGTH: 21
<212> TYPE: PRT
<213> ORGANISM: Artificial Sequence
<220> FEATURE:
<223> OTHER INFORMATION: Library Isolate

<400> SEQUENCE: 511

Gly Ser Glu Gln Leu Cys Phe Glu Tyr Gln Tyr Gly Gly Val Glu Cys
1               5                   10                  15

Phe Gly Pro Ala Pro
            20

<210> SEQ ID NO 512
<211> LENGTH: 21
<212> TYPE: PRT
<213> ORGANISM: Artificial Sequence
<220> FEATURE:
<223> OTHER INFORMATION: Library Isolate

<400> SEQUENCE: 512

Gly Ser Thr Gly Val Cys Ser Pro Ala Pro Tyr Gly Gly Glu Val Cys
1               5                   10                  15

Tyr His Phe Ala Pro
            20

<210> SEQ ID NO 513
<211> LENGTH: 21
<212> TYPE: PRT
<213> ORGANISM: Artificial Sequence
<220> FEATURE:
<223> OTHER INFORMATION: Library Isolate

<400> SEQUENCE: 513

Gly Ser His Asp Glu Cys Trp Glu Asp Ile Tyr Gly Gly Phe Thr Cys
1               5                   10                  15

Met Leu Met Ala Pro
            20

<210> SEQ ID NO 514
<211> LENGTH: 21
<212> TYPE: PRT
<213> ORGANISM: Artificial Sequence
<220> FEATURE:
<223> OTHER INFORMATION: Library Isolate

<400> SEQUENCE: 514

Gly Ser Gln His Thr Cys Phe Ser Asp Pro Tyr Gly Gly Glu Val Cys
1               5                   10                  15

Tyr Ala Asp Ala Pro
            20
```

<210> SEQ ID NO 515
<211> LENGTH: 21
<212> TYPE: PRT
<213> ORGANISM: Artificial Sequence
<220> FEATURE:
<223> OTHER INFORMATION: Library Isolate

<400> SEQUENCE: 515

Gly Ser Trp Glu Val Cys Glu Asn Ser Asn Tyr Gly Gly Gln Ile Cys
1               5                   10                  15

Tyr Trp Phe Ala Pro
            20

<210> SEQ ID NO 516
<211> LENGTH: 21
<212> TYPE: PRT
<213> ORGANISM: Artificial Sequence
<220> FEATURE:
<223> OTHER INFORMATION: Library Isolate

<400> SEQUENCE: 516

Gly Ser His Glu Met Cys Trp Ser Asp Val Trp Gly Gly Leu Thr Cys
1               5                   10                  15

Met Thr Met Ala Pro
            20

<210> SEQ ID NO 517
<211> LENGTH: 21
<212> TYPE: PRT
<213> ORGANISM: Artificial Sequence
<220> FEATURE:
<223> OTHER INFORMATION: Library Isolate

<400> SEQUENCE: 517

Gly Ser Leu Ser Leu Cys Lys Phe Phe Gly Asp Gly Ser Tyr Tyr Cys
1               5                   10                  15

Glu Pro Pro Ala Pro
            20

<210> SEQ ID NO 518
<211> LENGTH: 21
<212> TYPE: PRT
<213> ORGANISM: Artificial Sequence
<220> FEATURE:
<223> OTHER INFORMATION: Library Isolate

<400> SEQUENCE: 518

Gly Ser Thr Arg Phe Cys Glu Pro Tyr Gln Trp Gly Gly Glu Val Cys
1               5                   10                  15

Tyr Trp Lys Ala Pro
            20

<210> SEQ ID NO 519
<211> LENGTH: 21
<212> TYPE: PRT
<213> ORGANISM: Artificial Sequence
<220> FEATURE:
<223> OTHER INFORMATION: Library Isolate

<400> SEQUENCE: 519

Gly Ser Phe Ser Thr Cys Ala Thr Phe Pro Trp Thr Lys Phe Cys
1               5                   10                  15

Ser Asn Met Ala Pro
            20

<210> SEQ ID NO 520
<211> LENGTH: 21
<212> TYPE: PRT
<213> ORGANISM: Artificial Sequence
<220> FEATURE:
<223> OTHER INFORMATION: Library Isolate

<400> SEQUENCE: 520

Gly Ser His Glu Leu Cys Phe Glu Gly Thr Tyr Gly Gly Glu Val Cys
1               5                   10                  15

Phe Ser Met Ala Pro
            20

<210> SEQ ID NO 521
<211> LENGTH: 21
<212> TYPE: PRT
<213> ORGANISM: Artificial Sequence
<220> FEATURE:
<223> OTHER INFORMATION: Library Isolate

<400> SEQUENCE: 521

Gly Ser Leu Trp His Cys Phe Asn Asp Val Tyr Gly Gly Glu Asn Cys
1               5                   10                  15

Ile Pro Phe Ala Pro
            20

<210> SEQ ID NO 522
<211> LENGTH: 21
<212> TYPE: PRT
<213> ORGANISM: Artificial Sequence
<220> FEATURE:
<223> OTHER INFORMATION: Library Isolate

<400> SEQUENCE: 522

Gly Ser Gln Gln Tyr Cys Ile Pro Ala Glu Tyr Gly Gly Met Glu Cys
1               5                   10                  15

Tyr Pro Phe Ala Pro
            20

<210> SEQ ID NO 523
<211> LENGTH: 21
<212> TYPE: PRT
<213> ORGANISM: Artificial Sequence
<220> FEATURE:
<223> OTHER INFORMATION: Library Isolate

<400> SEQUENCE: 523

Gly Ser Ile Gln Asn Cys Trp Lys Tyr Glu Phe Gly Gly Ile Val Cys
1               5                   10                  15

Met Asp Met Ala Pro
            20

<210> SEQ ID NO 524
<211> LENGTH: 21
<212> TYPE: PRT
<213> ORGANISM: Artificial Sequence
<220> FEATURE:
<223> OTHER INFORMATION: Library Isolate

<400> SEQUENCE: 524

Gly Ser Val Ser Gly Cys Lys Glu Phe Trp Asn Ser Ser Gly Arg Cys
1               5                   10                  15

Phe Thr His Ala Pro
            20

```
<210> SEQ ID NO 525
<211> LENGTH: 21
<212> TYPE: PRT
<213> ORGANISM: Artificial Sequence
<220> FEATURE:
<223> OTHER INFORMATION: Library Isolate

<400> SEQUENCE: 525

Gly Ser Leu Trp Glu Cys Arg Gly Asp Phe Tyr Gly Gly Glu Val Cys
 1               5                  10                  15

Phe Asn Tyr Ala Pro
            20

<210> SEQ ID NO 526
<211> LENGTH: 21
<212> TYPE: PRT
<213> ORGANISM: Artificial Sequence
<220> FEATURE:
<223> OTHER INFORMATION: Library Isolate

<400> SEQUENCE: 526

Gly Ser Asn Leu Ile Cys Tyr Asp Tyr Tyr Gly Gly Gln Asp Cys
 1               5                  10                  15

Tyr His Asp Ala Pro
            20

<210> SEQ ID NO 527
<211> LENGTH: 21
<212> TYPE: PRT
<213> ORGANISM: Artificial Sequence
<220> FEATURE:
<223> OTHER INFORMATION: Library Isolate

<400> SEQUENCE: 527

Gly Ser Glu Gly Thr Cys Glu Glu Tyr Gln Tyr Gly Gly Ile Val Cys
 1               5                  10                  15

Trp Trp Gly Ala Pro
            20

<210> SEQ ID NO 528
<211> LENGTH: 21
<212> TYPE: PRT
<213> ORGANISM: Artificial Sequence
<220> FEATURE:
<223> OTHER INFORMATION: Library Isolate

<400> SEQUENCE: 528

Pro Gly Ser Gly Asp Cys Asp Trp Tyr Tyr Glu Trp Leu Phe Asp Cys
 1               5                  10                  15

Pro Leu Asn Ala Pro
            20

<210> SEQ ID NO 529
<211> LENGTH: 21
<212> TYPE: PRT
<213> ORGANISM: Artificial Sequence
<220> FEATURE:
<223> OTHER INFORMATION: Library Isolate

<400> SEQUENCE: 529

Gly Ser Asp Gln Met Cys Phe Asn Glu Ser Phe Gly Gly Gln Ile Cys
 1               5                  10                  15

Phe Tyr Ser Ala Pro
            20
```

```
<210> SEQ ID NO 530
<211> LENGTH: 21
<212> TYPE: PRT
<213> ORGANISM: Artificial Sequence
<220> FEATURE:
<223> OTHER INFORMATION: Library Isolate

<400> SEQUENCE: 530

Gly Ser Gly Met Ala Cys Met Ser Asp Pro Tyr Gly Gly Gln Val Cys
1               5                   10                  15

Tyr Ala Ile Ala Pro
            20

<210> SEQ ID NO 531
<211> LENGTH: 21
<212> TYPE: PRT
<213> ORGANISM: Artificial Sequence
<220> FEATURE:
<223> OTHER INFORMATION: Library Isolate

<400> SEQUENCE: 531

Gly Ser Glu Leu Thr Cys Trp Asp Ser Ala Tyr Gly Gly Asn Glu Cys
1               5                   10                  15

Phe Phe Phe Ala Pro
            20

<210> SEQ ID NO 532
<211> LENGTH: 21
<212> TYPE: PRT
<213> ORGANISM: Artificial Sequence
<220> FEATURE:
<223> OTHER INFORMATION: Library Isolate

<400> SEQUENCE: 532

Gly Ser His Phe Leu Cys Val Lys Glu Met Glu Gly Gly Glu Thr Cys
1               5                   10                  15

Tyr Tyr Ser Ala Pro
            20

<210> SEQ ID NO 533
<211> LENGTH: 21
<212> TYPE: PRT
<213> ORGANISM: Artificial Sequence
<220> FEATURE:
<223> OTHER INFORMATION: Library Isolate

<400> SEQUENCE: 533

Gly Ser Trp Glu Ile Cys Phe Ala Gly Pro Tyr Gly Gly Ser Trp Cys
1               5                   10                  15

Ile Pro Glu Ala Pro
            20

<210> SEQ ID NO 534
<211> LENGTH: 21
<212> TYPE: PRT
<213> ORGANISM: Artificial Sequence
<220> FEATURE:
<223> OTHER INFORMATION: Library Isolate

<400> SEQUENCE: 534

Gly Ser Ala Gln Tyr Cys Met Glu Ser Tyr Tyr Gly Gly Phe Thr Cys
1               5                   10                  15

Val Thr Leu Ala Pro
            20
```

<210> SEQ ID NO 535
<211> LENGTH: 21
<212> TYPE: PRT
<213> ORGANISM: Artificial Sequence
<220> FEATURE:
<223> OTHER INFORMATION: Library Isolate

<400> SEQUENCE: 535

Gly Ser Phe Asn Ala Cys Gly Phe Glu Glu Gly Leu Glu Trp Met Cys
1               5                   10                  15

Tyr Arg Gln Ala Pro
            20

<210> SEQ ID NO 536
<211> LENGTH: 21
<212> TYPE: PRT
<213> ORGANISM: Artificial Sequence
<220> FEATURE:
<223> OTHER INFORMATION: Library Isolate

<400> SEQUENCE: 536

Gly Ser Lys Leu Leu Cys Gln Tyr Trp Glu His Glu Trp Trp Pro Cys
1               5                   10                  15

Met Asn Glu Ala Pro
            20

<210> SEQ ID NO 537
<211> LENGTH: 21
<212> TYPE: PRT
<213> ORGANISM: Artificial Sequence
<220> FEATURE:
<223> OTHER INFORMATION: Library Isolate

<400> SEQUENCE: 537

Gly Ser Asn Met Asn Cys Gly Ala Glu Gln Gly Leu Glu Ser Leu Cys
1               5                   10                  15

Gly Trp Arg Ala Pro
            20

<210> SEQ ID NO 538
<211> LENGTH: 21
<212> TYPE: PRT
<213> ORGANISM: Artificial Sequence
<220> FEATURE:
<223> OTHER INFORMATION: Library Isolate

<400> SEQUENCE: 538

Gly Ser Asn Trp Val Cys Leu Ser Glu Gly Tyr Gly Gly Met Thr Cys
1               5                   10                  15

Tyr Pro Ser Ala Pro
            20

<210> SEQ ID NO 539
<211> LENGTH: 21
<212> TYPE: PRT
<213> ORGANISM: Artificial Sequence
<220> FEATURE:
<223> OTHER INFORMATION: Library Isolate

<400> SEQUENCE: 539

Gly Ser Pro Ser Thr Cys Ile Tyr Ser Ser Gly Leu Ile Val Asp Cys
1               5                   10                  15

Gly Leu Leu Ala Pro
            20

```
<210> SEQ ID NO 540
<211> LENGTH: 21
<212> TYPE: PRT
<213> ORGANISM: Artificial Sequence
<220> FEATURE:
<223> OTHER INFORMATION: Library Isolate

<400> SEQUENCE: 540

Gly Ser Thr Gln His Cys Trp Pro Ser Glu Tyr Gly Gly Met Thr Cys
1               5                   10                  15

Val Pro Ala Ala Pro
            20

<210> SEQ ID NO 541
<211> LENGTH: 21
<212> TYPE: PRT
<213> ORGANISM: Artificial Sequence
<220> FEATURE:
<223> OTHER INFORMATION: Library Isolate

<400> SEQUENCE: 541

Gly Ser Thr Trp Ala Cys Glu Glu Ile Ser Ala His His Thr Lys Cys
1               5                   10                  15

Thr Tyr Gln Ala Pro
            20

<210> SEQ ID NO 542
<211> LENGTH: 21
<212> TYPE: PRT
<213> ORGANISM: Artificial Sequence
<220> FEATURE:
<223> OTHER INFORMATION: Library Isolate

<400> SEQUENCE: 542

Gly Ser Tyr Thr Glu Cys Trp Glu Glu Asp Tyr Gly Gly Val Thr Cys
1               5                   10                  15

Phe Asn Val Ala Pro
            20

<210> SEQ ID NO 543
<211> LENGTH: 21
<212> TYPE: PRT
<213> ORGANISM: Artificial Sequence
<220> FEATURE:
<223> OTHER INFORMATION: Library Isolate

<400> SEQUENCE: 543

Gly Ser Asp Lys Phe Cys Phe Lys Asp Pro Trp Gly Gly Val Thr Cys
1               5                   10                  15

Tyr His Leu Ala Pro
            20

<210> SEQ ID NO 544
<211> LENGTH: 21
<212> TYPE: PRT
<213> ORGANISM: Artificial Sequence
<220> FEATURE:
<223> OTHER INFORMATION: Library Isolate

<400> SEQUENCE: 544

Gly Ser Asp Leu Asp Cys Trp Thr Asp Pro Tyr Gly Gly Glu Val Cys
1               5                   10                  15

Tyr Trp His Ala Pro
            20
```

```
<210> SEQ ID NO 545
<211> LENGTH: 21
<212> TYPE: PRT
<213> ORGANISM: Artificial Sequence
<220> FEATURE:
<223> OTHER INFORMATION: Library Isolate

<400> SEQUENCE: 545

Gly Ser Asp Tyr Glu Cys Tyr Asn Ala Trp Phe Gly Tyr Phe Asp Cys
1               5                   10                  15

Pro Gly Asp Ala Pro
            20

<210> SEQ ID NO 546
<211> LENGTH: 21
<212> TYPE: PRT
<213> ORGANISM: Artificial Sequence
<220> FEATURE:
<223> OTHER INFORMATION: Library Isolate

<400> SEQUENCE: 546

Gly Ser Leu Ser Thr Cys Trp Lys Gln Ala Tyr Gly Gly Val Trp Cys
1               5                   10                  15

Val Asp His Ala Pro
            20

<210> SEQ ID NO 547
<211> LENGTH: 21
<212> TYPE: PRT
<213> ORGANISM: Artificial Sequence
<220> FEATURE:
<223> OTHER INFORMATION: Library Isolate

<400> SEQUENCE: 547

Gly Ser Met Gln Leu Cys Arg Gln Trp Ala Tyr Gly Gly Gln Thr Cys
1               5                   10                  15

Tyr Trp Tyr Ala Pro
            20

<210> SEQ ID NO 548
<211> LENGTH: 21
<212> TYPE: PRT
<213> ORGANISM: Artificial Sequence
<220> FEATURE:
<223> OTHER INFORMATION: Library Isolate

<400> SEQUENCE: 548

Gly Ser Asn Gln Leu Cys Ile Thr Ala Gln Phe Gly Gly Gln Asp Cys
1               5                   10                  15

Tyr Pro Ile Ala Pro
            20

<210> SEQ ID NO 549
<211> LENGTH: 21
<212> TYPE: PRT
<213> ORGANISM: Artificial Sequence
<220> FEATURE:
<223> OTHER INFORMATION: Library Isolate

<400> SEQUENCE: 549

Gly Ser Pro Met Trp Cys Ala Pro Trp Pro Trp Gly Gly Glu His Cys
1               5                   10                  15

Val Gly Ser Ala Pro
            20
```

<210> SEQ ID NO 550
<211> LENGTH: 21
<212> TYPE: PRT
<213> ORGANISM: Artificial Sequence
<220> FEATURE:
<223> OTHER INFORMATION: Library Isolate

<400> SEQUENCE: 550

Gly Ser Gln Leu Leu Cys Gly Ser Glu Pro Glu Leu Ala Trp Met Cys
 1               5                  10                  15
Glu Gln Gly Ala Pro
            20

<210> SEQ ID NO 551
<211> LENGTH: 21
<212> TYPE: PRT
<213> ORGANISM: Artificial Sequence
<220> FEATURE:
<223> OTHER INFORMATION: Library Isolate

<400> SEQUENCE: 551

Gly Ser Gln Arg Gln Cys Trp Asp Asp Tyr Phe Gly Gly Ile Ile Cys
 1               5                  10                  15
Tyr Val Ile Asp Ala
            20

<210> SEQ ID NO 552
<211> LENGTH: 21
<212> TYPE: PRT
<213> ORGANISM: Artificial Sequence
<220> FEATURE:
<223> OTHER INFORMATION: Library Isolate

<400> SEQUENCE: 552

Gly Ser Arg Glu Val Cys Trp Gln Asp Phe Phe Gly Gly Met Val Cys
 1               5                  10                  15
Val Arg Asp Ala Pro
            20

<210> SEQ ID NO 553
<211> LENGTH: 21
<212> TYPE: PRT
<213> ORGANISM: Artificial Sequence
<220> FEATURE:
<223> OTHER INFORMATION: Library Isolate

<400> SEQUENCE: 553

Gly Ser Ser Gln Trp Cys Gln Arg Asp Phe Trp Gly Gly Asp Ile Cys
 1               5                  10                  15
Ile Asn Leu Ala Pro
            20

<210> SEQ ID NO 554
<211> LENGTH: 21
<212> TYPE: PRT
<213> ORGANISM: Artificial Sequence
<220> FEATURE:
<223> OTHER INFORMATION: Library Isolate

<400> SEQUENCE: 554

Gly Ser Thr Asp Ile Cys Trp Pro Gly Ser Tyr Gly Gly Glu Ile Cys
 1               5                  10                  15
Ile Pro Arg Ala Pro
            20

```
<210> SEQ ID NO 555
<211> LENGTH: 21
<212> TYPE: PRT
<213> ORGANISM: Artificial Sequence
<220> FEATURE:
<223> OTHER INFORMATION: Library Isolate

<400> SEQUENCE: 555

Gly Ser Thr Glu Tyr Cys Trp Pro Glu Pro His Gly Gly Gln Ala Cys
1               5                   10                  15

Ile Leu Leu Ala Pro
            20

<210> SEQ ID NO 556
<211> LENGTH: 21
<212> TYPE: PRT
<213> ORGANISM: Artificial Sequence
<220> FEATURE:
<223> OTHER INFORMATION: Library Isolate

<400> SEQUENCE: 556

Gly Ser Thr His Phe Cys Ile Asp Tyr Ile Trp Gly Gly Lys His Cys
1               5                   10                  15

Ile Ala Asp Ala Pro
            20

<210> SEQ ID NO 557
<211> LENGTH: 21
<212> TYPE: PRT
<213> ORGANISM: Artificial Sequence
<220> FEATURE:
<223> OTHER INFORMATION: Library Isolate

<400> SEQUENCE: 557

Gly Ser Thr Met Met Cys Trp Pro Ala His Tyr Gly Gly Asp Glu Cys
1               5                   10                  15

Phe Ala Leu Ala Pro
            20

<210> SEQ ID NO 558
<211> LENGTH: 21
<212> TYPE: PRT
<213> ORGANISM: Artificial Sequence
<220> FEATURE:
<223> OTHER INFORMATION: Library Isolate

<400> SEQUENCE: 558

Gly Ser Thr Gln Met Cys Phe Pro His Gln Tyr Gly Gly Gln Ser Cys
1               5                   10                  15

Tyr Ser Phe Ala Pro
            20

<210> SEQ ID NO 559
<211> LENGTH: 21
<212> TYPE: PRT
<213> ORGANISM: Artificial Sequence
<220> FEATURE:
<223> OTHER INFORMATION: Library Isolate

<400> SEQUENCE: 559

Gly Ser Val Glu Gly Cys Trp Val Glu Asp Gln Thr Ser Pro Phe Cys
1               5                   10                  15

Trp Ile Asp Ala Pro
            20
```

<210> SEQ ID NO 560
<211> LENGTH: 21
<212> TYPE: PRT
<213> ORGANISM: Artificial Sequence
<220> FEATURE:
<223> OTHER INFORMATION: Library Isolate

<400> SEQUENCE: 560

Gly Ser Trp Tyr Thr Cys Trp Asp Glu Ala Ser Gly Gly Gln Val Cys
1               5                   10                  15

Tyr Gln Leu Ala Pro
            20

<210> SEQ ID NO 561
<211> LENGTH: 21
<212> TYPE: PRT
<213> ORGANISM: Artificial Sequence
<220> FEATURE:
<223> OTHER INFORMATION: Library Isolate

<400> SEQUENCE: 561

Gly Ser Tyr Asn Leu Cys Tyr Pro Glu Ile Tyr Gly Gly Gln Val Cys
1               5                   10                  15

Tyr Arg Met Ala Pro
            20

<210> SEQ ID NO 562
<211> LENGTH: 21
<212> TYPE: PRT
<213> ORGANISM: Artificial Sequence
<220> FEATURE:
<223> OTHER INFORMATION: Library Isolate

<400> SEQUENCE: 562

Gly Ser Tyr Ser Gln Cys Phe Pro Asp Pro Phe Gly Gly Thr Thr Cys
1               5                   10                  15

Phe Val Ser Ala Pro
            20

<210> SEQ ID NO 563
<211> LENGTH: 21
<212> TYPE: PRT
<213> ORGANISM: Artificial Sequence
<220> FEATURE:
<223> OTHER INFORMATION: Library Isolate

<400> SEQUENCE: 563

Gly Ser Ser Met Gln Cys Phe Asn Arg Val Ser Gln Leu Val Asp Cys
1               5                   10                  15

Glu Thr Ala Ala Pro
            20

<210> SEQ ID NO 564
<211> LENGTH: 21
<212> TYPE: PRT
<213> ORGANISM: Artificial Sequence
<220> FEATURE:
<223> OTHER INFORMATION: Library Isolate

<400> SEQUENCE: 564

Gly Ser Ala Lys Thr Cys Arg Ser Tyr Trp Ala Gln Ser Gly Tyr Cys
1               5                   10                  15

Tyr Glu Tyr Ala Pro
            20

```
<210> SEQ ID NO 565
<211> LENGTH: 21
<212> TYPE: PRT
<213> ORGANISM: Artificial Sequence
<220> FEATURE:
<223> OTHER INFORMATION: Library Isolate

<400> SEQUENCE: 565

Gly Ser Ala Gln Thr Cys Trp Asp Tyr Val Tyr Gly Gly Phe Phe Cys
 1               5                   10                  15

Leu Asn Thr Ala Pro
            20

<210> SEQ ID NO 566
<211> LENGTH: 21
<212> TYPE: PRT
<213> ORGANISM: Artificial Sequence
<220> FEATURE:
<223> OTHER INFORMATION: Library Isolate

<400> SEQUENCE: 566

Gly Ser Ala Trp Asp Cys Phe Gln Gln Asp Thr Tyr Ser Thr His Cys
 1               5                   10                  15

His Trp Arg Ala Pro
            20

<210> SEQ ID NO 567
<211> LENGTH: 21
<212> TYPE: PRT
<213> ORGANISM: Artificial Sequence
<220> FEATURE:
<223> OTHER INFORMATION: Library Isolate

<400> SEQUENCE: 567

Gly Ser Ala Trp Asn Cys Glu Met Leu Asp Pro Trp Ser Thr Gln Cys
 1               5                   10                  15

Ser Trp Asp Ala Pro
            20

<210> SEQ ID NO 568
<211> LENGTH: 21
<212> TYPE: PRT
<213> ORGANISM: Artificial Sequence
<220> FEATURE:
<223> OTHER INFORMATION: Library Isolate

<400> SEQUENCE: 568

Gly Ser Ala Trp Val Cys His Pro Glu Gln Glu Gly Gly Thr Thr Cys
 1               5                   10                  15

Tyr Trp Val Ala Pro
            20

<210> SEQ ID NO 569
<211> LENGTH: 21
<212> TYPE: PRT
<213> ORGANISM: Artificial Sequence
<220> FEATURE:
<223> OTHER INFORMATION: Library Isolate

<400> SEQUENCE: 569

Gly Ser Asp Glu Leu Cys Trp Pro Gln Glu Phe Gly Gly Trp Val Cys
 1               5                   10                  15

Ile Gln Gly Ala Pro
            20
```

<210> SEQ ID NO 570
<211> LENGTH: 21
<212> TYPE: PRT
<213> ORGANISM: Artificial Sequence
<220> FEATURE:
<223> OTHER INFORMATION: Library Isolate

<400> SEQUENCE: 570

Gly Ser Asp Phe Gln Cys Phe Asn Trp Glu Gly Tyr Pro Thr Asn Cys
1               5                   10                  15

Tyr Ser Asn Ala Pro
            20

<210> SEQ ID NO 571
<211> LENGTH: 21
<212> TYPE: PRT
<213> ORGANISM: Artificial Sequence
<220> FEATURE:
<223> OTHER INFORMATION: Library Isolate

<400> SEQUENCE: 571

Gly Ser Asp Lys Lys Cys Trp Pro Ser Pro Tyr Gly Gly Gln Ile Cys
1               5                   10                  15

Trp Ala Val Ala Pro
            20

<210> SEQ ID NO 572
<211> LENGTH: 21
<212> TYPE: PRT
<213> ORGANISM: Artificial Sequence
<220> FEATURE:
<223> OTHER INFORMATION: Library Isolate

<400> SEQUENCE: 572

Gly Ser Asp Gln Leu Cys Phe Asp Gln Arg Trp Gly Gly Gln Val Cys
1               5                   10                  15

Val Phe Gly Ala Pro
            20

<210> SEQ ID NO 573
<211> LENGTH: 21
<212> TYPE: PRT
<213> ORGANISM: Artificial Sequence
<220> FEATURE:
<223> OTHER INFORMATION: Library Isolate

<400> SEQUENCE: 573

Gly Ser Asp Ser Gly Cys Lys Glu Phe Trp Asn Ser Ser Asp Arg Cys
1               5                   10                  15

Tyr Thr His Ala Pro
            20

<210> SEQ ID NO 574
<211> LENGTH: 21
<212> TYPE: PRT
<213> ORGANISM: Artificial Sequence
<220> FEATURE:
<223> OTHER INFORMATION: Library Isolate

<400> SEQUENCE: 574

Gly Ser Glu Trp Ile Cys Trp Ser Ser Phe Phe Gly Gly Glu Thr Cys
1               5                   10                  15

Thr Pro Lys Ala Pro
            20

-continued

<210> SEQ ID NO 575
<211> LENGTH: 21
<212> TYPE: PRT
<213> ORGANISM: Artificial Sequence
<220> FEATURE:
<223> OTHER INFORMATION: Library Isolate

<400> SEQUENCE: 575

Gly Ser Glu Trp Asn Cys Leu Asn Asn Thr Pro Tyr Gln Thr Thr Cys
1               5                   10                  15

Ser Trp Arg Ala Pro
            20

<210> SEQ ID NO 576
<211> LENGTH: 21
<212> TYPE: PRT
<213> ORGANISM: Artificial Sequence
<220> FEATURE:
<223> OTHER INFORMATION: Library Isolate

<400> SEQUENCE: 576

Gly Ser Glu Trp Arg Cys Trp Pro Asp Val Phe Gly Gly Gln Met Cys
1               5                   10                  15

Phe Asn Met Ala Pro
            20

<210> SEQ ID NO 577
<211> LENGTH: 21
<212> TYPE: PRT
<213> ORGANISM: Artificial Sequence
<220> FEATURE:
<223> OTHER INFORMATION: Library Isolate

<400> SEQUENCE: 577

Gly Ser Glu Tyr Glu Cys Tyr Pro Asp Trp Tyr Gly Gly Glu Val Cys
1               5                   10                  15

Val Gln Lys Ala Pro
            20

<210> SEQ ID NO 578
<211> LENGTH: 21
<212> TYPE: PRT
<213> ORGANISM: Artificial Sequence
<220> FEATURE:
<223> OTHER INFORMATION: Library Isolate

<400> SEQUENCE: 578

Gly Ser Phe Glu Ala Cys Trp Glu Glu Ala Tyr Gly Gly Leu Thr Cys
1               5                   10                  15

Trp His Asp Ala Pro
            20

<210> SEQ ID NO 579
<211> LENGTH: 21
<212> TYPE: PRT
<213> ORGANISM: Artificial Sequence
<220> FEATURE:
<223> OTHER INFORMATION: Library Isolate

<400> SEQUENCE: 579

Gly Ser Phe Glu Glu Cys Met Pro Tyr Arg Tyr Gly Gly Gln Thr Cys
1               5                   10                  15

Phe Met Ile Ala Pro
            20

```
<210> SEQ ID NO 580
<211> LENGTH: 21
<212> TYPE: PRT
<213> ORGANISM: Artificial Sequence
<220> FEATURE:
<223> OTHER INFORMATION: Library Isolate

<400> SEQUENCE: 580

Gly Ser Phe Trp Thr Cys Val Asp Thr Asn Trp His Thr Thr Glu Cys
 1               5                  10                  15

Phe His Ser Ala Pro
            20

<210> SEQ ID NO 581
<211> LENGTH: 21
<212> TYPE: PRT
<213> ORGANISM: Artificial Sequence
<220> FEATURE:
<223> OTHER INFORMATION: Library Isolate

<400> SEQUENCE: 581

Gly Ser Gly Gln Met Cys Trp His Gly Gln Tyr Gly Gly Thr Ile Cys
 1               5                  10                  15

Val Ala Met Ala Pro
            20

<210> SEQ ID NO 582
<211> LENGTH: 21
<212> TYPE: PRT
<213> ORGANISM: Artificial Sequence
<220> FEATURE:
<223> OTHER INFORMATION: Library Isolate

<400> SEQUENCE: 582

Gly Ser Gly Trp Val Cys Lys Gln Gln Gly Pro His Lys Thr Glu Cys
 1               5                  10                  15

Leu Phe Met Ala Pro
            20

<210> SEQ ID NO 583
<211> LENGTH: 21
<212> TYPE: PRT
<213> ORGANISM: Artificial Sequence
<220> FEATURE:
<223> OTHER INFORMATION: Library Isolate

<400> SEQUENCE: 583

Gly Ser His Asp Glu Cys Trp Glu Asp Ile Tyr Gly Gly Phe Thr Cys
 1               5                  10                  15

Met Pro Tyr Gly Ser
            20

<210> SEQ ID NO 584
<211> LENGTH: 21
<212> TYPE: PRT
<213> ORGANISM: Artificial Sequence
<220> FEATURE:
<223> OTHER INFORMATION: Library Isolate

<400> SEQUENCE: 584

Gly Ser His Val Val Cys Trp Asp Asp Pro Tyr Gly Gly Glu Ser Cys
 1               5                  10                  15

Tyr Asn Thr Ala Pro
            20
```

<210> SEQ ID NO 585
<211> LENGTH: 21
<212> TYPE: PRT
<213> ORGANISM: Artificial Sequence
<220> FEATURE:
<223> OTHER INFORMATION: Library Isolate

<400> SEQUENCE: 585

Gly Ser Ile Asp Ile Cys Thr Asp Ser Tyr Trp Gly Gly Ile Thr Cys
1               5                   10                  15

Tyr Lys Phe Ala Pro
            20

<210> SEQ ID NO 586
<211> LENGTH: 21
<212> TYPE: PRT
<213> ORGANISM: Artificial Sequence
<220> FEATURE:
<223> OTHER INFORMATION: Library Isolate

<400> SEQUENCE: 586

Gly Ser Lys Trp Ile Cys Val Asp Val Lys Trp Gly Gly Ser Ala Cys
1               5                   10                  15

Tyr Asp Ile Ala Pro
            20

<210> SEQ ID NO 587
<211> LENGTH: 21
<212> TYPE: PRT
<213> ORGANISM: Artificial Sequence
<220> FEATURE:
<223> OTHER INFORMATION: Library Isolate

<400> SEQUENCE: 587

Gly Ser Leu Trp Glu Cys Arg Ile Asp Tyr Tyr Gly Gly Glu Val Cys
1               5                   10                  15

Phe Ile Asp Ala Pro
            20

<210> SEQ ID NO 588
<211> LENGTH: 21
<212> TYPE: PRT
<213> ORGANISM: Artificial Sequence
<220> FEATURE:
<223> OTHER INFORMATION: Library Isolate

<400> SEQUENCE: 588

Gly Ser Leu Trp Thr Cys Val Leu Ser Val Tyr Gly Gly Glu Asp Cys
1               5                   10                  15

Tyr Asn Leu Ala Pro
            20

<210> SEQ ID NO 589
<211> LENGTH: 21
<212> TYPE: PRT
<213> ORGANISM: Artificial Sequence
<220> FEATURE:
<223> OTHER INFORMATION: Library Isolate

<400> SEQUENCE: 589

Gly Ser Met Thr Met Cys Gly Ala Glu Pro Asp Leu Trp Tyr Met Cys
1               5                   10                  15

Tyr Gly Ile Ala Pro
            20

<210> SEQ ID NO 590
<211> LENGTH: 21
<212> TYPE: PRT
<213> ORGANISM: Artificial Sequence
<220> FEATURE:
<223> OTHER INFORMATION: Library Isolate

<400> SEQUENCE: 590

Gly Ser Asn Gln Tyr Cys Met Pro Tyr Asp Trp Gly Gly Glu Met Cys
1               5                   10                  15

Phe Glu Val Ala Pro
            20

<210> SEQ ID NO 591
<211> LENGTH: 21
<212> TYPE: PRT
<213> ORGANISM: Artificial Sequence
<220> FEATURE:
<223> OTHER INFORMATION: Library Isolate

<400> SEQUENCE: 591

Gly Ser Asn Val Phe Cys Ser Glu Gly Pro Phe Gly Gly Glu Ile Cys
1               5                   10                  15

Tyr Gly Ile Ala Pro
            20

<210> SEQ ID NO 592
<211> LENGTH: 21
<212> TYPE: PRT
<213> ORGANISM: Artificial Sequence
<220> FEATURE:
<223> OTHER INFORMATION: Library Isolate

<400> SEQUENCE: 592

Gly Ser Asn Trp Ala Cys Phe Ile Glu Ala Met Gly Gly Trp Thr Cys
1               5                   10                  15

Ala Pro Arg Pro Thr
            20

<210> SEQ ID NO 593
<211> LENGTH: 21
<212> TYPE: PRT
<213> ORGANISM: Artificial Sequence
<220> FEATURE:
<223> OTHER INFORMATION: Library Isolate

<400> SEQUENCE: 593

Gly Ser Asn Trp Thr Cys Phe Ile Asp Ser Phe Gln Gly Glu Thr Cys
1               5                   10                  15

Tyr Pro Phe Ala Pro
            20

<210> SEQ ID NO 594
<211> LENGTH: 21
<212> TYPE: PRT
<213> ORGANISM: Artificial Sequence
<220> FEATURE:
<223> OTHER INFORMATION: Library Isolate

<400> SEQUENCE: 594

Gly Ser Asn Trp Trp Cys His Ser Glu Ala Phe Gly Gly His Thr Cys
1               5                   10                  15

Tyr Asn Ala Ala Pro
            20

-continued

<210> SEQ ID NO 595
<211> LENGTH: 21
<212> TYPE: PRT
<213> ORGANISM: Artificial Sequence
<220> FEATURE:
<223> OTHER INFORMATION: Library Isolate

<400> SEQUENCE: 595

Gly Ser Pro Cys Ala Cys Asn Asn Ser Tyr Gly His Ser Asp Asp Cys
 1               5                  10                  15

Asp His Leu Ala Pro
            20

<210> SEQ ID NO 596
<211> LENGTH: 21
<212> TYPE: PRT
<213> ORGANISM: Artificial Sequence
<220> FEATURE:
<223> OTHER INFORMATION: Library Isolate

<400> SEQUENCE: 596

Gly Ser Pro Gly Asn Cys Lys Asp Phe Trp Ala Trp Ser Leu Gln Cys
 1               5                  10                  15

Phe Ser Phe Ala Pro
            20

<210> SEQ ID NO 597
<211> LENGTH: 21
<212> TYPE: PRT
<213> ORGANISM: Artificial Sequence
<220> FEATURE:
<223> OTHER INFORMATION: Library Isolate

<400> SEQUENCE: 597

Gly Ser Pro Arg Trp Cys Tyr Phe Ser Ser Gly Ile Met Lys Asp Cys
 1               5                  10                  15

Asp Ile Leu Ala Pro
            20

<210> SEQ ID NO 598
<211> LENGTH: 21
<212> TYPE: PRT
<213> ORGANISM: Artificial Sequence
<220> FEATURE:
<223> OTHER INFORMATION: Library Isolate

<400> SEQUENCE: 598

Gly Ser Pro Thr Tyr Cys Gln Phe His Ser Gly Val Val Thr Leu Cys
 1               5                  10                  15

Ser Met Phe Ala Pro
            20

<210> SEQ ID NO 599
<211> LENGTH: 21
<212> TYPE: PRT
<213> ORGANISM: Artificial Sequence
<220> FEATURE:
<223> OTHER INFORMATION: Library Isolate

<400> SEQUENCE: 599

Gly Ser Gln Glu Ile Cys Phe Asn Ser Gln Tyr Gly Gly Gln Val Cys
 1               5                  10                  15

Phe Asp Ser Ala Pro
            20

-continued

```
<210> SEQ ID NO 600
<211> LENGTH: 21
<212> TYPE: PRT
<213> ORGANISM: Artificial Sequence
<220> FEATURE:
<223> OTHER INFORMATION: Library Isolate

<400> SEQUENCE: 600
```

Gly Ser Gln Met Ile Cys Tyr Pro His Val Phe Gly Gly Gln Asp Cys
 1               5                  10                  15

Phe Pro Gly Ala Pro
            20

```
<210> SEQ ID NO 601
<211> LENGTH: 21
<212> TYPE: PRT
<213> ORGANISM: Artificial Sequence
<220> FEATURE:
<223> OTHER INFORMATION: Library Isolate

<400> SEQUENCE: 601
```

Gly Ser Gln Trp Thr Cys Thr Glu Leu Ser Asp Val Met Thr His Cys
 1               5                  10                  15

Ser Tyr Thr Ala Pro
            20

```
<210> SEQ ID NO 602
<211> LENGTH: 21
<212> TYPE: PRT
<213> ORGANISM: Artificial Sequence
<220> FEATURE:
<223> OTHER INFORMATION: Library Isolate

<400> SEQUENCE: 602
```

Gly Ser Arg Val Asn Cys Gly Ala Glu Asp Asp Leu Ser Phe Leu Cys
 1               5                  10                  15

Met Thr Glu Ala Pro
            20

```
<210> SEQ ID NO 603
<211> LENGTH: 21
<212> TYPE: PRT
<213> ORGANISM: Artificial Sequence
<220> FEATURE:
<223> OTHER INFORMATION: Library Isolate

<400> SEQUENCE: 603
```

Gly Ser Ser Gly Asp Cys Ile Glu Met Tyr Asn Asp Trp Tyr Tyr Cys
 1               5                  10                  15

Thr Ile Leu Ala Pro
            20

```
<210> SEQ ID NO 604
<211> LENGTH: 21
<212> TYPE: PRT
<213> ORGANISM: Artificial Sequence
<220> FEATURE:
<223> OTHER INFORMATION: Library Isolate

<400> SEQUENCE: 604
```

Gly Ser Ser Trp Glu Cys Gly Glu Phe Gly Asp Thr Thr Ile Gln Cys
 1               5                  10                  15

Asn Trp Val Ala Pro
            20

```
<210> SEQ ID NO 605
<211> LENGTH: 21
<212> TYPE: PRT
<213> ORGANISM: Artificial Sequence
<220> FEATURE:
<223> OTHER INFORMATION: Library Isolate

<400> SEQUENCE: 605

Gly Ser Ser Trp Gln Cys Phe Ser Glu Ala Pro Ser Gly Ala Thr Cys
 1               5                  10                  15

Val Pro Ile Ala Pro
            20

<210> SEQ ID NO 606
<211> LENGTH: 21
<212> TYPE: PRT
<213> ORGANISM: Artificial Sequence
<220> FEATURE:
<223> OTHER INFORMATION: Library Isolate

<400> SEQUENCE: 606

Gly Ser Ser Trp Gln Cys Val Gln Val Asp Asp Phe His Thr Glu Cys
 1               5                  10                  15

Ser Phe Met Ala Pro
            20

<210> SEQ ID NO 607
<211> LENGTH: 21
<212> TYPE: PRT
<213> ORGANISM: Artificial Sequence
<220> FEATURE:
<223> OTHER INFORMATION: Library Isolate

<400> SEQUENCE: 607

Gly Ser Ser Trp Thr Cys Val Phe Tyr Pro Tyr Gly Gly Glu Val Cys
 1               5                  10                  15

Ile Pro Asp Ala Pro
            20

<210> SEQ ID NO 608
<211> LENGTH: 21
<212> TYPE: PRT
<213> ORGANISM: Artificial Sequence
<220> FEATURE:
<223> OTHER INFORMATION: Library Isolate

<400> SEQUENCE: 608

Gly Ser Thr Glu Leu Cys Val Pro Tyr Gln Trp Gly Gly Glu Val Cys
 1               5                  10                  15

Val Ala Gln Ala Pro
            20

<210> SEQ ID NO 609
<211> LENGTH: 21
<212> TYPE: PRT
<213> ORGANISM: Artificial Sequence
<220> FEATURE:
<223> OTHER INFORMATION: Library Isolate

<400> SEQUENCE: 609

Gly Ser Thr Val Tyr Cys His Asn Glu Tyr Phe Gly Gly Gln Val Cys
 1               5                  10                  15

Phe Thr Ile Ala Pro
            20
```

```
<210> SEQ ID NO 610
<211> LENGTH: 21
<212> TYPE: PRT
<213> ORGANISM: Artificial Sequence
<220> FEATURE:
<223> OTHER INFORMATION: Library Isolate

<400> SEQUENCE: 610

Gly Ser Thr Tyr Gly Cys Glu Tyr Tyr Met Pro Phe Gln His Lys Cys
 1               5                  10                  15

Ser Val Glu Ala Pro
            20

<210> SEQ ID NO 611
<211> LENGTH: 21
<212> TYPE: PRT
<213> ORGANISM: Artificial Sequence
<220> FEATURE:
<223> OTHER INFORMATION: Library Isolate

<400> SEQUENCE: 611

Gly Ser Trp Trp Gly Cys Phe Pro Tyr Ser Trp Gly Gly Glu Ile Cys
 1               5                  10                  15

Thr Ser Ile Ala Pro
            20

<210> SEQ ID NO 612
<211> LENGTH: 21
<212> TYPE: PRT
<213> ORGANISM: Artificial Sequence
<220> FEATURE:
<223> OTHER INFORMATION: Library Isolate

<400> SEQUENCE: 612

Gly Ser Trp Trp Asn Cys Val Asp Thr Ser Phe His Thr Thr Gln Cys
 1               5                  10                  15

Lys Tyr Ala Ala Pro
            20

<210> SEQ ID NO 613
<211> LENGTH: 21
<212> TYPE: PRT
<213> ORGANISM: Artificial Sequence
<220> FEATURE:
<223> OTHER INFORMATION: Library Isolate

<400> SEQUENCE: 613

Gly Ser Tyr Phe Met Cys Gln Asp Gly Phe Trp Gly Gly Gln Asp Cys
 1               5                  10                  15

Phe Tyr Ile Ala Pro
            20

<210> SEQ ID NO 614
<211> LENGTH: 21
<212> TYPE: PRT
<213> ORGANISM: Artificial Sequence
<220> FEATURE:
<223> OTHER INFORMATION: Library Isolate

<400> SEQUENCE: 614

Gly Ser Tyr Met Trp Cys Thr Glu Ser Lys Phe Gly Gly Ser Thr Cys
 1               5                  10                  15

Phe Asn Leu Ala Pro
            20
```

```
<210> SEQ ID NO 615
<211> LENGTH: 20
<212> TYPE: PRT
<213> ORGANISM: Artificial Sequence
<220> FEATURE:
<223> OTHER INFORMATION: Library Isolate

<400> SEQUENCE: 615

Gly Ser Gly Ala Tyr Ser His Leu Leu Glu Tyr His Ala Val Cys Lys
 1               5                  10                  15

Asn Val Ala Pro
            20

<210> SEQ ID NO 616
<211> LENGTH: 21
<212> TYPE: PRT
<213> ORGANISM: Artificial Sequence
<220> FEATURE:
<223> OTHER INFORMATION: Library Isolate

<400> SEQUENCE: 616

Pro Gly Ser Trp Thr Cys Gln Asn Tyr Glu Pro Trp Ala Thr Thr Cys
 1               5                  10                  15

Val Tyr Asp Ala Pro
            20

<210> SEQ ID NO 617
<211> LENGTH: 22
<212> TYPE: PRT
<213> ORGANISM: Artificial Sequence
<220> FEATURE:
<223> OTHER INFORMATION: Library Isolate

<400> SEQUENCE: 617

Ala Gln Asp Trp Tyr Tyr Asp Glu Ile Leu Gly Arg Gly Gly Arg Gly Gly Arg
 1               5                  10                  15

Gly Gly Gly Lys
            20
```

KDR AND VEGF/KDR BINDING PEPTIDES AND THEIR USE IN DIAGNOSIS AND THERAPY

RELATED APPLICATIONS

This application is a continuation of U.S. application Ser. No. 10/661,156, filed Sep. 11, 2003, which is a continuation-in-part of U.S. application Ser. No. 10/382,082, filed Mar. 3, 2003, (now abandoned), and a continuation-in-part of International Application No. PCT/US03/06731, which designated the United States and was filed on Mar. 3, 2003. U.S. application Ser. No. 10/382,082 and International Application No. PCT/US03/06731 claim the benefit of U.S. Provisional Application No. 60/360,851, filed Mar. 1, 2002, and U.S. Provisional Application No. 60/440,411, filed Jan. 15, 2003. The entire teachings of the above applications are incorporated herein by reference.

BACKGROUND OF THE INVENTION

In the developing embryo, the primary vascular network is established by in situ differentiation of meso-dermal cells in a process called vasculogenesis. After embryonic vasculogenesis however, it is believed that all subsequent generation of new blood vessels, in the embryo or in adults, is governed by the sprouting or splitting of new capillaries from the pre-existing vasculature in a process called angiogenesis (Pepper, M. et al., 1996. *Enzyme Protein,* 49:138-162; Risau, W., 1997. *Nature,* 386:671-674). Angiogenesis is not only involved in embryonic development and normal tissue growth and repair, it is also involved in the female reproductive cycle, establishment and maintenance of pregnancy, and in repair of wounds and fractures. In addition to angiogenesis that takes place in the normal individual, angiogenic events are involved in a number of pathological processes, notably tumor growth and metastasis, and other conditions in which blood vessel proliferation is increased, such as diabetic retinopathy, psoriasis and arthropathies. Angiogenesis is so important in the transition of a tumor from hyperplastic to neoplastic growth, that inhibition of angiogenesis has shown promise as a cancer therapy (Kim, K. et al., 1993. *Nature,* 362:841-844).

Tumor-induced angiogenesis is thought to depend on the production of pro-angiogenic growth factors by the tumor cells, which overcome other forces that tend to keep existing vessels quiescent and stable (Hanahan, D. and Folkman, J., 1996. *Cell,* 86:353-364). The best characterized of these pro-angiogenic agents is vascular endothelial growth factor (VEGF) Neufeld, G. et al., 1999. *FASEB J.,* 13:9-22).

VEGF is produced naturally by a variety of cell types in response to hypoxia and some other stimuli. Many tumors also produce large amounts of VEGF, and/or induce nearby stromal cells to make VEGF (Fukumura, D. et al. 1998. *Cell,* 94:715-725). VEGF, also referred to as VEGF-A, is synthesized as five different splice isoforms of 121, 145, 165, 189, and 206 amino acids. $VEGF_{121}$ and $VEGF_{165}$ are the main forms produced, particularly in tumors (see, Neufeld, G. et al 1999, supra). $VEGF_{121}$ lacks a basic domain encoded by exons 6 and 7 of the VEGF gene and does not bind to heparin or extracellular matrix, unlike $VEGF_{165}$.

VEGF family members act primarily by binding to receptor tyrosine kinases. In general, receptor tyrosine kinases are glycoproteins having an extracellular domain capable of binding one or more specific growth factors, a transmembrane domain (usually an alpha helix), a juxtamembrane domain (where the receptor may be regulated, e.g., by phosphorylation), a tyrosine kinase domain (the catalytic component of the receptor), and a carboxy-teal tail, which in many receptors is involved in recognition and binding of the substrates for the tyrosine kinase. There are three endothelial cell-specific receptor tyrosine kinases known to bind VEGF: VEGFR-1 (Flt-1), VEGFR-2 (KDR or Flk-1), and VEGFR-3 (Flt4). Flt-1 and KDR have been identified as the primary high affinity VEGF receptors. While Flt-1 has higher affinity for VEGF, KDR displays more abundant endothelial cell expression (Bikfalvi, A. et al., 1991. *J. Cell. Physiol.,* 149: 50-59). Moreover, KDR is thought to dominate the angiogenic response and is therefore of greater therapeutic and diagnostic interest (see, Neufeld G. et at 1999, supra) Expression of KDR is highly upregulated in angiogenic vessels, especially in tumors that induce a strong angiogenic response (Veikkola, T. et at, 2000. *Cancer Res.,* 60:203-212).

KDR is made up of 1336 amino acids in its mature form. Because of glycosylation, it migrates on an SDS-PAGE gel with an apparent molecular weight of about 205 kDa. KDR contains seven immunoglobulin-like domains in its extracellular domain, of which the first three are the most important in VEGF binding (Neufeld, G. et at 1999, supra). VEGF itself is a homodimer capable of binding to two KDR molecules simultaneously. The result is that two KDR molecules become dimerized upon binding and autophosphorylate, becoming much more active. The increased kinase activity in turn initiates a signaling pathway that mediates the KDR-specific biological effects of VEGF.

From the foregoing, it can be seen that not only is the VEGF binding activity of KDR in vivo critical to angiogenesis, but the ability to detect KDR upregulation on endothelial cells or to detect VEGF/KDR binding complexes would be extremely beneficial in detecting or monitoring angiogenesis, with particular diagnostic applications such as detecting malignant tumor growth. It would also be beneficial in therapeutic applications such as targeting tumoreidal agents or angiogenesis inhibitors to a tumor site or targeting agonists of KDR, VEGF/KDR, or angiogenesis to a desired site.

SUMMARY OF THE INVENTION

The present invention relates to polypeptides and compositions useful for detecting and targeting primary receptors on endothelial cells for vascular endothelial growth factor (VEGF), i.e., vascular endothelial growth factor receptor-2 (VEGFR-2, also known as kinase domain region (KDR) and fetal liver kinase-1 (Flk-1)), and for imaging and targeting complexes formed by VEGF and KDR. The involvement of VEGF and KDR in angiogenesis makes the VEGF/KDR and KDR binding polypeptides of the present invention particularly useful for imaging important sites of angiogenesis, e.g., neoplastic tumors, for targeting substances, e.g., therapeutics, including radiotherapeutics, to such sites, and for treating certain disease states, including those associated with inappropriate angiogenesis.

A group of polypeptides has been discovered that bind to KDR or VEGF/KDR complex (referred to herein as "KDR binding polypeptides" or "KDR binding moieties" and homologues thereof). Such KDR and VEGF/KDR binding polypeptides will concentrate at the sites of angiogenesis, thus providing a means for detecting and imaging sites of active angiogenesis, which can include sites of neoplastic tumor growth. Such KDR and VEGF/KDR binding polypeptides provide novel therapeutics to inhibit or promote, e.g., angiogenesis. The preparation, use and screening of such polypeptides, for example as imaging agents or as fusion partners for KDR or VEGF/KDR-homing therapeutics, is described in detail herein.

In answer to the need for improved materials and methods for detecting, localizing, measuring and possibly affecting (inhibiting or enhancing), e.g., angiogenesis, it has been surprisingly discovered that seven families of non-naturally occurring polypeptides bind specifically to KDR or VEGF/KDR complex. Appropriate labeling of such polypeptides provides detectable imaging agents that can bind, e.g., at high concentration, to KDR-expressing endothelial cells or cells exhibiting VEGF/KDR complexes, providing angiogenesis-specific imaging agents. The KDR and VEGF/KDR binding polypeptides of the instant invention can thus be used in the detection and diagnosis of such angiogenesis-related disorders. Conjugation or fusion of such polypeptides with effective agents such as VEGF inhibitors or tumoricidal agents can also be used to treat pathogenic tumors, e.g., by causing the conjugate or fusion to "home" to the site of active angiogenesis, thereby providing an effective means for treating pathogenic conditions associated with angiogenesis.

This invention pertains to KDR and VEGF/KDR binding polypeptides, and includes use of a single binding polypeptide as a monomer or m a multimeric or polymeric construct as well as use of more than one binding polypeptide of the invention in multimeric or polymeric constructs. Binding polypeptides according to this invention are useful in any application where binding, detecting or isolating KDR or VEGF/KDR complex, or fragments thereof retaining the polypeptide binding site, is advantageous. A particularly advantageous use of the binding polypeptides disclosed herein is in a method of imaging angiogenesis in vivo. The method entails the use of specific binding polypeptides according to the invention for detecting a site of angiogenesis, where the binding polypeptides have be detectably labeled for use as imaging agents, including magnetic resonance imaging (MRI) contrast agents, x-ray imaging agents, radiopharmaceutical imaging agents, ultrasound imaging agents, and optical imaging agents.

Another advantageous use of the KDR and VEGF/KDR complex binding polypeptides disclosed herein is to target therapeutic agents (including compounds capable of providing a therapeutic, radiotherapeutic or cytotoxic effect), or delivery vehicles for therapeutics (including drugs, genetic material, etc.) to sites of angiogenesis or other tissue expressing KDR.

Constructs comprising two or more KDR or KDR/VEGF binding polypeptides show improved ability to bind the target molecule compared to the corresponding monomeric binding polypeptides. For example, as shown in Experiment D of Example 5, tetrameric constructs of KDR binding polypeptides provided herein showed improved ability to bind KDR-transfected 293H cells. Combining two or more binding polypeptides in a single molecular construct appears to improve the avidity of the construct over the monomeric binding polypeptides as shown by a decrease in $K_D$.

In addition, as demonstrated herein, constructs comprising two or more binding polypeptides specific for different epitopes of KDR and/or KDR/VEGF (e.g., "heteromeric" or "heteromultimeric" constructs, see U.S. Application No. 60/440,201, U.S. application Ser. No. 10/379,287, filed Mar. 3, 2003, and Attorney Docket No. 057637/01182 by Christophe Arbogast et al., filed Sep. 11, 2003, the contents of which are incorporated herein) were made. Constructs comprising two or more binding polypeptides provided herein are expected to bind to multiple sites on KDR or VEGF/KDR. The heteromeric constructs show superior binding ability over both the corresponding monomers and multimeric constructs comprising multiple copies of the same binding polypeptide. Furthermore, heteromeric constructs comprising two or more binding peptides specific for different epitopes, together with a Control peptide, wore also able to efficiently bind KDR-transfected 293H cells. Thus, inclusion of two or more binding polypeptides that recognize different epitopes further improves the avidity of the construct for the target molecule, as demonstrated by a decrease in $K_D$.

Heteromeric constructs of the binding polypeptides provided herein show improved ability to inhibit receptor tyrosine kinase function. Based on experiments described herein, dimeric and other multimeric constructs of the present invention comprising at least two binding polypeptides specific for different epitopes of KDR and/or KDR/VEGF complex are expected to inhibit the function of receptor tyrosine kinases. In particular, such constructs are expected to inhibit the function of VEGFR-2/KDR, VEGFR-1/Flt-1 and VEGFR-3/Flt-4.

For the purposes of the present invention, receptor tyrosine kinase function can include any one of: oligomerization of the receptor, receptor phosphorylation, kinase activity of the receptor, recruitment of downstream signaling molecules, induction of genes, induction of cell proliferation, induction of cell migration, or combination thereof. For example, heteromeric constructs of binding polypeptides provided herein inhibit VEGF-induced KDR receptor activation in human endothelial cells, demonstrated by the inhibition of VEGF-induced phosphorylation of the KDR receptor. In addition, heteromeric constructs of binding peptides provided herein inhibit VEGF-stimulated endothelial cell migration. As shown here targeting two or more distinct epitopes on KDR with a single binding construct greatly improves the ability of the construct to inhibit receptor function. Even binding peptides with weak ability to block receptor activity can be used to generate heteromeric constructs having improved ability to block VEGF-induced receptor function.

Therefore, the present invention also is drawn to constructs comprising two or more binding polypeptides. In one embodiment, the multimeric constructs comprise two or more copies of a single binding polypeptide. In another embodiment, the multimeric constructs of the present invention comprise two or more binding polypeptides, such that at least two of the binding polypeptides in the construct are specific for different epitopes of KDR and/or KDR/VEGF. These constructs are also referred to herein as "heteromeric constructs," "heteromultimers," etc. The constructs of the present invention can also include unrelated, or control peptide(s). The constructs can include two or more, three or more, or four or more binding polypeptides. Based on the teachings provided herein, one of ordinary skill in the art is able to assemble the binding polypeptides provided herein into multimeric constructs and to select multimeric constructs having improved properties, such as improved ability to bind the target molecule, or improved ability to inhibit receptor tyrosine kinase function. Such multimeric constructs having improved properties are included in the present invention.

Consensus sequences 1-14 have been determined based on the specific KDR and VEGF/KDR binding polypeptides shown in Tables 1-7. In specific embodiments, KDR and VEGF/KDR binding polypeptides of the invention comprise one or more of these sequences. Such preferred KDR or VEGF/KDR complex binding polypeptides include polypeptides with the potential to form a cyclic or loop structure between invariant cysteine residues comprising, or alternatively consisting of, an amino acid sequence selected from the group consisting of Consensus Sequences 1-5 below:

Consensus Sequence 1:
$X_1$-$X_2$-$X_3$-Cys-$X_5$-$X_6$-$X_7$-$X_8$-$X_9$-$X_{10}$-Cys-$X_{12}$-$X_{13}$-$X_{14}$
(TN8),
wherein $X_1$ is Ala, Arg, Asp, Gly, His, Leu, Lye, Pro, Ser, Thr, Trp, Tyr or Val;
$X_2$ is Asn, Asp, Glu, Gly, Ile, Leu, Lys, Phe, Ser, Thr, Trp, Tyr or Val;
$X_3$ is Asn, Asp, Gln, Glu, Ile, Lea, Met, Thr, Trp or Val;
$X_5$ is Ala, Arg, Asn, Asp, Gin, Glu, His, Ile, Lys, Phe, Pro, Ser, Trp or Tyr;
$X_6$ is Ala, Arg, Asn, Asp, Gin Glu, Gly, His, Ile, Lys, Met, Phe, Pro, Ser, Thr, Tip, Tyr or Val;
$X_7$ is Ala, Asn, Asp, Glu, Gly, His, Ile, Leu, Lys, Phe, Pro, Ser. Thr, Tip, Tyr or Val;
$X_8$ is Ala, Asp, Glu, Gly, Leu, Phe, Pro, Ser, Thr, Trp or Tyr;
$X_9$ is Arg, Gln, Glu, Gly, Ile, Leu, Met, Pro, Thr, Trp, Tyr or Val;
$X_{10}$ is Ala, Arg, Gin, Gin, Gly, Ms, Ile, Leu, Lys, Met, Phe, Tip or Tyr;
$X_{12}$ is Arg, Asp, Cys, Gin, Glu, His, Ile, Leu, Lys, Met, Phe, Pro, Ser, Thr, Trp, Tyr or Val;
$X_{13}$ is Arg, Asn, Asp, Gln, Glu, Gly, His, Ile, Leu, Lys, Met, Phe, Ser, Thr, Trp or Tyr; and
$X_{14}$ is Gln, Glu, Gly, His, Ile, Leu, Lys, Met, Phe, Pro, Ser, Thr, Trp or Tyr,
and wherein the polypeptide binds KDR or a VEGF/KDR complex; or Consensus Sequence 2:
$X_1$-$X_2$-$X_3$-Cys-$X_5$-$X_6$-$X_7$-$X_8$-$X_9$-$X_{10}$-$X_{11}$-$X_{12}$-$X_{13}$-$X_{14}$-Cys-$X_{16}$-$X_{17}$-$X_{18}$ (TN12),
wherein $X_1$ is Ala, Asn, Asp, Gly, Leu, Pro, Ser, Trp or Tyr (preferably Asn, Asp, Pro or Tyr);
$X_2$ is Ala, Arg, Asn, Asp, Gly, His, Phe, Pro, Ser, Trp or Tyr (preferably Asp, Gly, Pro, Ser or Trp);
$X_3$ is Ala, Asn, Asp, Gln, Glu, Gly, His, Leu, Lys, Met, Phe, Ser, Thr, Tip, Tyr or Val (preferably Trp);
$X_5$ is Arg, Asp, Gln, Glu, Gly, His, Ile, Lys, Met, Thr, Trp or Val preferably Glu, Ile or Tyr);
$X_6$ is Ala, Arg, Asn, Cys, Glu, Ile, Leu, Met, Phe, Ser, Trp or Tyr (preferably Glu, Phe or Tyr);
$X_7$ is Arg, Asn, Asp, Gln Glu, His, Ile, Leu, Pro, Ser, Thr, Trp, Tyr or Val (preferably Glu);
$X_8$ is Ala, Asn, Asp, Gln Glu, Gly, His, Met, Phe, Pro, Ser, Trp, Tyr or Val (preferably Gln or Ser);
$X_9$ is Asp, Gln, Glu, Gly, His, Ile, Leu, Met, Phe, Pro, Ser, Thr, Trp or Tyr (preferably Asp);
$X_{10}$ is Ala, Arg, Asn, Asp, Gln, Glu, Gly, Leu, Lys, Met, Phe, Pro, Ser, Thr, Trp, Tyr or Val (preferably Lys or Ser);
$X_{11}$ is Ala, Arg, Asn, Asp, Gln, Glu, Gly, His, Lys, Trp, Tyr or Val preferably Gly or Tyr);
$X_{12}$ is Ala, Arg, Gln, Gly, His, Ile, Lys, Met, Phe, Ser, Thr, Trp, Tyr or Val (preferably Trp or Thr);
$X_{13}$ is Arg, Gln, Glu, His, Leu, Lys, Met, Phe, Pro, Thr, Trp or Val (preferably Glu or Trp);
$X_{14}$ is Arg, Asn, Asp, Gln, His, Ile, Met, Phe, Pro, Thr, Trp, Tyr or Val (preferably Phe);
$X_{16}$ is Ala, Asn, Asp, Gln, Glu, Gly, Lys, Met, Phe, Ser, Thr, Tip, Tyr or Val (preferably Asp);
$X_{17}$ is Arg, Asn, Asp, Cys, Gly, His, Phe, Pro, Ser, Trp or Tyr (preferably Pro or Tyr); and
$X_{18}$ is Ala, Asn, Asp, Gly, His, Leu, Phe, Pro, Ser, Trp or Tyr (preferably Asn, Pro or Trp),
and wherein the polypeptide binds KDR or a VEGF/KDR complex; or Consensus Sequence 3:
$X_1$-$X_2$-$X_3$-Cys-$X_5$-$X_6$-$X_7$-Gly-$X_9$-Cys-$X_{11}$-$X_{12}$-$X_{13}$ (TN7),
wherein $X_1$ is Gly or Trp;
$X_2$ is Ile, Tyr or Val;
$X_3$ is Gln, Glu Thr or Trp;
$X_5$ is Asn, Asp or Glu;
$X_6$ is Glu, His, Lys or Phe;
$X_7$ is Asp, Gln, Leu, Lys Met or Tyr;
$X_9$ is Arg, Gln, Leu, Lys or Val;
$X_{11}$ is Arg, Phe, Ser, Trp or Val;
$X_{12}$ is Glu, His or Ser; and
$X_{13}$ is Glu, Gly, Trp or Tyr,
and wherein the polypeptide binds KDR or a VEGF/KDR complex; or Consensus Sequence 4:
$X_1$-$X_2$-$X_3$-Cys-$X_5$-$X_6$-$X_7$-$X_8$-$X_9$-$X_{10}$-$X_{11}$-Cys-$X_{13}$-$X_{14}$-$X_{15}$ (TN9),
wherein $X_1$ is Arg, Asp, Gly, Ile, Met, Pro or Tyr (preferably Tyr);
$X_2$ is Asp, Gly, His, Pro or Trp (preferably Gly or Tip);
$X_3$ is Gly, Pro, Phe, Thr or Trp (preferably Pro);
$X_5$ is Ala, Asp, Lys, Ser, Trp or Val (preferably Lys);
$X_6$ is Asn, Glu, Gly, His or Leu;
$X_7$ is Gln, Glu, Gly, Met, Lys, Phe, Tyr or Val (preferably Met);
$X_8$ is Ala, Asn, Asp, Gly, Leu, Met, Pro, Ser or Thr;
$X_9$ is His, Pro or Trp (preferably Pro);
$X_{10}$ is Ala, Gly, His, Leu, Trp or Tyr (preferably His or Trp);
$X_{11}$ is Ala, Asp, Gln, Leu, Met, Thr or Trp;
$X_{13}$ is Ala, Lys, Ser, Trp or Tyr (preferably Trp);
$X_{14}$ is Asp, Gly, Leu, His, Met, Thr, Trp or Tyr (Preferably His, Trp, or Tyr); and
$X_{15}$ is Asn, Gln, Glu, Leu, Met, Pro or Trp (preferably Glu, Met or Trp),
and wherein the polypeptide binds KDR or a VEGF/KDR complex; or Consensus Sequence 5: (MTN13; SEQ ID NO: 1)
$X_1$-$X_2$-$X_3$-Cys-$X_5$-$X_6$-$X_7$-$X_8$-Ser-Gly-Pro-$X_{12}$-$X_{13}$-$X_{14}$-$X_{15}$-Cys-$X_{17}$-$X_{18}$-$X_{19}$,
wherein $X_1$ is Arg, Glu, His, Ser or Trp;
$X_2$ is Asn, Asp, Leu, Phe, Thr or Val;
$X_3$ is Arg, Asp, Glu, His, Lys or Thr;
$X_5$ is Asp, Glu, His or Thr;
$X_6$ is Arg, His, Lys or Phe;
$X_7$ is Gln, Ile, Lys, Tyr or Val;
$X_8$ is Gln, Ile, Leu, Met or Phe;
$X_{12}$ is Asn, Asp, Gly, His or Tyr;
$X_{13}$ is Gln, Gly, Ser or Thr;
$X_{14}$ is Glu, Lys, Phe or Ser;
$X_{15}$ is Glu, Ile, Ser or Val;
$X_{17}$ is Glu, Gly, Lys, Phe, Ser or Val;
$X_{18}$ is Arg, Asn, Ser or Tyr; and
$X_{19}$ is Asp, Gln, Glu, Gly, Met or Tyr, and wherein the polypeptide binds KDR or a VEGF/KDR complex.

Further analysis of the polypeptides isolated from the TN8 library (see Consensus Sequence 1) revealed sub-families of preferred binding polypeptides, which are described by the Consensus Sequences 6, 7 and 8 as follows:

```
Consensus Sequence 6:
X1-X2-X3-Cys-X5-X6-X7-X8-X9-Tyr-Cys-X12-X13-X14,
wherein
```

$X_1$ is Ala, Arg, Asp, Leu, Lys, Pro, Ser or Val;
$X_2$ is Asn, Asp, Glu, Lys, Thr or Ser (preferably Asn, Asp, Glu or Lys);
$X_3$ is Ile, Leu or Trp;
$X_5$ is Ala, Arg, Glu, Lys or Ser (preferably Glu);
$X_6$ is Ala, Asp, Gln, Glu, Thr or Val (preferably Asp or Glu);
$X_7$ is Asp or Glu;
$X_8$ is Trp or Tyr;
$X_9$ is Thr or Tyr preferably Tyr);
$X_{12}$ is Glu, Met, Phe, Trp or Tyr (preferably Trp, Phe, Met, or Tyr);
$X_{13}$ is Ile, Leu or Met; and
$X_{14}$ is Ile, Leu, Met, Phe or Thr (preferably Thr or Leu),
and wherein the polypeptide binds KDR or a VEGF/KDR complex; or

```
Consensus Sequence 7:
                                        (SEQ ID NO: 2)
Trp-Tyr-Trp-Cys-X5-X6-X7-Gly-X9-X10-Cys-X12-X13-
X14,
wherein
```

$X_5$ is Asp, Gln or His;
$X_6$ is His or Tyr (preferably Tyr);
$X_7$ is Ile, His or Tyr;
$X_9$ is Ile, Met or Val;
$X_{10}$ is Gly or Tyr;
$X_{12}$ is Asp, Lys or Pro;
$X_{13}$ is Gln, Gly or Trp; and
$X_{14}$ is Phe, Ser or Thr,
and wherein the polypeptide binds KDR or a VEGF/KDR complex; or

```
Consensus Sequence 8:
X1-X2-X3-Cys-X5-X6-X7-X8-Gly-X10-Cys-X12-X13-X14,
wherein
```

$X_1$ is Gly, Leu, His, Thr, Trp or Tyr (preferably Trp, Tyr, Leu or His);
$X_2$ is Ile, Leu, Thr, Trp or Val (preferably Val, Ile or Leu);
$X_3$ is Asp, Glu, Gln, Trp or Thr, (preferably Glu, Asp or Gln);
$X_5$ is Ala, Arg, Asn, Asp, His, Phe, Trp or Tyr (preferably Tyr, Trp or Phe);
$X_6$ is Ala, Asp, Gln, His, Lys, Met, Ser, Thr, Trp, Tyr or Val;
$X_7$ is Ala, Asn, Asp, Glu, Gly, His, Ile, Leu, Lys, Phe, Pro, Ser, Thr or Val;
$X_8$ is Asp, Phe, Ser, Thr, Trp or Tyr (preferably Thr, Ser or Asp);
$X_{10}$ is Ala, Arg, Gln, His, Ile, Leu, Lys, Met, Phe, Trp or Tyr (preferably Arg or Lys);
$X_{12}$ is Arg, Gln, His, Ile, Lys, Met, Phe, Thr, Trp, Tyr or Val (preferably Tyr, Trp, Phe, Ile or Val);
$X_{13}$ is Arg, Asn, Asp, Glu, His, Met, Pro, Ser or Thr; and
$X_{14}$ is Arg, Gln, Glu, Gly, Phe, Ser, Trp or Tyr, and wherein the polypeptide binds KDR or a VEGF/KDR complex.

Further analysis of the polypeptides isolated from the TN12 library (see Consensus Sequence 2) revealed sub-families of preferred binding polypeptides, which are described by Consensus Sequences 9-12 and 9A as follows:

```
Consensus Sequence 9:
                                        (SEQ ID NO: 3)
X1-X2-X3-Cys-X5-X6-X7-X8-Trp-Gly-Gly-X12-X13-Cys-
X15-X16-X17 (TN11, i.e., 11-mer binders isolated
from the TN12 library),
wherein
```

$X_1$ is Ser, Phe, Trp, Tyr or Gly (preferably Ser);
$X_2$ is Arg, Gly, Ser or Trp (preferably Arg);
$X_3$ is Ala, Glu, Ile or Val (preferably Val or Ile);
$X_5$ is Ala, Phe or Trp (preferably Trp or Phe);
$X_6$ is Glu or Lys (preferably Glu);
$X_7$ is Asp, Ser, Trp or Tyr (preferably Asp, Trp or Tyr);
$X_8$ is Phe; Pro or Ser preferably Ser);
$X_{12}$ is Gln or Glu (preferably Glu);
$X_{13}$ is Ile, Phe or Val;
$X_{15}$ is Gln, Ile, Leu, Phe or Tyr (preferably Phe, Tyr or Leu);
$X_{16}$ is Arg, Gly or Pro (preferably Arg); and
$X_{17}$ is Gln, His, Phe, Ser, Tyr or Val preferably Tyr, Phe, His or Val),
and wherein the polypeptide binds KDR or a VEGF/KDR complex; or

```
Consensus Sequence 9A:
                                        SEQ ID NO: 3
X1-X2-X3-Cys-X5-X6-X7-X8-X9-X10-X11-X12-X13-Cys-
X15-X16-X17 (TN11, i.e., 11-mer binders isolated
from the TN12 library;),
wherein
```

$X_1$ is Ala, Arg, Asn, Asp, Gln, Glu, Gly, His, Ile, Leu, Lys, Met, Phe, Pro, Ser, Thr, Trp, Tyr or Val;
$X_2$ is Ala, Arg, Asn, Asp, Gln, Glu, Gly, His, Leu, Lys, Met, Phe, Ser, Thr, Trp, Tyr or Val;
$X_3$ is Ala, Arg, Asn, Asp, Gln, Glu, Gly, His, Ile, Leu, Lys, Met, Phe, Thr, Trp, Tyr or Val;
$X_5$ is Ala, Arg, Asp, Gln, Glu, Gly, His, Ile, Leu, Lys, Met, Phe, Ser, Trp, Tyr or Val;
$X_6$ is Ala, Arg, Asn, Asp, Gln, Glu, Gly, His, Ile, Leu, Lys, Met, Phe, Pro, Ser, Thr, Trp or Tyr;
$X_7$ is Ala, Arg, Asp, Asn, Gln, Glu, Gly, His, Ile, Leu, Met, Phe, Ser, Thr, Trp, Tyr or Val;
$X_8$ is Ala, Arg, Asp, Asn, Gln, Glu, Gly, His, Ile, Lys, Met, Phe, Pro, Ser, Thr, Trp, Tyr or Val;
$X_9$ is Ala, Asn, Asp, Gln, Glu, Gly, His, Met, Phe, Pro, Ser, Trp or Tyr;
$X_{10}$ is Asp, Gln, Glu, Gly, His, Ile, Leu, Phe, Ser, Thr, Trp, Tyr or Val;
$X_{11}$ is Ala, Gln, Glu, Gly, His, Ile, Leu, Lys, Met, Pro, Ser, Thr, Trp, Tyr or Val;
$X_{12}$ is Ala, Asn, Asp, Gln, Glu, Gly, His, Ile, Leu, Lys, Met, Phe, Pro, Ser, Thr, Trp, Tyr or Val;
$X_{13}$ is Ala, Arg, Asn, Asp, Cys, Gln, Glu, His, Ile, Leu, Lys, Met, Phe, Pro, Ser, Thr, Trp, Tyr or Val;
$X_{15}$ is Ala, Asp, Asn, Glu, Gly, Ile, His, Leu, Lys, Met, Phe, Pro, Ser, Thr, Trp, Tyr or Val;
$X_{16}$ is Ala, Arg, Asn, Asp, Gln, Glu, Gly, His, Ile, Leu, Lys, Met, Phe, Pro, Ser, Thr, Trp, Tyr or Val;

$X_{17}$ is Ala, Arg, Asp, Asn, Gln, Glu, Gly, His, Ile, Leu, Lys, Met, Phe, Pro, Ser, Thr, Tyr or Val, and wherein the polypeptide binds KDR or a VEGF/KDR complex, or

```
Consensus Sequence 10:
                                    (TN12; SEQ ID NO: 4)
Tyr-Pro-X3-Cys-X5-Glu-X7-Ser-X9-Ser-X11-X12-X13-

Phe-Cys-X16-X17-X18,
wherein
```

$X_3$ is Gly or Trp (preferably Trp);
$X_5$ is His or Tyr (preferably His, or Tyr);
$X_7$ is His, Leu or Thr;
$X_9$ is Asp or Leu (preferably Asp);
$X_{11}$ is Gly or Val (preferably Val);
$X_{12}$ is Thr or Val (preferably Thr));
$X_{13}$ is Arg or Trp (preferably Arg);
$X_{16}$ is Ala or Val (preferably Val);
$X_{17}$ is Asp or Pro (preferably Pro); and
$X_{18}$ is Gly or Trp (preferably Trp),
and wherein the polypeptide binds KDR or a VEGF/KDR complex; or

```
Consensus Sequence 11:
                                    (TN12; SEQ ID NO: 5)
X1-X2-X3-Cys-X5-X6-X7-X8-X9-X10-Gly-X12-Trp-X14-

Cys-X16-X17-X18,
wherein
```

$X_1$ is Asp, Gly, Pro or Ser (preferably Asp);
$X_2$ is Arg, Asn, Asp, Gly or Ser (preferably Asp, Asn, or Ser);
$X_3$ is Gly, Thr, Trp or Tyr (preferably Trp or Tyr);
$X_5$ is Glu, Met or Thr (preferably Glu);
$X_6$ is Ile, Leu, Met or Phe (preferably Met, Leu, or Phe);
$X_7$ is Arg, Asp, Glu, Met, Trp or Val;
$X_8$ is Asn, Gln, Gly, Ser or Val;
$X_9$ is Asp or Glu;
$X_{10}$ is Lys, Ser, Thr or Val (preferably Lys);
$X_{12}$ is Arg, Gln, Lys or Trp (preferably Trp, Arg, or Lys);
$X_{14}$ is Asn, Leu, Phe or Tyr (preferably Tyr, Phe, or Asn);
$X_{16}$ is Gly, Phe, Ser or Tyr (preferably Tyr or Phe);
$X_{17}$ is Gly, Leu, Pro or Ser (preferably Pro or Ser); and
$X_{18}$ is Ala, Asp, Pro, Ser, Trp or Tyr,
and wherein the polypeptide binds KDR or a VEGF/KDR complex; or

```
Consensus Sequence 12:
                                    (TN12; SEQ ID NO: 6)
Asn-Trp-X3-Cys-X5-X6-X7-X8-X9-X10-X11-X12-X13-X14-

Cys-X16-X17-X18,
wherein
```

$X_3$ is Glu or Lys;
$X_5$ is Glu or Gly;
$X_6$ is Trp or Tyr;
$X_7$ is Ser or Thr;
$X_8$ is Asn or Gln;
$X_9$ is Gly or Met;
$X_{10}$ is Phe or Tyr;
$X_{11}$ is Asp or Gln;
$X_{12}$ is Lys or Tyr;
$X_{13}$ is Glu or Thr;
$X_{14}$ is Glu or Phe;
$X_{16}$ is Ala or Val;

$X_{17}$ is Arg or Tyr; and
$X_{18}$ is Leu or Pro,
and wherein the polypeptide binds KDR or a VEGF/KDR complex.

Analysis of the binding polypeptides isolated from a linear display library (Lin20) defined two families of preferred embodiments including the amino acid sequences of Consensus Sequences 13 and 14 as follows:

```
Consensus Sequence 13:
Z1-X1-X2-X3-X4-X5-Z2  (Lin20),
wherein,
```

$Z_1$ is a polypeptide of at least one amino acid or is absent;
$X_1$ is Ala, Asp, Gln or Glu (preferably Gln or Glu);
$X_2$ is Ala, Asp, Gln, Glu Pro (preferably Asp, Glu or Gln);
$X_3$ is Ala, Leu, Lys, Phe, Pro, Trp or Tyr (preferably Trp, Tyr, Phe or Leu);
$X_4$ is Asp, Leu, Ser, Trp, Tyr or Val (preferably Tyr, Trp, Leu or Val);
$X_5$ is Ala, Arg, Asp, Glu, Gly, Leu, Trp or Tyr (preferably Trp, Tyr or Leu); and
$Z_2$ is a polypeptide of at least one amino acid or is absent,
and wherein the polypeptide binds KDR or a VEGF/KDR complex; or

```
Consensus Sequence 14:
                              (Lin20; SEQ ID NO: 7)
X1-X2-X3-Tyr-Trp-Glu-X7-X8-X9-Leu,
wherein,
``` the sequence can optionally have a N-terminal polypeptide, C-terminal polypeptide, or a polypeptide at both termed of at least one amino acid; and wherein $X_1$ is Asp, Gly or Ser (preferably Gly),
$X_2$ is Ile, Phe or Tyr;
$X_3$ is Ala Ser or Val;
$X_7$ is Gln, Glu, Ile or Val;
$X_8$ is Ala, Ile or Val (preferably Ile or Val);
$X_9$ is Ala, Glu, Val or Thr;
and wherein the polypeptide binds KDR or a VEGF/KDR complex.

Preferred embodiments comprising the Consensus Sequence 1 above, include polypeptides in which $X_3$ is Trp and the amino acid sequence of $X_7$-$X_{10}$ is Asp-Trp-Tyr-Tyr (SEQ ID NO:8). More preferred structures include polypeptides comprising Consensus Sequence 1, wherein $X_3$ is Trp and the amino acid sequence of $X_5$-$X_{10}$ is Glu-Glu-Asp-Trp-Tyr-Tyr (SEQ ID NO:9). Additional preferred polypeptides comprising Consensus Sequence 1 include polypeptides in which: $X_3$ is Trp and the amino acid sequence Of $X_5$-$X_{10}$ is Glu-Gln-Asp-Trp-Tyr-Tyr (SEQ ID NO:9), and the peptide $X_{13}$-$X_{14}$ is Ile-Thr, Of these preferred polypeptides, it is additionally preferred that $X_1$ will be Pro and $X_{12}$ will be one of Phe, Trp or Tyr.

Particular embodiments of the cyclic polypeptide families described above are disclosed in Tables 1, 2, 4, 5, 6 and 7, infra.

Additional cyclic polypeptides found to bind a KDR or VEGF/KDR target have a cyclic portion (or loop), formed by a disulfide bond between the two cysteine residues, consisting often amino acids, for example, as follows:

```
                                              (SEQ ID NO: 10)
Asn-Asn-Ser-Cys-Trp-Leu-Ser-Thr-Thr-Leu-Gly-Ser-

Cys-Phe-Phe-Asp, (SEQ ID NO: 11)
Asp-His-His-Cys-Tyr-Leu-His-Asn-Gly-Gln-Trp-Ile-

Cys-Tyr-Pro-Phe, (SEQ ID NO: 12)
Asn-Ser-His-Tyr-Ile-Trp-Asp-Gly-Met-Trp-Leu-Cys-

Phe-Pro-Asp.
```

Additional preferred embodiments include linear polypeptides capable of binding a KDR or VEGF/KDR target comprising, or alternatively consisting of, a polypeptide having an amino acid sequence selected from the group of amino acid sequences set forth in Table 3, infra.

The polypeptides of the invention can optionally have additional amino acids attached at either or both of the N- and C-terminal ends. In preferred embodiments, binding polypeptides according to the invention can be prepared having N-terminal and/or C-terminal flanking peptides of one or more, preferably two, amino acids corresponding to the flanking peptides of the display construct of the phage selectant from which the binding polypeptides were isolated. Preferred amino-terminal flanking peptides include Ala-Gly- (most preferably for TN7, TN8 and TN9 sequences), Gly-Ser- (most preferably for TN10 sequences), Gly-Asp- (most preferably for TN12 sequences), Ala-Gln- (most preferably for linear sequences), and Ser-Gly- (most preferably for MTN13 sequences). Preferred caboxy-terminal flanking peptides include -Gly-Thr (most preferably for TN7, TN8, TN9 sequences), -Ala-Pro (most preferably for TN10 sequences), -Asp-Pro (most preferably for TN12 sequences), -Gly-Gly (most preferably for linear sequences), and -Gly-Ser (most preferably for MTN13 sequences). Single terminal amino acids can also be added to the binding polypeptides of the invention, and preferred terminal amino acids will preferably correspond to the parental phage display construct e.g., most preferably, N-terminal amino acids will be selected from Gly- (most preferably for TN7, TN8, TN9, MTN13 sequences), Ser- (most preferably for TN10 sequences), Asp- (most preferably for TN12 sequences), and Gln- (most preferably for linear sequences), and most preferably C-terminal amino acids will be selected from -Gly (most preferably for TN7, TN8, TN9, MTN13 and linear sequences), -Ala (most preferably for TN10 sequences), and -Asp (most preferably for TN12 sequences). Conservative substitutions (i.e., substitute amino acids selected within the following groups: {Arg, His, Lys}, {Glu, Asp}, {Asn, Cys, Gln, Gly, Ser, Thr, Tyr}, {Ala, Ile, Leu, Met, Phe, Pro, Trp, Val}) for such flanking amino acids are also contemplated.

Examination of the sequence information and binding data from the isolates of libraries containing polypeptides with the potential to form loop structures (e.g., libraries designated TN7, TN8, TN9, TN10, TN12 and MTN13) identifies a series of KDR or VEGF/KDR complex binding polypeptides that may form loop structures. In to specific embodiments, cyclic KDR- or VEGF/KDR-binding polypeptides of the invention comprise, or alternatively, consist of, an amino acid sequence selected from Loop Consensus Sequences 15-19 as follows:

```
      Loop Consensus Sequence 15:
      Cys-X2-X3-X4-X5-X6-X7-Cys (TN8),
      wherein
```

$X_2$ is Ala, Arg, Asn, Asp, Gln, Glu, His, Ile, Lys, Phe, Pro, Ser, Trp or Tyr preferably Asp, Glu or Tyr);

$X_3$ is Ala, Arg, Asn, Asp, Gln, Glu, Gly, His, Ile, Lys, Met, Phe, Pro, Ser, Thr, Trp, Tyr or Val (preferably Glu, Met or Tyr);

$X_4$ is Ala, Asn, Asp, Glu, Gly, His, Ile, Leu, Lys, Phe, Pro, Ser, Thr, Trp, Tyr or Val (preferably Asp);

$X_5$ is Ala, Asp, Glu, Gly, Leu, Phe, Pro, Ser, Thr, Trp or Tyr (preferably Trp or Thr);

$X_6$ is Arg, Gln, Glu, Gly, Ile, Leu, Met, Pro, Thr, Trp, Tyr or Val (preferably Gly or Tyr); and $X_7$ is Ala, Arg, Gln, Glu, Gly, His, Ile, Leu, Lys, Met, Phe, Trp or Tyr (preferably Lys or Tyr), and wherein the polypeptide binds KDR or a VEGF/KDR complex; or

```
Loop Consensus Sequence 16:
Cys-X2-X3-X4-X5-X6-X7-X8-X9-X10-X11-Cys (TN12),
wherein
```

$X_2$ is Arg, Asp, Gln, Glu, Gly, His, Ile, Lys, Met, Thr, Trp, Tyr or Val (preferably Glu, Ile or Tyr);

$X_3$ is Ala, Arg, Asn, Cys, Glu, Ile, Leu, Met, Phe, Ser, Trp or Tyr (preferably Glu, Phe or Tyr);

$X_4$ is Arg, Asn, Asp, Gln, Glu, His, Ile, Leu, Pro, Ser, Thr, Trp, Tyr or Val (preferably Glu);

$X_5$ is a Asn, Asp, Gin, Gln, Gly, His, Met, Phe, Pro, Ser, Trp, Tyr or Val (preferably Gln or Ser);

$X_6$ is Asp, Gln, Glu, Gly, His, Ile, Leu, Met, Phe, Pro, Ser, Thr, Trp or Tyr (preferably Asp);

$X_7$ is Ala, Arg, Asn, Asp, Gln, Glu, Gly, Leu, Lys, Met, Phe, Pro, Ser, Thr, Trp, Tyr or Val (preferably Lys or Ser);

$X_8$ is Ala, Arg, Asn, Asp, Gln, Glu, Gly, His, Lys, Trp, Tyr or Val (preferably Gly or Tyr);

$X_9$ is Ala, Arg, Gln, Gly, His, Ile, Lys, Met, Phe, Ser, Thr, Trp, Tyr or Val (preferably Trp or Thr);

$X_{10}$ is Arg, Gln, Glu, His, Leu, Lys, Met, Phe, Pro, Thr, Trp or Val (preferably Glu or Trp); and $X_{11}$ is Arg, Asn, Asp, Glu, His, Ile, Leu, Met, Phe, Pro, Thr, Trp, Tyr or Val (preferably Phe), and wherein the polypeptide binds KDR or a VEGF/KDR complex; or

```
      Loop Consensus Sequence 17:
      Cys-X2-X3-X4-Gly-X6-Cys (TN7),
      wherein
```

$X_2$ is Asn, Asp or Glu;

$X_3$ is Glu, His, Lys or Phe;

$X_4$ is Asp, Gln, Leu, Lys, Met or Tyr; and $X_6$ is Arg, Gln, Leu, Lys or Val, and wherein the polypeptide binds KDR or a VEGF/KDR complex; or

```
      Loop Consensus Sequence 18:
      Cys-X2-X3-X4-X5-X6-X7-X8-Cys (TN9),
      wherein
```

$X_2$ is Ala, Asp, Lys, Ser, Trp or Val (preferably Lys);

$X_3$ is Asn, Glu, Gly, His or Leu;

$X_4$ is Gln, Glu, Gly, Met, Lys, Phe, Tyr or Val (preferably Met);

$X_5$ is Ala, Asn, Asp, Gly, Leu, Met, Pro, Ser or Thr;

$X_6$ is His, Pro or Trp (preferably Pro or Trp);

$X_7$ is Ala, Gly, His, Leu, Trp or Tyr (preferably Trp); and $X_8$ is Ala, Asp, Gln, Leu, Met, Thr or Trp, and wherein the polypeptide binds KDR or a VEGF/KDR complex, or

```
Loop Consensus Sequence 19:
                        (MTN13; SEQ ID NO: 13)
Cys-X2-X3-X4-X5-Ser-Gly-Pro-X9-X10-X11-X12-Cys,
wherein
```

$X_2$ is Asp, Glu, His or Thr;
$X_3$ is Arg, His, Lys or Phe;
$X_4$ is Gln, Ile, Lys, Tyr or Val;
$X_5$ is Gln, Ile, Leu, Met or Phe;
$X_9$ is Asn, Asp, Gly, His or Tyr;
$X_{10}$ is Gln, Gly, Ser or Thr;
$X_{11}$ is Glu, Lys, Phe or Ser; and
$X_{12}$ is Glu, Ile, Ser or Val,
and wherein the polypeptide binds KDR or a VEGF/KDR complex.

Preferred embodiments of the cyclic peptides of Loop Consensus Sequence 15 include KDR and/or VEGF/KDR complex binding polypeptides comprising Loop Consensus Sequences 20-22 as follows:

```
Loop Consensus Sequence 20:
Cys-X2-X3-X4-X5-X6-Tyr-Cys (TN8),
wherein
```

$X_2$ is Ala, Arg, Glu, Lys or Ser (preferably Glu);

$X_3$ is Ala, Asp, Gln, Glu, Thr or Val preferably Asp or Glu);
$X_4$ is Asp or Glu;
$X_5$ is Trp or Tyr; and
$X_6$ is Thr of Tyr (preferably Tyr); or

```
Loop Consensus Sequence 21:
Cys-X2-X3-X4-Gly-X6-X7-Cys (TN8),
wherein
```

$X_2$ is Asp, Gln or His;
$X_3$ is His or Tyr (preferably Tyr);
$X_4$ is His, Ile or Tyr;
$X_6$ is Ile, Met or Val; and
$X_7$ is Gly or Tyr; or

```
Loop Consensus Sequence 22:
Cys-X2-X3-X4-X5-Gly-X7-Cys (TN8), wherein
```

$X_2$ is Ala, Arg, Asn, Asp, His, Phe, Trp or Tyr (preferably Tyr, Trp or Phe);
$X_3$ is Ala, Asp, Gln, His, Lys, Met, Ser, Thr, Trp, Tyr or Val;
$X_4$ is Ala, Asn, Asp, Gln, Glu, Gly, His, Ile, Leu, Lys, Pro, Ser, Thr or Val;
$X_5$ is Asp, Phe, Ser, Thr, Trp or Tyr (preferably Thr, Ser or Asp); and
$X_7$ is Ala, Arg, Gln, His, Ile, Leu, Lys, Met, Phe, Trp or Tyr preferably Arg or Lys).

Preferred embodiments of the cyclic peptides of Loop Consensus Sequence 16 include KDR and/or VEGF/KR complex binding polypeptides comprising sequences of Loop Consensus Sequences 23-26 as follows:

```
Loop Consensus Sequence 23:
Cys-X2-X3-X4-X5-Trp-Gly-Gly-X9-X10-Cys (TN11,
``` i.e., 11-mers based on isolates of the TN12 library SEQ ID NO: 14), wherein $X_2$ is Ala, Phe or Trp (preferably Trp or Phe);
$X_3$ is Glu or Lys (preferably Glu);
$X_4$ is Asp, Ser, Trp or Tyr (preferably Asp, Trp or Tyr);
$X_5$ is Phe, Pro or Ser (preferably Ser);
$X_9$ is Gln or Glu (preferably Glu); and
$X_{10}$ is Ile, Phe or Val; or

```
Loop Consensus Sequence 24:
Cys-X2-Glu-X4-Ser-X6-Ser-X8-X9-X10-Phe-Cys (TN12;
```

SEQ ID NO: 15), wherein $X_2$ is His or Tyr;
$X_4$ is Leu, His or Thr;
$X_6$ is Asp or Leu (preferably Asp);
$X_8$ is Gly or Val (preferably Val);
$X_9$ is Thr or Val (preferably Thr); and
$X_{10}$ is Arg or Trp (preferably Arg); or

```
Loop Consensus Sequence 25:
Cys-X2-X3-X4-X5-X6-X7-Gly-X9-Trp-X11-Cys (TN12;
```

SEQ ID NO: 16), wherein $X_2$ is Glu, Met or Thr (preferably Glu);
$X_3$ is Ile, Leu, Met or Phe (preferably Met, Leu or Phe);
$X_4$ is Arg, Asp, Glu, Met, Trp or Val;
$X_5$ is Asn, Gln, Gly, Ser or Val;
$X_6$ is Glu or Asp;
$X_7$ is Lys, Ser, Thr or Val (preferably Lys);
$X_9$ is Arg, Gln, Lys or Trp (preferably Trp, Arg or Lys); and
$X_{11}$ is Asn, Leu, Phe or Tyr (preferably Tyr, Phe or Asn); or

```
Loop Consensus Sequence 26:
Cys-X2-X3-X4-X5-X6-X7-X8-X9-X10-X11-Cys (TN12), wherein
```

$X_2$ is Glu or Gly;
$X_3$ is Trp or Tyr;
$X_4$ is Ser or Thr;
$X_5$ is Asn or Gln;
$X_6$ is Gly or Met;
$X_7$ is Phe or Tyr;
$X_8$ is Asp or Gln;
$X_9$ is Lys or Tyr,
$X_{10}$ is Glu or Thr; and
$X_{11}$ is Glu or Phe.

Preferred embodiments of the cyclic peptides of Loop Consensus Sequence 17 include KDR and/or VEGF/KDR complex binding polypeptides comprising sequences of Loop Consensus Sequence 27 as follows:

```
Loop Consensus Sequence 27:
Cys-X2-X3-X4-Gly-X6-Cys (TN7), wherein
```

15

$X_2$ is Asn, Asp or Glu;
$X_3$ is Glu, His, Lys or Phe;
$X_4$ is Asp, Gln, Leu, Lys, Met or Tyr; and
$X_6$ is Arg, Gln, Leu, Lys or Val.

Preferred embodiments of the cyclic peptides of Loop Consensus Sequence 18 include KDR and/or VEGF/KDR complex binding polypeptides comprising sequences of Loop Consensus Sequence 28 as follows:

```
Loop Consensus Sequence 28:
Cys-X2-X3-X4-X5-X6-X7-X8-Cys  (TN9), wherein
```

$X_2$ is Ala, Lys, Ser, Trp or Val (preferably Lys);
$X_3$ is Asn, Glu, Gly, His or Leu;
$X_4$ is Glu, Gly, Lys, Met or Tyr (preferably Met);
$X_5$ is Ala, Asn, Asp, Leu, Met, Pro or Ser;
$X_6$ is His, Pro or Trp (preferably Pro);
$X_7$ is His, Leu, Trp or Tyr (preferably Trp or His); and
$X_8$ is Ala, Asp, Gln, Leu, Met, Thr or Trp.

Preferred embodiments of the cyclic peptides of Loop Consensus Sequence 19 include KDR and/or VEGF/KDR complex binding polypeptides comprising sequences of Loop Consensus Sequence 29 as follows:

```
Loop Consensus Sequence 29:
Cys-X2-X3-X4-X5-Ser-Gly-Pro-X9-X10-X11-X12-Cys (MTN13; SEQ ID NO: 17), wherein
```

$X_2$ is Asp, Glu, His or Thr;
$X_3$ is Arg, His, Lys or Phe;
$X_4$ is Gln, Ile, Lys, Tyr or Val;
$X_5$ is Gln, Ile, Leu, Met or Phe;
$X_9$ is Asn, Asp, Gly, His or Tyr;
$X_{10}$ is Gln, Gly, Ser or Thr;
$X_{11}$ is Glu, Lys, Phe or Ser; and
$X_{12}$ is Glu, Ile, Ser or Val.

Chemical or physical modifications, as well as any sequence modifications, described herein are encompassed for use with any of the specific sequences disclosed herein and/or any specific sequences that conform to any of the consensus sequences described herein.

The KDR and VEGF/KDR binding polypeptides described above can optionally have additional amino acids attached at either or both of the N- and C-terminal ends and can be modified, optimized or employed in multimeric constructs. Further, the invention includes homologues of the KDR and VEGF/KDR complex binding peptides as defined herein.

Another aspect of the present invention relates to modifications of the foregoing polypeptides to provide specific angiogenesis imaging agents by detectably labeling a polypeptide according to the present invention. Such detectable labeling can involve radiolabeling, enzymatic labeling, or labeling with MRI paramagnetic chelates or microparticles or superparamagnetic particles; incorporation into ultrasound bubbles, microparticles, microspheres, emulsions, or liposomes; or conjugation with optical dyes.

In another aspect of the present invention, methods for isolating KDR or KDR-expressing cells using the present binding polypeptides are provided.

Additionally, the KDR and VEGF/KDR complex binding polypeptides of the invention can be used as therapeutic agents, either as the sole bioactive agent in a pharmaceutically acceptable composition or conjugated to (or in combination with) other therapeutic agents to treat diseases or conditions involving KDR or VEGF/KDR complex, angiogenesis or diseases associated with a number of pathogens, including, for example, malaria, HIV, SIV, Simian hemorrhagic fever, etc.

When the binding peptides disclosed herein are used as therapeutic agents, it may be advantageous to enhance the serum residence time of the peptides. This can be accomplished by: a) conjugating to the peptide a moiety, such as maleimide, that reacts with free sulfhydryl groups on serum proteins, such as serum albumin, b) conjugating to the peptide a moiety, such as a fatty acid, that binds non-covalently to serum proteins, especially serum albumin, c) conjugating to the peptide a polymer, such as PEG, that is known to enhance serum residence time, and/or d) fusing DNA that encodes the KDR-binding peptide to DNA that encodes a serum protein such as human serum albumin or an antibody and expressing the encoded fusion protein.

In another aspect of the invention, methods of screening polypeptides identified by phage display for their ability to bind to cells expressing the target are provided. These methods permit rapid screening of the binding ability of polypeptides, including polypeptides with monomeric affinities that are too low for evaluation in standard cell-binding assays. Additionally, these methods may be used to rapidly assess the stability of the peptides in the presence of serum.

In another embodiment of the invention, a multimeric polypeptide construct having the ability to bind to KDR or VEGF/KDR complex comprising at least one amino acid sequence selected from any of the polypeptides described above is envisioned. In a particular embodiment, the polypeptide comprises an amino acid sequence selected from the group consisting of: SEQ ID NOS: 20-86, 87-136, 187-192, 193-203, 207-259 and 505-516. In a particular embodiment, the amino acid sequence selected from the group consisting of: SEQ ID NOS: 137-186. In one embodiment, the amino acid sequence further comprises N-terminal and/or C-terminal flanking peptides of one or more amino acids. In another embodiment, the amino acid sequence comprises a modification selected from the group consisting of: an amino acid substitution, and amide bond substitution, a D-amino acid substitution, a glycosylated amino acid, a disulfide mimetic substitution, an amino acid translocation, a retroinverso peptide, a peptoid, a retro-inverso peptoid, and a synthetic peptide. In another embodiment, the polypeptide can be conjugated to a detectable label or a therapeutic agent, optionally further comprising a linker or spacer between the polypeptide and the detectable label or the therapeutic agent. In a particular embodiment, the detectable label or the therapeutic agent is selected from the group consisting of an enzyme, a fluorescent compound, a liposome, an optical dye, a paramagnetic metal ion, a superparamagnetic particle, an ultrasound contrast agent and a radionuclide. In one embodiment, the therapeutic agent or detectable label comprises a radionuclide, including, for example, $^{18}$F, $^{124}$I, $^{125}$I, $^{131}$I, $^{123}$I, $^{77}$Br, $^{76}$Br, $^{99m}$Tc, $^{51}$Cr, $^{67}$Ga, $^{68}$Ga, $^{47}$Sc, $^{51}$Cr, $^{167}$Tm, $^{141}$Ce, $^{111}$In, $^{168}$Yb, $^{175}$Yb, $^{140}$La, $^{90}$Y, $^{88}$Y, $^{153}$Sm, $^{166}$Ho, $^{165}$Dy, $^{166}$Dy, $^{62}$Cu, $^{64}$Cu, $^{67}$Cu, $^{97}$Ru, $^{103}$Ru, $^{186}$Re, $^{188}$Re, $^{203}$Pb, $^{211}$Bi, $^{212}$Bi, $^{213}$Bi, $^{214}$Bi, $^{105}$Rh, $^{109}$Pd, $^{117m}$Sn, $^{149}$Pm, $^{161}$Tb, $^{177}$Lu, $^{198}$Au or $^{199}$Au. In a particular embodiment, the therapeutic agent or detectable label further comprises a chelator, such as, for example, a compound selected from the group consisting of: formula 20, 21, 22, 23a, 23b, 24a, 24b, and 25. In a particular embodiment, the detectable label comprises an ultrasound contrast agent that can comprise, for example, a phospholipid stabilized microbubble or a microballoon comprising a gas. Alternatively, the detectable label can comprise one or more paramagnetic metal ions or a superparamagnetic particle and one or more chelators.

In another embodiment, the invention is directed to an ultrasound contrast agent comprising at least one KDR or VEGF/KDR complex binding polypeptide comprising an amino acid sequence of one of the following and optionally further comprising N-terminal and/or C-terminal flanking peptides of one or more amino acids described herein. In a particular embodiment, the gas filled microvesicles comprise phospholipid stabilized microbubbles or microballoons. In one embodiment, the phospholipid stabilized microbubbles or microballoons father comprise a fluorinated gas.

In another embodiment, the invention is directed to a scintigraphic imaging agent comprising at least one KDR or VEGF/KDR complex binding polypeptide comprising an amino acid sequence of one of the following and optionally further comprising N-terminal and/or C-terminal flanking peptides of one or more amino acids described herein. In a particular embodiment, the scintigraphic imaging agent can comprise at least one radionuclide useful in scintigraphic imaging and at least one KDR or VEGF/KDR complex binding moiety comprising a polypeptide of the invention. In a particular embodiment, the scintigraphic imaging agent can comprise at least one chelator selected from the group consisting of: formula 20, 21, 22, 23a, 23b, 24a, 24b and 25. In one embodiment, the radionuclide is selected from the group consisting of $^{99m}$Tc and $^{111}$In.

In another embodiment, the invention is directed to an agent useful in radiotherapy comprising at least one KDR or VEGF/KDR complex binding polypeptide comprising an amino acid sequence of one of the following and optionally her comprising N-terminal and/or C-terminal flanking peptides of one or more amino acids described herein.

In another embodiment, the invention is directed to an agent useful in radiotherapy comprising at least one radionuclide useful in radiotherapy and at least one KDR or VEGF/KDR complex binding moiety comprising a polypeptide of the invention. In a particular embodiment, the agent can comprise at least one chelator selected from the group consisting of: formula 20, 21, 22, 23a, 23b, 24a, 245 and 25. In a particular embodiment, the radionuclide is selected from the group consisting of: $^{177}$Lu, $^{90}$Y, $^{13}$Sm and $^{165}$Ho.

In another embodiment, the invention is directed to a method of synthesizing a polypeptide or a multimeric polypeptide construct having the ability to bind KDR or VEGF/KDR complex comprising a cyclic polypeptide formed by introducing an amide bond between two side chains.

In another embodiment, the invention is directed to a method of synthesizing a polypeptide or a multimeric polypeptide construct having the ability to bind KDR or VEGF/KDR complex comprising a polypeptide and a linker comprising at least one glycosylated amino acid selected from the group consisting or serine, threonine and homoserine.

In another embodiment, the invention is directed to a method of synthesizing a multimeric polypeptide construct having the ability to bind KDR or VEGF/KDR complex selected from the group consisting of D1, D2, D3, D4, D5, D6, D7, D8, D9, D10, D11, D12, D13, D14, D15, D16, D17, D18, D19, D20, D21, D22, D23, D24, D25, D26, D27, D28, D29, D30 and D31, comprising: a) treating a purified peptide monomer with glutaric acid bis-N-hydroxysuccinimidyl ester; and b) contacting the peptide monomer in (a) with a second peptide monomer in the presence of N,N-(Diispropyl) aminomethylpolystyrene, thereby forming the multimeric polypeptide.

In another embodiment, the invention is directed to a multimeric polypeptide having the ability to bind to KDR or VEGF/KDR complex selected from the group consisting of: D1, D2, D3, D4, D5, D6, D7, D8, D9, D10, D11, D12, D13, D14, D15, D16, D17, D18, D19, D20, D21, D22, D23, D24, D25, D26, D27, D28, D29, D30 and D31.

In another embodiment, the invention is directed to a dimeric polypeptide construct having the ability to bind to KDR or VEGF/KDR, wherein each peptide of the dimer comprises a sequence of a polypeptide of the invention. In a particular embodiment, the amino acid sequence of the polypeptide is selected from the group consisting of: SEQ ID NOS: 20-86, 87-136, 187-192, 193-203, 207-259 and 505-516. In a particular embodiment, the amino acid sequence of the polypeptide is selected from the group consisting of: SEQ ID NOS: 137-186. Any of the dimmers of the invention can comprise N-terminal and/or C-terminal flanking peptides of one or more amino acids, as well as a modification such as, for example, an amino acid substitution, and amide bond substitution, a D-amino acid substitution, a glycosylated amino acid, a disulfide mimetic substitution, an amino acid translocation, a retroinverso peptide, a peptoid, a retro-inverso peptoid or a synthetic peptide. The dimeric constructs of the invention can be conjugated to a detectable label or a therapeutic agent, optionally further comprising a linker or spacer between the polypeptide and the detectable label or the therapeutic agent. The detectable label or the therapeutic agent can be, for example, an enzyme, a fluorescent compound, a liposome, an optical dye, one or more paramagnetic metal ions or a superparamagnetic particle, an ultrasound contrast agent or one or more radionuclides. In a particular embodiment, the therapeutic agent or detectable label comprises one or more radionuclides. In a particular embodiment, a dimeric construct can be labeled with one or more radionuclides such as, for example, $^{18}$F, $^{124}$I, $^{125}$I, $^{131}$I, $^{123}$I, $^{77}$Br, $^{76}$Br, $^{99m}$Tc, $^{51}$Cr, $^{67}$Ga, $^{68}$Ga, $^{47}$Sc, $^{51}$Cr, $^{167}$Tm, $^{141}$Ce, $^{111}$In, $^{168}$Yb, $^{175}$Yb, $^{140}$La, $^{90}$Y, $^{88}$Y, $^{153}$Sm, $^{166}$Ho, $^{165}$Dy, $^{166}$Dy, $^{62}$Cu, $^{64}$Cu, $^{67}$Cu, $^{97}$Ru, $^{103}$Ru, $^{186}$Re, $^{188}$Re, $^{203}$Pb, $^{211}$Bi, $^{212}$Bi, $^{213}$Bi, $^{214}$Bi, $^{105}$Rh, $^{109}$Pd, $^{117m}$Sn, $^{149}$Pm, $^{161}$Tb, $^{177}$Lu, $^{198}$Au or $^{199}$Au. In a particular embodiment, each peptide of the dimer is selected from an amino acid sequence selected from the group consisting of the sequences listed in Tables 1-11 and 27.

In another embodiment, the invention is directed to a multimeric polypeptide having the ability to bind to KDR or VEGF/KDR complex, wherein the multimeric polypeptide comprises at least one peptide monomer comprising an amino acid sequence selected from the group consisting of those sequences listed in Tables 1-11 and 27.

In another embodiment, the invention is directed to a method of inhibiting VEGF-induced vascular permeability comprising administering and agent comprising a peptide of the invention. In a particular embodiment the agent comprises D10.

These and other aspects of the present invention will become apparent with reference to the following detailed description.

BRIEF DESCRIPTION OF THE DRAWINGS

The patent or application file contains at least one drawing executed in color. Copies of this patent or patent application publication with color drawings will be provided by the Office upon request and payment of the necessary fee.

FIGS. 1A and 1B are graphs illustrating the saturation binding curves of binding peptide/neutravidin-HRP complexes. FIG. 1A illustrates the saturation binding curve for SEQ ID NO:264 and SEQ ID NO:294. FIG. 1B illustrates the saturation binding curve for SEQ ID NO:277 and SEQ ID NO:356. All peptides had a C-terminal biotin and JJ spacer (di(8-amino-3,6-dioxaoctanoic acid)).

FIG. 3 illustrates peptide structures, with and without both spacer (di(8-amino-3,6-dioxaoctanoic acid) "JJ") and biotin tested in Example 5((a) biotinylated SEQ ID NO:264 with a JJ spacer; (b) SEQ ID NO:264 with an N-terminal biotin; (c) biotinylated SEQ ID NO:294 with the JJ spacer (d) biotinylated SEQ ID NO:294).

FIG. 8 illustrates structures of binding polypeptide sequences tested in Example 6: SEQ ID NOS:294, 368, 369, 337, 371 and 372.

FIGS. 25A and 25B show the kinetic analysis of fluorescein labeled SEQ ID NO:277 binding to murine KDR-Fc. All sensograms are fit to the 1:1 Langmuir model.

FIGS. 34A-F depict preferred structures of chelators.

FIG. 67A: Diamonds: D6 alone at the indicated concentrations. Squares: D6 at the indicated concentrations plus 100 nM Adjunct A (constant). FIG. 67B shows the structure of Adjunct A.

FIG. 69 is a schematic showing Scheme 2 (synthesis of Peptide 4).

FIGS. 79A-G show derivatives of binding peptides of the invention.

FIGS. 87A-C are schematic representations depicting synthesis schemes and structures for Dimer D30. FIG. 87A shows the synthesis scheme for the preparation of Compound 3. FIG. 87B shows the synthesis scheme for dimer D30: Preparation of Ac-VCWEDSWGGEVCFRYDPGGGK (SEQ ID NO:337) {[PnAO6-Glut-K(-Glut-JJ-NH(CH$_2$)$_4$—(S)—CH(Ac-AQDWYYDEILJGRGGRGGRGG (SEQ ID NO:478)-NH)C(=O)NH$_2$]—NH$_2$}—NH$_2$: D30 from Compound 3 and Compound 4. FIG. 87C shows the structure of dimer D30.

FIGS. 88A-D are schematic representations depicting synthesis schemes and structures for dimer D31. FIG. 88A shows the synthesis scheme for the preparation of Compound 2. FIG. 88B shows the synthesis scheme for the preparation of Compound 4 (a peptide related to SEQ ID NO:374). FIG. 88C depicts the synthesis scheme and structure for dimer D31 (i.e., Preparation of Ac AGPTWCEDDWYYCWLF-GTGGGK (SEQ ID NO:277) [Ac-VCWEDSWGGEVC-FRYDPGGGK (SEQ ID NO:337) [SGS-Glut-SGS—(S)—NH(CH$_2$)$_4$—CH(Biotin-JJ-NH)—C(=O)]—NH$_2$]—NH$_2$). FIG. 88D shows the structure of D31.

DETAILED DESCRIPTION OF THE INVENTION

Figure 1B:
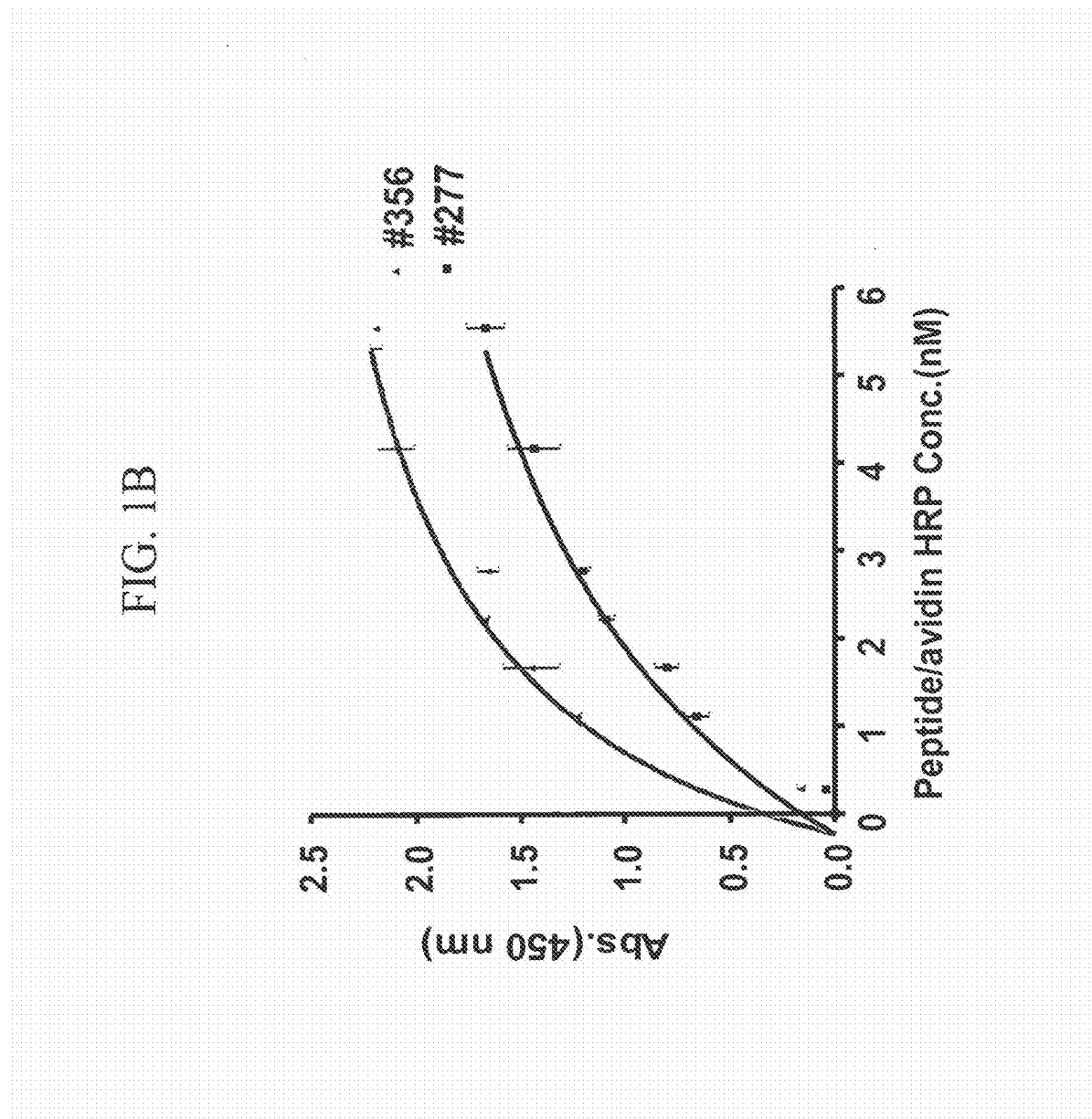

A description of preferred embodiments of the invention follows. While this invention has been particularly shown and described with references to preferred embodiments thereof, it will be understood by those skilled in the art that various changes in form and details may be made therein without departing from the scope of the invention encompassed by the appended claims.

DEFINITIONS

In the following sections, the term "recombinant" is used to describe non-naturally altered or manipulated nucleic acids, host cells transfected with exogenous nucleic acids, or polypeptides expressed non-naturally, through manipulation of isolated DNA and transformation of host cells. Recombinant is a term that specifically encompasses DNA molecules that have been constructed in vitro using genetic engineering techniques, and use of the term "recombinant" as an adjective to describe a molecule, construct vector, cell, polypeptide or polynucleotide specifically excludes naturally occurring such molecules, constructs, vectors, cells, polypeptides or polynucleotides.

The term "bacteriophage" is defined as a bacterial virus containing a DNA core and a protective shell built up by the aggregation of a number of different protein molecules. The terms "bacteriophage" and "phage" are used herein interchangeably.

The term "polypeptide" is used to refer to a compound of two or more amino acids joined through the main chain (as opposed to side chain) by a peptide amide bond (—C(:O)NH—). The term "peptide" is used interchangeably herein with "polypeptide" but is generally used to refer to polypeptides having fewer than 40, and preferably fewer than 25 amino acids.

The term "binding polypeptide" as used herein refers to any polypeptide capable of forming a binding complex with another molecule. An equivalent term sometimes used herein is "binding moiety". "KDR binding polypeptide" is a polypeptide that forms a complex in vitro or in vivo with vascular endothelial growth factor receptor-2 (or KDR, Flk-1) "VEGF/KDR complex binding polypeptide" is a polypeptide that forms a complex in vitro or in vivo with a binding complex formed between vascular endothelial growth factor (VEGF) and KDR, in particular the complex of homodimeric VEGF and one or two KDR molecules that is believed to form at the surface of endothelial cells during angiogenesis. Specific examples of KDR and VEGF/KDR binding polypeptides include but are not limited to the peptides presented in Tables 1-7, infra, and include hybrid and chimeric polypeptides incorporating such peptides. Also included within the definition of KDR and VEGF/KDR complex binding polypeptides are polypeptides that are modified or optimized as disclosed herein.

Specific examples of such modifications are discussed in detail infra, but include substitution of amino acids for those in the parent polypeptide sequence to optimize properties, obliterate an enzyme cleavage site, etc.; C- or N-terminal amino acid substitutions or elongations, e.g., for the purpose of linking the binding polypeptide to a detectable imaging label or other substrate, examples of which include, e.g., addition of a polyhistidine "tail" in order to assist in purification; truncations, amide bond changes; translocations; retroinverso peptides; peptoids; retroinversopeptoids, the use of N-terminal or C-terminal modifications or linkers, such as polyglycine or polylysine segments; alterations to include functional groups, notably hydrazide (—NH—NH$_2$) functionalities or the C-terminal linker -Gly-Gly-Gly-Lys (SEQ ID NO:18), to assist in immobilization of binding peptides according to this invention on solid supports or for attachment of fluorescent dyes; pharmacokinetic modifications, structural modifications to retain structural features, formation of salts to increase water solubility or case of formulation, and the like.

In addition to the detectable labels described further herein, other suitable substrates for the binding polypeptides include a tumoricidal agent or enzyme, a liposome (e.g., loaded with a therapeutic agent, an ultrasound appropriate gas, or both), or a solid support well, plate, bead, tube, slide, filter or dish. Moreover, dimers or multimers of one or more KDR or VEGF/KDR binding polypeptides can be formed. Such constructs may, for example, exhibit increased ability to bind to KDR. All such modified binding polypeptides are also considered KDR or VEGF/KDR complex binding polypeptides so long as they retain the ability to bind the KDR or VEGF/KDR targets.

"Homologues" of the binding polypeptides described herein can be produced using any of the modification or optimization techniques described herein or known to those skilled in the art. Such homologous polypeptides will be understood to fall within the scope of the present invention and the definition of KDR and VEGF/KDR complex binding polypeptides so long as the substitution, addition, or deletion of amino acids or other such modification does not eliminate its ability to bind either KDR or VEGF/KDR complex. The term "homologous", as used herein, refers to the degree of sequence similarity between two polymers (i.e., polypeptide molecules or nucleic acid molecules). Where the same nucleotide or amino acid residue or one with substantially similar properties (i.e., a conservative substitution) occupies a sequence position in the two polymers under comparison, then the polymers are homologous at that position. For example if the amino acid residues at 60 of 100 amino acid positions in two polypeptide sequences match or are homologous then the two sequences are 60% homologous. The homology percentage figures referred to herein reflect the maximal homology possible between the two polymers, i.e., the percent homology when the two polymers are so aligned as to have the greatest number of matched (homologous) positions. Polypeptide homologues within the scope of the present invention will be at least 70% and preferably greater than 80% homologous to at least one of the KDR or VEGF/KDR binding sequences disclosed herein.

The term "binding" refers to the determination by standard assays, including those described herein, that a binding polypeptide recognizes and binds reversibly to a given target. Such standard assays include, but are not limited to equilibrium dialysis, gel filtration, and the monitoring of spectroscopic changes that result from binding.

The term "specificity" refers to a binding polypeptide having a higher binding affinity for one target over another. The term "KDR specificity" refers to a KDR binding moiety having a higher affinity for KDR than for an irrelevant target. The term "VEGF/KDR specificity" refers to a VEGF/KDR complex binding moiety having a higher affinity for a VEGF/KDR complex than for another given target. Binding specificity can be characterized by a dissociation equilibrium constant ($K_D$) or an association equilibrium constant ($K_a$) for the two tested target materials, or can be any measure of relative binding strength, The binding polypeptides according to the present invention are specific for KDR or VEGF/KDR complex and preferably have a $K_D$ for KDR or VEGF/KDR complex that is lower than 10 μM, more preferably less than 1.0 μM, most preferably less than 0.5 μM or even lower.

The term "patient" as used herein refers to any mammal, especially humans.

The term "pharmaceutically acceptable" carrier or excipient refers to a non-toxic carrier or excipient that can be administered to a patient, together with a compound of this invention, such that it does not destroy the biological or pharmacological activity thereof.

The following common abbreviations are used throughout this specification: 9-fluorenylmethyloxycarbonyl (fmoc or Fmoc), 1-hydroxybenzotriazole (HOBt), N,N'-diisopropylcarbodiimide (DIC), acetic anhydride ($Ac_2O$), (4,4-dimethyl-2,6-dioxocyclohex-1-ylidene)-3-methylbutyl (ivDde), trifluoroacetic acid (TFA), Reagent B (TFA:$H_2O$:phenol:triisopropylsilane, 88:5:5:2), N,N-diisopropylethylamine (DIEA), O-(1H-benzotriazole-1-yl)-N,N,N',N'-tetramethyluronium hexafluorophosphate (HBTU), O-(7-azabenzotriazol-1-yl)-1,1,3,3-tetramethyluronium hexafluorphosphate (HATU), N-hydroxysuccinimide (NHS), solid phase peptide synthesis (SPPS), dimethyl sulfoxide (DMSO), dichloromethane (DCM), dimethylformamide (DMF), and N-methylpyrrolidinone (NMP).

DETAILED DESCRIPTION OF THE INVENTION

The present invention provides novel binding moieties that bind KDR or a complex of VEGF and KDR. Such binding moieties make possible the efficient detection, imaging and localization of activated endothelial cells exhibiting upregulated KDR expression and binding to VEGF. Such endothelial cells are characteristic of active angiogenesis, and therefore the polypeptides described herein provide a means of detecting, monitoring and localizing sites of angiogenesis. In particular, the binding polypeptides of this invention, when appropriately labeled, are useful for detecting, imaging and localizing tumor-induced angiogenesis. Thus, the binding polypeptides can be used to form a variety of diagnostic and therapeutic agents for diagnosing and treating neoplastic tumor growth or other pathogenic instances of angiogenesis. In addition, the binding polypeptides can themselves be used as therapeutic agents.

Specific KDR and VEGF/KDR complex binding polypeptides according to the present invention were isolated initially by screening of phage display libraries, that is, populations of recombinant bacteriophage transformed to express an exogenous peptide on their surface. In order to isolate new polypeptide binding moieties for a particular target, such as KDR or VEGF/KDR, screening of large peptide libraries, for example using phage display techniques, is especially advantageous, in that very large numbers (e.g., $5 \times 10^9$) of potential binders can be tested and successful binders isolated in a short period of time.

In order to prepare a phage library of displaying polypeptides to screen for binding polypeptides such as KDR or VEGF/KDR complex binding polypeptides, a candidate binding domain is selected to serve as a structural template for the peptides to be displayed in the library. The phage library is made up of a multiplicity of analogues of the parental domain or template. The binding domain template may be a naturally occurring or synthetic protein, or a region or domain of a protein. The binding domain template may be selected based on knowledge of a known interaction between the binding domain template and the binding target but this is not critical. In fact, it is not essential that the domain selected to act as a template for the library have any affinity for the target at all: Its purpose is to provide a structure from which a multiplicity (library) of similarly structured polypeptides (analogues) can be generated, which multiplicity of analogues will hopefully include one or more analogues that exhibit the desired binding properties (and any other properties screened for).

In selecting the parental binding domain or template on which to base the variegated amino acid sequences of the library, the most important consideration is how the variegated peptide domains will be presented to the target, i.e., in what conformation the peptide analogues will come into contact with the target. In phage display methodologies, for example, the analogues will be generated by insertion of synthetic DNA encoding the analogues into phage, resulting in display of the analogue on the surfaces of the phage. Such libraries of phage, such as M13 phage, displaying a wide variety of different polypeptides, can be prepared using techniques as described, e.g. in Kay et al., *Phage Display of Peptides and Proteins: A Laboratory Manual* (Academic Press, Inc., San Diego, 1996) and U.S. Pat. No. 5,223,409 (Ladner et al.), incorporated herein by reference.

In isolating the specific polypeptides according to this invention, seven cyclic peptide (or "loop") libraries, designated TN6/VI, TN7/IV, TN8/IX, TN9/IV, TN10/IX, TN12/I, and MTN13/I, and a linear library, designated Lin20, were used. Each library was constructed for expression of diversified polypeptides on M13 phage. The seven libraries having a "TN" designation were designed to display a short, variegated exogenous peptide loop of 6, 7, 8, 9, 10, 12 or 13 amino acids, respectively, on the sue of M13 phage, at the amino terminus of protein m. The libraries are designated TN6/VI (having a potential $3.3 \times 10^{12}$ amino acid sequence diversity), TN7/IV (having a potential $1.2 \times 10^{14}$ amino acid sequence diversity), TN8/IX (having a potential $2.2 \times 10^{15}$ amino acid sequence diversity), TN9/IV (having a potential $4.2 \times 10^{16}$ amino acid sequence diversity), TN10/IX (having a potential $3.0 \times 10^{16}$ amino acid sequence diversity), TN12/I (having a sequence diversity of $4.6 \times 10^{19}$), MTN13/I (having a potential $8.0 \times 10^{17}$ amino acid sequence diversity), and Lin20 (having a potential $3.8 \times 10^{25}$ amino acid sequence diversity).

The TN6/VI library was constructed to display a single microprotein binding loop contained in a 12-amino acid template. The TN6/VI library utilized a template sequence of $Xaa_1$-$Xaa_2$-$Xaa_3$-$Xaa_5$-$Xaa_6$-$Xaa_7$-$Xaa_8$-Cys-$Xaa_{10}$-$Xaa_{11}$-$Xaa_{12}$. The amino acids at positions 2, 3, 5, 6, 7, 8, 10, and 11 of the template were varied to permit any amino acid except cysteine (Cys). The amino acids at positions 1 and 12 of the template were varied to permit any amino acid except cysteine (Cys), glutamic acid (Glu), isoleucine (Ile), lysine (Lys), methionine (Met), and threonine (Thr).

The TN7/IV library was constructed to display a single microprotein binding loop contained in a 13-amino acid template. The TN7/IV library utilized a template sequence of $Xaa_1$-$Xaa_2$-$Xaa_3$-Cys-$Xaa_5$-$Xaa_6$-$Xaa_7$-$Xaa_8$-$Xaa_9$-Cys-$Xaa_{11}$-$Xaa_{12}$-$Xaa_{13}$. The amino acids at amino acid positions 1, 2, 3, 5, 6, 7, 8, 9, 11, 12, and 13 of the template were varied to permit any amino acid except cysteine (Cys).

The TN8/IX library was constructed to display a single microprotein binding loop contained in a 14-amino acid template. The TN8/IX library utilized a template sequence of $Xaa_1$-$Xaa_2$-$Xaa_3$-Cys-$Xaa_5$-$Xaa_6$-$Xaa_6$-$Xaa_7$-$Xaa_8$-$Xaa_9$-$Xaa_{10}$-Cys-$Xaa_{12}$-$Xaa_{13}$-$Xaa_{14}$. The amino acid at position 1, 2, 3, 5, 6, 7, 8, 9, 10, 12, 13, and 14 in the template were varied to pet any amino acid except cysteine (Cys).

The TN9/IV library was constructed to display a single microprotein binding loop contained in a 15-amino acid template. The TN9/IV library utilized a template sequence $Xaa_1$-$Xaa_2$-$Xaa_3$-Cys-$Xaa_5$-$Xaa_6$-$Xaa_7$-$Xaa_8$-$Xaa_9$-$Xaa_{10}$-$Xaa_{11}$-Cys-$Xaa_{13}$-$Xaa_{14}$-$Xaa_{15}$. The amino acids at position 1, 2, 3, 5, 6, 7, 8, 9, 10, 11, 13, 14 and 15 in the template were varied to permit any amino acid except cysteine (Cys).

The TN10/IX (library was constructed to display a single microprotein binding loop contained in a 16-amino acid template. The TN10/IX library utilized a template sequence $Xaa_1$-$Xaa_2$-$Xaa_3$-Cys-$Xaa_5$-$Xaa_6$-$Xaa_7$-$Xaa_8$-$Xaa_9$-$Xaa_{10}$-$Xaa_{11}$-$Xaa_{12}$-Cys-$Xaa_{14}$-$Xaa_{15}$-$Xaa_{16}$. The amino acids at positions 1, 2, 15, and 16 in the template were varied to permit any amino acid selected from a group of 10 amino acids: D, P, H, L, N, P, R, S, W, or Y). The amino acids at positions 3 and 14 in the template were varied to permit any amino acid selected from a group of 14 amino acids: A, D, F, G, H, L, N, P, Q, R, S, V, W, or Y). The amino acids at positions 5, 6, 7, 8, 9, 10, 11, and 12 in the template were varied to permit any amino acid except cysteine (Cys).

The TN12/I library was constructed to display a single microprotein binding loop contained in an 18-amino acid template. The TN12/I library utilized a template sequence $Xaa_1$-$Xaa_2$-$Xaa_3$-Cys-$Xaa_5$-$Xaa_6$-$Xaa_7$-$Xaa_8$-$Xaa_9$-$Xaa_{10}$-$Xaa_{11}$-$Xaa_{12}$-$Xaa_{13}$-$Xaa_{14}$Cys-$Xaa_{16}$-$Xaa_{17}$-$Xaa_{18}$. The amino acids at position 1, 2, 17, and 18 in the template were varied to permit any amino acid selected from a group of 12 amino acids: A, D, F, G, H, L, N, P, R, S, W, or Y). The amino acids at positions 3, 5, 6, 7, 8, 9, 10, 11, 12, 13, 14, and 16 were varied to permit any amino acid except cysteine (Cys).

The MTN13/I library was constructed to display a single microprotein binding loop contained in a 19-amino acid template featuring two variable regions of equal size (i.e., eight amino acids) separated by a constant region of three amino acids (Ser-Gly-Pro). The MTN13/I library utilized a template sequence $Xaa_1$-$Xaa_2$-$Xaa_3$-Cys-$Xaa_5$-$Xaa_6$-$Xaa_7$-$Xaa_8$-Ser-Gly-Pro-$Xaa_{12}$-$Xaa_{13}$-$Xaa_{14}$-$Xaa_{15}$-Cys-$Xaa_{17}$-$Xaa_{18}$-$Xaa_{19}$ (SEQ ID NO:19). The amino acids at position 1, 2, 3, 5, 6, 7, 8, 12, 13, 14, 15, 17, 18, and 19 in the template were varied to permit any amino acid except cysteine (Cys).

The Lin20 library was constructed to display a single linear peptide in a 20-amino acid template. The amino acids at each position in the template were varied to permit any amino acid except cysteine (Cys).

The binding polypeptides provided herein can include additions or truncations in the N- and/or C-termini. Such modified binding polypeptides are expected to bind KDR or VEGF/KDR complex. For example, the -GGGK linker present at the N-terminus of some of the binding polypeptides provided herein is an optional linker. Therefore, polypeptides having the same sequence, except without the terminal -GGGK sequence, are also encompassed by the present invention. In addition, binding polypeptides comprising the loop portion of the templates and sequences provided herein are expected to bind KDR and/or VEGF/KDR complex and are also encompassed by the present invention. The loop portion of the templates and sequences includes the sequences between and including the two cysteine residues that are expected to form a disulfide bond, thereby generating a peptide loop structure, Furthermore, the binding polypeptides of the present invention can include additional amino acid residues at the N- and/or C-termini.

The phage display libraries were created by making a designed series of mutations or variations within a coding sequence for the polypeptide template, each mutant sequence encoding a peptide analogue corresponding in overall structure to the template except having one or more amino acid variations in the sequence of the template. The novel variegated (mutated) DNA provides sequence diversity, and each transformant phage displays one variant of the initial template amino acid sequence encoded by the DNA, leading to a phage population (library) displaying a vast number of different but structurally related amino acid sequences. The amino acid variations are expected to alter the binding properties of the binding peptide or domain without significantly altering its structure, at least for most substitutions. It is preferred that the amino acid positions that are selected for variation (variable amino acid positions) will be surface amino acid positions, that is, positions in the amino acid sequence of the domains that, when the domain is in its most stable conformation, appear on the outer surface of the domain (i.e., the surface exposed to solution). Most preferably the amino acid positions to be varied will be adjacent or close together so as to maximize the effect of substitutions.

As indicated previously, the techniques discussed in Kay et al., *Phage Display of Peptides and Proteins: A Laboratory Manual* (Academic Press, Inc., San Diego, 1996) and U.S. Pat. No. 5,223,409 are particularly useful in preparing a library of potential binders corresponding to the selected parental template. The seven libraries discussed above were prepared according to such techniques, and they were screened for KDR or VEGF/KDR complex binding polypeptides against an immobilized target, as explained in the examples to follow.

In a typical screen, a phage library is contacted with and allowed to bind the target, or a particular subcomponent thereof. To facilitate separation of binders and non-binders, it is convenient to immobilize the target on a solid support. Phage bearing a target-binding moiety form a complex with the target on the solid support whereas non-binding phage remain in solution and may be washed away with excess buffer. Bound phage are then liberated from the target by changing the buffer to an extreme pH (pH 2 or pH 10), changing the ionic strength of the buffer, adding denaturants, or other known means. To isolate the binding phage exhibiting the polypeptides of the present invention, a protein elution was performed, i.e., some phage were eluted from target using VEGF in solution (competitive elution); and also, very high affinity binding phage that could not be competed off incubating with VEGF overnight were captured by using the phage still bound to substrate for infection of *E. coli* cells.

The recovered phage may then be amplified through infection of bacterial cells and the screening process repeated with the new pool that is now depleted in non-binders and enriched in binders. The recovery of even a few binding phage is sufficient to carry the process to completion. After a few rounds of selection, the gene sequences encoding the binding moieties derived from selected phage clones in the binding pool are determined by conventional methods, described below, revealing the peptide sequence that imparts binding affinity of the phage to the target. When the selection process works, the sequence diversity of the population fails with each round of selection until desirable binders remain. The sequences converge on a small number of related binders, typically 10-50 out of the more than 10 million original candidates from each library. An increase in the number of phage recovered at each round of selection, and of course, the recovery of closely related sequences are good indications that convergence of the library has occurred in a screen. After a set of binding polypeptides is identified, the sequence information may be used to design other secondary phage libraries, biased for members having additional desired properties.

Formation of the disulfide binding loop is advantageous because it leads to increased affinity and specificity for such peptides. However, in serum, the disulfide bond might be opened by free cysteines or other thiol-containing molecules. Thus, it may be useful to modify the cysteine residues to replace the disulfide cross-link with another less reactive linkage. The —$CH_2$—S—S—$CH_2$— cross-link has a preferred geometry in which the dihedral bond between sulfurs is close to 90 degrees, but the exact geometry is determined by the context of other side groups and the binding state of the molecule. Preferred modifications of the closing cross-link of the binding loop will preserve the overall bond lengths and angles as much as possible. Suitable such alternative cross-links include thioether linkages such as —$CH_2$—S—$CH_2$—$CH_2$—, —$CH_2$—$CH_2$—S—$CH_2$—, —$CH_2$—$CH_2$—S—$CH_2$—$CH_2$—; lactam linkages such as —$CH_2$—NH—CO—$CH_2$—and —$CH_2$—CO—NH—$CH_2$—; ether linkages such as —$CH_2$—$CH_2$—O—$CH_2$—$CH_2$—; alkylene bridges such as —$(CH_2)_n$— (where n=4, 5, or 6); the linkage —$CH_2$—NH—CO—NH—$CH_2$—, and solar groups known in the art.

Although polypeptides containing a stable disulfide-linked binding loop are most preferred, linear polypeptides derived from the foregoing sequences may be readily prepared, e.g., by substitution of one or both cysteine residues, which may retain at least some of the KDR or VEGF/KDR binding activity of the original polypeptide containing the disulfide linkage. In making such substitutions for Cys, the amino acids Gly, Ser, and Ala are preferred, and it is also preferred to substitute both Cys residues, so as not to leave a single Cys that may cause the polypeptide to dimerize or react with other free thiol groups in a solution. All such linearized derivatives that retain KDR or VEGF/KDR binding properties are within the scope of this invention.

Direct synthesis of the polypeptides of the invention may be accomplished using conventional techniques, including solid-phase peptide synthesis, solution-phase synthesis, etc. Solid-phase synthesis is preferred. See Stewart et al., *Solid-Phase Peptide Synthesis* (W. H. Freeman Co., San Francisco, 1989); Merrifield, *J. Am. Chem. Soc.*, 85:2149-2154 (1963), Bodanszky and Bodanszky, *The Practice of Peptide Synthesis* (Springer-Verlag, New York, 1984), incorporated herein by reference.

Polypeptides according to the invention may also be prepared commercially by companies providing peptide synthesis as a service (e.g., BACHEM Bioscience, Inc., King of Prussia, Pa.; Quality Controlled Biochemicals, Inc., Hopkinton, Mass.) Automated peptide synthesis machines, such as manufactured by Perkin-Elmer Applied Biosystems, also are available.

The polypeptide compound is preferably purified once it has been isolated or synthesized by either chemical or recombinant techniques. For purification purposes, there a many standard methods that may be employed, including reversed-phase high-pressure liquid chromatography RP-HPLC) using an alkylated silica column such as $C_4$-, $C_8$- or $C_{18}$-silica. A gradient mobile phase of increasing organic content is generally used to achieve purification, for example, acetonitrile in an aqueous buffer, usually containing a small amount of trifluoroacetic acid. Ion-exchange chromatography can also be used to separate peptides based on their charge. The degree of purity of the polypeptide may be determined by various methods, including identification of a major large peak on HPLC. A polypeptide that produces a single peak that is at least 95% of the input material on an HPLC column is preferred. Even more preferable is a polypeptide that produces a single pea that is at least 97%, at least 98%, at least 99% or even 99.5% or more of the input material on an HPLC column.

In order to ensure that the peptide obtained using any of the techniques described above is the desired peptide for use in compositions of the present invention, analysis of the peptide composition may be carried out. Such composition analysis may be conducted using high resolution mass spectrometry to determine the molecular weight of the peptide. Alternatively, the amino acid content of the peptide can be confirmed by hydrolyzing the peptide in aqueous acid, and separating, identifying and quantifying the components of the mixture using HPLC, or an amino acid analyzer. Protein sequenators, which sequentially degrade the peptide and identify the amino acids in order, may also be used to determine the sequence of the peptide.

KDR or VEGF/KDR complex binding polypeptides according to the present invention also may be produced using recombinant DNA techniques, utilizing nucleic acids (polynucleotides) encoding the polypeptides according to this invention and then expressing them recombinantly, i.e., by manipulating host cells by introduction of exogenous nucleic acid molecules in known ways to cause such host cells to produce the desired KDR or VEGF/KDR complex binding polypeptides. Such procedures are within the capability of those skilled in the art (see Davis et al., *Basic Methods in Molecular Biology*, (1986)), incorporated by reference. Recombinant production of short peptides such as those described herein may not be practical in comparison to direct synthesis, however recombinant means of production may be very advantageous where a KDR or VEGF/KDR complex binding moiety of this invention is incorporated in a hybrid polypeptide or fusion protein.

In the practice of the present invention, a determination of the affinity of the KDR or VEGF/KDR complex binding moiety for KDR or VEGF/KDR complex relative to another protein or target is a useful measure, and is referred to as specificity for KDR or VEGF/KDR complex. Standard assays for quantitating binding and determining affinity include equilibrium dialysis, equilibrium binding, gel filtration, or the monitoring of numerous spectroscopic changes (such as a change in fluorescence polarization) that may result from the interaction of the binding moiety and its target. These techniques measure the concentration of bound and free ligand as a function of ligand (or protein) concentration. The concentration of bound polypeptide ([Bound]) is related to the concentration of free polypeptide ([Free]) and the concentration of binding sites for the polypeptide, i.e., on KDR or VEGF/KDR complex, (N), as described in the following equation:

$$[Bound]=N\times[Free]/((1/K_a)+[Free]).$$

A solution of the data to this equation yields the association constant, $K_a$, a quantitative measure of the binding affinity. The association constant, $K_a$ is the reciprocal of the dissociation constant, $K_D$. The $K_D$ is more frequently reported in measurements of affinity. Preferred KDR or VEGF/KDR complex binding polypeptides have a $K_D$ for KDR or VEGF/KDR complex in the range of 1 nanomolar (nM) to 100 micromolar (µM), which includes $K_D$ values of less than 10 nM, less than 20 nM, less than 40 nM, less than 60 nM, less than 80 nM, less than 1 µM, less than 5 µM, less than 10 µM, less than 20 µM, less than 40 µM, less than 60 µM, and less than 80 µM.

Where KDR or VEGF/KDR complex binding moieties are employed as imaging agents, other aspects of binding specificity may become more important. Imaging agents operate in a dynamic system in that binding of the imaging agent to the target (KDR or VEGF/KDR complex, e.g., on activated endothelium) may not be in a stable equilibrium state throughout the imaging procedure. For example, when the imaging agent is initially injected, the concentration of imaging agent and of agent-target complex rapidly increases. Shortly after injection, however, the circulating (free) imaging agent starts to clear through the kidneys or liver, and the plasma concentration of imaging agent begins to drop. This drop in the concentration of free imaging agent in the plasma eventually causes the agent-target complex to dissociate. The usefulness of an imaging agent depends on the difference in rate of agent-target dissociation relative to the clearing rate of the agent. Ideally, the dissociation rate will be slow compared to the clearing rate, resulting in a long imaging time during which there is a high concentration of agent-target complex and a low concentration of free imaging agent (background signal) in the plasma.

Quantitative measurement of dissociation rates may be easily performed using several methods known in the art, such as fiber optic fluorimetry (see, e.g., Anderson & Miller, *Clin. Chem.*, 34(7):1417-21 (1938)), surface plasmon resonance (see, Malmborg et al., *J. Immunol. Methods*, 198(1): 51-7 (1996) and Schuck, *Current Opinion in Biotechnology*, 8:498-502 (1997)), resonant mirror, and grating coupled planar waveguiding (see, e.g., Hutchinson, *Molec. Biotechnology*, 3:47-54 (1995)). Automated biosensors are commercially available for measuring binding kinetics: BIAcore surface plasmon resonance sensor (Biacore AB, Uppsala SE), IAsys resonant mirror sensor (Fisons Applied Sensor Technology, Cambridge GB), BIOS-1 grated coupled planar waveguiding sensor (Artificial Sensor Instruments, Zurich CH).

Methods of Screening Polypeptides Identified by Phage Display for Their Ability to Bind to Cells Expressing the Target:

In another aspect of the invention, methods of screening binding polypeptides identified by phage display for their ability to bind to cells expressing the target (and not to cells that do not express the target) are provided. These methods address a significant problem associated with screening peptides identified by phage display: frequently the peptides so identified do not have sufficient affinity for the target to be screened against target-expressing cells in conventional assays. However, ascertaining that a particular phage-identified peptide binds to cells that express the target (and does not bind to cells that do not) is a critical piece of information in identifying binding peptides that are potential in vivo targeting moieties, The method takes advantage of the increase in affinity and avidity associated with multivalent binding and permits screening of polypeptides with low affinities against target-expressing cells.

The method generally consists of preparation and screening of multimeric constructs including one or more binding polypeptides. For example, polypeptides identified by phage display as binding to a target are biotinylated and complexed with avidin, streptavidin or neutravidin to form tetrameric constructs. These tetrameric constructs are then incubated with cells that express the desired target and cells that do not, and binding of the turmeric construct is detected. Binding may be detected using any method of detection known in the art. For example, to detect binding the avidin, streptavidin, or neutravidin may be conjugated to a detectable marker (e.g., a radioactive label, a fluorescent label, or an enzymatic label that undergoes a color change, such as HRP (horse radish peroxidase), TMB (tetramethyl benzidine) or alkaline phosphatase).

The biotinylated peptides are preferably complexed with neutravidin-HRP. Neutravidin exhibits lower non-specific binding to molecules than the other alternatives due to the absence of lectin binding carbohydrate moieties and cell adhesion receptor-binding RYD domain in neutravidin. See, Hiller et al., *Biochem. J*, 248:167-171 (1987); Alon et al., *Biochem. Biophys. Res. Commun.* 170:1236-41 (1990).

The tetrameric constructs can be screened against cells that naturally express the target or cells that have been engineered via recombinant DNA technologies to express the target (e.g., transfectants, transformants, etc.). If cells that have been transfected to express the target are used, mock-transfected cells (i.e., cells transfected without the genetic material encoding the target) may be used as a control.

The tetrameric complexes may optionally be screened in the presence of serum. Thus, the assay may also be used to rapidly evaluate the effect of serum on the binding of peptides to the target.

The methods disclosed herein are particularly useful in preparing and evaluating combinations of distinct binding polypeptides for use in dimeric or multimeric targeting constructs that contain two or more binding polypeptides. Use of biotin/avidin complexes allows for relatively easy preparation of tetrameric constructs containing one to four different binding peptides. Furthermore, it has now been found that affinity and avidity of a targeting construct may be increased by inclusion of two or more targeting moieties that bind to different epitopes on the same target. The screening methods described herein are useful in identifying combinations of binding polypeptides that may have increased affinity when included in such multimeric constructs.

In a preferred embodiment, the screening methods described herein may be used to screen KDR and VEGF/KDR complex binding polypeptides identified by phage display, such as those described herein. As described in more detail in Example 5 infra, these methods may be used to assess the specific binding of KDR binding polypeptides to cells that express KDR or have been engineered to express KDR. Tetrameric complexes of biotinylated KDR binding polypeptides of the invention and neutravidin-HRP may be prepared and screened against cells transfected to express KDR as well as mock transfected cells (without any KDR).

As shown in Example 5, the assay can be used to identify KDR binding polypeptides that bind specifically to KDR-expressing cells (and do not bind to cells that do not express KDR) even when the monodentate $K_D$ of the polypeptide is on the order of 200 nM-300 nM. The assay may be used to screen homotetrameric constructs containing four copies of a single KDR binding polypeptide of the invention as well as heterotetrameric constructs (e.g., constructs containing two or more different KDR binding polypeptides). The methods described herein are particularly useful for assessing combinations of KDR binding polypeptides for use in multimeric constructs, particularly constructs containing two or more KDR binding polypeptides that bind to different epitopes of KDR.

The assay may also be used to assess the effect of serum on the KDR binding polypeptides. Indeed, using the screening methods disclosed herein, KDR binding polypeptides, such as SEQ ID NOS:264, 294, and 356, were identified whose binding is not significantly affected by serum.

Modification or Optimization of KDR and VEGF/KDR Complex Binding Polypeptides.

As discussed, modification or optimization of KDR and VEGF/KDR complex binding polypeptides is within the scope of the invention and the modified or optimized polypeptides are included within the definition of "KDR and VEGF/KDR complex binding polypeptides". Specifically, a polypeptide sequence identified by phage display can be modified to optimize its potency, pharmacokinetic behavior, stability and/or other biological, physical and chemical properties.

Substitution of Amino Acid Residues

For example, one can make the following isosteric and/or conservative amino acid changes in the part polypeptide sequence with the expectation that the resulting polypeptides would have a similar or improved profile of the properties described above:

Substitution of alkyl-substituted hydrophobic amino acids: Including alanine, leucine, isoleucine, valine, norleucine, S-2-aminobutyric acid, S-cyclohexylalanine or other simple alpha-amino acids substituted by an aliphatic side chain from C1-10 carbons including branched, cyclic and straight chain alkyl, alkenyl or alkynyl substitutions.

Substitution of aromatic-substituted hydrophobic amino acids: Including phenylalanine, tryptophan, tyrosine, biphenylalanine, 1-naphthylalanine, 2-naphthylalanine, 2-benzothienylalanine, 3-benzothienylalanine, histidine, amino, alkylamino, dialkylamino, aza, halogenated (fluoro, chloro, bromo, or iodo) or alkoxy (from C1-C4)-substituted forms of the previous listed aromatic amino acids, illustrative examples of which are: 2-, 3- or 4-aminophenylalanine, 2-, 3- or 4-chlorophenylalanine, 2-, 3- or 4-methylphenylalanine, 2-, 3- or 4-methoxyphenylalanine, 5-amino-, 5-chloro-, 5-methyl- or 5-methoxytryptophan 2'-, 3'-, or 4'-amino-, 2'-, 3'-, or 4'-chloro-, 2, 3, or 4-biphenylalanine, 2'-, 3'-, or 4'-methyl-2,3 or 4-biphenylalanine, and 2- or 3-pyridylalanine.

Substitution of amino acids containing basic functions: Including arginine, lysine, histidine, ornithine, 2,3-diaminopropionic acid, homoarginine, alkyl, alkenyl, or aryl-substituted (from C1-C10 branched, linear, or cyclic) derivatives of the previous amino acids, whether the substituent is on the heteroatoms (such as the alpha nitrogen or the distal nitrogen or nitrogens, or on the alpha carbon, in the pro-R position for example. Compounds that serve as illustrative examples include: N-epsilon-isopropyl-lysine, 3-(4-tetrahydropyridyl)-glycine, 3-(4-tetrahydropyridyl)-alanine, N,N-gamma, gamma'-diethyl-homoarginine. Included also are compounds such as alpha methyl arginine, alpha methyl 2,3-diaminopropionic acid, alpha methyl histidine, alpha methyl ornithine where alkyl group occupies the pro-R position of the alpha carbon. Also included are the amides formed from alkyl, aromatic, heteroaromatic (where the heteroaromatic group has one or more nitrogens, oxygens or sulfur atoms singly or in combination) carboxylic acids or any of the many well-known activated derivatives such as acid chlorides, active esters, active azolides and related derivatives) and lysine, ornithine, or 2,3-diaminopropionic acid.

Substitution of acidic amino acids: Including aspartic acid, glutamic acid, homoglutamic acid, tyrosine, alkyl, aryl, arylalkyl and heteroaryl sulfonamides of 2,4-diaminopriopionic acid, ornithine or lysine and tetrazole-substituted alkyl amino acids.

Substitution of side chain amide residues: Including asparagine, glutamine, and alkyl or aromatic substituted derivatives of asparagine or glutamine.

Substitution of hydroxyl containing amino acids: Including serine, threonine, homoserine, 2,3-diaminopropionic acid, and allyl or aromatic substituted derivatives of serine or threonine. It is also understood that the amino acids within each of the categories listed above may be substituted for another of the same group.

Substitution of Amide Bonds

Another type of modification within the scope of the patent is to substitute the amide bonds within the backbone of the polypeptide. For example, to reduce or eliminate undesired proteolysis, or other degradation pathways that diminish serum stability, resulting in reduced or abolished bioactivity, or to restrict or increase conformational flexibility, it is common to substitute amide bonds within the backbone of the peptides with functionality that mimics the existing conformation or alters the conformation in the manner desired. Such modifications may produce increased binding affinity or improved pharmacokinetic behavior. It is understood that those knowledgeable in the art of peptide synthesis can make the following amide bond changes for any amide bond connecting two amino acids with the expectation that the resulting peptides could have the same or improved activity: insertion of alpha-N-methylamides or peptide amide backbone thioamides, removal of the carbonyl to produce the cognate secondary amines, replacement of one amino acid with an aza-amino acid to produce semicarbazone derivatives, and use of E-olefins and substituted E-olefins as amide bond surrogates.

Introduction of D-Amino Acids

Another approach within the scope of the patent is the introduction of D-alanine, or another D-amino acid, distal or proximal to the labile peptide bond. In this case it is also understood to those skilled in the art that such D-amino acid substitutions can, and at times, must be made, with D-amino acids whose side chains are not conservative replacements for those of the L-amino acid being replaced. This is because of the difference in chirality and hence side-chain orientation, which may result in the accessing of a previously unexplored region of the binding site of the target that has moieties of different charge hydrophobicity, steric requirements etc. than that serviced by the side chain of the replaced L-amino acid.

Modifications to Improve Pharmacokinetic or Pharmacodynamic Properties

It is also understood that use of the KDR or VEGF/KDR complex binding polypeptide in a particular application may necessitate modifications of the peptide or formulations of the peptide to improve pharmacokinetic and pharmacodynamic behavior. It is expected that the properties of the peptide may be changed by attachment of moieties anticipated to bring about the desired physical or chemical properties. Such moieties may be appended to the peptide using acids or amines, via amide bonds or urea bonds, respectively, to the N- or C-terminus of the peptide, or to the pendant amino group of a suitably located lysine or lysine derivative, 2,3-diaminopropionic acid, ornithine, or other amino acid in the peptide that possesses a pendant amine group or a pendant alkoxyamine or hydrazine group. The moieties introduced may be groups that are hydrophilic, basic, or nonpolar alkyl or aromatic groups depending on the peptide of interest and the extant requirements for modification of its properties.

Glycosylation of Amino Acid Residues

Yet another modification within the scope of the invention is to employ glycosylated amino acid residues (e.g., serine, threonine or asparagine residues), singly or in combination in the either the binding moiety (or moieties) or the linker moiety or both. Glycosylation, which may be carried out using standard conditions, can be used to enhance solubility, alter pharmacokinetics and pharmacodynamics or to enhance binding via a specific or non-specific interaction involving the glycosidic moiety. In another approach glycosylated amino acids such as O-(2-acetamido-2-deoxy-3,4,6-tri-O-acetyl-β-D-glucopyranosyl) serine or the analogous threonine derivative (either the D- or L- amino acids) can be incorporated into the peptide during manual or automated solid phase peptide synthesis, or in manual or automated solution phase peptide synthesis. Similarly D- or L-N$^\gamma$-(2-acetamido-2-deoxy-3,4,6-tri-O-acetyl-β-D-glucopyranosyl)-asparagine can be employed. The use of amino acids glycosylated on a pendant oxygen, nitrogen or sulfur function by the agency of suitably functionalized and activated carbohydrate moieties that can be employed in glycosylation is anticipated. Such carbohydrate functions could be monosaccharides, disaccharides or even larger assemblies of oligosaccharides (Kihlberg, Jan. (2000) Glycopeptide synthesis. In: Fmoc Solid Phase Peptide Synthesis—A Practical Approach (Chan, W. C. and White, P. D. Eds) Oxford University Press, New York, N.Y. Chap. 8, pp 195-213).

Also anticipated is the appendage of carbohydrate functions to amino acids by means other than glycosylation via activation of a leaving group at the anomeric carbon. Linkage of the amino acid to the glycoside is not limited to the formation of a bond to the anomeric carbon of the carbohydrate function. Instead, linkage of the carbohydrate moiety to the amino acid could be through any suitable, sufficiently reactive oxygen atom, nitrogen atom, carbon atom or other pendant atom of the carbohydrate function via methods employed for formation of C-heteroatom, C—C or heteroatom-heteroatom (examples are S—S, O—N, N—N, P—O, P—N) bonds known in the art.

Formation of Salts

It is also within the scope of the invention to form different salts that may increase the water solubility or the ease of formulation of these peptides. These may include, but are not restricted to, N-methylglucamine (meglumine), acetate, oxalates, ascorbates, etc.

Structural Modifications that Retain Structural Features

Yet another modification within the scope of the invention is truncation of cyclic polypeptides. The cyclic nature of many polypeptides of the invention limits the conformational space available to the peptide sequence, particularly within the cycle. Therefore truncation of the peptide by one or more residues distal or even proximal to the cycle, at either the N-terminal or C-terminal region may provide truncated peptides with similar or improved biological activity. A unique sequence of amino acids, even as small as three amino acids, which is responsible for the binding activity, may be identified, as noted for RGD peptides (see, e.g., Plow et al., *Blood*, 70(1): 110-5 (1987); Oldberg et al., *Journal of Biological Chemistry*, 263(36):19433-19436 (1988); Taub et al., *Journal of Biological Chemistry*, 264(1):259-65 (1989); Andrieux et al., *Journal of Biological Chemistry*, 264(16):9258-65 (1989); and U.S. Pat. Nos. 5,773,412 and 5,759,996, each of which is incorporated herein by reference).

It has also been shown in the literature that large peptide cycles can be substantially shortened, eliminating extraneous amino acids, but substantially including the critical binding residues. See, U.S. Pat. No. 5,556,939, incorporated by reference herein.

The shortened cyclic peptides can be formed using disulfide bonds or amide bonds of suitably located carboxylic acid groups and amino groups.

Figure 26:
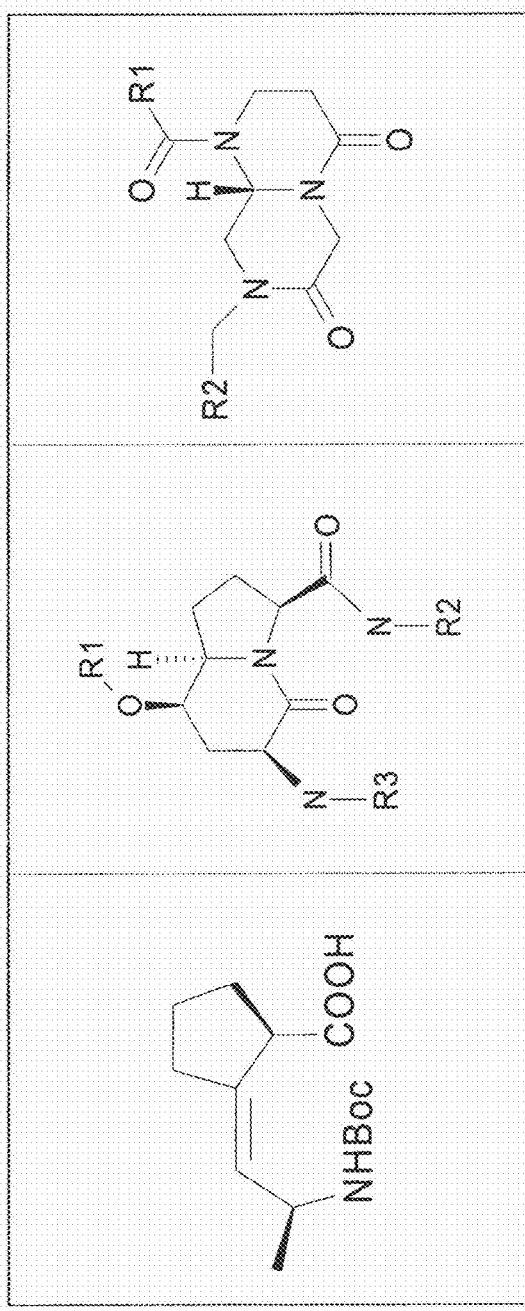
FIG. 26 depicts examples of alpha, beta, gamma or delta dipeptide or turn mimics (such as α, β, γ, or δ turn mimics), shown in panels 1, 2 and 3.

Furthermore, D-amino acids can be added to the peptide sequence to stabilize turn features (especially in the case of glycine). In another approach alpha, beta, gamma or delta dipeptide or turn mimics (such as α, β, γ, or δ turn mimics), some of which are shown in schematics 1, 2 and 3 as shown in FIG. 26, can be employed to mimic structural motifs and tan features in a peptide and simultaneously provide stability from proteolysis and enhance other properties such as, for example, conformational stability and solubility (structure 1: Hart et al. *J. Org. Chem.*, 64, 2998-2999 (1999); structure 2: Hanessian et al., "Synthesis of a Versatile Peptidomimetic Scaffold" in *Methods in Molecular Medicine, Vol 23: Peptidomimetics Protocols*, W. M. Kazmierski, Ed. (Humana Press Inc., Totowa, N.J., 1999), Chapter 10, pp. 161-174; structure 3: WO 01/16135).

Substitution of Disulfide Mimetics

Also with the scope of the invention is the substitution of disulfide mimetics for disulfide bonds within the KDR or VEGF/KDR complex binding peptides of the invention.

When disulfide-containing peptides are employed in generating $^{99m}$Tc-based radiopharmaceuticals, a significant problem is the presence of the disulfide bond. The integrity of the disulfide bond is difficult to maintain dug procedures designed to incorporate $^{99m}$Tc via routes that are reliant upon the reduction of pertechnetate ion and subsequent incorporation of the reduced Tc species into substances bearing Tc-specific chelating groups. This is because the disulfide bond is rather easily reduced by the reducing agents commonly used in kits devised for one-step preparation of radiopharmaceuticals. Therefore, the ease with which the disulfide bond can be reduced during Tc chelation may require substitution with mimetics of the disulfide bonds. Accordingly, another modification within the scope of the invention is to substitute the disulfide moiety with mimetics utilizing the methods disclosed herein or known to those skilled in the art, while retaining the activity and other desired properties of the KDR-binding polypeptides of the invention:

1) Oxime Linker

Figure 27:
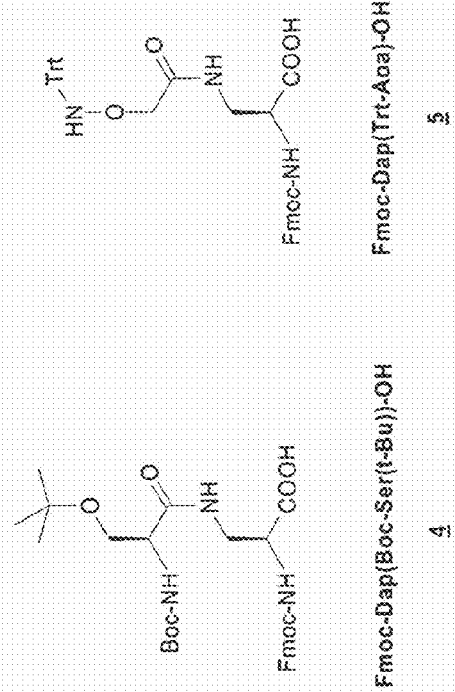
FIG. 27 shows an oxime linker. The amino acids containing an aminoalcohol function (4), and containing an alkoxyamino function (5), are incorporated into the peptide chain, not necessarily at the end of the peptide chain.

The oxime moiety has been employed as a linker by investigators in a number of contexts. Of the most interest is the work by Mutter et al (Wahl and Mutter, *Tetrahedron Lett.*, 37:6861-6864 (1996)). The amino acids 4, containing an aminoalcohol function, and 5, containing an alkoxyamino function, are incorporated into the peptide chain not necessarily at the end of the peptide chain (FIG. 27). After formation of the peptide the sidechain protecting groups are removed. The aldehyde group is unmasked and an oxime linkage is formed.

2) Lanthionine Linker

Lanthionines are cyclic sulfides, wherein the disulfide linkage (S—S) is replaced by a carbon-sulfur (C—S) linkage. Thus, e lability to reduction is far lower. Lanthionines have been prepared by a number of methods since 1971.

Preparation of Lanthionines Using Bromoacetylated Peptides

Figure 28:
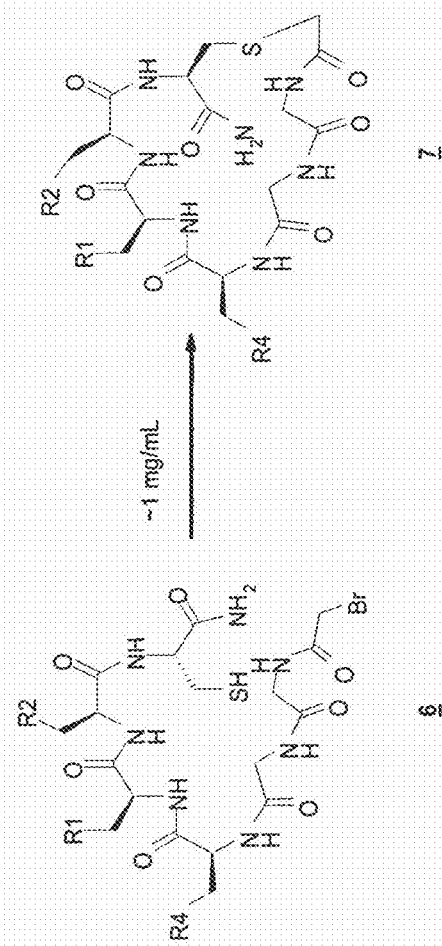
FIG. 28 shows an example of cyclization of cysteine with a pendant bromoacetamide function.

Lanthionines are readily prepared using known methods. See, for example, Robey et al., *Anal. Biochem.*, 177:373-377 (1989); Inman et al., *Bioconjugate Chem.*, 2:458-463 (1991); Ploinsky et al., *Med. Chem.*, 35:4185-4194 (1992); Mayer et al., "Peptides, Frontiers of Peptide Science", in Proceedings of the 15$^{th}$ American Peptide Symposium, Tam & Kaumaya (Eds.), Jun. 14-19, 1995, Nashville, Tenn. (Klumer Academic Pub., Boston), pp. 291-292; Wakao et al., Jpn. Kokai Tokyo Koho, JP 07300452 A2 (1995). Preparation of peptides using Boc automated peptide synthesis followed by coupling the peptide terminus with bromoacetic acid gives bromoacetylated peptides in good yield. Cleavage and deprotection of the peptides is accomplished using HF/anisole. If the peptide contains a cysteine group its reactivity can be controlled with low pH. If the pH of the medium is raised to 6-7 then either polymerization or cyclization of the peptide takes place. Polymerization is favored at high (100 mg/mL) concentration whereas cyclization is favored at lower concentrations (1 mg/mL), e.g., 6 cyclizes to 7 (Scheme 1; FIG. 28).

Inman et al. demonstrated the use of N$^α$-(Boc)-N$^ε$-[N-(bromoacetyl)-β-alanyl]-L-lysine as a carrier of the bromoacetyl group that could be employed in Boc peptide synthesis thus allowing placement of a bromoacetyl bearing moiety anywhere in a sequence. In preliminary experiments they found that peptides with 4-6 amino acids separating the bromoacetyl-lysine derivative from a cysteine tend to cyclize, indicating the potential utility of this strategy.

Preparation of Lanthionines Via Cysteine Thiol Addition to Acrylamides

Several variants of this strategy may be implemented. Resin-bound serine can be employed to prepare the lanthionine ring on resin either using a bromination-dehydrobromination-thiol addition sequence or by dehydration with disuccinimidyl carbonate followed by thio addition (Ploinsky et al., *M. J. Med. Chem.*, 35:4185-4194 (1992); Mayer et al., "Peptides, Frontiers of Peptide Science", in Proceedings of the 15$^{th}$ American Peptide Symposium, Tam & Kaumaya (Eds.), Jun. 14-19, 1995, Nashville, Tenn. (Klumer Academic Pub., Boston), pp. 291-292). Conjugate addition of thiols to acrylamides has also been amply demonstrated and a reference to the addition of 2-mercaptoethanol to acrylamide is provided (Wakao et al., Jpn. Kokai Tokyo Koho, JP 07300452 AZ (1995)).

3) Diaryl Ether or Diarylamine Linkage: Diaryl Ether Linkage from Intramolecular Cyclization of Aryl Boronic Acids and Tyrosine Recently the reaction of arylboronic acids with phenols, amines and heterocyclic amines in the presence of cupric acetate, in air, at ambient temperature, in dichloromethane using either pyridine or triethylamine as a base to provide to unsymmetrical diaryl ethers and the related ambles in good yields (as high as 98%) has been reported. See, Evans et al., *Tetrahedron Lett.*, 39:2937-2940 (1998); Chan et al., *Tetrahedron Lett.*, 39:2933-2936 (1998); Lam et al., *Tetrahedron Lett.*, 39:2941-2944 (1998). In the case of N-protected tyrosine derivatives as the phenol component the yields were also as high as 98%. This demonstrates that amino acid amides (peptides) are expected to be stable to the transformation and that yields are high. Precedent for an intramolecular reaction exists in view of the facile intramolecular cyclizations of peptides to lactams, intramolecular biaryl ether formation based on the S$_N$Ar reaction and the generality of intramolecular cyclization reactions under high dilution conditions or on resin, wherein the pseudo-dilution effect mimics high dilution conditions.

Figure 29:
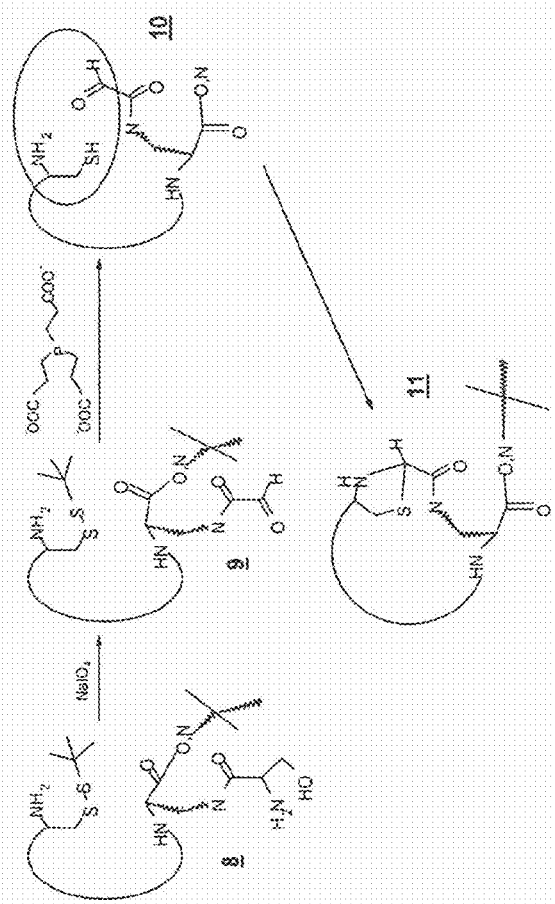
FIG. 29 is a schematic showing the formation of cyclic peptides with a thiazolidine linkage via intramolecular reaction of peptide aldehydes with cysteine moieties.

4) Formation of Cyclic Peptides with a Thiazolidine Linkage via Intramolecular Reaction of Peptide Aldehydes with Cysteine Moieties Another approach that may be employed involves intramolecular cyclization of suitably located vicinal amino mercaptan functions (usually derived from placement of a cysteine at a terminus of the linear sequence or tethered to the sequence via a side-chain nitrogen of a lysine, for example) and aldehyde functions to provide thiazolidines that result in the formation of a bicyclic peptide; one ring of which is that formed by the residues in the main chain, and the second ring being the thiazolidine ring, Scheme 2 (FIG. 29) provides an example. The required aldehyde function can be generated by sodium metaperiodate cleavage of a suitably located vicinal aminoalcohol function, which can be present as an unprotected serine tethered to the chain by appendage to a side chain amino group of a lysine moiety. In some cases the required aldehyde function is generated by unmasking of a protected aldehyde derivative at the C-terminus or the N-terminus of the chain. An example of this strategy is found in: Botti et al., *J. Am. Chem. Soc.*, 118:10018-10034 (1996).

5) Lactams Based on Intramolecular Cyclization of Pendant Amino Groups with Carboxyl Groups on Resin.

Macrocyclic peptides have been prepared by lactam formation by either head to tail or by pendant group cyclization. The basic strategy is to prepare a fully protected peptide wherein it is possible to remove selectively an amine protecting group and a carboxy protecting group. Orthogonal protecting schemes have been developed. Of those that have been developed the allyl, trityl and Dde methods have been employed most. See, Mellor et al., "Synthesis of Modified Peptides", in Fmoc Solid Phase Synthesis: A Practical Approach, White and Chan (eds) (Oxford University Press, New York, 2000), Chapt. 6, pp. 169-178. The Dde approach is of interest because it utilizes similar protecting groups for both the carboxylic acid function (Dmab ester) and the amino group (Dde group). Both are removed with 2-10% hydrazine in DMF at ambient temperature. Alternatively, the Dde can be used for the amino group and the allyl group can be used for the carboxyl.

Figure 30:
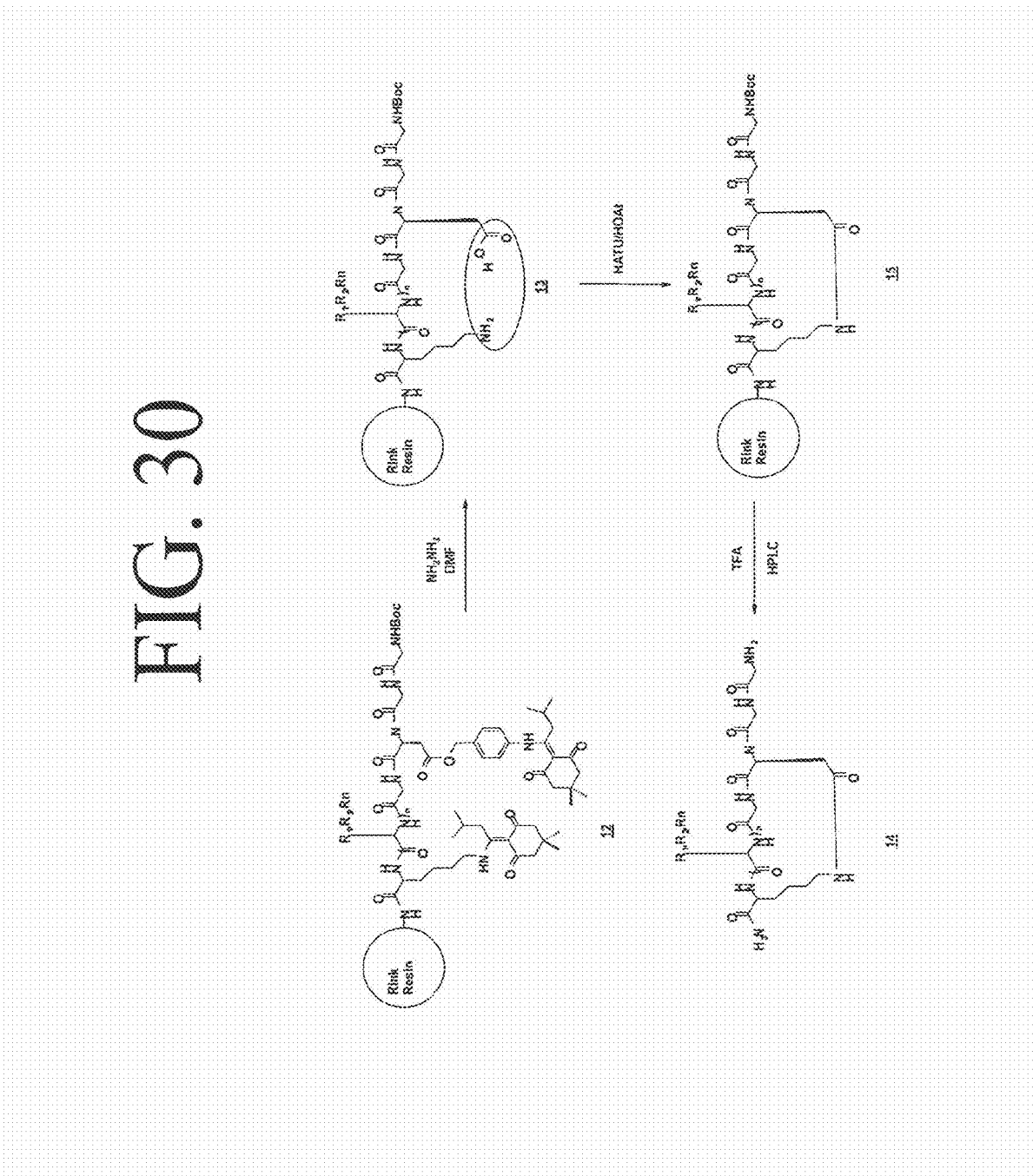
FIG. 30 is a schematic showing lactam surrogate for the disulfide bond via quasiorthogonal deprotection of Lys and Asp followed by on-resin cyclization and cleavage from resin.

A lactam function, available by intramolecular coupling via standard peptide coupling reagents (such as HATU, PyBOP etc), could act as a surrogate for the disulfide bond. The Dde/Dmab approach is shown in FIG. 30.

Thus, a linear sequence containing, for example, the Dde-protected lysine and Dmab ester can be prepared on a Tentagel-based Rink amide resin at low load (~0.1-0.2 mmol/g). Deprotection of both functions with hydrazine is then followed by on-resin cyclization to give the desired products.

Figure 31:
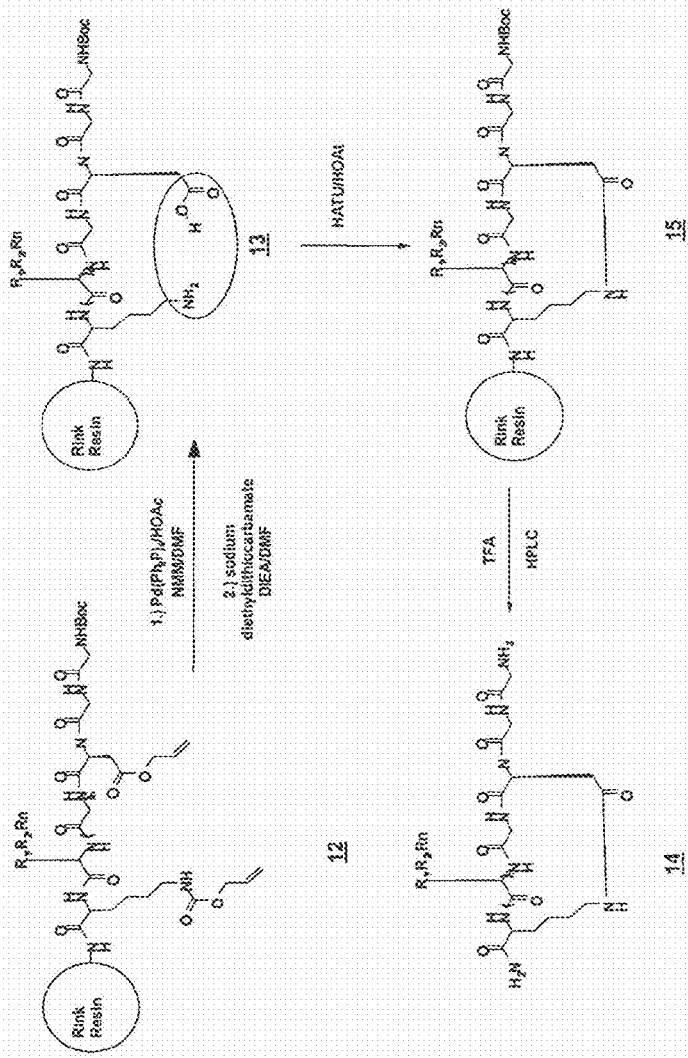
FIG. 31 is a schematic showing lactam surrogate for the disulfide bond via quasiorthogonal deprotection of Lys and Asp using allyl-based protecting groups followed by on-resin cyclization and cleavage from resin.

In the allyl approach, shown in FIG. 31, the pendant carboxyl that is to undergo cyclization is protected as an allyl ester and the pendant amino group is protected as an alloc group. On resin, both are selectively unmasked by treatment with palladium tris-triphenylphosphine in the presence of N-methylmorpholine and acetic acid in DMF. Residual palladium salts are removed using sodium diethyldithiocarbamate in the presence of DIEA in DMF, followed by subsequent washings with DMF. The lactam ring is then formed employing HATU/HOAt in the presence of N-methylmorpholine. Other coupling agents can be employed as described above. The processing of the peptide is then carried out as described above to provide the desired peptide lactam.

Subsequently cleavage from resin and purification can also be carried out. For functionalization of the N-terminus of the peptide, it is understood that amino acids, such as trans-4-(iV-Dde)methylaminocyclohexane carboxylic acid, trans-4-iV-Dde)methylaminobenzoic acid, or their alloc congeners can be employed. Yet another approach is to employ the safety catch method to intramolecular lactam formation during cleavage from the resin.

Thus, a linear sequence containing, for example, the Dde-protected lysine and Dmab ester may be prepared on a Tentagel-based Rink amide resin at low load (~0.1-0.2 mmol/g). Deprotection of both functions with hydrazine is then followed by on-resin cyclization to give the desired products. Subsequently cleavage from resin and purification may also be carried out. For functionalization of the N-terminus of the peptide it is understood that diamino acids such as trans-4(iv-Dde)methylaminocyclohexane carboxylic acid or trans-4-(iv-Dde)methylamino benzoic acid would be required. An alternative scenario is to employ the safety catch method to intramolecular lactam formation during cleavage from the resin.

6) Cyclic Peptides Based on Olefin Metathesis

Figure 32:
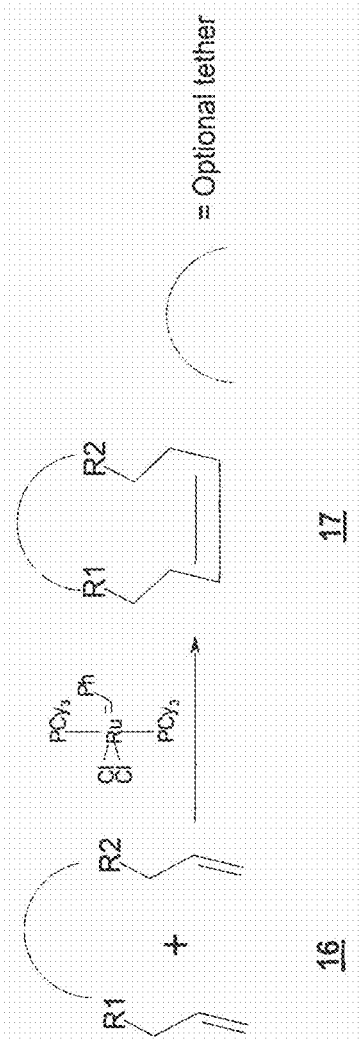
FIG. 32 is a schematic depicting Grubbs Olefin Metathesis Cyclization.

The Grubbs reaction (FIG. 32) involves the metathesis/cyclization of olefin bonds and is illustrated as shown below. See, Schuster et al., *Angewandte. Chem. Int. Edn Engl.,* 36:2036-2056 (1997); Miller et al., J. Am. Chem. Soc., 118: 9606-9614 (1996).

It is readily seen (FIG. 32) that if the starting material is a diolefin (16) that the resulting product will be cyclic compound 17. The reaction has in fact been applied to creation of cycles from olefin-functionalized peptides. See, e.g., Pernerstorfer et al., *Chem. Commun.,* 20:1949-50 (1997); see, also, Covalent capture and stabilization of cylindrical β-sheet peptide assemblies, Clark et al., *Chem. Eur. J.,* 5(2):782-792 (1999); Highly efficient synthesis of covalently cross-linked peptide helices by ring-closing metathesis, Blackwell et al., *Angew. Chem., Int. Ed.,* 37(23):3281-3284 (1998); Synthesis of novel cyclic protease Inhibitors using Grubbs olefin metathesis, Ripka et at, *Med. Chem. Lett.,* 8(4):357-360 (1998); Application of Ring-Closing Metathesis to the Synthesis of Rigidified Amino Acids and Peptides, Miller et al., *J. Am. Chem. Soc.,* 118(40):9606-9614 (1996); Supramolecular Design by Covalent Capture, Design of a Peptide Cylinder via Hydrogen-Bond-Promoted Intermolecular Olefin Metathesis, Clark et al., *J. Am. Chem. Soc.,* 117(49): 12364-12365 (1995); Synthesis of Conformationally Restricted Amino Acids and Peptides Employing Olefin Metathesis, Miller et al., *J. Am. Chem. Soc.,* 117(21):5855-5856 (1995). One can prepare either C-allylated amino acids or possibly N-allylated amino acids and employ them in this reaction in order to prepare carba-bridged cyclic peptides as surrogates for disulfide bond containing peptides. One may also prepare novel compounds with olefinic groups. Functionalization of the tyrosine hydroxyl with an olefin-containing tether is one option. The lysine ϵ-amino group is another option with appendage of the olefin-containing unit as part of an acylating moiety, for example. If instead the lysine side chain amino group is alkylated with an olefin containing tether, it can still function as a point of attachment for a reporter as well. The use of 5-pentenoic acid as an acylating agent for the lysine, ornithine, or diaminopropionic side chain amino groups is another possibility. The length of the olefin-containing tether can also be varied in order to explore structure activity relationships.

Manipulation of Peptide Sequences

Other modifications within the scope of the invention include common manipulations of peptide sequences, which can be expected to yield peptides with similar or improved biological properties. These include amino acid translocations (swapping amino acids in the sequence), use of retroinverso peptides in place of the original sequence or a modified original sequence, peptoids and retro-inverso peptoid sequences. Structures wherein specific residues are peptoid instead of peptidic, which result in hybrid molecules, neither completely peptidic nor completely peptoid, are anticipated as well.

Linkers

Additional modifications within the scope of the invention include introduction of linkers or spacers between the targeting sequence of the KDR or VEGF/KDR complex binding peptide and the detectable label or therapeutic agent. Use of such linkers/spacers may improve the relevant properties of the binding peptide (e.g., increase serum stability, etc.). These linkers may include, but are not restricted to, substituted or unsubstituted alkyl chains, polyethylene glycol derivatives, amino acid spacers, sugars, or aliphatic or aromatic spacers common in the art. Furthermore, linkers that are combinations of the moieties described above, can also be employed to confer special advantage to the properties of the peptide. Lipid molecules with linkers may be attached to allow formulation of ultrasound bubbles, liposomes or other aggregation based constructs. Such constructs mould be employed as agents for targeting and delivery of a diagnostic reporter, a therapeutic agent (e.g., a chemical "warhead" for therapy) or a combination of these.

Multimeric Constructs of KDR and VEGF/KDR Complex Binding Polypeptides

Constructs employing dimers, multimers or polymers of one or more VEGF or VEGF/KDR complex binding polypeptides of the invention are also contemplated. Indeed, there is ample literature evidence that the binding of low potency peptides or small molecules can be substantially increased by the formation of dimers and multimers. Thus, dimeric and multimeric constructs (both homogeneous and heterogeneous) are within the scope of the instant invention. Indeed, as discussed in more detail in the Examples, it is within the scope of the present invention to include multiple KDR or VEGF/KDR complex binding polypeptide sequences in a dimeric or multimeric construct. Moreover, as shown in Example 4 infra, these constructs can exhibit improved binding compared to a monomeric construct. The polypeptide sequences in the dimeric constructs may be attached at their N- or C-terminus or the N-epsilon nitrogen of a suitably placed lysine moiety (or another function bearing a selectively derivatizable group such as a pendant oxyamino or other nucleophilic group), or may be joined together via one or more linkers employing the appropriate attachment chemistry. This coupling chemistry may include amide, urea, thiourea, oxime, or aminoacetylamide (from chloro- or bromoacetamide derivatives, but is not so limited. For example, ally of the following methods may be utilized to prepare dimeric or multimeric constructs of KDR or VEGF/KDR complex binding polypeptides of the invention. Modified polypeptides and peptide-derived molecules are shown, for example, in FIGS. 79A-79G, Method A Fully protected KDR-binding peptides can be built up on Ellman-type safety catch resin using automated or manual Fmoc peptide synthesis protocols. Backes et al., *J. Am. Chem. Soc.*, 118(12):3055-56 (1996). Separately, using standard methods known in the art of peptide synthesis, a di-lysine derivative can be constructed on 2-chlorotrityl resin. See, for example, Fields et al, "Principles and Practice of Solid Phase Synthesis" in *Synthetic Peptides, A Users Guide, Grant*, Ed. (W.H. Freeman Co., New York, 1992), Chapt. 3, pp. 77-183; Barlos et al., "Convergent Peptide Synthesis" in *Fmoc Solid Phase Peptide Synthesis*, Chan, W. C. and White, P. D., Eds. (Oxford University Press, New York, 2000), Chapt 9, pp. 215-228. Liberation of this from the 2-chlorotrityl resin without removal of the sidechain protecting groups, activation of the carboxyl group and coupling to any amine-functionalized labeling group provides a di-lysine derivative whose protected pendant nitrogen atoms may be unmasked to give two free amino groups. The prior-mentioned safety-catch resin is activated and the desired N-deprotected labeling group-functionalized di-lysine derivative is added to the activated safety-catch resin. The pendant amino groups are acylated by the carboxy-terminus of the safety-catch resin-bound peptide, which is now detached from the resin and an integral part of the di-lysine structure. An excess of the safety-catch resin-bound peptide can be employed to insure complete reaction of the amino groups of the di-lysine construct Optimization of the ratio of the reacting partners in this scheme optimizes the yield. The protecting groups on the KDR-binding peptides are removed employing trifluoroacetic acid based cleavage protocols.

The synthesis of dimeric and multimeric constructs wherein two or more KDR-binding peptides are present in one construct is easily accomplished. Orthogonal protection schemes (such as an allyloxycarbonyl group on one nitrogen and an Fmoc group on the other, or employing the Fmoc group in conjunction with the iV-Dde protecting group on the other, for example) can be employed to distinguish the pendant nitrogen atoms of the di-lysine derivatives described above. Unmasking of one of the amino groups, followed by reaction of the resulting product with an activated safety-catch resin-bound KDR-binding peptide as described above, provides a di-lysine construct having a single KDR-binding peptide attached. Removal of the second protecting group unmasks the remaining nitrogen. See, also, Mellor et al., "Synthesis of Modified Peptides" in *Fmoc Solid Phase Peptide Synthesis*, Chan, W. C. and White, P. D., Eds. (Oxford University Press, New York, 2000), Chapt. 6, pp. 169-176. The resulting product may be reacted with a second safety-catch resin bearing another KDR-binding peptide to provide a fully-protected homodimeric construct, which after removal of protecting groups with trifluoroacetic acid, provides the desired material.

Method B

A KDR-binding peptide is assembled on a Rink-amide resin by automated or manual peptide coupling methods, usually employing Fmoc peptide synthesis protocols. The peptide may possess a C-terminus or N-terminus functionalized with a linker or a linker-labeling group construct that may possess an additional nucleophilic group such as the s-amino group of a lysine moiety, for example. Cleavage of the protecting groups is accomplished employing trifluoroacetic acid with appropriate modifiers depending on the nature of the peptide. The fully deprotected peptide is then reacted with a large excess of a bifunctional electrophile such as the commercially available glutaric acid bis-N-hydroxysuccinimide ester (Tyger Scientific, Inc.). The resulting monoamidated, mono-N-hydroxysuccinimidyl ester of glutaric acid is then treated with an additional equivalent of the same peptide, or an equivalent of a different Knit-binding peptide. Purification of the resulting material by HPLC affords the desired homodimeric construct bearing a suitable labeling group.

Method C

A modular scheme can be employed to prepare dimeric or higher multimeric constructs bearing suitable labeling groups as defined above. In a simple illustration, fmoc-lysine (iV-Dde) Rink amide resin is treated with piperidine to remove the fmoc moiety. Then a labeling function, such as biotin, 5-carboxyfluorescein or N,N-Dimethyl-Gly-Ser(O-t-Bu)-Cys(Acm)-Gly-OH is coupled to the nitrogen atom. The resin is next treated with hydrazine to remove the iV-Dde group. After thorough washing, the resin is treated with cyanuric chloride and a hindered base such as diisopropylethylamine in a suitable solvent such as DMF, NW or dichloromethane to provide a monofunctionalized dichlorotriazine bound to the resin. Subsequent successive displacement of the remaining chlorine atoms by two equivalents of a KDR-binding peptide provides a resin-bound homo-dimeric labeling group-functionalized construct. Falorni et al., *Tetrahedron Lett.*, 39(41): 7607-7610 (1998); Johnson et al., *Tetrahedron Let.*, 54(16): 40974106 (1998); Stankova et al., *Mol. Diversity*, 2(1/2):75-80 (1996). The incoming peptides may be protected or unprotected as the situation warrants. Cleavage of protecting groups is accomplished employing trifluoroacetic acid-based deprotection reagents as described above, and the desired materials are purified by high performance liquid chromatography.

It is understood that in each of these methods lysine derivatives may be serially employed to increase the multiplicity of the multimers. The use of related, more rigid molecules bearing the requisite number of masked, or orthogonally protected nitrogen atoms to act as scaffolds to vary the distance between the KDR-binding peptides, to increase the rigidity of the construct (by constraining the motion and relative positions of the KDR-binding peptides relative to each other and the reporter) is entirely within the scope of methods A-C and all other methods described herein. The references cited above are incorporated by reference herein in their entirety.

Uses for KDR or VEGF/KDR Complex Binding Polypeptides:

The KDR or VEGF/KDR complex binding moieties according to this invention will be extremely useful for detection and/or imaging of KDR or VEGF/KDR complex in vitro or in vivo, and particularly for detection and/or imaging of sites of angiogenesis, in which VEGF and KDR are intimately involved, as explained above. Any suitable method of assaying or imaging KDR or VEGF/KDR complex may be employed. The KDR and VEGF/KDR complex binding moieties of the invention also have utility in the treatment of a variety of disease states, including those associated with angiogenesis or those associated with a number of pathogens. The KDR and VEGF/KDR complex binding moieties of the invention may themselves be used as therapeutics or may be used to localize one or more therapeutic agents (e.g., a chemotherapeutic, a radiotherapeutic, genetic material, etc.) to KDR expressing cells, including sites of angiogenesis.

In Vitro:

For detection of KDR or VEGF/KDR complex in solution, a binding polypeptide according to the invention can be detectably labeled, e.g., fluorescently labeled, enzymatically labeled, or labeled with a radioactive or paramagnetic metal, then contacted with the solution, and thereafter formation of a complex between the binding polypeptide and the KDR or VEGF/KDR complex target can be detected. As an example, a fluorescently labeled KDR or VEGF/KDR complex binding peptide may be used for in vitro KDR or VEGF/KDR complex detection assays, wherein the peptide is added to a solution to be tested for KDR or VEGF/KDR complex under conditions allowing binding to occur. The complex between the fluorescently labeled KDR or VEGF/KDR complex binding peptide and KDR or VEGF/KDR complex target can be detected and quantified by measuring the increased fluorescence polarization arising from the KDR or VEGF/KDR complex-bound peptide relative to that of the free peptide.

Alternatively, a sandwich-type "ELISA" assay may be used, wherein a KDR or VEGF/KDR complex binding polypeptide is immobilized on a solid support such as a plastic tube or well, then the solution suspected of containing KDR or VEGF/KDR complex target is contacted with the immobilized binding moiety, non-binding materials are washed away, and complexed polypeptide is detected using a suitable detection reagent, such as a monoclonal antibody recognizing KDR or VEGF/KDR complex. The monoclonal antibody is detectable by conventional means known in the art, including being detectably labeled, e.g., radiolabeled, conjugated with an enzyme such as horseradish peroxidase and the like, or fluorescently labeled, etc.

For detection or purification of soluble KDR or VEGF/KDR complex in or from a solution, binding polypeptides of the invention can be immobilized on a solid substrate such as a chromatographic support or other matrix material, then the immobilized binder can be loaded or contacted with the solution under conditions suitable for formation of a binding polypeptide:KDR complex or binding polypeptide:VEGF/KDR complex. The non-binding portion of the solution can be removed and the complex may be detected, e.g., using an anti-KDR or anti-VEGF/KDR complex antibody, or an anti-binding polypeptide antibody, or the KDR or VEGF/KDR complex target may be released from the binding moiety at appropriate elution conditions.

The biology of angiogenesis and the roles of VEGF and KDR in initiating and maintaining it have been investigated by many researchers and continues to be an active field for research and development. In furtherance of such research and development, a method of purifying bulk amounts of KDR or VEGF/KDR complex in pure form is desirable, and the binding polypeptides according to this invention are especially useful for that purpose, using the general purification methodology described above.

In Vivo:

Diagnostic Imaging

A particularly preferred use for the polypeptides according to the present invention is for creating visually readable images of KDR expressing tissue, such as, for example, neoplastic tumors, which require angiogenesis for survival and metastasis, or other sites of angiogenic activity. The KDR and VEGF/KDR complex binding polypeptides disclosed herein may be converted to imaging reagents by conjugating the polypeptides with a label appropriate for diagnostic detection, optionally via a linker. Preferably, a peptide exhibiting much greater specificity for KDR or VEGF/KDR complex than for other serum proteins is conjugated or linked to a label appropriate for the detection methodology to be employed. For example, the KDR or VEGF/KDR complex binding polypeptide may be conjugated with or without a linker to a paramagnetic chelate suitable for magnetic resonance imaging (MRI), with a radiolabel suitable for x-ray, PET or scintigrapic imaging (including a chelator for a radioactive metal), with an ultrasound contrast agent (e.g., a stabilized microbubble, a ultrasound contrast agent, a microsphere or what has been referred to as a gas filled "liposome") suitable for ultrasound detection, or with an optical imaging dye.

Suitable linkers can be substituted Or unsubstituted alkyl chains, amino acid chains (e.g., polyglycine), polyethylene glycols, polyamides, and other simple polymeric linkers known in the art.

In general, the technique of using a detectably labeled KDR or VEGF/KDR complex binding moiety is based on the premise that the label generates a signal that is detectable outside the patient's body, For example, when the detectably labeled KDR or VEGF/KDR complex binding moiety is administered to the patient in which it is desirable to detect, e.g., angiogenesis, the high affinity of the KDR or VEGF/KDR complex binding moiety for KDR or VEGF/KDR complex causes the binding moiety to bind to the site of angiogenesis and accumulate label at the site of angiogenesis. Sufficient time is allowed for the labeled binding moiety to localize at the site of angiogenesis. The signal generated by the labeled peptide is detected by a scanning device that will vary according to the type of label used, and the signal is then converted to an image of the site of angiogenesis.

In another embodiment, rather than directly labeling a KDR or VEGF/KDR complex binding polypeptide with a detectable label or radiotherapeutic construct, the peptide(s) of the invention can be conjugated with, for example, avidin, biotin, or an antibody or antibody fragment that will bind the detectable label or radiotherapeutic. For example, one or more KDR-binding peptides can be conjugated to streptavidin (potentially generating multivalent binding) for in vivo binding to KDR-expressing cells. After the unbound targeting construct has cleared from the body, a biotinylated detectable label or radiotherapeutic construct (e.g., a chelate molecule complexed with a radioactive metal) can be infused and will rapidly concentrate at the site where the targeting construct is bound. This approach in some situations can reduce the time required after administering the detectable label until imaging can take place. It can also increase signal to noise ratio in the target site, and decrease the dose of the detectable label or radiotherapeutic construct required. This is particularly useful when a radioactive label or radiotherapeutic is used as the dose of radiation that is delivered to normal but radiation-sensitive sites in the body, such as bone-marrow, kidneys, and liver is decreased. This approach, sometimes referred to as pre-targeting or two-step, or three-step approaches was reviewed by S. F. Rosebrough in *Q. J. Nucl. Med.*, 40:234-251 (996), which is incorporated by reference herein.

A. Magnetic Resonance Imaging (MRI)

The KDR or VEGF/KDR complex binding moieties of the present invention can advantageously be conjugated with one or more paramagnetic metal chelates in order to form a contrast agent for use in MRI. Preferred paramagnetic metal ions have atomic numbers 21-29, 42, 44, or 57-83. A is includes ions of the transition metal or lanthanide series that have one, and more preferably five or more, unpaired electrons and a magnetic moment of at least 1.7 Bohr magneton. Preferred paramagnetic metals include, but are not limited to, chromium (III), manganese (II), manganese (III), iron (II), iron (III), cobalt (II), nickel (II), copper (II), praseodymium (III), neodymium (III), samarium (III), gadolinium (III), terbium (III), dysprosium (III), holmium (III), erbium (III), europium (III) and ytterbium (III), chromium (III), iron (III), and gadolinium (III). The trivalent cation, $Gd^{3+}$, is particularly preferred for MM contrast agents, due to its high relaxivity and low toxicity, with the further advantage that it exists in only one biologically accessible oxidation state, which minimizes undesired metabolism of the metal by a patient. Another useful metal is $Cr^+$, which is relatively inexpensive. Gd(III) chelates have been used for clinical and radiologic MR applications since 1988, and approximately 30% of MR exams currently employ a gadolinium-based contrast agent. Additionally, heteromultimers of the present invention also can be conjugated with one or more superparamagnetic particles.

The practitioner will select a metal according to dose required to detect angiogenesis and considering other factors such as toxicity of the metal to the subject (Tweedle et al., *Magnetic Resonance Imaging* (*2nd ed.*), vol. 1, Partain et al., Eds. (W.B. Saunders Co. 1988), pp. 796-797). Generally, the desired dose for an individual metal will be proportional to its relaxivity, modified by the biodistribution, pharmacokinetics and metabolism of the metal.

The paramagnetic metal chelator(s) is a molecule having one or more polar groups that act as a ligand for, and complex with, a peramagnetic metal. Suitable chelators are known in the art and include acids with methylene phosphonic acid groups, methylene carbohydroxamine acid groups, carboxyethylidene groups, or carboxymethylene groups. Examples of chelators include, but are not limited to, diethylenetriamine-pentaacetic acid (DTPA), 1,4,7,10-tetraazacyclo-tetradecane-1,4,7,10-tetraacetic acid (DOTA), 1-substituted 1,4,7-tricarboxymethyl-1,4,7,10-teraazacyclododecane (DO3A), ethylenediaminetetraacetic acid (EDTA), and 1,4,8,11-tetra-azacyclotetradecane-1,4,8,11-tetraacetic acid (TETA). Additional chelating ligands are ethylene bis-(2-hydroxy-phenylglycine) (EHPG), and derivatives thereof, including 5-Cl-EHPG, 5Br-EHPG, 5-Me-EHPG, 5t-Bu-EHPG, and 5sec-Bu-EHPG; benzodiethylenetriamine pentaacetic acid (benzo-DTPA) and derivatives thereof including dibenzo-DTPA, phenyl-DTPA, diphenyl-DTPA, benzyl-DTPA, and dibenzyl DTPA; bis-2 (hydroxybenzyl)-ethylene-diaminediacetic acid (HBED) and derivatives thereof, the class of macrocyclic compounds, which contain at least 3 Carbon atoms, more preferably at least 6, and at least two heteroatoms (O and/or N), which macrocyclic compounds can consist of one ring, or two or three rings joined together at the hetero ring elements, e.g., benzo-DOTA, dibenzo-DOTA, and benzo-NOTA, where NOTA is 1,4,7-triazacyclononane N,N',N''-triacetic acid, benzo-TETA, benzo-DOTMA, where DOTMA is 1,4,7,10-tetraaazacyclotetradecane-1,4,7,10-tetra(methyl tetraacetic acid), and benzo-TETMA, where TETMA is 1,4,8,11-tetraazacyclotetradecane-1,4,8,11-(methyl tetraacetic acid); derivatives of 1,3-propylene-diaminetetraacetic acid (PDTA) and triethylenetetraminehexaacetic acid (TTHA); derivatives of 1,5,10-N,N',N''-tris(2,3-dihydroxybenzoyl)-tricatecholate (LICAM); and 1,3,5-N,N',N''-tris(2,3-dihydroxybenzoyl)aminomethylbenzene (MECAM). A preferred chelator for use in the present invention is DTPA, and the use of DO3A is particularly preferred. Examples of representative chelators and chelating groups contemplated by the present invention are described in WO 98/18496, WO 86/06605, WO 91/03200, WO 95/28179, WO 96/23526, WO 97/36619, PCT/US98/01473, PCT/US98/20182, and U.S. Pat. Nos. 4,899,755, 5,474,756, 5,846,519 and 6,143,274, all of which are hereby incorporated by reference.

In accordance with the present invention, the chelator of the MRI contrast agent is coupled to the KDR or VEGF/KDR complex binding polypeptide. The positioning of the chelate(s) should be selected so as not to interfere with the binding affinity or specificity of the KDR or VEGF/KDR complex binding polypeptide. Preferably, the chelate(s) will be appended either to the N-terminus or the C-terminus, however the chelate(s) may also be attached anywhere within the sequence. In preferred embodiments, a chelator having a free central carboxylic acid group (e.g., DTPA-Asp(β-COOH)-)OtBu) makes it easy to attach at the N-terminus of the peptide by formation of an amide bond. The chelate(s) can also be attached at the C-terminus with the aid of a linker. Alternatively, isothiocyanate conjugation chemistry can be employed as a way of linking the appropriate isothiocyanate group bearing DTPA to a free amino group anywhere within the peptide sequence.

In general, the KDR or VEGF/KDR complex binding moiety can be bound directly or covalently to the metal chelator (or other detectable label), or it may be coupled or conjugated to the metal chelator using a linker, which may be, without limitation, amide, urea, acetal, ketal, double ester, carbonyl, carbamate, thiourea, sulfone, thioester, ester, ether, disulfide, lactone, imine, phosphoryl, or phosphodiester linkages; substituted or unsubstituted saturated or unsaturated alkyl chains; linear, branched, or cyclic amino acid chains of a single amino acid or different amino acids (e.g., extensions of the N- or C-terminus of the KDR or VEGF/KDR complex binding moiety); derivatized or underivatized polyethylene glycol, polyoxyethylene, or polyvinylpyridine chains; substituted or unsubstituted polyamide chains; derivatized or underivatized polyamine, polyester, polyethylenimine, polyacrylate, poly(vinyl alcohol), polyglycerol, or oligosaccharide (e.g., dextran) chains; alternating block copolymers, malonic, succinic, glutaric, adipic and pimelic acids; caproic acid; simple diamines and dialcohols; any of the other linkers disclosed herein; or any other simple polymeric linkers known in the art (see, e.g., WO 98/18497, WO 98/18496). Preferably the molecular weight of the linker can be tightly controlled. The molecular weights can range in size from less than 100 to greater than 1000. Preferably the molecular weight of the linker is less than 100. In addition, it may be desirable to utilize a linker that is biodegradable in vivo to provide efficient routes of excretion for the imaging reagents of the present invention. Depending on their location within the linker, such biodegradable functionalities can include ester, double ester, amide, phosphoester, ether, acetal, and ketal functionalities.

In general, known methods can be used to couple the metal chelate(s) and the KDR or VEGF/KDR complex binding moiety using linkers. See, e.g., WO 95/28967, WO 98/18496, WO 98/18497 and discussion therein. The KDR or VEGF/KDR complex binding moiety can be linked through its N- or C-terminus via an amide bond, for example, to a metal coordinating backbone nitrogen of a metal chelate or to an acetate arm of the metal chelate itself. The present invention contemplates liking of the chelate on any position, provided the metal chelate retains the ability to bind the metal tightly in order to minimize toxicity. Similarly, the KDR or VEGF/KDR complex binding moiety may be modified or elongated in order to generate a locus for attachment to a metal chelate, provided such modification or elongation does not eliminate its ability to bind KDR or VEGF/KDR complex.

MRI contrast reagents prepared according to the disclosures herein may be used in the same manner as conventional MRI contrast reagents. When imaging a site of angiogenesis, certain MR techniques and pulse sequences may be preferred to enhance the contrast of the site to the background blood and tissues. These techniques include (but are not limited to), for example, black blood angiography sequences that seek to make blood dark, such as fast spin echo sequences (see, e.g., Alexander et al., *Magnetic Resonance in Medicine*, 40(2): 298-310 (1998)) and flow-spoiled gradient echo sequences (see, e.g., Edelman et al., *Radiology*, 177(1): 45-50 (1990)). These methods also include flow independent techniques that enhance the difference in contrast, such as inversion-recovery prepared or saturation-recovery prepared sequences that will increase the contrast between angiogenic tumor and background tissues. Finally, magnetization transfer preparations may also improve contrast with these agents (see, e.g., Goodrich et al., *Investigative Radiology*, 31(6): 323-32 (1996)).

The labeled reagent is administered to the patient in the form of an injectable composition. The method of administering the MRI contrast agent is preferably parenterally, meaning intravenously, inaarterially, intrathecally, interstitially, or intracavitarilly. For imaging active angiogenesis, intravenous or intraarterial administration is preferred. For MRI, it is contemplated that the subject will receive a dosage of contrast agent sufficient to enhance the MR signal at the site of angiogenesis at least 10%. After injection with the KDR or VEGF/KDR complex binding moiety-containing MRI reagent, the patient is scanned in the MRI machine to determine the location of any sites of angiogenesis. In therapeutic settings, upon angiogenesis (e.g., tumor) localization, a tumorcidal agent or anti-angiogenic agent (e.g., inhibitors of VEGF) can be immediately administered, if necessary, and the patient can be subsequently scanned to visualize tumor regression or arrest of angiogenesis.

B. Ultrasound Imaging

When ultrasound is transmitted through a substance, the acoustic properties of the substance will depend upon the velocity of the transmissions and the density of the substance. Changes in the acoustic properties will be most prominent at the interface of different substances (solids, liquids, gases). Ultrasound contrast agents are intense sound wave reflectors because of the acoustic differences between the agent and the surrounding tissue. Gas containing or gas generating ultrasound contrast agents are particularly useful because of the acoustic difference between liquid (e.g., blood) and the gas-containing or gas generating ultrasound contrast agent. Because of their size, ultrasound contrast agents comprising microbubbles, ultrasound contrast agents, and the like may remain for a longer time in the blood stream after injection than other detectable moieties; a targeted KDR or VEGF/KDR complex-specific ultrasound agent therefore may demonstrate superior imaging of sites of angiogenesis.

In this aspect of the invention, the KDR or VEGF/KDR complex binding moiety may be lied to a material that is useful for ultrasound imaging For example, the KDR or VEGF/KDR complex binding polypeptides may be linked to materials employed to form vesicles (e.g., microbubbles, ultrasound contrast agents, microspheres, etc.), or emulsions containing a liquid or gas that functions as the detectable label (e.g., an echogenic gas or material capable of generating an echogenic gas). Materials for the preparation of such vesicles include surfactants, lipids, sphingolipids, oligolipids, phospholipids, proteins, polypeptides, carbohydrates, and synthetic or natural polymeric materials. See, e.g. WO 98/53857, WO 98/18498, WO 98/18495, WO 98/18497, WO 98/18496, and WO 98/18501, incorporated herein by reference in their entirety.

Figure 33:
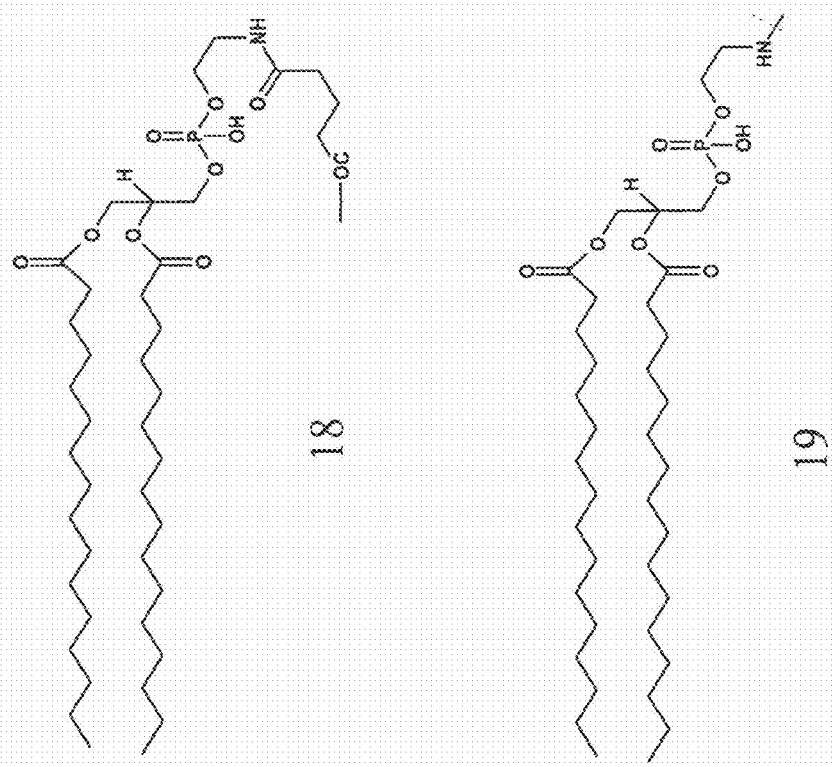
FIG. 33 shows phospholipid structures.

For contrast agents comprising suspensions of stabilized microbubbles (a preferred embodiment), phospholipids, and particularly stabilized phospholipids are preferred. The preferred gas-filled microbubbles of the invention can be prepared by means known in the art, such as, for example, by a method described in any one of the following patents: EP 554213, U.S. Pat. Nos. 5,413,774, 5,578,292, EP 744962, EP 682530, U.S. Pat. Nos. 5,556,610, 5,846,518, 6,183,725, EP 474833, U.S. Pat. Nos. 5,271,928, 5,380,519, 5,531,980, 5,567,414, 5,658,551, 5,643,553, 5,911,972, 6,110,443, 6,136,293, EP 619743, U.S. Pat. Nos. 5,445,813, 5,597,549, 5,686,060, 6,187,288, and 5,908,610, which are incorporated by reference herein in their entirety. In a preferred embodiment, at least one of the phospholipid moieties has the structure 18 or 19 (FIG. 33) and described in U.S. Pat. No. 5,686,060, which is herein incorporated by reference. In ultrasound applications the contrast agents formed by phospholipid stabilized microbubbles can be adminstered, for example, in doses such that the amount of phospholipid injected is in the range 0.1 to 200 µg/kg body weight, preferably from about 0.1 to 30 µg/kg.

Examples of suitable phospholipids include esters of glycerol with one or two molecules of fatty acids (the same or different) and phosphoric acid, wherein the phosphoric acid residue is in tun bonded to a hydrophilic group, such as choline, serine, inositol, glycerol, ethanolamine, and the like groups. Fatty acids present in the phospholipids are in general long chain aliphatic acids, typically containing from 12 to 24 carbon atoms, preferably from 14 to 22, that may be saturated or may contain one or more unsaturations. Examples of suitable fatty acids are lauric acid, myristic acid, palmitic acid, stearic acid, arachidic acid, behenic acid, oleic acid, linoleic acid, and linolenic acid. Mono esters of phospholipid are also known in the art as the "lyso" forms of the phospholipids.

Further examples of phospholipids are phosphatidic acids, i.e., the diesters of glycerol-phosphoric acid with fatty acids, sphingomyelins, i.e., those phosphatidylcholine analogs where the residue of glycerol diester with fatty acids is replaced by a ceramide chain, cardiolipins, i.e. the esters of 1,3-diphosphatidylglycerol with a fatty acid, gangliosides, cerebrosides, etc. As used herein, the term phospholipids includes either naturally occurring, semisynthetic or synthetically prepared products that can be employed either singularly or as mixtures. Examples of naturally occurring phospholipids are natural lecithins (phosphatidylcholine (PC) derivatives) such as, typically, soya bean or egg yolk lecithins.

Examples of semisynthetic phospholipids are the partially or rally hydrogenated derivatives of the naturally occurring lecithins.

Examples of synthetic phospholipids are e.g., dilauryloyl-phosphatidylcholine ("DLPC"), dimyristoylphosphatidylcholine ("DMPC"), dipalmitoyl-phosphatidylcholine ("DPPC"), diarachidoylphosphatidylcholine ("DAPC"), distearoyl-phosphatidylcholine ("DSPC"), 1-myristoyl-2-palmitoylphosphatidylcholine ("MPPC"), 1-palmitoyl-2-myristoylphosphatidylcholine ("PMPC"), 1-palmitoyl-2-stearoylphosphatid-ylcholine ("PSPC"), 1-stearoyl-2-palmitoyl-phosphatidylcholine ("SPPC"), dioleoylphosphatidylycholine ("DOPC"), 1,2 Distearoyl-sn-glycero-3-Ethylphosphocholine (Ethyl-DSPC), dilauryloyl-phosphatidylglycerol ("DLPG") and its alkali metal salts, diarachidoylphosphatidylglycerol ("DAPG") and its alkali metal salts, dimyristoylphosphatidylglycerol ("DMPG") and its alkali metal salts, dipalmitoyl-phosphatidylglycerol ("DPPG") and its alkali metal salts, distearolyphosphatidylglycerol ("DSPG") and its alkali metal salts, dioleoylphosphatidylglycerol ("DOPG") and its alkali metal salts, dimyrstoyl phosphatidic acid ("DMPA") and its alkali metal salts, dipalmitoyl phosphatidic acid ("DPPA") and its alkali metal salts, distearoyl phosphatidic acid ("DSPA"), diarachidoyl phosphatidic acid ("DAPA") and its alai metal salts, dimyristoyl phosphatidyl-ethanolamine ("DMPE"), dipalmitoyl phosphatidylethanolamine ("DPPE"), distearoyl phosphatidyl-ethanolamine ("DSPE"), dimyristoyl phosphatidylserine ("DMPS"), diarachidoyl phosphatidylserine ("DAPS"), dipalmitoyl phosphatidylserine ("DPPS"), distearoylphosphatidylserine ("DSPS"), diolcoylphosphatidylserine ("DOPS"), dipalmitoyl sphingomyelin ("DPSP"), and distearoyl sphingomyelin ("DSSP").

Other preferred phospholipids include dipalmitoylphosphatidylcholine, dipalmitoylphosphatidic acid and dipalmitoylphosphatidylserine. The compositions also may contain PEG-4000 and/or palmitic acid. Any of the gases disclosed herein or known to the skilled artisan may be employed; however, inert gases, such as $SF_6$ or fluorocarbons like $CF_4$, $C_3F_8$ and $C_4F_{10}$, are preferred.

The preferred microbubble suspensions of the present invention may be prepared from phospholipids using known processes such as a freeze-drying or spray-drying solutions of the crude phospholipids in a suitable solvent or using the processes set forth in EP 554213; U.S. Pat. Nos. 5,413,774; 5,578,292; EP 744962; EP 682530; U.S. Pat. Nos. 5,556,610; 5,846,518; 6,183,725; EP 474833; U.S. Pat. Nos. 5,271,928; 5,380,519; 5,531,980; 5,567,414; 5,658,551; 5,643,553; 5,911,972; 6,110,443; 6,136,293; EP 619743; U.S. Pat. Nos. 5,445,813; 5,597,549; 5,686,060; 6,187,288; and 5,908,610, which are incorporated by reference herein in their entirety. Most preferably, the phospholipids are dissolved in an organic solvent and the solution is dried without going through a liposome formation stage. This can be done by dissolving the phospholipids in a suitable organic solvent together with a hydrophilic stabilizer substance or a compound soluble both in the organic solvent and water and freeze-drying or spray-drying the solution. In this embodiment the criteria used for selection of the hydrophilic stabilizer is its solubility in the organic solvent of choice. Examples of hydrophilic stabilizer compounds soluble in water and the organic solvent are, e.g., a polymer, like polyvinyl pyrrolidone (PVP), polyvinyl alcohol (PVA), polyethylene glycol (PEG), etc., malic acid, glycolic acid, maltol, and the like. Such hydrophilic compounds also aid in homogenizing the microbubbles size distribution and enhance stability under storage. Any suitable organic solvent may be used as long as its boiling point is sufficiently low and its melting point is sufficiently high to facilitate subsequent drying. Typical organic solvents include, for example, dioxane, cyclohexanol, tertiary butanol, tetrachlorodifluoro ethylene ($C_2Cl_4F_2$) or 2-methyl-2-butanol. 2-methyl-2-butanol and $C_2Cl_4F_2$ are preferred.

Prior to formation of the suspension of microbubbles by dispersion in an aqueous carrier, the freeze dried or spray dried phospholipid powders are contacted with air or another gas. When contacted with the aqueous carrier the powdered phospholipids whose structure has been disrupted will form lamellarized or laminarized segments that will stabilize the microbubbles of the gas dispersed therein. This method permits production of suspensions of microbubbles that are stable even when stored for prolonged periods and are obtained by simple dissolution of the dried laminarized phospholipids (which have been stored under a desired gas) without shaking or any violent agitation.

Alternatively, microbubbles can be prepared by suspending a gas into an aqueous solution at high agitation speed, as disclosed e.g. in WO 97/29783. A further process for preparing microbubbles is disclosed in co-pending European patent application no. 03002373, herein incorporated by reference, which comprises preparing an emulsion of an organic solvent in an aqueous medium in the presence of a phospholipid and subsequently lyophilizing said emulsion, after optional washing and/or filtration steps.

Additives known to those of ordinary skill in the art can be included in the suspensions of stabilized microbubbles. For instance, non-film forming surfactants, including polyoxypropylene glycol and polyoxyethylene glycol and similar compounds, as well as various copolymers thereof; fatty acids such as myristic acid, palmitic acid, stearic acid, arachidic acid or their derivatives, ergosterol, phytosterol, sitosterol, lanosterol, tocopherol, propyl gallate, ascorbyl palmitate and butylated hydroxytoluene may be added. The amount of these non-film forming surfactants is usually up to 50% by weight of the total amount of surfactants but preferably between 0 and 30%.

Other gas containing suspensions include those disclosed in, for example, U.S. Pat. No. 5,798,091, WO 97/29783, also EP 881 915, incorporated herein by reference in their entirety. These agents may be prepared as described in U.S. Pat. No. 5,798,091 or WO97/29783.

Another preferred ultrasound contrast agent comprises ultrasound contrast agents. The term "microballoon" refers to gas filled bodies with a material boundary or envelope. More on microballoon formulations and methods of preparation may be found in EP 324938 (U.S. Pat. No. 4,844,882); U.S. Pat. Nos. 5,711,933; 5,840,275; 5,863,520; 6,123,922; 6,200, 548; 4,900,540; 5,123,414; 5,230,882; 5,469,854; 5,585,112; 4,718,433; 4,774,958; WO 95/01187; U.S. Pat. Nos. 5,529, 766; 5,536,490 and 5,990,263, the contents of which are incorporated herein by reference.

The preferred microballoons have an envelope including a biodegradable physiologically compatible polymer or, a biodegradable solid lipid. The polymers useful for the preparation of the microballoons of the present invention can be selected from the biodegradable physiologically compatible polymers, such as any of those described in any of the following patents: EP 458745, U.S. Pat. Nos. 5,711,933, 5,840, 275, EP 554213, U.S. Pat. Nos. 5,413,774 and 5,578,292, the entire contents of which are incorporated herein by reference. In particular, the polymer can be selected from biodegradable physiologically compatible polymers, such as polysaccharides of low water solubility, polylactides and polyglycolides and their copolymers, copolymers of lactides and lactones such as ε-caprolactone, γ-valerolactone and polypeptides. Other suitable polymers include poly(ortho)esters (see e.g., U.S. Pat. Nos. 4,093,709; 4,131,648; 4,138,344; 4,180,646); polylactic and polyglycolic acid and their copolymers, for instance DEXON (see J. Heller, Biomaterials 1 (1980), 51 poly(DL-lactide-co-ε-caprolactone), poly(DL-lactide-co-γ-valerolactone), poly(DL-lactide-co-γ-butyrolactone), poly-alkylcyanoacrylates; polyamides, polyhydroxybutyrate; polydioxanone; poly-β-aminoketones (A. S. Angeloni, P. Ferruti, M. Tramontini and M. Casolaro, The Mannich bases in polymer synthesis: 3. Reduction of poly(beta-aminoketone)s to poly(gamma-aminoalohol)s and their N-alkylation to poly(gamma-hydroxyquaternary ammonium salt)s, Polymer 23, pp 1693-1697, 1982.); polyphosphazenes (Allcock, Harry R. Polyphosphazenes: new polymers with inorganic backbone atoms (Science 193:1214-19 (1976)) and polyanhydrides The microballoons of the present invention can also be prepared according to the methods of WO-A-96/15815, incorporated herein by reference, where the microballoons are made from a biodegradable membrane comprising biodegradable lipids, preferably selected from mono-di-, tri-glycerides, fatty acids, sterols, waxes and mixtures thereof. Preferred lipids are di- or tri-glycerides, e.g., di- or tri-myristin, -palmityn or -stearin, in particular tripalmitin or tristearin. The microballoons may employ any of the gases disclosed herein of known to the skilled artisan; however, inert gases such as fluorinated gases are preferred. The microballoons may be suspended in a pharmaceutically acceptable liquid carrier with optional additives known to those of ordinary skill in the art and stabilizers.

Other gas-containing contrast agent formulations include microparticles (especially aggregates of microparticles) having gas contained therein or otherwise associated therewith (for example being adsorbed on the surface thereof and/or contained within voids, cavities or pores therein). Methods for the preparation of these agents are as described in EP 0122624; EP 0123235; EP 0365467; U.S. Pat. Nos. 5,558,857; 5,607,661; 5,637,289; 5,558,856; 5,137,928; WO 95/21631 or WO 93/13809, incorporated herein by reference in their entirety.

Any of these ultrasound compositions should also be, as far as possible, isotonic with blood. Hence, before injection, small amounts of isotonic agents may be added to any of above ultrasound contrast agent suspensions. The isotonic agents are physiological solutions commonly used in medicine and they comprise aqueous saline solution (0.9% NaCl), 2.6% glycerol solution, 5% dextrose solution, etc. Additionally, the ultrasound compositions may include standard pharmaceutically acceptable additives, including, for example, emulsifying agents, viscosity modifiers, cryoprotectants, lyoprotectants, bulking agents etc.

Any biocompatible gas may be used in the ultrasound contrast agents useful in the invention. The term "gas" as used herein includes any substances (including mixtures) substantially in gaseous form at the normal human body temperature. The gas may thus include, for example, air, nitrogen, oxygen, $CO_2$, argon, xenon or krypton, fluorinated gases (including for example, perfluorocarbons, $SF_6$, $SeF_6$) a low molecular weight hydrocarbon (e.g., containing from 1 to 7 carbon atoms), for example, an alkane such as methane, ethane, a propane, a butane or a pentane, a cycloalkane such as cyclopropane, cyclobutane or cyclopentene, an alkene such as ethylene, propane, propadiene or a butene, or an alkyne such as acetylene or propyne and/or mixtures thereof. However, fluorinated gases are preferred. Fluorinated gases include materials that contain at least one fluorine atom such as $SF_6$, freons (organic compounds containing one or more carbon atoms and fluorine, i.e., $CF_4$, $C_2F_6$, $C_3F_8$, $C_4F_8$, $C_4F_{10}$, $CBrF_3$, $CCl_2F_2$, $C_2ClF_5$, and $CBrClF_2$) and perfluorocarbons. The term perfluorocarbon refers to compounds containing only carbon and fluorine atoms and includes, in particular, saturated, unsaturated, and cyclic perfluorocarbons. The saturated perfluorocarbons, which are usually preferred, have the formula $C_nF_{n+2}$, where n is from 1 to 12, preferably from 2 to 10, most preferably from 3 to 8 and even more preferably from 3 to 6. Suitable perfluorocarbons include, for example, $CF_4$, $C_2F_6$, $C_3F_8$ $C_4F_8$, $C_4F_{10}$, $C_5F_{12}$, $C_6F_{12}$, $C_7F_{14}$, $C_8F_{18}$, and $C_9F_{20}$. Most preferably the gas or gas mixture comprises $SF_6$ or a perfluorocarbon selected from the group consisting of $C_3F_8$ $C_4F_8$, $C_4F_{10}$, $C_5F_{12}$, $C_6F_{12}$, $C_7F_{14}$, $C_8F_{18}$, with $C_4F_{10}$ being particularly preferred. See also WO 97/29783, WO 98/53857, WO 98/18498, WO 98/18495, WO 98/18496, WO 98/18497, WO 98/18501, WO 98/05364, WO 98/17324.

In certain circumstances it may be desirable to include a precursor to a gaseous substance (e.g., a material that is capable of being converted to a gas in vivo, often referred to as a "gas precursor"). Preferably the gas precursor and the gas it produces are physiologically acceptable. The gas precursor may be pH-activated, photo-activated, temperature activated, etc. For example, cerin perfluorocarbons may be used as temperature activated gas precursors. These perfluorocarbons, such as perfluoropentane, have a liquid/gas phase transition temperature above room temperature (or the temperature at which the agents are produced and/or stored) but below body temperature; thus they undergo a phase shift and are converted to a gas within the human body.

As discussed, the gas can comprise a mixture of gases. The following combinations are particularly preferred gas mixtures: a mixture of gases (A) and (B) in which, at least one of the gases (B), present in an amount of between 0.5-41% by vol., has a molecular weight greater than 80 daltons and is a fluorinated gas and (A) is selected from the group consisting of air, oxygen, nitrogen, carbon dioxide and mixtures thereof, the balance of the mixture being gas A.

Since ultrasound vesicles may be larger than the other detectable labels described herein, they may be linked or conjugated to a plurality of KDR or VEGF/KDR complex binding polypeptides in order to increase the targeting efficiency of the agent. Attachment to the ultrasound contrast agents described above (or known to those skilled in the art) may be via direct covalent bond between the KDR or VEGF/KDR complex binding polypeptide and the material used to make the vesicle or via a linker, as described previously. For example, see WO 98/53857 generally for a description of the attachment of a peptide to a bifunctional PEG linker, which is then reacted with a liposome composition. See also, Lanza et al., *Ultrasound in Med. & Bio.*, 23(6):863-870 (1997).

A number of methods may be used to prepare suspensions of microbubbles conjugated to KDR or VEGF/KDR complex binding polypeptides. For example, one may prepare maleimide-derivatized microbubbles by incorporating 5% (w/w) of N-MPB-PE (1,2-dipalmitoyl-sn-glycero-3-phosphoethanolamine-4-(p-maleimido-phenyl butyramide), (Avanti Polar-Lipids, Inc) in the phospholipid formulation. Then, solutions of mercaptoacetylated KDR-binding peptides (10 mg/mL in DMF), which have been incubated in deacetylation solution (50 mM sodium phosphate, 25 mM EDTA, 0.5 M hydroxylamine.HCl, pH 7.5) are added to the maleimide-activated microbubble suspension. After incubation in the dark under gentle agitation, the peptide conjugated microbubbles may be purified by centrifugation.

Compounds that can be used for derivatization of microbubbles typically include the following components: (a) a hydrophobic portion, compatible with the material forming the envelope of the microbubble or of the microballoon, in order to allow an effective incorporation of the compound in the envelope of the vesicle; said portion is represented typically by a lipid moiety (dipalmitin, distearoyl); and (b) a spacer (typically PEGs of different molecular weights), which may be optional in some cases (for example, microbubbles may for instance present difficulties to be freeze dried if the spacer is too long) or preferred in some others (e.g., peptides may be less active when conjugated to a microballoon with short spacers); and (c) a reactive group capable of reacting with a corresponding rig moiety on the peptide to be conjugated (e.g., maleimido with the —SH group of cysteine).

Alternatively, KDR-binding polypeptide conjugated microbubbles may be prepared using biotin/avidin. For example, avidin-conjugated microbubbles may be prepared using a maleimide-activated phospholipid microbubble suspension, prepared as described above, which is added to mercaptoacetylated-avidin (which has been incubated with deacetylation solution). Biotinylated KDR or VEGF/KDR complex-binding peptides (prepared as described herein) are then added to the suspension of avidin-conjugated microbubbles, yielding a suspension of microbubbles conjugated to KDR or VEGF/KDR complex-binding peptides.

Unless it contains a hyperpolarized gas, known to require special storage conditions, the lyophilized residue may be stored and transported without need of temperature control of its environment and in particular it may be supplied to hospitals and physicians for on site formulation into a ready-to-use administrable suspension without requiring such users to have special storage facilities. Preferably in such a case it can be supplied in the form of a two-component kit, which can include two separate containers or a dual-chamber container. In the former case preferably the container is a conventional septum-sealed vial, wherein the vial containing the lyophilized residue of step b) is sealed with a septum through which the carrier liquid may be injected using an optionally prefilled syringe. In such a case the syringe used as the container of the second component is also used then for injecting the contrast agent. In the latter case, preferably the dual-chamber container is a dual-chamber syringe and once the lyophilizate has been reconstituted and then suitably mixed or gently shaken, the container can be used directly for injecting the contrast agent. In both cases means for directing or permitting application of sufficient bubble forming enter into the contents of the container are provided. However, as noted above, in the stabilised contrast agents according to the invention the size of the gas microbubbles is substantially independent of the amount of agitation energy applied to the reconstituted dried product. Accordingly, no more than gentle hand shaking is generally required to give reproducible products with consistent microbubble size.

It can be appreciated by one of ordinary skilled in the art that other two-chamber reconstitution systems capable of combining the dried powder with the aqueous solution in a sterile manner are also within the scope of the present invention. In such systems, it is particularly advantageous if the aqueous phase can be interposed between the water-insoluble gas and the environment, to increase shelf life of the product. Where a material necessary for forming the contrast agent is not already present in the container (e.g. a targeting ligand to be linked to the phospholipid during reconstitution), it can be packaged with the other components of the kit, preferably in a form or container adapted to facilitate ready combination with the other components of the kit.

No specific containers, vial or connection systems are required; the present invention may use conventional containers, vials and adapters. The only requirement is a good seal between the stopper and the container. The quality of the seal, therefore, becomes a matter of primary concern; any degradation of seal integrity could allow undesirable substances to enter the vial. In addition to assuring sterility, vacuum retention is essential for products stoppered at ambient or reduced pressures to assure safe and proper reconstitution. As to the stopper, it may be a compound or multicomponent formulation based on an elastomer, such as poly(isobutylene) or butyl rubber.

Ultrasound imaging techniques that can be used in accordance with the present invention include known techniques, such as color Doppler, power Doppler, Doppler amplitude, stimulated acoustic imaging, and two- or three-dimensional imaging techniques. Imaging may be done in harmonic (resonant frequency) or fundamental modes, with the second harmonic preferred.

In ultrasound applications the contrast agents formed by phospholipid stabilized microbubbles may, for example, be administered in doses such that the amount of phospholipid injected is in the range 0.1 to 200 µg/kg body weight, preferably from about 0.1 to 30 µg/kg. Microballoons-coining contrast agents are typically administered in doses such that the amount of wall-forming polymer or lipid is from about 10 µg/kg to about 20 mg/kg of body weight.

As shown in the Examples, ultrasound contrast agents conjugated to KDR binding moieties of the invention, such as, for example, those comprising SEQ ID NOS:356, 294 and 480 and the diner D23, are able to bind to KDR-expressing tissue and thus are useful in providing an image of such tissue. Indeed, compounds of the invention, such as phospholipid stabilized microbubbles conjugated to the heterodimer D23, can be used to image angiogenic tissue in vivo.

C. Optical Imaging, Sonoluminescence or Photoacoustic Imaging

In accordance with the present invention, a number of optical parameters may be employed to determine the location of KDR or VEGF/KDR complex with in vivo light imaging after injection of the subject with an optically-labeled KDR or VEGF/KDR complex binding polypeptide. Optical parameters to be detected in the preparation of an image may include transmitted radiation, absorption, fluorescent or phosphorescent emission, light reflection, changes in absorbance amplitude or maxima, and elastically scattered radiation. For example, biological tissue is relatively translucent to light in the near infrared (NIR) wavelength range of 650-1000 nm. NIR radiation can penetrate tissue up to several centimeters, permitting the use of the KDR or VEGF/KDR complex binding polypeptides of the present invention for optical imaging of KDR or VEGF/KDR complex in vivo.

The KDR or VEGF/KDR complex binding polypeptides may be conjugated with photolabels, such as optical dyes, including organic chromophores or fluorophores, having extensive delocalized ring systems and having absorption or emission maxima in the range of 400-1500 nm. The KDR or VEGF/KDR complex binding polypeptide may alternatively be derivatized with a bioluminescent molecule. The preferred range of absorption maxima for photolabels is between 600 and 1000 nm to minimize interference with the signal from hemoglobin. Preferably, photoabsorption labels should have large molar absorptivities, e.g., >$10^5$ cm$^{-1}$M$^{-1}$, while fluorescent optical dyes will have high quantum yields, Examples of optical dyes include, but are not limited to those described in WO 98/18497, WO 98/18496, WO 98/18495, WO 98/18498, WO 98/53857, WO 96/17628, WO 97/18841, WO 96/23524, WO 98/47538, and references cited therein. The photolabels may be covalently linked directly to the KDR or VEGF/KDR complex binding peptide or lined to the KDR or VEGF/KDR complex binding peptide via a linker, as described previously.

After injection of the optically-labeled KDR or VEGF/KDR complex binding moiety, the patient is scanned with one or more light sources (e.g., a laser) in the wavelength range appropriate for the photolabel employed in the agent. The light used may be monochromatic or polychromatic and continuous or pulsed. Transmitted, scattered, or reflected light is detected via a photodetector tuned to one or multiple wavelengths to determine the location of KDR or VEGF/KDR complex in the subject. Changes in the optical parameter may be monitored over time to detect accumulation of the optically-labeled reagent at the site of angiogenesis. Standard image processing and detecting devices may be used in conjunction with the optical imaging reagents of the present invention.

The optical imaging reagents described above may also be used for acousto-optical or sonoluminescent imaging performed with optically-labeled imaging agents (see, U.S. Pat. No. 5,171,298, WO 98/576663 and references cited therein). In acousto-optical imaging, ultrasound radiation is applied to the subject and affects the optical parameters of the transmitted, emitted, or reflected light. In sonoluminescent imaging, the applied ultrasound actually generates the light detected. Suitable imaging methods using such techniques are described in WO 98/57666.

D. Nuclear Imaging (Radionuclide Imaging) and Radiotherapy

The KDR or VEGF/KDR complex binding moieties may be conjugated with a radionuclide reporter appropriate for scintigraphy, SPECT, or PET imaging and/or with a radionuclide appropriate for radiotherapy. Constructs in which the KDR or VEGF/KDR complex binding moieties are conjugated with both a chelator for a radionuclide useful for diagnostic imaging and a chelator useful for radiotherapy are with the scope of the invention.

For use as a PET agent a peptide is complexed with one of the various positron emitting metal ions such as $^{51}$Mn, $^{52}$Fe, $^{60}$Cu, $^{68}$Ga, $^{72}$As, $^{94m}$Tc, or $^{110}$In. The binding moieties of the invention can also be labeled by halogenation using radionuclides such as $^{18}$F, $^{124}$I, $^{125}$I, $^{131}$I, $^{123}$I, $^{77}$Br , and $^{76}$Br. Preferred metal radionuclides for scintigraphy or radiotherapy include $^{99m}$Tc, $^{51}$Cr, $^{67}$Ga, $^{68}$Ga, $^{47}$Sc, $^{51}$Cr, $^{167}$Tm, $^{141}$Ce, $^{111}$In, $^{168}$Yb, $^{175}$Yb, $^{140}$La, $^{90}$Y, $^{88}$Y, $^{153}$Sm, $^{166}$Ho, $^{165}$Dy, $^{166}$Dy, $^{62}$Cu, $^{64}$Cu, $^{67}$Cu, $^{97}$Ru, $^{103}$Ru, $^{186}$Re, $^{188}$Re, $^{203}$Pb, $^{211}$Bi, $^{212}$Bi, $^{213}$Bi, $^{214}$Bi, $^{105}$Rh, $^{109}$Pd, $^{117m}$Sn, $^{149}$Pm, $^{161}$Tb, $^{177}$Lu, $^{198}$Au and $^{199}$Au. The choice of metal will be determined based on the desired therapeutic or diagnostic application. For example, for diagnostic purposes the preferred radionuclides include $^{64}$Cu, $^{67}$Ga, $^{68}$Ga, $^{99m}$Tc and $^{111}$In. For therapeutic purposes, the preferred radionuclides include $^{64}$Cu, $^{90}$Y, $^{105}$Rh, $^{111}$In, $^{117m}$Sn, $^{149}$Pm, $^{153}$Sm, $^{161}$Tb, $^{166}$Dy, $^{166}$Ho, $^{175}$Yb, $^{177}$Lu, $^{186/188}$Re, and $^{199}$Au. $^{99m}$Tc is particularly preferred for diagnostic applications because of its low cost, availability, imaging properties, and high specific activity. The nuclear and radioactive properties of Tc-99m make this isotope an ideal scintigraphic imaging agent. This isotope has a single photon energy of 140 keV and a radioactive half-life of about 6 hours, and is readily available from a $^{99}$Mo—$^{99m}$Tc generator.

The metal radionuclides may be chelated by, for example, linear, macrocyclic, terpyridine, and $N_3S$, $N_2S_2$, or $N_4$ chelants (see also, U.S. Pat. Nos. 5,367,080, 5,364,613, 5,021,556, 5,075,099, 5,886,142), and other chelators known in the art including, but not limited to, HYNIC, DTPA, EDTA, DOTA, DO3A, TETA, and bisamino bisthiol (BAT) chelators (see also U.S. Pat. No. 5,720,934). For example, $N_4$ chelators are described in U.S. Pat. Nos. 6,143,274; 6,093,382; 5,608,110; 5,665,329; 5,656,254; and 5,688,487. Certain $N_3S$ chelators are described in PCT/CA94/00395, PCT/CA94/00479, PCT/CA95/00249 and in U.S. Pat. Nos. 5,662,885; 5,976,495; and 5,780,006. The chelator may also include derivatives of the chelating ligand mercapto-acetyl-acetyl-glycyl-glycine (MAG3), which contains an $N_3S$, and $N_2S_2$ systems such as MAMA (monoamidemonoaminedithiols), DADS ($N_2S$ diaminedithiols), CODADS and the like. These ligand systems and a variety of others are described in Liu and Edwards, Chem. Rev., 99:2235-2268 (1999) and references therein.

The chelator may also include complexes containing ligand atoms that are not donated to the metal in a tetradentate array. These include the boronic acid adducts of technetium and rhenium dioximes, such as are described in U.S. Pat. Nos. 5,183,653; 5,387,409; and 5,118,797, the disclosures of which are incorporated by reference herein, in their entirety.

In another embodiment, disulfide bonds of a KDR or VEGF/KDR complex binding polypeptide of the invention are used as two ligands for chelation of a radionuclide such as $^{99m}$Tc. In this way the peptide loop is expanded by the introduction of Tc (peptide-S-S-peptide changed to peptide-S-Tc-S-peptide). This has also been used in other disulfide containing peptides in the literature (Chen et al., J Nucl. Med., 42:1847-1855 (2001)) while maintaining biological activity. The other chelating groups for Tc can be supplied by amide nitrogens of the backbone, another cystine amino acid or other modifications of amino acids.

Figure 34A:
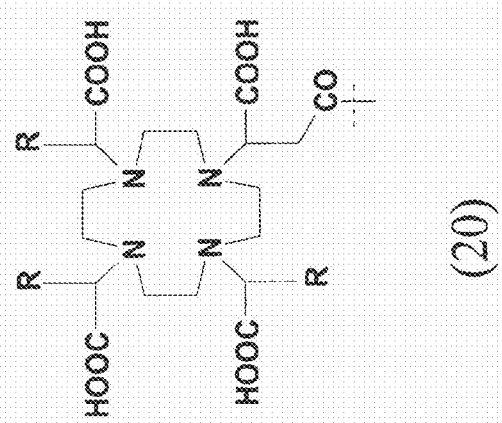
Figure 34B:
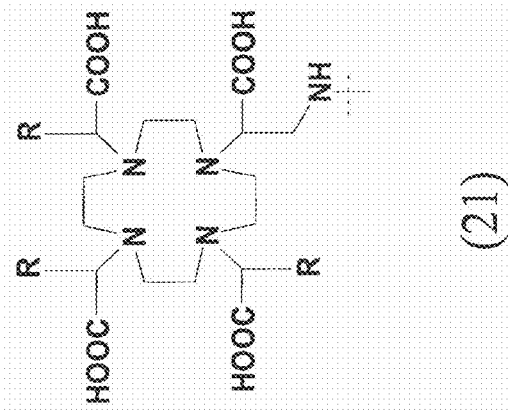
Figure 34C:
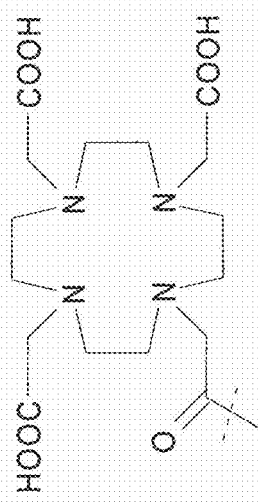
Figure 34D:
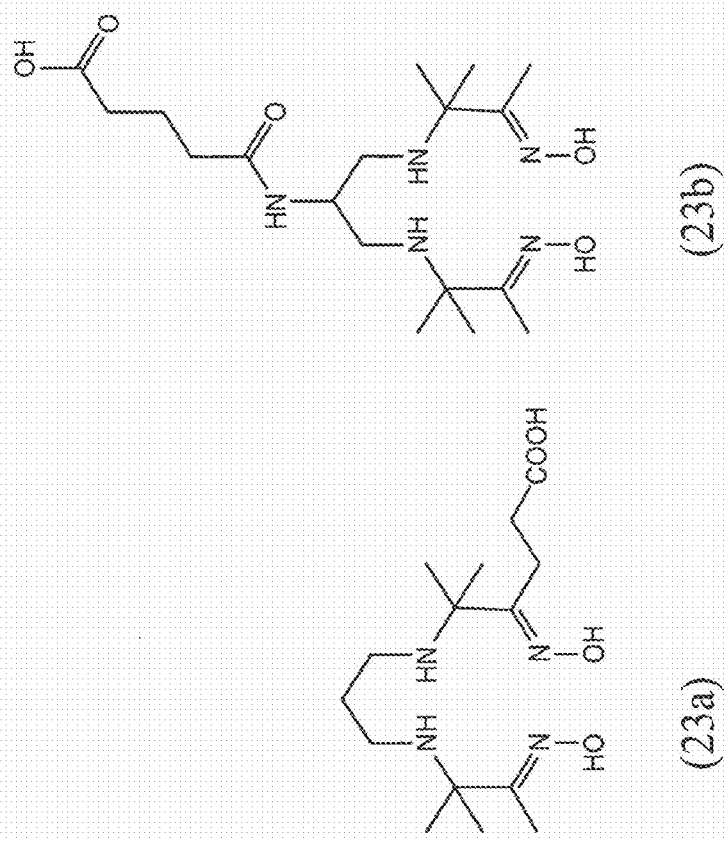
Figure 34F:
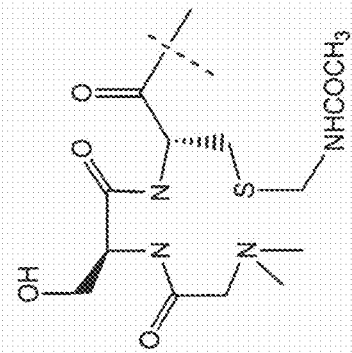
Figure 35:
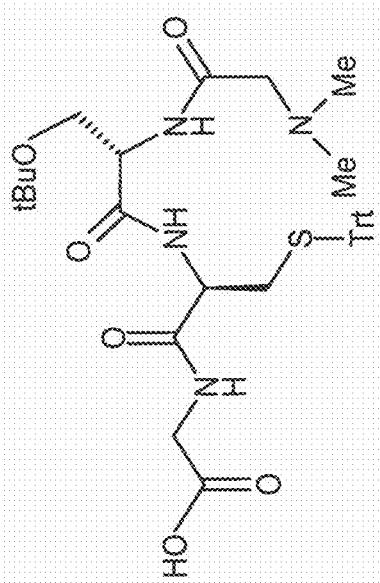
FIG. 35 shows the structure of a chelating agent.
Figure 36:
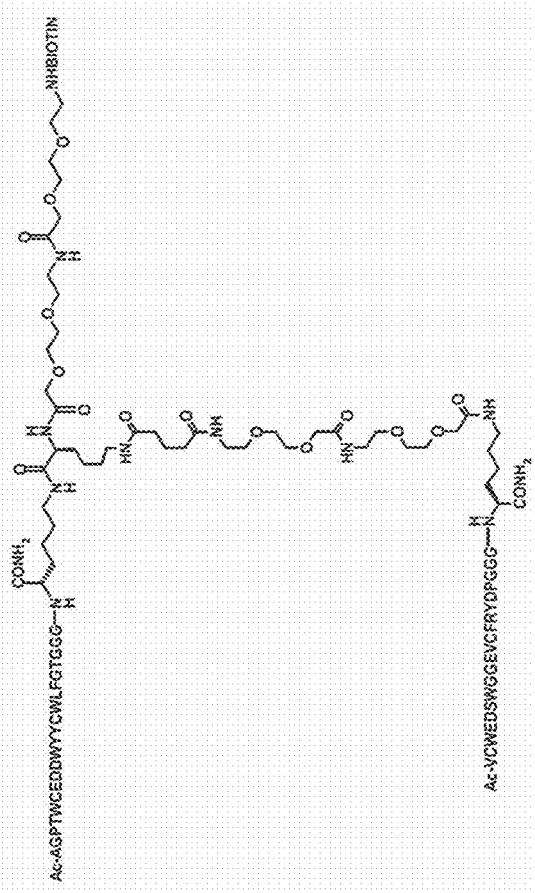
FIG. 36 shows dimer 1 (D-1; Ac-AGPTWCBDDWYY-CWLFGTGGGK (SEQ ID NO:277)[(Biotin-JJK-(O═)C(CH$_2$)$_3$C(═O)-JJ-NH(CH$_2$)$_4$—(S)—CH((Ac-VCWED-SWGGEVCFRYDPGGGK (SEQ ID NO:337))-NR)CONH$_2$]—NH$_2$).
Figure 37:
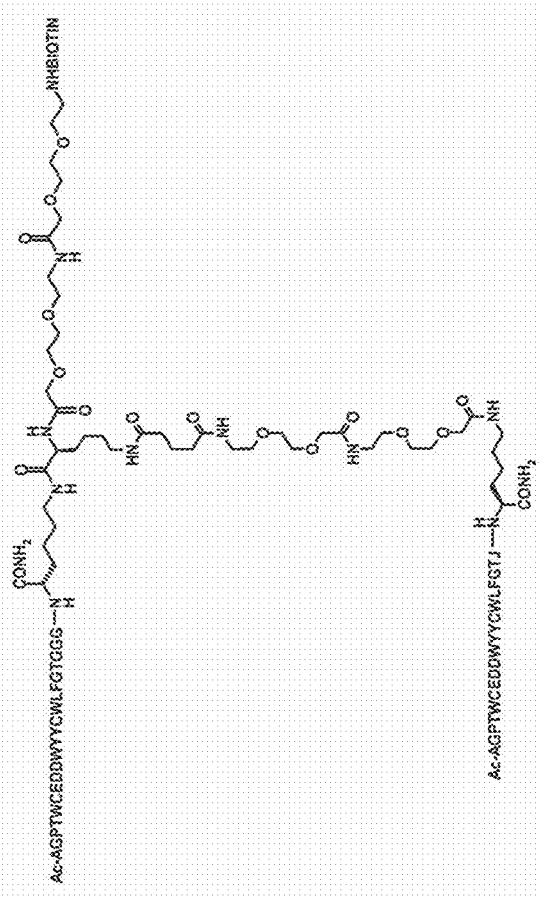
FIG. 37 shows dimer 2 (D2; Ac-AGPTWCEDDWYY-CWLFGTTGGGK (SEQ ID NO:277) [(Biotin-JJK-(O═)C(CH$_2$)$_3$C(═O)-JJ-NH(CH$_2$)$_4$—(S)—CH((Ac-AGPTWCEDDWYYCWLFGTJK (SEQ ID NO:493))-NH)CONH$_2$]—NH$_2$).
Figure 38:
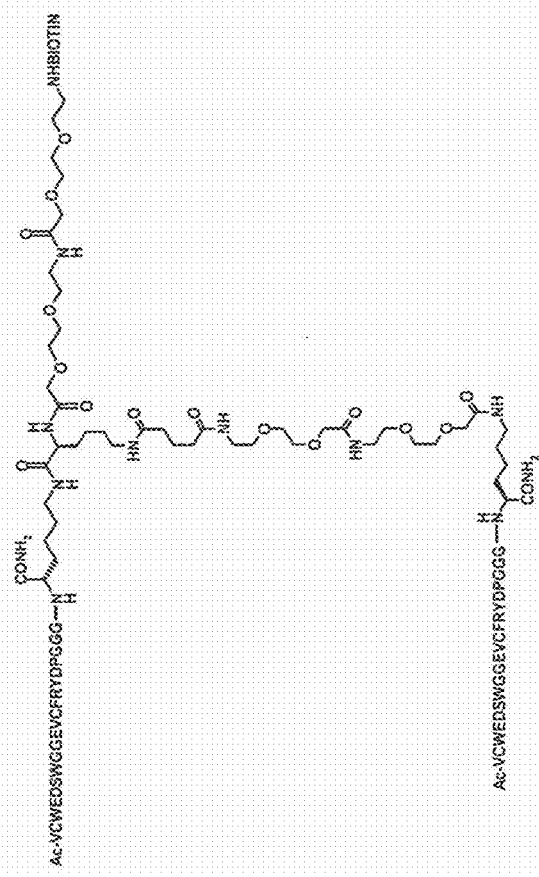
FIG. 38 shows dimer 3 (D3; Ac-VCWEDSWGGEVC-FRYDPGGGK (SEQ ID NO:337)[(Biotin-JJK-(O═)C(CH$_2$)$_3$C(═O)-JJ-NH(CH$_2$)$_4$—(S)—CH((Ac-VCWED-SWGGEVCFRYDPGGGYK (SEQ ID NO:337))-NH)CONH$_2$]—NH$_2$).
Figure 39:
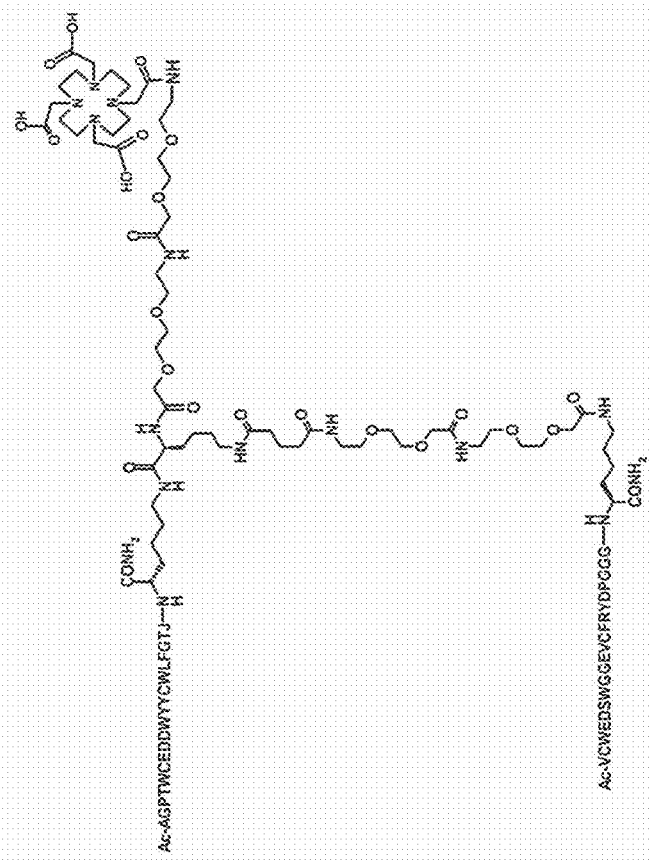
FIG. 39 shows dimer 4 (D4; Ac-AGPTWCEDDWYY-CWLFGTJK (SEQ ED NO:338)[DOTA-JJK-(O═)C(CH$_2$)$_3$C(═O)-JJ-NH(CH$_2$)$_4$—(S)—CH((Ac-VCWEDSWGGEV-CFRYDPGGGK (SEQ ID NO:337))-NH)CONH$_2$]—NH$_2$)
Figure 40:
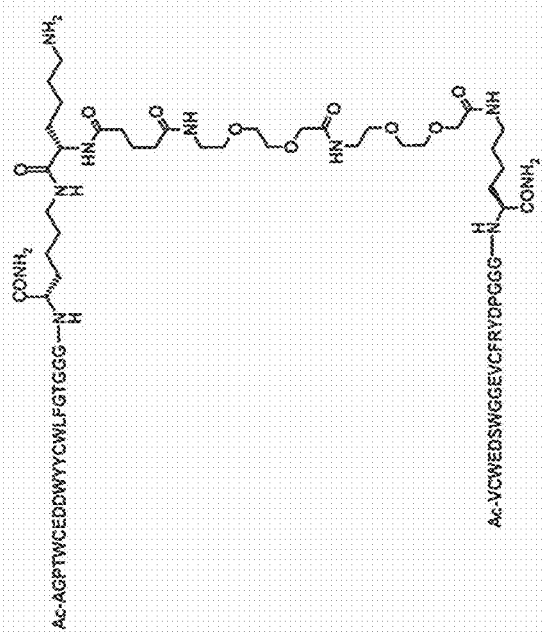
FIG. 40 shows dimer 5 (D5; Ac-VCWEDSWGGEVC-FRYDPGGGK (SEQ ID NO:337) (JJ-C(═O)(CH$_2$)$_3$C(═O)—K—NH(CH$_2$)$_4$—(S)—CH((Ac-AGPTWCEDDW-YYCWLFGTGGGK (SEQ ID NO:277))-NH)CONH$_2$—NH$_2$).
Figure 41:
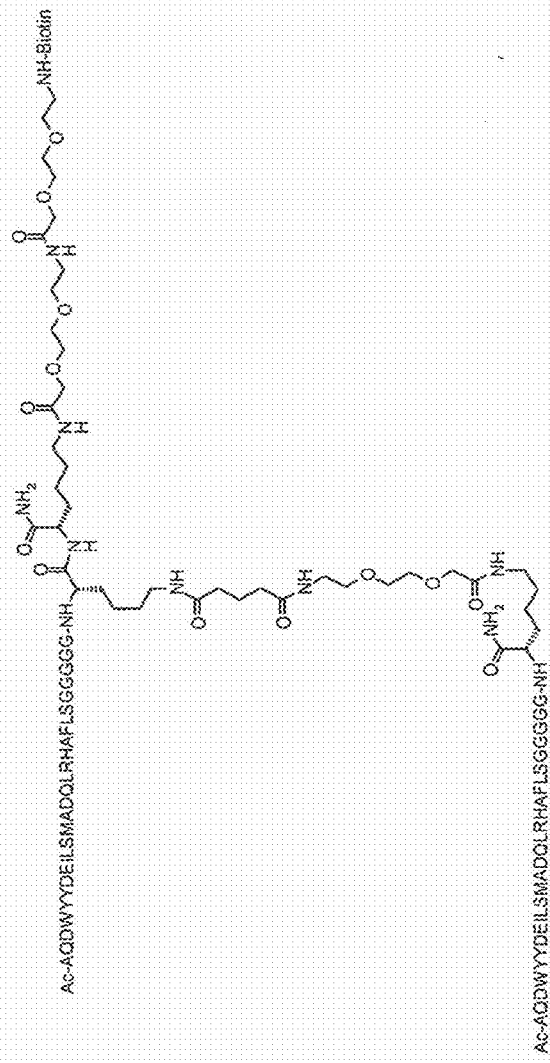
FIG. 41 shows dimer 8 (D8; AcAQDWYYDEILS-MADQLRHAFLSGGGGK (SEQ ID NO:356) {Ac-AQDW-YYYYDEILSMADQLRHAFLSGGGGK (SEQ ID NO:356)(J-Glut-)-NH$_2$}K(Biotin-JJ)-NH$_2$).
Figure 42:
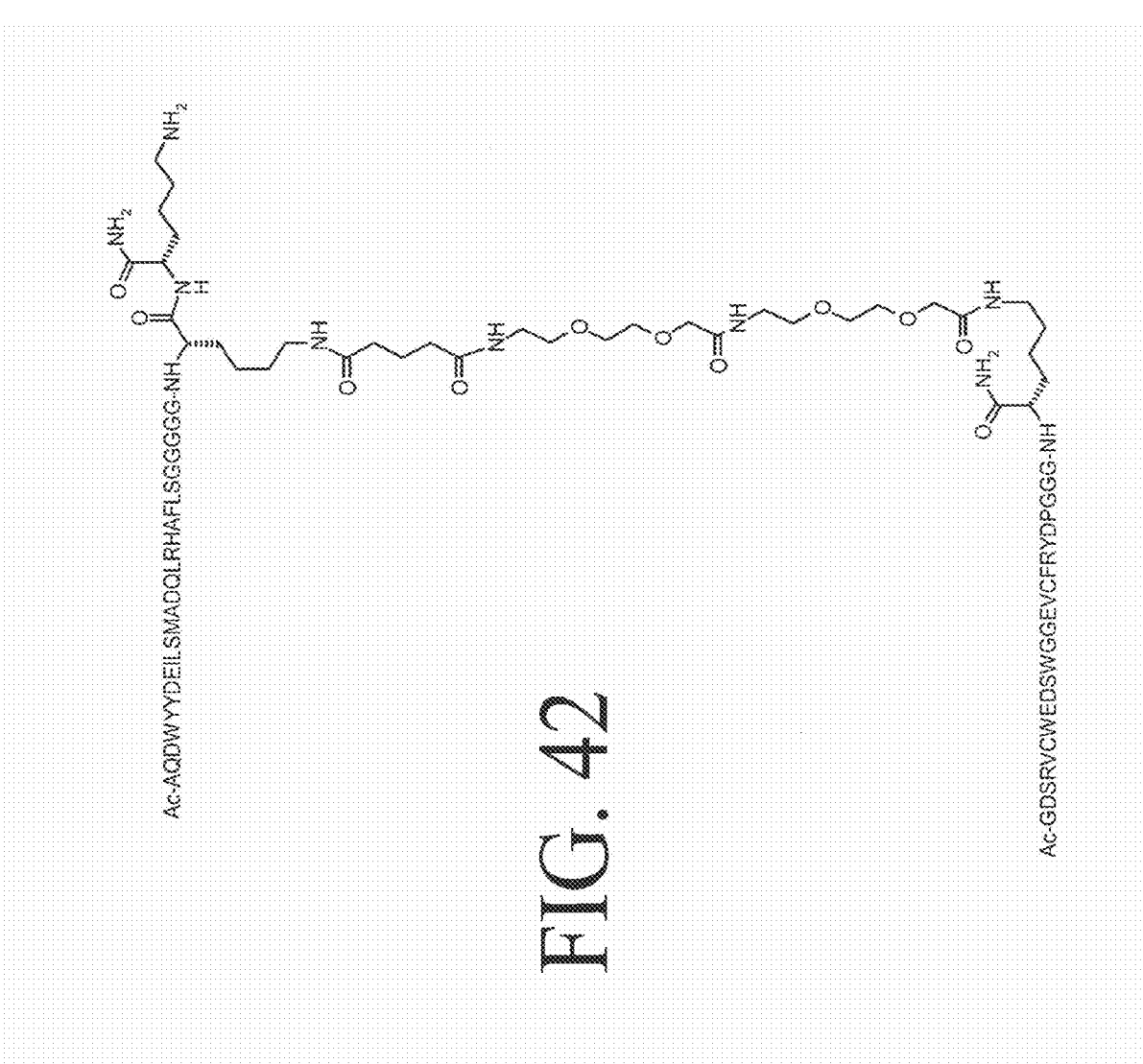
FIG. 42 shows dimer 9 (D9; Ac-AQDWYYDEILS-MADQLRHAFLSGGGGK (SEQ ID NO:356) {[Ac-GD-SRVCWEVDSWGGEVCFRYDPGGGKu (SEQ ID NO:294)(JJ-Glut-)]-NH$_2$}K—NH$_2$).
Figure 43:
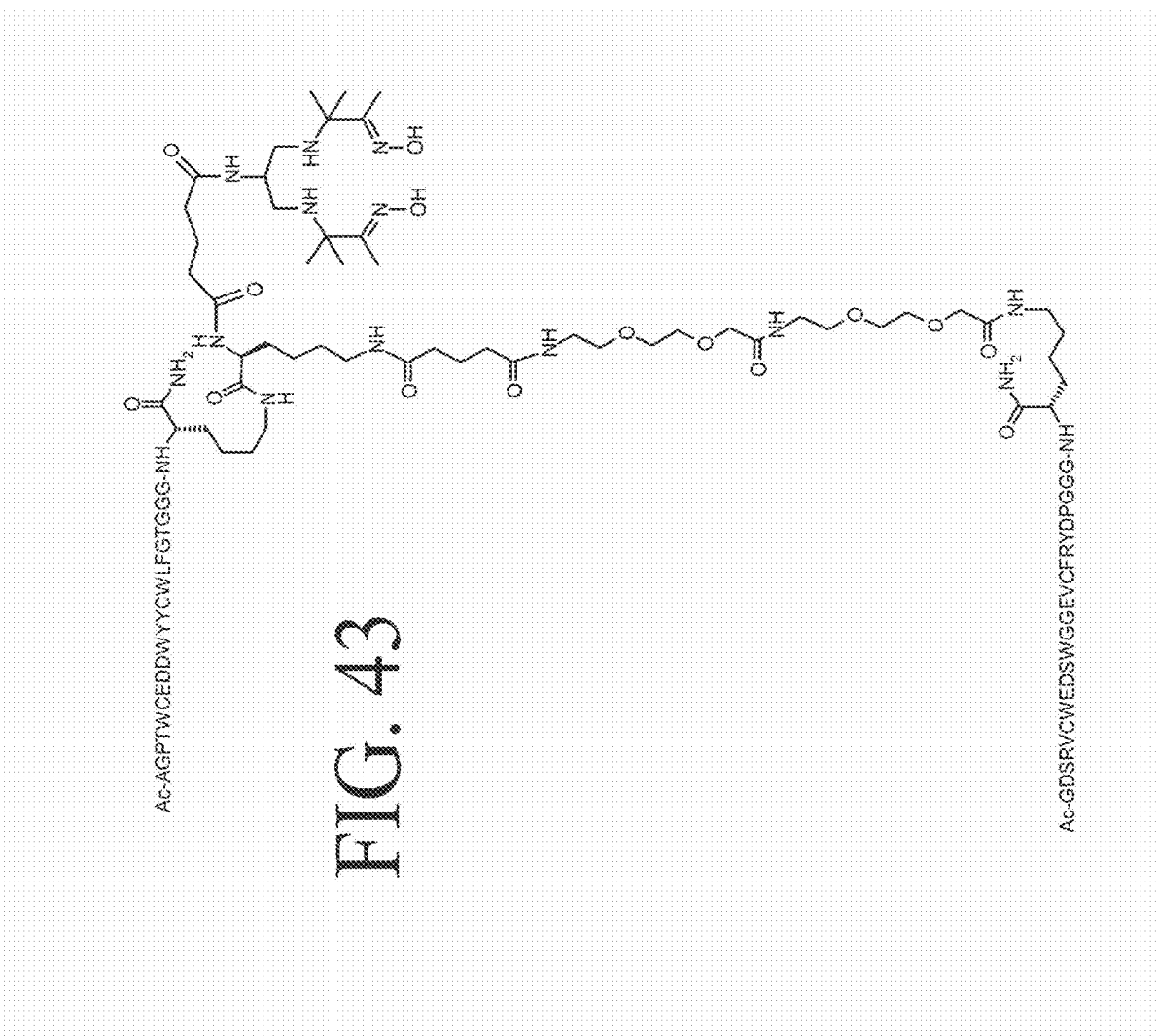
FIG. 43 shows dimer 10 (D10Ac-AGPTWCEDDWYY-CWLFGTGGGK (SEQ ID NO:277){[Ac-GDSRVCWED-SWGGEVCFRYDPGGGK(SEQ ID NO:294)(JJ-Glut-NH(CH$_2$)$_4$—(S)—CH(PnAO6-Glut-NH)(C═O—)]—NH$_2$}—NH$_2$).
Figure 44:
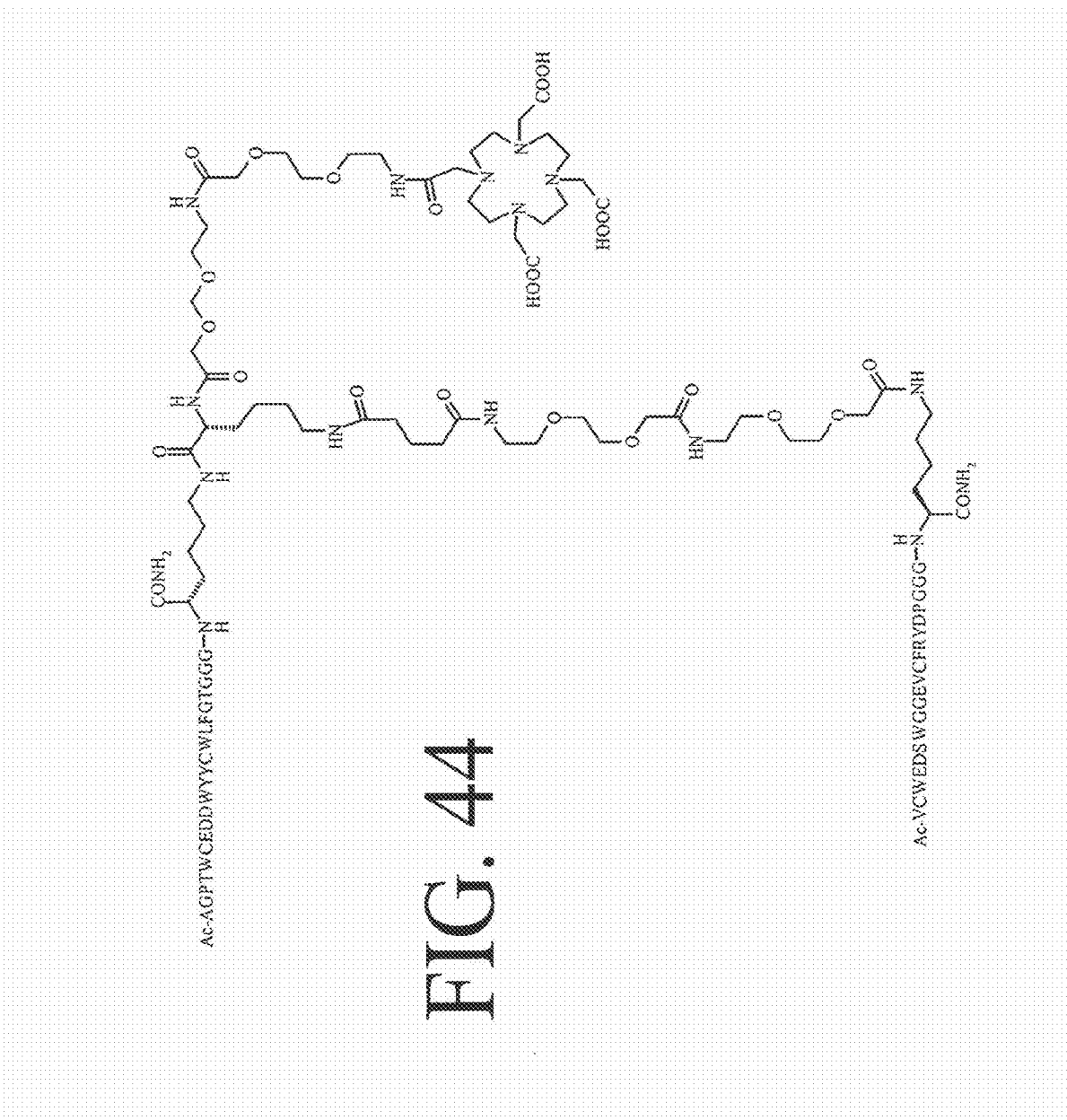
FIG. 44 shows dimer 11 (D11; AC-AGPTWCEDDWYY-CWLFGTGGGK (SEQ ID NO:277) {Ac-VCWEDSWG-GEVCFRYDPGGGK (SEQ ID NO:337)[JJ-Glut-NH(CH$_2$)$_4$—(S)—CH(DOTA-JJ-NH—)(C═O—]—NH$_2$}—NH$_2$).
Figure 45:
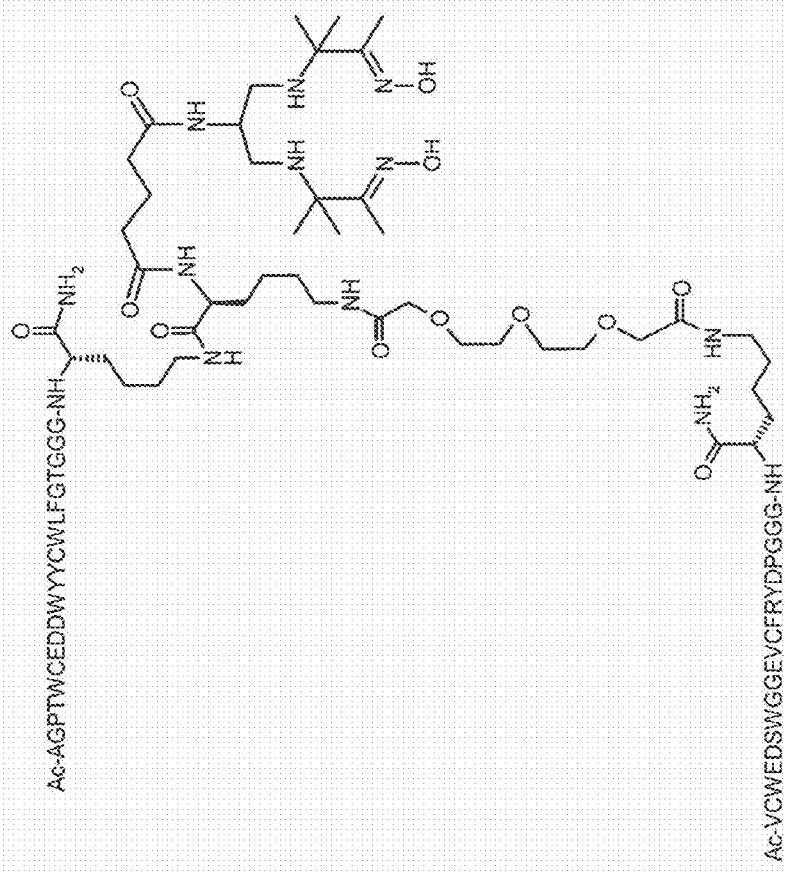
FIG. 45 shows dimer 12 (D12; Ac-AGPTWCEDDWYY-CWLFGTGGGK (SEQ ID NO:277) {[PnAO6-Glut-K(Ac-VCWEDSWGGEVCFRYDPGGGK (SEQ D NO:337) (—C(═O)CH$_2$(OCH$_2$CH$_2$)$_2$OCH$_2$C(═O)—)—NH$_2$]}—NH$_2$).
Figure 46:
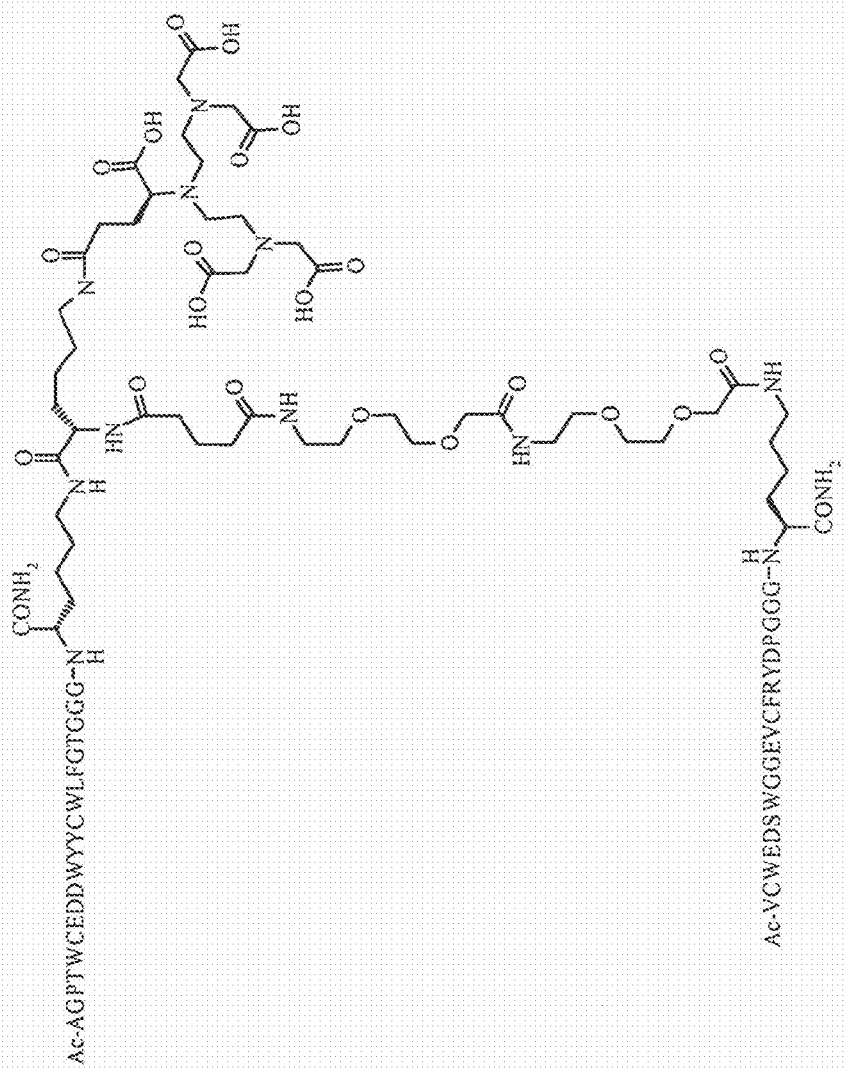
FIG. 46 shows dimer 13 (D3; Ac-AGPTWCEDDWYY-CWLFGTGGGK (SEQ ID NO:277) {Ac-VCWEDSWG-GEVCFRYDPGGGK (SEQ ID NO:337) [JJ-Glut-K(BOA)]-NH$_2$}—NH$_2$).
Figure 47:
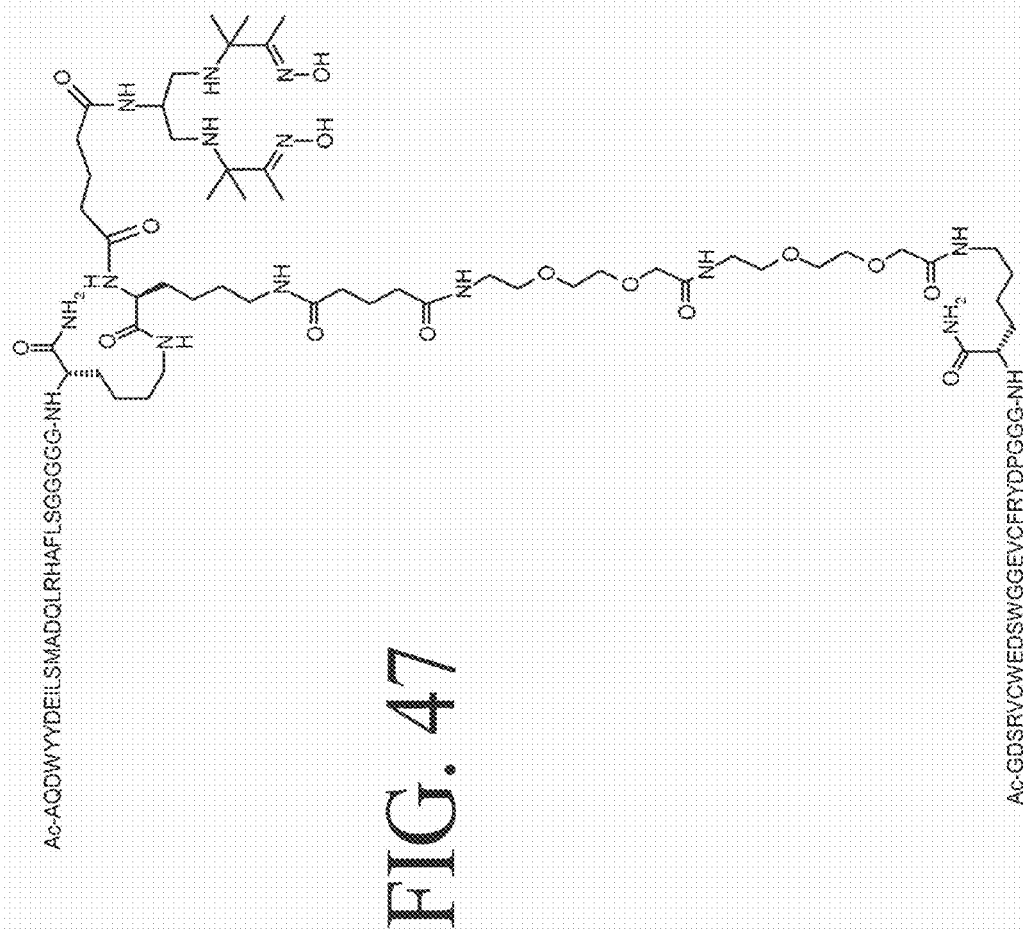
FIG. 47 shows dimer 14 (D14; Ac-AQDWYYDEILS-MADQLRHAFLSGGGGK (SEQ ID NO:356) {PnAO6-Glut-K[Ac-GDSRVCWEDSWGGEVCFRYDPGGGK (SEQ ID NO:477) (JJ-Glut)-NH$_2$]}—NH$_2$).
Figure 48:
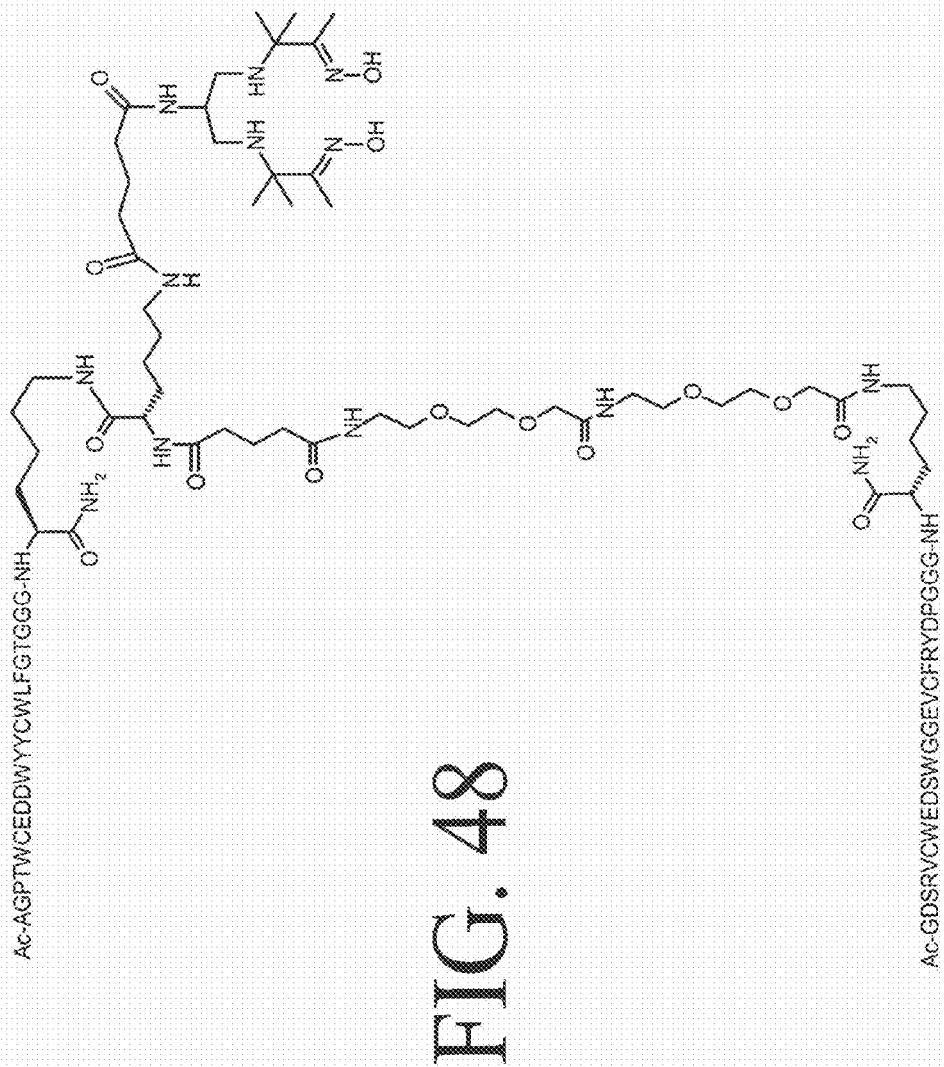
FIG. 48 shows dimer 15 (D15; Ac-AGPTWCEDDWYY-CWLFGTGGGK (SEQ ID NO:277){[Ac-GDSRVCWED-SWGGEVCFRYDPGGGK (SEQ ID NO:294)[JJ-Glut]-NH$_2$]-K(PnAO6-Glut)}-NH$_2$).
Figure 49:
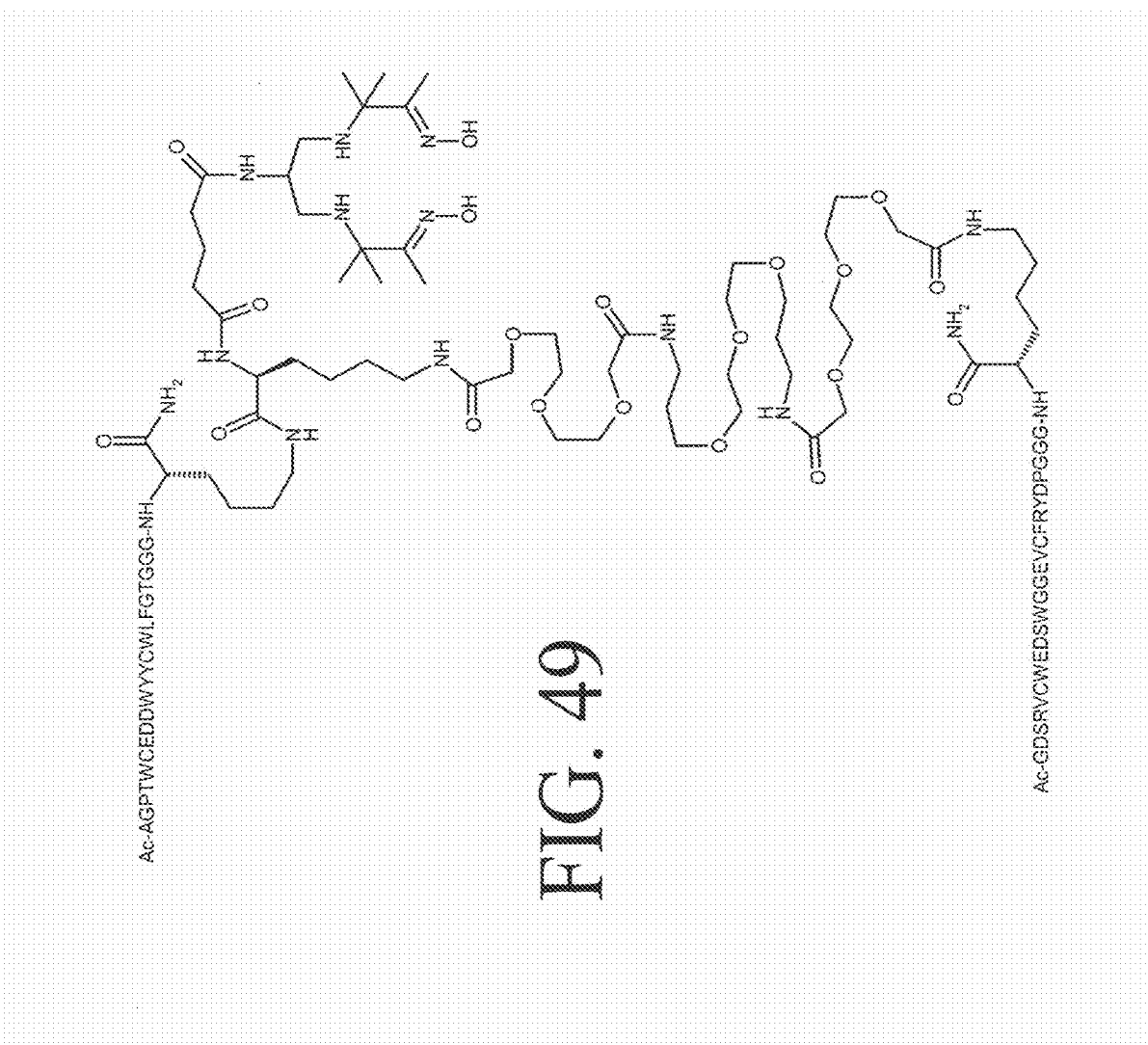
FIG. 49 shows dimer 16 (D6; Ac-AGPTWCEDDWYY-CWLFGTGGGK (SEQ ID NO:277) {PnAO6-Glut-K [Ac-GDSRVCWEDSWGGEVCFRYDPGGGK (SEQ ID NO:294) [—C(═O)CH$_2$O(CH$_2$CH$_2$O)$_2$CH$_2$C(═O)NH(CH$_2$)$_3$O(CH$_2$CH$_2$O)$_2$(CH$_2$)$_3$NH C(═O)CH$_2$O(CH$_2$CH$_2$O)$_2$CH$_2$C(═O)—]—NH$_2$]}—NH$_2$).
Figure 50:
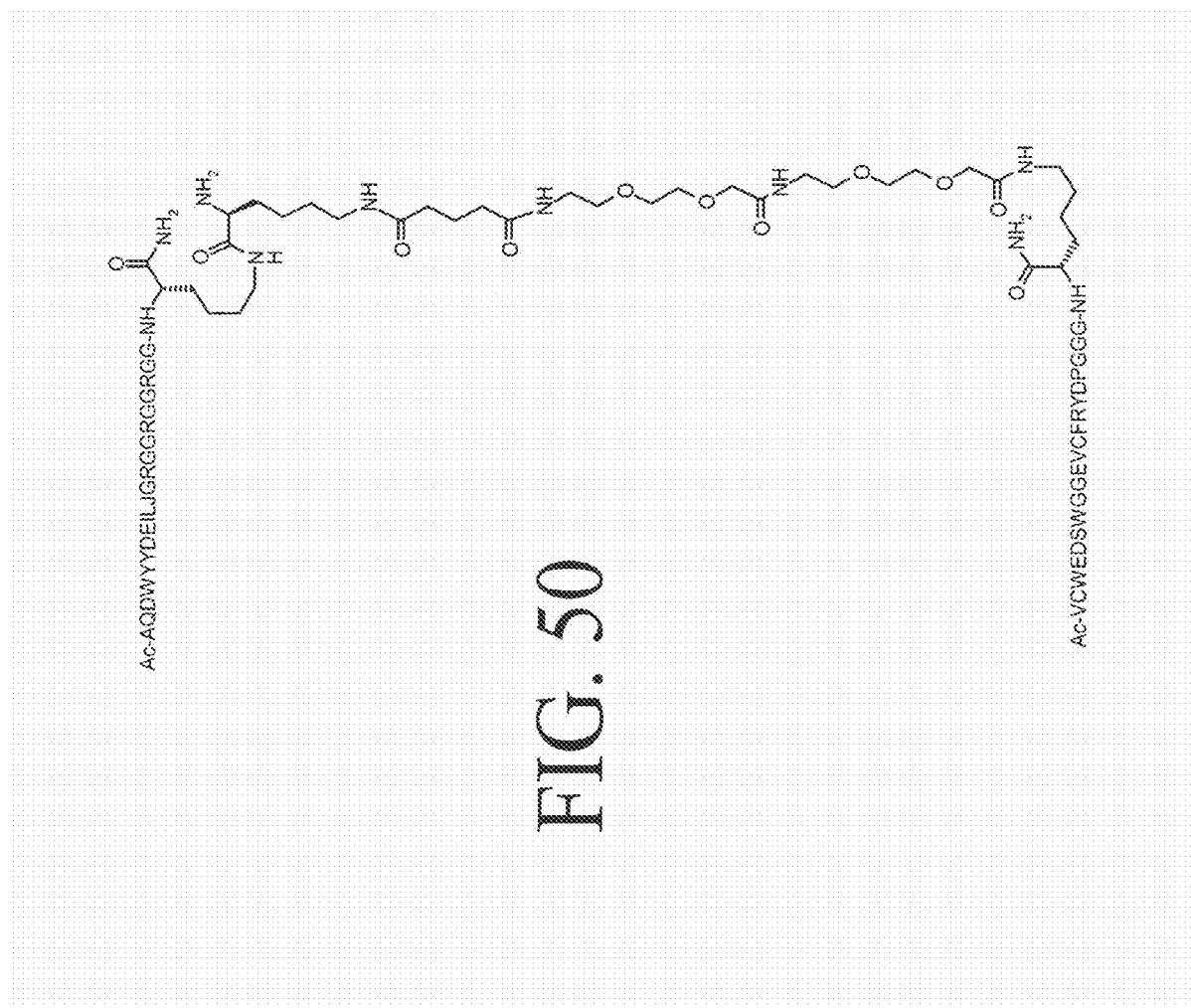
FIG. 50 shows dimer 17 (D17; Ac-AQDWYYDEILJGRG-GRGGRGGK (SEQ ID NO:478) {K[Ac-VCWEDSWG-GEVCFRYDPGGGK (SEQ ID NO:337) (JJ-Glut)-NH$_2$]}—NH$_2$).
Figure 51:
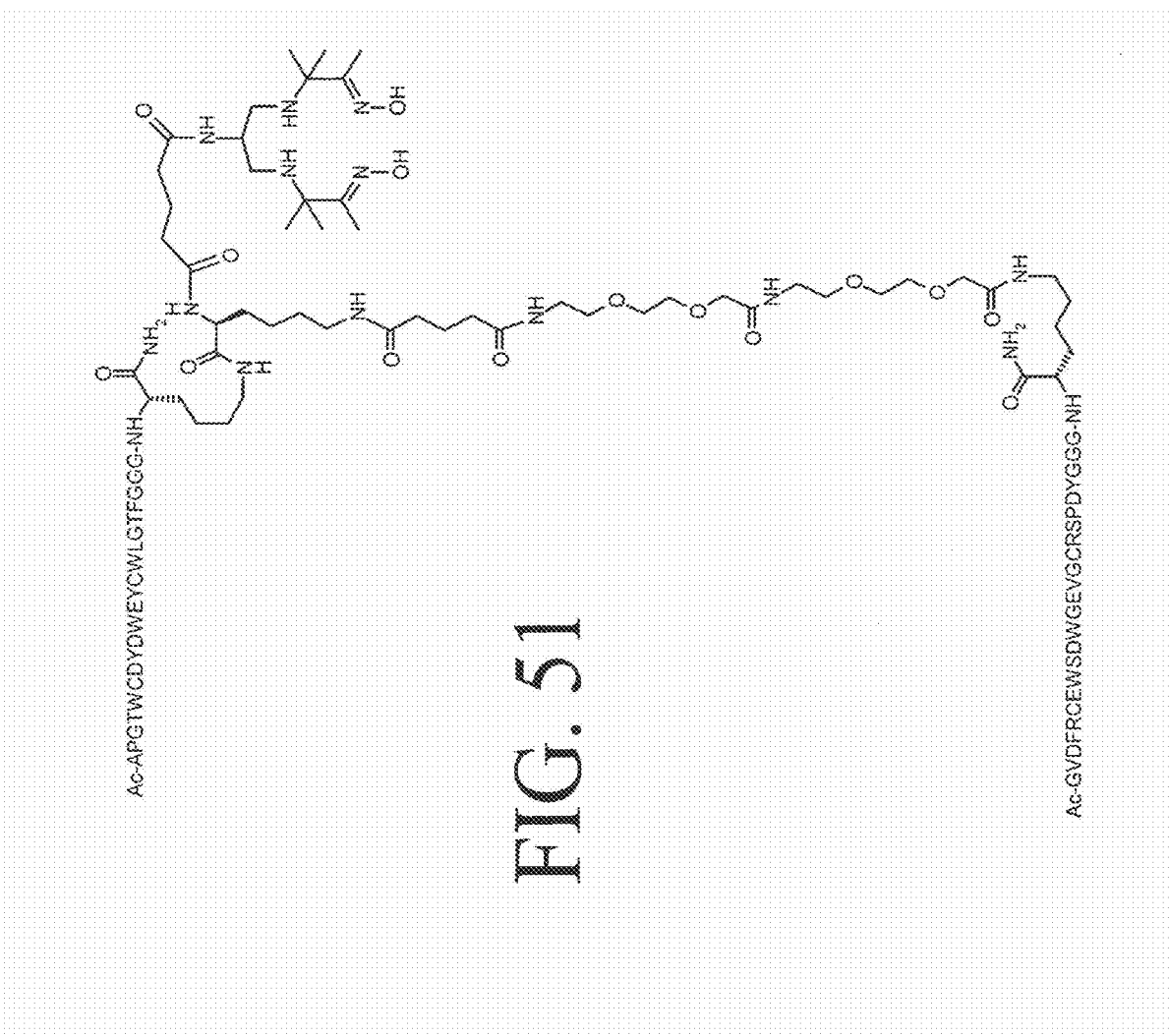
FIG. 51 shows diner 18 (D18; Ac-APGTWCDYDWEY-CWLGTFGGGK (SEQ ID NO:497) {PnAO6-Glut-K[Ac-GVDFRCEWSDWGEVGCRSPDYGGGK (SEQ ID NO:489) (JJ-Glut)-NH$_2$]}—NH$_2$).
Figure 52:
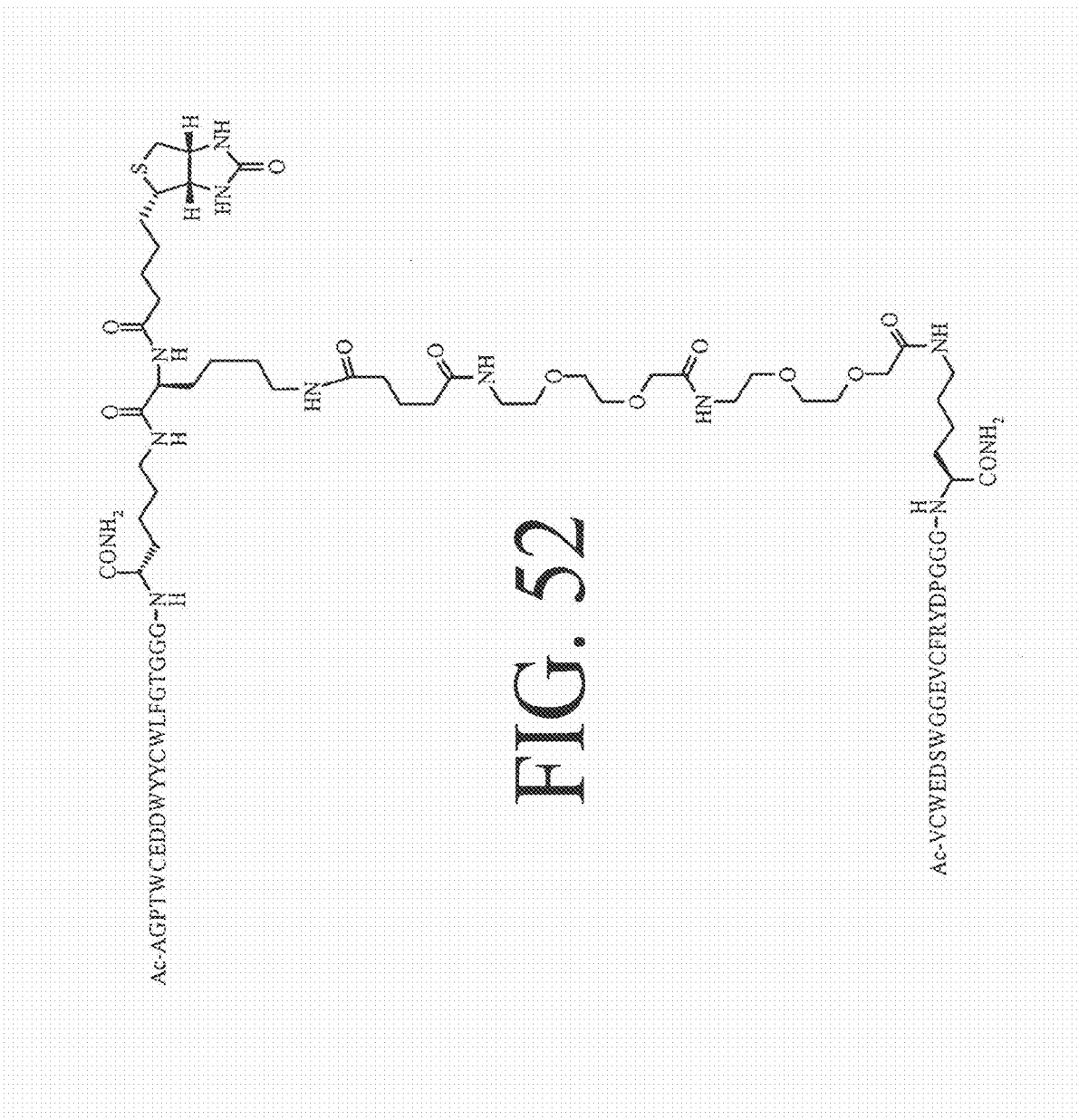
FIG. 52 shows dimer 19(D19; Ac-AGPTWCEDDWYY-CWLFGTGGGK (SEQ ID NO:277) {Biotin-K[A-VCWED-SWGGEVCFRYDPGGGK (SEQ ID NO:337) (JJ-Glut)-NH$_2$]}—NH$_2$).
Figure 53:
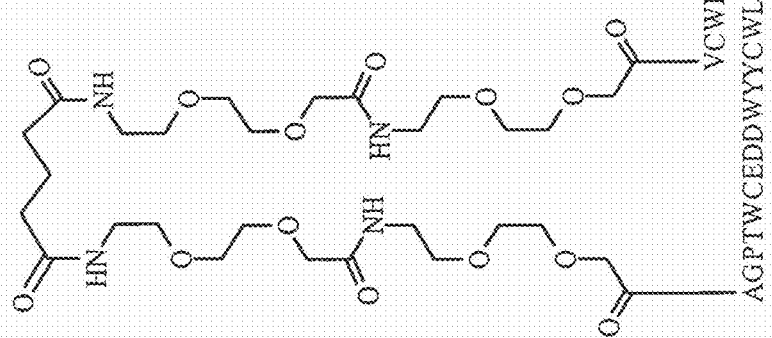
FIG. 53 shows dimer 20 (D20 (((-JJ)-AGPTWCEDDW-YYCWLGTGGGGK (SEQ ID NO:480)-NH$_2$)-Glut-JJ) VCWEDSWFFEVCFRYDPGGG (SEQ ID NO:370)-NH$_2$).
Figure 54:
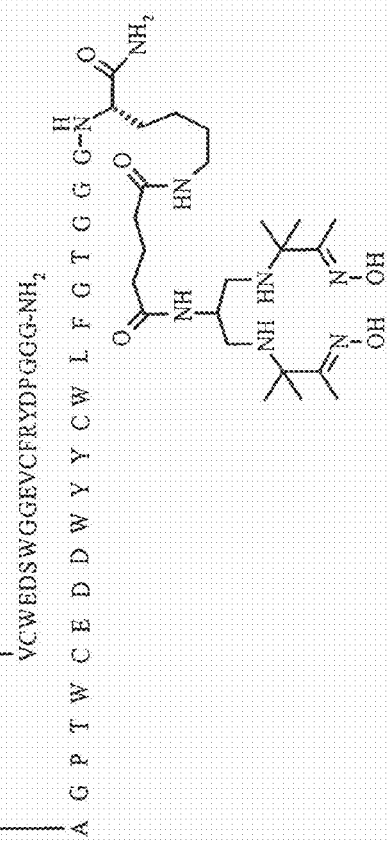
FIG. 54 shows dimer 21 (D21; [(-JJ)-AGPTWCEDDW-YYCWLFGTGGGGK (SEQ ID NO:480) (PnAO6-Glut)-NH$_2$]-Glut-(JJ)-VCWEDSWGGEVCFRYDPGGG (SEQ ID NO:370)-NH$_2$).
Figure 55:
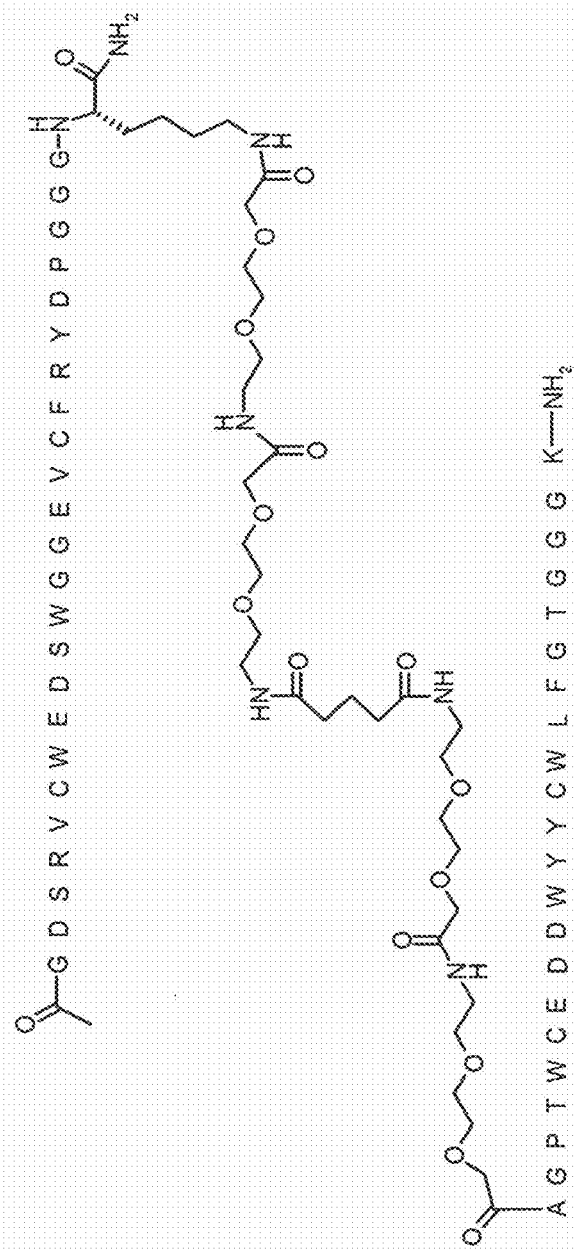
FIG. 55 shows dimer 22 (D22; Ac-GDSRVCWEDSWG-GEVCFRYDPGGGK (SEQ ID NO:294) {JJ-Glut-JJ-AGPTWCEDDWYYCWLFTGGGK (SEQ ID NO:481)-NH$_2$}—NH$_2$).
Figure 56:
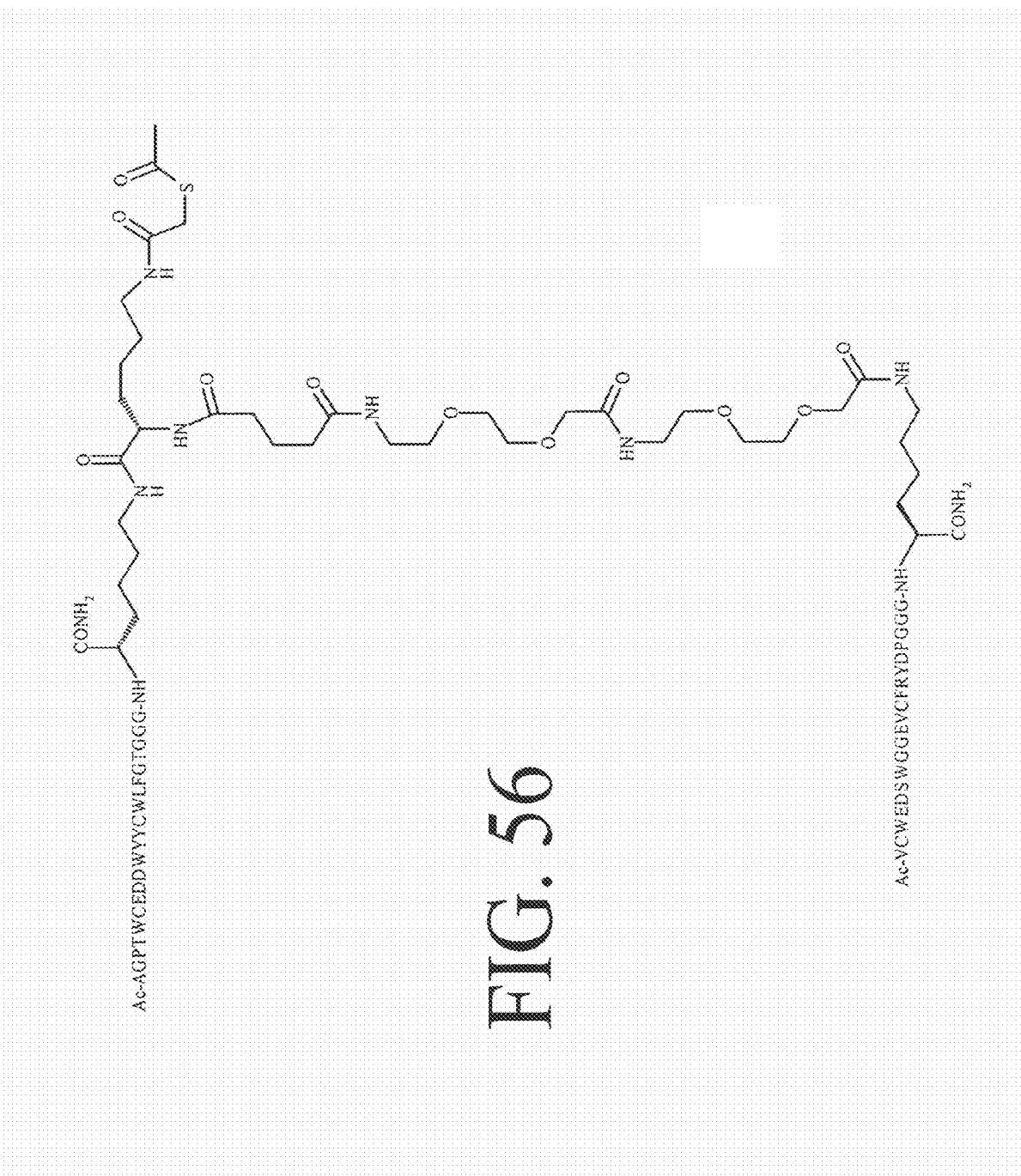
FIG. 56 shows dimer 23 (23; Ac-AGPTWCEDDWYY-CWLFGTGGGK (SEQ ID NO:277) {Ac-VCWEDSWG-GEVCFRYDPGGGK (SEQ ID NO:337) [JJ-Glut-K(SATA)]-NH$_2$}—NH$_2$. D23 is dimer D5 functionalized with the SATA (S-Acetylthioacetyl) group).
Figure 57:
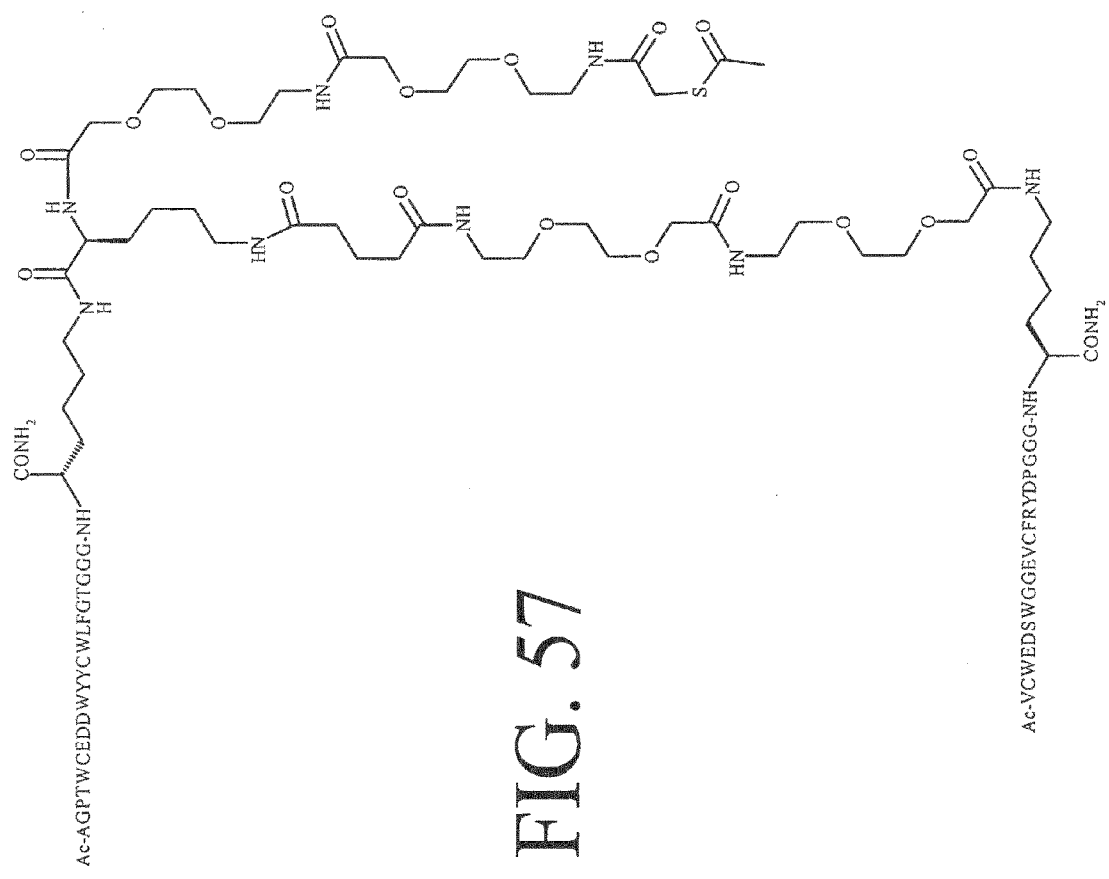
FIG. 57 shows dimer 24 (D24; Ac-AGPTWCEDDWYY-CWLFGTGGGK (SEQ ID NO:277) {SATA-JJK[Ac-VCWEDSWGGEVCFRYDPGGK (SEQ ID NO:337) (JJ-Glut)-NH$_2$]}—NH$_2$).
Figure 58:
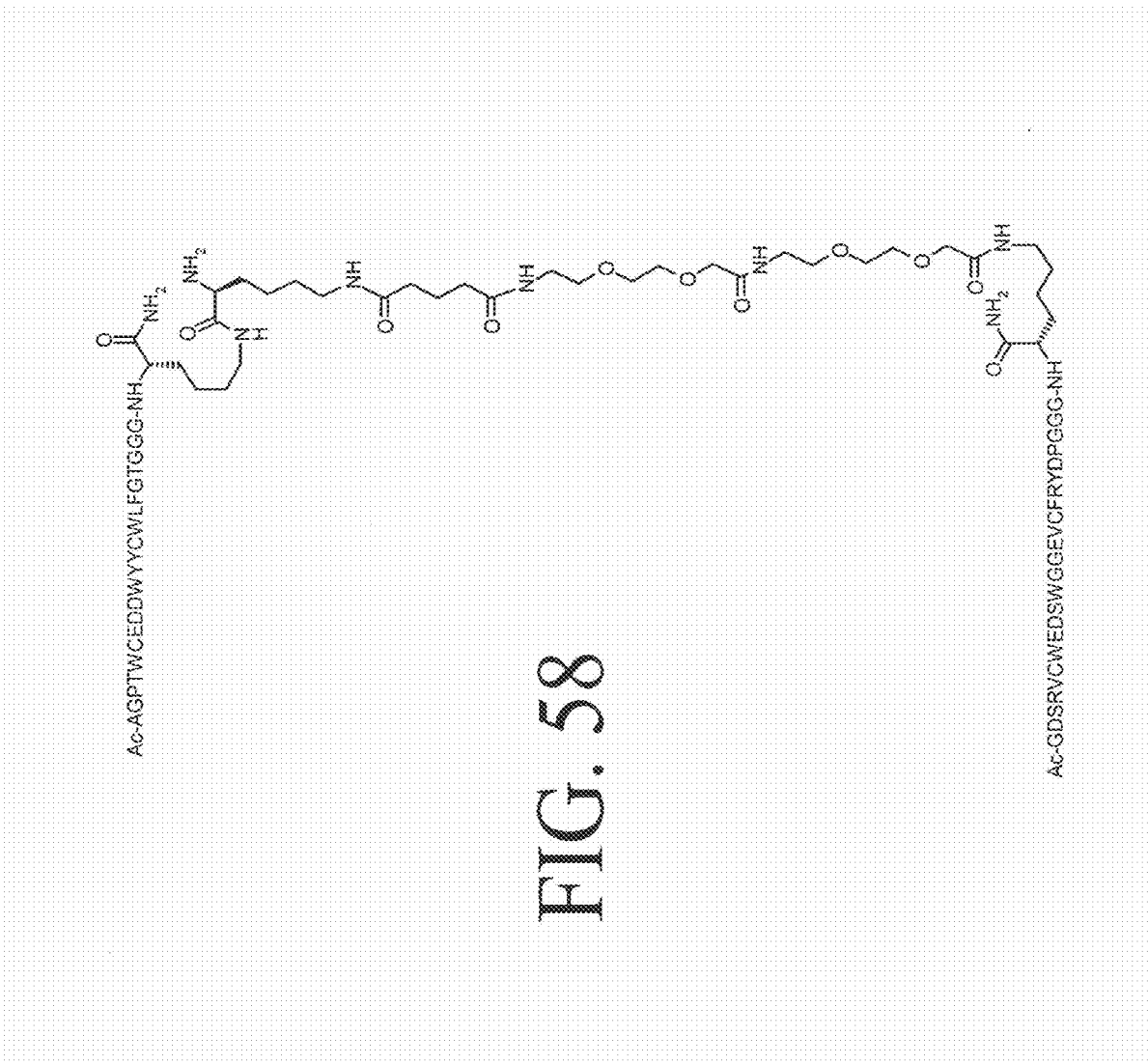
FIG. 58 shows dimer 25 (D25; Ac-AGPTWCEDDWYY-CWLFGTGGGK (SEQ ID NO:277) {Ac-GDSRVCWED-SWGGEVCFRYDPGGGK (SEQ ID NO:294) [JJ-Glut-NH(CH$_2$)4-(S)—CH(NH$_2$)C(═O)—]—NH$_2$}—NH$_2$).
Figure 59:
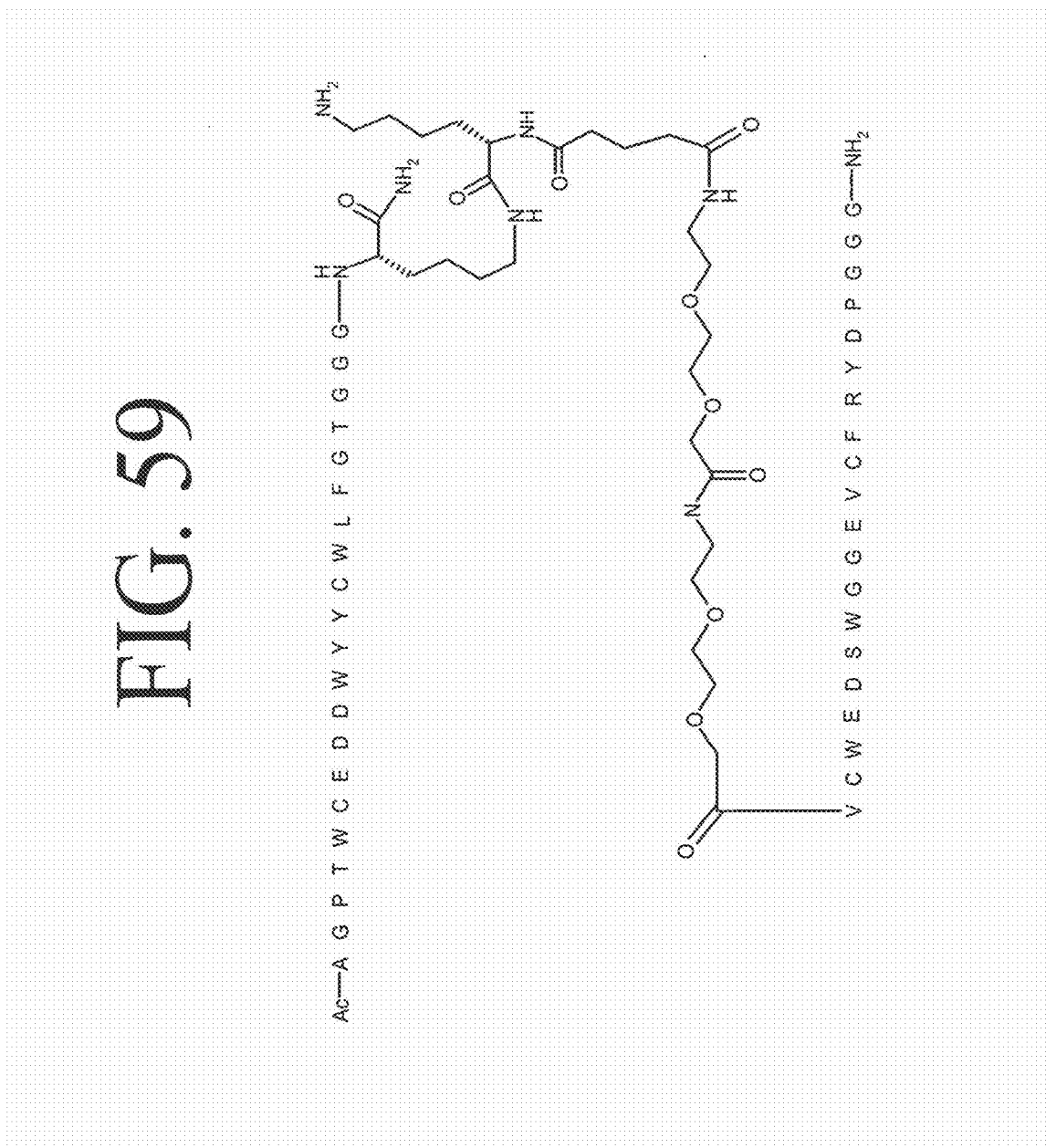
FIG. 59 shows dimer 26 (D26; AGPTWCEDDWYY-CWLFGTGGGK (SEQ ID NO:277) {(-Glut-JJ-VCWED-SWGGEVCFRYDPGGG (SEQ ID NO:370)-NH$_2$)—K}—NH$_2$).
Figure 60:
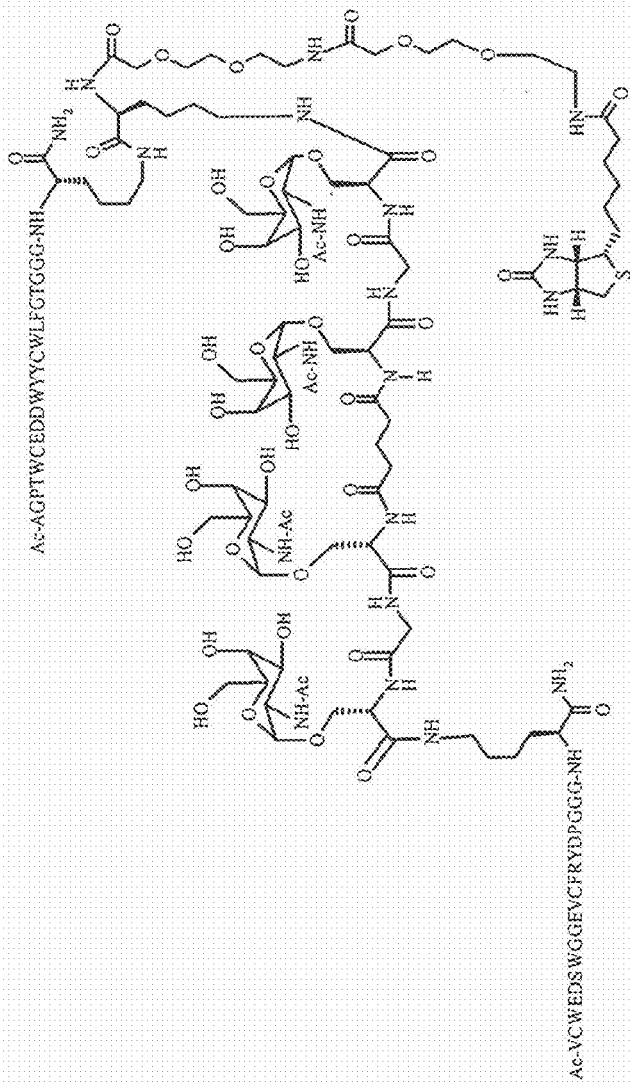
FIG. 60 shows dimer 27 (D27; Ac-AGPTWCEDDWYY-CWLFGTGGGK (SEQ DD NO:277) {Ac-VCWEDSWG-GEVCFRYDPGGGK (SEQ ED NO:337)[S(GalNAc-alpha-D)-G-S(GalNAc-alpha-D)-Glut-S(GalNAc-alpha-D)-G-S(GalNAc-alpha-D)-NH(CH$_2$)$_4$—(S)—CH(Biotin-JJNH—)C(═O)—]—NH$_2$}—NH$_2$).
Figure 61:
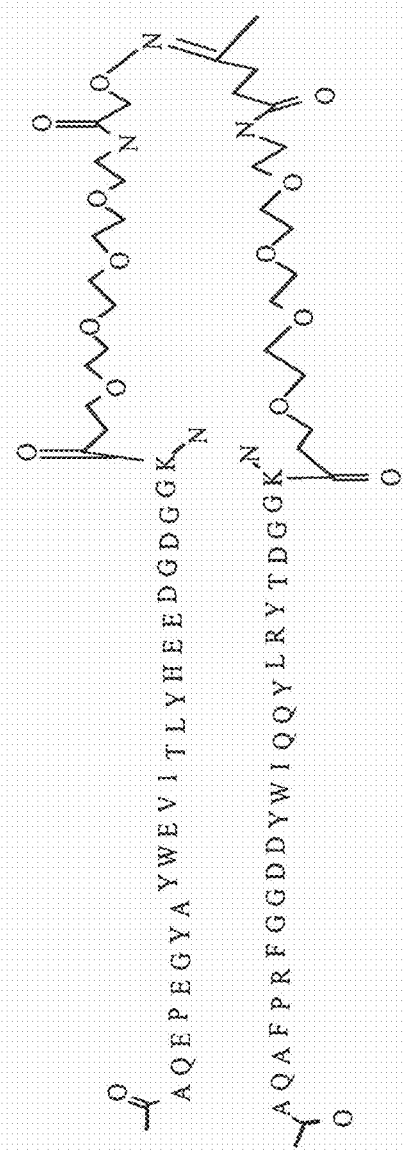
FIG. 61 shows dimer 28 (D28; comprising AQEPEGYAY-WEVITLYHEEDGDGGK (SEQ ID NO:305) and AQAF-PRFGGDDYWIQQYLRYTDGGK (SEQ ID NO:306)).
Figure 62:
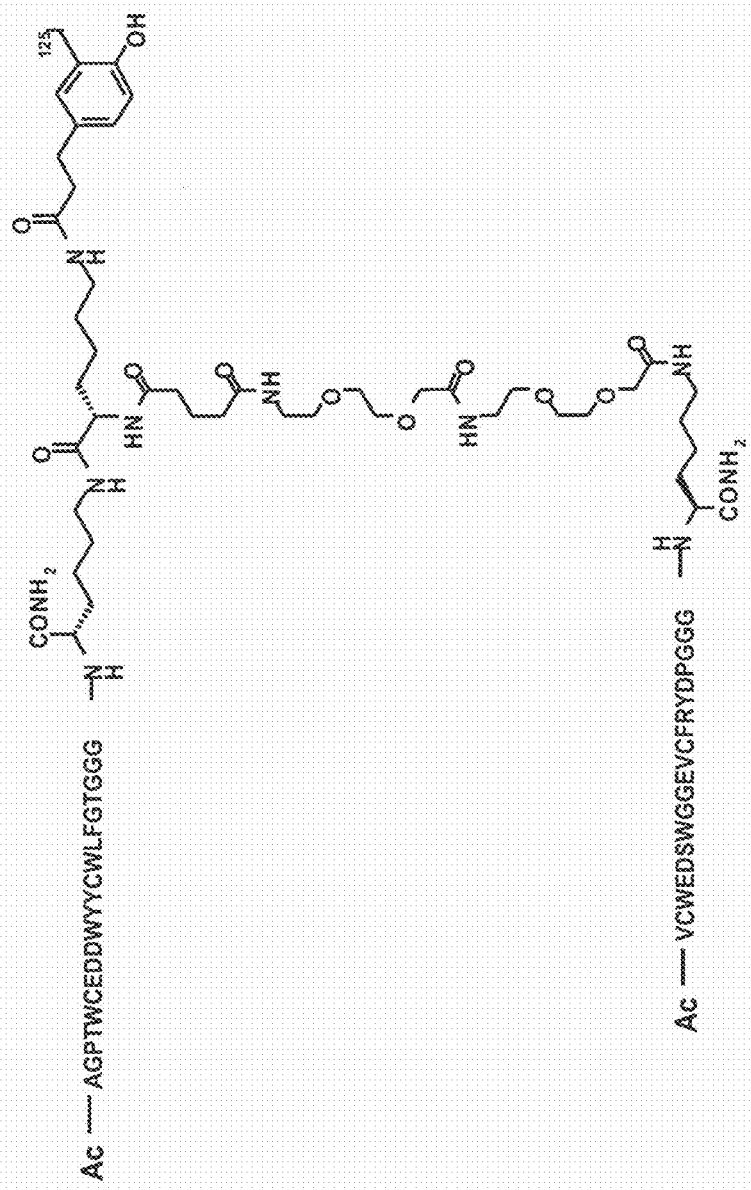
FIG. 62 shows dimer 29 (D29; comprising AGPTWCED-DWYYCWLFGTGGGK (SEQ ID NO:277) and VCWED-SWGGEVCFRYDPGGGK (SEQ ID NO:337)).
Figure 63:
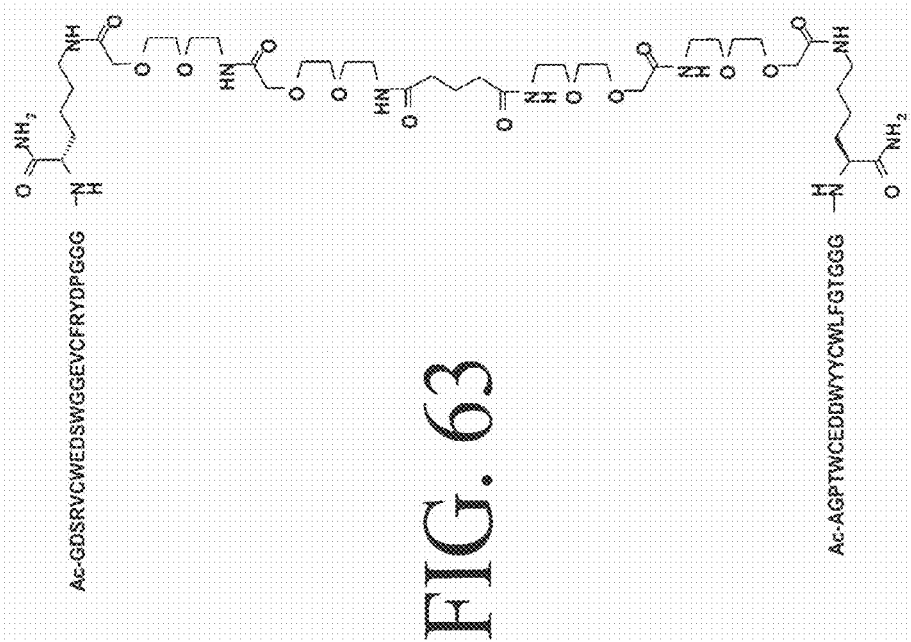
FIG. 63 shows dimer 6 (D6; comprising GDSRVCWED-SWGGEVCFRYDPGGGK (SEQ ID NO:294) and AGPTWCEDDWYYCWLFGTGGGK (SEQ ID NO:277)).

Particularly preferred metal chelators include those of Formula 20, 21, 22, 23a, 23b, 24a, 24b and 25 (FIGS. 34A-F) and FIG. 35. Formulas 20-22 (FIGS. 34A-C) are particularly useful for lanthanides such as paramagnetic $Gd^{3+}$ and radioactive lanthanides such as $^{177}$Lu, $^{90}$Y, $^{153}$Sm, $^{111}$In, or $^{166}$Ho. Formulas 23a-24b (FIGS. 34D and F) and FIG. 35 are particularly useful for radionuclides $^{99m}$Tc, $^{186}$Re, or $^{188}$Re. Formula 25 (FIG. 34F) and the structure shown in FIG. 35 are particularly useful for $^{99m}$Tc. These and other metal chelating groups are described in U.S. Pat. Nos. 6,093,382 and 5,608,110, which are incorporated by reference herein in their entirety. Additionally, the chelating group of formula 22 (FIG. 34C) is described in, for example, U.S. Pat. No. 6,143,274; the chelating group of formula 24 is described in, for example, U.S. Pat. Nos. 5,627,286 and 6,093,382, and the chelating groups of formula 25 and FIG. 35 are described in, for example, U.S. Pat. Nos. 5,662,885; 5,780,006; and 5,976,495.

In the above Formulas 24a and 24b (FIG. 34E), X is either $CH_2$ or O, Y is $C_1$-$C_{10}$ branched or unbranched alky, aryl, aryloxy, arylamino, arylaminoacyl, or arylalkyl comprising $C_1$-$C_{10}$ branched or unbranched alkyl groups, hydroxy or $C_1$-$C_{10}$ branched or unbranched polyhydroxyalkyl groups, $C_1$-$C_{10}$ branched or unbranched hydroxy or polyalkoxyalkyl or polyhydroxy-polyalkoxyalkyl groups; J is C(=O)—, OC(=O)—, $SO_2$—, NC(=O)—, NC(=S)—, N(Y), NC(=NCH$_3$)—, NC(=NH)—, N=N—, homopolyamides or heteropolyamines derived from synthetic or naturally occurring ammo acids, and n is 1-100. Other variants of these structures are described, for example, in U.S. Pat. No. 6,093,382. The disclosures of each of the foregoing patents, applications and references are incorporated by reference herein, in their entirety.

The chelators may be covalently linked directly to the KDR or VEGF/KDR complex binding moiety or linked to the KDR or VEGF/KDR complex binding polypeptide via a linker, as described previously, and then directly labeled with the radioactive met of choice (see, WO 98/52618, U.S. Pat. Nos. 5,879,658, and 5,849,261).

Complexes of radioactive technetium are particularly useful for diagnostic imaging and complexes of radioactive rhenium are particularly useful for radiotherapy. In forming a complex of radioactive technetium with the reagents of this invention, the technetium complex, preferably a salt of Tc-99m pertechnetate, is reacted with the reagent in the presence of a reducing agent. Preferred reducing agents are dithionite, stannous and ferrous ions; the most preferred reducing agent is stannous chloride. Means for preparing such complexes are conveniently provided in a kit form comprising a sealed vial containing a predetermined quantity of a reagent of the invention to be labeled and a sufficient amount of reducing agent to label the reagent with Tc-99m. Alternatively, the complex may be formed by reacting a peptide of this invention conjugated with an appropriate chelator with a preformed labile complex of technetium and another compound known as a transfer ligand. This process is known as ligand exchange and is well known to those skilled in the art. The labile complex may be formed using such transfer ligands as tartrate, citrate, gluconate or mannitol, for example. Among the Tc-99m pertechnetate salts useful with the present invention are included the a metal salts such as the sodium salt, or ammonium salts or lower alkyl ammonium salts.

Preparation of the complexes of the present invention where the metal is radioactive rhenium may be accomplished using rhenium starting materials in the +5 or +7 oxidation state. Examples of compounds in which rhenium is in the Re(VII) state are $NH_4ReO_4$ or $KReO_4$. Re(V) is available as, for example, $[ReOCl_4](NBu_4)$, $[ReOCl_4](AsPh_4)$, $ReOCl_3(PPh_3)_2$ and as $ReO_2(pyridine)_4^+$, where Ph is phenyl and Bu is n-butyl. Other rhenium reagents capable of forming a rhenium complex may also be used.

Radioactively-labeled scintigraphic imaging agents provided by the present invention are provided having a suitable amount of radioactivity. In forming Tc-99m radioactive complexes, it is generally preferred to form radioactive complexes in solutions containing radioactivity at concentrations of from about 0.01 mCi to 100 mCi per mL.

Generally, the unit dose to be administered has a radioactivity of about 0.01 mCi to about 100 mCi, preferably 1 mCi to 20 mCi. The solution to be injected at unit dosage is from about 0.01 mL to about 10 mL.

Typical doses of a radionuclide-labeled KDR or VEGF/KDR complex binding imaging agents according to the invention provide 10-20 mCi. After injection of the KDR or VEGF/KDR complex-specific radionuclide imaging agent into the patient, a gamma camera calibrated for the gamma ray energy of the nuclide incorporated in the imaging agent is used to image areas of uptake of the agent and quantify the amount of radioactivity present in the site. Imaging of the site in vivo can take place in a matter of a few minutes. However, imaging can take place, if desired, hours or even longer, after the radiolabeled peptide is injected into a patient. In most instances, a sufficient amount of the administered dose will accumulate in the area to be imaged within about 0.1 of an hour to permit the taking of scintiphotos.

Proper dose schedules for the radiotherapeutic compounds of the present invention are known to those skilled in the art. The compounds can be administered using many methods that include, but are not limited to, a single or multiple IV or IP injections, using a quantity of radioactivity that is sufficient to cause damage or ablation of the targeted KDR-expressing tissue, but not so much that substantive damage is caused to non-target (normal tissue). The quantity and dose required is different for different constructs, depending on the energy and half-life of the isotope used, the degree of uptake and clearance of the agent from the body and the mass of the tumor. In general, doses can range from a single dose of about 30-50 mCi to a cumulative dose of up to about 3 Curies.

The radiotherapeutic compositions of the invention can include physiologically acceptable buffers, and can require radiation stabilizers to prevent radiolyic damage to the compound prior to injection. Radiation stabilizers are known to those skilled in the art, and may include, for example, para-aminobenzoic acid, ascorbic acid, gentistic acid and the like.

A single, or multi-vial kit that contains all of the components needed to prepare the complexes of this invention, other than the radionuclide, is an integral part of this invention.

A single-vial kit preferably contains a chelating ligand, a source of stannous salt, or other pharmaceutically acceptable reducing agent, and is appropriately buffered with pharmaceutically acceptable acid or base to adjust the pH to a value of about 3 to about 9. The quantity and type of reducing agent used would depend highly on the nature of the exchange complex to be formed. The proper conditions are well known to those that are skilled in the art. It is preferred that the kit contents be in lyophilized form. Such a single vial kit may optionally contain labile or exchange ligands such as gluco-heptonate, gluconate, mannitol, malate, citric or tartaric acid and can also contain reaction modifiers such as diethylenetri-amine-pentaacetic acid (DPTA), ethylenediamine tetraacetic acid (EDTA), or α, β, or γ cyclodextrin that serve to improve the radiochemical purity and stability of the final product. The kit may also contain stabilizers, bulking agents such as mannitol, that are designed to aid in the freeze-drying process, and other additives known to those skilled in the art.

A multi-vial kit preferably contains the same general components but employs more than one vial in reconstituting the radiopharmaceutical. For example, one vial may contain all of the ingredients that are required to form a labile Tc(V) complex on addition of pertechnetate (e.g., the stannous source or other reducing agent). Pertechnetate is added to this vial, and after waiting an appropriate period of time, the contents of this vial are added to a second vial that contains the ligand, as well as buffers appropriate to adjust the pH to its optimal value. After a reaction time of about 5 to 60 minutes, the complexes of the present invention are formed. It is advantageous that the contents of both vials of this multi-vial kit be lyophilized. As above, reaction modifiers, exchange ligands, stabilizers, bulking agents, etc. may be present in either or both vials.

As shown in the Examples, compounds of the invention comprising a radionuclide, particularly heteromultimers such as D10 conjugated to a radionuclide (optionally via a chelator), are useful in imaging KDR or VEGF/KDR complex expressing tissue (such as angiogenic tissue).

Additionally, the Examples establish that compounds of the invention conjugated to a therapeutic radionuclide, particularly heteromultimers such as D13 conjugated to a chelator and complexed with a therapeutic radionuclide, are useful in radiotherapy of tumors expressing KDR.

Other Therapeutic Applications

The KDR or VEGF/KDR complex binding polypeptides of the present invention can be used to improve the activity of therapeutic agents such as anti-angiogenic or tumorcidal agents against undesired angiogenesis such as occurs in neoplastic tumors, by providing or improving their affinity for KDR or VEGF/KDR complex and their residence time at a KDR or VEGF/KDR complex on endothelium undergoing angiogenesis. In this aspect of the invention, hybrid agents are provided by conjugating a KDR or VEGF/KDR complex binding polypeptide according to the invention with a therapeutic agent. The therapeutic agent may be a radiotherapeutic, discussed above, a drug, chemotherapeutic or tumorcidal agent, genetic material or a gene delivery vehicle, etc. The KDR or VEGF/KDR complex binding polypeptide portion of the conjugate causes the therapeutic to "home" to the sites of KDR or VEGF/KDR complex (i.e., activated endothelium), and to improve the affinity of the conjugate for the endothelium, so that the therapeutic activity of the conjugate is more localized and concentrated at the sites of angiogenesis. Such conjugates will be useful in treating angiogenesis-associated diseases, especially neoplastic tumor growth and metastasis, in mammals, including humans, which method comprises administering to a mammal in need thereof an effective amount of a KDR or VEGF/KDR complex binding polypeptide according to the invention conjugated with a therapeutic agent. The invention also provides the use of such conjugates in the manufacture of a medicament for the treatment of angiogenesis associated diseases in mammals, including humans.

Suitable therapeutic agents for use in this aspect of the invention include, but are not limited to: antineoplastic agents, such as platinum compounds (e.g., spiroplatin cisplatin, and carboplatin), methotrexate, adriamycin, mitomycin, ansamitocin, bleomycin, cytosine, arabinoside, arabinosyl adenine, mercaptopolylysine, vincristine, busulfan, chlorambucil, melphalan (e.g., PAM, L-PAM, or phenylalanine mustard), mercaptopurine, mitotane, procarbazine hydrochloride, dactinomycin (actinomycin D), daunorubicin hydrochloride, doxorubicin hydrochloride, taxol, mitomycin, plicamycin (mithramycin), aminoglutethimide, estramustine phosphate sodium, flutamide, leuprolide acetate, megestrol acetate, tamoxifen citrate, testoiactone, trilostane, amsacrine (m-AMSA), aparaginase (L-aparaginase), Erwina aparaginase, etoposide (VP-16), interferon cx-2a, Interferon cx-2b, teniposide (VM-26, vinblastine sulfate (VLB), vincristine sulfate, bleomycin sulfite, adriamycin, and arabinosyl, anti-angiogenic agents such as tyrosine kinase inhibitors with activity toward signaling molecules important in angiogenesis and/or tumor growth such as SU5416 and SU6668 (Sugen/Pharmacia & Upjohn), endostatin (EntreMed), angiostatin (EntreMed), Combrestatin (Oxigene), cyclosporine, 5-fluorouracil, vinblastine, doxorubicin, paclitaxel, daunorubcin, immunotoxins; coagulation factors; antivirals such as acyclovir, amantadine azidothymidine (AZT or Zidovudine), ribavirin and vidarabine monohydrate (adenine arabinoside, ara-A); antibiotics, antimalarials, antiprotozoans such as chloroquine, hydroxychloroquine, metroidazole, quinine and meglumine antimonate; anti-inflammatories such as diflunisal, ibuprofen, indomethacin, meclofenamate, mefenamic acid, naproxen, oxyphenbutazone, phenylbutazone, piroxicam, sulindac, tolmetin, aspirin and salicylates.

The KDR or VEGF/KDR complex binding polypeptides of the present invention may also be used to target genetic material to KDR-expressing cells. Thus, they may be useful in gene therapy, particularly for treatment of diseases associated with angiogenesis. In this embodiment, genetic material or one or more delivery vehicles containing genetic material useful in treating an angiogenesis-related disease may be conjugated to one or more KDR binding moieties of the invention and administered to a patient. The genetic material may include nucleic acids, such as RNA or DNA, of either natural or synthetic origin, including recombinant RNA and DNA and antisense RNA and DNA. Types of genetic material that may be used include, for example, genes carried on expression vectors such as plasmids, phagemids, cosmids, yeast artificial chromosomes (YAC's) and defective or "helper" viruses, antigene nucleic acids, both single and double stranded RNA and DNA and analogs thereof, such as phosphorothioate and phosphorodithioate oligodeoxynucleotides. Additionally, the genetic material may be combined, for example, with lipids, proteins or other polymers. Delivery vehicles for genetic material may include, for example, a virus particle, a retroviral or other gene therapy vector, a liposome, a complex of lipids (especially cationic lipids) and genetic material, a complex of dextran derivatives and genetic material, etc.

In a preferred embodiment the constructs of the invention are utilized in gene therapy for treatment of diseases associated with angiogenesis. In this embodiment, genetic material, or one or more delivery vehicles containing genetic material, e.g., useful in treating an angiogenesis-related disease, can be conjugated to one or more KDR or VEGF/KDR complex binding polypeptides or multimers (e.g. homomultimers or heteromultimers) of the invention and administered to a patient.

Constructs including genetic material and the KDR-binding polypeptides of the invention may be used, in particular, to selectively introduce genes into angiogenic endothelial cells, which may be useful not only to treat cancer, but also after angioplasty, where inhibition of angiogenesis may inhibit restenosis.

Therapeutic agents and the KDR or VEGF/KDR complex binding moieties of the invention can be linked or fused in known ways, using the same type of linkers discussed elsewhere in this application. Preferred linkers will be substituted or unsubstituted alkyl chains, amino acid chains, polyethylene glycol chains, and other simple polymeric linkers known in the art. More preferably, if the therapeutic agent is itself a protein, for which the encoding DNA sequence is known, the therapeutic protein and KDR or VEGF/KDR complex binding polypeptide may be coexpressed from the same synthetic gene, created using recombinant DNA techniques, as described above. The coding sequence for the KDR or VEGF/KDR complex binding polypeptide may be fused in frame with that of the therapeutic protein, such that the peptide is expressed at the amino- or carboxy-terminus of the therapeutic protein, or at a place between the termini, if it is determined that such placement would not destroy the required biological function of either the therapeutic protein or the KDR or VEGF/KDR complex binding polypeptide. A particular advantage of this general approach is that concatamerization of multiple, tandemly arranged KDR or VEGF/KDR complex binding polypeptides is possible, thereby increasing the number and concentration of KDR or VEGF/KDR complex binding sites associated with each therapeutic protein. In his manner KDR or VEGF/KDR complex binding avidity is increased, which would be expected to improve the efficacy of the recombinant therapeutic fusion protein.

Similar recombinant proteins containing one or more coding sequences for a KDR and VEGF/KDR complex binding polypeptide may be useful in imaging or therapeutic applications. For example, in a variation of the pre-targeting applications discussed infra, the coding sequence for a KDR or VEGF/KDR complex binding peptide can be fused in frame to a sequence encoding an antibody (or an antibody fragment or recombinant DNA construct including an antibody, etc.) that, for example, binds to a chelator for a radionuclide (or another detectable label). The antibody expressing the KDR or VEGF/KDR complex binding polypeptide is then administered to a patient and allowed to localize and bind to KDR-expressing tissue. After the non-binding antibodies have been allowed to clear, the chelator-radionuclide complex (or other detectable label), which the antibody recognizes is administered, permitting imaging of or radiotherapy to the KDR-expressing tissues. Additionally, the coding sequence for a KDR or VEGF/KDR complex binding peptide may be fused in frame to a sequence encoding, for example, serum proteins or other proteins that produce biological effects (such as apoptosis, coagulation, internalization, differentiation, cellular stasis, immune system stimulation or suppression, or combinations thereof. The resulting recombinant proteins are useful in imaging, radiotherapy, and therapies directed against cancer and other diseases that involve angiogenesis or diseases associated with the pathogens discussed herein.

Additionally, constructs including KDR or KDR/VEGF complex binding polypeptides of the present invention can themselves be used as therapeutics to treat a number of diseases. For example, where binding of a protein or other molecule (e.g., a growth factor, hormone etc.) is necessary for or contributes to a disease process and a binding moiety inhibits such binding, constructs including such binding moieties could be useful as therapeutics. Similarly, where binding of a binding moiety itself inhibits a disease process, constructs containing such binding moieties could also be useful as therapeutics.

As binding of VEGF and activation of KDR is necessary for angiogenic activity, in one embodiment constructs including KDR complex binding polypeptides that inhibit the binding of VEGF to KDR (or otherwise inhibit activation of KDR) may be used as anti-angiogenic agents. Some peptides of the invention that inhibit activation of KDR are discussed in Example 9 infra. Certain constructs of the invention including multimers and heteromultimers that inhibit activation of KDR are also discussed in the Examples. A particularly preferred heteromultimer is the heterodimer-containing construct D1 (structures provided by the examples). Other preferred heterodimer constructs include D4, D5, D6, D10, D13, D17, D23, D27, D30 and D31 (structures provided in the Examples below). The binding polypeptides and constructs thereof of the present invention are useful as therapeutic agents for treating conditions that involve endothelial cells. Because an important function of endothelial cells is angiogenesis, or the formation of blood vessels, the polypeptides and constructs thereof are particularly useful for treating conditions that involve angiogenesis. Conditions that involve angiogenesis include, for example, solid tumors, tumor metastases and benign tumors. Such tumors and related disorders are well known in the art and include, for example, melanoma, central nervous system tumors, neuroendocrine tumors, sarcoma, multiple myeloma as wells as cancer of the breast, lung, prostate, colon, head & neck, and ovaries. Additional tumors and related disorders are listed in Table I of U.S. Pat. No. 6,025,331, issued Feb. 15, 2000 to Moses, et al., the teachings of which are incorporated herein by reference. Benign tumors include, for example, hemangiomas, acoustic neuromas, neurofibromas, trachomas, and pyogenic granulomas. As shown in Example 15, compounds of the invention, including heteromultimers such as D6, are useful in treating and/or slowing the growth of certain tumors.

Other relevant diseases that involve angiogenesis include for example, rheumatoid arthritis, psoriasis, and ocular diseases, such as diabetic retinopathy, retinopathy of prematurity, macular degeneration, corneal graft rejection, neovascular glaucoma, retrolental fibroplasia, rebeosis, Osler-Webber Syndrome, myocardial angiogenesis, plaque neovascularization, telangiectasia, hemophiliac joints, angiofibroma and wound granulation. Other relevant diseases or conditions that involve blood vessel growth include intestinal adhesions, atherosclerosis, scleroderma, and hypertropic scars, and ulcers. Furthermore, the binding polypeptides and constructs thereof of the present invention can be used to reduce or prevent uterine neovascularization required for embryo implantation, for example, as a birth control agent. Heteromultimers of this invention can also be useful for treating vascular permeability events that can result when VEGF binds KDR. In renal failure, for example, it has been shown that anti-VEGF antibodies can reverse damage. In a similar way, the compounds of the present invention can reverse renal permeability pathogenesis in, for example, diabetes.

Furthermore, the KDR or VEGF/KDR complex binding polypeptides of the present invention may be useful in treating diseases associated with certain pathogens, including, for example, malaria, HIV, SW, Simian hemorrhagic fever virus, etc. Sequence homology searches of KDR-binding peptides identified by phage display using the BLAST program at NCBI has identified a number of homologous proteins known or expected to be present on the surface of pathogenic organisms. Homologies were noted between the polypeptides of the invention and proteins from various malaria strains, HIV, SIV, simian hemorrhagic fever virus, and an enterohemorrhagic *E. coli* strain. Some of the homologous proteins, such as PfEMP1 and EBL-1, are hypermutable adhesion proteins known to play roles in virulence. These proteins possess multiple binding sites that are capable of binding to more than one target molecule on the host's surface. Their high mutation and recombination rates allow them to quickly develop new binding sites to promote survival and/or invasion. Similarly, proteins such as gp120 of HIV (which also has homology to some of the KDR-binding peptides disclosed herein) play critical roles in the adhesion of pathogens to their hosts. Although not reported previously, it is possible that many of the pathogen proteins with homology to the KDR-binding peptides disclosed herein also bind to KDR. Comparison of the pathogen protein sequences with the corresponding peptide sequences may suggest changes in the peptide sequence or other modifications that will enhance its binding properties. Additionally, the KDR-binding peptide sequences disclosed herein may have usefulness in blocking infection with the pathogen species that possesses the homology. Indeed, a similar strategy is being employed to block HIV infection by trying to prevent virus envelope proteins from binding to their known cellular surface targets such as CD4. See, Howie et al., "Synthetic peptides representing discontinuous CD4 binding epitopes of HIV-1 gp120 that induce T cell apoptosis and block cell death induced by gp1200", *FASEB J,* 12(11):991-998 (1998). Thus, KDR may represent a previously unknown target for a number of pathogens, and the KDR binding peptides of the invention may be useful in treating the diseases associated with those pathogens.

The binding polypeptides and constructs thereof can be administered to an individual over a suitable time course depending on the nature of the condition and the desired outcome. The binding polypeptides and constructs thereof can be administered prophylactically, e.g., before the condition is diagnosed or to an individual predisposed to a condition. The binding polypeptides and constructs thereof can be administered while the individual exhibits symptoms of the condition or after the symptoms have passed or otherwise been relieved (such as after removal of a tumor). In addition, the binding polypeptides and constructs thereof of the present invention can be administered a part of a maintenance regimen % for example to prevent or lessen the recurrence or the symptoms or condition. As described below, the binding polypeptides and constructs thereof of the present invention can be administered systemically or locally.

The quantity of material administered will depend on the seriousness of the condition. For example, for treatment of an angiogenic condition, e.g., in the case of neoplastic tumor growth, the position and size of the tumor will affect the quantity of material to be administered. The precise dose to be employed and mode of administration must per force in view of the nature of the complaint be decided according to the circumstances by the physician supervising treatment. In general, dosages of the agent conjugate of the present invention will follow the dosages that are routine for the therapeutic agent alone, although the improved affinity of a binding polypeptide or heteromultimer of the invention for its target may allow a decrease in the standard dosage.

Such conjugate pharmaceutical compositions are preferably formulated for parenteral administration, and most preferably for intravenous or intra-arterial administration. Generally, and particularly when administration is intravenous or intra-arterial pharmaceutical compositions may be given as a bolus, as two or more doses separated in time, or as a constant or non-linear flow infusion.

As used herein the term "therapeutic" includes at least partial alleviation of symptoms of a given condition. The binding polypeptides and constructs thereof of the present invention do not have to produce a complete alleviation of symptoms to be useful. For example, treatment of an individual can result in a decrease in the size of a tumor or diseased area, or prevention of an increase in size of the tumor or diseased area. Treatment can result in reduction in the number of blood vessels in an area of interest or can prevent an increase in the number of blood vessels in an area of interest. Treatment can also prevent or lessen the number or size of metastatic outgrowths of the main tumor(s).

Symptoms that can be alleviated include physiological characteristics such as VEGF receptor activity and migration ability of endothelial cells. The binding polypeptides and constructs thereof of the present invention can inhibit activity of VEGF receptors, including VEGFR-2/KDR, VEGFR-1/Flt-1 and VEGFR-3/Flt-4. Such inhibition can be detected, for example, by measuring the phosphorylation state of the receptor in the presence of or after treatment with the binding polypeptides or constructs thereof. Such inhibition can also be detected by measuring the ability of endothelial cells to migrate in the presence of or after treatment with the binding polypeptides or constructs thereof. Based on the teachings provided herein one of ordinary skill in the art would know how and be able to administer a suitable dose of binding polypeptide or construct thereof as provided herein, and measure the effect of treatment on the parameter of interest. For example, the size of the area of interest (e.g., the tumor or lesion) can be measured before and after treatment. In another embodiment, the phosphorylation state of the relevant receptor, or the migration ability of endothelial in an area of interest can be measured in samples taken from the individual. The VEGF receptors or endothelial cells can be isolated from the sample and used in assays described herein.

The dosage of the polypeptides and constructs thereof may depend on the age, sex, health, and weight of the individual, as well as the nature of the condition and overall treatment regimen. The biological effects of the polypeptides and constructs thereof are described herein. Therefore, based on the biological effects of the binding polypeptides and constructs provided herein, and the desired outcome of treatment, the preferred dosage is determinable by one of ordinary skill in the art through routine optimization procedures. Typically, the daily regimen is in the range of about 0.1 µg/kg to about 1 mg/kg.

The binding polypeptides and constructs thereof provided herein can be administered as the sole active ingredient together with a pharmaceutically acceptable excipient, or can be administered together with other binding polypeptides and constructs thereof, other therapeutic agents, or combination thereof. In addition, the binding polypeptides and constructs thereof can be conjugated to therapeutic agents, for example, to improve specificity, residence time in the body, or therapeutic effect. Such other therapeutic agents include, for example, other anti-angiogenic compounds, and tumoricidal compounds. The therapeutic agent can also include antibodies.

Furthermore, the binding polypeptide or constructs thereof of the present invention can be used as an endothelial cell homing device. Therefore, the binding polypeptide or constructs thereof can be conjugated to nucleic acid encoding, for example, a therapeutic polypeptide, in order to target the nucleic acid to endothelial cells. Once exposed to the nucleic acid conjugated binding-polypeptide, the endothelial cell can internalize and express the conjugated nucleic acid, thereby delivering the therapeutic peptide to the target cells.

In another embodiment of the invention, the therapeutic agent can be associated with an ultrasound contrast agent composition, said ultrasound contrast agent including the KDR or VEGF/KDR complex binding peptides of the invention linked to the material employed to form the vesicles (particularly microbubbles or microballoons) comprising the contrast agent. For example, the therapeutic agent can be associated with the contrast agent and delivered as described in U.S. Pat. No. 6,258,378, herein incorporated by reference. Thus, after administration of the ultrasound contrast agent and the optional imaging of the contrast agent bound to the pathogenic site expressing the KDR or VEGF/KDR complex, the pathogenic site can be irradiated with an energy beam (preferably ultrasonic, e.g., with a frequency of from 0.3 to 3 MHz), to rupture or burst of microvesicles. The therapeutic effect of the therapeutic agent can thus be advantageously enhanced by the energy released by the rapture of the microvesicles, in particular causing an effective deliver of the therapeutic agent to the targeted pathogenic site.

The binding polypeptides and constructs thereof can be administered by any suitable route. Suitable routes of administration include, but are not limited to, topical application, transdermal, parenteral, gastrointestinal, intravaginal, and transalveolar. Compositions for the desired route of administration can be prepared by any of the methods well known in the pharmaceutical arts, for example, as described in *Remington: The Science and Practice of Pharmacy,* $20^{th}$ ed., Lippincott, Williams and Wilkins, 2000.

For topical application, the binding polypeptides can be suspended, for example, in a cream, gel or rinse that allows the polypeptides or constructs to penetrate the skin and enter the blood stream, for systemic delivery, or contact the area of interest, for localized delivery. Compositions suitable for topical application include any pharmaceutically acceptable base in which the polypeptides are at least minimally soluble.

For transdermal administration, the polypeptides can be applied in pharmaceutically acceptable suspension together with a suitable transdermal device or "patch." Examples of suitable transdermal devices for administration of the polypeptides of the present invention are described, for example, in U.S. Pat. No. 6,165,458, issued Dec. 26, 2000 to Foldvari, et al., and U.S. Pat. No. 6,274,166B1, issued Aug. 4, 2001 to Sintov, et al., the teachings of which are incorporated herein by reference.

For parenteral administration, the polypeptides can be injected intravenously, intramuscularly, intraperitoneally, or subcutaneously. Typically, compositions for intravenous administration are solutions in sterile isotonic aqueous buffer. Other pharmaceutically acceptable carriers include, but are not limited to, sterile water, saline solution, and buffered saline (including buffers like phosphate or acetate), alcohol, vegetable oils, polyethylene glycols, gelatin, lactose, amylose, magnesium stearate, talc, silicic acid, paraffin, etc. Where necessary, the composition may also include a solubilizing agent and a local anaesthetic such as lidocaine to ease pain at the site of the injection, preservatives, stabilizers, wetting agents, emulsifiers, salts, lubricants, etc. as long as they do not react deleteriously with the active compounds. Similarly, the composition may comprise conventional excipients, i.e. pharmaceutically acceptable organic or inorganic carrier substances suitable for parenteral, enteral or intranasal application that do not deleteriously react with the active compounds. Generally, the ingredients will be supplied either separately or mixed together in unit dosage form, for example, as a dry lyophilized powder or water free concentrate in a hermetically sealed container such as an ampoule or sachette indicating the quantity of active agent in activity units. Where the composition is to be administered by infusion, it can be dispensed with an infusion bottle containing sterile pharmaceutical grade "water for injection" or saline. Where the composition is to be administered by injection, an ampoule of sterile water for injection or saline may be provided so that the ingredients may be mixed prior to administration.

For gastrointestinal and intravaginal administration, the polypeptides can be incorporated into pharmaceutically acceptable powders, pills or liquids for ingestion, and suppositories for rectal or vaginal administration.

For transalveolar, buccal or pulmonary administration, the polypeptides can be suspended in a pharmaceutically acceptable excipient suitable for aerosolization and inhalation or as a mouthwash. Devices suitable for transalveolar administration such as atomizers and vaporizers are also included within the scope of the invention. Suitable formulations for aerosol delivery of polypeptides using buccal or pulmonary routes can be found, for example in U.S. Pat. No. 6,312,665B11, issued Nov. 6, 2001 to Pankaj Modi, the teachings of which are incorporated herein by reference.

In addition, the polypeptides of the present invention can be administered nasally or ocularly, where the polypeptide is suspended in a liquid pharmaceutically acceptable agent suitable for dropwise dosing.

The polypeptides of the present invention can be administered such that the polypeptide is released in the individual over an extended period of time (sustained or controlled release). For example, the polypeptide can be formulated into a composition such that a single administration provides delivery of the polypeptide for at least one week, or over the period of a year or more. Controlled release systems include monolithic or reservoir-type microcapsules, depot implants, osmotic pumps, vesicles, micelles, liposomes, transdermal patches and iontophoretic devices. In one embodiment, the polypeptides of the present invention are encapsulated or admixed in a slowly degrading, non-toxic polymer. Additional formulations suitable for controlled release of the polypeptides provided herein are described in U.S. Pat. No. 4,391,797, issued Jul. 5, 1983, to Folkman, et al., the teachings of which are incorporated herein by reference.

Another suitable method for delivering the polypeptides of the present to an individual is via in vivo production of the polypeptide. A gene encoding the polypeptide can be administered to the individual such that the encoded polypeptide is expressed. The gene can be transiently expressed. In a particular embodiment, the gene encoding the polypeptide is transfected into cells that have been obtained from the patient, a method referred to as ex vivo gene therapy. Cells expressing the polypeptide are then returned to the patients body. Methods of ex Vivo gene therapy are well known in the art and are described, for example, in U.S. Pat. No. 4,391,797, issued Mar. 21, 1998 to Anderson, et al., the teachings of which are incorporated herein by reference.

Isolation, formulation and use of KDR or VEGF/KDR complex binding moieties in accordance with this invention will be further illustrated in the following examples. The specific parameters included in the following examples are intended to illustrate the practice of the invention, and they are not presented to in any way limit the scope of the invention.

EXAMPLES

Methods for the Examples

The following methods were employed in Examples 4-10. The following common abbreviations are used: 9-fluorenylmethyloxycarbonyl (Fmoc), 1-hydroxybenzotriazole (HOBt), N,N'-diisopropylcarbodiimide (DIC), N-methylpyrrolidinone (NMP), acetic anhydride ($Ac_2O$), (4,4-dimethyl-2,6-dioxocyclohex-1-ylidene)-3-methylbutyl (ivDde), trifluoroacetic acid (TFA), Reagent B (TFA:$H_2O$:phenol:triisopropylsilane 88:5:5:2), diisopropylethylamine (DIEA), O-(1H-benzotriazole-1-yl)-N,N,N',N'-tetramethyluronium hexafluorophosphate (HBTU), O-(7-azabenzotriazol-1-yl)-1,1,3,3-tetramethyluronium hexafluorophosphate (HATU), N-hydroxysuccinimide (NHS), solid phase peptide synthesis (SPPS), dimethyl sulfoxide (DMSO), dichloromethane (DCM), dimethylformamide (DMF), human serum albumin (HSA), and radiochemical purity (RCP).

Method 1 for the ACT 357 MPS and ACT 496 MOS Synthesizers

The peptides were synthesized on NovaSyn TGR (Rink amide) resin (0.2 mmol/g) using the Advanced ChemTech ACT 357 or ACT 496 Synthesizers employing Fmoc peptide synthesis protocols, specifically using HOBt/DIC as the coupling reagents and NMP as the solvent. The Fmoc was removed by treating the Nova-Syn TGR (Rink amide-available from NovaBiochem, San Diego Calif.) resin-bound peptide with 25% piperidine in DMF twice (4 min and 10 min). All amino acids were dissolved in NMP (DMF was added when the amino acid was not soluble in pure NMP). The concentration of the amino acid was 0.25M, and the concentrations for HOBt and DIC respectively were 0.5 M.

For a 0.04 mmol Scale Synthesis:

A typical amino acid coupling cycle (not including wash steps) was to dispense piperidine solution (2.4 mL) to each well and mix for 4 min, then empty all wells. NMP (320 µL), HOBt solution (320 µL, 4 eq), amino acid (640 µL, 4 eq) and DIC (320 µL, 4 eq) solutions were dispensed to each well. The coupling time was 3 h; then the resin was washed. The cycle was repeated for each amino acid. After the last amino acid coupling, the resin-bound peptide was treated with 25% piperidine to remove the Fmoc protecting group. After washing, the resin bound peptide was capped with 1.0M $Ac_2O$ (1.2 mL per well) and diisopropylethylamine in DMF, optionally including varying amounts of HOBt in the mixture for 30 min. The resin was washed with methanol and then dichloromethane and dried. Cleavage of the peptides from the resin and side-chain deprotection was accomplished using Reagent B for 4.5 h. The cleavage solutions were collected and the resins were washed with an additional aliquot of Reagent B. The combined solutions were concentrated to dryness. Ether was added to the residue with swirling or stirring to precipitate the peptides. The ether was decanted, and solid was collected. This procedure was repeated 2-3 times to remove impurities. The crude linear peptides were dissolved in DMSO and water mixtures, and purified by HPLC (column: Waters Associates Xterra C18, 19×50 mm; solvents: $H_2O$ with 0.1% TFA and $CH_3CN$ with 0.1% TFA; UV 220 µm; Flow rate: 50-60 mL/min) The solutions containing the peptide were lyophilized to give the desired peptides as white fluff lyophilizates (>90% purity). The purified linear di-cysteine containing peptides were dissolved in water, mixtures of water-acetonitrile, or mixtures of water-DMSO at concentrations between 0.1 mW/mL and 2.0 mg/mL. The choice of solvent was a function of the solubility of the crude peptide in the solvent. The pH of the solution was adjusted to pH 7.5-8.5 with aqueous ammonia, aqueous ammonium carbonate or aqueous ammonium bicarbonate. The mixture was stirred vigorously in air for 24-48 hrs. In the case of non-DMSO containing solvent systems, the pH of the solution was adjusted to pH 2 with aqueous trifluoroacetic acid. The mixture was lyophilized to provide the crude cyclic disulfide containing peptide. The cyclic disulfide peptide was then dissolved to a volume of 1-2 mL in aqueous (0.1% TEA) containing a minimum of acetonitrile (0.1% TFA). The resulting solution was loaded onto a reverse phase column and the desired compound obtained by a gent elution of acetonitrile into water, employing a C18, or C8 reverse phase semi-preparative or preparative HPLC column. In the case of the DMSO-containing solutions, the solution was diluted until the DMSO concentration was minimal without precipitation of the peptide. The resulting mixture was quickly acidified to pH 2 with dilute trifluoroacetic acid and loaded onto the reverse phase HPLC system and purified as described. Fractions containing the desired materials were pooled and the peptides isolated by lyophilization.

Method 2 for the ACT 357 MPS and ACT 496 MOS Synthesizers

The peptides were synthesized as in Method 1 with the following changes. HBTU/HOBt/DIEA were used as the coupling reagent and NMP as the solvent. A low load (~0.2 mmol/g) Fmoc-GGGK(Boc)-NovSyn-TGR-resin-prepared from the above-described Nova-Syn TGR resin was employed for peptide synthesis on 0.01 mmol scale. For a 0.01 mmol scale synthesis:

After the Fmoc group was removed, a standard coupling procedure used a solution of HOBt (720 µl, 6 eq), amino acid (804 µl, 6.6 eq), HBTU (720 µl, 6 eq) and DIEA (798 µl, 13.3 eq). The mixture was agitated for 15 min., emptied and the resin washed. After all couplings and after cleavage and purification as above, the solutions containing desired linear peptides were lyophilized to give the peptides (>90% purity) as white fluffy solids. The crude ether-precipitated linear di-cysteine containing peptides were cyclized by dissolution in water, mixtures of aqueous acetonitrile (0.1% TFA), or aqueous DMSO and adjustment of the pH of the solution to pH 7.5-8.5 by addition of aqueous ammonia, aqueous ammonium carbonate, or aqueous ammonium bicarbonate solution. The peptide concentration was between 0.1 and 2.0 mg/mL. The mixture was stirred in air for 24-48 hrs., acidified to a pH 2 with aqueous trifluoroacetic acid, and then purified by preparative reverse phase HPLC employing a gradient of acetonitrile into water. Fractions containing the desired material were pooled and the peptides were isolated by lyophilization.

Method 3 for the ACT 496 MOS Synthesizer

The peptides were synthesized by using an Advanced ChemTech ACT 496 MOS Synthesizer as in method 1. The low load (~0.2 mmol/g) GGGK(Boc)-NovaSyn-TGR resin was employed for peptide synthesis. The coupling solvent was NMP/DMSO 8:2. The synthesis was performed at a 0.02 mmol scale using a coupling time of 3 h. The crude linear peptides were further processed as described for Method 1.

Method 4 for the ACT 496 MOS Synthesizer

The peptides were synthesized using method 3 on the ACT 496 with HBTU/DIEA as the coupling reagents, and NMP as the solvent. 2,4,6-collidine as a 1 M solution was used as the base. The low load Fmoc-GGGK(ivDde)-Novsyn-TGR resin (~0.2 mmol/g) was used for peptide synthesis. The coupling time was 30 minutes. The crude linear peptides were further processed as described for Method 1.

Method 5 for the ABI 433A Synthesizer

Synthesis of peptides was carried out on a 0.25 mmol scale using the FastMoc protocol (Applied Biosystems Inc). In each cycle of this protocol, 1.0 mmol of a dry protected amino acid in a cartridge was dissolved in a solution of 0.9 mmol of HBTU, 2 mmol of DIEA, and 0.9 mmol of HOBt in DM with additional NMP added. The peptides were made using 0.1 mmol of NovaSyn TGR (Rink amide) resin (resin substitution 0.2 mmol/g). The coupling time in this protocol was 21 min. Fmoc deprotection was carried out with 20% piperidine in NMP. At the end of the last cycle, the synthesized peptide was acetylated using acetic anhydride/DIEA/HOBt/NMP. The peptide resin was washed and dried for further manipulations or cleaved from the resin (using reagent B). Generally, the cleaved peptides were cyclized as in Method 1 before purification.

Method 6

Biotinylation of Resin-Bound Peptides

The peptides were prepared using Method 5. The ivDde protecting group on the C-terminal lysine was selectively removed by treatment with 10% hydrazine in DMF. The resin was then treated with a solution of Biotin-N-hydroxysuccinimidyl ester in DMF in the presence of DIEA. After washing, the resin was dried and cleavage was performed using Reagent B. The resin was filtered off and the filtrate concentrated to dryness. The biotinylated peptide was dissolved in neat DMSO and treated with DIEA and stirred for 4-6 hours to effect disulfide cyclization. The crude mixture was purified by preparative HPLC.

In a typical experiment, 200 mg of the resin -bound peptide was treated with 10% hydrazine in DMF (2×20 mL) and washed with DMF (2×20 mL) and then with dichloromethane (1×20 mL). The resin was resuspended in DMF (10 mL) and treated with a solution of Biotin-NHS ester (0.2 mmol, 5 equivalents) and DIEA (0.2 mmol), and the resin was mixed with the reagents for 4 h. The completion of the reaction was checked by the ninhydrin test. The peptide was then released from the resin by treatment with Reagent B (10 mL) for 4 h. The resin was filtered off, Reagent B was removed in vacuo and the peptide was precipitated by addition of anhydrous ether. The solid formed was collected, washed with ether and dried. The solid was dissolved in anhydrous DMSO and the mixture was adjusted to pH 7.5 with DIEA and stirred for 4-6 h to effect disulfide cyclization. The disulfide cyclization reaction was monitored by analytical HPLC. After completion of the cyclization, the mixture solution was diluted with 25% acetonitrile in water and directly purified by HPLC on a reverse phase C18 column using a gradient of acetonitrile into water (both containing 0.1% TEA). Fractions were analyzed by analytical HPLC and those containing the pure product were collected and lyophilized to obtain the required biotinylated peptide.

Method 7

Biotinylation of Purified Peptides

The purified peptide (10 mg, prepared by methods 1-5) containing a free amino group was dissolved in anhydrous DMF or DMSO (1 mL) and Biotin-NHS ester (5 equivalents) and DIEA (5 equivalents) were added. The reaction was monitored by HPLC and after the completion of the reaction (1-2 h.), the crude reaction mixture was directly purified by preparative HPLC. Fractions were analyzed by analytical HPLC, and those containing the pure product were collected and lyophilized to obtain the required biotinylated peptide.

Method 8

Biotinylation of Resin-Bound Peptides Containing Linkers

In a typical experiment, 400 mg of the resin- containing peptide (made using the ABI 433A Synthesizer and bearing an ivDde-protected lysine) was treated with 10% hydrazine in DMF (2×20 mL). The resin was washed with DMF (2×20 mL) and DCM (1×20 mL). The resin was resuspended in DMF (10 mL) and treated with Fmoc-aminodioxaoctanoic acid (0.4 Mmol), HOBt (0.4 mmol), DIC (0.4 mmol), DIEA (0.8 mmol) with mixing for 4 h. After the reaction, the resin was washed with DMF (2×10 mL) and with DCM (1×10 mL). The resin was then treated with 20% piperidine in DMF (2×15 µL) for 10 min. each time. The resin was washed and the coupling with Fmoc-diaminodioxaoctanoic acid and removal of the Fmoc protecting group were repeated once more. The resulting resin, containing a peptide with a free amino group, was treated with a solution of Biotin-NHS ester (0.4 mmol, 5 equivalents) and DIEA (0.4 mmol, 5 equivalents) in DMF for 2 hours. The peptide-resin was washed and dried as described previously and then treated with reagent B (20 mL) for 4 h. The mixture was filtered, and the filtrate concentrated to dryness. The residue was stirred with ether to produce a solid that was collected, washed with ether and dried. The solid was dissolved in anhydrous DMSO and the pH adjusted to 7.5 with DIEA. The mixture was stirred for 4-6 hr to effect the disulfide cyclization reaction, which was monitored by analytical HPLC. After the completion of the cyclization, the DMSO solution was diluted with 25% acetonitrile in water and applied directly to a reverse phase C-18 column. Purification was effected using a gradient of acetonitrile into water (both containing 0.1% TFA). Fractions were analyzed by analytical HPLC, and those containing the pure product were collected and lyophilized to provide the required biotinylated peptide.

Method 9

Formation of 5-Carboxyfluorescein-Labeled Peptides

Peptide-resin obtained via Method 5 containing an ivDde protecting group on the epsilon nitrogen of lysine, was mixed with a solution of hydrazine in DMF (10% hydrazine/DMF, 2×10 mL, 10 min) to remove the ivDde group. The epsilon nitrogen of the lysine was labeled with fluorescein-5-isothiocyanate (0.12 mmol) and diisopropylethylamine (0.12 mmol) in DMF . The mixture was agitated for 12 h (fluorescein-containing compounds were protected from light). The resin was then washed with DMF (3×10 ml) and twice with $CH_2Cl_2$ (10 mL) and dried under nitrogen for 1 h. The peptide was cleaved from the resin using reagent B for 4 h and the solution collected by filtration. The volatiles were removed under reduced pressure, and the residue was dried under vacuum. The peptide was precipitated with ether, collected and the precipitate was dried under a stream of nitrogen. The precipitate was added to water (1 mg/mL) and the pH of the mixture was adjusted to 8 with 10% aqueous meglumine. Cyclization of the peptide was carried out for 48 h and the solution was freeze-dried. The crude cyclic peptide was dissolved in water and purified by RP-HPLC on a $C_{18}$ column with a linear gradient of acetonitrile into water (both phases contained 0.1% TFA). Fractions containing the pure product were collected and freeze-dried. The peptides were characterized by ES-MS and the purity was determined by RP-HPLC (linear gradient of acetonitrile into water/0.1% TEA).

Method 10A

Preparation of Peptidic Chelate for Binding to Tc by Coupling of Single Amino Acids Peptides were synthesized starting with 0.1 mmol of NovaSyn-TGR resin (0.2 mmol/g substitution). Deprotected (ivDde) resin was then treated according to the protocol A for the incorporation of Fmoc-Gly-OH, Fmoc-Cys(Acm)-OH and Fmoc-Ser(tBu)-OH.

Protocol A for Manual Coupling of Single Amino Acid:
1. Treat with 4 equivalents of corresponding Fmoc-amino acid and 4.1 equivalents of HOBt and 4.1 equivalents of DIC for 5 h.
2. Wash with DMF (3×10 mL)
3. Treat with 20% piperidine in DMF (2×10 mL, 10 min.)
4. Wash with DMF (3×10 µl)

The Fmoc-protected peptide loaded resin was then treated with 20% piperidine in DMF (2×10 mL, 10 min.) and washed with DMF (3×10 mL). A solution of N,N-dimethylglycine (0.11 mmol), HATU (1 mmol), and DIEA (0.11 mmol) in DMF (10 mL) was then added to the peptide loaded resin and the manual coupling was continued for 5 h. After the reaction the resin was washed with DMF (3×10 mL) and $CH_2Cl_2$ (3×10 nm) and dried under vacuum.

Method 10B

Figure 86:
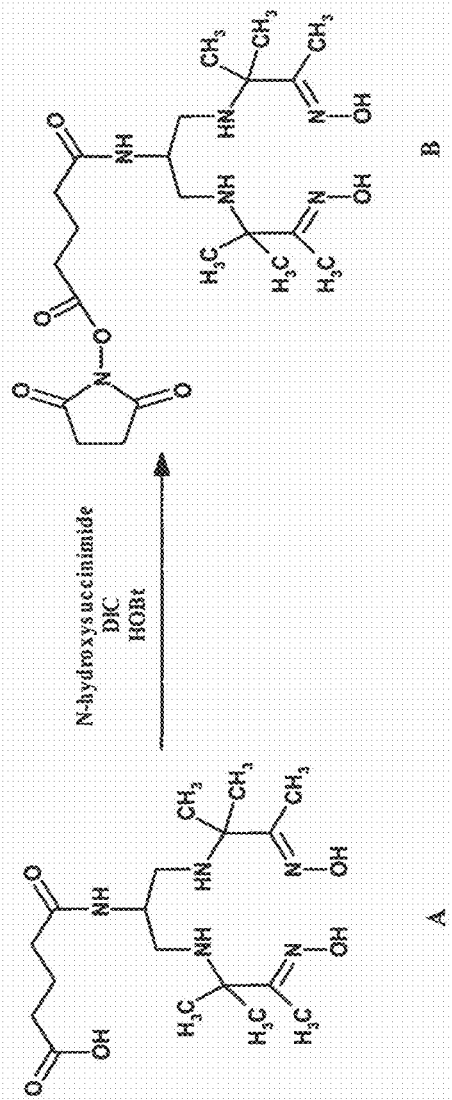
FIG. 86 is a schematic representation of the synthesis scheme used to prepare 4-{2-(2-Hydroxyimino-1,1-dimethylpropylamino)-1-[(2-hydroxyimino-1,1-dimethylpropylamino)-methyl]-ethylcarbamoyl}-butyric acid, N-hydroxysuccimide ester (Compound B) using 4-{2-(2-Hydroxyimino-1,1-dimethyl-propylamino)-1-[(2-hydroxyimino-1,1-dimethyl-propylamino)-methyl]-ethylcarbamoyl}-butyric acid as a starting reagent.

Preparation of Peptidic Chelate for Binding to Tc by Appendage of the Glutaryl-PnAO6 Chelator to the Peptide Preparation of 4-{2-(2-Hydroxyimino-1,1-dimethyl-propylamino)-1-[(2-hydroxyimino-1,1-dimethyl-propylamino)-methyl]-ethylcarbamoyl}-butyric acid, N-hydroxysuccinimide ester (Compound B, FIG. 86).

4-{2-(2-Hydroxyimino-1,1-dimethyl-propylamino)-1-[(2-hydroxyimino-1,1-dimethyl-propylamino)-methyl]-ethylcarbamoyl}-butyric acid (Compound A. FIG. 86) (40 mg) was dissolved in DMF (700 µL). N-Hydroxysuccinimide (1.5 equiv, 17.2 mg) and 1,3-diisopropylcarbodiimide (1.5 equiv, 24 µL) were added. The progress of the reaction was monitored by mass spectroscopy. After 17 h, the reaction was complete. The volatiles were removed in vacuo and the residue was washed with ether (5×) to remove the unreacted NHS. The residue was dried to provide compound B, which was used directly without further treatment or purification. See FIG. 86 for reaction scheme.

Functionalization of Peptides with 4-{2-(2-Hydroxyimino-1,1-dimethylpropylamino)-1-[(2-hydroxyimino-1,1-dimethyl-propylamino)-methyl]-ethylcarbamoyl}-butyric acid, N-hydroxsuccinimide ester (Compound B)

The peptide (prepared, for example, by Methods 1-13) is dissolved in DMF and treated with compound B and DIEA sufficient to maintain the basicity of the mixture. The progress of the reaction is monitored by HPLC and mass spectroscopy. At completion of the reaction the volatiles are removed in vacuo and the residue is either purified by reverse phase HPLC or processed further by selective removal of side chain protecting groups or subjected to cleavage of all remaining protecting groups as required by the next steps in the synthesis scheme.

Method 11

Formation of Mercaptoacetylated Peptides Using S-Acetylthioglycolic acid N-Hydroxysuccinimide Ester S-acetylthioglycolic acid N-hydroxysuccinimide ester (SATA) (0.0055 mmol) was added to a solution of a peptide (0.005 mmol, obtained from Methods 1-5 with a free amine) in DMF (0.25 mL) and the reaction mixture was stirred at ambient temperature for 6 h. The volatiles were removed under vacuum and the residue was purified by preparative HPLC using acetonitrile-water containing 0.1% TFA. Fractions containing the pure product were collected and freeze-dried to yield the mercaptoacetylated peptide. The mercaptoacetylated peptide was characterized by ESI-MS and the purity was determined by reverse phase HPLC analysis employing a linear gradient of acetonitrile into water (both containing 0.1% TA).

Examples of SATA-modified peptides include, but are not limited to:

```
SATA-modified SEQ ID NO: 480
Ac-AGPTWCEDDWYYCWLFGTGGGGK(SATA-JJ)-NH2

SATA-modified SEQ ID NO: 356
Ac-AQDWYYDEILSMADQLRHAFLSGGGGCK(SATA)-NH2

SATA-modified SEQ ID NO: 356
Ac-AQDWYYDEILSMADQLRHAFLSGGGGK(SATA-JJ)-NH2
```

Method 12

Formation of Mercaptoacetylated Peptides Using S-Acetylthioglycolic Acid

Purified peptides from method 5, after disulfide cyclization, was coupled with S-acetylthioglycolic acid (0.5-10 eq.)/HOBt (1.5-10 eq.)/DIC (1.5-10 eq.) in NMP for 2-16 hours at room temperature. The mixture was then purified by preparative HPLC; the factions containing pure peptide were combined and lyophilized. In the case of compounds with another lysine protected by an ivDde group, the deprotection reaction employed 2% hydrazine in DMSO for 3 h at room temperature. Purification of the reaction mixture afforded pure peptide.

In the case when preparing a compound with S-acetylthioglycolic acid coupled to two aminodioxaoctanoic acid groups and the peptide, the purified peptide from method 5 (having a free amino group), was coupled to AcSCH$_2$CO—(NH—CH$_2$—CH$_2$—O—CH$_2$—CH$_2$—O—CH$_2$—CO)$_2$—OH (30 eq.)/HOBt (30 eq.)/DIC (30 eq.) in NMP for 40 hours at room temperature. The mixture was purified, and the ivDde group was removed. A second purification gave the final product as a white lyophilizate.

Alternatively Fmoc aminodioxaoctanoic acid was coupled twice successively to the peptide (produced by method 5) followed by Fmoc removal and coupling to S-acetylthioglycolic acid.

Method 13

Preparation of Homodimers and Heterodimers

The required purified peptides were prepared by SPPS using Method 5. To prepare homodimers, half of the peptide needed to prepare the dimer was dissolved in DMF and treated with 10 equivalents of glutaric acid bis N-hydroxysuccinimidyl ester. The progress of the reaction was monitored by HPLC analysis and mass spectroscopy. At completion of the reaction, the volatiles were removed in vacuo and the residue was washed with ethyl acetate to remove unreacted bis-NHS ester. The residue was dried, re-dissolved in anhydrous DMF and treated with another half portion of the peptide in the presence of 2 equivalents of DIEA. The reaction was allowed to proceed for 24 h. This mixture was applied directly to a Waters Associates C-18 XTerra reverse phase HPLC column and purified by elution with a linear gradient of acetonitrile into water (both containing 0.1% TFA).

In the case of heterodimers, one of the monomers was reacted with the bis NHS ester of glutaric acid and after washing off the excess of bis NHS ester, the second peptide was added in the presence of DIEA After the reaction, the mixture was purified by preparative HPLC.

Example 1

Library Screening Against KDR and KDR/VEGF Complex Targets

Chimeric fusions of Ig Fc region with human KDR (#357-KD-05), murine KDR (#443-KD-050), human VEGFR-1 (#321-FL-050), human VEGFR-3 (#349-F4-050), and human Trail R4 (#633-TR-100) were purchased in carrier-free form (no BSA) from R & D Systems (Minneapolis, Minn.). Trail R4 Fc is an irrelevant Fc fusion protein with the same Fc fusion region as the target Fc fusion (KDR Fc) and is used to deplete the libraries of Fe binders. VEGF$_{165}$ (#100-20) was purchased in carrier-free form from Peprotech (Rocky Hill, N.J.). Protein A Magnetic Beads (#100.02) were purchased from Dynal (Oslo, Norway). Heparin (#H-3393) was purchased from Sigma Chemical Company (St. Louis, Mo.). A 2-component tetramethyl benzidine (TMB) system was purchased from KPL (Gaithersburg, Md.).

In the following procedures, microtiter plates were washed with a Bio-Tek 404 plate washer (Winooski, Vt.). ELISA signals were read with a Bio-Tek plate reader (Winooski, Vt.). Agitation of 96-well plates was on a LabQuake shaker (Lab-industries, Berkeley, Calif.).

Eight M13 phage display libraries were prepared for screening against immobilized KDR and VEGF/KDR targets: Cyclic peptide display libraries TN6/VI, TN7/IV, TN8/IX, TN9/IV, TN10/IX, TN12/I, and MTN13/I, and a linear display library, Lin20. The design of these libraries has been described, supra.

The DNA encoding the library was synthesized with constant DNA on either side so that the DNA can be PCR amplified using Taq DNA polymerase (Perkin-Elmer, Wellesley, Mass.), cleaved with NcoI and PstI and ligated to similarly cleaved phage display vector. XL1-Blue MFR' *E. coli* cells were transformed with the ligated DNA. All of the libraries were constructed in same manner.

KDR Selection Protocol in the Presence of Heparin

Protein A Magnetic Beads were blocked once with 1×PBS (pH 7.5), 0.01% Tween-20, 0.1% HSA (Blocking Buffer) for 30 minutes at room temperature and then washed five times with 1×PBS (pH 7.5), 0.01% Tween-20, 5 μg/m heparin (PBSTH Buffer).

The cyclic peptide, or "constrained loop", libraries were pooled for the initial screening into two pools: TN6/VI, TN7/IV and TN8/IX were in one pool; TN9/IV, TN10/IX and TN12/I were in the second pool. The two pooled libraries and the linear library (Lin20) were depleted against Trail R4 Fc fusion (an irrelevant Fc fusion) and then selected against KDR Fc fusion. $10^{11}$ plaque forming units (pfu) from each library per 100 μL PBSTH were pooled together, e.g., 3 pooled libraries would result in a total volume of ~350 μl in PBSTH.

To prepare the irrelevant Fc fusion beads, 500 μl of Trail R4-Fc fusion (0.1 μg/μl stock in PBST (no heparin)) were added to 1000 μl of washed, blocked protein A magnetic beads. The fusion was allowed to bind to the beads overnight with agitation at 4° C., The next day, the magnetic beads were washed 5 times with PBSTH. Each phage pool was incubated with 50 μl of Trail R4 Fe fusion beads on a Labquake shaker for 1 hour at room temperature (RT). After incubation, the phage supernatant was removed and incubated with another 50 μL of Trail R4 beads. This was repeated for a total of 5 rounds of depletion, to remove non-specific FP fusion and bead binding phage from the libraries.

To prepare the KDR target beads, 500 μl of KDR-Fc fusion (0.1 μg/μl stock in to PBST (no heparin)) were added to 500 μL of washed, blocked beads. The KDR-Fc fusion was allowed to bind overnight with agitation at 4° C. The next day, the beads were washed 5 times with PBSTH. Each depleted library pool was added to 100 μL of KDR-Fc beads and allowed to incubate on a LabQuake shaker for 1 hour at RT. Beads were then washed as rapidly as possible with 5×1 mL PBSTH using a magnetic stand (Promega) to separate the beads from the wash buffer. Phage still bound to beads after the washing were eluted once with 250 μl of VEGF (50 μg/mL, ~1 μM) in PBSTH for 1 hour at RT on a LabQuake shaker. The 1-hour elution was removed and saved. After the first elution, the beads were incubated again with 250 μl of VEGF (50 μg/mL, ~1 μM) overnight at RT on a LabQuake shaker. The two VEGF elutions were kept separate and a small aliquot taken from each for titering. Each elution was mixed with an aliquot of XL1-Blue MRF' (or other F' cell line) E. coli cells that had been chilled on ice after having been grown to mid-logarithmic phase. The remaining beads after VEGF elution were also mixed with cells to amplify the phage still bound to the beads, i.e., KDR-binding phage that had not been competed off by the two VEGF incubations (1-hour and overnight (O/N) elutions). After approximately 15 minutes at room temperature, the phage/cell mixtures were spread onto bio-Assay Dishes (243×243×18 mm, Nalge Nunc) containing 250 mL of NZCYM agar with 50 μg/mL of ampicillin. The plate was incubated overnight at 37° C. The next day, each amplified phage culture was harvested from its respective plate. Over the next day, the input, output and amplified phage cultures were tied for FOI (i.e., Fraction of Input=phage output divided by phage input).

In the first round, each pool yielded three amplified eluates. These eluates were panned for 2-3 more additional rounds of selection using ~$10^{10}$ input phage/round according to the same protocol as described above. For each additional round, the KDR-Fc beads were prepared the night before the round was initiated. For the elution step in subsequent rounds, the amplified elution re-screen on KDR-Fc beads was always eluted in the same manner, and all other elutions were treated as washes. For example, for the amplified elution recovered by using the still-bound beads to infect E. coli, the 1-hour and overnight VEGF elutions were performed and then discarded as washes. Then the beads were used to again infect E. coli and produce the next round amplified elution. Using this procedure, each library pool only yielded three final elutions at the end of the selection. Two pools and one linear library, therefore, yielded a total of 9 final elutions at the end of the selection.

This selection procedure was repeated for all libraries in the absence of heparin in all binding buffers, i.e., substituting PBST (PBS (pH 7.5), 0.01% Tween-20) for PBSTH in all steps.

KDR Selection Protocol in the Absence of Heparin

A true TN11/1 library was used to screen for KDR binders. The same selection protocol as above (KDR Selection Protocol in the Presence of Heparin) was used, except heparin was omitted. The three elution conditions were VEGF elation (1 uM; 1 hr; same as original protocol), Dimer D6 elution (0.1 uM; 1 hr), and then bead elution (same as above). TN11/1 alone was used in the selection and screening. For selected peptides, see Table 27 and Consensus Sequence 9A.

KDR:VEGF Complex Selection Protocol in the Presence of Heparin

Protein A magnetic beads were blocked once with Blocking Buffer for 30 minutes at room temperature and then washed five times with PBSTH.

Two pools of constrained loop libraries and a linear library (Lin20) were prepared as before and ten depleted against KDR Fc fusion alone, instead of Trail-R4 Fc fusion, to remove binders to the receptor without bound VEGF. Once depleted, the libraries were selected against the KDR:$VEGF_{165}$ complex.

To prepare KDR-Fc fusion depletion beads, 1 mL of KDR-Fc fusion (0.1 μg/μL stock in PBST (no heparin)) was added to 1 mL of washed, blocked beads. The fusion was allowed to bind overnight with agitation at 4° C. The next day, the beads were washed 5 times with PBSTH. Each phage pool was incubated with 50 μl of KDR-Fc fusion beads on a LabQuake shaker for 1 hour at RT. After incubation, the phage supernatant was removed and incubated with another 50 μl of KDR-Fc beads. This was repeated for a total of 5 rounds of depletion.

To prepare the KDR:VEGF complex beads, 300 μL of KDR-Fc fusion beads from above were incubated with 15 μL of VEGF (1 mg/mL). VEGF was allowed to bind for 1 hour at RT. The beads were washed 5 times with PBSTH. Each depleted library pool was added to 100 M of KDR:VEGF complex beads and allowed to incubate on a LabQuake shaker for 1 hour at RT. Beads were then washed as rapidly as possible with 5×1 mL PBSTH using a magnetic stand (Promega) to separate the beads from the wash buffer. To elute the phage still bound after washing, the beads were mixed with cells to amplify the phage still bound to the beads. After approximately 15 minutes at room temperature, the phage/cell mixtures were spread onto Bio-Assay Dishes (243×243×18 nm, Nalge Nunc) containing 250 mL of NZCYM agar with 50 μg/mL of ampicillin. The plate was incubated overnight at 37° C. The next day, each amplified phage culture was harvested from its respective plate. Over the next day, the input, output and amplified phage cultures were titered for FOI. This selection protocol was repeated for two additional rounds using $10^{10}$ input phage from each amplified elution.

KDR and KDR/VEGF Screening Assay

100 µl of KDR-Fc fusion or Trail R4-Fc fusion (1 µg/mL) were added to duplicate Immulon II plates, to every well, and allowed to incubate at 4° C. overnight. Each plate was washed twice with PBST PBS, 0.05% Tween-20). The wells were filled to the top with 1×PBS, 1% BSA and allowed to incubate at RT for 2 hours. Each plate was washed once with PBST (PBS, 0.05% Tween-20).

To assess binding to KDR:VEGF complex, another set of KDR plates was prepared as above and then 100 µl of VEGF (1 µg/mL) in PBST was added to each KDR well and allowed to incubate at RT for 30 minutes. Each plate was then washed with PBST (PBS, 0.05% Tween-20).

Once the plates were prepared, each overnight phage culture was diluted 1:1 (or to $10^{10}$ pfu if using purified phage stock) with PBS, 0.05% Tween-20, 1% BSA. 100 µl of each diluted culture was added and allowed to incubate at RT for 2-3 hours. Each plate was washed 5 times with PBST. The binding phage were visualized by adding 100 µl of a 1:10,000 dilution of HRP-anti-M13 antibody conjugate (Pharmacia), diluted in PBST, to each well, then incubating at room temperature for 1 hr. Each plate was washed 7 times with PBST (PBS, 0.05% Tween-20), then the plates were developed with Imp substrate (~10 minutes) and the absorbance signal (630 nm) detected with plate reader.

KDR and VEGF/KDR complex binding phage were recovered, amplified, and the sequences of the display peptides responsible for the binding were determined by standard DNA sequencing methods. The binding peptides of the phage isolates are set forth in Tables 1-7, infra.

After isolation of KDR and VEGF/KDR complex isolates in initial selection rounds, certain isolates were selected to act as templates for the construction of secondary libraries, from which additional high affinity binding polypeptides were isolated. In a secondary TN8 library, the phage isolate sequence PKWCEEDWYYCMIT (SEQ ID NO:21) was used as a template to construct a library that allowed one-, two-, and three-base mutations to the parent sequence at each variable codon. In a secondary TN12 library, the phage isolate sequence SRVCWEDSWGGEVCFRY (SEQ ID NO:88) was used as a template to construct a library that allowed one-, two-, and three-base mutations to the parent sequence at each variable codon. In a another TN8 secondary library, a recurrent motif from the initial TN8 sequences was kept constant (WVEC-TG-C-; SEQ ID NO:260) and all of the other codon positions (i.e., at "-") were allowed to vary (all possible 20 amino acids) using NNK codon substitution, where N stands for any nucleotide and K stands for any keto nucleotide (0 or T).

Using a method of peptide optimization by soft randomization as described by Fairbrother et al., *Biochemistry*, 37(51):17754-17764 (1998), two libraries were prepared based on the SEQ ID NO:21 and SEQ ID NO:88 sequences. At each residue position, each nucleotide within a particular codon was allowed to evolve by adding fixed amounts of the other three nucleotides that did not correspond to the nucleotide of the parent codon. This nucleotide mixing is accomplished in the synthesis of the template DNA used to make the library. For these libraries, the parent nucleotide within each codon was maintained at 64% for SEQ ID NO:21 and 67% for SEQ ID NO:885 whereas the other nucleotides were added at the remainder frequency divided by three. Since the parent nucleotides are in the majority, the overall consensus sequence for the whole library should still contain the parental sequence. Inspection of individual isolates, however, shows that multiple mutations are possible, thus allowing selection of peptides with improved binding ability compared to the parent sequence.

For the third library, the TN8 motif described above was kept constant and all of the other positions in were allowed to vary with NNK substitution in the template oligonucleotide, To extend the substitution, NNK diversity was also permitted in the two flanking amino acid positions, thus adding variable amino acid positions N-terminal and C-terminal to the display peptide. The secondary library template, therefore, encoded a display peptide of the following sequence: Xaa-Xaa-Trp-Val-Glu-Cys-Xaa-Xaa-Xaa-Thr-Gly-Xaa-Cys-Xaa-Xaa-Xaa-Xaa-Xaa (SEQ ID NO:261), where Xaa can be any amino acid. Unlike the previous two libraries, where the consensus sequence remains the parental sequence this library was quite diverse in all allowed positions and only resembled the parent motif in the residues that were held constant.

A total of $2 \times 10^{11}$ pfu from each library was used as before, except the elution strategy was changed. Competition elution of bound phage was performed using the parental peptide (50 µM) that was used to make the particular secondary library (i.e., peptides of SEQ ID NOS:21, 88, and 40, respectively). Binding phage were eluted through three steps: (1) elution for 1 hour at room temperature, the eluted phage being used to infect cells for amplification, (2) elution overnight, wherein fresh competition elution peptide was added to the bound phage and incubated at 4° C. overnight with mixing, the eluted phage being then used to infect cells for amplification, and (3) the remaining beads (bearing undated binding phage) were used to infect cells directly. Three rounds of selections were performed. Plaques were picked from rounds 2 and 3 and analyzed by ELISA and sequencing. KDR positive isolates were assayed further for competition with 50 µM free parent peptide. Those peptides that showed minimal competition with the parent peptide were deemed higher affinity binders and were synthesized These sequences are listed in the following table as SEQ ID NOS:22-33 for the TN8 secondary library and SEQ ID NOS:89-95 for the TN12 secondary library.

TABLE 1

TN8/IXLibrary Isolates

| Sequence | SEQ ID NO: | Elutlon | Class |
|---|---|---|---|
| DSWCSTEYTYCEMI | 20 | 1 HR | NA |
| PKWCEEDWYYCMIT | 21 | 1 HR | (III) |
| SDWCRVDWYYCWLM | 22 | O/N | III |
| ANWCEEDWYYCFIT | 23 | O/N | III |
| ANWCEEDWYYCWIT | 24 | O/N | III |
| PDWCEEDWYYCWIT | 25 | O/N | III |
| SNWCEEDNYYCYIT | 26 | O/N | HI |
| PDWCAADWYYCYIT | 27 | O/N | III |
| PEWCEVDWYYCWLL | 28 | CELL | III |
| PTWCEDDWYYCWLF | 29 | O/N | III |
| SKWCEQDWYYCWLL | 30 | CELL | III |
| RNWCEEDWYYCFIT | 31 | O/N | III |
| VNWCEEDWYYCWIT | 32 | O/N | III |
| ANWCEEDWYYCYIT | 33 | O/N | III |

TABLE 1-continued

TN8/IX Library Isolates

| Sequence | SEQ ID NO: | Elution | Class |
|---|---|---|---|
| VWECAKTFPFCHWF | 34 | 1 HR | I |
| VTVCYEGTRTCEWH | 35 | 1 HR | NA |
| WVECRYSTGLCINY | 36 | O/N | NA |
| WYWCDYYGIGCKWT | 37 | 1 HR | NA |
| WVECWWKSGQCYEF | 38 | 1 HR, CELL | (II) |
| WIQCDMETGLCTHG | 39 | 1 HR, CELL | II |
| WVECFMDTGACYTF | 40 | CELL, O/N | II |
| WLECYAEFGHCYNF | 41 | CELL, O/N | II |
| WIECDMLTQMCKHG | 42 | CELL | NA |
| SVECFMDTGACYTF | 43 | CELL | I |
| WIQCNSITGHCTSG | 44 | CELL | II |
| WIECYHPDGICYHF | 45 | CELL | (III) |
| QAWVECYAETGYCWPRSW | 46 | NA | NA |
| VGWVECYQSTGFCYHSRD | 47 | NA | NA |
| FTWVECHQATGRCVEWTT | 48 | NA | NA |
| DWWVECRVGTGLCYRYDT | 49 | NA | NA |
| DSWVECDAQTGFCYSFLY | 50 | NA | NA |
| GGWVECYWATGRCIEFAG | 51 | NA | NA |
| ERWVECRAETGFCYTWVS | 52 | NA | NA |
| GGWVECRAETCHCQEYRL | 53 | NA | NA |
| VAWVECYQTTGKCYTFRG | 54 | NA | NA |
| EGWVECFANTGACFTYPR | 55 | NA | NA |
| GVECYKHSGMCRSW | 56 | O/N | II |
| GVWCDMVTGWCYHG | 57 | CELL | II |
| WIECHYKTGHCIHS | 58 | CELL | II |
| DFNCKMIDGFCLLK | 59 | 1 HR | II |
| WIQCDRKAGRCSRG | 60 | CELL | II |
| TITCWMDTGHCMHE | 61 | CELL | II |
| GINCYPATGKCQMG | 62 | CELL | II |
| WTECHYATGKCHSF | 63 | CELL | II |
| LNICKEDWYYCFLL | 64 | 1 HR | I/III |
| GITCYSATGKCQMW | 65 | CELL | II |
| WVQCASDTGKCIMG | 66 | CELL | II |
| TGNCQEDWYYCWYF | 67 | CELL | II |
| KELCEDDWYYCYLM | 68 | 1 HR | I/III |
| HWECYSDTGKCWFF | 69 | O/N | II |
| GITCYSDTGKCFSF | 70 | CELL | II |
| AVTCWALTGECVEE | 71 | O/N | II |

TABLE 1-continued

TN8/IX Library Isolates

| Sequence | SEQ ID NO: | Elution | Class |
|---|---|---|---|
| YVDCYYDTGRCYHQ | 72 | CELL | II |
| WYWCQYHGVCPQS* | 73 | 1 HR | I/III |
| LVMCISPEGYCYEI | 74 | O/N | II |
| LIECYAHTGLCFDF | 75 | O/N | II |
| HWWCAFQPQECEYW | 76 | 1 HR | III |
| HYECNYPEGKCYFY | 77 | CELL | II |
| WYWCHHIGMYCDGF | 78 | 1 HR | III |
| WEWCPIDAWECIML | 79 | 1 HR | II |
| WLECYTEFGECYNF | 80 | 1 HR | II |
| WVECWWKYCQCYEF | 81 | 1 HR | II |
| PNTCETFDLYCWWI | 82 | 1 HR | II |
| WIICDGNLGWCWEG | 83 | O/N | II |
| GEQCSNLAVACCST | 84 | O/N | II |
| WVECYDPWGWCWEW | 85 | CELL | NA |
| WYWCMHYGLGCPYR | 86 | CELL | NA |

TABLE 2

TN12/I Library Isolates*

| Sequence | SEQ ID NO: | Elution | Class |
|---|---|---|---|
| YPWCHELSDSVTRFCVPW | 87 | 1 HR | (III) |
| SRVCWEDSWGGEVCFRY | 88 | 1 HR | (III) |
| SRVGWEYSWGGEVCYRV | 89 | O/N | III |
| FGECWEYFWGGEFCLRV | 90 | CELL | III |
| WRICWESSWGGEVCIGH | 91 | CELL | III |
| YGVCWEYSWGGEVCLRF | 92 | CELL | III |
| SSVCFEYSWGGEVCFRY | 93 | CELL | III |
| SRVCWEYSWGGQICLGY | 94 | CELL | III |
| FSVCWEYSWGGEVCLRQ | 95 | CELL | III |
| DHMCRSPDYODHVFCMYW | 96 | CELL | (II) |
| PPLCYFVGTQEWHHCNPF | 97 | CELL | (II) |
| WWECKREEYRNTTWCAWA | 98 | CELL | II |
| DSYCMMNEKGWNNCYLY | 99 | CELL | NA |
| PAQCWESNYQCIFFCDNP | 100 | CELL | II? |
| GSWCEMRQCVGKWNCFSD | 101 | CELL | II |
| GWACAKWPWGGEICQPS | 102 | CELL | (II) |
| ASTCVFHDHPYFPMCQDN | 103 | CELL | I/III |
| PDTCTMWGDSGRWYCFPA | 104 | CELL | (II) |
| NWKCEYTQGYDYTECVYL | 105 | O/N | II |

TABLE 2-continued

TN12/I Library Isolates*

| Sequence | SEQ ID NO: | Elution | Class |
|---|---|---|---|
| NWECGWSNMFQKEFCARP | 106 | 1 HR | (III) |
| SGYCEFESDTGRWFCSSW | 107 | O/N | II |
| GGWCQLVDHSWWWCGDS | 108 | O/N | II |
| DNWCEIVVEKQQWFCYGS | 109 | O/N | II |
| YPGCYETSLSGVWFCADG | 110 | CELL | II |
| GWCQMDAQGIWSCWAD | 111 | 1 HR | II |
| DRWCMLDQEKGWWLCGPP | 112 | CELL | II |
| NSECGCPNMLHKEFCARH | 113 | 1 HR | I/III |
| PFWCKFQQSKAMFPCSWF | 114 | 1 HR | II |
| YPWCHEHSDSVTRFCVPW | 115 | 1 HR | III |
| SDLCYNQSGWWELCYFD | 116 | O/N | I/II? |
| LGYCMYDYENRGNTCYPP | 117 | O/N | II |
| YYQCQRYWDCKTWWCEYN | 118 | 1 HR | I/III |
| DSWCELEHQSGIWRCDFW | 119 | CELL | II |
| DWACDEYWSAYSVLCKHP | 120 | CELL | II |
| LSLCYNDMHGWWEHCQWY | 121 | CELL | II |
| YSHCIETSMENIWFCDFD | 122 | CELL | II |
| PPFCIYQEPSGQWWCYDH | 123 | CELL | II |
| PGWCDFSPQLGQWMCDWF | 124 | CELL | II |
| LDNCIWNVWKGVQDCEYS | 125 | O/N | II |
| AGWCEYVAPQGAWRCFHN | 126 | CELL | II |
| WDDCIWHMWLKKKDCNSG | 127 | O/N | II |
| PGHCEYIWIDEQPWCVRL | 128 | CELL | III |
| YSDCLFQLWKGSVCPPS | 129 | CELL | II |
| YFFCSFADVAYESCHPL | 130 | CELL | NA |
| NYMCESEDHTYMFPCWWY | 131 | CELL | NA |
| DAVCYNPWPKYWETCEYN | 132 | CELL | NA |
| NYMCEYEDHTYMLTCECN | 133 | CELL | NA |
| WDDCIYSMWNVHTVCDR | 134 | CELL | NA |
| NWKCDAHQEGRIHICWGY | 135 | CELL | NA |
| NGSCWYDFGWETEICFHN | 136 | CELL | II |

TABLE 3

Lin20 Library Isolates*

| Sequence | SEQ ID NO: | Elution | Class |
|---|---|---|---|
| QVQYQFFLGTPRYEQWDLDK | 137 | CELL | II |
| EPEGYAYWEVITLYEEEDGD | 138 | CELL | (II) |
| WYYDWFHNQRKPPSDWIDNL | 139 | 1 HR | III |
| AFPRFGGDDYWIQQYLRYTD | 140 | 1 HR | (III) |
| GDYVYWEIIELTGATDHTPP | 141 | O/N | (III) |
| RGDYQEQYWHQQLVEQLKLL | 142 | 1 HR | (III) |
| RSWYLGPPYYEEIIDPIPN | 143 | CELL | II |
| PSNSWAAVWEDDMQRLMRQH | 144 | CELL | II |
| PRLGDDFEEAPPLEWWWAHF | 145 | CELL | II |
| MPPGFSYWEQVVLHDDAQVL | 146 | CELL | II |
| KKEDAQQYWTDYVPSYLYR | 147 | 1 HR | III? |
| WVTKQQFIDTYGRKEWTILF | 148 | CELL | II |
| WLYDYWDRQQKSEEFKFWSQ | 149 | 1 HR | III |
| PVTDWTPHHPKAPDVWLFYT | 150 | 1 HR | III? |
| EWYWTEEVGMKHGPFV | 151 | 1 HR | I/III |
| DALEAPKRDWYYDWFLNHSP | 152 | 1 HR | III |
| PDNWKEFYESGWKYPSLYKPL | 153 | 1 HR | NA |
| EWAQYWHDLRQQYMLDYIQ | 154 | 1 HR | I/III |
| AFEIEYWDSVRNKIWQHFPD | 155 | 1 HR | I/III |
| AFPRFGGDDYWIQOYLRYTF | 158 | 1 HR | I/III |
| AHMPPWRPVAVDALFDWVE | 157 | CELL | NA |
| AHMPPWWPLAVDAQEDWFE | 158 | CELL | NA |
| AQMPPWWPLAVDALFDWFE | 159 | CELL | II |
| ARMGPDWEEAPPHEWGWADG | 160 | CELL | II |
| DWYWQRERDKLREHYDDAFW | 161 | 1 HR | I/III |
| DWYWREWMPMHAQFLADDW | 162 | 1 HR | I/III |
| DWYYDEILSMADQLRHAFLS | 163 | 1 HR | III |
| EEQQALYPGCEPAEHWVYAG | 164 | 1 HR | III |
| FDVVNWGDGIWYAYPS | 165 | CELL | II |
| FPSQMWQQKVSHHFFQHKGY | 166 | CELL | II |
| GSDHVRVDNYWWNGMAWEIF | 167 | 1 HR | II |
| ISPWREMSGWGMPWITAVPH | 168 | 1 HR | I/III |
| LEEVFEDFQDFWYTEHIIVDR | 169 | 1 HR | II |
| MPPGFSYWEQAALHDDAQDL | 170 | CELL | II |
| PEDSEAWYWLNYRPTMFHQL | 171 | 1 HR | I/III? |
| QIEYVNDKWYWTGGYWNVPF | 172 | 1 HR | II |
| QVQYQFILGTPRYEQWDPDK | 173 | CELL | II |
| RDEWGWTGVPYECEMGYQIS | 174 | 1 HR | II |
| STNGDSFVYWEEVELVDHPY | 175 | O/N | II |
| SYEQWLPQYWAQYKSNYFL | 176 | 1 HR | I/III? |

TABLE 3-continued

Lin20 Library Isolates*

| Sequence | SEQ ID NO: | Elution | Class |
|---|---|---|---|
| TKWGPNPEEWQYWYSHYASS | 177 | 1 HR | I/III? |
| VSKGSIDVCEGISYWEIIEL | 178 | 1 HR | III |
| WESDYWDQMRQQLKTAYMKV | 179 | 1 HR | I/III |
| WYHDGLHNERKPPSHWIDNV | 180 | 1 HR | III |
| APAWTFGTNWRSIQRVDSLT | 181 | CELL | NA |
| EGWFRNPQEIMGFGDSWDKP | 182 | CELL | NA |
| GWDLSVNRDKRWFWPWSSRE | 183 | CELL | NA |
| KSGVDAVGWHIPVWLKKYWF | 184 | CELL | NA |
| GMDLYQYWASDDYWGRHQEL | 185 | CELL | NA |
| GVDIWHYWKSSTRYFHQ | 186 | CELL | NA |

TABLE 4

TN7/IV Library Isolates

| Sequence | SEQ ID NO: | Elution | Class |
|---|---|---|---|
| GVECNHMGLCVSW | 187 | CELL | II |
| GITCDELGRCVHW | 188 | CELL | II |
| WIQCNHQGQCFHG | 189 | CELL | II |
| WIECNKDGKCWHY | 190 | CELL | II |
| WVECNHKGLCREY | 191 | CELL | II |
| WYWCEFYGVCSEE | 192 | 1 HR | I/III |

TABLE 5

TN9/IV Library Isolates

| Sequence | SEQ ID NO: | Elution | Class |
|---|---|---|---|
| IDFCKGMAPWLCADM | 193 | 1 HR | (III) |
| PWTCWLEDHLACAML | 194 | CELL | II |
| DWGCSLGNWYWCSTE | 195 | CELL | NA |
| MPWCSEVTWGWCKLN | 196 | CELL | II |
| RGPCSGQPWHLCYYQ | 197 | O/N | II |
| PWGCDHFGWAWCKGM | 198 | O/N | NA |
| MPWCVEKDHWDCWWW | 199 | CELL | NA |
| PGPCKGYMPHQCWYM | 200 | CELL | NA |
| YGPCAEMSPWLCWYP | 201 | CELL | NA |
| YGPCKNMPPWMCWHE | 202 | CELL | NA |
| GHPCKGMLPHTCWYE | 203 | CELL | NA |

TABLE 6

TN10/IX Library Isolates

| Sequence | SEQ ID NO: | Elution | Class |
|---|---|---|---|
| NNSCWLSTTLGSCFFD | 204 | O/N | NA |
| DHHCYLHNGQWICYPF | 205 | CELL | (III) |
| NSHCYIWDGMWLCFPD | 206 | CELL | (II) |

TABLE 7

MTNI3/I Library Isolates

| Sequence | SEQ ID NO: | Elution | Class |
|---|---|---|---|
| SNKCDHYQSGPHGKICVNY | 207 | CELL | NA |
| SNKCDHYQSGPYGEVCFNY | 208 | CELL | NA |
| RLDCDKVFSGPYGKVCVSY | 209 | CELL | NA |
| RLDCDKVFSQPDTSCGSQ | 210 | CELL | NA |
| RLDCDKVFSGPHGKICVRY | 211 | CELL | NA |
| RLDCDKVFSGPHGKICVNY | 212 | CELL | NA |
| RVDCDKVISGPHGKICVNY | 213 | CELL | NA |
| RTTCHHQISGPHGKICVNY | 214 | CELL | NA |
| EFHCHHIMSGPHGKICVNY | 215 | CELL | NA |
| HNRCDFKMSQPHGKICVNY | 216 | CELL | NA |
| WQECTKVLSGPGTFECSYE | 217 | CELL | NA |
| WQECTKVLSGPGQFSCVYG | 218 | CELL | NA |
| WQECTKVLSGPGQFECEYM | 219 | CELL | NA |
| WQECTKVLSGPWSFECKYD | 220 | CELL | NA |
| WDRCERQISGPGQFSCVYG | 221 | CELL | NA |
| WQECTKVLSGPGQFLCSYG | 222 | CELL | NA |
| RLDCDMVFSCPRGKICVNY | 223 | CELL | NA |
| KRCDTTHSGPHGIVCVVY | 224 | CELL | NA |
| SNKCDHYQSGPYGAVCLHY | 225 | CELL | NA |
| SPHCQYKISGPFGPVCVNY | 226 | CELL | NA |
| AHQCHHWTSGPYGEVCFNY | 227 | CELL | NA |
| YDKCSSRFSGPFGEICVNY | 228 | CELL | NA |
| MGGCDFSFSGPFGQICGRY | 229 | CELL | NA |
| RTTCHHQISGPFGDVCVSY | 230 | CELL | NA |
| WYRCDFNMSGPDFTECLYP | 231 | CELL | NA |
| WMQCNMSASGPKDMYCEYD | 232 | CELL | NA |
| GISCKWIWSGPDRWKCHHF | 233 | CELL | NA |
| WQVCKPYVSGPAAESCKYE | 234 | CELL | NA |
| GWWCYRNDSGPKPFHCRIK | 235 | CELL | NA |
| EGWCWFIDSGPWKTWCEKQ | 230 | CELL | NA |
| FPKCKFDFSGPPWYQCNTK | 237 | CELL | NA |

TABLE 7-continued

MTNI3/I Library Isolates

| Sequence | SEQ ID NO: | Elution | Class |
|---|---|---|---|
| RLDCDKVFSGPYGRVCVKY | 238 | CELL | NA |
| RLDCDKVFSGPYGNVCVNY | 239 | CELL | NA |
| RLDCDKVFSGPSMGTCKLQ | 240 | CELL | NA |
| RTTCHHHISGPHGKICVNY | 241 | CELL | NA |
| QFGCEHIMSGPHGKICVNY | 242 | CELL | NA |
| PVHCSHTISGPHGKICVNY | 243 | CELL | NA |
| SVTCHFQMSGPHCKICVNY | 244 | CELL | NA |
| PRGCQHMISGPHGKICVNY | 245 | CELL | NA |
| RTTCHHQISGPHGQICVNY | 246 | CELL | NA |
| WTICHMELSGPHGKICVNY | 247 | CELL | NA |
| FITCALWLSGPHGKICVNY | 248 | CELL | NA |
| MGGCDFSFSGPHGKICVNY | 249 | CELL | NA |
| KDWCHTTFSGPHGKICVNY | 250 | CELL | NA |
| AWGCDNMMSGPHGKICVNY | 251 | CELL | NA |
| SNKCDHIMSGPHGKICVNY | 252 | CELL | NA |
| SNKCDHYQSCPFGDICVMY | 253 | CELL | NA |
| SNKCDHYQSGPFGDVCVSY | 254 | CELL | NA |
| SNKCDHYQSGPFGDICVSY | 255 | CELL | NA |
| RTTCHHQISGPFGPVCVNY | 256 | CELL | NA |
| RTTCHHQISGPYGDICVKY | 257 | CELL | NA |
| PHGKICVNYGSESADPSYIE | 258 | CELL | NA |
| RYKCPRDLSGPPYOPCSPQ | 259 | CELL | NA |

TABLE 27

TN11/1 Library Isolates

| Sequence | SEQ ID NO | Elution | # of isolates |
|---|---|---|---|
| GSNNVCMDDSYGGTTCYSMAP | 505 | D6 | 107 |
| GSYNQCYGDYWGGETCYLIAP | 506 | Bead | 93 |
| GSRVNCGAEDGLSFLCMMDAP | 507 | Bead | 40 |
| GSIWDCQISEYGGEDCYLVAP | 508 | D6 | 29 |
| GSYWHCMDDFFGGETCFATAP | 509 | D6 | 28 |
| GSGEYCFPSIYGGETCYAHAP | 510 | D6 | 24 |
| GSEQLCFEYQYGGOVECFGPAP | 511 | D6 | 21 |
| GSTGVCSPAPYGGEVCYHFAP | 512 | D6 | 20 |
| GSHDECWEDIYGGFTCMLMAP | 513 | D6 | 19 |
| GSQHTCFSDPYGGEVCYADAP | 514 | D6 | 18 |
| GSWEVCENSNYGGQICYWFAP | 515 | D6 | 18 |

TABLE 27-continued

TN11/1 Library Isolates

| Sequence | SEQ ID NO | Elution | # of isolates |
|---|---|---|---|
| GSHEMCWSDVWGGLTCMTMAP | 516 | D6 | 15 |
| GSLSLCKFFGDGSYYCEPPAP | 517 | D6 | 14 |
| GSTRFCEPYQWGGEVCYWKAP | 518 | D6 | 14 |
| GSFSTCATFPWTTKFCSNMAP | 519 | VEGF | 12 |
| GSHELCFEGTYGGEVCFSMAP | 520 | D6 | 12 |
| GSLWHCFNDVYGGENCIPFAP | 521 | VEGF | 12 |
| GSOQYCIPAEYGGMECYPFAP | 522 | Bead | 11 |
| GSIQNCWKYEFGGIVCMDMAP | 523 | D6 | 9 |
| GSVSGCKEFWNSSGRCFTHAP | 524 | D6 | 9 |
| GSLWECRGDFYGGEVCFNYAP | 525 | D6 | 8 |
| GSNLICYDYYYCCQDCYHDAP | 526 | D6 | 8 |
| GSEGTCEEYQYGGIVCWWGAP | 527 | D6 | 7 |
| PGSGDCDWYYEWLFDCPLNAP | 528 | VEGF | 7 |
| GSDQMCFNESFGGQICFYSAP | 529 | VEGF | 6 |
| GSGMACMSDPYGGQVCYAIAP | 530 | D6 | 5 |
| GSELTCWDSAYGGNECPFFAP | 531 | VEGF | 4 |
| GSHFLCVKEMEGGETCYYSAP | 532 | VEGF | 4 |
| GSWEICFAGPYGGSWCIPEAP | 533 | Bead | 4 |
| GSAQYCMESYYGGFTCVTLAP | 534 | Bead | 3 |
| GSFNACGFEEGLEWNCYRQAP | 535 | D6 | 3 |
| GSKLLCQYWEHEWWPCMNEAP | 536 | VEGF | 3 |
| GSNMNCGAEQGLESLCGWRAP | 537 | VEGF | 3 |
| GSNWVCLSEGYGGMTCYPSAP | 538 | VEGF | 3 |
| GSPSTCIYSSGLIVDCGLLAP | 539 | VEGF | 3 |
| GSTQHCWPSEYGGMTCVPAAP | 540 | D6/VEGF | 3 |
| GSTWACEEISAHHTKCTYQAP | 541 | VEGF/Bead | 3 |
| GSYTECWEEDYGGVTCFNVAP | 542 | Bead | 3 |
| GSDKFCFKDPWGGVTCYHLAP | 543 | D6 | 2 |
| GSDLDCWTDPYGGEVCYWHAP | 544 | D6 | 2 |
| GSDYECYNAWFGYFDCPGDAP | 545 | VEGF/Bead | 2 |
| GSLSTCWKQAYGGVWCVDHAP | 546 | VEGF | 2 |
| GSMQLCRQWAYGGQTCYWYAP | 547 | D6 | 2 |
| GSNQLCITAQFGGQDCYPIAP | 548 | VEGF | 2 |
| GSPMWCAPWPWGGEHCVGSAP | 549 | VEGF | 2 |
| GSQLLCGSEPELAWMCEQGAP | 550 | VEGF | 2 |
| GSQRQCWDDYFGGIICYVIDA | 551 | VEGF | 2 |
| GSREVCWQDFFGGMVCVRDAP | 552 | Bead | 2 |

TABLE 27-continued

TN11/1 Library Isolates

| Sequence | SEQ ID NO | Elution | # of isolates |
|---|---|---|---|
| GSSQWCQRDFWGGDICINLAP | 553 | VEGF | 2 |
| GSTDICWPGSYGGEICIPRAP | 554 | VEGF | 2 |
| GSTEYCWPEPHGGQACILLAP | 555 | VEGF | 2 |
| GSTHFCIDYIWGGKHCIADAP | 556 | VEGF | 2 |
| GSTMMCWPAHYGGDECFALAP | 557 | VEGF | 2 |
| GSTQMCFPHQYGGQSCYSFAP | 558 | VEGF | 2 |
| GSVEGCWVEDQTSPPCWIDAP | 559 | VEGF | 2 |
| GSWYTCWDEASGGQVCYQLAP | 560 | VEGF | 2 |
| GSYNLCYPEIYGGQVCYRMAP | 561 | D6 | 2 |
| GSYSQCFPDPFGGTTCFVSAP | 562 | D6 | 2 |
| GSSMQCFNRVSQLVDCETAAP | 563 | VEGF | 2 |
| GSAKYCRSYWAQSGYCYEYAP | 564 | D6 | 1 |
| GSAQTCWDYVYGGFFCLNTAP | 565 | VEGF | 1 |
| GSAWDCFQQDTYSTHCHWRAP | 566 | VEGF | 1 |
| GSAWNCEMLDPWSTQCSWDAP | 567 | VEGF | 1 |
| GSAWVCHPEQEGGTTCYWVAP | 568 | VEGF | 1 |
| GSDELCWPQEFGGWVCIQGAP | 569 | Bead | 1 |
| GSDFQCFNWEGYPTNCYSNAP | 570 | D6 | 1 |
| GSDKKCWPSPYGGQICWAVAP | 571 | VEGF | 1 |
| GSDQLCFDQRWGGQVCVFGAP | 572 | VEGF | 1 |
| GSDSGCKEFWNSSDRCYTHAP | 573 | D6 | 1 |
| GSEWICWSSFFGGETCTPKAP | 574 | VEGF | 1 |
| GSEWNCLNNTPYQTTCSWRAP | 575 | Bead | 1 |
| GSEWRCWPDVFGGQMCFNMAP | 576 | VEGF | 1 |
| GSEYECYPDWYGGEVCVQKAP | 577 | VEGF | 1 |
| GSFEACWEEAYGGLTCWHDAP | 578 | D6 | 1 |
| GSFEECMPYRYGGQTCFMIAP | 579 | D6 | 1 |
| GSFWTCVDTNWHTTECFMSAP | 580 | VEGF | 1 |
| GSGQMCWHGQYGGTICVAMAP | 581 | VEGF | 1 |
| GSGWVCKQQGPHKTECLFMAP | 582 | VEGF | 1 |
| GSEDECWEDIYGGFTCMPYGS | 583 | D6 | 1 |
| GSHVVCWDDPYGGESCYNTAP | 584 | VEGF | 1 |
| GSIDICTDSYWGGITCYKFAP | 585 | D6 | 1 |
| GSKWICVDVKWGGSACYDIAP | 586 | VEGF | 1 |
| GSLWECRIDYYGGEVCFIDAP | 587 | VEGF | 1 |
| GSLWTCVLSVYGGEDCYNLAP | 588 | VEGF | 1 |
| GSMTMCGAEPDLWYMCYGIAP | 589 | VEGF | 1 |
| GSNQYCMPYDWGGEMCFEVAP | 590 | D6 | 1 |
| GSNVFCSEGPFGGEICYGIAP | 591 | VEGF | 1 |
| GSNWACFIEAMGGWTCAPRPT | 592 | VEGF | 1 |
| GSNWTCFIDSFQGETCYPFAP | 593 | VEGF | 1 |
| GSNWWCHSEAFGGHTCYNAAP | 594 | VEGF | 1 |
| GSPCACNNSYGHSDDCDHLAP | 595 | VEGF | 1 |
| GSPGNCKDFWAWSLQCFSFAP | 596 | VEGF | 1 |
| GSPRWCYFSSGIMFWCDILAF | 597 | VEGF | 1 |
| GSPTYCQFHSGVVTLCSMFAP | 598 | VEGF | 1 |
| GSQEICFNSQYGGQVCFDSAP | 599 | D6 | 1 |
| GSQMICYPHVFGGQDCFPGAP | 600 | VEGF | 1 |
| GSQWTCTELSDVMTHCSYTAP | 601 | VEGF | 1 |
| GSRVNCGAEDDLSFLCMTEAP | 602 | VEGF | 1 |
| GSSGDCIEMYNDWYYCTTLAP | 603 | Bead | 1 |
| GSSWECGEFGDTTIQCNWVAP | 604 | VEGF | 1 |
| GSSWQCFSEAPSGATCVPIAP | 605 | VEGF | 1 |
| GSSWQCVQVDDFHTECSFMAP | 606 | VEQF | 1 |
| GSSWTCVFYPYGGEVCIPDAP | 607 | D6 | 1 |
| GSTELCVPYQWGGEVCVAQAP | 608 | D6 | 1 |
| GSTVYCHNEYFGGQVCFTIAP | 609 | VEGF | 1 |
| GSTYGCEYYMPFQHKCSVEAP | 610 | VEGE | 1 |
| GSWWGCFPYSWGGEICTSIAP | 611 | D6 | 1 |
| GSWWNCVDTSFHTTQCKYAAP | 612 | VEGF | 1 |
| GSYFMCQDGFWGGQDCFYIAP | 613 | VEGF | 1 |
| GSYMWCTESKFGGSTCFNLAP | 614 | VEGF | 1 |
| GSGAYSHLLEYHAVCKNVAP | 615 | VEGF | 1 |
| PGSWTCQNYEPWATTCVYDAP | 616 | VEGF | 1 |

*During the course of DNA synthesis, there is always a small percentage of incomplete couplings at each cycle. Since the libraries used for these experiments were constructed using TRIM technology to couple trinucleotides (codons) instead of nucleotides, the library template DNA often has a small percentage of deleted codons. In the case of the TN12 library, for instance, it has been observed that approximately 5.3% of the total library is phage expressing a cyclic 11-mer, rather than a 12-mer and indeed some phage expressing 11-mers were isolated in the selections described above (see Table 2).

In the foregoing tables, Class I peptides only bind KDR in the absence of heparin and therefore presumably target the heparin binding domain of KDR; Class II peptides bind in the presence or absence of heparin or VEGF, and therefore presumably bind at a non-involved site on KDR; Class III peptides exhibit binding characteristics that are not affected by heparin but are perturbed in the presence of VEGF, and therefore presumably these bind either to VGF or the VEGF binding domain of KDR. NA signifies data not available. In the elution column, 1 HR, O/N, and Cell stand for 1 hour VEGF, overnight VEGF, and bead infection elutions, respectively. In some cases, a particular isolate sequence was observed in two different elutions. For the isolates identified by second generation library, VEGF elutions were substituted with peptide elutions (see below).

Example 2

Peptide Synthesis and Fluorescein Labeling

Selected KDR or VEGF/KDR complex binding peptides corresponding to positive phage isolates were synthesized on solid phase using 9-fluorenylmethoxycarbonyl protocols and purified by reverse phase chromatography. Peptide masses were confirmed by electrospray mass spectrometry, and peptides were quantified by absorbance at 280 nm. For synthesis, two N-terminal and two C-terminal amino acids from the phage vector sequence from which the peptide was excised were retained, and a -Gly-Gly-Gly-Lys-NH$_2$ linker (SEQ ID NO:262) was added to the C-terminus of each peptide. Each peptide was N-terminally acetylated. For peptides with selected lysine residues, these were protected with 1-(4,4-dimethyl-2,6-dioxocyclohex-1-ylidene)-3-methylbutyl (ivDde), which allows selective coupling to the C-terminal lysine, is not removed during peptide cleavage, and can be removed after coupling with 2% hydrazine in DMF or 0.5 M hydroxylamine, pH 8, in water.

Each peptide was labeled with fluorescein on the C-terminal lysine using fluorescein (N-hydroxysuccinimide ester derivative) or fluorescein isothiocyanate (FITC) in DMF, 2% diisopropylethylamine (DIPEA). If the peptide contained an ivDde protected lysine, the reaction was quenched by the addition of 2% hydrazine, which reacts with all free NHS-fluorescein and removes the internal protecting group. For all other peptides, the reaction was quenched by the addition of an equal volume of 0.5 M hydroxylamine, pH 8. The quenched reactions were then diluted with water to less than 10% DMF and then purified using C18 reverse phase chromatography. The peptides were characterized for purity and correct mass on an LC-MS system (BP 1100 HPLC with in-line SCIEX AP150 single quadrapole mass spectrometer).

Example 3

Fluorescence Anisotropy Measurements and BiaCore Assays

Fluorescence anisotropy measurements were performed in 384-well microplates in a volume of 10 µl in binding buffer (PBS, 0.01% Tween-20, pH 7.5) using a Tecan Polarion fluorescence polarization plate reader. In some cases, heparin (0.5 µg/mL) or 10% human serum was added to the binding buffer (data not shown). The concentration of fluorescein labeled peptide was held constant (20 nM) and the concentration of KDR-Fc (or similar target) was varied. Binding mixtures were equilibrated for 10 minutes in the microplate at 30° C. before measurement. The observed change in anisotropy was fit to the equation below via nonlinear regression to obtain the apparent K$_D$. This equation (1) assumes that the synthetic peptide and KDR form a reversible complex in solution with 1:1 stoichiometry.

$$r_{obs} = r_{free} + (r_{bound} - r_{free}) \frac{(K_D + KDR + P) - \sqrt{(K_D + KDR + P)^2 - 4 \cdot KDR \cdot P}}{2 \cdot P}, \quad (1)$$

where $r_{obs}$ is the observed anisotropy, $r_{free}$ is the anisotropy of the free peptide, $r_{bound}$ is the anisotropy of the bound peptide, $K_D$ is the apparent dissociation constant, KDR is the total KDR concentration, and P is the total fluorescein-labeled peptide concentration. $K_D$ was calculated in a direct binding assay ($K_{D,B}$) (see Table 8), and therefore these values represent KDR binding to the fluorescein labeled peptide.

For BiaCore determinations of $K_D$, KDR-Fc (or other protein targets) was cross-linked to the dextran surface of a CM5 sensor chip by the standard amine coupling procedure (0.5 mg/nm solutions diluted 1:20 with 50 mM acetate, pH 6.0, R$_L$ KDR-Fc=12859). Experiments were performed in HBS-P buffer (0.01 M HEPES, pH 7.4, 0.15 M NaCl, 0.005% polysorbate 20 (v/v)). Peptide solutions quantitated by extinction coefficient were diluted to 400 nM in HBS-P. Serial dilutions were performed to produce 200, 100, 50, and 25 nM solutions. For association, peptides were injected at 20 µl/min. for 1 minute using the kinject program. Following a 1-minute dissociation, any remaining peptide was stripped from the target surface with a quick injection of 1M NaCl for 25 sec. at 50 µl/min. All samples were injected in duplicate. Between each peptide series a buffer injection and a non-target binding peptide injection served as additional controls. Sensorgrams were analyzed using the simultaneous $k_a/k_d$ fitting program in the BIAevaluation software 3.1. Apparent $K_D$ by is method is set forth as BiaK$_D$ in Table 8. Unlike the fluorescence anisotropy experiments above, the unlabeled peptide was used for all testing using this assay and therefore, these values represent KDR binding to the unlabeled peptide. Binding affinities determined for the synthesized polypeptides are set forth in Table 8, below. The putative disulfide-constrained cyclic peptide moieties of the polypeptides are in bold.

TABLE 8

Binding Affinities for Synthesized Peptides

| Sequence | K$_{D,B}$ (µM) | BiaK$_D$ (µM) | SEQ ID NO: |
|---|---|---|---|
| TN8 | | | |
| AGDSWCSTEYTYCEMIGTGGGK | >2 | | 263 |
| AGPKWCEEDWYYCMITGTGGGK | 0.28 | 0.027 | 264 |
| AGVWECAKTFPFCHWFGTGGGK | 2.60 | | 265 |
| AGWVECWWKSGQCYEFGTGGGK | 1.3 | | 266 |
| AGWLECYAEFGHCYNFGTGGGK | >10 | | 267 |
| AGWIQCNSITGHCTSGGTGGGK | 0.24 | | 268 |
| AGWIECYHPDGICYHFGTGGGK | 0.32 | 0.32 | 269 |
| AGSDWCRVDWYYCWLMGTGGGK | 0.064 | | 270 |
| AGANWCEEDWYYCFITGTGGGK | 0.310 | | 271 |
| AGANWCEEDWYYCWITGPGGGK | 0.097 | | 272 |
| AGPDWCEEDWYYCWITGTGGGK | 0.075 | | 273 |
| AGSNWCEEDWYYCYITGTGGGK | 0.046 | | 274 |
| AGPDWCAADWYYCYITGTGGGK | 0.057 | | 275 |
| AGPEWCEVDWYYCWLLGTGGGK | 0.075 | | 276 |
| AGPTWCEDDWYYCWLFGTGGGK | 0.0032 | 0.079 | 277 |
| AGSKWCEQDWYYCWLLGTGGGK | 0.400 | | 278 |
| AGRNWCEEDWYYCFITGTGGGK | 0.190 | | 279 |
| AGVNWCEEDWYYCWITGTGGGK | 0.260 | | 280 |
| AGANWCEEDWYYCYITGTGGGK | 0.180 | | 281 |
| AGQAWVECYAETGYCWPRSWGTGGGK | 0.71 | | 282 |
| AGQAWIECYAEDGYCWPRSWGTGGGK | 1.40 | | 283 |

TABLE 8-continued

Binding Affinities for Synthesized Peptides

| Sequence | $K_{D,B}$ (µM) | Bia$K_D$ (µM) | SEQ ID NO: |
|---|---|---|---|
| AGVGWVECYQSTGFCYHSRDGTGGGK | 1.30 | | 284 |
| AGFTWVECHqATGRCVEWTTGTGGGK | 2.00 | | 285 |
| AGDNWVECRVGTGLCYRYDTGTGGGK | 0.93 | | 286 |
| AGDSWVECDAQTGFCYSFLYGTGGGK | 2.30 | | 287 |
| AGGGWVECYWATGRCIEFAGGTGGGK | NB | | 288 |
| AGERWVECRAETGFCYTWVSGTGGGK | 2.10 | | 289 |
| AGGGWVECRAETGHCQEYRLGTGGGK | 1.60 | | 290 |
| AGVAWVECYQTTGKCYTFRGGTGGGK | ~2 | | 291 |
| AGEGWVECFANTGACFTYPRGTGGGK | 2.10 | | 292 |

TN12

| | | | |
|---|---|---|---|
| GDYPWCHELSDSVTRFCVPWDPGGGK | 0.98 | 0.18 | 293 |
| GDSRVCWEDSWGGEVCFRYDPGGGK | 0.069 | 0.12 | 294 |
| GDDHMCRSPDYQDHVFCMYWDPGGGK | 0.48 | 0.14 | 295 |
| GDPPLCYFVGTQEWHHCNPFDPGGGK | 0.60 | | 296 |
| GDDSYCMMNEKGWWNCYLYDPGGGK | 1.3 | | 297 |
| GDPAQCWESNYQGIFFCDNPDPGGGK | 2.3 | | 298 |
| GDGSWCEMRQDVGKWNCFSDDPGGGK | 0.62 | 0.18 | 299 |
| GDGWACAKWPWGGEICQPSDPGGGK | 1.0 | 1.5 | 300 |
| GDPDTCTMWGDSGRWYCFPADPGGGK | 0.49 | 0.26 | 301 |
| GDNWKCEYTQGYDYTECVYLDPGGGK | 0.82 | | 302 |
| GDNWECGWSNMFQKEFCARPDPGGGK | 0.21 | 0.99 | 303 |
| GDWWECKREEYRNTTWCAWADPGGGK | | | 486 |
| GDSSVCFEYSWGGEVCFRYDPGGGK | 0.058 | | 487 |
| GDSRVCWEYSWGGQICLGYDPGGGK | 0.32 | | 488 |

Lin20

| | | | |
|---|---|---|---|
| AQQVQYQFFLGTPRYEQWDLDKGGK | 1.7 | | 304 |
| AQEPEGYAYWEVITLYHEEDGDGGK | 0.27 | 0.73 | 305 |
| AQAFPRFGGDDYWIQQYLRYTDGGK | 0.53 | 0.25 | 306 |
| AQGDYVYWEIIELTGATDHTPPGGK | 0.18 | | 307 |
| AQRGDYQEQYWHQQLVEQLKLLGGK | 0.31 | 5.3 | 308 |
| AQRSWYLGPPYYEEWDPIPNGGK | 1.8 | | 309 |
| AQDWYYDEILSMADQLRHAFLSGGGK | | 0.05 | 310 |

TN9

| | | | |
|---|---|---|---|
| AGIDFCKGMAPWLCADMGTGGGK | 0.73 | 0.18 | 311 |
| AGPWTCWLRDHLACAMLGTGGGK | 3.9 | | 312 |
| AGDWGCSLGNWYWCSTEGTGGGK | 2.0 | | 313 |

TN10

| | | | |
|---|---|---|---|
| GSDHHCYLHNGQWICYPFAPGGGK | 0.26 | 0.15 | 314 |
| GSNSHCYIWDGHWLCFPDAPGGGK | 0.74 | | 315 |

MTN13

| | | | |
|---|---|---|---|
| SGRLDCDKVFSGPYGKVCVSYGSGGGK | 1.05 | | 316 |
| SGRLDCDKVFSGPHGKICVNYGSGGGK | ~2 | | 317 |
| SGRTTCHHQISGPHGKICVNYGSGGGK | 0.65 | | 318 |
| SGAHQCHHWTSGPYGEVCFNYGSGGGK | ~2 | | 319 |

For the analysis of those peptides that bind specifically to KDR/VEGF complex, each peptide was tested for binding to the complex in both assays (fluorescence anisotropy/Biacore) as above. In the anisotropy assay, KDR-VEGF complex was formed by mixing together a two fold molar excess of VEGF with KDR-Fc. This mixture was then used in the direct binding titration using a fluorescein labeled peptide as done previously. As a control, each peptide was also tested for binding to KDR and VEGF alone to assess their specificity for complex, Since none of the peptides bound VEGF to any extent, the presence of excess VEGF in the assay should not affect the $K_D$ determination. As shown in Table 9, below, all of the peptides showed a dramatic, binding preference, binding for KDR/VEGF complex over VEGF. Some of them, however, did show some residual binding to free KDR. To confirm the anisotropy results, the unlabeled peptides were tested in Biacore as before, except the chip was saturated with VEGF to form KDR/VEGF complex prior to the injection of the peptides. In the peptides tested, the Bia$K_D$ was within at least 2-fold of the anisotropy measurement.

TABLE 9

KDR/VEGF Complex Specific Peptides

| SEQ ID NO: Sequence | $K_D$, B (KDR) | $K_D$, B (VEGF) | $K_D$, B (KDR/ VEGF) | Bia$K_D$ (KDR/ VEGF) |
|---|---|---|---|---|
| 320 AGMPWCVEKDHWDCWWWGTGGGK | NB | 10 | 0.14 | |
| 321 AGPGPCKGYMPHQCWYMGTGGGK | 0.4 | NB | 0.06 | 0.08 |
| 322 AGYGPCAEMSPWLCWYPGTGGGK | 3.7 | NB | 0.13 | |
| 323 AGYGPCKNMPPWMCWHEGTGGGK | 1.8 | NB | 0.18 | 0.42 |
| 324 AGGHPCKGMLPHTCWYEGTGGGK | >10 | NB | 3.3 | |
| 325 AQAPAWTFGTNWRSIQRVDSLTGGGGK | NB | NB | 0.84 | |
| 326 AQEGWFRNPQEIMGFGDSWDKPGGGGGK | NB | NB | 1.4 | |

The putative disulfide-constrained cyclic peptide moiety is underscored.

Example 4

Preparation of KDR and VEGF/KDR Complex Binding Polypeptides

Utilizing the methods set forth above, biotinylated versions the KDR and VEGF/KDR complex binding polypeptides set forth in Table 10 were prepared. The letter "J" in the peptide sequences refers to a spacer or linker group, 8-amino-3,6-dioxaoctanoyl.

The ability of the biotinylated polypeptides (with the JJ spacer) to bind to KDR was assessed using the assay set forth in Example 5, following the procedures disclosed therein. Several biotinylated peptides bound well to the KDR-expressing cells: SEQ ID NO:356 $K_D$ 1.81 nM+/−0.27) SEQ ID NO:264 $K_D$ 14.87+/−5.0 nM, four experiment average), SEQ ID NO:294+spacer $K_D$ 10.00+/−2.36 nM, four experiment average), SEQ ID NO:301 ($K_D$ 4.03+/−0.86 nM, three experiment average), SEQ ID NO:337 ($K_D$ 6.94+/−1.94 nM, one experiment), and SEQ ID NO:338 ($K_D$ 3.02+−0.75 nM, one experiment).

TABLE 10

KDR, VEGF/KDR Complex Binding Polypeptides

| SEQ ID NO: | Structure (or) Sequence | Mol. Wt. | MS |
|---|---|---|---|
| 294 | Ac-GDSRVCWEDSWGGEVCFRYDPGGGK-NH$_2$ | 2801.98 | 1399.6 [M − H]$^-$ |
| 329 | Ac-AGMPWCVEKDHWDCWWGTGGGK-NH$_2$ | 2730.14 | — |
| 311 | Ac-AGIDFCKGMAPWLCADMGTGGGK-NH$_2$ | 2324.02 | — |
| 264 | Ac-AGPKWCEEDWYYCMITGTGGGK-NH$_2$ | 2361 | — |
| 266 | Ac-AGWVECWWKSGQCYEFGTGGGK-NH$_2$ | 2474.06 | — |
| 330 | Ac-AQEGWFRNPQEIMGFGDSWDKPGGGK-NH$_2$ | 2934.35 | — |
| 299 | Ac-GDGSWCEMRQDVGK(iv-Dde)WNCFSDDP-GGGK-NH$_2$ | 3075.29 | 1537.5 [M$^{2-}$] |
| 299 | Ac-DGSWCEMRQDVGKWNCFSDDPGGGK-NH$_2$ | 2869.16 | — |
| 303 | Ac-GDNWECGWSNMPQK(iv-Dde)EFCARPDP-GGGK-NH$_2$ | 3160.36 | 1579.6 [M$^{2-}$] |
| 303 | Ac-GDNWECGWSNMFQKEFCARPDPGGGK-NH$_2$ | 2954.23 | — |
| 294 | Ac-GDSRVCWEDSWGGEVCFRYDPGGGK(Biotin)-NH$_2$ | 3030.29 | 1512.4 [M$^{2-}$] |
| 331 | Ac-AQRGDYQEQYWHQQLVEQLK(iv-Dde)LLGGGK-NH$_2$ | 3318.71 | 1659.1 [M$^{2-}$] |
| 331 | Ac-AQRGDYQEQYWHQQLVEQLKLLGGGK-NH$_2$ | 3112.58 | — |
| 332 | Ac-AGWYWCDYYGIGCK(iv-Dde)WTGGGK-NH$_2$ | 2673.18 | |
| 333 | Ac-AGWYWCDYYGIGCKWTGTGGGK-NH$_2$ | 2467.05 | |
| 334 | Ac-AQWYYDWFHNQRKPPSDWIDNLGGGK-NH$_2$ | 3218.51 | — |
| 323 | Ac-AGYGPCKNMPPWMCWHEGTGGGK-NH$_2$ | 2502.05 | — |
| 335 | Ac-AGPKWCEEDWYYCMITGTGGGK(N,N-Dimethyl-Gly-Ser-Cys(Acm)-Gly)-NH$_2$ | 2836.204 | 2833.4 [M − H]$^-$ |
| 264 | Ac-AGPK(iv-Dde)WCEEDWYYCMITGTGGGK-NH$_2$ | 2698.11 | 2695.7 [M − H]$^-$; 1347.8 [M − 2H]$^{2-}$/2 |
| 336 | Ac-WQPCPWESWTFCWDPGGGK(AcSCH$_2$C(=O))-NH2 | 2422.71 | 2420.7 [M − H]$^-$, 1209.9 [M − 2H]/2 |
| 264 | Ac-AGPKWCEEDWYYCMITGTGGGK(Biotin)-NH$_2$ | 2718.13 | 2833.4 (M − H)$^-$ |
| 264 | Ac-AGPKWCEEDWYYCMITGTGGGK(Biotin-JJ)-NH$_2$ | 3008.44 | 1502.6.4 (M − 2H)$^{2-}$/2 |
| 264 | Ac-AGPKWCEEDWYYCMITGTGGGK(AcSCH$_2$C(=O))-NH$_2$ | 2608.96 | 1304, [M − 2H]$^{2-}$/2 |
| 294 | Ac-GDSRVCWEDSWGGEVCFRYDPGGGK(Biotin-JJ)-NH$_2$ | 3316.4 | 1657.8, [M − 2]$^{2-}$/2 |
| 294 | Ac-GDSRVCWEDSWGGEVCFRYDPGGGK(AcSCH$_2$C(=O))-NH$_2$ | 2917.15 | 1457.4, [M − 2H]$^{2-}$/2 |
| 294 | Biotin-JJGDSRVCWEDSWQGEVCFRYDPGGGK-NH$_2$ | 3272.34 | 1636.7, [M − 2H]$^{2-}$/2 |
| 264 | Ac-AGPKWCEEDWYYCMITGT-GGGK(AcSCH$_2$C(=O)-JJ)-NH$_2$ | 2899.28 | 1449.2, [M − 2H]$^{2-}$/2 |
| 277 | Ac-AGPTWCEDDWYYCWLFGTGGGK(Biotin-JJ)-NH$_2$ | 3066.27 | 1532.8, [M − 2H]$^{2-}$/2 |
| 337 | Ac-VCWEDSWGGEVCFRYDPGGGK(Biotin-JJ)-NH$_2$ | 2903.24 | 1449.3, (M − 2H)$^{2-}$/2; 965.8, (M − 3H)$^{3-}$/3 |
| 338 | Ac-AGPTWCEDDWYYCWLFGTJK(Biotin-JJ)-NH$_2$ | 3042.44 | 1519.7, (M − 2H)$^{2-}$/2−; 1012.8 (M − 3H)$^{3-}$/3 |

TABLE 10-continued

KDR, VEGF/KDR Complex Binding Polypeptides

| SEQ ID NO: | Structure (or) Sequence | Mol. Wt. | MS |
|---|---|---|---|
| 294 | Ac-GDSRVCWEDSWGGEVCFRYDPGGGK (AcSCH$_2$C(=O)-JJ)- NH$_2$ | 3208.48 | 1602.6, [M − 2H]$^{2-}$/2 |
| 339 | Ac-AGPTWCEDDWYYCWLFGTGGGK(N,N-Dimethyl-Gly-Ser-Cys(Acm)-Gly-JJ)- NH$_2$ | 3242.33 | 1621.5, [M − 2H]$^{2-}$/2 |
| 277 | Ac-AGPTWCEDDWYYCWLFGTGGGK (AcSCH$_2$C(=O)-JJ)- NH$_2$ | 2907.29 | 1453.1, [M − 2H]$^{2-}$/2 |
| 340 | Ac-AQAHMPPWRPVAVDALFDWVEGG-GGGK(Biotin-JJ)- NH$_2$ | 3404.64 | 1701.6, [M − 2H]$^{2-}$/2 |
| 341 | Ac-AQAHMPPWWPLAVDAQEDWFEGG-GGGK(Biotin-JJ)- NH$_2$ | 3493.59 | 1746.2, [M − 2H]$^{2-}$/2 |
| 342 | Ac-AQAQMPPWWPLAVDALFDWFEGG-GGGK(Biotin-JJ)- NH$_2$ | 3487.64 | 1743.2, [M − 2H]$^{2-}$/2 |
| 343 | Ac-AQDWYWREWMPMKAQFLADDWGG-GGGK(Biotin-JJ)- NH$_2$ | 3751.64 | 1874.3, [M − 2H]$^{2-}$/2 |
| 344 | Ac-AQK(ivDde)K(iv-Dde)EDAQQWYWTDYVPSY-LYRGGGGGK(Biotin-JJ)- NH$_2$ | 4220.06 | 2108.9, [M − 2H]$^{2-}$/2 |
| 345 | Ac-AQPVTDWTPHHPK(iv-Dde)APDVWLFYT-GGGGGK(Biotin-JJ)- NH$_2$ | 3781.86 | 1890.4, [M − 2H]$^{2-}$/2 |
| 346 | Ac-AQDALEAPK(iv-Dde)RDWYYDWFLNHSP-GGGGGK(Biotin-JJ)- NH$_2$ | 3897.85 | 1948.0, [M − 2H]$^{2-}$/2 |
| 347 | Ac-KWCEEDWYYCMITGTGGGK(Biotin-JJ)- NH$_2$ | 2781.2 | 1390.0, [M − 2H]$^{2-}$/2 |
| 348 | Ac-AGPKWCEEDWYYCMIGGGK(Biotin-JJ)- NH$_2$ | 2747.15 | 1373.5, [M − 2H]$^{2-}$/2 |
| 349 | Ac-KWCEEDWYYCMIGGGK(Biotin-JJ)- NH$_2$ | 2522.04 | 1260.8, [M − 2H]$^{2-}$/2 |
| 350 | Ac-AQPDNWK(iv-Dde)EFYESGWK(iv-Dde)-YPSLYK(iv-Dde)PLGGGGGK(Biotin-JJ)- NH$_2$ | 4377.2 | 2188.4, [M − 2H]$^{2-}$/2 |
| 351 | Ac-AQMPPGFSYWEQVVLHDDAQVLGG-GGGK(Biotin-JJ)- NH$_2$ | 3499.7 | 1749.2, [M − 2H]$^{2-}$/2 |
| 352 | Ac-AQARMGDDWEEAPPHEWGWADGG-GGGK(Biotin-JJ)- NH$_2$ | 3480.5 | 1740.2, [M − 2H]$^{2-}$/2 |
| 353 | Ac-AQPEDSEAWYWLNYRPTMFHQLGG-GGGK(Biotin-JJ)- NH$_2$ | 3751.7 | 1875.8, [M − 2H]$^{2-}$/2 |
| 354 | Ac-AQSTNGDSFVYWEEVELVDHPGG-GGGK(Biotin-JJ)- NH$_2$ | 3554.6 | 1776.4, [M − 2H]$^{2-}$/2 |
| 355 | Ac-AQWESDYWDQMRQQLK(iv-Dde)TAYMK(iv-Dde)VGGGGGK(Biotin-JJ)- NH$_2$ | 4187.02 | 2093.0, [M − 2H]$^{2-}$/2 |
| 356 | Ac-AQDWYYDEILSMADQLRHAFLSGGGGGK(Biotin-JJ)- NH$_2$ | 3641.69 | 1820.9, [M − 2H]$^{2-}$/2 |

The putative disulfide constrained cyclic peptide is indicated in bold.

Example 5

Binding of KDR Binding Peptides/Avidin HRP Complex to KDR Transfected 293H Cells To determine the binding of peptides identified by phage display to KDR expressed in transiently-transfected 293H cells, a novel assay that measures the binding of biotinylated peptides complexed with neutravidin HRP to KDR on the surface of the transfected cells was developed. This assay was used to screen the biotinylated peptides set forth in Example 4. Neutravidin HRP was used instead of streptavidin or avidin because it has lower nonspecific binding to molecules other than biotin due to the absence of lectin binding carbohydrate moieties and also due to the absence of the cell adhesion receptor-binding RYD domain in neutravidin.

In the experiments described herein, tetrameric complexes of KDR-binding peptides SEQ ID NO:294, SEQ ID NO:264, SEQ ID NO:277 and SEQ ID NO:356 and a control peptide, which does not bind to KDR, were prepared and tested for their ability to bind 293H cells that were transiently-transfected with KDR. All four tetrameric complexes of KDR-binding peptides were biotinylated and contained the JJ spacer, and bound to the KDR-expressing cells; however, SEQ ID NO:356 exhibited the best $K_D$ (1.81 nM). The tetrameric complexes of KDR-binding peptides SEQ ID NO:294, SEQ ID NO:264 exhibited improved binding over monomers of the same peptides Moreover, inclusion of a spacer between the KDR-binding peptide and the biotin was shown to improve binding in Experiment B.

In Experiment C, it was shown that this assay can be used to assess the effect of serum on binding of peptides of the invention to KDR and VEGF/KDR complex. The binding of SEQ ID NO:264, SEQ ID NO:294, and SEQ ID NO:356 was not significantly affected by the presence of serum, while the binding of SEQ ID NO:277 was reduced more than 50% in the presence of serum.

In Experiment D, it was shown that this assay is useful in evaluating distinct combinations of KDR and VEGF/KDR complex binding polypeptides for use in multimeric targeting constructs that contain more than one KDR and VEGF/KDR complex binding polypeptide Moreover, Experiments D and E establish that tetrameric constructs including two or more KDR binding peptides that bind to different epitopes exhibited superior binding to "pure" tetrameric constructs of the targeting peptides alone.

Experiment A

Preparation of mRNA & 5' RACE Ready cDNA Library

HUVEC cells were grown to almost 80% confluence in 175 cm$^2$ tissue culture flasks (Becton Dickinson, Biocoat, cat #6478) and then 10 ng/mL of bFGF (Oncogene, cat #PF003) was added for 24 h to induce expression of KDR. mRNA was isolated using the micro-fast track 2.0 kit from Invitrogen (cat. # K1520-02). 12 µg of mRNA (measured by absorbance at 260 nM) was obtained from two flasks (about 30 million cells) following the kit instructions. Reverse transcription to generate cDNA was performed with 2 µg of mRNA, oligo dT primer (5'-(T)$_{25}$GC-3') and/or smart II oligo (5'AAG-CAGTGGTAACAACGCAGAGTACGCGGG-3') (SEQ ID NO:357) using Moloney Murine Leukemia Virus (MMLV) reverse transcriptase. The reaction was performed in a total volume of 20 µl and the reaction mix contained 2 µl of RNA, 1 µl smart II oligo, 1 µl of oligo dT primer, 4 µl of 5× fast-strand buffer (250 mM Tris HCl pH 8.3, 375 mM KCl, 30 mM MgCl$_2$) 1 µl DTT (20 mM, also supplied with reverse transcriptase), 1 µl dNTP mix (10 mM each of dATP, dCTP, dGTP, and dTTP in ddH$_2$O, Stratagene, cat. # 200415), 9 µl ddH$_2$O and 1 µl MMLV reverse transcriptase (Clonetech, cat #8460-1). The reverse transcription reaction was performed for 90 minutes at 42° C., and the reaction was stopped by adding 250 µl of tricine-EDTA buffer (10 mM tricine, 1.0 mM EDTA). The reverse transcription product, a 5' RACE ready cDNA library, can be stored for 3 months at −20° C. Note that all water used for DNA and RNA application was DNAse and RNAse free from USB (cat. # 70783).

Cloning of s-KDR into TOPOII Vector

In order to clone s-KDR, a 5' oligo (G ATG GAG AGC AAG GTG CTG CTG G) (SEQ ID NO:358) and a 3' oligo (C CAA GTT CGT CTT TTC CTG GGC A) (SEQ ID NO:359) were used. These were designed to amplify the complete extracellular domain of KDR (~2.2 kbps) from the 5' RACE ready cDNA library (prepared above) using polymerase chain reaction (PCR) with pfu polymerase (Stratagene, cat. # 600135). The PCR reaction was done in total volume of 50 µl and the reaction mix contained 2 µl 5' RACE ready cDNA library, 1 µl 5' oligo (10 µM), 1 µl 3' oligo (10 µM), 5 µl 10×PCR buffer [PCR buffer (200 mM Tris-HCl pH 8.8, 20 mM MgSO$_4$, 100 mM KCl, 100 mM (NH$_4$)$_2$SO$_4$) supplied with pfu enzyme plus 1% DMSO and 8% glycerol], 1 µl dNTP mix (10 mM) and 40 µl ddH$_2$O. The PCR reaction was performed by using a program set for 40 cycles of 1 minute at 94° C., 1 minute at 68° C. and 4 minutes at 72° C. The PCR product was purified by extraction with 1 volume of phenol, followed by extraction with 1 volume of chloroform and precipitated using 3 volume of ethanol and 1/10 volume of 3M sodium acetate. The PCR product was resuspended in 17 µl of ddH$_2$O, the 2 µl of 10× Taq polymerase buffer (100 mM Tris-HCl pH 8.8, 500 mM KCl, 15 mM MgCl$_2$, 0.01% gelatin) and 1 µl of Taq polymerase (Stratagene, cat. # 600131) was added to generate an A overhang to each end of the product. After incubating for 1 hour at 72° C. the modified product was cloned directly into a TOPOII vector (InVitrogen, Carlsbad, Calif.) following the manufacturer's protocol to give TOPO-sKDR. The TOPO vector allows easy cloning of PCR products because of the A-overhang in Taq (PCR enzyme)-treated PCR products.

Cloning the Transmembrane and Cytoplasmic Domains of KDR into TOPO II Vector

In order to clone the transmembrane and cytoplasmic domains of KDR, a 5' oligo (TCC CCC GGG ATC ATT ATT CTA GTA GGC ACG GCG GTG) (SEQ ID NO:360) and a 3' oligo (C AGG AGG AGA GCT CAG TGT GGT C) (SEQ ID NO:361) were used. These were designed to amplify the complete transmembrane and cytoplasmic domains of KDR (~1.8 kbps) from the 5' RACE ready cDNA library (described above) using polymerase chain reaction (PCR) with pfu polymerase. PCR reaction conditions and the program were exactly the same as described above for s-KDR. Just as with the s-KDR sequence, the PCR product was purified using phenol chloroform extraction, treated with Taq polymerase and cloned into TOPOII vector from Invitrogen to give TOPO-CYTO.

Cloning of Full-Length KDR into pcDNA6 Vector

To create the full-length receptor, the extracellular domain and the cytoplasmic domain (with trans-membrane domain) were amplified by PCR separately from TOPO-sKDR and TOPO-CYTO respectively and ligated later to create the full-length receptor. An oligo with a NotI site at the 5' end of the extracellular domain (A TAA GAA TOC GGC CGC AGG ATG GAG AGC AAG GTG CTG CTG G) (SEQ ID NO:362) and an oligo complimentary to the 3' end of the extracellular domain (TTC CAA GTT CGT CTT TTC CTG GGC ACC) (SEQ ID NO:363) were used to amplify by PCR the extracellular domain from TOPO-sKDR. Similarly, the 5' oligo (ATC ATT ATT CTA GTA GGC ACG GCG GTG) (SEQ ID NO:364) and the 3' oligo, with a NotI site (A TAA GAA TGC GGC CGC AAC AGG AGG AGA OCT CAG TGT GOT C) (SEQ ID NO:365), were used to amplify by PCR the cytoplasmic domain of KDR (with transmembrane domain) from TOPO-CYTO. Both PCR products were digested with NotI and ligated together to create the full-length receptor. The cDNA encoding the full-length receptor was purified on an agarose gel and ligated into the Not I site of the pcDNA6NA5/V5-HisC vector. Purification of DNA and ligation was done as described earlier for psKDR. The ligation reaction was used to transform a culture of DH5α bacteria and a number of individual clones were analyzed for the presence and orientation of insert by restriction analysis of purified plasmid from each clone with EcoRI enzyme.

Cell Culture 293H cells were obtained from Invitrogen (cat. # 11631) and grown as monolayer culture in their recommended media plus 1 mL/L pen/strep (Invitrogen, cat #15140-148). All the cells were grown in presence of antibiotic for everyday culture but were split into antibiotic free media for 16-20 hours prior to transfection.

Preparation of DNA for Transfection

*E. coli* bacteria DH5α containing pf-KDR was streaked onto LB with 50 µg/mL ampicillin (LB agar from US biologicals, cat. # 75851 and ampicillin from Sigma, cat. #A2804) plates from a glycerol stock and plates were loft in a 37° C. incubator to grow overnight. Next morning, a single colony was picked from the plate and grown in 3 mL of LB/ampicillin media (LB from US biologicals, cat # US75852) at 37° C. After 8 hours, 100 µl of bacterial culture from the 3 mL tube was transferred to 250 mL of LB/ampicillin media for overnight incubation at 37° C. Bacteria were grown up with circular agitation in a 500 mL bottle (Beckman, cat. # 355605) at 220 rpm in a Lab-Line incubator shaker. The next day, the bacterial culture was processed using maxi-prep kit (QIAGEN, cat. # 12163). Generally, about 1 mg of plasmid DNA (as quantitated by absorbance at 260 nm) was obtained from 250 mL of bacterial culture.

Transfection of 293H Cells in 96 Well Plate

Transfection was done as recommended in the lipofectamine 2000 protocol (Invitrogen, cat# 11668-019) using a poly-D-lysine-coated 96 well plate. 320 ng of KDR DNA (pc-DNA6-fKDR)/per well in 0.1 mL was used for 96 well transfection. Transfection was done in serum-containing media, the transfection reagent mix was removed from cells after 6-8 hours and replaced with regular serum-containing medium. Transfection was done in black/clear 96-well plates (Becton Dickinson, cat. # 354640). The left half of the plate (48 wells) were mock-transfected (with no DNA) and the right half of the plate was transfected with KDR cDNA. The cells were 80-90% confluent at the time of transfection and completely confluent next day, at the time of the assay, otherwise the assay was aborted.

Preparation of M199 Media

In order to prepare M199 media for the assay, one M199 medium packet (GIBCO, cat. # 31100-035), 20 mL of 1 mM HEPES (GIBCO, cat. #15630-080) and 2 gm of DIFCO Gelatin (DIFCO, cat. #0143-15-1) were added to 950 mL of ddH$_2$O and the pH of the solution was adjusted to 7.4 by adding approximately 4 mL of 1N NaOH. After pH adjustment, the M199 media was warmed to 37° C. in a water bath for 2 hours to dissolve the gelatin, then filter sterilized using 0.2 µm filters (Corning, cat #43109), and stored at 4° C. to be used later in the assay.

Preparation of SoftLink Soft Release Avidin-Sepharose

SoftLink soft release avidin-sepharose was prepared by centifuging the sepharose obtained from Promega (cat. # V2011) at 12,000 rpm for 2 minutes, washing twice with ice cold water (centrifuging in-between the washes) and resuspending the pellet in ice cold water to make a 500% slurry in ddH$_2$O. A fresh 50% slurry of avidin-sepharose was prepared for each experiment.

Preparation of Peptide/Neutravidin HRP Solution

Biotinylated peptides SEQ ID NOS:294, 264, 277, 356, and the non-binding biotinylated control peptide were used to prepare 250 µM stock solutions in 50% DMSO and a 33 µM stock solution of neutravidin-HRP was prepared by dissolving 2 mg of neutravidin-HRP (Pierce, cat. # 31001) in 1 mL of ddH$_2$O (all polypeptides contained the JJ spacer). Peptide stock solutions were stored at −20° C., whereas the Neutravidin HRP stock solution was stored at −80° C. To prepare peptide/neutravidin-HRP complexes, 10 µl of 250 µM biotinylated peptide stock solution and 10 µl of 33 µM neutravidin-HRP were added to 1 mL of M199 medium. This mixture was incubated on a rotator at 4° C. for 60 minutes, followed by addition of 50 µl of soft release avidin-sepharose (50% slurry in ddH$_2$O) to remove excess peptides and another incubation for 30 minutes on a rotator at 4° C. Finally, the soft release avidin-sepharose was pelleted by centrifuging at 12,000 rpm for 5 minutes at room temperature, and the resulting supernatant was used for the assays. Fresh peptide/neutravidin-HRP complexes were prepared for each experiment.

Preparation of Peptide/Neutravidin HRP Dilutions for the Assay

For saturation binding experiments, 120 µl, 60 µl, 20 µl, 10 µl, 8 µl, 6 µl, 4 µl, and 1 µl of peptide/neutravidin HRP complex were added to 1.2 mL aliquots of M199 medium to create dilutions with final concentrations of 33.33 nM, 16.65 nM, 5.55 nM, 2.78 nM, 1.67 nM, 1.11 nM and 0.28 nM complex, respectively.

Preparation of Blocking Solution for Transfected 293H Cells

Blocking solution was prepared by adding 20 mL of M199 medium to 10 mg of lyophilized unlabeled neutravidin (Pierce, cat. # 31000). Fresh blocking solution was used for each experiment.

Assay to Detect the Binding of Peptide/Neutravidin-HRP 24 hours after transfection, each well of the 293H cells was washed once with 100 µl of M199 medium and incubated with 80 µl of blocking solution at 37° C. After one hour, cells were washed twice with 100 µl of M199 media and incubated with 70 µl of peptide/neutravidin-HRP dilutions of control peptide, SEQ ID NO:264, SEQ ID NO:294, SEQ ID NO:277, and SEQ ID NO:356 for two and half hours at room temperature. Bach dilution was added to three separate wells of mock as well as KDR-transfected 293H cells (two plates were used for each saturation binding experiment). After incubation at room temperature, plates were transferred to 4° C. for another half-hour incubation. Subsequently, cells were washed 5 times with ice-cold M199 media and once with ice-cold PBS (in that order). After the final wash, 100 µl of ice cold TMB solution (KPL, cat. # 50-76-00) was added to each well and each plate was incubated for 30 minutes at 37° C. in an air incubator. Finally, the HRP enzyme reaction was stopped by adding 50 µl of 1N phosphoric acid to each well, and binding was quantitated by measuring absorbance at 450 nm using a microplate reader BioRad Model 3550).

Binding of Peptide/Neutravidin HRP to KDR-Transfected Cells

Figure 2:
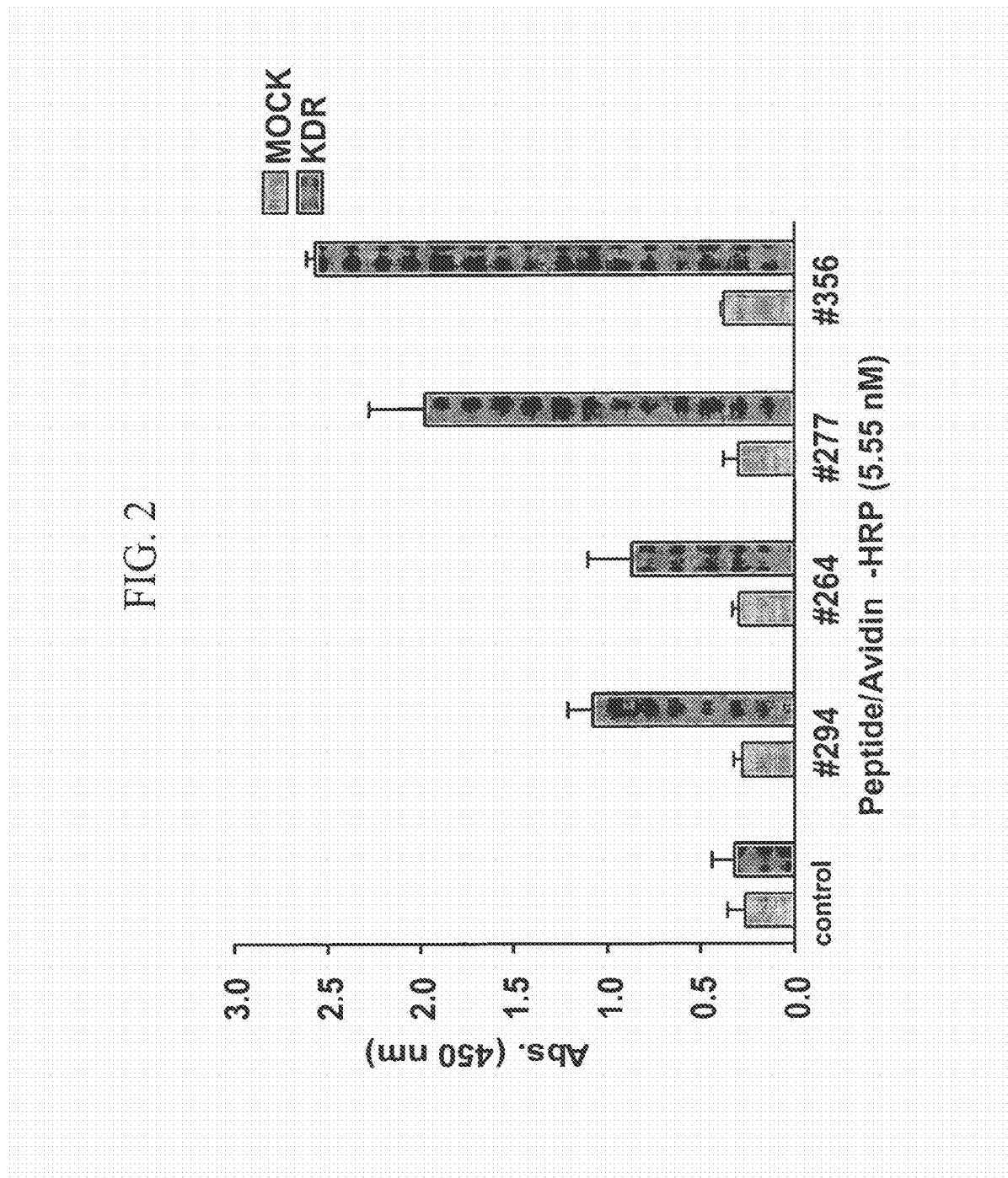
FIG. 2 is a graph illustrating the binding of peptide/neutravidin-HRP complexes: control (biotinylated with spacer, and SEQ ID NOS:264, 294, 277 and 356) to KDR-transfected and Mock-transfected 293H cells at a single concentration (5.55 nM). All peptides had a C-terminal biotin and JJ spacer.

In this assay, complexes of control peptide, SEQ, ID NO:264, SEQ ID NO:294, SEQ ID NO:277, and SEQ ID NO:356 peptides, each biotinylated with the JJ spacer and conjugated with neutravidin-HRP, were prepared as described above and tested for their ability to bind 293H cells that were transiently-transfected with KDR. During the peptide/neutravidin complex preparation, a 7.5-fold excess of biotinylated peptides over neutravidin-HRP was used to make sure that all four biotin binding sites on neutravidin were occupied. After complex formation, the excess of free biotinylated peptides was removed using soft release avidin-sepharose to avoid any competition between fee biotinylated peptides and neutravidin HRP-complexed biotinylated peptides. The experiment was performed at several different concentrations of peptide/neutravidin-HRP, from 0.28 nM to 33.33 nM, to generate saturation binding curves for SEQ ID NO:264 and SEQ ID NO:294 (FIG. 1A) and 0.28 to 5.55 nM to generate saturation binding curve for SEQ ID NO:277 and SEQ ID NO:356 (FIG. 1B). In order to draw the saturation binding curve, the background binding to mock-transfected cells was subtracted from the binding to KDR-transfected cells for each distinct peptide/neutravidin HRP complex at each concentration tested. Therefore, absorbance on the Y-axis of FIG. 1 is differential absorbance (KDR minus mock) and not the absolute absorbance. Analysis of the saturation binding data in FIG. 1 using Graph Pad Prism software (version 3.0) yielded a K$_D$ of 10.00 nM (+/−2.36) for the tetrameric SEQ ID NO:294, 14.87 nM (+/−5.066) for the tetrameric SEQ ID NO:264, 4.031 nM (+/−0.86) for the tetrameric SEQ ID NO:277, and 1.814 nM (+/−0.27) for the tetrameric SEQ ID NO:356 peptide Complexes. These binding constants are, as expected, lower than those measured by FP against the KDRFc construct for the related monodentate peptides SEQ ID NO:294 (69 nM), SEQ ID NO:264 (280 mM), SEQ ID NO:310 (51 nM), but similar to monodentate peptide SEQ ID NO:277 (3 nM). As expected, no saturation of binding for the control (non-binder) peptide/neutravidin HRP-complex was observed. The binding of peptide/neutravidin HRP complexes (FIG. 2) at a single concentration (5.55 nM) was plotted to demonstrate that a single concentration experiment can be used to differentiate between a KDR binding peptide (SEQ ID NOS:264, 294 and 277) from a non-binding peptide.

Experiment B

Experiment B was designed to look at the requirement of spacer (JJ, Table 10) between the KDR binding sequences (SEQ ID NOS:294 and 264) and biotin. In this experiment biotinylated peptides with and without spacer JJ were tested (e.g., biotinylated SEQ ID NO:264 with the JJ spacer, biotinylated SEQ ID NO:264 without the JJ spacer, SEQ ID NO:294 with a spacer, and biotinylated SEQ ID NO:294 without the spacer), and a non-KDR binding, biotinylated control peptide (with and without spacer, prepared as set forth above) was used as a control. The peptide structure of all the KDR-binding sequences tested in this experiment is shown in FIG. 3.

This experiment was performed as set forth in Experiment A described above, except that it was only done at a single concentration of 2.78 nM.

Figure 4:
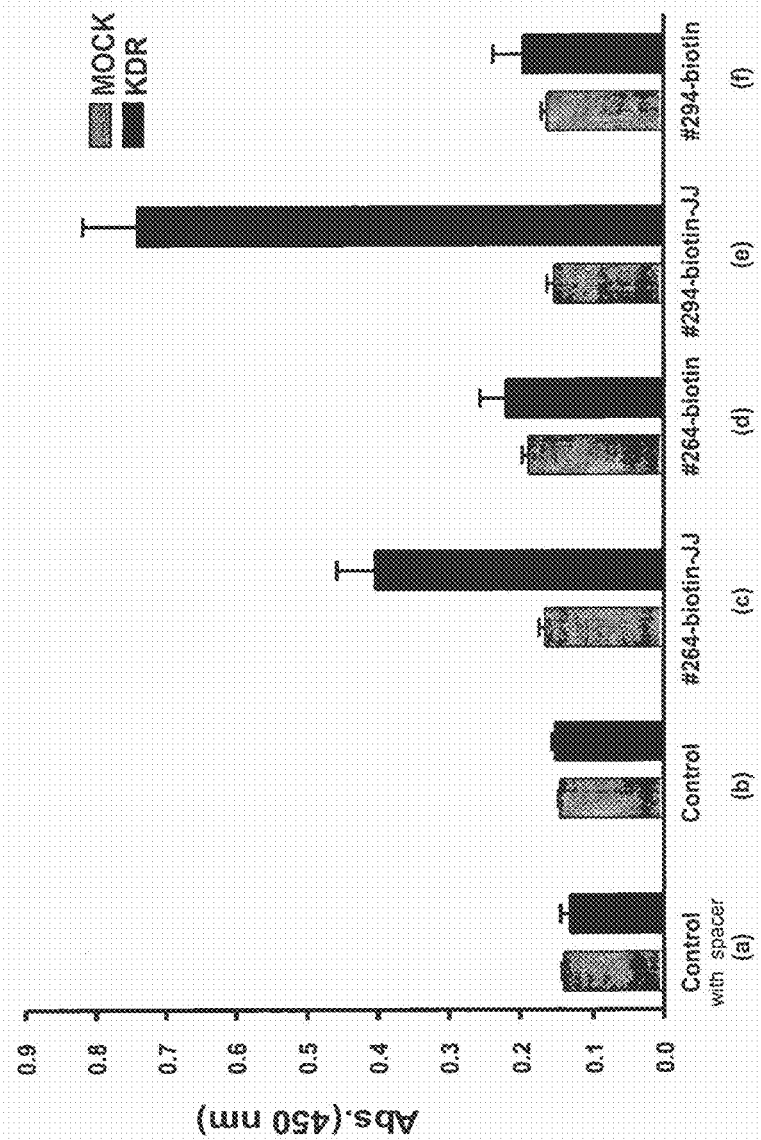
FIG. 4 is a bar graph illustrating binding of peptide/neutravidin HRP complexes to KDR-transfected and mock-transfected 293H cells at single a concentration (2.78 nM); peptides include (a) control (with spacer); (b) control; (c) biotinylated SEQ ID NO:264 with a JJ spacer; (d) SEQ ID NO:264 with an N-terminal biotin; and (e) biotinylated SEQ ID NO:294 with the JJ spacer; and (f) biotinylated SEQ ID NO:294.

Results: It is evident from the results shown in the FIG. 4 that the spacer enhances binding of SEQ ID NO:294 and SEQ ID NO:264. The spacer between the binding sequence and biotin can be helpful in enhancing binding to target molecule by multiple mechanisms. First, it could help reduce the steric hindrance between four biotinylated peptides after their binding to a single avidin molecule. Second, it could provide extra length necessary to reach multiple binding sites available on a single cell.

Experiment C

Experiment C was designed to look at the serum effect on the binding of SEQ ID NOS: 294, 264, 277 and 356. In this procedure, biotinylated peptide/avidin HRP complexes of SEQ ID NOS:294, 264, 277 and 356 were tested in M199 media (as described above in Experiment A) with and without 40% rat serum. This experiment was performed as described for Experiment A except that it was only done at single concentration of 6.66 nM for SEQ ID NOS: 294 and 264, 3.33 nM for SEQ ID NO:277 and 2.22 nM for SEQ ID NO:356. Each of the polypeptides were biotinylated and had the JJ spacer.

Figure 5:
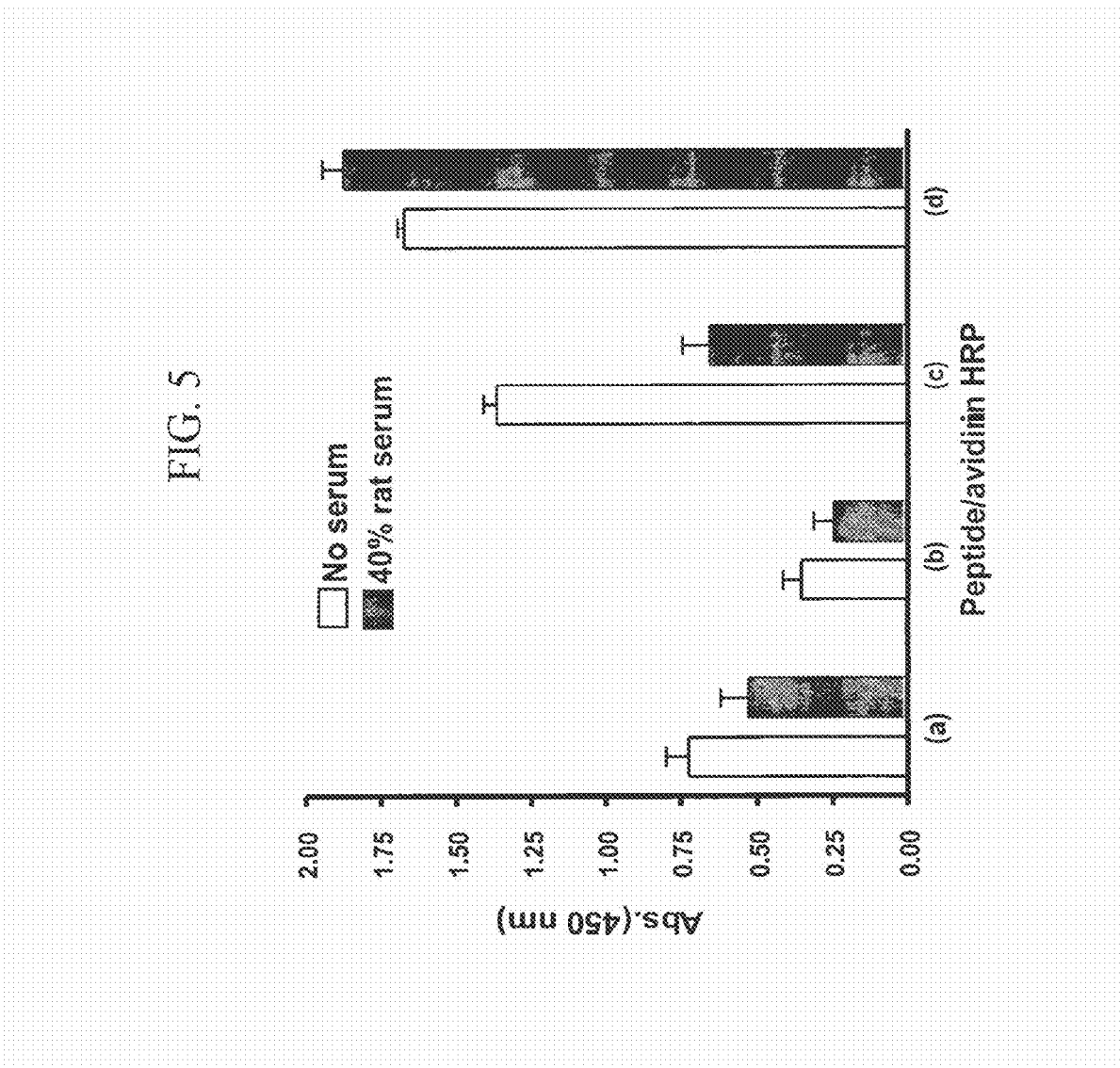
FIG. 5 is a bar graph illustrating specific binding (binding to KDR transfected cells minus binding to Mock transfected cells) of peptide/neutravidin-HRP complexes with and without 40% rat serum. (a) SEQ ID NO:294; (b) SEQ ID NO:264; (c) SEQ ID NO:277; (d) SEQ ID NO:356. Concentration of peptide/avidin HRP solutions was 6.66 nM for (a) and (b), 3.33 nM for (c), and 2.22 nM for (d). All peptides had a C-terminal biotin and JJ spacer.
Figure 97:
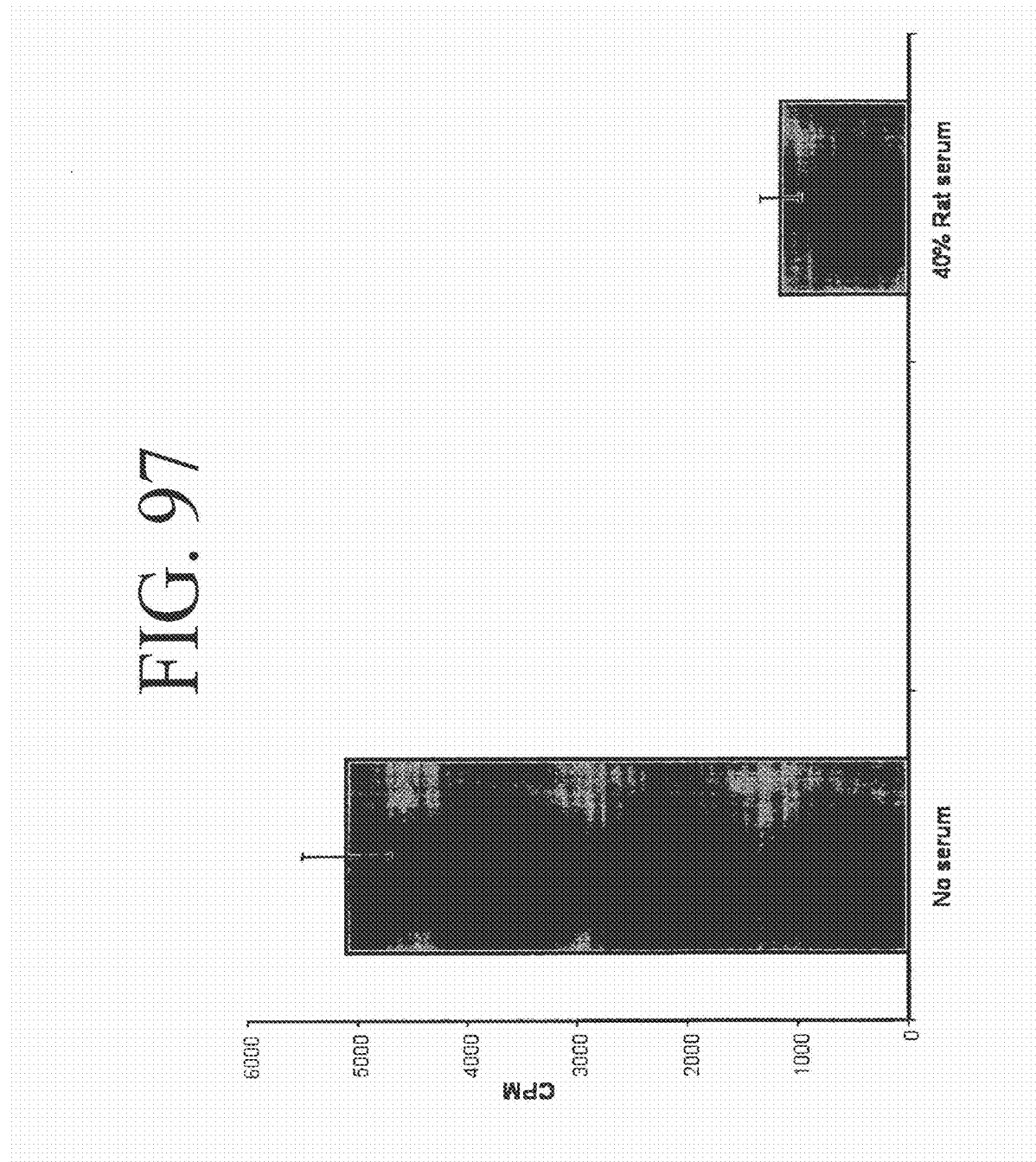
FIG. 97 is a bar graph demonstrating that Tc-labeled SEQ ID NO:277 with Tc-chelate binding to KDR-transfected 293H cells is inhibited by about 80% in the presence of 40% rat serum.

Results: Results in FIG. 5 indicate that binding of SEQ ID NO:264, SEQ ID NO:294, and SEQ ID NO:356 was not significantly affected by 40% rat serum, whereas binding of SEQ ID NO:277 (c) was more than 50% lower in presence of 40% rat serum. More than an 80% drop in the binding of Tc-labeled SEQ ID NO:277 with Tc-chelate was observed in the presence of 40% rat serum (FIG. 97). Since the serum effect on the binding of Tc-labeled SEQ ID NO:277 is mimicked in the avidin HRP assay disclosed herein, this assay may be used to rapidly evaluate the serum effect on the binding of peptide(s) to KDR.

Experiment D

Experiment D was designed to evaluate the binding of tetrameric complexes of KDR and VEGF/KDR complex binding polypeptides SEQ ID NO:294 and SEQ ID NO:264, particularly where the constructs included at least two KDR binding polypeptides. The KDR binding peptides and control binding peptide were prepared as described above. This experiment was performed using the protocol set forth for Experiment A, except the procedures set forth below were unique to this experiment.

Preparation of Peptide/Neutravidin Solutions: 250 µM stock solutions of biotinylated peptides SEQ ID NOs:264, 294 and control peptide were prepared in 50% DMSO and a 33 µM stock solution of Neutravidin HRP was prepared by dissolving 2 mg of Neutravidin HRP (Pierce, cat. # 31001) in 1 mL of ddH$_2$O. Peptide stock solutions were stored at −20° C., whereas the Neutravidin HRP stock solution was stored at −80° C. The sequences of the biotinylated peptides are shown above. To prepare peptide/neutravidin HRP complexes, a total 5.36 µL of 250 µM biotinylated peptide stock solution (or a mixture of peptide solutions, to give peptide molecules four times the number of avidin HRP molecules) and 10 µL of 33 µM Neutravidin HRP were added to 1 mL of M 199 medium. This mixture was incubated on a rotator at 4° C. for 60 minutes, followed by addition of 50 µL of soft release avidin-sepharose (50% slurry in ddH$_2$O) to remove excess peptides and another incubation for 30 minutes on a rotator at 4° C. Finally, the soft release avidin-sepharose was pelleted by centrifuging at 12,000 rpm for 5 minutes at room temperature, and the resulting supernatant was used for the assays. Fresh peptide/neutravidin HRP complexes were prepared for each experiment.

Assay to Detect the Binding of Peptide/Neutravidin HRP: 24 hours after transfection, each well of the 293H cells was washed once with 100 µL of M199 medium and incubated with 80 µL of blocking solution at 37 C. After one hour, cells were washed twice with 100 µL of M199 media and incubated with 70 µL of 3.33 nM peptide (or peptide mix)/neutravidin HRP solutions (prepared by adding 10 µL of stock prepared earlier to 1 mL of M199 media) for two and half hours at room temperature. Each dilution was added to three separate wells of mock as well as KDR-transfected 293H cells. After incubation at room temperature, plates were transferred to 4 C for another half-hour incubation. Subsequently, cells were washed five times with ice-cold M199 media and once with ice-cold PBS (in that order). After the final wash, 100 µL of ice cold TMB solution (KPL, Gaithersburg, Md.) was added to each well and each plate was incubated for 30 minutes at 37 C in an air incubator. Finally, the HRP enzyme reaction was stopped by adding 50 µL of 1N phosphoric acid to each well, and binding was quantitated by measuring absorbance at 450 nm using a microplate reader (BioRad Model 3550).

Figure 6:
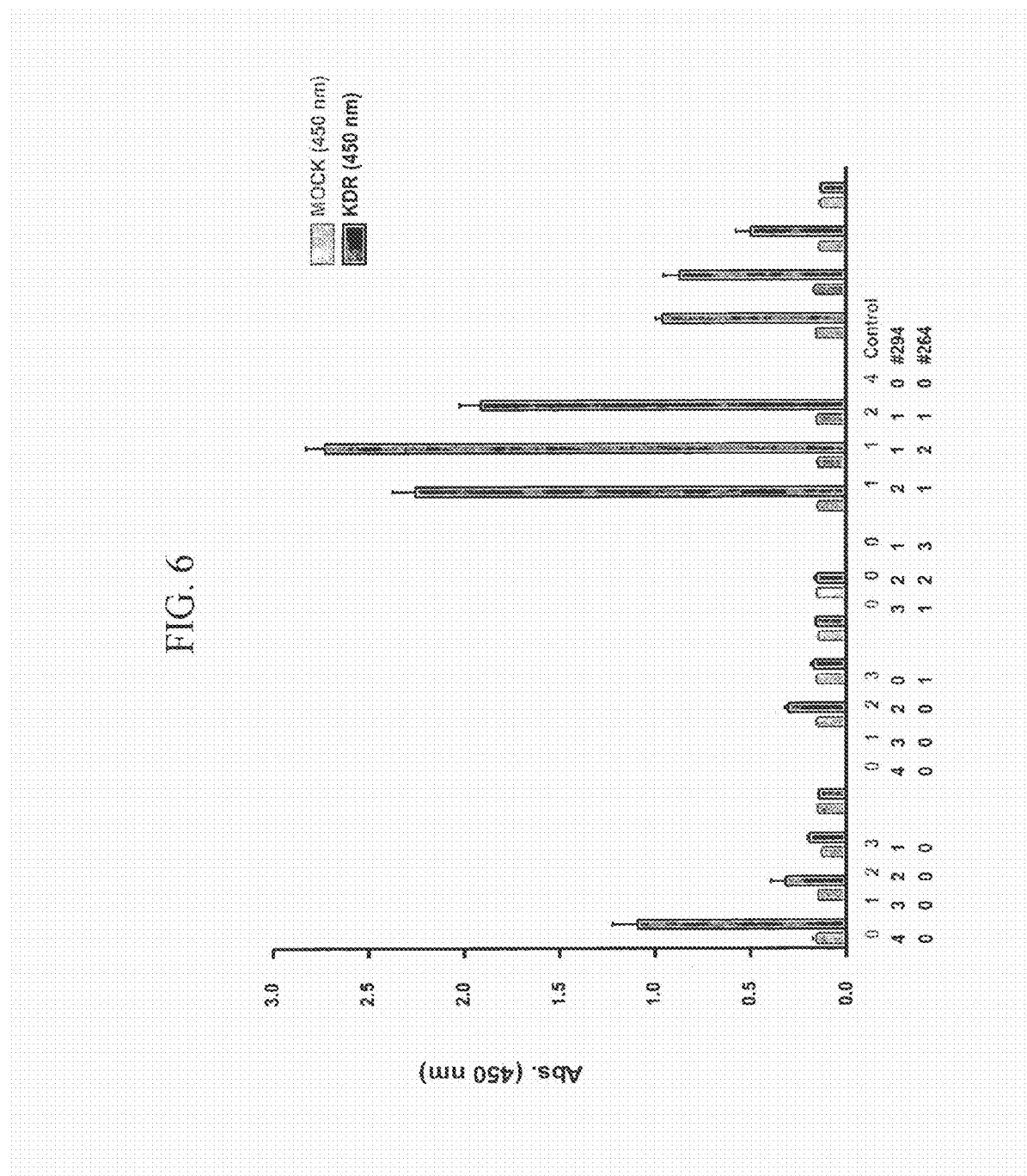
FIG. 6 is a bar graph illustrating binding of polypeptide/avidin-HRP solutions (SEQ ID NO:294 and/or SEQ ID NO:264) to mock- and KDR-transfected cells plotted as absorbance at 450 nm. The proportions of control and KDR binding peptides used to form each tetrameric complex are indicated in the legend for each tested multimer.

Results: This experiment establishes that SEQ ID NO:294 and SEQ ID NO:264 bind to KDR in multimeric fashion, and cooperate with each other for binding to KDR in 293H transfected cells. A biotinylated control peptide that does not bind to KDR was used. As expected, a tetrameric complex of the control peptide with avidin-HRP did not show enhanced binding to KDR-transfected cells. Tetrameric complexes of SEQ ID NO:294 and SEQ ID NO:264 bound to KDR-transfected cells significantly better than to mock-transfected cells (see FIG. 6). SEQ ID NO:294 tetramers, however, bound much better than SEQ ID NO:264 tetramers. If the control peptide was added to the peptide mixture used to form the tetrameric complexes, the binding to the KDR-transfected cells decreased. The ratio of specific binding of tetramer to monomer, dimer and trimer was calculated by dividing the specific binding (obtained by subtracting the binding to mock transfected cells from KDR transfected cells) of tetramer, trimer and dimer with that of monomer. Results indicate that there is co-operative effect of multimerization of SEQ ID NOS:264, 294 and 356 on the binding to KDR-transfected cells.

|  | Tetramer | Trimer | Dimer |
| --- | --- | --- | --- |
| SEQ ID NO: 264 | 45.4 | 5 | 4.3 |
| SEQ ID NO: 294* | 38.6 | 7.1 | 2.7 |
| SEQ ID NO: 277 | 1 | 1.1 | 1.1 |
| SEQ ID NO: 356 | 16 | 5.7 | 2.3 |

*monomeric peptide binding at 2.22 nM was zero, therefore ratios were calculated using binding at 5.55 nM.

A mixture of 25% non-binding control peptide with 75% SEQ ID NO:264 did not bind significantly over background to KDR-transfected cells, indicating that multivalent binding is critical for the SEQ ID NO:264/avidin-HRP complex to remain bound to KDR throughout the assay. This phenomenon also held true for SEQ ID NO:294, where substituting 50% of the peptide with control peptide in the tetrameric complex abolished almost all binding to KDR on the transfected cells.

Surprisingly, a peptide mixture composed of 50% control peptide with 25% SEQ ID NO:294 and 25% SEQ ID NO:264 bound quite well to KDR-transfected cells relative to mock-transfected cells, indicating that there is a great advantage to targeting two sites or epitopes on the same target molecule. Furthermore, it was noted that tetrameric complexes containing different ratios of SEQ ID NO:294 and SEQ ID NO:264 (3:1, 2:2, and 1:3) all bound much better to KDR-transfected cells than pure tetramers of either peptide, in agreement with the idea that targeting two distinct sites on a single target molecule is superior to multimeric binding to a single site. This may be because multimeric binding to a single target requires that the multimeric binding entity span two or more separate target molecules that are close enough together for it to bind them simultaneously, whereas a multimeric binder that can bind two or more distinct sites on a single target molecule does not depend on finding another target molecule within its reach to achieve multimeric binding.

Experiment E

Experiment E was designed to confirm that SEQ ID NO:294 and SEQ ID NO:264 bind to distinct sites (epitopes) on KDR. If these peptides bind to the same site on KDR, then they should be able to compete with each other; however, if they bind to different sites they should not compete. This experiment was performed using a single concentration of SEQ ID NO:264/avidin HRP (3.33 nM) solution in each well and adding a varying concentration (0-2.5 µM) of biotinylated control peptide with spacer, SEQ ID NO:264 and SEQ ID NO:294, none of which were complexed with avidin.

Figure 7:
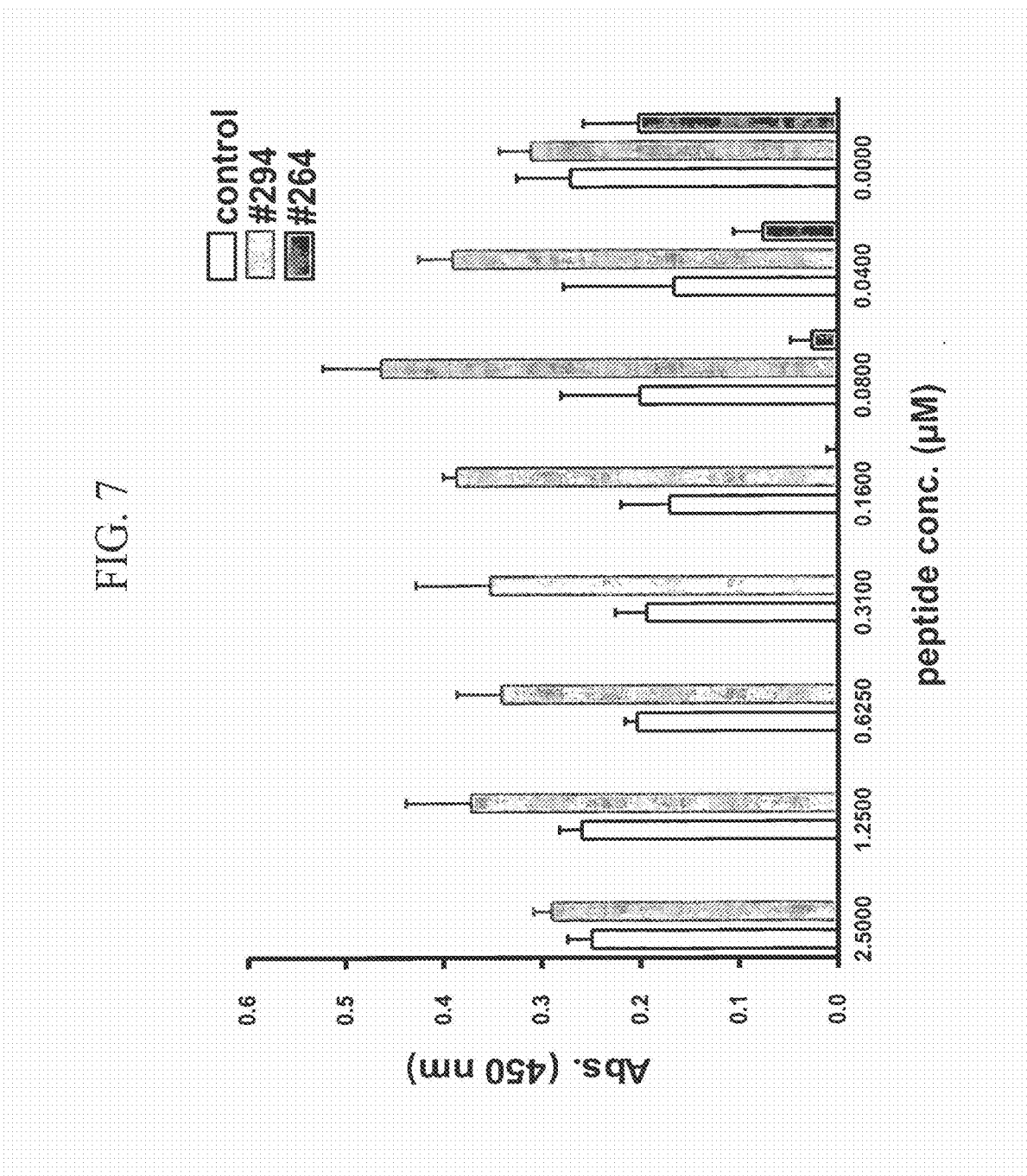
FIG. 7 is a bar graph illustrating specific binding of a peptide comprising SEQ ID NO:294, and a biotinylated SEQ ID NO:264 with a JJ spacer/avidin-HRP complex to KDR transfected cells (background binding to mock-transfected cells subtracted), plotted as absorbance at 450 nm. Increasing concentrations (as indicated in the X axis) of uncomplexed peptides were added to the assay as indicated. Free SEQ ID NO:264 was able to decrease the binding of the SEQ ID NO:264 complex to KDR-transfected cells.

Results: It is evident from FIG. 7 that SEQ ID NO:264 does compete with SEQ ID NO:264/avidin HRP solution for binding to recombinant KDR-Fc fusion protein whereas control peptide and SEQ ID NO:294 do not compete with SEQ ID NO:264/avidin HRP solution for binding to recombinant KDR-Fc fusion protein. Thus, SEQ ID NO:264 and SEQ ID NO:294 bind to distinct and complementary sites on KDR.

Example 6

Binding of Analogs of a KDR-Binding Peptide to KDR-Expressing Cells

N-terminal and C-terminal truncations of a KDR binding polypeptide were made and the truncated polypeptides tested for binding to KDR-expressing cells. The synthesized polypeptides are shown in FIG. 8. Binding of the polypeptides to KDR-expressing cells was determined following the procedures of Example 3.

All of the peptides were N-terminally acetylated and fluoresceinated for determining apparent $K_D$ according to the method described above (Example 3). The results indicate that, for the SEQ ID NO:294 (FIG. 8) polypeptide, the C-terminal residues outside the disulfide-constrained loop contribute to KDR binding.

Example 7

Bead-Binding Assay to Confirm Ability of Peptides Identified by Phage Display to Bind KDR-Expressing Cells The following procedures were performed to assess the ability of KDR-binding peptides to bind to KDR-expressing cells. In this procedure, KDR-binding peptides containing SEQ ID NOS:2644, 337, 363, and 373 were conjugated to fluorescent beads, and their ability to bind to KDR-expressing 293H cells was assessed. The experiments show these peptides can be used to bind particles such as beads to KDR-expressing sites. The results indicate that the binding of both KDR binding sequences improved with the addition of a spacer.

Protocol

Biotinylation of an anti-KDR antibody: Anti-KDR from Sigma (V-9134), as ascites fluid, was biotinylated using a kit from Molecular Probes (F-6347) according to the manufacturer's instructions.

Preparation of peptide-conjugated fluorescent beads: 0.1 mL of a 0.2 mM stock solution of each biotinylated peptide (prepared as set forth above, in 50% DMSO) was incubated with 0.1 mL of Neutravidin-coated red fluorescent microspheres (2 micron diameter, custom-ordered from Molecular Probes) and 0.2 mL of 50 mM MES (Sigma M-8250) buffer, pH 6.0 for 1 hour at room temperature on a rotator. As a positive control, biotinylated anti-KDR antibody was incubated with the Neutravidin-coated beads as above, except that 0.03 mg of the biotinylated antibody preparation in PBS (Gibco #14190-136) was used instead of peptide solution. Beads can be stored at 4° C. until needed for up to 1 week.

Binding Assay From the above bead preparations, 0.12 mL was spun for 10 minutes at 2000 rpm in a microcentrifuge at room temperature. The supernatant was removed and 0.06 mL of M pH 6.0 was added. Each bead solution was then vortexed and sonicated in a water bath 15 min. To 1.47 mL of DMEM, high glucose (GIBCO #11965-084) with 1×MEM Non-Essential Amino Acids Solution (NEAA) (GIBCO 11140-050) and 40% FBS (Hyclone SH30070.02) 0.03 mL of the sonicated bead preparations was added. 96-well plates seeded with 293H cells that have been mock-transfected in columns 1 to 6, and KDR-transfected in columns 7 to 12 (as in Example 5), were drained and washed once with DMEM, high glucose with 1×NEAA and 40% FBS. To each well 0.1 mL of bead solution was added, six wells per bead preparation. After incubating at room temperature for 30 minutes, the wells were drained by inverting the plates and washed four times with 0.1 mL PBS with $Ca^{++}Mg^{++}$ (GIBCO #14040-117) with shaking at room temperature for 5 minutes each wash. After draining, 0.1 mL of PBS was added per well. The plates were then read on a Packard FluoroCount fluorometer at excitation 550 nm/emission 620 nm. Unconjugated neutravidin beads were used as a negative control while beads conjugated with a biotinylated anti-KDR antibody were used as the positive control for the assay.

To calculate the number of beads bound per well, a standard curve with increasing numbers of the same fluorescent beads was included in each assay plate. The standard curve was used to calculate the number of beads bound per well based on the fluorescence intensity of each well.

Figure 9:
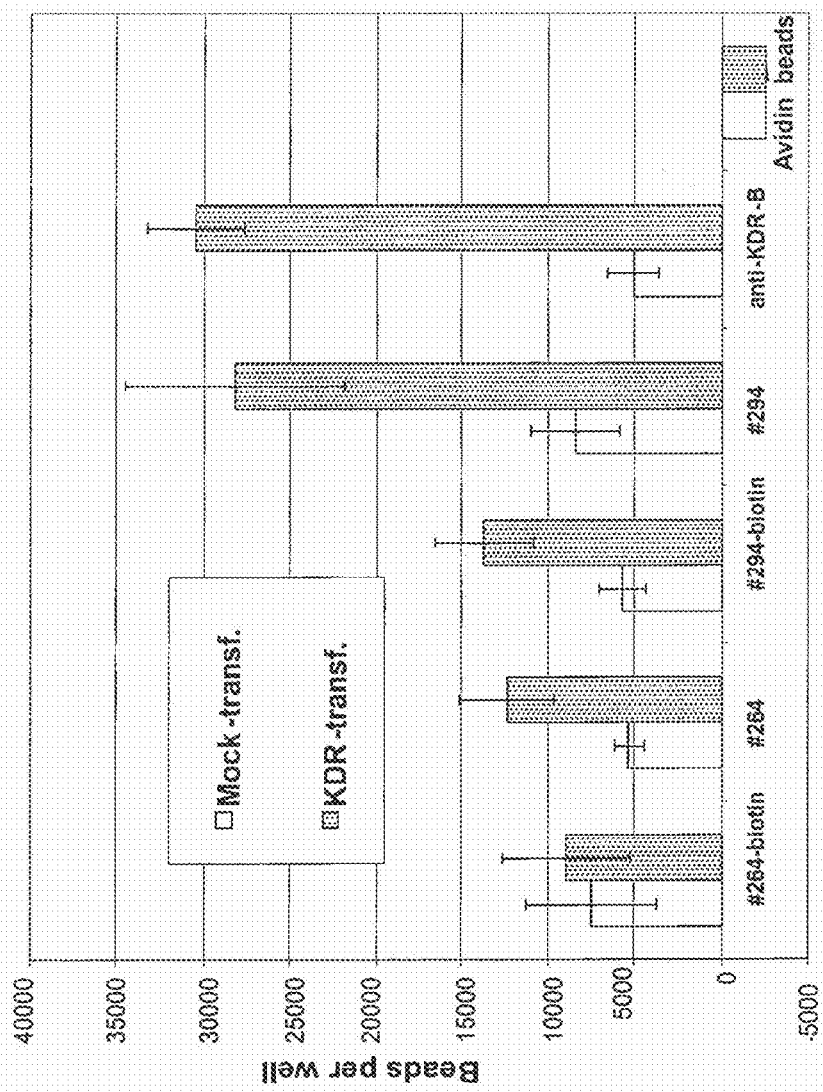
FIG. 9 is a bar graph illustrating the binding of fluorescent beads to KDR-transfected and mock-transfected cells. Neutravidin-coated beads with the indicated ligands attached were tested for binding to KDR-expressing and non-expressing 293H cells.

Results: The positive control beads with anti-KDR attached clearly bound preferentially to the KDR-expressing cells while avidin beads with nothing attached did not bind to either cell type (FIG. 9). Biotinylated SEQ ID NO:264 beads did not bind to the KDR-transfected cells significantly more than to mock-transfected cells, but adding a hydrophilic spacer between the peptide moiety and the biotin group (biotinylated SEQ ID NO:264 with a JJ spacer beads) enhanced binding to KDR cells without increasing the binding to mock-transfected cells. Biotinylated SEQ ID NO:294 beads showed greater binding to KDR-transfected cells, and adding a hydrophilic spacer between the peptide portion and the biotin of the molecule biotinylated SEQ ID NO:294 with the JJ spacer) significantly improved the specific binding to KDR in the transfected cells. Thus, the peptide sequences of both SEQ ID NO:264 and SEQ ID NO:294 can be used to bind particles such as beads to KDR-expressing sites. Addition of a hydrophilic spacer between the peptide and the group used for attachment to the particle should routinely be tested with new targeting molecules as it improved the binding for both of the peptides evaluated here.

Example 8

Competition of KDR Binding Peptides and $^{125}$I-Labeled VEGF for Binding to KDR-Transfected 293H Cells KDR-binding polypeptides were next assessed for their ability to compete with $^{125}$I-labeled VEGF for binding to KDR expressed by transfected 293H cells. The results indicate that KDR-binding polypeptide SEQ ID NO:263 (Ac-AGDSWCSTEYTYCEMIGTGGGK-NH$_2$) did not compete significantly with $^{125}$I-labeled VEGF, and SEQ ID NOS:294, 264, and SEQ ID NO:277 competed very well with $^{125}$I-labeled VEGF, inhibiting 96.29±2.97% and 104.48±2.074% of $^{125}$I-labeled VEGF binding.

Transfection of 293H cells: 293H cells were transfected using the protocol described in Example 5. Transfection was done in black/clear 96-well plates (Becton Dickinson, cat. # 354640). The left half of the plates (48 wells) were mock-transfected (with no DNA) and the right half of the plates were transfected with KDR cDNA. The cells were 80-90% confluent at the time of transfection and completely confluent the next day, at the time of the assay; otherwise the assay was aborted.

Preparation of M199 media: M199 medium was prepared as described in Example 5.

Preparation of peptide solutions: 3 mM stock solutions of peptides SEQ ID NO:294, SEQ ID NO:263, SEQ ID NO:264 and SEQ ID NO:277 were prepared as described above in 50% DMSO.

Preparation of $^{125}$I-labeled VEGF solution for the assay: 25 µCi of lyophilized $^{125}$I-labeled VEGF (Amersham, cat. # IM274) was reconstituted with 250 µl of ddH$_2$O to create a stock solution, which was stored at –80 C for later use. For each assay, a 300 pM solution of $^{125}$I-labeled VEGF was made fresh by diluting the above stock solution in M199 medium. The concentration of $^{125}$I-labeled VEGF was calculated daily based on the specific activity of the material on that day.

Preparation of 30 µM and 0.3 µM peptide solution in 300 pM $^{125}$-labeled VEGF: For each 96 well plate, 10 mL of 300 pM $^{125}$I-labeled VEGF in M199 medium was prepared at 4° C. Each peptide solution (3 mM, prepared as described above) was diluted 1:100 and 1:10000 in 300 µl of M199 media with 300 µM $^{125}$I-labeled VEGF to prepare 30 µM and 0.3 µM peptide solutions containing 300 µM of $^{125}$I-labeled VEGF. Once prepared, the solutions were kept on ice until ready to use. The dilution of peptides in M199 media containing 300 pM $^{125}$I-labeled VEGF was done freshly for each experiment.

Assay to detect competition with $^{125}$I-labeled VEGF in 293H cells: Cells were used 24 hours after transfection, and to prepare the cells for the assay, they were washed 3 times with room temperature M199 medium and placed in the refrigerator. After 15 minutes, the M199 medium was removed from the plate and replaced with 75 µl of 300 pM $^{125}$I-labeled VEGF in M199 medium (prepared as above) with the polypeptides. Each dilution was added to three separate wells of mock and KDR transfected cells. After incubating at 4° C. for 2 hours, the plates were washed 5 times with cold binding buffer, gently blotted dry and checked under a microscope for cell loss. 100 µl of solubilizing solution (2% Triton X-100, 10% Glycerol, 0.1% BSA) was added to each well and the plates were incubated at room temperature for 30 minutes. The solubilizing solution in each well was mixed by pipeting up and down, and transferred to 1.2 mL tubes. Each well was washed twice with 100 µl of solubilizing solution and the washes were added to the corresponding 1.2 mL tube. Each 1.2 mL tube was then transferred to a 15.7×100 cm tube to be counted in an LKB Gamma Counter using program 54 ($^{125}$I window for 1 minute).

Competition of peptides with $^{125}$I-labeled VEGF in 293H cells: The ability of KDR-binding peptides SEQ ID NO:294, SEQ ID NO:263, SEQ ID NO:264 and SEQ ID NO:277 to specifically block $^{125}$I-labeled VEGF binding to KDR was assessed in mock-transfected and KDR-transfected cells. SEQ ID NO:263 was used in the assay as a negative control, as it exhibited poor binding to KDR in the FP assays described herein and would therefore not be expected to displace or compete with VEGF. To calculate the specific binding to KDR, the binding of $^{125}$I-labeled VEGF to mock-transfected cells was subtracted from KDR-transfected cells. Therefore, the binding of $^{125}$I-labeled VEGF to sites other than KDR (which may or may not be present in 293H cells) is not included when calculating the inhibition of $^{125}$I-labeled VEGF binding to 293H cells by KDR-binding peptides. Percentage inhibition was calculated using formula [(Y1−Y2)*100/Y1], where Y1 is specific binding to KDR-transfected 29311 cells in the absence peptides, and Y2 is specific binding to KDR-transfected 293H cells in the presence of peptides or DMSO. Specific binding to KDR-transfected 293H cells was calculated by subtracting binding to mock-transfected 293H cells from binding to KDR-transfected 293H cells.

Figure 10:
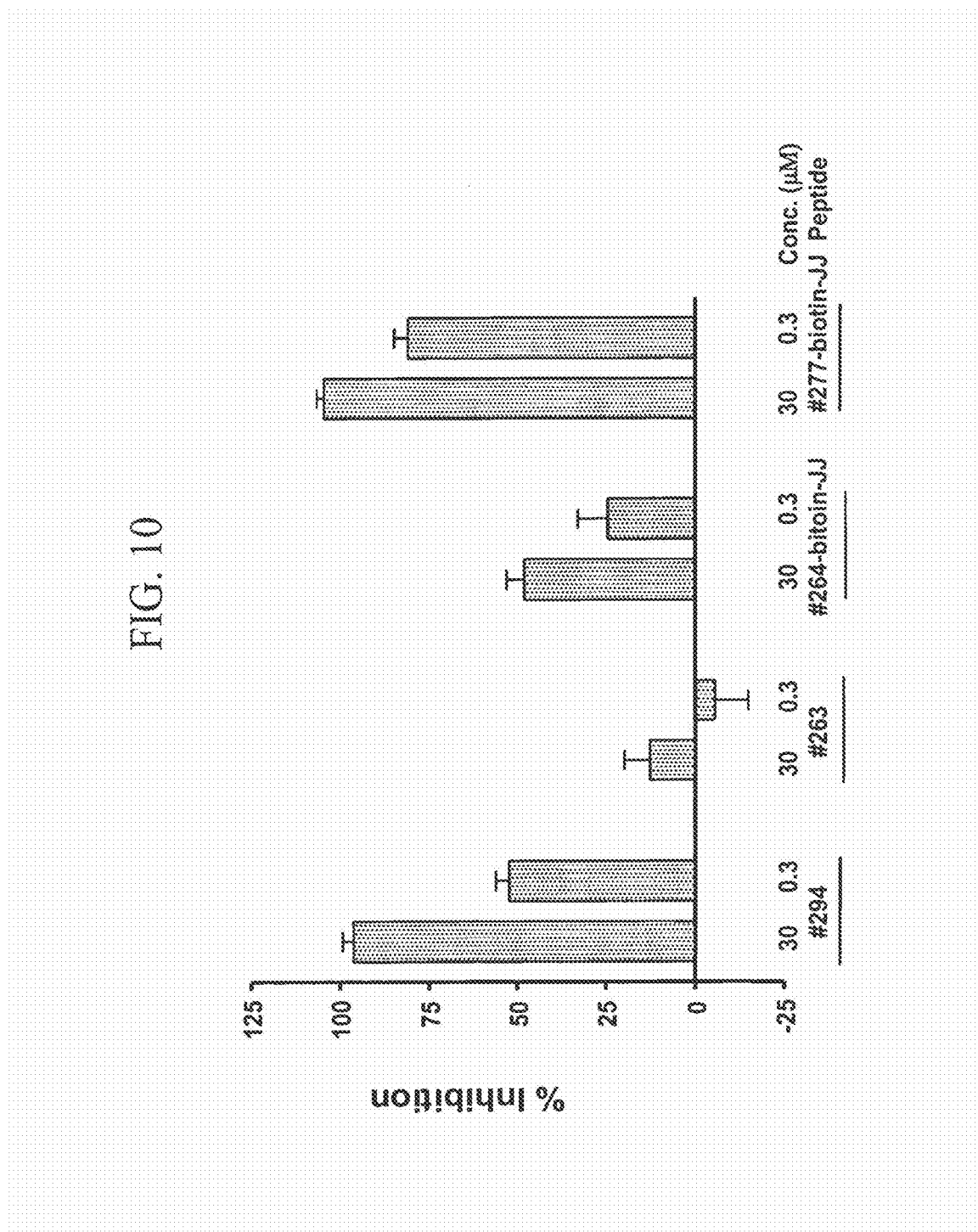
FIG. 10 is a bar graph illustrating percent inhibition of $^{125}$I-labeled VEGF binding by binding polypeptides (a) acetylated SEQ ID NO:294 (without the modified C-terminus, GDSRVCWEDSWGGEVCFRYDP; SEQ ID NO: 374); (b) SEQ ID NO:263 (without the modified C-terminus, AGD-SWCSTEYTYCEMIGT; SEQ ID NO:375); (c) biotinylated SEQ ID NO:264 with a JJ spacer; and (d) SEQ ID NO:277 (biotinylated with the JJ spacer), at two concentrations (30 µM and 0.3 µM), to KDR-expressing 293H transfectants.

As shown in FIG. 10, in 293 cells, SEQ ID NO:263, which due to its relatively high $K_d$ (>2 µM) was used as a negative control, did not compete significantly with $^{125}$I-labeled VEGF, 12.69±7.18% at 30 µM and −5.45±9.37% at 0.3 µM (FIG. 10). At the same time, SEQ ID NOS:294 and 277 competed very well with $^{125}$I-labeled VEGF, inhibiting 96.29±2.97% and 104.48±2.074% of $^{125}$I-labeled VEGF binding at 30 µM and 52.27±3.78% and 80.96±3.8% at 0.3 µM (FIG. 10) respectively. The percentage inhibition with SEQ ID NO:264 was 47.95±5.09% of $^{125}$I-labeled VEGF binding at 30 µM and 24.41±8.43% at 0.3 µM (FIG. 10). Thus, the three strongly KDR-binding polypeptides did compete with VEGF, and their potency increased with their binding affinity. This assay will be useful for identifying peptides that bind tightly to KDR but do not compete with VEGF, a feature that may be useful for imaging KDR in tumors, where there is frequently a high local concentration of VEGF that would otherwise block the binding of KDR-targeting molecules.

Example 9

Inhibition of VEGF-Induced KDR Receptor Activation by Peptides Identified by Phage Display The ability of KDR-binding peptides identified by phage display to inhibit VEGF induced activation (phosphorylation) of KDR was assessed using the following assay. A number of peptides of the invention were shown to inhibit activation of KDR in monomeric and/or tetrameric constructs. As discussed supra, peptides that inhibit activation of KDR may be useful as anti-angiogenic agents.

Protocol

Human umbilical vein endothelial cells (HUVECs) (Biowhittaker Catalog #CC-2519) were obtained frozen on dry ice and stored in liquid nitrogen until thawing. These cells were thawed, passaged, and maintained as described by the manufacturer in EGM-MV medium (Biowhittaker Catalog #CC-3125). Cells seeded into 100 mm dishes were allowed to become confluent, then cultured overnight in basal EBM medium lacking serum (Biowhittaker Catalog #CC-3121). The next morning, the medium in the dishes was replaced with 10 mL fresh EBM medium at 37 C containing either no additives (negative control), 5 ng/mL VEGF (Calbiochem Catalog #676472 or Peprotech Catalog #1020) (positive control), or 5 ng/mL VEGF plus the indicated concentration of the KDR-binding peptide (prepared as described above). In some cases, a neutralizing anti-KDR antibody (Catalog #AF357, R&D Systems) was used as a positive control inhibitor of activation. In such cases, the antibody was pre-incubated with the test cells for 30 min at 37° C. prior to the addition of fresh medium containing both VEGF and the antibody. After incubating the dishes 5 min. in a 37° C. tissue culture incubator they were washed three times with ice-cold D-PBS containing calcium and magnesium and placed on ice without removing the last 10 mL of Delbecco's phosphate buffered saline (D-PBS). The first dish of a set was drained and 0.5 mL of Triton lysis buffer was added (20 mM Tris base pH 8.0, 137 mM NaCl, 10% glycerol, 1% Triton X-100, 2 mM EDTA (ethylenediaminetetraacetic acid), 1 mM PMSF (phenylmethylsulfonylfluoride), 1 mM sodium orthovanadate, 100 mM NaF, 50 mM sodium pyrophosphate, 10 µg/mL leupeptin, 10 µg/mL aprotinin). The cells were quickly scraped into the lysis buffer using a cell scraper (Falcon, Cat No. #353087), dispersed by pipetting up and down briefly, and the resulting lysate was transferred to the second drained dish of the pair. Another 0.5 mL of lysis buffer was used to rinse out the first dish then transferred to the second dish, which was then also scraped and dispersed. The pooled lysate from the two dishes was transferred to a 1.5 mL Eppindorf tube. The above procedure was repeated for each of the controls and test samples (KDR-binding peptides), one at a time. The lysates were stored on ice until all the samples had been processed. At this point samples were either stored at −70° C. or processed to the end of the assay without interruption.

The lysates, freshly prepared or frozen and thawed, were precleared by adding. 20 µl of protein A-sepharose beads (Sigma 3391, preswollen in D-PBS, washed three times with a large excess of D-PBS, and reconstituted with 6 mL D-PBS to generate a 50% slurry) and rocking at 4° C. for 30 min. The beads were pelleted by centrifugation for 2 min. in a Picofuge (Stratgene, Catalog #400550) at 2000×g and the supernatants transferred to new 1.5 mL tubes. Twenty µg of anti-Flk-1 antibody (Santa Cruz Biotechnology, Catalog #sc-504) was added to each tube, and the tubes were incubated overnight (16-18 hr.) at 4 C on a rotator to immunoprecipitate KDR. The next day 40 µl of protein A-sepharose beads were added to the tubes that were then incubated 4 C for 1 hr. on a rotator. The beads in each tube were subsequently washed three times by centrifuging for 2 min. in a Picofuge, discarding the supernatant, and dispersing the beads in 1 ml freshly added TBST buffer (20 mM Tris base pH 7.5, 137 mM NaCl, and 0.1% Tween 20). After centrifuging and removing the liquid from the last wash, 40 µl of Laemmli SDS-PAGE sample buffer (Bio-Rad, Catalog #161-0737) was added to each tube and the tubes were capped and boiled for 5 min. After cooling, the beads in each tube were pelleted by centrifuging and the supernatants containing the immunoprecipitated KDR were transferred to new tubes and used immediately or frozen and stored at −70 C for later analysis.

Detection of phosphorylated KDR as well as total KDR in the immunoprecipitates was carried out by immunoblot analysis. Half (20 µL) of each immunoprecipitate was resolved on a 7.5% precast Ready Gel (Bio-Rad, Catalog #161-1154) by SDS-PAGE according to the method of Laemmli (*Nature*, 227:680-685 (1970)).

Using a Bio-Rad mini-Protean 3 apparatus (Catalog #165-3302), the resolved proteins in each gel were electroblotted to a PVDF membrane (Bio-Rad, Cat. No. 162-0174) in a Bio-Rad mini Trans-Blot cell (Catalog #170-3930) in CAPS buffer (10 mM CAPS, Sigma Catalog #C-6070, 1% ACS grade methanol, pH 11.0) for 2 hr. at 140 mA according to the method of Matsudaira (*J. Biol. Chem.*, 262:10035-10038 (1987)). Blots were blocked at room temperature in 5% Blotto-TBS (Pierce Catalog #37530) pre-warmed to 37° C. for 2 hr. The blots were first probed with an anti-phosphotyrosine antibody (Transduction Labs, Catalog #P11120), diluted 1:200 in 5% Blotto-TBS with 0.1% Tween 20 added for 2 hr. at room temp. The unbound antibody was removed by washing the blots four times with D-PBS containing 0.11% Tween 20 (D-PBST), 5 min. per wash. Subsequently, blots were probed with an HRP-conjugated sheep anti-mouse antibody (Amersham Biosciences Catalog #NA931) diluted 1:25,000 in 5% Blotto-TBS with 0.1% Tween 20 added for 1 hr. at room temp., and washed four times with D-PBST. Finally, the blots were incubated with 2 mL of a chemiluminescent substrate (ECL Plus, Amersham Catalog #RPN2132) spread on top for 2 min., drip-drained well, placed in plastic sheet protector (C-Line Products, Catalog #62038), and exposed to X-ray film (Kodak BioMax ML, Cat No. 1139435) for varying lengths of time to achieve optimal contrast.

To confirm that similar amounts of KDR were compared in the assay, the blots were stripped by incubating for 30 min. at 37° C. in TBST with its pH adjusted to 2.4 with HCl, blocked for 1 hr. at room temp. with 5% Blotto-TBS with 0.1% Tween 20 (Blotto-TBST), and reprobed with an anti-Flk-1 polyclonal antibody (Catalog #sc-315 from Santa Cruz Biotech), 1:200 in 5% Blotto-TBST with 1% normal goat serum (Life Tech Catalog #16210064) for 2 hr. at room temp. The unbound antibody was removed by washing the blots four times with D-PBST, 5 min. per wash. Subsequently, the blots were probed with an HRP-conjugated donkey anti-rabbit secondary antibody (Amersham Biosciences Catalog #NA34) diluted 1:10,000 in 5% Blotto-TBST for 1 hr. at room temp., and washed four times with D-PBST. Finally, the blots were incubated with 2 mL of chemiluminescent substrate and exposed to X-ray film as described above.

Figure 11:
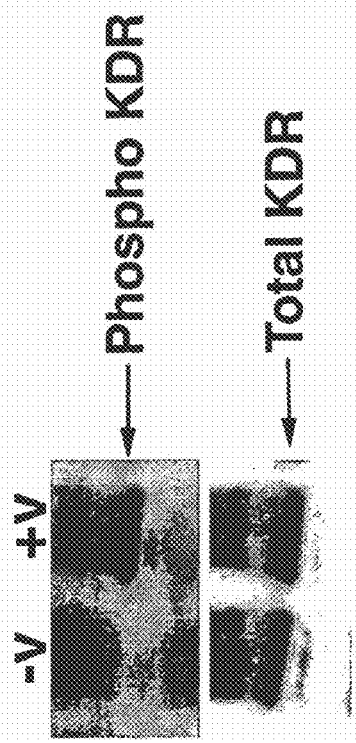
FIG. 11 depicts chemiluminescent detection on film demonstrating that activated (phosphorylated) KDR was not detected in immunoprecipitates from unstimulated (−V) HUVECs, but was abundant in immunoprecipitates from VEGF-stimulated (+V) HUVECs (upper panel). Reprobing the blot with anti-KDR demonstrated that comparable amounts of total KDR were present in both immunoprecipitates (lower panel).

Results: Immunoblots of KDR immunoprocipitates prepared from HUVECs with and without prior VEGF stimulation demonstrated that activated (phosphorylated) KDR could be detected when the HUVECs were stimulated with VEGF. An anti-phosphotyrosine antibody (PY-20) detected no phosphorylated proteins close to the migration position of KDR from unstimulated HUVECs on the blots, but after five minutes of VEGF stimulation, an intense band was consistently observed at the expected location (FIG. 11, upper panel). When the blots were stripped of bound antibodies by incubation in acidic solution then reprobed with an anti-KDR antibody (sc-315), the identity of the phosphorylated protein band was confirmed to be KDR. Moreover, it was observed that immunoprecipitates from unstimulated HUVECs contained about as much total KDR as immunoprecipitates from VEGF-stimulation HUVECs (FIG. 11, lower panel).

The foregoing results indicate that the phosphorylated KDR detected was formed from preexisting KDR through autophosphorylation of KDR dimers resulting from VEGF binding, as five minutes is not enough time to synthesize and process a large glycosylated cell-surface receptor such as KDR.

Figure 12:
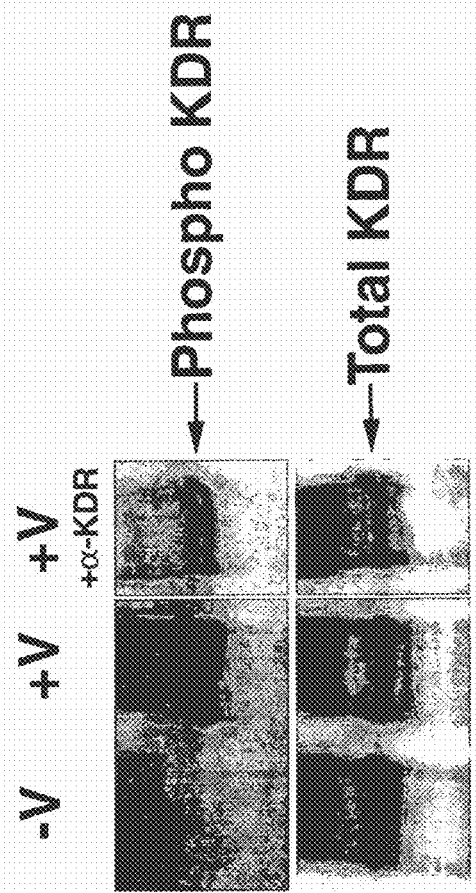
FIG. 12 depicts chemiluminescent detection on film demonstrating the ability of an anti-KDR antibody (1 µg/mL; indicated as "α-KDR") to partially block VEGF-mediated phosphorylation.

The ability of this assay to detect agents capable of blocking the VEGF activation of KDR was assessed by adding a series of compounds to HUVECs in combination with VEGF and measuring KDR phosphorylation with the immunoblot assay described above. As negative and positive controls, immunoprecipitates from unstimulated HUVECs and from HUVECs stimulated with VEGF in the absence of any test compounds were also tested in every assay. When a neutralizing anti-KDR antibody (Catalog #AF-357 from R&D Systems) was combined with the VEGF, the extent of KDR phosphorylation was greatly reduced (FIG. 12, upper panel), indicating that the antibody was able to interfere with the ability of VEGF to bind to and activate KDR. This result was expected since the ability of the antibody to block VEGF-induced DNA synthesis is part of the manufacturer's quality control testing of the antibody. Re-probing the blot with an anti-KDR antibody (FIG. 12, lower panel) indicated that slightly less total KDR was present in the VEGF+antibody-treated lane (+V+α-KDR) relative to the VEGF-only-treated lane (+V), but the difference was not great enough to account for the much lower abundance of phosphorylated KDR in the antibody-treated lane.

Figure 13:
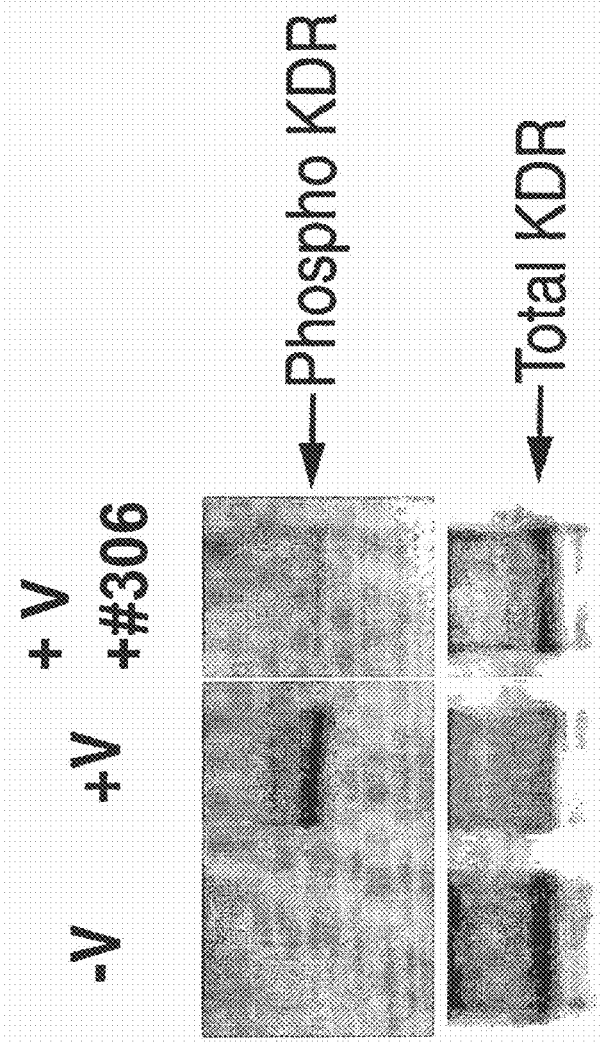
FIG. 13 depicts chemiluminescent detection on film demonstrating the ability of a KDR-binding polypeptide SEQ ID NO:306 (10 µM) to block VEGF-mediated KDR phosphorylation.

To assess the potency of a linear KDR-binding peptide (AFPRFGGDDYWIQQYLRYTD, SEQ ID NO:140) identified by phage display, the assay was repeated with a synthetic peptide containing the KDR-binding sequence, Ac-AQAF-PRFGGDDYWIQQYLRYTDGGGK-NH$_2$ (SEQ ID NO:306) in the presence of VEGF. SEQ ID NO:306 was able to inhibit the VEGF-induced phosphorylation of KDR. Re-probing the blot for total KDR showed that there is even more total KDR in the VEGF+SEQ ID NO:306-treated cells (+V+SEQ ID NO:306) than in the VEGF only-treated cells (+V) (FIG. 13, lower panel). Thus, it is clear that the decreased phosphorylation of KDR in the presence of SEQ ID NO:306 is; not due to differential sample loading, but rather the ability of the polypeptide to inhibit VEGF-activation of KDR.

Repeating the foregoing assay, the following polypeptides demonstrated at least a 50% inhibition of VEGF-induced KDR phosphorylation at 10 μM:

```
                                            (SEQ ID NO: 269)
    Ac-AGWIECYHPDGICYHFGTGGGK-NH₂

(SEQ ID NO: 267)
    Ac-AGWLECYAEFGHCYNFGTGGGK-NH₂

(SEQ ID NO: 294)
    Ac-GDSRVCWEDSWGGEVCFRYDPGGGK-NH₂

(SEQ ID NO: 366 having a blocked K)
    Ac-GDWWECK(ivDde)REEYRNTTWCAWADPGGGK-NH₂

(SEQ ID NO: 301)
    Ac-GDPDTCTMWGDSGRWYCFPADPGGGK-NH₂

(SEQ ID NO: 305)
    Ac-AQEPEGYAYWEVITLYHEEDGDGGK-NH₂

(SEQ ID NO: 306)
    Ac-AQAFPRPGGDDYWIQQYLRYTDGGK-NH₂

(SEQ ID NO: 307)
    Ac-AQGDYVYWEIIELTGATDHTPFGGK-NH₂.
```

SEQ ID NOS: 269 and 294 were the most potent compounds in the assay, producing at least a 50% inhibition of VEGF-induced KDR phosphorylation at 1 μM.

The following peptides were tested in the assay and did not produce significant inhibition of KDR activation at 10 μM:

```
                                            (SEQ ID NO: 264)
    Ac-AGPK(ivDde)WCEEDWYYCMITGTGGGK-NH₂

(SEQ ID NO: 314)
    Ac-GSDRHCYLHNGQWICYPFAPGGGK-NH₂

(SEQ ID NO: 293)
    Ac-GDYPWCHELSDSVTRFCVPWDPGGGK-NH₂

(SEQ ID NO: 295)
    Ac-GDDHMCRSPDYQDEWFCMYWDPGGGK-NH₂

(SEQ ID NO: 296)
    Ac-GDPPLCYFVGTQEWHHCNPFDPGQGK-NH₂

(SEQ ID NO: 299)
    Ac-GDGSWCEMRQDVGK(ivDde)WNCFSDDIPGGGK-NH₂

(SEQ ID NO: 331)
    Ac-AQRGDYQEQYWHQQLVEQLK(ivDde)LLGGGK-NH₂

(SEQ ID NO: 303)
    Ac-GDNWECGWSNMFQK(ivDde)EFCARPDPGGGK-NH₂

(SEQ ID NO: 367)
    Ac-AGPGPCK(ivDde)GYMPHQCWYMGTGGGK-NH₂

(SEQ ID NO: 322)
    Ac-AGYGPCAEMSPWLCWYPGTGGGK-NH₂.
```

In addition, tetrameric complexes of biotinylated derivatives of SEQ ID NOS:294 and 277 (prepared as described above) produced at least a 50% inhibition of VEGF-induced KDR phosphorylation at 10 nM.

Example 10

Binding of Tc-Labeled SEQ ID NO:339 to KDR-Transfected 293H Cells

The ability of Tc-labeled SEQ ID NO:339 to bind KDR was assessed using KDR-transfected 293H cells. Tc-labeled SEQ ID NO:277 (i.e., Ac-AGPTW CEDDWYYCWLFGT-GGGK (N,N-dimethyl-Gly-Ser-Cys-Gly-di(aminodioxaocta-))-NH$_2$) bound significantly better to KDR transfected 293H cells than to mock transfected 293H cells and binding increased with concentration of Tc-labeled SEQ ID NO:339 in a linear manner.

Preparation of Peptidic Chelate for Binding to Tc by SPPS (FIG. 35)

To a 250 mL of SPPS reaction vessel was added 6.64 mmol of H-Gly-2-Cl-trityl resin (0.84 mmol/g, Novabiochem). It was swelled in 80 mL of DMF for 1 h. For each coupling cycle the resin was added 26.6 mmol of DIEA, 26.6 mmol of a Fmoc-amino acid in DMF (EM Science), 26.6 mmol of HOBT Novabiochem) in DMF, and 26.6 mmol of DIC. The total volume of DMF was 80 mL. The reaction mixture was shaken for 4 h. The resin then was filtered and washed with DMF (3×80 ml). A solution of 20% piperidine in DM (80 mL) was added to the resin and it was shaken for 10 min. The resin was filtered and this piperidine treatment was repeated. The resin finally was washed with DMF (3×80 mL) and ready for next coupling cycle. At the last coupling cycle, N,N-dimethyl glycine (Aldrich) was coupled using HATU/DIEA activation. Thus, to a suspension of N,N-dimethyl glycine (26.6 mmol) in DMF was added a solution of 26.6 mmol of HATU (Perseptive Biosystems) in DMF and 53.1 mmol of DIEA. The clear solution was added to the resin and shaken for 16 h. Following the synthesis, the resin was filtered and washed with DMF (3×80 mL), CH$_2$Cl$_2$ (3×80 mL) and dried. The resin was mixed with 80 mL of AcOH/CF$_3$CH$_2$OH/DCM (1/1/8, v/v/v) and shaken for 45 min. The resin was filtered and the filtrate was evaporated to a paste. Purification of the crude material by silica gel chromatography using 25% MeOH/DCM afforded 2.0 g of the final product.

Coupling of the Peptidic Chelate to the Peptide (Fragment Coupling)

Diisopropylcarbodiimide (0.0055 mmol) was added to a mixture of purified Me$_2$N-Gly-Cys-(Trt)-Ser(tBu)-Gly-OH and hydroxybenzotriazole (0.055 mmol) in DMF (0.25 mL), and the mixture was stirred at RT for 6 h. The peptide (0.005 mmol) in DMF (0.25 mL) was then added to the reaction mixture, and stirring was continued for an additional 6 h. DMF was removed under vacuum and the residue was treated with reagent B and stirred for 3 h. TFA was removed under reduced pressure and the residue was purified by preparative HPLC using acetonitrile-water containing 0.1% TFA. Fractions containing the pure product were collected and freeze dried to yield the peptide. The peptide was characterized by ES-MS and the purity was determined by RP-HPLC (acetonitrile-water/0.1% TFA) gradient.

Synthesis of $^{99m}$Tc-Labeled SEQ ID NO:339

A stannous gluconate solution was prepared by adding 2 mL of a 20 µg/mL SnCl$_2$.2H$_2$O solution in nitrogen-purged 1N HCl to 1.0 mL of nitrogen-purged water containing 13 mg of sodium glucoheptonate. To a 4 mL autosampler vial was added 20-40 µl (20-40 µg) of SEQ ID NO:339 ligand dissolved in 50/50 ethanol/H$_2$O, 6-12 mCi of $^{99m}$TcO$_4^-$ in saline and 100 µl of stannous glucoheptonate solution. The mixture was heated at 100° C. for 22 min. The resulting radiochemical purity (RCP) was 10-47% when analyzed using a Vydac C18 Peptide and Protein column that was eluted at a flow rate of 1 mL/min. with 66% H$_2$O (0.1% TFA)/34% ACN (0.085% TFA). The reaction mixture was purified by HPLC on a Vydac C18 column (4.6 mm×250 mm) at a flow rate of 1 mL/min., using 0.1% TFA in water as aqueous phase and 0.085% TFA in acetonitrile as the organic phase. The following gradient was used: 29.5% org. for 35 min., ramp to 85% over 5 min., hold for 10 min. The fraction containing $^{99m}$Tc SEQ ID NO:339 was collected into 500 µl of a stabilizing buffer containing 5 mg/mL ascorbic acid and 16 mg/mL hydroxypropyl-α-cyclodextrin in 50 mM phosphate buffer. The mixture was concentrated using a speed vacuum apparatus to remove acetonitrile, and 200 µl of 0.1% HSA in 50 mM pH 5 citrate buffer was added. The resulting product had an RCP of 100%. Prior to injection into animals, the compound was diluted to the desired radioconcentration with normal saline.

Transfection of 293H Cells 293H cells were transfected using the protocol described above. Transfection was done in black/clear 96-well plates (Becton Dickinson, cat. #354640). The left half of the plates (48 wells) were mock-transfected (with no DNA) and the right half of the plate was transfected with KDR cDNA. The cells were 80-90% confluent at the time of transfection and completely confluent the next day, at the time of the assay; otherwise the assay was aborted.

Preparation of Opti-MEMI Media with 0.1% HSA

Opti-MEMI was obtained from Invitrogen (cat. #11058-021) and human serum albumin (HSA) was obtained from Sigma (cat. # A-3782). To prepare opti-MEMI media with 0.1% HSA, 0.1% w/v HSA was added to opti-MEMI, stirred at room temperature for 20 min. and then filter sterilized using 0.2 µm filter.

Preparation of Tc-Labeled SEQ ID NO:339 Dilutions for the Assay

Stock solution of Tc-labeled SEQ ID NO:339 (117 µCi/mL) was diluted 1:100, 1:50, 1:25 and -1:10 in opti-MEMI with 0.1% HSA to provide solutions with final concentration of 1.17, 2.34, 4.68 and 11.7 µCi/mL of Tc-labeled. SEQ ID NO:339.

Assay to Detect the Binding of Tc-Labeled SEQ ID NO:339

Cells were used 24 hours after transfection, and to prepare the cells for the assay, they were washed once with 100 µl of room temperature opti-MEMI with 0.1% HSA. After washing, the opti-MEMI with 0.1% HSA was removed from the plate and replaced with 70 µl of 1.17, 2.34, 4.68 and 11.7 µCi/mL of Tc-labeled SEQ ID NO:339 (prepared as above). Each dilution was added to three separate wells of mock- and KDR-transfected cells. After incubating at room temperature for 1 hour, the plates were transferred to 4° C. for 15 minutes and washed 5 times with 100 µl of cold binding buffer (opti-MEMI with 0.1% HSA), gently blotted dry and checked under a microscope for cell loss. 100 µl of solubilizing solution (2% Triton X-100, 10% Glycerol, 0.1% BSA) was added to each well and the plates were incubated at 37° C. for 10 minutes. The solubilizing solution in each well was mixed by pipeting up and down, and transferred to 1.2 ml tubes. Each well was washed once with 100 µl of solubilizing solution and the washes were added to the corresponding 1.2 mL tube. Each 1.2 mL tube was then transferred to a 15.7×100 cm tube to be counted in an LKB Gamma Counter using program 12 (Tc-window for 20 sec).

Binding of Tc-Labeled SEQ ID NO:339 to KDR Transfected Cells

The ability of Tc-labeled SEQ ID NO:339 to specifically bind to KDR was assessed using transiently transfected 293H cells.

Figure 14:
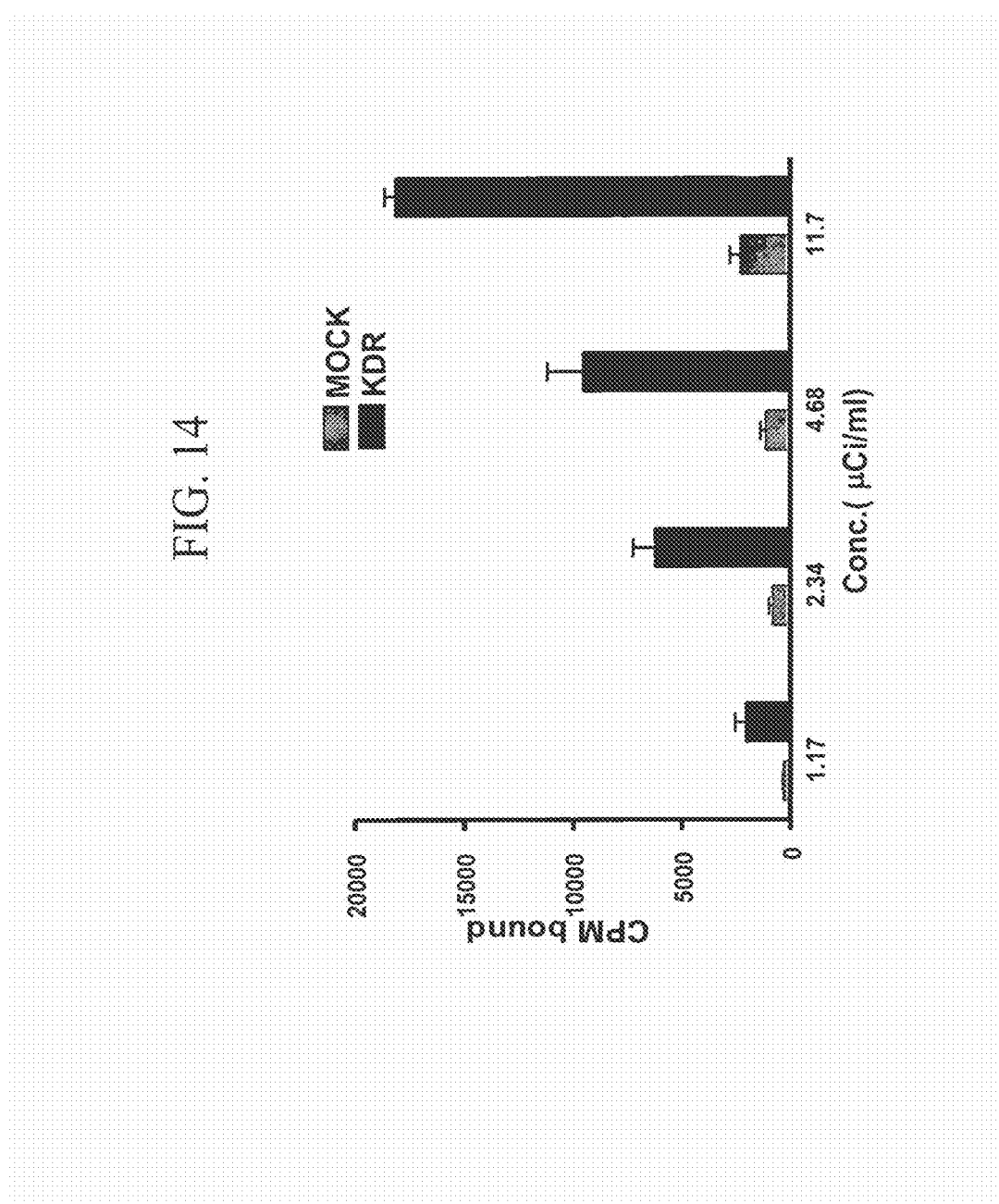
FIG. 14 is a bar graph showing binding of a Tc-labeled polypeptide (SEQ ID NO:339) to KDR-transfected 293H cells.
Figure 96:
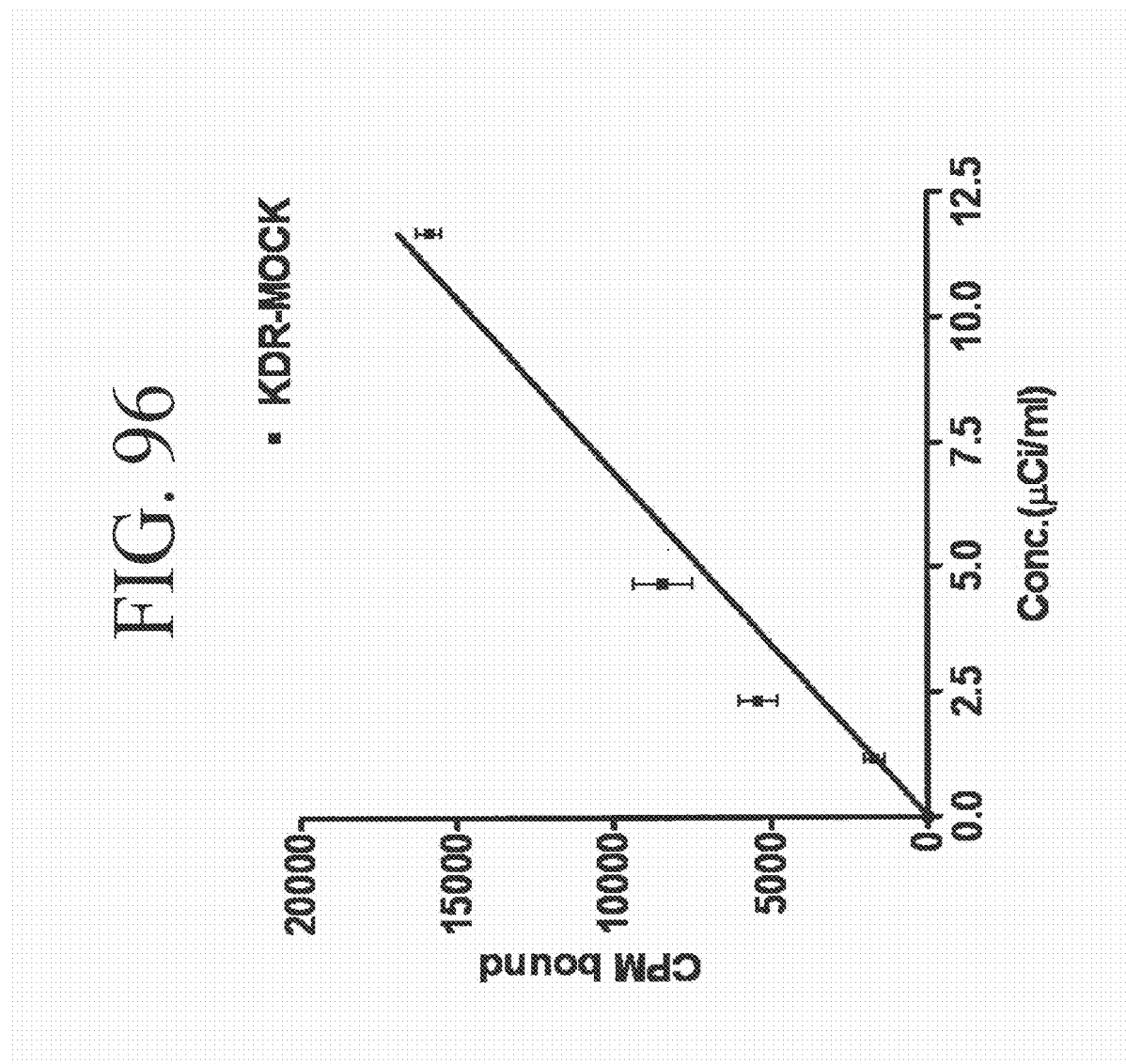
FIG. 96 is a graph showing the specific binding of a Tc-labeled polypeptide (SEQ ID NO:339) to KDR-transfected 293H cells after subtracting the binding to mock-transfected 293H cells.

As shown in FIG. 14, Tc-labeled SEQ ID NO:339 bound significantly better to KDR transfected 293H cells as compared to mock transfected 293H cells. To calculate specific binding to KDR, the binding of Tc-labeled SEQ ID NO:339 polypeptide to mock-transfected cells was subtracted from the binding to KDR-transfected cells. A linear increase in the specific binding of Tc-labeled SEQ ID NO:339 to KDR was observed with increasing concentration of Tc-labeled SEQ ID NO:339 (FIG. 96). Linear binding was not surprising because concentration of Tc-labeled SEQ ID NO:339 was only ~100 pM (even at the highest concentration, 11.7 µCi/mL, tested in the assay), which is far below the $K_D$ value of ~3-4 nM of SEQ ID NO:277 (as calculated using avidin HRP assay), so no saturation of binding would be expected.

Example 11

Preparation of Peptides and Dimeric Peptide Construction

The following methods were used for the preparation of individual peptides and dimeric peptide constructs described in the following Examples (11-15).

Automated Peptide Synthesis

Peptide synthesis was carried out on a ABI-433A Synthesizer (Applied Biosystems Inc., Foster City, Calif.) on a 0.25 mmol scale using the FastMoc protocol. In each cycle of this protocol preactivation was accomplished by dissolution of 1.0 mmol of the requisite dry $N^\alpha$-Fmoc side-chain protected amino acid in a cartridge with a solution of 0.9 mmol of HBTU, 2 mmol of DIEA, and 0.9 mmol of HOBt in a DMF-NMP mixture. The peptides were assembled on NovaSyn TGR (Rink amide) resin (substitution level 0.2 mmol/g). Coupling was conducted for 21 min. Fmoc deprotection was carried out with 20% piperidine in NMP. At the end of the last cycle, the N-terminal Fmoc group was removed and the fully protected resin-bound peptide was acetylated using acetic anhydride/DIEA/HOBt/NMP.

Cleavage, Side-Chain Deprotection and Isolation of Crude Peptides

Cleavage of the peptides from the resin and side-chain deprotection was accomplished using Reagent B for 4.5 h at ambient temperature. The cleavage solutions were collected and the resins were washed with an additional aliquot of Reagent B. The combined solutions were concentrated to dryness. Diethyl ether was added to the residue with swirling or stirring to precipitate the peptides. The liquid phase was decanted, and solid was collected. This procedure was repeated 2-3 times to remove impurities and residual cleavage cocktail components.

Cyclization of Di-Cysteine Peptides

The crude ether-precipitated linear di-cysteine containing peptides were cyclized by dissolution in water, mixtures of aqueous acetonitrile (0.1% TFA), aqueous DMSO or 100% DMSO and adjustment of the pH of the solution to 7.5-8.5 by addition of aqueous ammonia, aqueous ammonium carbonate, aqueous ammonium bicarbonate solution or DMA. The mixture was stirred in air for 16-48 h, acidified to pH 2 with aqueous trifluoroacetic acid and then purified by preparative reverse phase HPLC employing a gradient of acetonitrile into water. Fractions containing the desired material were pooled and the purified peptides were isolated by lyophilization.

Preparation of Peptides Containing Linkers

In a typical experiment, 400 mg of the resin-bound peptide bearing an ivDde-protected lysine) was treated with 10% hydrazine in DMF (2×20 mL). The resin was washed with DMF (2×20 mL) and DCM (1×20 mL). The resin was resuspended in DMF (10 mL) and treated with Fmoc-8-amino-3,6-dioxaoctanoic acid (0.4 mmol), HOBt (0.4 mmol), DIC (0.4 mmol) and DIEA (0.8 mmol) with mixing for 4 h. After the reaction, the resin was washed with DMF (2×10 mL) and with DCM (1×10 mL). The resin was then treated with 20% piperidine in DMF (2×15 ml) for 10 min each time. The resin was washed and the coupling with Fmoc-8-amino-3,6-dioxaoctanoic acid and Fmoc protecting group removal were repeated once more.

The resulting resin-bound peptide with a free amino group was washed and dried and then treated with reagent B (20 mL) for 4 h. The mixture was filtered and the filtrate concentrated to dryness. The residue was stirred with ether to produce a solid, which was washed with ether and dried. The solid was dissolved in anhydrous DMSO and the pH adjusted to 7.5 with DIEA. The mixture was stirred for 16 h to effect the disulfide cyclization and the reaction was monitored by analytical HPLC. After completion of the cyclization, the reaction mixture was diluted with 25% acetonitrile in water and applied directly to a reverse phase C-18 column. Purification was effected using a gradient of acetonitrile into water (both containing 0.1% TFA). Fractions were analyzed by HPLC and those containing the pure product were combined and lyophilized to provide the required peptide.

Preparation of Biotinylated Peptides Containing Linkers

In a typical experiment, 400 mg of the resin-bound peptide bearing an ivDde-protected lysine, was treated with 10% hydrazine in DMF (2×20 mL). The resin was washed with DMF (2×20 mL) and DCM (1×20 ml). The resin was resuspended in DMF (10 mL) and treated with Fmoc-8-amino-3,6-dioxaoctanoic acid (0.4 mmol), HOBt (0.4 mmol), DIC (0.4 mmol) and DIEA (0.8 mmol) with mixing for 4 h. After the reaction, the resin was washed with DMF (2×10 ml) and with DCM (1×10 mL). The resin was then treated with 20% piperidine in DMF (2×15 mL) for 10 min each time. The resin was washed and the coupling with Fmoc-8-amino-3,6-dioxaoctanoic acid and removal of the Fmoc protecting group were repeated once more.

The resulting resin-bound peptide with a free amino group was treated with a solution of Biotin-NHS ester (0.4 mmol, 5 equiv.) and DIEA (0.4 mmol, 5 equiv.) in DMF for 2 h. The resin was washed and dried as described previously and then treated with Reagent B (20 mL) for 4 h. The mixture was filtered and the filtrate concentrated to dryness. The residue was stirred with ether to produce a solid that was collected, washed with ether, and dried. The solid was dissolved in anhydrous DMSO and the pH adjusted to 7.5 with DIEA. The mixture was stirred for 4-6 h to effect the disulfide cyclization, which was monitored by HPLC. Upon completion of the cyclization, the reaction mixture was diluted with 25% acetonitrile in water and applied directly to a reverse phase C-18 column. Purification was effected using a gradient of acetonitrile into water (both containing 0.1% TFA). Fractions were analyzed by HPLC and those containing the pure product were collected and lyophilized to provide the required biotinylated peptide.

Preparation of DOTA-Conjugated Peptides for Labeling with Selected Gadolinium or Indium Isotopes In a typical experiment, 400 mg of the resin-bound peptide bearing an $N^\epsilon$-ivDde-protected lysine moiety was treated with 10% hydrazine in DMF (2×20 mL). The resin was washed with DMF (2×20 mL) and DCM (1×20 mL). The resin was resuspended in DMF (10 mL) and treated with Fmoc-8-amino-3,6-dioxaoctanoic acid (0.4 mmol), HOBt (0.4 mmol), DIC (0.4 mmol), DIEA (0.8 mmol) with mixing for 4 h. After the reaction, the resin was washed with DMF (2×10 mL) and with DCM (1×10 mL). The resin was then treated with 20% piperidine in DMF (2×15 mL) for 10 min each time. The resin was washed and the coupling with Fmoc-8-amino-3,6-dioxaoctanoic acid and removal of the Fmoc protecting group were repeated once. The resulting resin-bound peptide with a free amino group was resuspended in DMF (10 mL) and treated with a solution of 1,4,7,10-tetraazacyclododecane-1,4,7,10-tetraacetic acid-1,4,7-tris-t-butyl ester (DOTA-tris-t-butyl ester, 0.4 mmol, 5 equiv.), HOBt (0.4 mmol), DIC (0.4 mmol) and DIEA (0.8 mmol) in DMF (10 mL) with mixing for 4 h. Upon completion of the reaction, the resin was washed with DMF (2×10 mL) and with DCM (1×10 mL) and treated with Reagent B (20 mL) for 4 h. The mixture was filtered and the filtrate concentrated to dryness. The residue was stirred in ether to produce a solid that was collected, washed with ether, and dried. The solid was dissolved in anhydrous DMSO and the pH adjusted to 7.5 with DIEA. The mixture was stirred for 16 h to effect the disulfide cyclization, which was monitored by HPLC. Upon completion of the cyclization, the mixture was diluted with 25% acetonitrile in water and applied directly to a reverse phase C-18 HPLC column. Purification was effected using a gradient of acetonitrile into water (both containing 0.1% TFA). Fractions were analyzed by HPLC and those containing the pure product were combined and lyophilized to provide the required biotinylated peptide.

The following monomeric peptides of Table 11 were prepared by the above methods, "PnAO6", as used herein, refers to 3-(2-amino-3-(hydroxyimino-1,1-dimethyl-propylamino)-propylamino)-3-methylbutan-2-one oxime.

TABLE 11

Sequence or Structure of Monomeric Peptides and Peptide Derivatives

| Structure or Sequence | SEQ. ID NO: or dimer |
|---|---|
| Ac-AGPTWCEDDWYYCWLFGTGGGK(BiotinJJ-K)-NH$_2$ | 277 |
| (Ac-AGPTWCEDDWYYCWLFGTGGGKK(BiotinJJ)- NH$_2$) | 373 |
| Ac-AGPTWCEDDWYYCWLFGTJK(DOTAJJ-K)-NH$_2$ | 493 |
| Ac-AGPTWCEDDWYYCWLFGTJK(JJ)-NH$_2$ | 493 |
| Ac-AGPTWCEDDWYYCWLFGTGCGK[K(ivDde)]-NH$_2$ | 373 |
| Ac-VCWEDSWGGEVCFRYDPGGGK(Biotin-JJK)-NH$_2$ | 337 |
| (Ac-VCWEDSWGGEVCFRYDPGGGKK(Biotin-JJ)-NH$_2$) | 494 |
| Ac-VCWEDSWGGEVCFRYDPGGGK(JJ)-NH$_2$ | 337 |
| Ac-AQDWYYDEILSMADQLRHAFLSGGGGGK(J)-NH$_2$ Seq 12 derivative | 356 |
| Ac-AQDWYYDEILSMADQLRHAFLSGGGGGKK(ivDde) Application seq 12 derivative | 495 |
| Ac-GDSRVCWEDSWGGEVCFRYDPGGGK(JJ)-NH$_2$ Seq 5 derivative | 294 |
| Ac-GDSRVCWEDSWGGEVCFRYDPGGGK(JJ)-NH$_2$ Seq 5 deriv | 294/D10 |
| Ac-AGPTWCEDDWYYCWLFGTGGGK[(PnAO6-C(=O)(CH$_2$)$_3$O(=O)-K]-NH$_2$ A Seq 11 derivative | 277/D10 |
| Ac-AGPTWCEDDWYYCWLFGTGGGK[(DOTA-JJK(iV-Dde)]-NH2 A Seq 11 derivative | 277/D11 |
| Ac-AGPTWCEDDWYYCWLFGTGGGK[(PnAO6-C(=O)(CH$_2$)$_3$C(=O))K]-NH$_2$ A Seq 11 derivative | 476/D12 |
| Ac-VCWEDSWGGEVCFRYDPGGGK-NH$_2$ A Seq 5 derivative specifically: Seq 5 residues 5-25 | 337/D12 |
| Ac-AGPTWCEDDWYYCWLFGTGGGK[K(BOA)]-NH$_2$ Seq 11 derivative | 277/D13 |
| Ac-AQDWYYDEISMADQLRHAFLSGGGGK[PnAO6-C(=O)(CH$_2$)$_3$C(=O)-K(iV-Dde)]-NH$_2$ Application seq 12 derivative | 356/D14 |
| Ac-GDSRVCWEDSWGGEVCFRYDPGGGK(JJ)-NH$_2$ Seq 5 deriv linker = Glut | 294/D15 |
| Ac-AGPTWCEDDWYYCWLFGTGGGK-[PnAO6-C(=O)(CH$_2$)$_3$C(=O)-K]-NH$_2$ A Seq 11 derivative, new sequence | 277/D16 |

TABLE 11-continued

Sequence or Structure of Monomeric Peptides and Peptide Derivatives

| Structure or Sequence | SEQ. ID NO: or dimer |
|---|---|
| Ac-AQDWYYEILJGRGGRGGRGGK[K(ivDde)]-NH$_2$<br>A Seq 12(1-9) derivative | 496/D17 |
| Ac-APGTWCDYDWEYCWLGTFGGGK[(6PnAO-<br>C(=O)(CH$_2$)$_3$C(=O)-K]-NH$_2$ A scrambled Seq 11<br>derivative used as a control. | 497/D18 |
| Ac-GVDFRCEWSDWGEVGCRSPDYGGGK(JJ)-NH$_2$ A<br>scrambled Seq 5 derivative. | 489/D18 |
| Ac-AGPTWCEDDWYYCWLFGTGGGK(Biotin-K)-NH$_2$,<br>A Seq 11 derivative | 294/D19 |
| JJAGPTWCEDDWYYCWLFGTGGGK(iV-Dde)-NH$_2$<br>(SEQ ID NO: 277) | 277/D20 |
| JJVCWEDSWGGEVCFRYDPGGG-NH$_2$ | 370/D20 |
| JJAGPTWCEDDWYYCWLFGTGGGK(iV-Dde)-NH$_2$ | 277/D21 |
| Ac-AGPTWCEDDWYYCWLFGTGGGK[K(SATA)]-NH$_2$ | 373/D22 |
| Ac-AGPTWCEDDWYYCWLGTGGGK[SATA-JJ-K]-NH$_2$ | 339/D23 |
| Ac-GDSRVCWEDSWGGEVCFRYDPGGGK(JJ)-NH$_2$ | 294/D24 |
| H$_2$N-AGPTWCEDDWYYCWLFGTGGGK[K(iV-Dde)]-NH$_2$ | 373/D25 |
| Ac-AGPTWCEDDWYYCWLFGTGGGK{Biotin-JJK[NH$_2$-<br>Ser(GalNAc(Ac)$_3$-alpha-D)-Gly-Ser(GalNAc<br>(Ac)$_3$alpha-D]}-NH$_2$ | 339/D26 |
| Ac-VCWEDSWGGEVCFRYDPGGGK(NH$_2$-Ser(GalNAc(Ac)$_3$-<br>alpha-D)-Gly-Ser(GalNAc(Ac)$_3$-alpha-D)-NH$_2$ | 337/D26 |
| Ac-GSPEMCMMFPFLYPCNHHAPGGGK[(PnAO6)-<br>C(=O)(CH$_2$)$_3$C(=O)-K]}-NH$_2$ A modified cMet<br>Binding Sequence | 482/D27 |

Example 12

Preparation of Homodimeric and Heterodimeric Constructs

The purified peptide monomers mentioned above in Example 8 were used in the preparation of various homodimeric and heterodimeric constructs.

Preparation of Homodimer-Containing Constructs

To prepare homodimeric compounds, half of the peptide needed to prepare the dimer was dissolved in DMF and treated with 10 equivalents of glutaric acid bis-N-hydroxysuccinimidyl ester. The progress of the reaction was monitored by HPLC analysis and mass spectroscopy. At completion of the reaction, the volatiles were removed in vacuo and the residue was washed with ethyl acetate to remove the unreacted bis-NHS ester. The residue was dried, redissolved in anhydrous DMF and treated with another half portion of the peptide in the presence of 2 equivalents of DIEA. The reaction was allowed to proceed for 24 h. This mixture was applied directly to a YMC reverse phase HPLC column and purified by elution with a linear gradient of acetonitrile into water (both containing 0.1% TFA).

Preparation of Heterodimer-Containing Constructs

In the case of heterodimers, one of the monomers ("A") was reacted with the bis-NHS ester of glutaric acid and after washing off the excess of bis-NHS ester (as described for the homodimeric compounds), the second monomer ("B") was added in the presence of DIEA. After the reaction the mixture was purified by preparative HPLC. Typically, to a solution of glutaric acid bis N-hydroxysuccinimidyl ester (0.02 mmol, 10 equivalents) in DMF (0.3 mL) was added a solution of peptide "A" and DIEA (2 equiv) in DMF (0.5 mL) and the mixture was stirred for 2 h. The progress of the reaction was monitored by HPLC analysis and mass spectroscopy. At completion of the reaction, the volatiles were removed in vacuo and the residue was washed with ethyl acetate (3×1.0 mL) to remove the unreacted bis-NHS ester. The residue was dried, re-dissolved in anhydrous DMF (0.5 mL) and treated with a solution of peptide "B" and DIEA (2 equiv) in DMF (0.5 mL) for 24 h. The mixture was diluted with water (1:1, v/v) and applied directly to a YMC C-18 reverse phase HPLC column and purified by elution with a linear gradient of acetonitrile into water (both containing 0.1% TFA). Fractions were analyzed by analytical HPLC and those containing the pure product were combined and lyophilized to obtain the required dimer. The dimers depicted in FIGS. 36-63 were prepared by this method (structure, name, compound reference number as described in the "Brief Description of the Drawings").

For the preparation of the dimer D5, after the coupling reaction of the individual peptides, 50 μL of hydrazine was added to the reaction mixture (to expose the lysine N$^\epsilon$-amino group) and the solution was stirred for 2 min. The reaction mixture was diluted with water (1.0 mL) and the pH was adjusted to 2 with TFA. This was then purified by the method described above.

The HPLC analysis data and mass spectral data for the dimeric peptides are given in Table 12 below.

TABLE 12

Analytical Data for Homodimeric and Heterodimeric Peptide Constructs
HPLC Analysis System

| | Retention Time (System) | Mass Spectral data (API-ES, -ion) |
|---|---|---|
| D1 | 8.98 min. (A) | 1987.7 (M − 3H)/3, 1490.6 (M − 4H)/4, 1192.3 (M − 5H)/5 |
| D2 | 16.17 min (B) | 2035.3 (M − 3H)/3, 1526.1 (M − 4H)/4, 1220.7 (M − 5H)/5 |
| D3 | 8.74 min (C) | 1933.6 (M − 3H)/3, 1449.9 (M − 4H)/4, 1159.4 (M − 5H)/5 |
| D4 | 10.96 min (D) | 2032.8 (M − 3H)/3 |
| D5 | 6.57 min (E) | 1816.2 (M − 3H)/3, 1361.8 (M − 4H)/4, 1089.4 (M − 5H)/5, 907.7 (M − 6H)/6 |
| D6 | | |
| D7 | | |
| D8 | 4.96 min; (F) | 2379.3 [M − 3H]/3 |
| D9 | 5.49 min; (G) | 2146.4 [M − 3H]/3 |
| D10 | 5.44 min; (H) | 2082.7 [M − 3H]/3, 1561.7 [M − 4H]/4, 1249.1 [M − 5H]/5, 1040.7 [M − 6H]/6 |
| D11 | 7.23 min; (E) | 2041.8 [M − 3H]/3, 1531.1 [M − 4H]/4, 1224.6 [M − 5H]/5 |
| D12 | 5.84 min; (H) | 1877.1 [M − 3H]/3, 1407.6 [M − 4H]/4, 1125.9 [M − 5H]/5, 938.1 [M − 6H]/6. |
| D13 | 5.367 min; (E) | 1965.3 [M − 3H]/3, 1473.8 [M − 4H]/4, 1178.8 [M − 5H]/5, 982.2 [M − 6H]/6 |
| D14 | 4.78 min; (I) | 2275.0 [M − 3H]/3, 1362.8 [M − 5H]/5 |
| D15 | 5.41 min; (H) | 1561.3 [M − 4H]/4, 1249.1 [M − 5H]/5, 1040.8 [M − 6H]/6, 891.8 [M − 7H]/7. |
| D16 | 5.44 min; (J) | 2150.8 [M − 3H]/3, 1613.1 [M − 4H]/4, 1289.9 [M − 5H]/5, 1074.8 [M − 6H]/6, 920.9 [M − 7H]/7. |
| D17 | 4.78 min; (K) | 1789.4 [M − 3H]/3, 1347.7 [M − 4H]/4. |
| D18 | 4.74 min; (L) | 2083.1 [M − 3H]/3, 1562.7 [M − 4H]/4, 1249.5 [M − 5H]/5. |
| D19 | 7.13 min; (O) | 1891.9 [M − 3H]/3, 1418.4 [M − 4H]/4, 1134.8 [M − 5H]/5, 945.5 [M − 6H]/6. |
| D20 | 9.7 min; (P) | 2700.4 [M − 2H]/2, 1799.3 [M − 3H]/3 |
| D21 | 6.1 min; (P) | 2891.3 [M − 2H]/2, 1927.2 [M − 3H]/3, 1445.1 [M − 4H]/4, 1155.8 [M − 5H]/5. |
| D22 | 6.23 min; (Q) | 1994.4 [M − 3H]/3, 1495.7 [M − 4H]/4, 1196.3 [M − 5H]/5 |
| D23 | 7.58 min; (J) | 1854.4 [M − 3H]/3, 1390.8 [M − 4H]/4, 1112.7 [M − 5H]/5, 927 [M − 6H]/6 |
| D24 | 8.913 min; (R) | 1952.1 [M − 3H]/3, 1463.4 [M − 4H]/4, 1171.1 [M − 5H]/5, 975.3 [M − 6H]/6 |
| D25 | 5.95 min; (E) | 1954.9 [M − 3H]/3, 1466.1 [M − 4H]/4, 1172.4 [M − 5H]/5, 976.8 [M − 6H]/6. |
| D26 | 6.957 min; (S) | 1759.1 [M − 3H]/3, 1319.6 [M − 4H]/4, 1055.1 [M − 5H]/5 |
| D27 | 5.5 min; (M) | 2317.6 [M − 3H]/3, 1737.2 [M − 4H]/4, 1389.3 [M − 5H]/5, 1157.7 [M − 6H]/6 |
| D30 | 4.29 min (T) | [M + H]: 5782.3, [M + 4H]/4: 1146.6, [M + 5H]/5: 1157.4, [M + 6H]/6: 964.7 |
| D31 | 6.6 min (U) | [M − 3H]/3: 2045.3. |
| Monomer Compound 2 | 6.0 min (U) | [M − 2H]/2: 1307.4 |
| Monomer Compound 4 (SEQ ID NO: 374-related sequence) | 5.3 min (U) | [M − 2H]/2: 1307.4 |

TABLE 13

Dimer sequences and linkers

| Dimer # | Sequence |
|---|---|
| D1 (FIG. 36) | Ac-AGPTWCEDDWYYCWLFGTGGGK(SEQ ID NO: 277)[(Biotin-JJK-(O=)C(CH₂)₃C(=O)-JJ-NH(CH₂)₄-(S)-CH((Ac-VCWEDSWGGEVCFRYDPGGGK(SEQ ID NO: 337))-NH)CONH₂]-NH₂) |
| D2 (FIG. 37) | Ac-AGPTWCEDDWYYCWLFGTGGGK(SEQ ID NO: 277)[(Biotin-JJK-(O=)C(CH₂)₃C(=O)-JJ-NH(CH₂)₄-(S)-CH((Ac-AGPTWCEDDWYYCWLFGTJK (SEQ ID NO: 493))-NH)CONH₂]-NH₂ |
| D3 (FIG. 38) | Ac-VCWEDSWGGEVCFRYDPGGGK(SEQ ID NO: 337)[(Biotin-JJK-(O=)C(CH₂)₃C(=O)-JJ-NH(CH₂)₄-(S)-CH((Ac-VCWEDSWGGEVCFRYDPGGGK(SEQ ID NO: 337))-NH)CONH₂]-NH₂ |
| D4 (FIG. 39) | Ac-AGPTWCEDDWYYCWLFGTJK(SEQ ID NO: 338)[DOTA-JJK-(O=)C(CH₂)₃C(=O)-JJ-NH(CH₂)₄-(S)-CH((Ac-VCWEDSWGGECFRYDPGGGK(SEQ ID NO: 337))-NH)CONH₂]-NH₂ |

TABLE 13-continued

Dimer sequences and linkers

Figure 64:
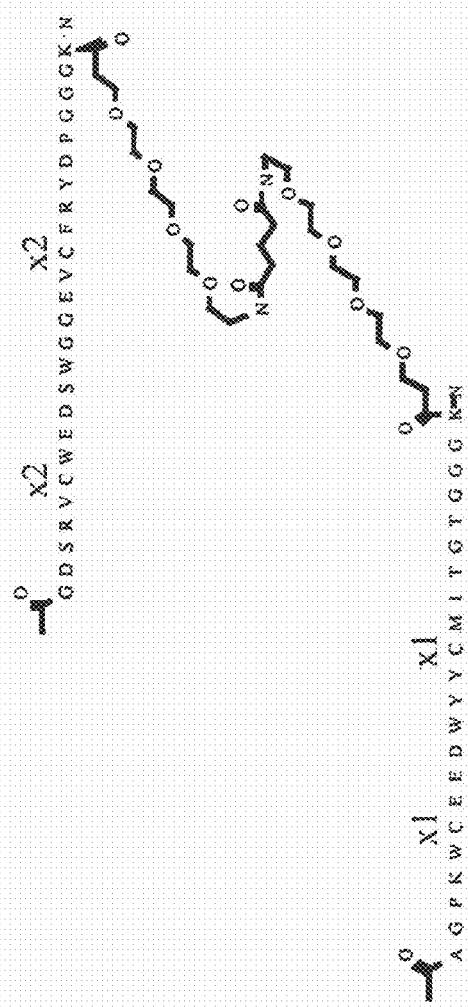
FIG. 64 shows dimer 7 (D7; comprising GDSRVCWED-SWGGEVCFRYDPGG (SEQ ID NO:294) and AGPKW-CEEDWYYCMITGTGGGK (SEQ ID NO:264)).

| Dimer # | Sequence |
|---|---|
| D5 (FIG. 40) | Ac-VCWEDSWGGEVCFRYDPGGGK(SEQ ID NO: 337)(JJ-C(=O)(CH$_2$)$_3$C(=O)—K—NH(CH$_2$)$_4$—(S)—CH((Ac-AGPTWCEDDWYYCWLFGTGGGK(SEQ ID NO: 277))-NH)CONH$_2$)—NH$_2$ |
| D6 (FIG. 63) | GDSRVCWEDSWGGEVCFRYDFGGGK (SEQ ID NO: 294) - AGPTWCEDDWYYCWLFGTGGGK (SEQ ID NO: 277) (see FIG. 63 for linkage) |
| D7 (FIG. 64) | GDSRVCWEDSWGGEVCFRYDPGGGK (SEQ ID NO: 294) - AGPKWCEEDWYYCMITGTGGGK (SEQ ID NO: 264) (see FIG. 64 for linkage) |
| D8 (FIG. 41) | Ac-AQDWYYDEILSMADQLRHAFLSGGGGGK{Ac-AQDWYYDEILSMADQLRHAFLSGGGGGK(J-Glut)-NH$_2$}K(Biotin-JJ)-NH$_2$ |
| D9 (FIG. 42) | Ac-AQDWYYDEILSMADQLRHAFLSGGGGGK{[Ac-GDSRVCWEDSWGGEVCFRYDFGGGK(JJ-Glut-)]-NH$_2$}K—NH$_2$ |
| D10 (FIG. 43) | Ac-AGPTWCEDDWYYCWLFGTGGGK[Ac-GDSRVCWEDSWGGEVCFRYDPGGGK(JJ-Glut-NH(CH$_2$)$_4$—(S)—CH(PnAO6-Glut-NH)(C=O—)]-NH$_2$]-NH$_2$ |
| D11 (FIG. 44) | Ac-AGPTWCEDDWYYCWLFGTGGGK{Ac-VCWEDSWGGEVCFRYDPGGGK[JJ-Glut-NH(CH$_2$)$_4$—(S)—CH(DOTA-JJ-NH—)(C=O)-NH$_2$}-NH$_2$ |
| D12 (FIG. 45) | Ac-AGPTWCEDDYCWLFGTGGGK{[PnAO6-Glut-K(Ac-VCWEDSWGGEVCFRYDPGGGK(—C(=O)CH$_2$(OCH$_2$CH$_2$)$_2$OCH$_2$C(=O)-NH$_2$]-NH$_2$ |
| D13 (FIG. 46) | Ac-AGPTWCEDDWYYCWLFGTGGGK{Ac-VCWEDSWGGEVCFRYDPGGGK[JJ-Glut-K(BOA)-NH$_2$]-NH$_2$: Dimer 13 (D13) |
| D14 (FIG. 47) | Ac-AQDWYYDEILSMADQLRHAFLSGGGGGK{PnAO6-Glut-K[Ac-GSDRVCWEDSWGGEVCFRYDPGGGK(JJ-Glut)-NH$_2$]}-NH$_2$ |
| D15 (FIG. 48) | Ac-AGPTWCEDDWYYCWLFGTGGGK{[[Ac-GDSRVCWEDSWGGEVCFRYDPGGGKJJ-Glut]-NH$_2$]-K(PnAO6-Glut)}-NH$_2$ |
| D16 (FIG. 49) | Ac-AGPTWCEDDWYYCWLFGTGGGGK{PnAO6-Glut-K[Ac-GDSRVCWEDSWGGEVCFRYDPGGGK[—C(=O)CH$_2$O(CH$_2$CH$_2$O)$_2$CH$_2$C(=O)NH(CH$_2$)$_3$O(CH$_2$CH$_2$O)$_2$(CH$_2$)$_3$NHC(=O)CH$_2$O(CH$_2$CH$_2$O)$_2$CH$_2$(=O)-NH$_2$]}-NH$_2$ |
| D17 (FIG. 50) | Ac-AQDWYYDEILJGRGGRGGRGGK{K[Ac-VCWEDSWGGEVCFRYDPGGGK(JJ-Glut)-NH$_2$]}-NH$_2$ |
| D18 (FIG. 51) | Ac-AGPTWCDYDWEYCWLGTFGGGK{PnAO6-Glut-K[Ac-GVDFRCEWSDWGEVGCRSPDYGGGK(JJ-Glut)-NH$_2$]}-NH$_2$ |
| D19 (FIG. 52) | Ac-AGPTWCEDDWYYCWLFGTGGGK{Biotin-K[Ac-VCWEDSWGGEVCFRYDPGGGK(JJ-Glut)-NH$_2$]}-NH$_2$ |
| D20 (FIG. 53) | (-JJAGPTWCEDDWYYCWLFGTGGGGK-NH$_2$)-Glut-VCWEDSWGGEVCFRYDPGGG-NH$_2$ |
| D21 (FIG. 54) | [-JJAGPTWCEDDWYYCWLFGTGGGGK(PnAO6-Glut)-NH$_2$]-Glut-VCWEDSWGGEVCFRYDPGGG-NH$_2$ |
| D22 (FIG. 55) | Ac-GDSRVCWEDSWGGEVCFRYDPGGGK(JJ-Glut-JJ-AGPTWCEDDWYYCWLFTGGGK—NH$_2$)-NH$_2$ |
| D23 (FIG. 56) | Ac-AGPTWCEDDWYYCWLFGTGGGK{Ac-VCWEDSWGGEVCFRYDPGGGK[JJ-Glut-K(SATA)]-NH$_2$}-NH$_2$ |
| D24 (FIG. 57) | Ac-AGPTWCEDDWYYCWLFGTGGGK{SATA-JJK[Ac-VCWEDSWGGEVCFRYDPGGGK(JJ-Glut)-NH$_2$]}-NH$_2$ |
| D25 (FIG. 58) | Ac-AGPTWCEDDWYYCWLFGTGGGK{Ac-GDSRVCWEDSWGGEVCFRYDPGGGK[JJ-Glut-NH(CH$_2$)$_4$—(S)—CH(NH$_2$)C(=O)-NH$_2$}-NH$_2$ |
| D26 (FIG. 59) | AGPTWCEDDWYYCWLFGTGGGGK{(-Glut-JJ-VCWEDSWGGEVCFRYDPGGG-NH$_2$)—K}-NH$_2$ |

TABLE 13-continued

Dimer sequences and linkers

Figure 87B:
Figure 87C:
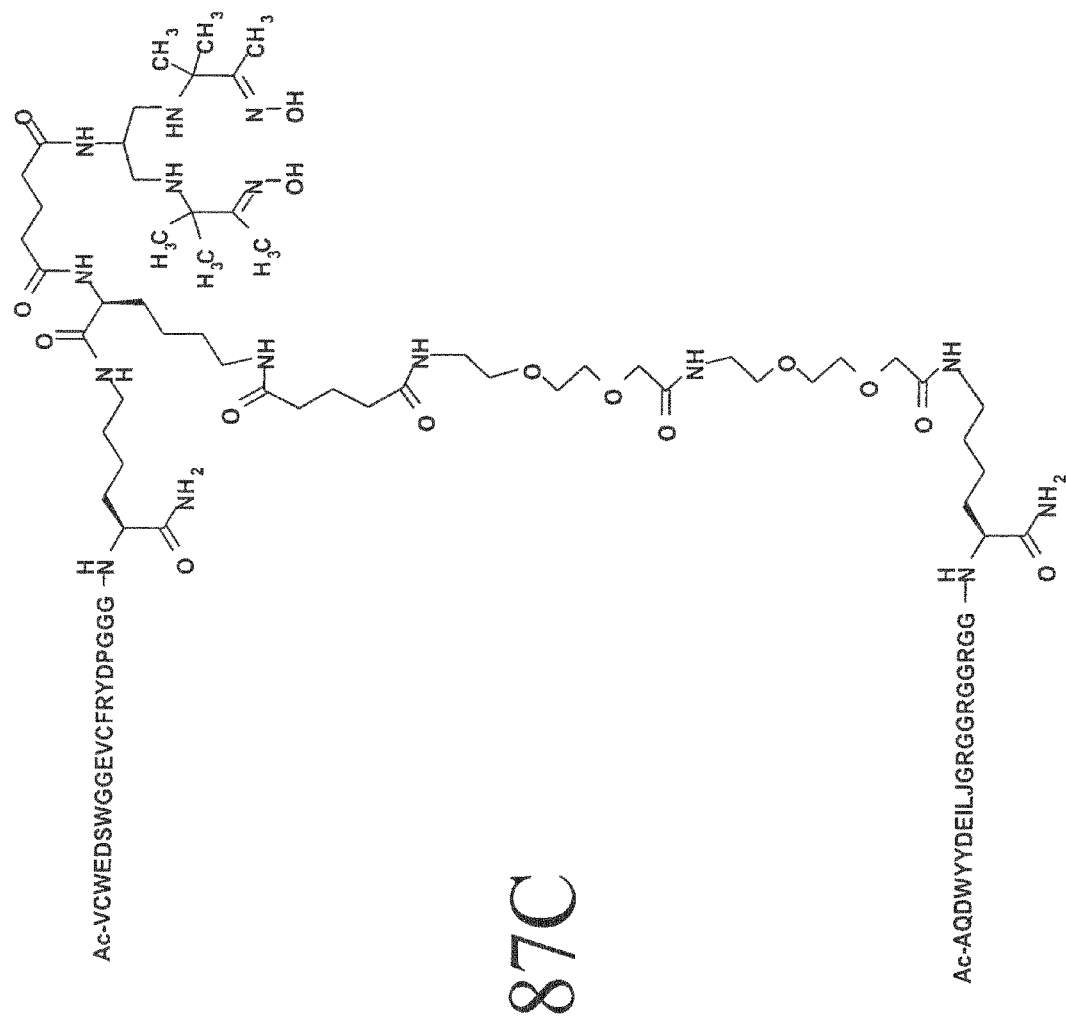

| Dimer # | Sequence |
|---|---|
| D27 (FIG. 60) | Ac-AGPTWCEDDWYYCWLFGTGGGGK{Ac-VCWEDSWGGEVCFRYDPGGGK[S(GalNAc(Ac)$_3$-alpha-D)-G-S(GalNAc(Ac)$_3$-alpha-D)-Glut-S(GalNAc(Ac)$_3$-alpha-D)-G-S(GalNAc(Ac)$_3$-alpha-D)-NH(CH$_2$)$_4$—(S)—CH(Biotin-JJNH—)C(=O)]- NH$_2$}-NH$_2$ |
| D28 (FIG. 61) | AQEPEGYAYWEVITLYHEEDGDGGK (SEQ ID NO: 305) - AQAFPRFGGDDYWIQQYLRYTDGGK (SEQ ID NO: 306) (see FIG. 61 for linkage) |
| D29 (FIG. 62) | AGPTWCEDDWYYCWLFGTGGGK (SEQ ID NO: 277) - VCWEDSWGGEVCFRYDPGGGK (SEQ ID NO: 337) (see FIG. 62 for linkage) |
| D30 (FIG. 87C) | Ac-VCWEDSWGGEVCFRYDPGGGK (SEQ ID NO: 337){[PnAO$_6$-Glut-K(-Glut-JJ-NH(CH$_2$)$_4$—(S)—CH(Ac-AQDWYYDEILJGRGGRGGRGG(SEQ ID NO: 478)-NH)C(=O)NH$_2$]-NH$_2$}-NH$_2$ (see FIG. 87C) |
| D31 (FIG. 88D) | Ac-AGPTWCEDDWYYCWLFGTGGGK(SEQ ID NO: 277)[Ac-VCWEDSWGGEVCFRYDPGGGK(SEQ ID NO: 337)[SGS-Glut-SGS—(S)—NH(CH$_2$)$_4$—CH(Biotin-JJ-NH)—C(=C)]—NH$_2$]-NH$_2$ (see FIG. 88D) |

HPLC Analysis Systems

System A: Column: YMC C-4 (4.6×250 mm); Eluents: A: Water (0.1% TFA), B: ACN (0.1% TEA); Elution: initial condition, 25% B, linear gradient 25-60% B in 10 min; flow rate: 2.0 mL/min; detection; UV @ 220 nm.

System B: Column: YMC C-4 (4.6×250 mm); Eluents: A: water (0.1% TFA), B: ACN (0.1% TFA); Elution: initial condition, 25% B, linear gradient 25-60% B in 20 min; flow rate: 2.0 mL/min; detection, UV @ 220 nm.

System C: Column: YMC C-4 (4.6×250 mm); Eluents: A: water (0.1% TEA), B: ACN (0.1% TFA); Elution: initial condition, 30% B, linear gradient 30-60% B in 10 min; flow rate: 2.0 mL/min; detection: UV @ 220 nm.

System D: Column: YMC C-4 (4.6×250 mm); Eluents: A: water (0.1% TFA), B: ACN (0.1% TFA), Elution: initial condition, 20% B, linear gradient 20-60% B in 10 min; flow rate-2.0 mL/min; Detection: UV @ 220 nm.

System E, Column: Waters XTerra, 4.6×50 mm; Eluents: A: water (0.1% TFA), B: ACN (0.1% TFA); Elution: initial condition, 10% B, linear gradient 10-60% B in 10 min; flow rate: 3.0 mL/min; detection: UV @ 220 min.

System F: Column: Waters XTerra, 4.6×50 mm; Eluents: A: water (0.1% TFA), B: Acetonitrile (0.1% TFA); Elution: Initial condition, 30% B, Linear Gradient 30-70% B in 10 min; Flow rate: 3.0 mL/min; Detection: @ 220 nm.

System G: Column: Waters XTerra, 4.6×50 mm; Eluents: A: water (0.1% TFA), B: ACN (0.1% TFA); Elution: initial condition, 30% B, linear gradient 30-75% B in 10 min; flow rate: 3.0 mL/min; detection: UV @ 220 nm.

System H: Column: Waters XTerra, 4.6×50 mm; Eluents: A: water (0.1% TFA), B: ACN (0.1% TFA); Elution: initial condition, 20% B, linear gradient 20-52% B in 10 min; flow rate: 3.0 mL/min; detection: UV @ 220 nm.

System I: Column: Waters XTerra, 4.6×50 mm; Eluents: A: water (0.1% TFA), B: ACN (0.1% TFA); Elution: initial condition, 10% B, linear gradient 10-65% B in 10 min; flow rate: 3.0 mL/min; detection: UV @ 220 nm.

System J: Column: Waters XTerra, 4.6×50 mm; Eluents: A: water (0.1% TFA), B: ACN (0.1% TFA); Elution: initial condition, 20% B, linear gradient 20-60% B in 10 min; flow rate: 3.0 mL/min; detection: UV @ 220 nm.

System K: Column: Waters XTerra, 4.6×50 mm; Eluents: A: water (0.1% TFA), B: ACN (0.1% TFA); Elution: initial condition, 5% B, linear gradient 5-60% B in 10 min.; flow rate: 3.0 mL/min; detection: UV @ 220 nm.

System L: Column: Waters XTerra, 4.6×50 mm; Eluents: A: water (0.1% TFA), B: ACN (0.1% TFA); Elution: initial condition, 5% B, linear gradient 5-65% B in 10 min; flow rate: 3.0 mL/mint, detection: UV @ 220 nm.

System M: Column: Waters XTerra, 4.6×50 mm; Eluents: A: water (0.1% TFA), B: ACN (0.1% TFA); Elution: initial condition, 15% B, linear gradient 15-50% B in 10 min; flow rate: 3.0 mL/min; detection: UV 220 mm.

System N: Column: Waters XTerra, 4.6×50 mm; Eluents: A: water (0.1% TFA), B: ACN (0.1% TFA); Elution: initial condition, 10% B, linear gradient 20-80% B in 10 min; flow rate: 3.0 mL/min; detection: UV @ 220 nm.

System O: Column: YMC-C18, 4.6×250 mm; Eluents: A: water (0.1% TFA), B: ACN (0.1% TFA); Elution: initial condition, 30% B, linear gradient 30-60% B in 10 min; flow rate: 2.0 mL/min; detection: UV @ 220 nm.

System P: Column: YMC-C18, 4.6×250 mm, Eluents: A: water (0.1% TFA), B: ACN (0.1% TFA); Elution: initial condition, 20% B, linear gradient 20-80% B in 20 min; flow rate: 2.0 mL/min; detection: UV @ 220 nm.

System Q: Column: YMC-C18, 4.6×250 mm; Eluents: A: water (0.1% TEA), B: ACN (0.1% TFA); Elution: initial condition, 20% B, linear gradient 20-60% B in 6 min; flow rate: 2.0 mL/min; detection: UV @ 220 nm.

System R: Column: YMC-C18, 4.6×250 mm; Eluents: A: water (0.1% TFA), B: ACN (0.1% TFA); Elution: initial condition, 25% B, linear gradient 25-60% B in 10 min; flow rate: 2.0 mL/min; detection: UV @ 220 nm.

System S: Column: YMC-C18, 4.6×100 mm; Eluents: A: water (0.1% TFA), B: ACN (0.1% TFA); Elution: initial condition, 10% B, linear gradient 10-60% B in 10 min; flow rate: 3.0 mL/min; detection: UV @ 220 nm.

System T: Column: Waters XTerra, 4.6×50 mm; Eluents: A: water (0.1% TFA), B: ACN (0.1% TFA). Elation: initial condition, 5% B, linear gradient 5-65% B in 8 min; flow rate: 3.0 nm in; detection: UV @ 220 nm.

System U: Column: Waters XTerra, 4.6×50 mm; Eluents: A: water (0.1% TFA), B: ACN (0.1% TFA); Elution: initial condition, 15% B, linear gradient 15-50% B in 8 min; flow rate: 3.0 mL/min; detection: UV @ 220 nm.

Example 13

Figure 15:
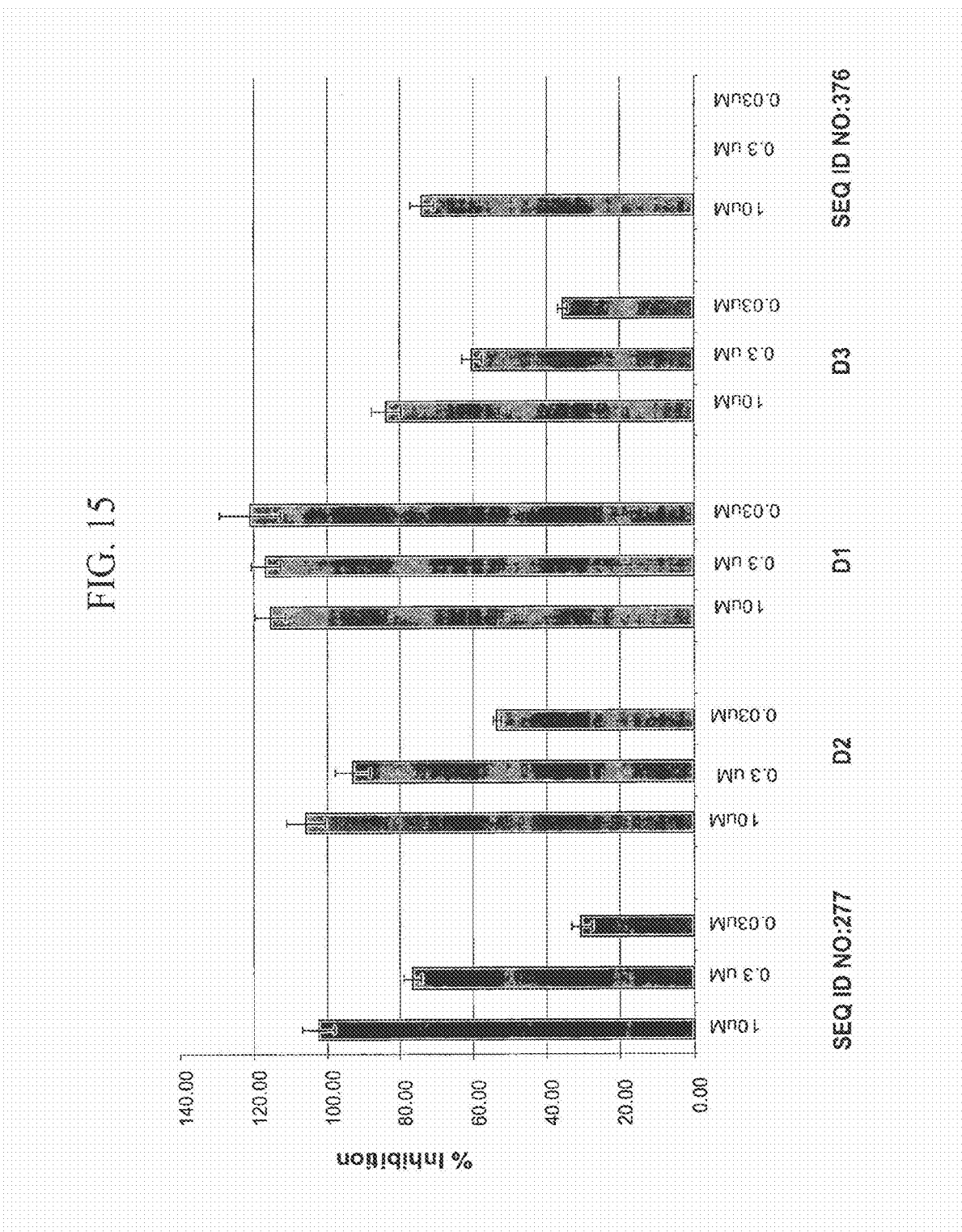
FIG. 15 is a graph showing the percentage inhibition of $^{125}$I-labeled VEGF binding by SEQ ID NO:277, D2, D1, D3, and AQDWYYDEILSMADQLRHAFLSGG (SEQ ID NO:376) at three different concentrations (10 µM, 0.3 µM, and 0.03 µM) to KDR-transfected 293H cells. The results are from one experiment carried out in triplicate+/−S.D.

Competition with $^{125}$I-VEGF for Binding to KDR on HUVECs and KDR-Transfected Cells The following experiment assessed the ability of KDR-binding peptides to compete with $^{125}$I-labeled VEGF for binding to KDR expressed by transfected 293H cells.
Protocol:
293H cells were transfected with the KDR cDNA or mock-transfected by standard techniques. The cells were incubated with $^{125}$I-VEGF in the presence or absence of competing compounds (at 10 µM, 0.3 µM, and 0.03 µM). After washing the cells, the bound radioactivity was quantitated on a gamma counter. The percentage inhibition of VEGF binding was calculated using the formula [(Y1−Y2)×100/Y1], where Y1 is specific binding to KDR-transfected 293H cells in the absence peptides, and Y2 is specific binding to KDR-transfected 293H cells in the presence of peptide competitors. Specific binding to KDR-transfected 293H cells was calculated by subtracting the binding to mock-transfected 293H cells from the binding to KDR-transfected 293H cells.
Results
As shown in FIG. 15, all of the KDR-binding peptides assayed were able to compete with $^{125}$I-VEGF for binding to KDR-transfected cells. The heterodimer (D1) was clearly the most effective at competing with $^{125}$I-VEGF, even over the two homodimers (D2 and D3), confirming the superior binding of D1.

Example 14

Receptor Activation Assay

Figure 16:
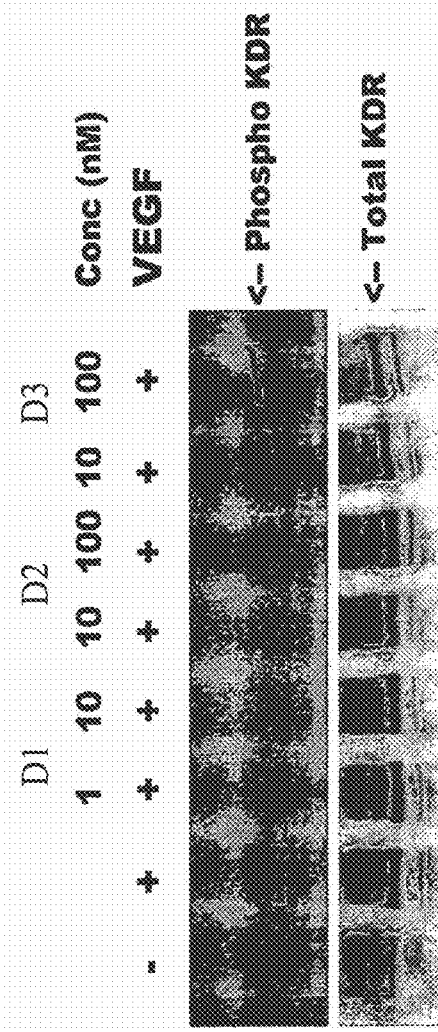
FIG. 16 is a photograph showing the ability of D1 to completely block the VEGF-induced phosphorylation of KDR in HUVECs at 10 nM and the majority of phosphorylation at 1 nM. Reprobing the blot for total KDR (lower panel) demonstrated that the effects of the tested compounds was not due to reduced sample loading. Homodimers (D2 and D3) composed of the two binding sequences contained in D1 did not interfere with the phosphorylation at up to 100 nM.

The ability of KDR-binding peptides to inhibit VEGF induced activation (phosphorylation) of KDR was assessed using the following assay.
Protocol
Dishes of nearly confluent HUVECs were placed in basal medium lacking serum or growth factors overnight. The dishes in group (c), below were then pretreated for 15 min in basal medium with a KDR-binding peptide, and then the cells in the dishes in groups (a), (b), and (c) were placed in fresh basal medium containing:
 (a) no additives (negative control),
 (b) 5 ng/mL VEGF (positive control), or
 (c) 5 ng/mL VEGF plus the putative competing/inhibiting peptide.
After 5 min of treatment, lysates were prepared from each set of dishes. KDR was immunoprecipitated from the lysates was analyzed sequentially by immunoblotting for phosphorylation with an anti-phosphotyrosine antibody, and for total KDR with an anti-KDR antibody (to control for sample loading).
Results
As shown in FIG. 16, D1 was able to completely block the VEGF-induced phosphorylation of KDR in HUVECs at 10 nM. More than half of the phosphorylation was inhibited by the compound at 1 mM. Homodimers D2 and D3, made up of the two individual binding moieties that are contained in D1, had no effect on phosphorylation at up to 100 nM, demonstrating the benefit of heterodimer constructs in blocking a receptor-ligand interaction. In multiple experiments, the $IC_{50}$ for D1 in this assay varied between 0.5 and 1 nM. A different heterodimer containing unrelated binding sequences, D28, a tail-to-tail heterodimer comprising the polypeptides of SEQ ID NO:305 and SEQ ID NO:306 (FIG. 61), had no effect on phosphorylation at 100 nM in spite of it's high binding affinity (11 nM for KDR by SPR), suggesting that the choice of KDR-binding moieties is important when constructing a multimer to compete with VEGF for binding to KDR. One of ordinary skill in the art would be able to construct suitable heteromultimers using the binding polypeptides provided herein and routine screening assays.

Even though the affinity of D1 for KDR is 10-fold higher than that of D2 (by SPR analysis), the $IC_{50}$ of D1 in the activation assay is at least 100-fold lower. This suggests that targeting two distinct epitopes on KDR with a single binding molecule can generate greater steric hindrance than a molecule with similar affinity that only binds to a single epitope on KDR and, therefore, improve the ability to inhibit VEGF induced KDR activity. Similarly, it should be pointed out that the two KDR-binding moieties within D1, when tested as monomeric free peptides (SEQ ID NO:277 and SEQ ID NO:337 in the receptor activation assay, had $IC_{50}$s of 0.1 and 1 micromolar, respectively. The $IC_{50}$ for the monomeric free peptides were 100 to 1000-fold higher than the $IC_{50}$ for D1 in the assay and 14 to 30-fold higher than the $K_D$s for the fluoresceinated derivatives of the monomeric peptides. Thus, creating a dimer containing two peptides with weak VEGF-blocking activity has resulted in a molecule with very potent VEGF-blocking activity that goes well beyond the increased binding affinity of D1.

Example 15

Migration Assay

Figure 17:
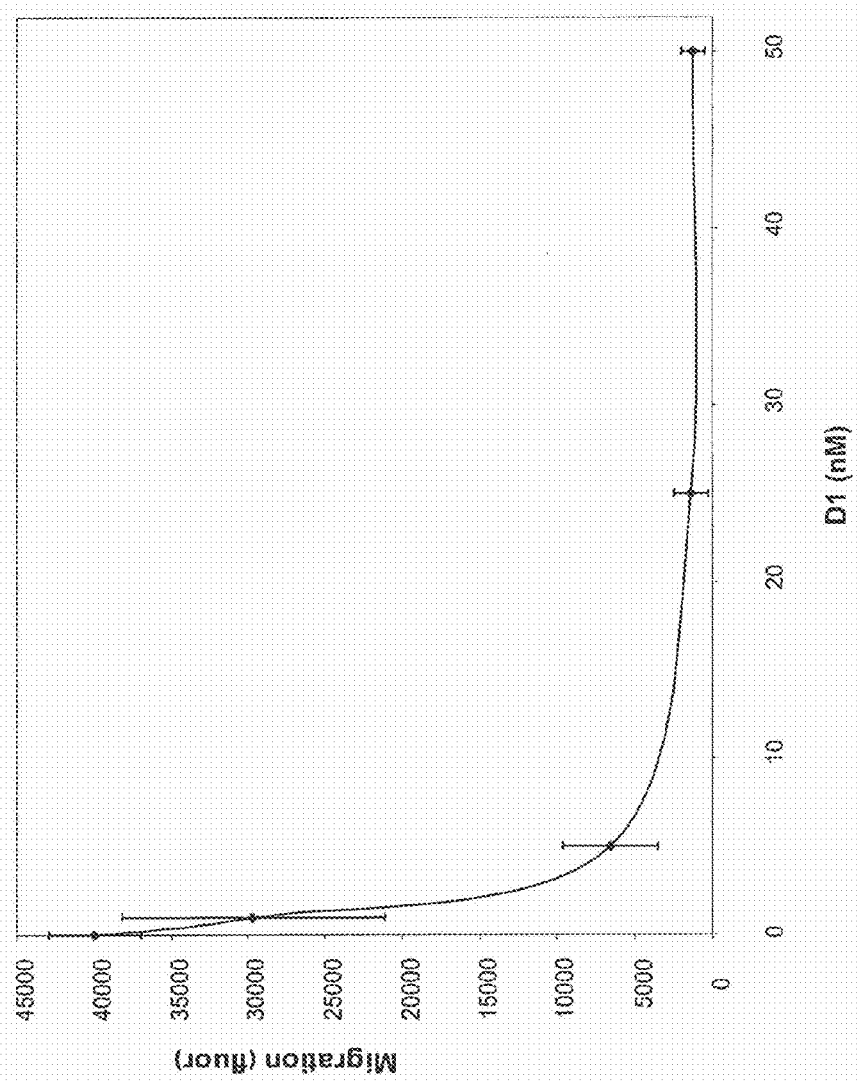
FIG. 17 is a graph showing that D1 potently blocks the migration/invasion of endothelial cells induced by VEGF. Migrating cells were quantitated by fluorescence measurement after staining the migrated cells with a fluorescent dye.

The following experiment assessed the ability of D1 to block the VEGF-induced migration of HUVECs in culture.
Protocol
Serum-starved HUVECs were placed, 100,000 cells per well, into the upper chambers of BD Matrigel-coated FluoroBlok 24-well insert plates (#354141). Basal medium, containing either nothing or different attractants such as VEGF (10 ng/mL) or serum (5% FBS) in the presence or absence of potential VEGF-blocking/inhibiting compounds, was added to the lower chamber of the wells. After 22 hours, quantitation of cell migration/invasion was achieved by post-labeling cells in the insert plates with a fluorescent dye and measuring the fluorescence of the invading/migrating cells in a fluorescent plate reader. The VEGF-induced migration was calculated by subtracting the migration that occurred when only basal medium was placed in the lower chamber of the wells.
Results:
VEGF induced a large increase in endothelial cell migration in the assay, which was potently blocked by D1. At 5 nM D1, the VEGF-stimulated endothelial cell migration was 84% blocked (see FIG. 17). At 25 nM D1, this migration was almost completely blocked. In other experiments, a known KDR inhibitor, SU-1498 (Strawn, L. et al. 1996, *Cancer Res.*, 56:3540-3545) was tested in the assay. SU-1498 at 3 micromolar did not block the VEGF-induced migration as well as D1 (47% blocked at 3 micromolar). D6 (structure shown below in Example 18), at 50 nM, also produced essentially complete inhibition of the migration stimulated by VEGF Serum was a very powerful attractant in the assay when used in place of VEGF, but its effect was not significantly diminished by D1, indicating that D1 specifically inhibits endothelial migration induced by VEGF.

Example 16

Preparation of Labeled Compounds

The following experiments describe methods used to prepare Tc, In, and I-labeled compounds.

Preparation of $^{99m}$Tc-378 (Ac-AGPTWC*EDDWYYC*WLFGTGGGK (PnAO6-NH—(O=)C(CH$_2$)$_3$C(=O)-JJ)-NH$_2$; SEQ ID NO:378).

SnCl$_2$2H$_2$O (20 mg) was dissolved in 1 mL of 1 N HCl, and 10 µL of this solution was added to 1 mL of a DTPA solution that was prepared by dissolving 10 mg of Ca Na$_2$ DTPA.2.5H$_2$O (Fluka) in 1 mL of water. The pH of the stannous DTPA solution was adjusted to pH 6-8 using 1N NaOH. SEQ ID NO:378 (50 µg in 50 µL of 10% DMF) was mixed with 20 µL of $^{99m}$TcO$_4^-$ (2.4 to 4 mCi, Syncor), followed by 100 µL of the stannous Sn-DTPA solution. After 30 minutes at RT, the radiochemical purity (RCP) was 93%. The product was purified on a Supelco Discovery C16 amide column (4×250 mm, 5 um pore size) eluted at a flow rate of 0.5 mL/min using an aqueous/organic gradient of 1 g/L ammonium acetate in water (A) and acetonitrile (B). The following gradient was used: 30.5% B to 35% B in 30 minutes, ramp up to 70% B in 10 min. The compound, which eluted at a retention time of 21.2 minutes was collected into 500 µL of 50 mM citrate buffer (pH 5.2) containing 1% ascorbic acid and 0.1% HSA, and acetonitrile was removed using a Speed Vacuum (Savant). After purification, the compound had an RCP of >98%.

Preparation of $^{111}$In—Ac-AGPTWCEDDWYYCWLF-GTJK(JJ-DOTA)-NH$_2$ (SEQ ID NO:338).

SEQ ID) NO:338 (50 µg in 50 µL of 10% DMF) was mixed with $^{111}$InCl$_3$ (50 µL, 400 µCi, Mallinckrodt) and 100 µL of 0.2M ammonium acetate or citrate buffer at a pH of 5.3. After being heated at 85° C. for 45 minutes, the radiochemical purity (RCP) ranged from 44% to 52.2% as determined using HPLC. The $^{111}$In-labeled compound was separated from unlabeled ligand using a Vydac C18 column (4.6×25 cm, 5 micron pore size) under following conditions: aqueous phase, 1 g/L ammonium acetate (pH 6.8); organic phase, acetonitrile. Gradient: 23% org. to 25% org. in 30 minutes, up to 30% org. in 2 minutes, hold for 10 minutes. The compound, which eluted at a retention time of 20.8 min, was collected into 200 µL of 50 nM citrate buffer (pH 5.2) containing 1% ascorbic acid and 0.1% HSA, and the acetonitrile was removed using a Speed Vacuum (Savant). After purification the compound had an RCP of >93%.

Preparation of $^{111}$In-D4

A histidine buffer was prepared by adjusting a 0.1M solution of histidine (Sigma) to pH 6.25 with concentrated ammonium hydroxide. Ammonium acetate buffer was prepared by adjusting a 0.2 M solution of ammonium acetate (99.99%, Aldrich) to pH 5.5 using concentrated HCl (J. T. Baker, Ultra Pure). High purity $^{111}$InCl$_3$ (100 µL, 1.2 mCi, Malinckrodt, Hazelwood, Mo.) was added to D4 (200 µg in 200 of 50% DMF, 10% DMSO, 20% acetonitrile and 20% water), followed by addition of 300 µL of histidine buffer. The fin pH was 5.5. After incubation of the reaction mixture at 85° C. for 45 minutes, the RCP was 20%.

Alternatively, $^{111}$InCl$_3$ provided with a commercially available OctreoScan™ Kit (134 µL, 0.6 mCi, Mallinkrodt) was added to D4 (135 µg) in 162 µL of 0.2M ammonium acetate buffer. The final pH was 5.5. After incubation of the reaction mixture at 85° C. for 45 min. the RCP was 20%.

Preparation of $^{125}$I-D5

D5 (200 µg), in 30 µL of DMF that had been previously adjusted to pH 8.5-9.0 using diisopropyl amine, was added to 1 mCi of mono-iodinated $^{125}$I Bolton-Hunter Reagent (NEX-120, Perkin-Elmer) that had been evaporated to dryness. The vial was shaken and then incubated on ice for 30 minutes with occasional . After this time, the RCP was 23%. $^{125}$I-D5 was purified by HPLC at a flow rate of 1 mL/min using a Vydac C18 column (4.6×250 mm, 5 micron pore size) under the following conditions. Aqueous phase: 0.1% TFA in water; organic phase: 0.085% TFA in acetonitrile. Gradient: 30% org. to 36% org. in 30 minutes, up to 60% org. in 5 minutes, hold for 5 minutes. The compound was collected into 200 µL of 50 mM citrate buffer (pH 5.2) containing 1% ascorbic acid and 0.1% HSA. Acetonitrile was removed using Speed Vacuum (Savant). The resulting compound had an RCP of 97% (see FIG. 65).

Preparation of $^{177}$Lu-D11

D11 (5 µL of a ~1 µg/µL solution in 0.05N NH$_4$OH/10% EtOH) was added to a glass insert microvial containing 80 µL of 0.2M NaOAc buffer, pH 5.6. Enough $^{177}$Lu was added to bring the ligand:Lu ratio to ≤2:1 (1-5 mCi). The vial was crimp-sealed and heated at 100° C. for 15-20 minutes, cooled for 5 minutes, and treated with 3 µL of 1% Na$_2$EDTA.2H$_2$O in H$_2$O. The entire reaction mixture was injected onto a Supelco Discovery RP Amide C16 column (4 mm×250 mm×5 µm). The following HPLC conditions were used: Column temperature=50° C., Solvent A=H$_2$O w/0.1% TFA, Solvent B=ACN w/0.085% TFA, gradient 0.6/0.25 mL/min A/B at t=0 minutes to 0.5/0.4 mL/min A/B at t=60 minutes . The retention time for D11 was ~40 minutes; that of $^{177}$Lu-D11 was ~42 minutes. The radioactive peak was collected into 0.7 mL of 0.05M citrate buffer, pH 5.3 containing 0.1% Human Serum Albumin Fraction V and 1.0% Ascorbic Acid, and the mixture was spun down in a Savant Speed Vac to remove organic solvents. Radiochemical purities of greater than 80% were obtained.

Preparation of $^{177}$Lu-D13

D13 (306 µg) was added to a 2-mL autosampler vial with a ~450 µL conical insert and dissolved in 0.01N NH$_4$OH (50 µL). To this was added 300 µL of 0.5M Ammonium Acetate containing Sodium Ascorbate, Sodium Gentisate, L-Methionine and L-Tryptophan each at 10 mg/mL, plus Human Serum Albumin Fraction V at 2 mg/mL, final pH=7.6 adjusted with NaOH. A 6.8 µL aliquot of $^{177}$LuCl$_3$ in 0.05N HCl (39.3 mCi) was added, the vial was crimp-sealed, warmed for 15 nm at 37 C, cooled for ~5 minutes, and 10 µL of 1% Na$_2$EDTA 2H$_2$O in H$_2$O was added. A 350 µL aliquot of the reaction mixture was injected onto a Supelco Discovery RP Amide C: column (4 mm×250 mm×5 µm). The following HPLC conditions were used: column temperature=37 C, Solvent A=H$_2$O containing 2 g/L NH$_4$OAc buffer, pH 7.0, Solvent B=80% ACN/20% H$_2$O, gradient 0.56/0.24 mL/min MB at t=0 minutes to 0.47/0.33 mL/min A/B at t=30 minutes. The retention time for D13 was ~28 minutes; the retention tine for $^{177}$Lu—BRU 1339 was ~29 minutes. The radioactive peak was collected into 1 mL of a buffer containing Sodium Ascorbate, Sodium Gentisate, L-Methionine and L-Tryptophan each at 10 mg/mL, plus Human Serum Albumin Fraction V at 2 mg/mL, final pH=7.6 adjusted with NaOH). It was then spun down ~40 minutes using a Speed Vacuum (Savant) to remove ACN. The RCP of the isolated product was 86%.

Preparation of $^{99m}$Tc-D10

SnCl$_2$ 2H$_2$O (20 mg) was dissolved in 1 mL of 1 N HCl, and 10 µL of this solution was added to 1 mL of a DTPA solution that was prepared by dissolving 10 mg of Ca Na$_2$ DTPA.2.5H$_2$O (Fluka) in 1 mL of water. D10 (100 µg in 100

µL of 50% DMF) was mixed with 75 µL of 0.1 M, pH 9 phosphate buffer and 50 µL of $^{99m}TcO_4^-$ (2.4 to 5 mCi, Syncor), followed by 100 µL of the stannous Sn-DTPA solution. After 15 min at RT, the radiochemical purity RCP) was 72%. The product was purified on a Supelco Discovery C16 amide column (4×250 mm, 5 um pore size) eluted at a flow rate of 0.7 mL/min using an aqueous/organic gradient of 0.1% TFA in water (A) and 0.085% TFA in acetonitrile (B; "ACN"). The following gradient was used: 30% B to 42% B in 36 min, ramp up to 70% B in 10 min. The compound, which eluted at a retention time of 32 min., was collected into 500 µL of 50 mM citrate buffer (pH 5.2) containing 0.2% HSA, and acetonitrile was removed using a Speed Vacuum (Savant). After purification, the compound had an RCP of >90%.

Preparation of $^{99m}Tc$-D12

$SnCl_2.2H_2O$ (20 mg) was dissolved in 1 mL of 1 N HCl, and 10 µL of this solution was added to 1 mL of a DTPA solution that was prepared by dissolving 10 mg of Ca Na$_2$ DTPA.2.5H$_2$O (Fluka) in 1 mL of water, D12 (100 µg in 100 µL of 50% DMF) was mixed with 75 µL of 0.1 M, pH 9 phosphate buffer and 60 µL of $^{99m}TcO_4^-$ (2.4 to 4 mCi, Syncor), followed by 100 µL of the stannous Sn-DTPA solution. After 10 min at 40° C., the radiochemical purity (RCP) was 16%. The product was purified on a Supelco Discovery C16 amide column (4×250 mm, 5 um pore size) eluted at a flow rate of 0.7 mL/min using an aqueous/organic gradient of 0.1% TFA in water (A) and 0.085% TFA in acetonitrile (B). The follow gradient was used: 30% B to 42% B in 36 min, ramp up to 70% B in 10 min. The compound, which eluted at a retention time of 37.1 min. was collected into 500 µL of 50 mM citrate buffer (pH 5.2) containing 0.2% HSA, and acetonitrile was removed using a Speed Vacuum (Savant). After purification, the compound had an RCP of >90%.

Preparation of $^{99m}Tc$-D14

$SnCl_2.2H_2O$ (20 mg) was dissolved in 1 mL of 1 N HCl, and 10 µL of this solution was added to 1 mL of a DTPA solution that was prepared by dissolving 10 mg of CaNa$_2$DTPA.2.5H$_2$O Fluka) in 1 mL of water. D14 (100 µg in 100 µL of 50% DMF) was mixed with 50 µL of $^{99m}TcO_4^-$ (6 mCi, Syncor) and 125 µL, of 0.1M phosphate buffer, pH 9 followed by 100 µL of the stannous Sn-DTPA solution. After 15 min at 40° C., the radiochemical purity (RCP) was 21%. The product was purified on a Vydac peptide C18 column (4.6×250 mm) eluted at a flow rate of 1 mL/min using an aqueous/organic gradient of 0.1% TFA in water (A) and 0.085% TFA in acetonitrile (B). The following gradient was used: 30% B to 45% B in 40 min. The compound, which eluted at a retention time of 34.9 min., was collected into 500 µL of 50 mM citrate buffer (pH 5.3) containing 0.2% HSA, and acetonitrile was removed using a Speed Vacuum (Savant). After purification, the compound had an RCP of 92.5%.

Preparation of $^{99m}Tc$-D18

$SnCl_2.2H_2O$ (20 mg) was dissolved in 1 mL of 1 N HCl, and 10 µL of this solution was added to 1 µL of a DTPA solution that was prepared by dissolving 10 mg of Ca Na$_2$ DTPA 2.5H$_2$O (Fluka) in 1 HL of water. D18 (100 µg in 100 µL of 50% DMF) was mixed with 50 µL of 0.1 M, pH 9 phosphate buffer and 90 µL of $^{99m}TcO_4^-$ (14 mCi, Syncor), followed by 100 µL of the stannous Sn-DTPA solution, The reaction was warmed for 20 minutes at 37 C. The entire reaction was injected on a Vydac 218TP54 C18 column (4.6×250 mm, 5 um silica) and eluted at a flow rate of 1.5 mL/min using an aqueous/organic gradient of 0.1% TFA in water (A) and 0.085% TFA in ACN (3). The following gradient was used: 32% to 39% B in 30 minutes, ramp up to 80% B in 2 min. The free ligand eluted at a retention time of 19 minutes. The complex, which eluted at 24 minutes, was collected into 500 µL of 50 mM citrate buffer (pH 5.3) containing 0.1% HSA and 1% Ascorbic Acid. ACN and excess TFA were removed using a Speed Vacuum (Savant) for 40 minutes. After purification, the compound had an RCP of 93%.

Preparation of $^{99m}Tc$-D30

$SnCl_2.2H_2O$ (20 mg) was dissolved in 1 mL of 1 N HCl, and 10 µL of this solution was added to 1 mL of a DTPA solution that was prepared by dissolving 10 mg of CaNa$_2$ DTPA.2.5H$_2$O (Fluka) in 1 mL of water. D30 (100 µg in 100 µL of DMF) was mixed with 150 µL of 0.1 M pH 8 phosphate buffer and 50 µL of $^{99m}TcO_4^-$ (5.2 mCi, Syncor), followed by 100 µL of the stannous Sn-DTPA solution. After 15 min at 100° C., the radiochemical purity (RCP) was 13%. The product was purified on a Vydac C18 peptide column (4.6×250 mm, 5 um pore size) eluted at a flow rate of 1 ml/min using an aqueous/organic gradient of 0.1% TFA in water (A) and 0.085% TFA in acetonitrile (B). The following gradient was used. 10% B to 50% B in 30 nm in, hold 50% B for 5 min, back to 70% B in 5 min. The compound, which eluted at a retention time of 33.2 min., was collected into 3 ml of 50 mM citrate buffer (pH 5.5) containing 0.2% HSA, and acetonitrile was removed using a Speed Vacuum (Savant). After purification, the compound had an RCP of 92.4%.

Example 17

Binding to KDR-Transfected Cells

An experiment was performed to test the ability of $^{125}$I-labeled D5 to bind to KDR-transfected 293H cells. In this experiment, different amounts of $^{125}$I-labeled D5 (1-4 µCi/mL, labeled with $^{125}$I-Bolton-Hunter reagent and HPLC-purified) were incubated with mock and KDR-transfected 293H cells in 96-well plates for 1 hr at room temperature. Binding was performed with and without 40% mouse serum to evaluate the serum effect on binding to KDR-transfected cells. After washing away the unbound compound, the cells in each well were lysed with 0.5 N NaOH and the lysates were counted with a gamma counter.

Figure 18:
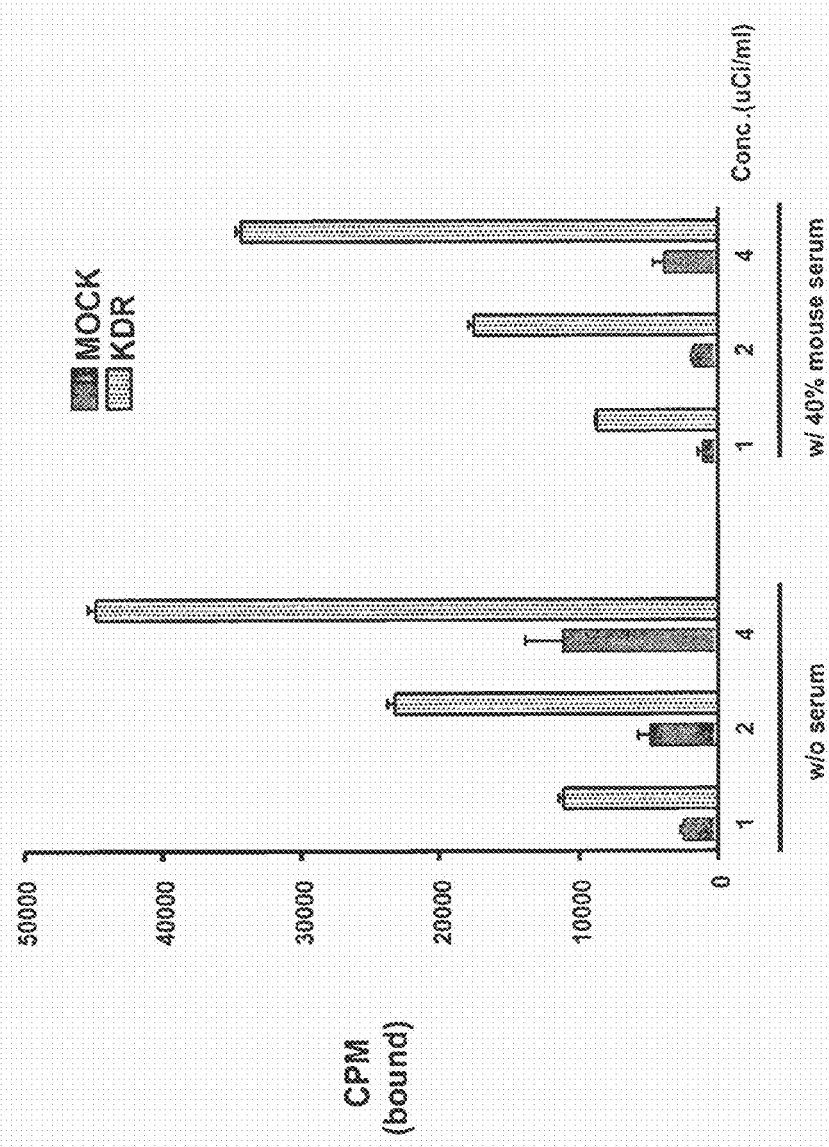
FIG. 18 is a graph showing the binding of $^{125}$I-labeled D5 to mock and KDR transfected 293H cells in the absence and presence of 40% mouse serum.
Figure 19:
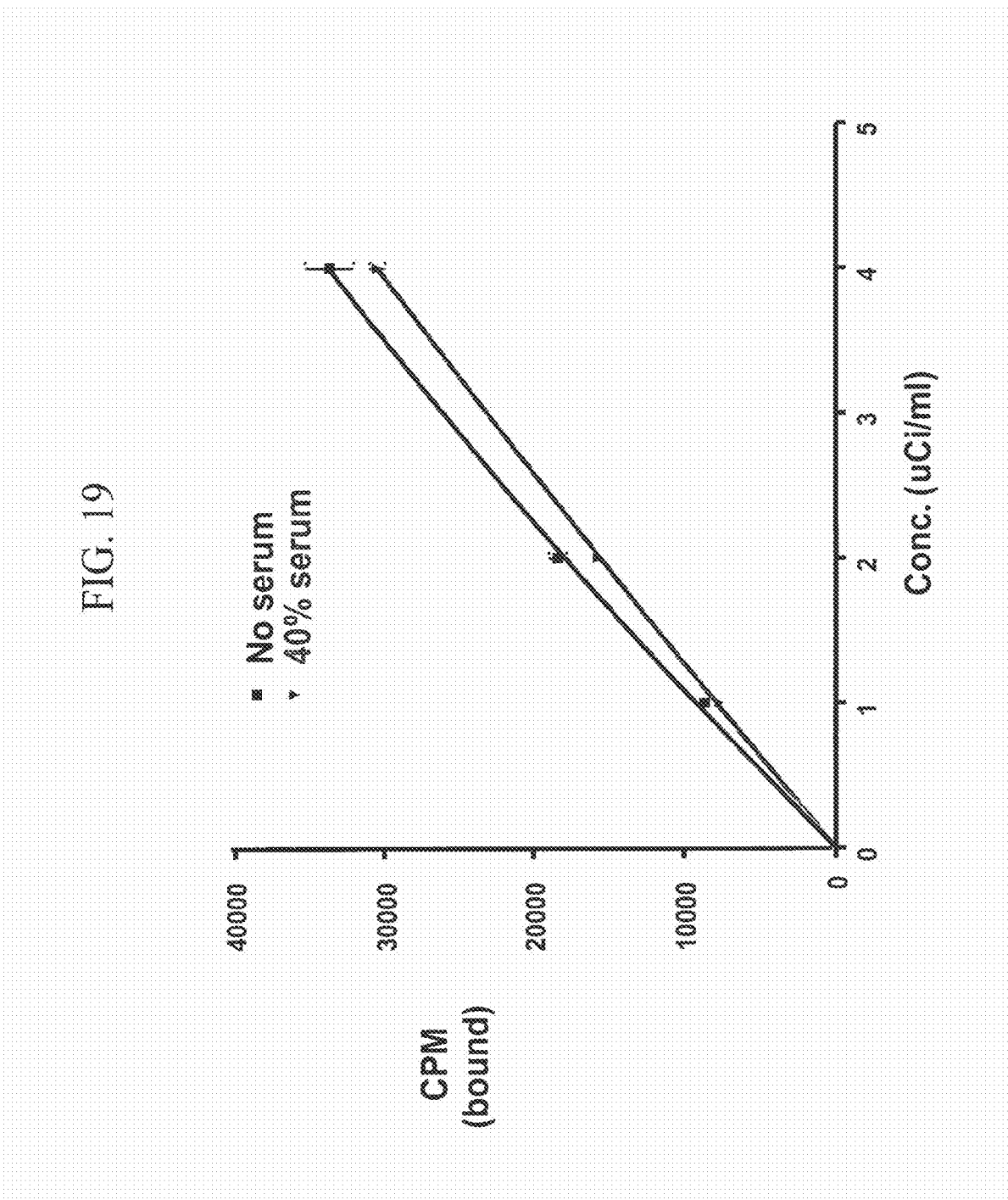
FIG. 19 is a graph showing the specific binding (KDR-MOCK) of $^{125}$I-labeled D5 to KDR-transfected 293H cells in the absence and presence of 40% mouse serum.

The results of this experiment are summarized in FIG. 18 and FIG. 19. $^{125}$I-labeled D5 is able to specifically bind to KDR-transfected cells, and its binding is not affected by the presence of 40% mouse serum. Somewhat more binding to KDR-transfected cells was observed in the absence of serum as compared to binding in the presence of 40% mouse serum. However, the binding of $^{125}$I-D5 to mock-transfected cells was also increased by about the same extent when serum was omitted during the assay, indicating that the increased binding in the absence of serum was non-specific (FIG. 18). Specific binding to KDR-transfected cells (after subtracting binding to mock-transfected cells) looked almost identical with or without mouse serum (as shown in FIG. 19). In this experiment, 10-14% of the total CPM added were specifically bound to KDR-transfected cells (data not shown).

Example 18

Biacore Analysis of Heterodimer Binding to KDR-Fc and Determination of Affinity Constant A peptide heterodimer (FIG. 63) composed of SEQ ID NO:277 and SEQ ID NO:294 was prepared as previously described in Example 12 using glutaric acid bis N-hydroxysuccinimidyl ester. The heterodimer was tested for binding to KDR-Fc using Biacore, and an affinity constant was determined as follows.

Three densities of KDR-Fc were cross-linked to the dextran surface of a CM5 sensor chip by the standard amine coupling procedure (0.5 mg/mL solution diluted 1:100 or 1:50 with 50 mM acetate, pH 6.0). Flow cell I was activated and then blocked to serve as a reference subtraction. Final immobilization levels achieved:

$R_L$ Fc 2 KDR-Fc=1607
$R_L$ Fc 3 KDR-Fc=3001
$R_L$ Fc 4 KDR-Fc=6319

Experiments were performed in PBS (5.5 mM phosphate, pH 7.65, 0.15 M NaCl)+0.005% P-20 (v/v)). D6 was diluted to 250 nM in PBS and serial dilutions were performed to produce 125, 62.5, 31.3 15.6, 7.8, and 3.9 nM solutions. All samples were injected in duplicate. For association, peptides were injected at 20 µl min for 12.5 minutes using the kinject program. Following a 10 minute dissociation, any remaining peptide was stripped from the KDR surface with a quickinject of 50 mM NaOH+1 M NaCl for 12 s at 75 µL/min. Sensorgrams were analyzed using BIAevaluation software 3.1 and a hyperbolic double rectangular regression equation in Sigma-Plot 6.0. Heterodimer steady state binding affinities ($K_{DAV}$) were determined at all three KDR immobilization densities (Table 14).

TABLE 14

Summary of Parameters

|  |  | $K_{D1}$ (nM) | $R_{max1}$ | $K_{DAV}$ (nM) | $R_{maxAV}$ | $R^{2*}$ |
|---|---|---|---|---|---|---|
| D6 | Vs. 1600RU | 46 | 13.1 | 1.5 | 12.6 | 0.995 |
|  | Vs. 3000RU | 25.5 | 21.2 | 0.665 | 22.7 | 0.991 |
|  | Vs. 6000RU | 17 | 61.3 | 0.662 | 62.2 | 0.993 |

From these data, it appears that at the higher immobilization densities, the heterodimer binds KDR with a sub-nanomolar affinity (~0.6 nM).

To assess the in vivo clearance of this peptide heterodimer, a small amount of material was iodinated using iodogen and Na$^{125}$I according to standard protocols (Pierce). One tube coated with the iodogen reagent was pre-wet with 1 mL of 25 mM Tris, 0.4M NaCl, pH 7.5. This was discarded and 100 µJ, of the same buffer added. Using a Hamilton syringe 11 µL of the $^{125}$I—NaI was transferred to the reaction tube. Based on original estimates of the Na$^{125}$I concentration of 143.555 mCi/mL, the 11 µL should contain about 1.5 mCi. After addition, the sample was swirled and set in a lead pig to incubate for 6 min with a swirl every 30 sec. After 6 min, the entire sample was transferred to the protein that was in an Eppendorf tube. The sample was swirled and set to incubate for 8 min, with a swirl every 30 sec. After 8 min. the reaction was quenched (terminated) with tyrosine (10 mg/mL, a saturated solution), allowed to sit for 5 min, and then 2 µL was removed for a standard.

Figure 21:
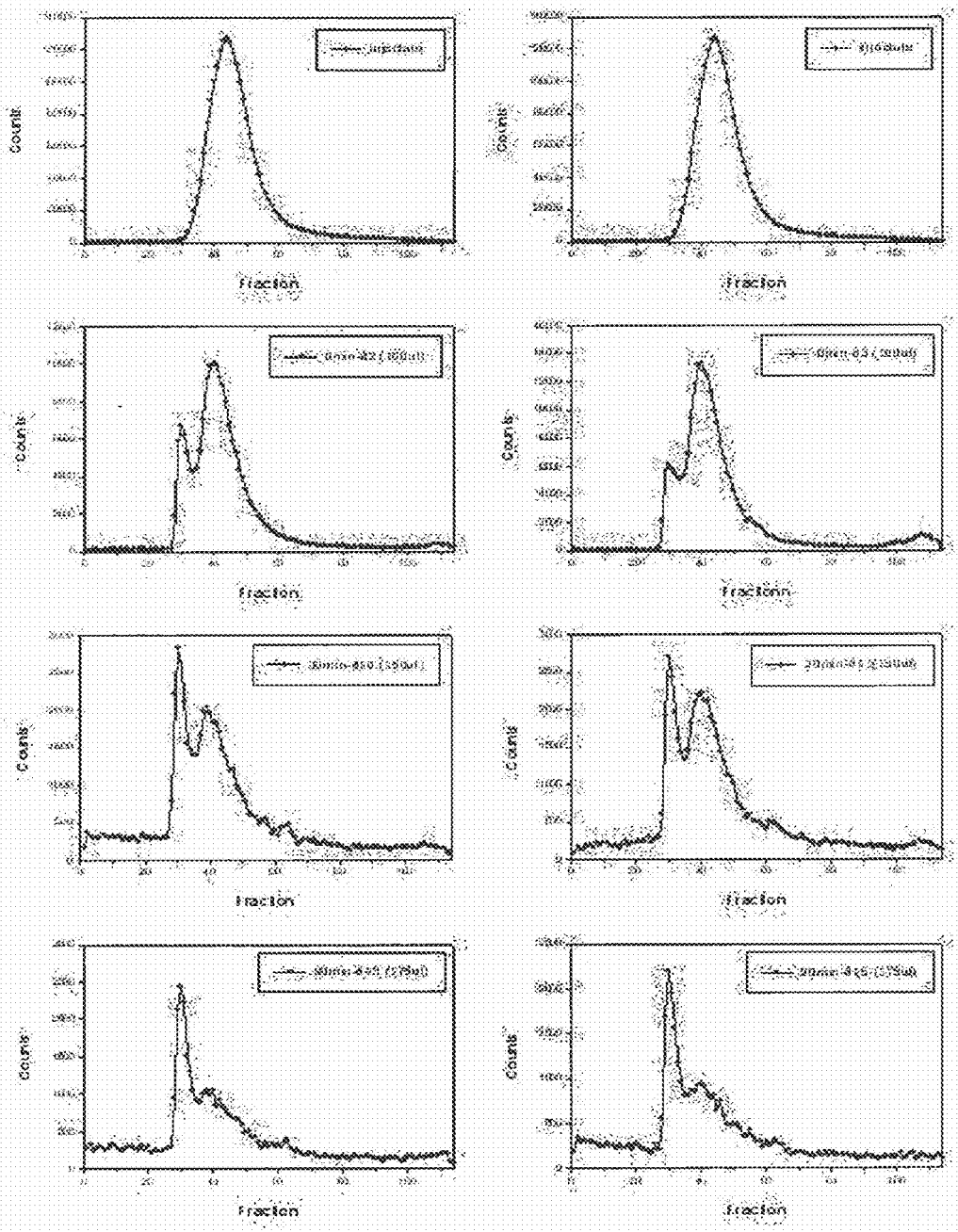
FIG. 21 shows SE-HPLC profiles of plasma from the Superdex peptide column. Top panel, sample injected; followed by 0 min, 30 min, and 90 min. The insert within each panel shows time point, animal number and volume injected for HPLC analysis.

For purification a 10 mL column of the D-salt polyacrylamide 1800 was used to separate the labeled peptide from labeled tyrosine. The column was first washed with 10 mL saline, then 5 mL of 25 mM Tris, 0.4M NaCl, pH 7.5 containing 2.5% HSA to block non-specific sites. After the HSA buffer wash, the column was eluted with 60 mL of the 25 mM Tris, 04 M NaCl buffer, and the column was stored overnight at 4° C. The labeled sample contained 1.355 mCi, as determined by the dose calibrator. The 2 µL sample that was removed as a standard contained 8.8 µCi. The peptide sample was applied to the D-salt 1800 column and eluted with the Tris/NaCl buffer, pH 7.5. The flow was controlled by applying single 0.5 mL aliquots for each fraction, #1-14, and then 1.0 mL for fractions 25-43. FIG. 21 shows the elution profile of activity versus fraction number. The peak of activity in fractions # 9, 10, and 11, was assumed to be the peptide. The radioactivity in 24 through ~40 is likely the labeled tyrosine. From this purification, fractions #9-12 were pooled together and used for the subsequent clearance study (concentration of $^{125}$I-D6 in pool is 7.023 µg/mL; 100 µL=0.702 µg with 8.6 µCi).

Figure 20:
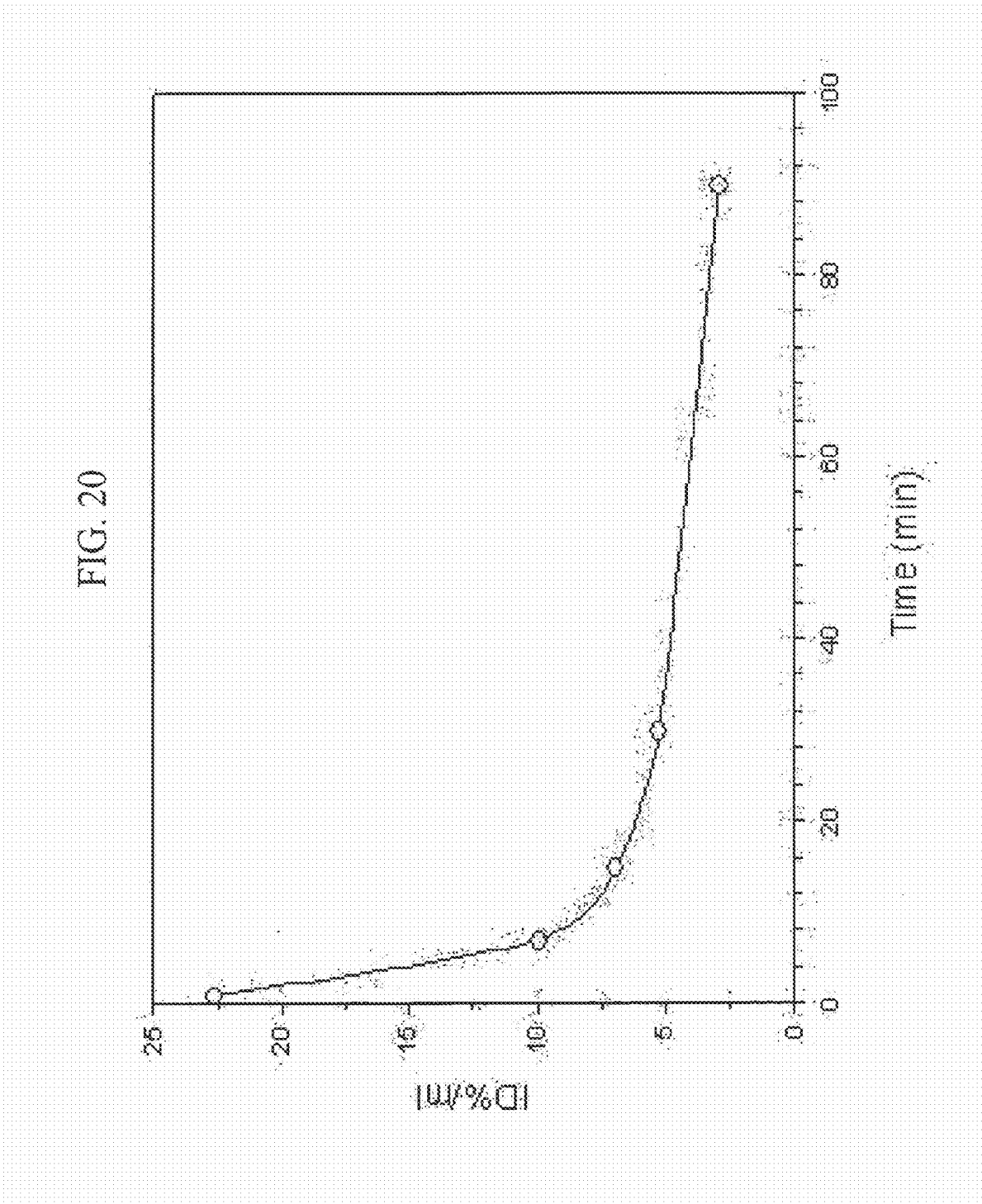
FIG. 20 is a graph of plasma clearance as percent injected dose per mL versus time.

A total of 15 mice were injected with 100 µL $^{125}$I-D6 and mice (in sets of 3) were sacrificed at the following time points: 0, 7, 15, 30, 90 minutes. After injection more than 2 µCi was found remaining in the syringe, so actual activity injected was about 6 µCi. With 6 µCi injected, the corresponding protein administered was ~0.5 µg per animal. Once sacrificed, the counts were determined in a 50 µL plasma sample from each animal. For each set of three animals at each time point, the counts were averaged, converted to % injected dose/ml plasma (ID %/mL), and then plotted to assess the rate of clearance (FIG. 20). This data was fit to either a 4 or 5 parameter equation to determine the biphasic half life of this molecule. The 4 parameter fit resulted in a $T_{1/2\alpha}$ of 2.55 minutes and a $T_{1/2\beta}$ of 64.66 minutes. The 5 parameter fit resulted in a $T_{1/2\alpha}$ of 2.13 minutes and a $T_{1/2\beta}$ of 23.26 minutes.

Larger volumes of plasma were also taken from mice sacrificed at the 0, 30, and 90 minute time points. These samples were injected onto a Superdex peptide column (Pharmacia) coupled to a radioactivity detector to assess the association of the peptide with serum proteins (FIG. 21). As shown, the labeled peptide does associate with higher MW proteins, which could explain its biphasic half life clearance behavior.

To help assess the potency of the peptide as an anti-angiogenesis inhibitor, D6 was tested in an endothelial cell proliferation assay using HUVECs and BrdU detection. Briefly, freshly isolated HUVECs (between pH3-6) were cultured in RPMI+10% FCS+1% antibiotics+1% L-glutamine+0.4% BBE (bovine brain extract) and seeded per well, 5000-10000/well in 100 µL. The cells were allowed to recover for 24 hrs prior to use. Then the cells were washed with PBS twice and treated for 48 hrs with anti-VEGF antibody (positive control) or peptides A, B and C (0.1 and 10 ug/mL) in RPMI+0.1% BSA+1% L-glutamine. The following 6 variables were tested in 2 series (n=4):

Series I: w/o VEGF
Series II: wt VEGF (30 ng/mL)
1. Standard medium: RPMI+10% FCS+1% antibiotics+ 1% L-glutamine+0.4% BBE
2. Negative control 1: RPMI (true starvation)
3. Negative control 2: RPMI+0.1% BSA+1% L-glutamine
4. Positive control: anti-VEGF 10 µg/mL in RPMI+0.1% BSA+1% L-glutamine
5. 0.1 µg/mL KDR peptides in RPMI+0.1% BSA+1% L-glutamine
6. 10 µg/mL KDR peptides in RPMI+0.1% BSA+1% L-glutamine Protocol:
1) cells are incubated for 48 hours under various conditions
2) 10 µL BrdU dilution (1:100 in EBM) is added to each well at 24 hours
3) incubate for another 24 hours (total 48 hrs)
4) aspirate the culture medium
5) add 100 µL, FixDenat (Roche Applied Science, Indianapolis, Ind.) to each well, incubate at room temperature for 30 min.
6) Discard FixDenat solution 7) 100 μL antibody-solution (PBS 1% BSA and anti-BrdU PO) added to each well.
8) incubate at RT for 90 minutes.
9) wash 3 times with PBS, 200 μL/well, 5 min.
10) add substrate solution (TMB), incubate for 10-30 minutes
11) transfer all to a flexible plate
12) stop the reaction by adding 2 M $H_2SO_4$, 25 μL/well
13) read absorbance at 450 nm within 5 minutes after stopping the reaction.

Background binding was determined by omitting the anti-BrdU antibody in 4 wells with control cells (cultured in complete medium; EBM+BulletKit (Clonetics, BioWhittaker, Inc., MD) and by complete labeling of cells that was not exposed to BrdU.

Figure 22:
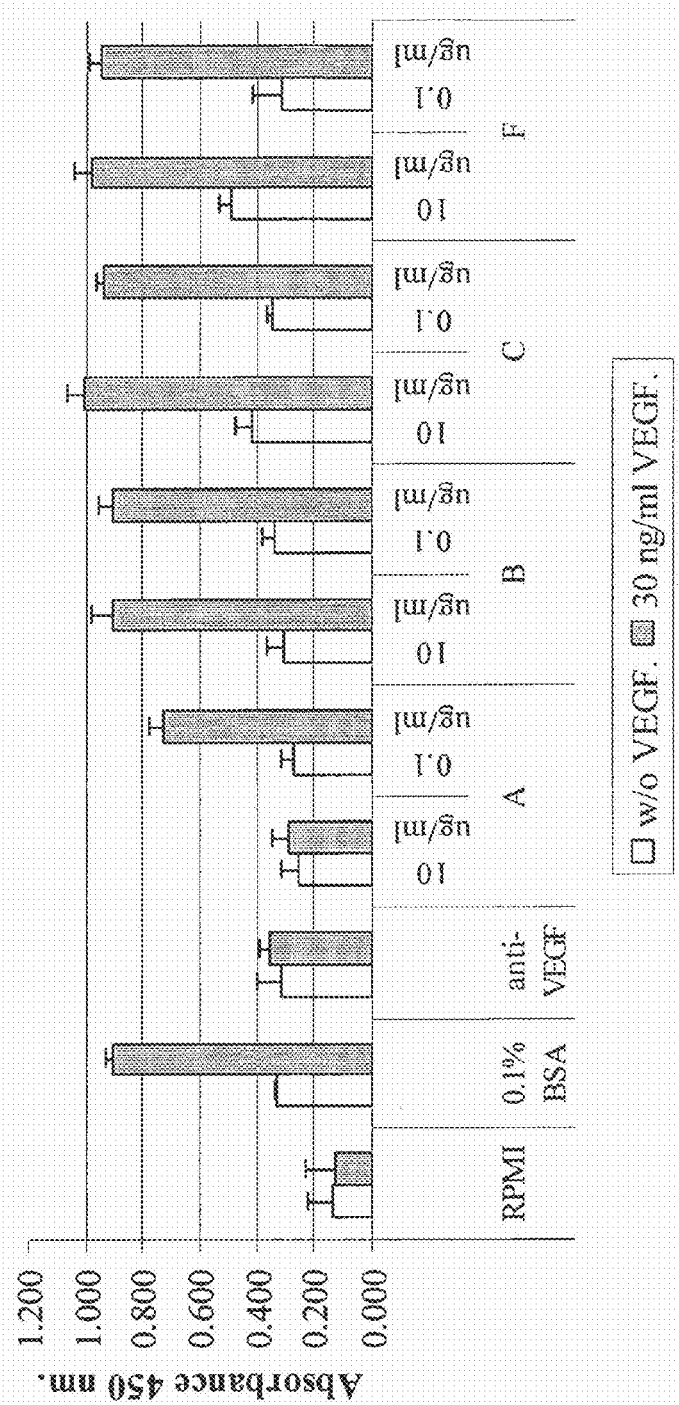
FIG. 22 is a graph showing the results of testing of KDR peptides in HUVEC proliferation assay. A: D6; B: SEQ ID NO:277; C: SEQ ID NO:377 (AEGTGDLHCYFPWVC-SLDPGPEGGGK SEQ ID NO:377; negative control); F: SEQ ID NO:377; negative control.

Of the two KDR binding peptide tested (D6 and SEQ ID NO:277) as shown in FIG. 22, D6 (A) completely inhibits HUVEC proliferation at 10 μg/mL in the presence of VEGF, similar to an anti-VEGF antibody (positive control). On the other hand, SEQ ID NO:277 (B, one of the peptides that make up the heterodimer) did not inhibit proliferation in this assay at the highest concentration tested (10 μg/mL). As a result, the heterodimer shows an enhanced ability to compete with VEGF in comparison with SEQ ID NO:277 alone.

Example 19

BIAcore Analysis—Murine KDR-Fc Binding of Peptide Dimers D1 and D7

Using BIAcore, the binding constants of peptide dimers D1 (a heterodimer of SEQ ID NO:277 and SEQ ID NO:294 and D7 (a heterodimer of SEQ ID NO:264 and SEQ ID NO 294; see FIG. 67) for murine KDR-Fc were determined.

Procedure

Three densities of recombinant murine KDR-Fc were cross-linked to the dextran surface of a CM5 sensor chip by the standard amine coupling procedure (0.5 mg/mL solution diluted 1:100 or 1:40 with 50 mM acetate, pH 6.0). Flow cell 1 was activated and then blocked to serve as a reference subtraction. Final immobilization levels achieved:

$R_L$ Fc 2 KDR-Fc=2770

$R_L$ Fc 3 KDR-Fc=5085

$R_L$ Fc 4 KDR-Fc=9265

Experiments were performed in PBS buffer (5.5 mM phosphate, pH 7.65, 0.15 M NaCl)+0.005% P-20 (v/v)). SEQ ID NO:277, run as a control, was diluted to 125 nM in PBS. Serial dilutions were performed to produce 62.5, 31.3, 15.6, 7.8, and 3.9 nM solutions. D1 and D6 were diluted to 50 nM in PBS and serial dilutions were performed to produce 25, 12.5, 6.25, 3.13, 1.56, 0.78, and 0.39 nM solutions. All samples were injected in duplicate. For association, peptides were injected at 30 μL/ml for 3 minutes using the kinject program. Following a 10 minute dissociation, any remaining peptide was stripped from the rmKDR-Fc surface with a quickinject of 50 mM NaOH+1 M NaCl for 12 s at 75 μL/min.

Figure 23A:
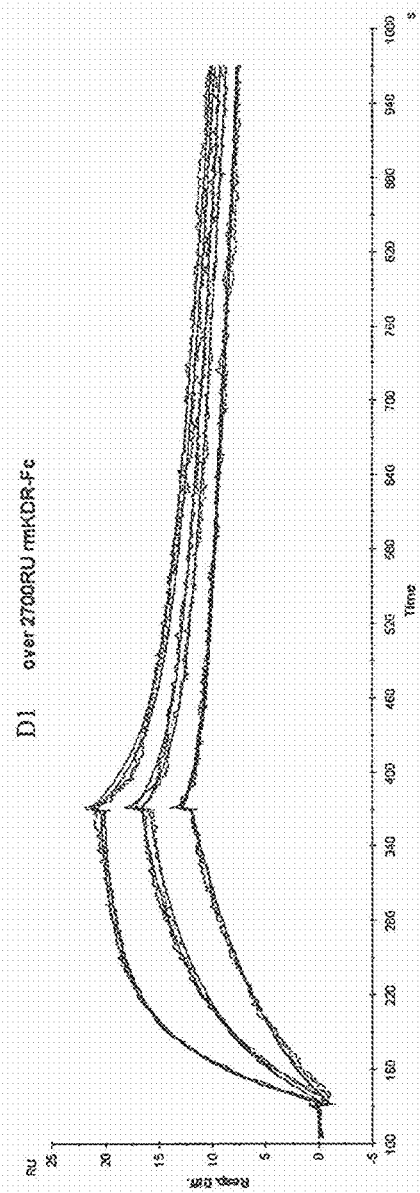
FIGS. 23A and 23B show the kinetic analysis of D1 (see FIG. 36), binding to murine KDR-Fc. All sensograms are fit to the bivalent analyte model.
Figure 23B:
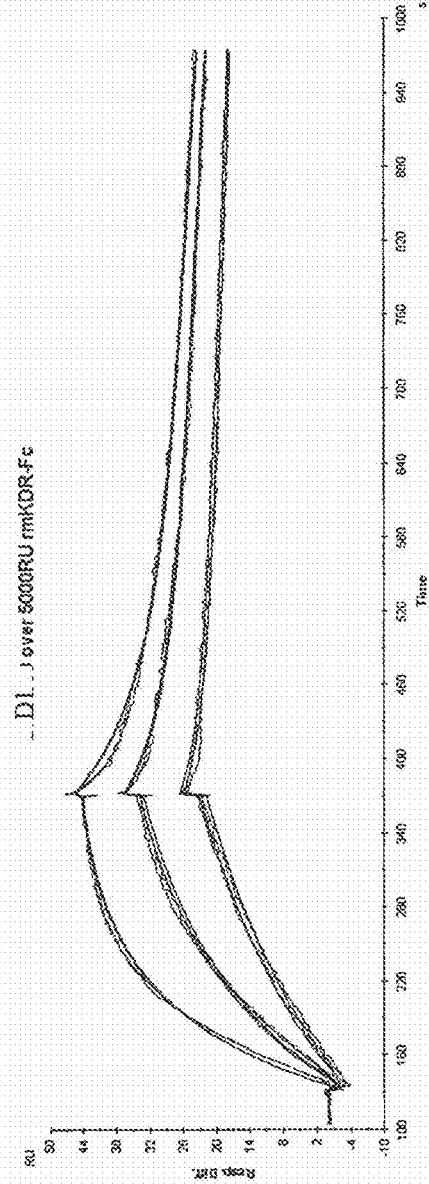
Figure 24A:
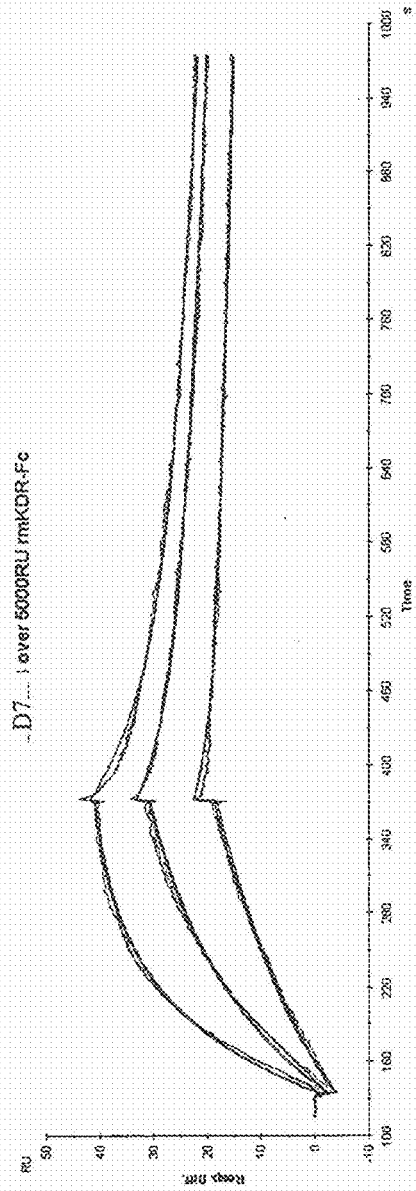
FIGS. 24A and 24B show the kinetic analysis of D7, a heterodimer of SEQ ID NO:264 and SEQ ID NO:294. All sensograms are fit to the bivalent analyte model.
Figure 24B:
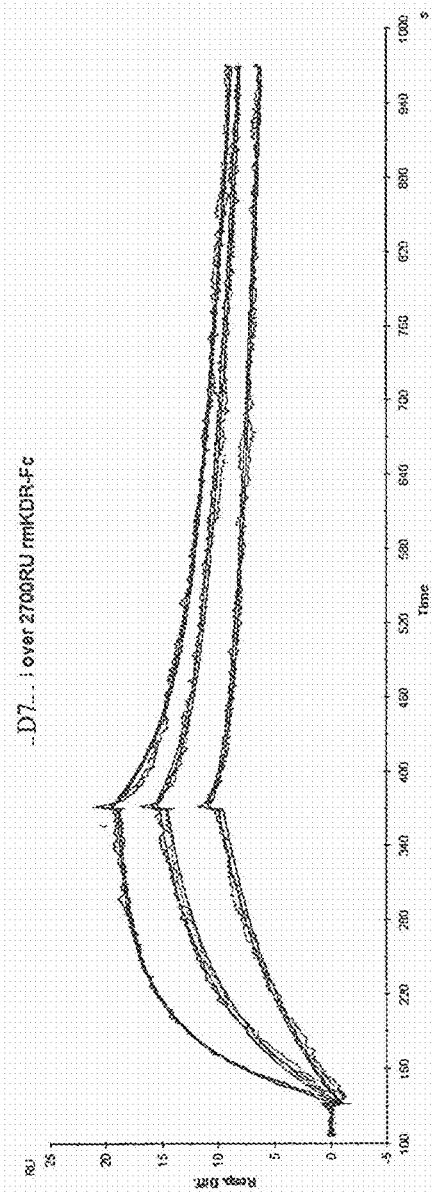
Figure 25B:
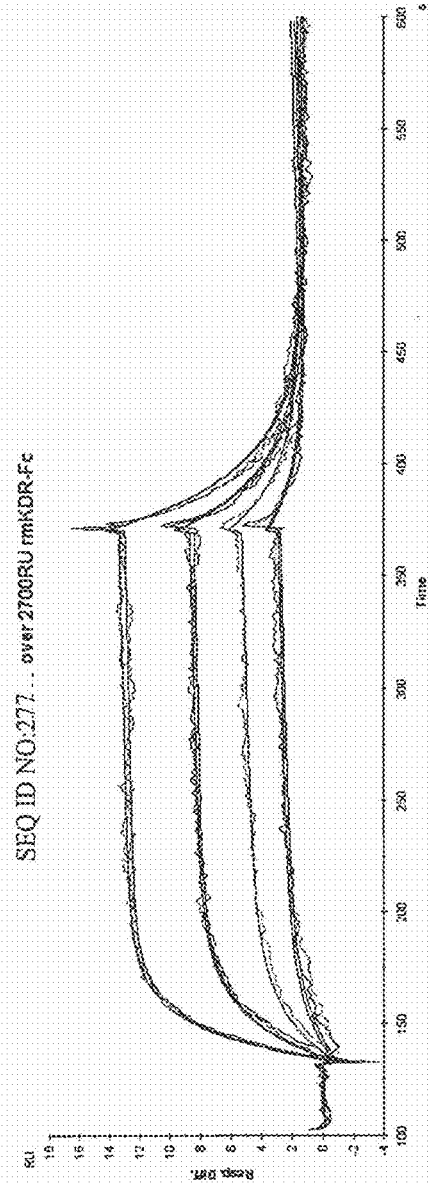

Sensorgrams were analyzed using the simultaneous $k_a/k_d$ fitting program in the BIAevaluation software 3.1. The Results are shown in Table 15 and FIGS. 23-25. The fact that about the same $K_{D2}$ constant was achieved for both heterodimers even when the density of receptor on the sensor chip was reduced by half is consistent with multimeric binding of the heterodimers to individual receptors rather than cross-link-type binding between receptors.

TABLE 15

Summary of Kinetic Parameters.

| | | ka1 (1/Ms) | Kd1 (1/s) | ka2 (1/RUs) | kd2 (1/s) | KD1[#] (nM) | KD2[‡] (nM) | Chi2[*] |
|---|---|---|---|---|---|---|---|---|
| D1 | vs. 2700RU | 7.94E+05 | 0.0139 | 3.31E-04 | 5.96E-04 | 17.5 | 0.751 | 0.077 |
| | vs. 5000RU | 5.54E+05 | 8.88E-03 | 1.17E-04 | 4.57E-04 | 16.0 | 0.825 | 0.323 |
| D7 | vs. 2700RU | 7.59E+05 | 0.011 | 3.36E-04 | 6.44E-04 | 14.5 | 0.848 | 0.082 |
| | vs. 5000RU | 5.21E+05 | 7.39E-03 | 1.17E-04 | 4.68E-04 | 14.2 | 0.898 | 0.278 |
| Fluorescein | vs. 2700RU | 1.02E+06 | 0.037 | — | — | 36.4 | — | 0.073 |
| SEQ ID NO: 277 | vs. 5000RU | 5.18E+05 | 0.0174 | — | — | 33.6 | — | 0.167 |

[#]$K_{D1}$ is a calculated $K_D$ based on $kd_1/ka_1$
[‡]$K_{D2}$ is a calculated $K_D$ based on $kd_2/ka_1$ (i.e., avidity factor)
[*]The chi2 value is a standard statistical measure of the closeness of the fit. For good fitting to ideal data, chi2 is of the same order of magnitude as the instrument noise in RU (typically <2).

Example 20

In Vivo Inhibition of Tumor Growth

Conditions are described providing methods for determining efficacy of three (3) concentrations for Test Article (binding peptide, D6) suspected of having anti-angiogenic activity on SW-480 human colon carcinoma cells using an in vivo xenograft tumor model.

Athymic nude mice are acceptable hosts for the growth of allogenic and heterogenic cells. Nude mice are required in *Points to Consider in the Characterization of Cell Lines used to Produce Biologicals* (*Points to Consider in the Characterization of Cell Lines used to Produce Biologicals*, FDA 1993).

D6 is a synthetic heterodimeric peptide suspected of having anti-angiogenic activity. This peptide binds to the human VEGF receptor 2 (KDR) with high affinity and competes with VEGF binding.

SW-480 Human Carinoma Cells

Colon carcinoma, SW-480, cells (ATCC) were cultured in Dulbecco's Modified Eagles Medium (DMEM) supplemented with 4 mM L-glutamine, 0.1 mM non-essential amino acids, 50 mg/mL Gentamicin, 250 mg/mL Fungizone and 10% heat inactivated fetal bovine serum at 37° C. in 95% air and 5% $CO_2$.

Exponentially growing cells were harvested, washed twice in phosphate buffered saline (PBS) to remove any traces of trypsin or serum. Cells were suspended in Hanks Balanced Salt Solution (HBSS) for injections.

Sterile phosphate buffered saline (BioWhittaker) was manufactured in accordance with cGMP regulations and was cell culture tested to assure compatibility; having a pH of 7.3-7.7 and an osmolarity of 271-287 mOsm/kg. PBS was the vehicle used to reconstitute Test Articles and for vehicle control injections.

Cisplatin (American Pharmaceutical Partners, Inc.; Los Angeles, Calif.) was prepared according to manufacture's specifications. Cisplatin was prepared in an aseptic fashion using a BL2 BioChem guard hood.

Test System

A. Species/Strain: *Mus musculus*, Crl:NU/NU-nuBR mice (nude mice)
B. Sex: Female
C. Age: 6-8 weeks at initiation of treatment
D). Weight Range: No weight requirement
E. Source: Animals were received from the Gnottobiotic Department at Charles River Laboratories, Wilmington, Mass.
F. Number: A total of 115 animals were received and injected for this study, with 90 mice used on study.
G. Method of Identification:
   Mice were uniquely numbered using an ear tag system. Additionally, cages were marked with cage cards minimally identifying group number, animal number, study number and IACUC protocol number.
H. Randomization:
   Animals were randomly assigned to treatment groups using Microsoft® Excel 97 SR-1 program.
I. Humane Care of Animals:
   Treatment and care of the animals were in accordance with the standard operating procedures of Charles River Laboratories, which adheres to the regulations outlined in the USDA Animal Welfare Act (9 CFR, Parts 1, 2, and 3) and the *Guide for the Care and Use of Laboratory Animals*.
   This study protocol was covered under the Charles River Laboratories Institutional Animal Care and Use Committee (IACUC Protocol Number: P071820011).

Animal Care

A. Diet and Drinking Water:
   Mice were fed gamma-irradiated rodent chow ad libitum. Tap water was sterilized and supplied via bottle and sipper tube ad libitum.
B. Animal Environment:
   Animals were housed by groups in semi-rigid isolators. Mice were housed in flat bottom caging containing five to ten animals. Cages contained gamma-irradiated contact bedding. The number of mice in each cage may have been altered due to the behavior of the mice, changes were noted in the isolator inventory. The housing conforms to the recommendations set forth in the *Guide for the Care and Use of Laboratory Animals*, National Academy Press, Washington, D.C., 1996 and all subsequent revisions.
   Environmental controls were set to maintain a temperature of 16-26° C. (70±8° F.) with a relative humidity of 30-70. A 12:12 hour light: dark cycle was maintained.
C. Acclimation:
   Once animals were received, they were allowed to acclimate to the laboratory environment for 24-hours prior to the study start. Mice were observed for signs of disease, unusual food and/or water consumption or other general signs of poor condition. At the time of animal receipt, animals were clinically observed and appeared to be healthy.

Experimental Design

A. General Description:
   Female athymic nude mice (Crl:NU/NU-nuBR) at 6-8 weeks of age were used in this study. A total of 115 mice were injected subcutaneously into the right lateral thorax with $5 \times 10^6$ SW-480, human colon carcinoma cells. When tumors reached a target window size of approximately 150±75 mg, 90 tumor-bearing mice were randomly selected and distributed into one of nine groups. Test Articles and vehicle were administered intraperitoneally (IP), Cisplatin was administered intravenously (IV). Tumor measurements were recorded twice weekly using hand-held calipers. Mice were monitored daily for signs of toxicity and morbidity. At study termination, animals were euthanized by carbon dioxide overdose and necropsied for tissue collection.
B. Group Assignments:
   A total of nine (9) groups were used in this study. Each group contained ten (10) tumor-bearing mice. Groups 1 and 2 contained untreated and vehicle treated negative control mice, respectively. Groups 3, 4, and 5 contained mice that received one of tree different concentrations of the D6 anti-angiogenic peptide. Group 9 contained mice that received cisplatin, a standard chemotherapeutic compound as a positive control.
C. Dosing Levels and Regiment:
   Dose levels for each group are provided in Table 16. Dosing began the same day that animals were randomly sorted into groups (Study Day 7). Each dose was removed from the dose vial using aseptic technique for each animal and the injection site was wiped with an alcohol swab prior to dose administration. Doses were administered with a 1.0 mL syringe and a 27-gauge×½" needle for each mouse
   The Test Article- and vehicle-treated mice received daily intraperitoneal AP) injections for 15 days. Cisplatin was administered every other workday for a total of five (5) doses via an intravenous route.

TABLE 16

Study Treatment Groups

| Group | Test Article | Concentration mg/kg | Number of Animals |
|---|---|---|---|
| 1 | Untreated | — | 10 |
| 2 | Vehicle | 0 | 10 |
| 3 | D6 | 0.05 | 10 |
| 4 | D6 | 0.5 | 10 |
| 5 | D6 | 5.0 | 10 |
| 9 | Cisplatin | 6.0 | 10 |

D. Clinical Observations of Animals:
   Clinical Observations of each animal were performed and recorded at least once daily for toxicity, morbidity and mortality. Morbidity included signs of illness such as, but not limited to, emaciation, dehydration, lethargy, hunched posture, unkempt appearance, dyspnea and urine or fecal staining.
E. Tumor Measurements:
   In accordance with the protocol tumor measurements were taken twice weekly throughout the study by measuring the length and width of tumors with calibrated calipers. Measurements oared a minimum of 3-4 days apart, except when animals were euthanized and measurements were taken; this sometimes resulted in an interval of less than 3 days. Tumor weights were calculated using the following formula: mg= $(L \times W^2)/2$. Animals were euthanized either when mean tumor weight was ≥1000 mg per group over two (2) consecutive measurements, or if tumors became ulcerated, impaired the animal's ability to ambulate or obtain food and water.

F. Unscheduled Euthanasia and Unexpected Deaths:

1. Unscheduled Euthanasia:

None of the animals required unscheduled euthanasia while on study.

2. Unexpected Deaths:

None of the animals died while on study.

G. Necropsy:

1. Euthanasia and Necropsy Order:

All mice in groups 1, 2, 3, 4, and 5 (50 total) were submitted for necropsy when tumors reached a group mean target size of ≥1000 mg over two (2) consecutive measurements within a group. Animals were submitted for necropsy to the Charles River Laboratories Health Monitoring Laboratory (HM), Wilmington, Mass. All animals were euthanized on Study Day 22, short of received the full 28 day treatment regiment with Test Articles because mean tumor size was ≥1000 mg in Test Article Treated Groups 3-8.

All animals were humanely euthanized by carbon dioxide ($CO_2$) inhalation.

2. Tissue Collection:

Tumors were dissected free of surrounding tissue and overlying skin. Additionally the kidneys were collected. Any abnormalities noted on the renal surfaces were noted.

Frozen blocks were made of tumors and kidneys for each animal. A representative section of the tissue (tumor, kidneys) was taken. Kidney sections included the cortex and medulla. Tissue sections were placed in the bottom of a labeled plastic-freezing mold. Tissue was embedded with OCT medium. Blocks were submerged into isopentane chilled with dry ice until frozen. Blocks were briefly examined for quality, and stored on dry ice.

Blocks were labeled with the animal number and a letter code corresponding to tissue (A=left kidney, B=right kidney; C=mass). Blocks from one animal were placed into a labeled bag.

Results

A. In-Life Measurements and Observations:

1. Clinical Observations, Morbidity and Mortality Summary Statement:

All animals appeared healthy and were within normal limits throughout the study. D6 showed no signs of toxicity at the doses used in this study.

Animals were euthanized on Study Day 22. All mice, except Group 9 mice, were euthanized prior to completing Test Article administration, because mean tumor size was ≥1000 mg in Groups 1-8. Group 9, Cisplatin-treated animals were euthanized on Study Day 22 when mean tumor weight was 995 mg. No animals died while on study.

2. Mass Palpation Summary Statement:

Throughout the study palpable masses were detected in all mice, with tumors progressively growing for the duration of the study. As expected tumors in untreated and vehicle treated negative control mice (Groups 1 and 2) grew the fastest, reaching a mean tumor size of 1000 mg on or before Study Day 20. In addition, animals treated with Cisplatin (Group 9) developed tumors that grew the slowest reaching a mean tumor size of 995 mg at study termination (Day 22).

Figure 65:
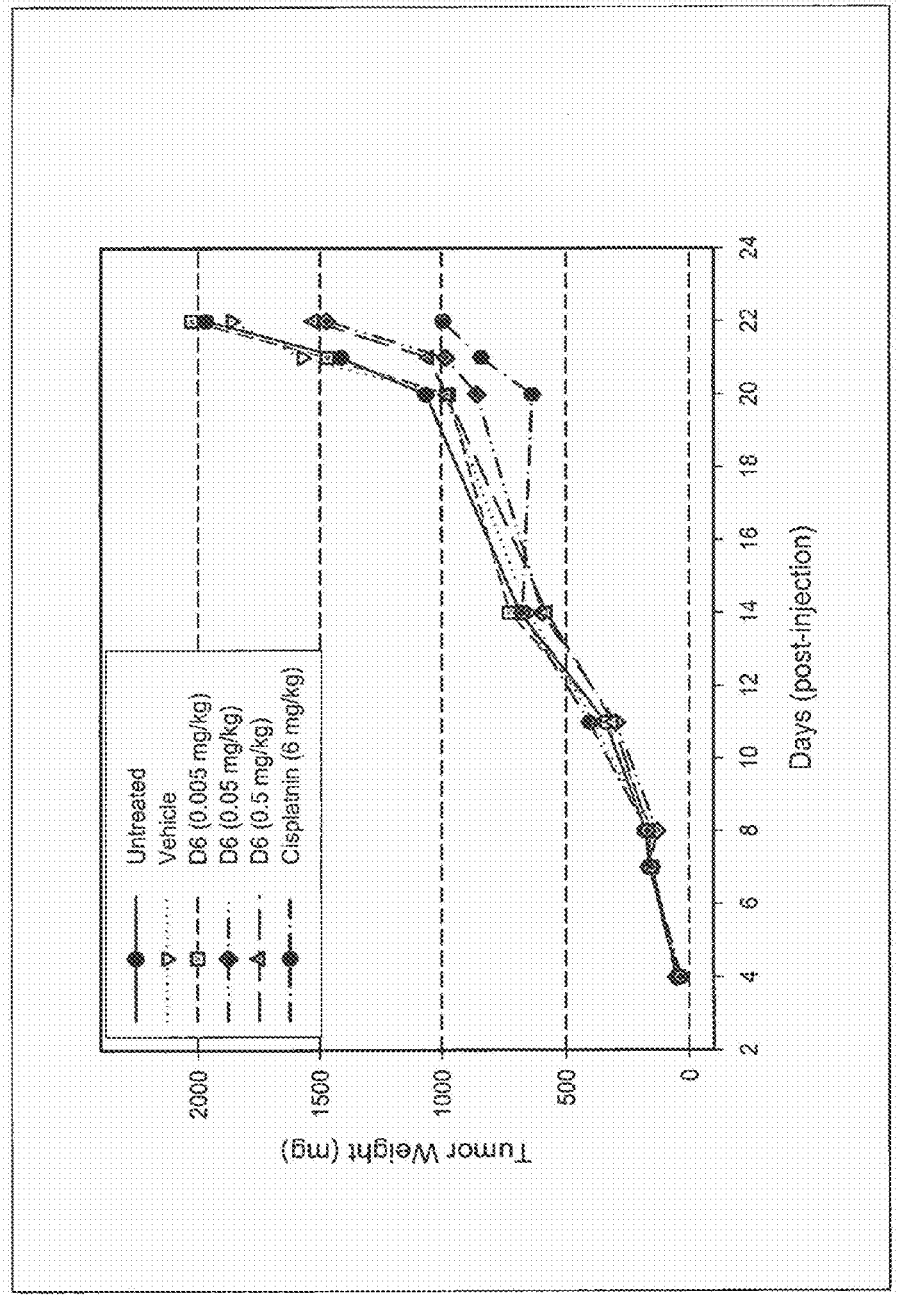
FIG. 65 is a graph showing the inhibition of tumor growth by D6 as a function of D6 concentration.

In general, except for Group 3 mice, all animals treated with Test Article resulted in slower tumor growth FIG. 65). Animals in Group 3, which were treated with the low dose of D6 (0.05 mg/kg) had tumors that grew at approximately the same rate as the tumors in untreated and vehicle treated animals in Groups 1 and 2. Animals treated with either higher doses of D6 (Groups 4 and 5) had tumors that grew slower; reaching a mean tumor size of 1000 mg on Study Day 21. When compared to control Groups 1 and 2 mice, Test Article treatment resulted in a delay of tumor growth of approximately 1 day.

B. Conclusions:

Data from this study validate the model used because tumor-bearing mice in negative control Groups 1 and 2 and positive control Group 9 responded as expected.

Throughout the study palpable masses were observed in all groups. In addition, all animals were healthy and within normal limits throughout the study. Furthermore, D6 did not adversely affect the animals. Therefore, these data would suggest that animals treated with D6 Test Article had tumors that grew slowly (approximately 1 day slower over the 22 day test period than controls). Also, since the Test Article did not show any significant toxic effects, higher concentrations of Test Article could also be used with potentially better tumor regression.

TABLE 17

| | | | Test Article | | | | |
|---|---|---|---|---|---|---|---|
| | Untreated Control | Vehicle Control | D6 0.005 mg/kg | D6 0.05 mg/kg | D6 0.5 mg/kg | Cisplatnin 6 mg/kg | |
| Days After Cell Injection  4 | 48 | 49 | 43 | 51 | 50 | 34 | Tumor Weights (mg) |
| 7 | 164 | 156 | 157 | 163 | 154 | 160 | |
| 8 | 180 | 164 | 156 | 133 | 168 | 173 | |
| 11 | 340 | 388 | 333 | 298 | 310 | 407 | |
| 14 | 684 | 648 | 726 | 596 | 577 | 675 | |
| 20 | 1064 | 986 | 973 | 857 | 978 | 635 | |
| 21 | 1412 | 1571 | 1468 | 983 | 1056 | 839 | |
| 22 | 1967 | 1863 | 2026 | 1474 | 1526 | 995 | |

Example 21

In Vitro Cell Proliferation Assay

Figure 84:
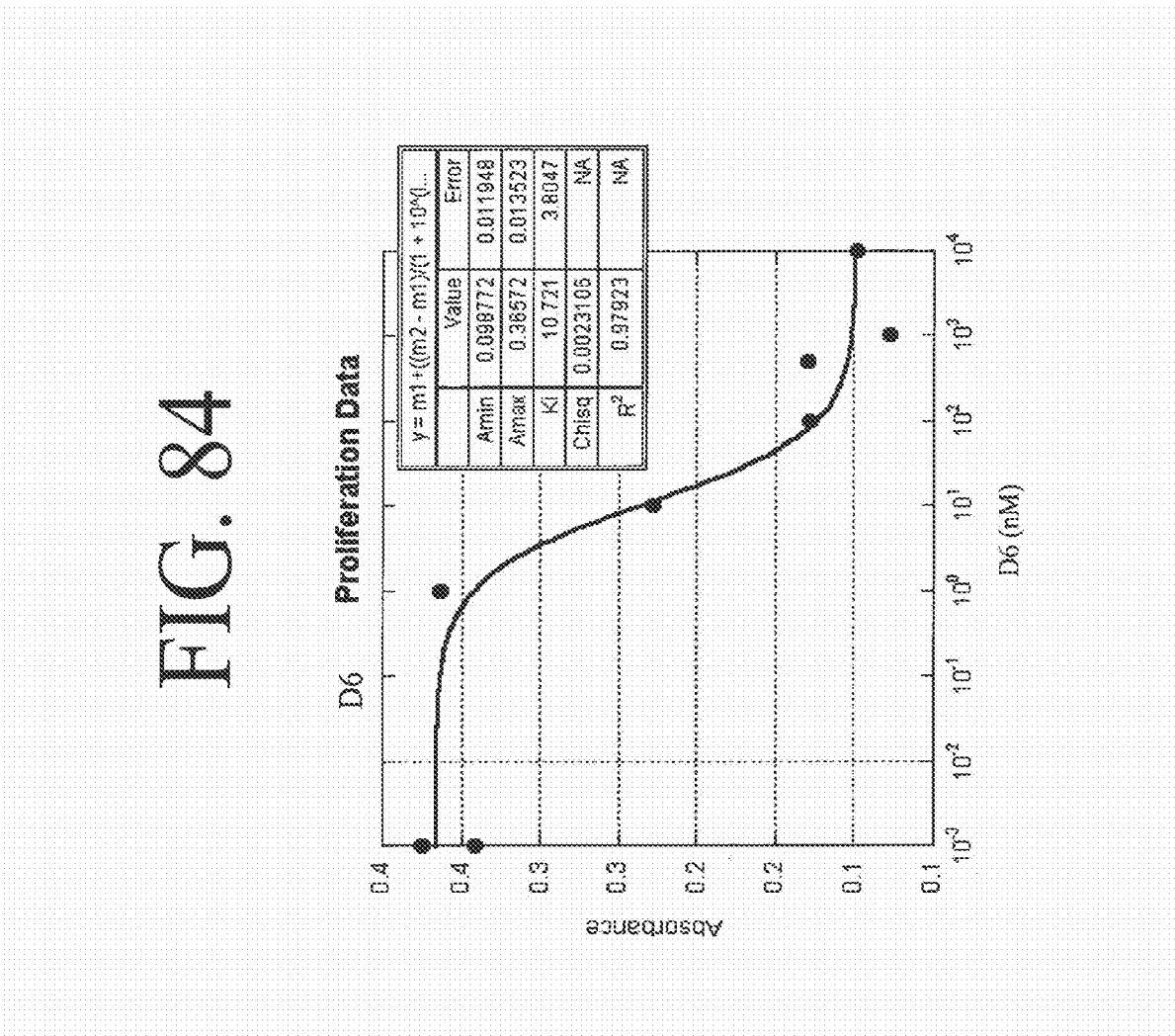
FIG. 84 is a graph showing the results of in vitro binding assays. Microvascular endothelial cells (MVECs, Cascade Biologics, Portland, Oreg.) were used to assess the in vitro efficacy of D6 and related analogues for their ability to inhibit VEGF-stimulated proliferation.

Microvascular endothelial cells (MVECs, Cascade Biologics, Portland, Oreg.) were used to assess the in vitro efficacy of D6 and related analogues for their ability to inhibit VEGF-stimulated proliferation. MVECs (passage 2) were grown to 90% confluency, trypsinized and plated in gelatin-coated 96-well microtiter plates at a density of $4\text{-}8 \times 10^3$ cells/well. Sixteen to 24 hours after plating, the cells were washed one time (200 μL/well) with media devoid of fetal bovine serum but containing 0.1% bovine serum albumin (BSA) Fresh BSA-containing media was added to each well and the cells were incubated for an additional 24 hours. After this 24 hour period of starvation, fresh BSA-containing media (containing 25 ng/mL VEGF) with or without D6 was added and the cells were incubated for an additional 48 hours at 37 C. To assess the dose response in this assay, multiple D6 concentrations were tested in duplicate wells. The media was removed and fresh BSA-containing media was added with or without BrdU and the cells were incubated for an additional 24 hours prior to determining the level of incorporation exactly as described by the manufacturer. Results are shown in FIG. 84.

Example 22

The following experiment assessed the ability of D25 and D27 to block the VEGF-induced migration of HUVECs in culture and demonstrated that the added glycosylation and/or distinct spacer structure used in D27 enhanced its potency.

Protocol: Serum-starved HUVECs were placed, 100,000 cells per well, into the upper chambers of BD fibronectin-coated FluoroBlok 24-well insert plates. Basal medium, with or without VEGF (10 ng/mL) in the presence or absence of D25 or D27, was added to the lower chamber of the wells. After 22 hours, quantitation of cell migration/invasion was achieved by post-labeling cells in the insert plates with a fluorescent dye and measuring the fluorescence of the invading/migrating cells in a fluorescent plate reader. The VEGF-induced migration was calculated for each experimental condition by subtracting the amount of migration that occurred when only basal medium was added to the lower chamber of the wells.

Figure 66:
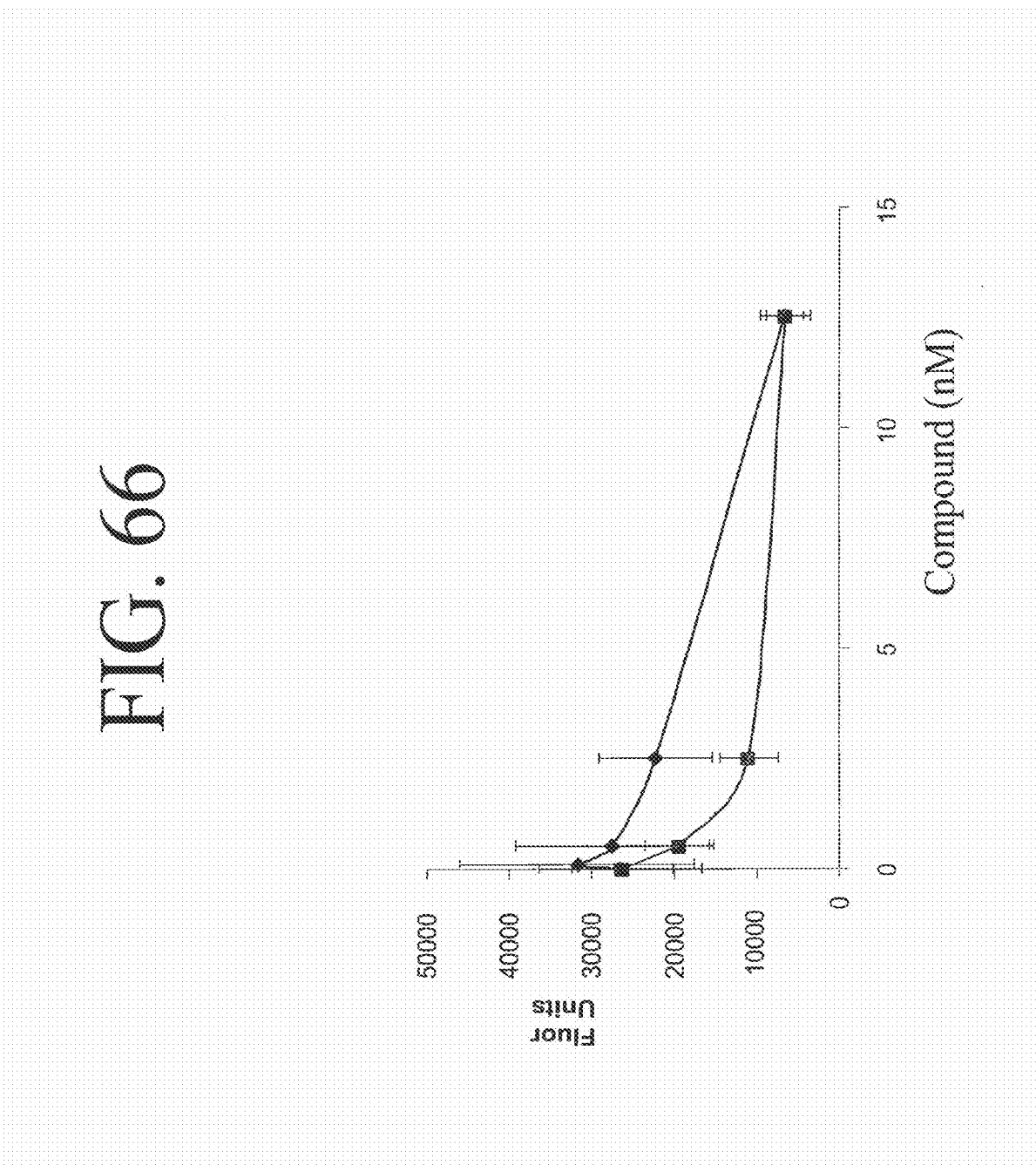
FIG. 66 shows that D27 (squares) with its glycosylation and modified spacer is able to block the effects of VEGF in the migration assay to block VEGF-stimulated migration even mote potently than D25 (diamonds), which lacks those chemical modifications.

Results: VEGF induced a large increase in endothelial cell migration in the assay, which was potently blocked by both D25 and D27 (FIG. 66). D27 was ten-fold more potent than D25 ($IC_{50}$ 0.5 nM and 5 nM respectively), indicating that the glycosylation of D27 and/or its distinct spacer properties has enhanced its ability to bind KDR and block the effects of VEGF.

Example 23

The following experiment assessed the ability of "Adjunct A" multimeric construct of TKPPR peptide (SEQ ID NO:503; binds to NP-1, a VEGF receptor that enhances the effects of VEGF mediated by KDR), to enhance the inhibition of the VEGF-induced migration of HUVECs in culture produced by D6. Adjunct A=5CF-Gly-N{[$CH_2CH_2C$(=O)-Gly-N($CH_2CH_2C$(O)-Adoa-Thr-Lys-Pro-Pro-Arg-OH]$_2$}$_2$ where Adoa=3,6-dioxa-8-aminooctanoyl, 5CF=5-carboxyfluoresceinyl. See FIG. 67B.

Protocol: Serum-starved HUVECs were placed, 100,000 cells per well, into the upper chambers of BD fibronectin-coated FluoroBlok 24-well insert plates. Basal medium, containing with or without VEGF (10 ng/mL) in the presence or absence of varying concentrations of D6, or varying concentrations of D6 in combination with a constant 100 nM Adjunct A (synthesized as described in WO 01/91805 A2) was added to the lower chamber of the wells. After 22 hours, quantitation of cell migration/invasion was achieved by post-labeling cells in the insert plates with a fluorescent dye and measuring the fluorescence of the invading/migrating cells in a fluorescent plate reader. VEGF-induced migration was calculated for each experimental condition by subtracting the amount of migration observed in the absence of VEGF.

Figure 67A:
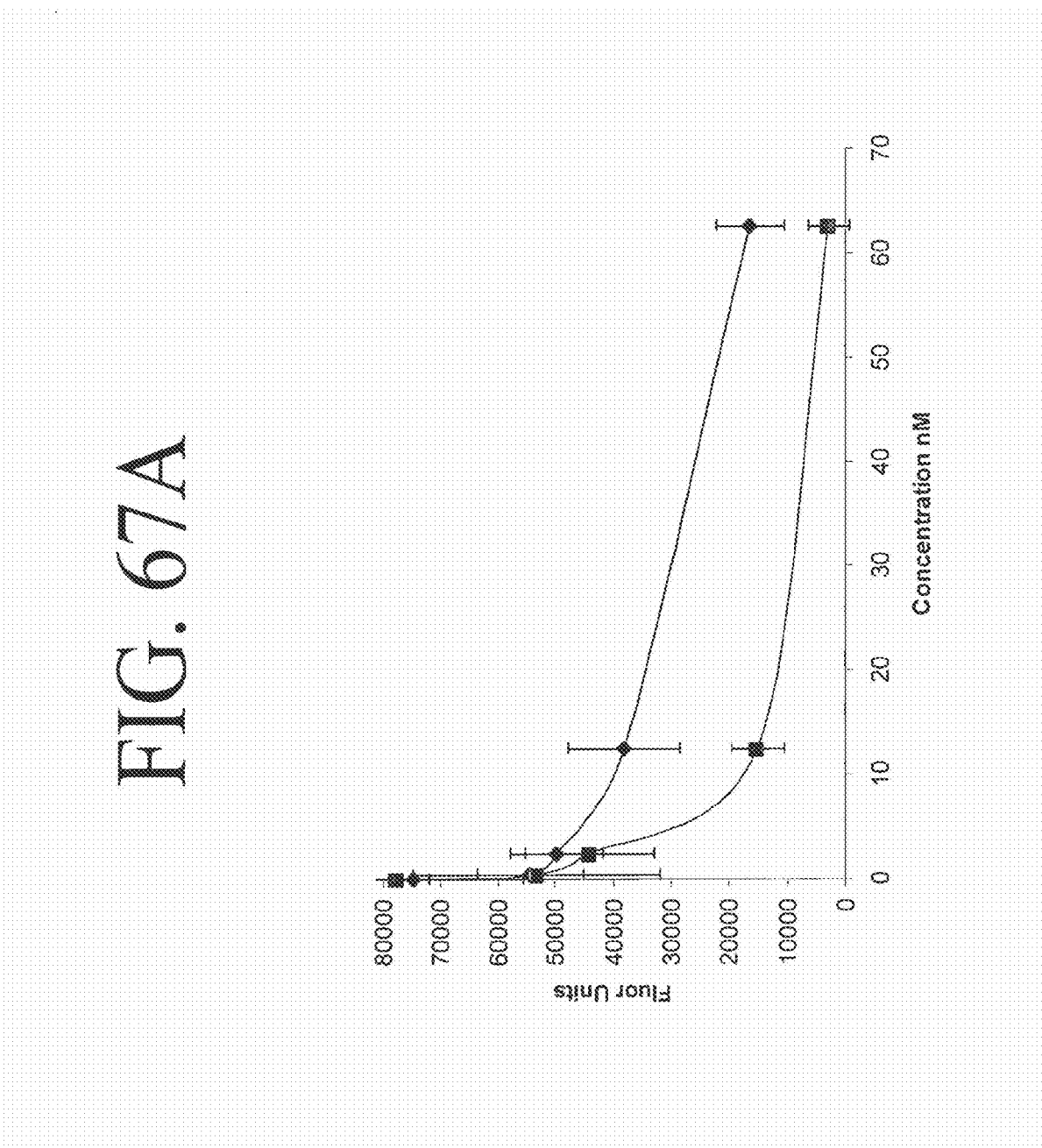
FIGS. 67A and 67B show that Adjunct A enhances the potency of D6 in blocking the biological effects of VEGF in a migration assay with cultured HUVECs.
Figure 67B:
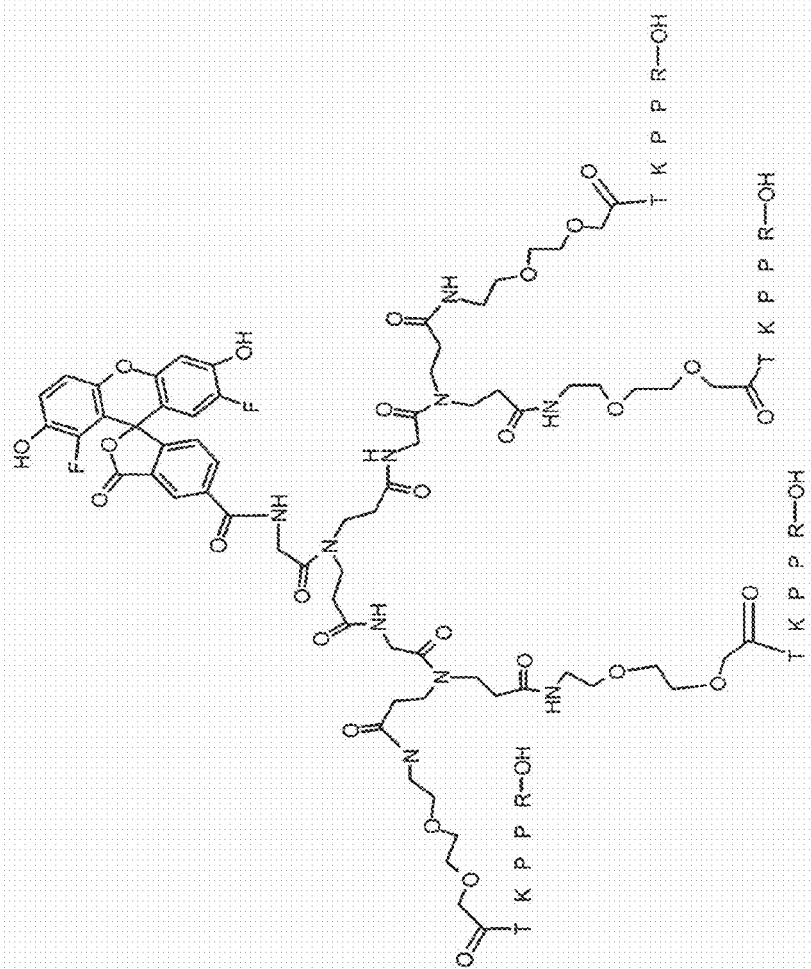

Results: VEGF induced a large increase in endothelial cell migration in the assay, which was potently blocked by D6 ($IC_{50}$ about 12.5 nM), but not by 100 nM Adjunct A alone (FIG. 67A). Surprisingly however, Adjunct A was able to enhance the potency of D6 by about ten-fold when used in the assay simultaneously with D6 ($IC_{50}$ about 2.5 nM). This indicates that compounds containing the TKPPR sequence (or similar) found in Adjunct A can be used to enhance the potency of certain compounds such as D6, which compete with VEGF for binding to KDR. In addition, a heteromultimer containing the peptide sequences found in D6 or similar) as well as the TKPPR sequence (or similar), in one or more repetitions, would likely possess enhanced activity in this assay. See U.S. patent application Ser. No. 09/871,974, incorporated by reference in its entirety, for details regarding the preparation of TKPPR constructs.

Example 24

Synthesis of D27

Figure 68:
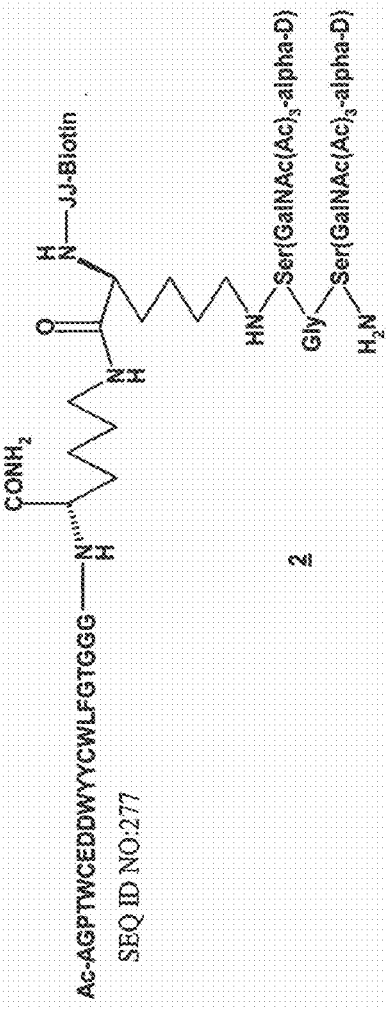
FIG. 68 is a schematic showing Scheme 1 (synthesis of Peptide 2).

Synthesis of 1 and 3 (see FIGS. 68 and 69)

Synthesis of the monomers were carried out as described in Method 5 on a 0.25 mmol scale employing as the starting resin Fmoc-GGGK(iV-Ddc)NH-PAL-PEG-PS resin. The peptide resin was washed and dried before cleavage or further derivatization by automated or manual methods.

Procedure Synthesis of Peptide 2 and Peptide 4 (see FIGS. 68 and 69)

Appendage of Biotin-JJ, Lysyl, Glycyl and Serinyl (GalNAc(Ac)-3-x-D moieties onto 1 and 3 was done by manual SPPS such as described in Method 6 and Method 8. The coupling of amino acids was carried out in DMF using HOBt/DIC activation (except for Ser(GalNAc(Ac)$_3$-α-D). Fmoc removal was carried out with 20% piperidine in DMF. All couplings were 5-16 hours duration. After each coupling, the completion was coned by the Kaiser test. In the case of Ser(GalNAc(Ac)$_3$-α-D the coupling was performed in DMF employing HATU/DIEA as the coupling agent. In cases where the Kaiser test indicated unreacted amino groups the coupling was repeated. Removal of the N-terminal Fmoc group and cleavage from resin was performed. The crude peptide was precipitated in ether and washed twice by ether and dried under vacuum. The linear crude peptide was directly cyclized by dissolving the peptide in DMSO (40 mg/mL). The pH of the solution was adjusted to X by addition of aqueous N-methylglucamine and the solution was stirred in air for 48 h at room temperature. The peptides were then purified employing gradient HPLC as described in Method 1 employing a Waters-YMC C-18 ODS preparative column (250 mm×4.6 mm i.d.). The pure product-containing fractions were combined and lyophilized to provide the needed peptides.

Figure 70:
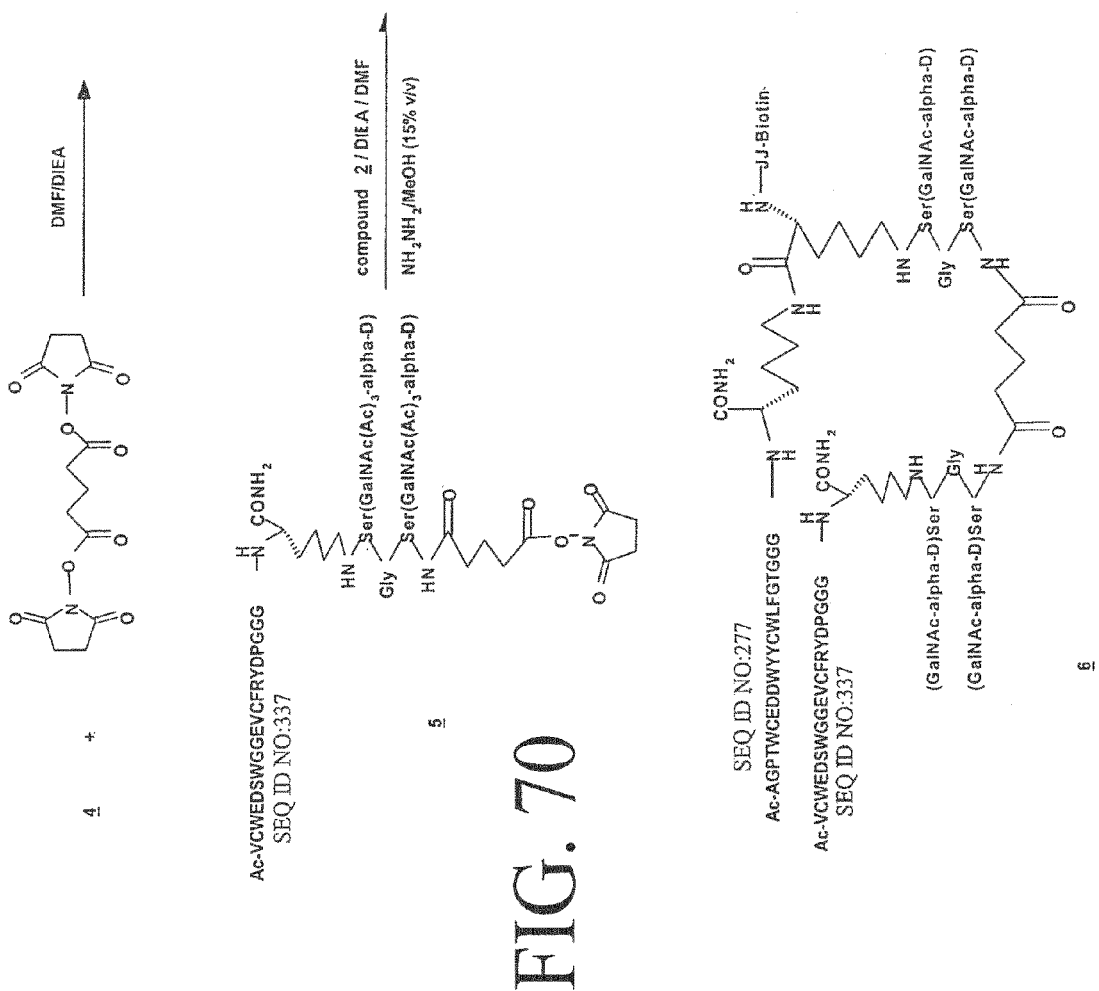
FIG. 70 is a schematic showing Scheme 3 (synthesis of D27).

Procedure: Synthesis of D27—Compound 6 (see FIG. 70)

To a solution of glutaric acid bis-NHS ester (0.122 mmol, Pierce Scientific Co.) in anhydrous DMF was added dropwise a solution of 4 in DMF (40 mg, 0.0122 mmol, DIEA was added to neutralize the trifluoroacetic acid bound to the peptide and N-hydroxysuccinimide formed dug the reaction). This 0.7 mL solution was stirred for 4 h. The reaction was monitored by HPLC and mass spectroscopy. DMF was removed under vacuum. The excess diester was removed by addition of ethyl acetate, which precipitated the peptide-monoester 5 while dissolving glutaric acid bis-NHS ester. The mixture was centrifuged and the liquid portion decanted. This was repeated twice. The residue was kept under vacuum for 10 min. The residue was dissolved in DMF and nixed with a solution of 2 (37 mg, 0.009 mmol) in DMF (pH 7). It was stirred at ambient temperature for 16 h. The volatiles were removed under high vacuum and the acetate functions were removed by treatment of the residue with 1 mL of hydrazine/MeOH (15/85, v/v) solution with stirring for 2.5 h at ambient temperature. Acetone was added to quench the excess of hydrazine and the volatiles were removed under vacuum. The resulting residue was dissolved in DMSO and purified by preparative HPLC as described above to provide 9 mg of the pure material.

Sequence and Analytical Data for Peptides 2, 4 and 6

| Compound identifier | Sequence | HPLC Ret. time (System) | Mass Spectrum (ESI, neg. ion) |
|---|---|---|---|
| Peptide 2: New Seq, a Seq 11 derivative | Ac-AGPTWCEDDWYYCWLFGTGGGK{Biotin-JJK[NH$_2$-Ser(GalNAc(Ac)$_3$-α-D)-Gly-Ser(GalNAc(Ac)$_3$-α-D)]}-NH$_2$ | 7.4 min (T) | 2041.3 [M − 2H]/2 |
| Peptide 4: New Seq, a Seq 5 derivative | Ac-VCWEDSWGGEVCFRYDPGGGK(NH$_2$ Ser(GalNAc(Ac)$_3$-α-D)-Gly-Ser(GalNAc(Ac)$_3$-α-D)-NH$_2$ | 8.0 min (T) | 1636.3 [M − 2H]/2 |
| D27 | Ac-AGPTWCEDDWYYCWLFGTGGGK{Ac-VCWEDSWGGEVCFRYDPGGGK[S(GalNAc-α-D)-G-S(GalNAc-α-D)-Glut-S(GalNAc-α-D)-G-S(GalNAc-α-D)-NH(CH$_2$)$_4$−(S)—CH(Biotin-JJNH−)C(=O)}- NH$_2$}-NH$_2$ | 5.50 min (M) | 1737.2 (M − 4H)/4; 1389.3 (M − 5H)/5; 1157.7 [M − 6H]/6 |

System T: Column: Waters XTerra, 4.6 x 50 mm; Eluents: A: Water (0.1% TFA), B: Acetonitrile (0.1% TFA): Elution: Initial condition, 15% B, Linear Gradient 15-50% B in 8 min; Flow rate: 3.0 mL/min; Detection: UV @ 220 nm.

Example 25

Demonstration of the Distinction Between Binding Affinity and Biological Potency Through In Vitro Assays The following experiments showed that heteromultimeric peptides can display much greater biological potency than a monomeric peptide with similar binding affinity to the same target.

Protocol experiment 1: 293H cells were transfected with the KDR cDNA or mock-transfected by standard techniques described in Example 5. The cells were incubated with $^{125}$I-VEGF in the presence or absence of SEQ ID NO: 504 or D1 (at 300, 30, 3, and 0.3 nM). After washing the cells, the bound radioactivity was quantitated on a gamma counter. The percentage inhibition of VEGF binding was calculated using the formula [(Y1−Y2)×100/Y1], where Y1 is specific binding to KDR-transfected 293H cells in the absence peptides, and Y2 is specific binding to KDR-transfected 293H cells in the presence of peptide competitors. Specific binding to KDR-transfected 293H cells was calculated by subtracting the binding to mock-transfected 293H cells from the binding to KDR-transfected 293H cells.

Protocol experiment 2: Serum-starved HUVECs were placed, 100,000 cells per well, into the upper chambers of BD fibronectin-coated FluoroBlok 24-well insert plates. Basal medium, with or without VEGF (10 ng/mL) in the presence or absence of increasing concentrations of SEQ ID NO:504 or D1, was added to the lower chamber of the wells. After 22 hours, quantitation of cell migration/invasion was achieved by post-labeling cells in the insert plates with a fluorescent dye and measuring the fluorescence of the invading/migrating cells in a fluorescent plate reader. VEGF-stimulated migration was derived by subtracting the basal migration measured in the absence of VEGF.

Figure 71:
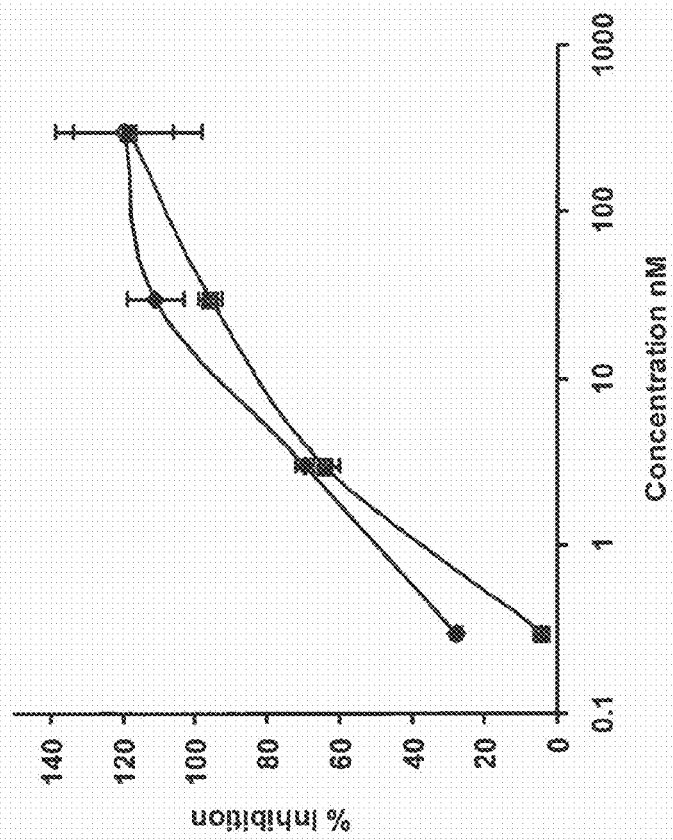
FIG. 71 depicts % inhibition±s.d. of specific $^{125}$I-VGF binding to KDR-transfected cells by SEQ ID NO:504 (squares) and D1 (diamonds).

Results experiment 1: As shown in FIG. 71, SEQ ID NO:504 AND D1 competed about equally well with $^{125}$I-VEGF for binding to KDR-transfected cells, indicating that they possess comparable binding affinities as well as a comparable ability to inhibit VEGF from binding to KDR.

Figure 72:
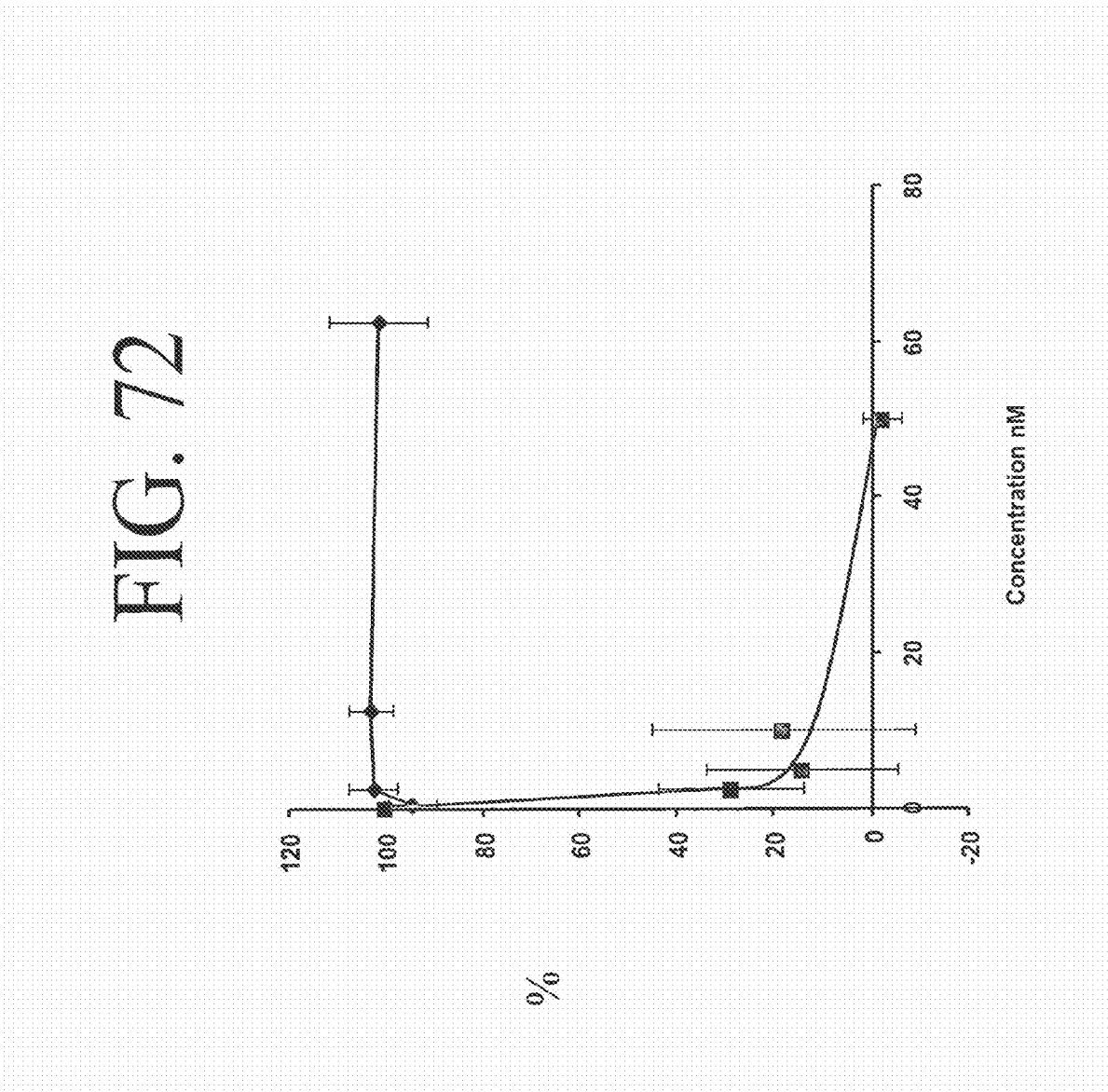
FIG. 72 depicts % maximum VEGF-stimulated migration±s.d. of HUVEC cells in the presence of the indicated concentrations of SEQ ID NO:504 (diamonds) or D1 (squares).

Results experiment 2: Despite the fact that both SEQ ID NO:504 and D1 potently block $^{125}$I-VEGF binding to KDR-expressing cells to the same degree (FIG. 72), the heterodimeric D1 was much more potent in blocking the biological effects of VEGF as demonstrated in an endothelial cell migration assay (FIG. 72) than the monomeric SEQ ID NO:504. At up to 62.5 nM, a peptide comprising SEQ ID NO:504 had no effect on VEGF-stimulated migration whereas D1 completely blocked VEGF-stimulated migration at 50 nM. These data suggest that heteromultimeric binding can more effectively block the biological activity of a ligand than a monomer, even when the monomer has a comparable ability to inhibit ligand binding to its receptor.

Example 26

Identification of Fragments of SEQ ID NO. 356 with KDR Binding Activity

The following experiment showed that fragments of SEQ ID NO:356 can maintain significant KDR binding activity.

Protocol 293H cells were transfected with the KDR cDNA or mock-transfected by standard techniques described in Example 6. Binding of the neutravidin-HRP complexes to the cells was carried out as in Example 6 with a complex concentration of 5.5 nM in the presence of 0 to 250 nM or 0 to 1000 nM of the following competing peptides: SEQ ID NOS:356, 462, 463, and 465. After determining the specific binding under each experimental condition, the IC$_{50}$ for each peptide was determined (where possible).

Results: As shown in Table 18, SEQ ID NO:462, composed of just the Asp-Trp-Tyr-Tyr (SEQ ID) NO:490) binding motif that is also shared with SEQ ID NO:286 along with the non-targeted Gly-Gly-Gly-Lys (SEQ II) NO:262) sequence that was added to most monomeric peptides synthesized based on phage display data, was the smallest fragment able to block peptide/neutravidin-HRP complex binding with an $IC_{50}$ below one micromolar. Surprisingly, a larger fragment comprising SEQ ID NO:356, failed to significantly inhibit complex binding at one micromolar. However, when a solubilising motif, $(Gly-Arg-Gly)_3$ was added to the latter peptide to make SEQ ID NO:465, it was able to compete with the complex for binding with an $IC_{50}$ of 175 nM, confirming that certain fragments of SEQ ID NO:356 containing the Asp-Trp-Tyr-Tyr (SEQ ID NO:490) motif retain KDR-binding activity.

TABLE 18

Fragments of SEQ ID NO: 356 in a displacement assay competing with a complex composed of binding peptide and neutravidin-HRP for binding to KDR-expressing cells.

| Fragment (SEQ ID NO) | $IC_{50}$, nM |
| --- | --- |
| 356 | 93 |
| 462 | 850 |
| 463 | >1000 |
| 465 | 175 |

Example 27

Cell Based Assay for Binding of KDR/VEGF Complex Binders

The ability of a KDR/VEGF complex-binding peptide to selectively bind to the KDR/VEGF complex was demonstrated.

Reagent Preparation

The reagents for this assay were prepared as described in Example 5 except where noted.

Preparation of Peptide-$^{125}$I-Neutravidin Solution

Biotinylated peptides SEQ D NOS:321, 320 and 323, and a biotinylated non-binding control peptide were used to prepare 1.25 μM stock solutions in 50% DMSO. A 33.33 nM stock solution of $^{125}$I-neutravidin was purchased from Amersham (Buckinghamshire, UK). A stock solution of 13.33 nM $^{125}$I-neutravidin/100 nM VEGF was prepared by mixing 850 mL of $^{125}$I-neutravidin with 22 μL of 10 μM VEGF and 1275 μL of M199 media. Another stock solution was prepared in the same manner, but lacking VEGF. To prepare 13.33 nM peptide-$^{125}$I-neutravidin complex solutions±VEGF, 500 μL of the $^{125}$I-neutravidin (with and without VEGF) stock solutions (prepared in last step) were mixed with 24 μL of 1.25 μM peptide solution of SEQ ID NOS:321, 320 and 323, or control peptide. The mixtures were incubated on a rotator at 4 C for 60 minutes, followed by addition of 50 μL of soft release avidin-sepharose (50% slimy in ddH$_2$O) to remove excess peptides and another incubation for 30 minutes on a rotator at 4 C. Finally, the soft release avidin-sepharose was pelleted by centrifuging at 12,000 rpm for 5 minutes at room temperature, and the resulting supernatants were used for the assays.

Binding of Peptide/Neutravidin HP to KDR-Transfected Cells

Figure 73:
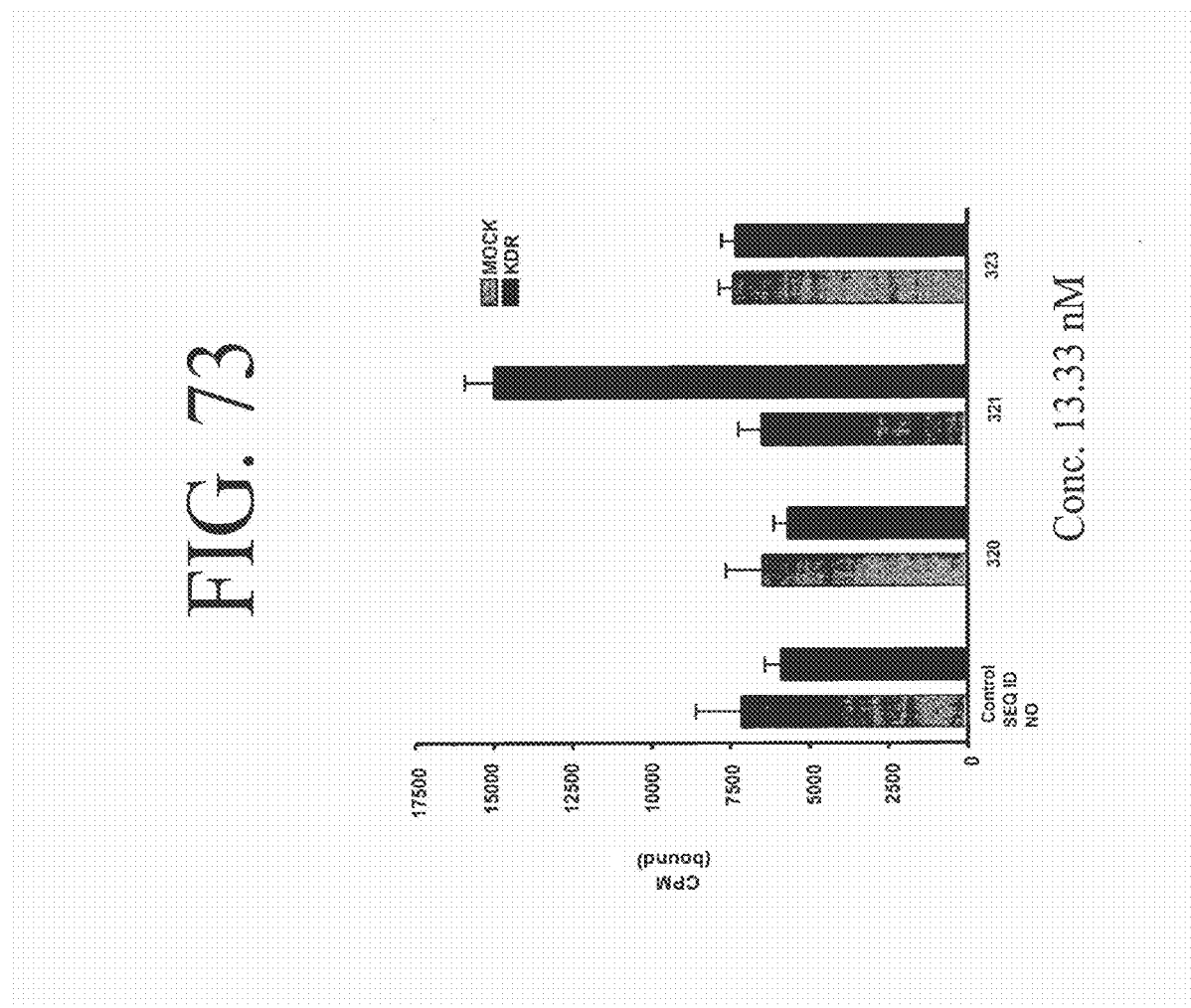
FIG. 73 is a graphical representation showing total binding of complexes of control peptide and the test peptides (SEQ ID NOS:321, 320 and 323) with $^{125}$I-streptavidin (in the presence of VEGF) to mock-transfected and KDR-transfected cells. Only the complex containing SEQ ID NO:321 showed specific binding (KDR-mock).
Figure 74:
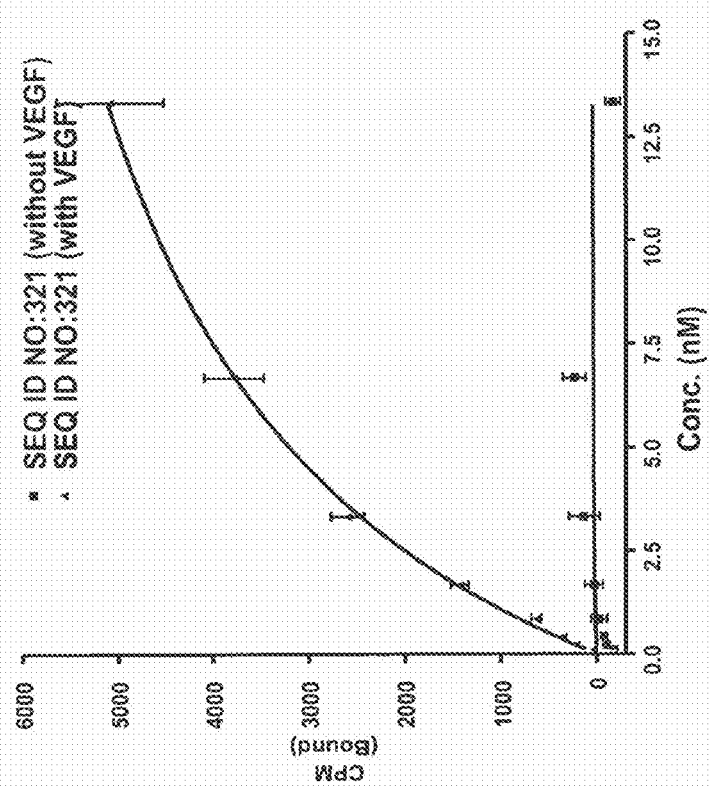
FIG. 74 is a graphical representation showing specific binding of complexes of peptide (SEQ ID NO:321) and $^{125}$I-streptavidin (in the absence and presence of VEGF) to KDR-transfected cells at various concentrations (0-13.33 nM of peptide-$^{125}$I-streptavidin complex.

Complexes of control peptide and the test peptides (SEQ ID NOS:321, 320 and 323) with $^{125}$I-neutravidin in the presence or absence of VEGF (prepared as above) were tested for their ability to bind 293H cells that were transiently-transfected with KDR. The complex of SEQ ID NO:321 with $^{125}$I-neutravidin specifically bound to KDR-transfected 293H cells as compared to mock transfected cells in the presence of VEGF (FIG. 73), but not where VEGF was omitted (FIG. 74). SEQ ID NO:321, was also the best KDR/VEGF complex binder among the peptides tested using fluorescence polarization and SPR (BIAcore) assays (Table 9). This example shows that peptide (SEQ ID NO:321) can specifically bind to the KDR/VEGF complex present on the cell surface. This establishes a utility for the assay as useful for targeting the KDR/VEGF complex in vitro and in vivo for diagnostic or therapeutic purposes. Since the KDR/VEGF binding peptide only detects the functional and active KDR receptor and not all the KDR present on cell surface, it will be useful in detecting and/or treating active angiogenesis in tumors, metastasis, diabetic retinopathy, psoriasis, and arthropathies.

Example 28

This example provides more evidence that heterodimeric peptides targeting two epitopes on KDR are superior to a homodimeric peptide that binds one of the two epitopes on the target molecule. The following experiment provides further evidence that heterodimeric constructs are superior to homodimeric peptides in their ability to block the biological effects of VEGF.

Protocol: Serum-starved HUVECs were placed, 100,000 cells per well, into the upper chambers of ED fibronectin-coated FluoroBlok 24-well insert plates. Basal medium, containing either nothing or VEGF in the presence or absence of increasing concentrations of homodimeric D8 or heterodimeric D17, was added to the lower chamber of the wells. After 22 hours, quantitation of cell migration/invasion was achieved by post-labeling cells in the insert plates with a fluorescent dye and measuring the fluorescence of the invading/migrating cells in a fluorescent plate reader.

Figure 75:
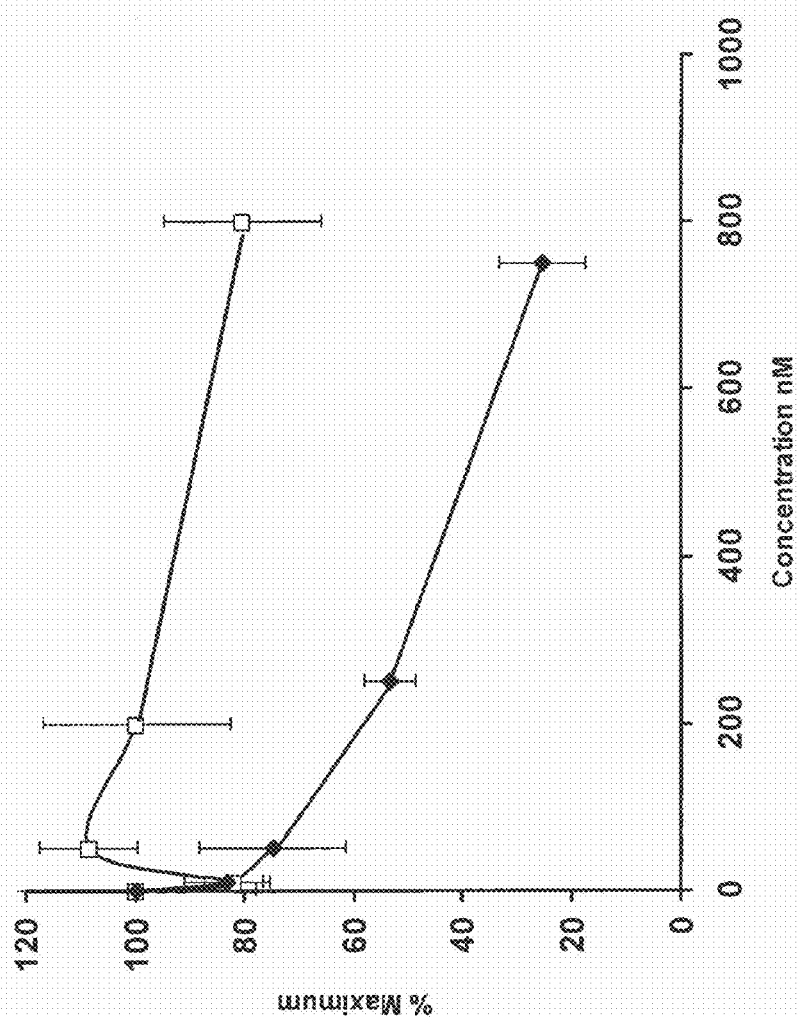
FIG. 75 shows that homodimeric D8 (squares) does not block the effects of VEGF in the migration assay as carried out in Example 28 as well the heterodimeric D17 (diamonds).

Results: As shown in FIG. 75, VEGF induced a large increase in endothelial cell migration in the assay, which was potently blocked by D17 but not D8. D17 blocked VEGF-induced migration with an $IC_{50}$ of about 250 nM while D8 had no significant effect on migration even at 800 nM. This is in spite of the fact that D8 used the fall targeting sequence found in SEQ ID NO:356 while D17 contained a truncated version of the SEQ ID NO:356 sequence (as seen in SEQ ID NO:465) with a lower affinity for KDR (as demonstrated in Example 26). Thus a heterodimer with the capability of binding two separate epitopes on KDR is more effective at blocking ligand binding to KDR than a homodimer containing the same or even more potent targeting sequences.

Example 29

Preparation of KDR-Binding Peptides in which the Disulfide Bond has been Replaced Disulfide bond substitution analogs of SEQ ID NO:301, where the Cys residues at position 6 and 13 are replaced by a pair of amino acids one with a carboxy-bearing side-chain (either Glu or Asp) and the other with an amino-bearing side chain [(Lys or Dpr (2,3-diaminopropanoic acid)] wee prepared. The cycle, encompassing the same sequence positions as those included in SEQ ID NO:301 (made by formation of the disulfide bond) was made by condensation of the side-chain amino and sidechain acid moieties, resulting in a lactam ring that bridges the residues 6-13 as does the disulfide bond of SEQ ID NO:301.

Table 19 below displays some examples of the substitutions made for Cys$^6$ and Cys$^{13}$ of SEQ ID NO:301 in lactam, analogs.

TABLE 19

Lactam Analogs of SEQ ID NO: 277

| Sequence | Position 6 | Position 13 | Difference in Ring Size vs SEQ ID NO: 277 |
|---|---|---|---|
| SEQ ID NO: 277 (parent seq) | Cys | Cys | — |
| 453 | Glu | Lys | 4 |
| 454 | Lys | Glu | 4 |
| 455 | Dpr | Asp | 0 |
| 456 | Asp | Dpr | 0 |
| 457 | Asp | Lys | 3 |

Synthesis of Resin Bound SEQ ID NO:453

Figure 76:
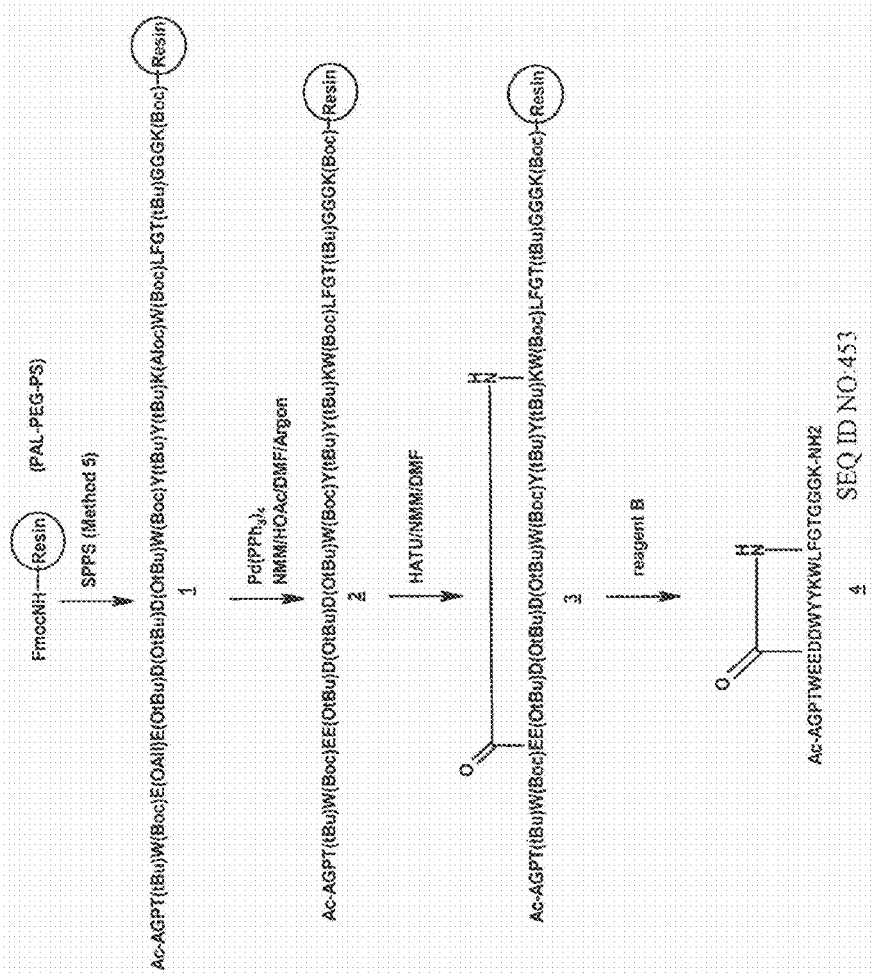
FIG. 76 is a schematic showing the synthesis of cyclic lactam peptides (sample procedure).

Synthesis of 1 was carried out using Method 5 on a 0.25 mmol scale. The peptide resin 1 was washed and dried for further derivatization manually (see FIG. 76).

Synthesis of 4 (SEQ ID NO: 453)

To 1 (240 mg, 0.06 mmol) was added NMM (N-methyl morpholine)/HOAc/DMF 1/2/10 (v/v/v) (65 mL). Palladium tris-triphenylphosphine [Pd(PPh$_3$)$_4$, 554.4 mg 0.48 mmol] was added and the resin was shaken for 20 h shielded from light. The resin was filtered and washed with a solution of sodium diethyldithiocarbamate (0.5 g)/DIEA (0.5 mL)/DMF (100 mL), and finally with DMF (3×70 mL). This treatment served to expose only the carboxy and amino groups of Glu6 and Lys13 that are required for the lactam forming reaction. The on-resin cyclization of 2 was carried out using HATU (114 mg, 0.3 mmol), NMM (66 µL, 0.6 mmol) and DMF (10 mL) for 3 h. The completion of the cyclization was monitored by Kaiser test. The peptide was cleaved from the peptide resin 3 using reagent B for 4 h. The resin was filtered and the filtrate was evaporated to a paste. The crude peptide was precipitated in ether and washed twice with ether. The cyclic peptide was purified by preparative reverse phase linear gradient HPLC using a Waters-YMC C-18 column (250 mm×30 mm i.d.) with CH$_3$CN into H$_2$O (both with 0.1% TFA) as the eluent. Lyophilization of the product-containing fractions afforded 8 mg of (SEQ ID NO:453). SEQ ID NOS:454, 455, 456 and 457 were prepared similarly.

Example 30

Replacement of a Disulfide Bridge while Retaining KDR-Binding Activity

The following experiment demonstrated that the lactam SEQ ID NO:454 replaced a chemically reactive disulfide bridge to maintain significant KDR binding activity.

Protocol: 293H cells were transfected with the KDR cDNA or mock-transfected by standard techniques described in Example 5. Neutravidin-HP complexes were prepared as in Example 5. Binding of the neutravidin-HRP complexes to the cells was carried out as in Example 5 with a complex concentration of 5.5 nM in the presence of 0 to 250 µM SEQ ID NO:277 or SEQ ID NO:454. After determining the specific binding under each experimental condition, the IC$_{50}$ for each peptide was determined.

Results: As shown in Table 20, SEQ ID NO:454, containing a lactam disulfide bridge replacement, was still able to compete with peptide-neutravidin-HRP complexes for binding to KDR although some affinity was lost (IC$_{50}$ 108 nM versus 13 nM).

TABLE 20

SEQ ID NO: 277 and SEQ ID NO: 454 (disulfide bridge replacement analog) in a displacement assay competing with a neutravidin-HRP/binding peptide complex for binding to KDR-expressing cells.

| Fragment (SEQ ID NO) | IC$_{50}$, nM |
|---|---|
| 277 | 13 |
| 454 | 108 |

Example 31

Use of the Neutravidin/Avidin HRP Assay with Biotinylated Peptides Identified by Phage Display Allows Identification of Peptides Capable of Binding to the Target Even where the Affinity of the Peptides is Too Low for Other Assays This example confirms that the neutravidin/HRP screening assay described herein is an effective technique for screening peptides whose affinity as monomers is too low for use in conventional screening assays, such as, for example, an ELISA.

Three different derivatives of SEQ ID NO:482, which was identified by phage display as a peptide that binds to cMet, were prepared as described in U.S. Patent Application No. 60/451,588 (incorporated herein by reference in its entirety), filed on the same date as U.S. patent application Ser. No. 10/382,082, of which the present application is a continuation-in-part.

These three peptides and a control peptide that does not bind to cMet, were tested as tetrameric complexes with neutravidin HRP for their ability to bind cMet-expressing MB-231 cells. All three tetrameric complexes of cMet-binding peptides bound to the MB231 cells as compared to control peptide.

Cell Culture: MDA-MB231 cells were obtained from ATCC and grown as monolayer culture in their recommended media plus 1 mL/L pen/strep (InVitrogen, Carlsbad, Calif.). Cells were split the day before the assay, 35000 cells were added to each well of a 96 well plate. The rest of the experiment was conducted as in Example 6, except as noted below.

Figure 77:
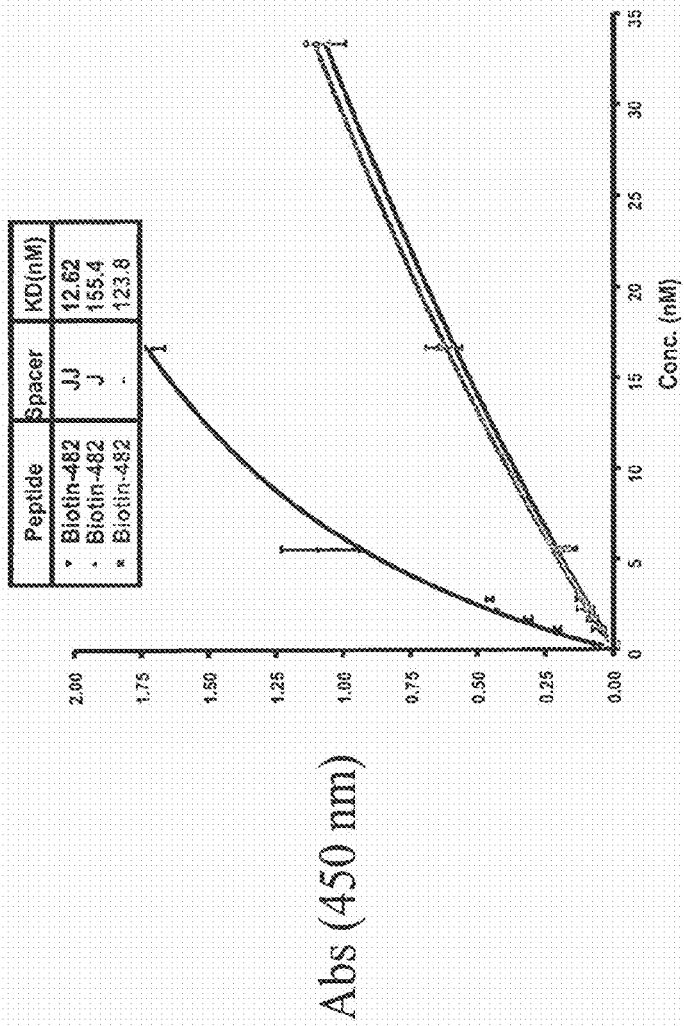
FIG. 77 is a graphical representation showing binding of SEQ ID NO:482 derivatives with different spacer length and biotin Derivatives have none, one J and two J spacers, respectively, in between the SEQ ID NO:482 targeting sequence and biotin.

Binding of Peptide/Neutravidin HRP to MDA-MB-231 Cells
Complexes of control peptide, and SEQ ID NO:482 derivatives with 0, 1 or 2 J spacers with neutravidin-HRP were prepared as described above and tested for their ability to bind MDA-MB-231 cells. During the peptide/neutravidin-HRP complex preparation, a 7.5-fold excess of biotinylated peptides over neutravidin-HRP was used to make sure that all four biotin binding sites on neutravidin were occupied. After complex formation, the excess of free biotinylated peptides was removed using soft release avidin-sepharose to avoid any competition between free biotinylated peptides and neutravidin HRP-complexed biotinylated peptides. The experiment was performed at several different concentrations of peptide/neutravidin-HRP, from 0.28 nM to 33.33 nM, to generate saturation binding curves for derivatives with no or one spacer (FIG. 77) and 0.28 to 16.65 nM to generate a saturation binding curve for the derivative with two spacers (FIG. 77). In order to draw the saturation binding curve, the background binding of the control peptide/neutravidin HRP complex was subtracted from the binding of the binding derivative peptide/neutravidin-HRP complexes for each concentration tested. Therefore, absorbance on the Y-axis of FIG. 77 is differential absorbance (cMet-binding peptide minus control peptide)

and not the absolute absorbance. Analysis of the saturation binding data in FIG. 77 using Graph Pad Prism software (version 3.0) yielded a $K_D$ of 12.62 nM (+/−3.16) for the tetrameric derivative with two spacers, 155.4 mM (+/−86.56) for the tetrameric derivative with one spacer and 123.8 nM (+/−37.71) for the tetrameric derivative without a spacer. These binding constants are, as expected, lower than that measured by FP for the related monodentate peptide SEQ ID NO:482 (880 nM).

Results: As was the case where the binding target was KDR, the neutravidin-HRP assay with biotinylated peptides identified with phage display was useful for identifying peptides capable of binding to an immobilized target even when the affinity of the monomeric binding sequence is too low for an ELISA-type assay (with washing steps after binding) to work well (see FIG. 77).

Example 32

Binding of Tc-Labeled Heterodimeric Polypeptides to KDR-Transfected 293H Cells

The ability of Tc-labeled D10 to bind KDR was assessed using KDR-transfected 293H cells. The results show that Tc-labeled DIG binds significantly better to KDR transfected 293H cells than to mock transfected 293H cells, and good binding was maintained in the presence of 40% mouse serum. In addition, a derivative of Tc-labeled D10 with its amino acid sequence scrambled, D18, was shown to possess no affinity for KDR-expressing cells, confirming the specificity of the DIG binding to those cells.

Transfection of 293H Cells 293H cells were transfected using the protocol described in Example 5. Transfection was done in black/clear 96-well plates (Becton Dickinson, cat. # 354640). The cells in one half of the plate (48 wells) were mock-transfected (without DNA) and the cells in the other half of the plate were transfected with KDR cDNA. The cells were 80-90% confluent at the time of transfection and completely confluent the next day, at the time of the assay (the assay was aborted if these conditions were not satisfied).

Preparation of Opti-MEMI Media with 0.1% HSA

Opti-MEMI was obtained from InVitrogen (Carlsbad, Calif.) and human serum albumin (USA) was obtained from Sigma (St. Louis, Mo.). Opti-MEMI media was prepared by adding 0.1% HSA, 0.1% w/v HSA to opti-MEMI, followed by stirring at room temperature for 20 minutes. The media was filter sterilized using 0.2 μM filter.

Preparation of Tc-Labeled Peptide Dilutions for the Assay

D10 and D18 were diluted in opti-MEMI with 0.1% HSA to provide solutions with final concentrations of 1.25, 2.5, 5.0, and 10 μCi/mL of each Tc-labeled heterodimer. A second set of dilutions was also prepared using a mixture of 40% mouse serum/60% opti-MEMI with 0.1% HSA as the diluent.

Assay to Detect the Binding of the Tc-Labeled Heterodimers

Cells were used 24 h after transfection, and to prepare the cells for the assay, they were washed once with 100 μL of room temperature opti-MEMI with 0.1% HSA. After washing, the opti-MEMI with 0.1% HSA was removed from the plate and replaced with 70 μL of 1.25, 2.5, 5.0 and 10 μCi/mL of Tc-labeled D10 or D18 (prepared as above with both diluent solutions), Each dilution was added to three separate wells of mock- and KDR-transfected cells. After incubating at room temperature for 1 h, the plates were washed 5 times with 100 μL of cold binding buffer (opti-MEMI with 0.1% HSA). 100 μL of solubilizing solution (0.5 N NaOH) was added to each well and the plates were incubated at 37 C for 10 minutes. The solubilizing solution in each well was mixed by pipetting up and down, and transferred to 1.2 mL tubes. Each well was washed once with 100 μL of solubilizing solution and the washes were added to the corresponding 1.2 mL tube. Each 1.2 mL tube was then transferred to a 15.7 mm×100 cm tube to be counted in an LKB Gamma Counter.

Binding of Tc-Labeled Peptide to KDR Transfected Cells

Figure 78:
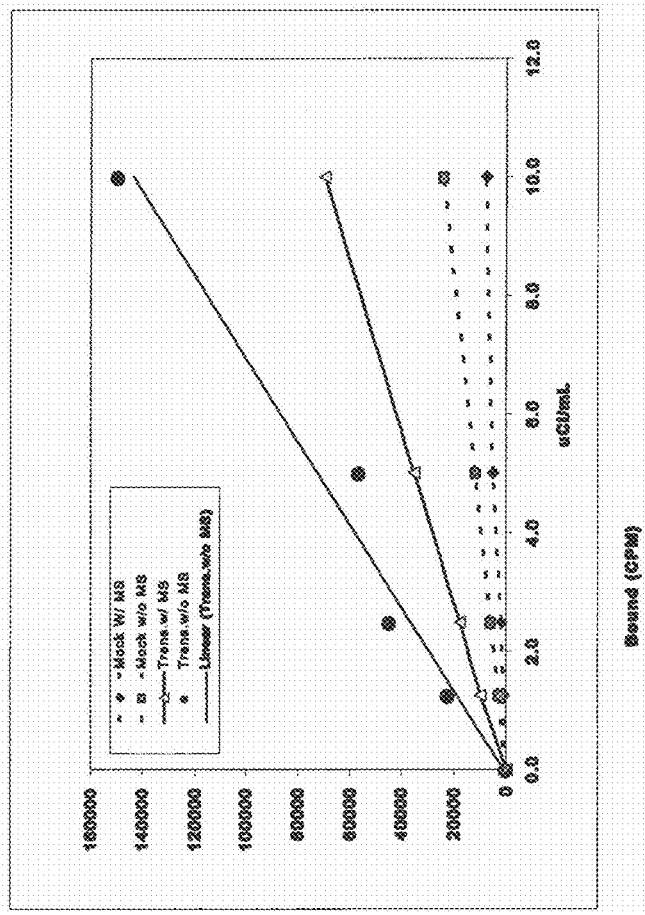
FIG. 78 depicts the binding of Tc-labeled D10 to KDR-transfected 293H cells as described in Example 32. Mock=mock-transfected. Trans=KDR-transfected. MS=mouse serum.

The ability of Tc-labeled D10 and D18 to bind specifically to KDR was demonstrated using transiently transfected 293H cells. As shown in FIG. 78, Tc-labeled D10 bound better to KDR transfected 293H cells, as compared to mock-transfected (with a scrambled peptide) 293H cells in both the presence and absence of 400/, mouse serum although there was some inhibition in the presence of serum. The total specific binding of this Tc-labeled heterodimer to KDR-expressing cells was greater than that observed previously with a Tc-labeled monomeric peptide (Example 10). Tc-labeled D18 the scrambled peptide, displayed no affinity for either mock-transfected or KDR-transfected 293H cells (not shown), confirming the specificity of D10 binding.

Example 33

Binding of a Lu-Labeled Heterodimeric Polypeptide to KDR-Transfected 293H Cells

The ability of Lu-labeled D13 to bind KDR was assessed using KDR-transfected 293H cells. The results show that Lu-labeled D13 binds better to KDR transfected 293H cells than to mock transfected 29311 cells, and significant binding was maintained in the presence of 40% mouse serum.

Transfection of 293H Cells 293H cells were transfected using the protocol described in Example 5. Transfection was performed in black/clear 96-welt plates (Becton Dickinson, San Jose, Calif.). The cells in one half of the plate (48 wells) were mock-transfected (without DNA) and the cells in the other half of the plate were transfected with KDR cDNA. The cells were 80-90% confluent at the time of transfection and completely confluent the next day, at the time of assay (the assay was aborted if these conditions were not satisfied).

Preparation of Opti-MEMI Media with 0.11% HSA

Opti-MEMI was prepared as in Example 32.

Preparation of Lu-Labeled Peptide Dilutions for the Assay

A stock solutions of Lu-labeled D13 was diluted in opti-MEMI with 0.1% HSA to provide solutions with final concentrations of 1.25, 2.5, 5.0, and 10 μCi/mL of labeled heterodimer. A second set of dilutions was also prepared using a mixture of 40% mouse serum/60% opti-MEMI with 0.1% HSA as the diluent.

Assay to Detect the Binding of the Lu-Labeled Heterodimers

Detection of binding was measured as detailed in Example 32 except that Lu-labeled D13 was used in place of the Tc-labeled heterodimers.

Binding of Lu-Labeled Peptide to KDR Transfected Cells

Figure 95:
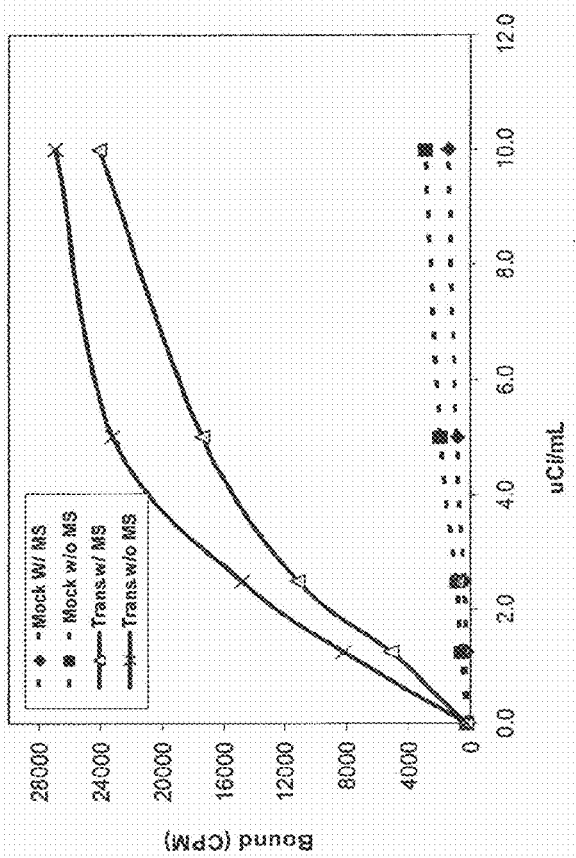
FIG. 95 is a graph depicting the binding of Lu-D13 to KDR-transfected 293H cells. Mock=mock-transfected. Trans=KDR-transfected. MS=mouse serum.

The ability of Lu-labeled D13 to bind specifically to KDR was demonstrated using transiently-transfected 293H cells. As shown in FIG. 95, Lu-labeled D13 bound significantly better to KDR transfected 293H cells, as compared to mock-transfected 293H cells in both the presence and absence of 40% mouse serum, although there was some binding inhibition in the presence of serum.

Example 34

Radiotherapy with a Lu-Labeled Heterodimeric Peptide in tumor-bearing Mice

In this example, the ability of Lu-labeled D13 to inhibit the growth of PC3 cell tumors implanted in nude mice is demonstrated.

Animal Model

PC3 cells from ATCC, grown as recommended by the supplier, were injected subcutaneously between the shoulder blades of nude mice. When their tumors reached 100-400 mm$^3$, twelve mice were injected i.v. with 500 microcuries of Lu-labeled D13 and their growth monitored for an additional 18 days. Mice were sacrificed if they lost 20% or more of their body weight or their tumors exceeded 2000 mm$^3$. Tumor growth in the treated mice was compared with the average tumor growth in 37 untreated nude mice implanted with PC3 tumors.

Results

Figure 80:
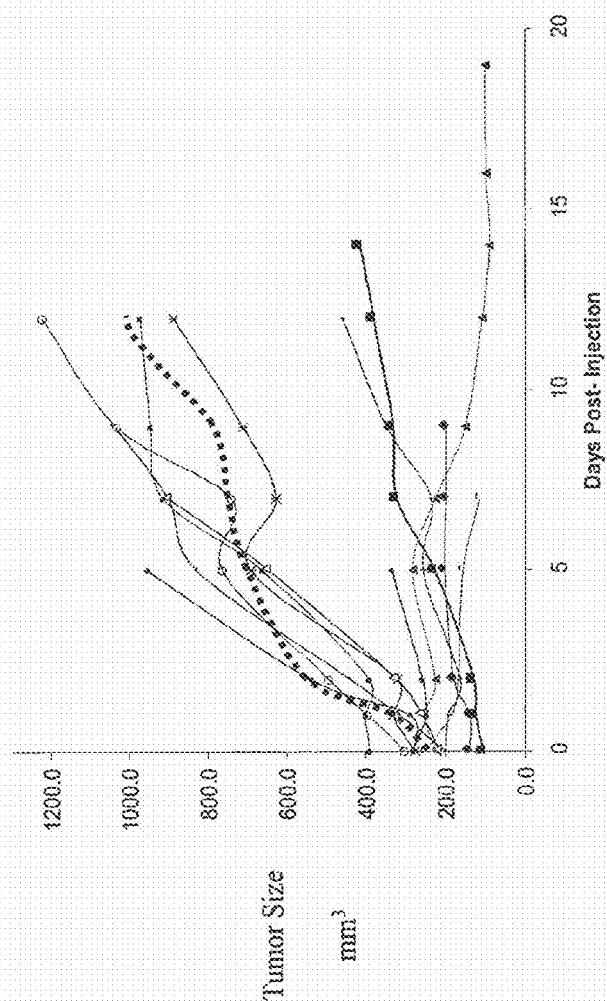
FIG. 80 summarizes the results of a radiotherapy study with D13 conducted in nude mice implanted with PO$_3$ tumors. Each plotted line represents the growth over time for an individual tumor in a treated mouse, except for the heavy dashed line, which represents the average tumor growth in a set of untreated mice, as described in Example 34.

In 6 of the 12 treated mice in the study, the tumors experienced a significant or complete growth delay (FIG. 80) relative to untreated tumor mice, indicating that D13 was effective in slowing PC3 tumor growth under the conditions employed.

Example 35

Preparation of Ultrasound Contrast Agents Conjugated to KDR-Binding Peptides Ultrasound contrast agents comprising phospholipid-stabilized microbubbles conjugated to KDR-binding polypeptides of the invention were prepared as described below.

200 mg of DSPC (distearoylphosphatidylcholine), 275 mg of DPPG.Na (distearoylphosphatidylglycerol sodium salt), 25 mg of N-APB-PE were solubilized at 60 C in 50 mL of Hexan/isopropanol (42/8). The solvent was evaporated under vacuum, and then PEG-4000 (35.046) was added to the lipids and the mixture was solubilized in 106.92 g of t-butyl alcohol at 60 C. in a water bath. The solution was filled in vials with 1.5 mL of solution. The samples were rapidly frozen at −45 C and lyophilized. The air in the headspace was replaced with a mixture of $C_4F_{10}$/Air (50/50) and vials capped and crimped. The lyophilized samples were reconstituted with 10 mL saline solution (0.9%-NaCl) per vial.

Peptide Conjugation

Peptides, e.g., SEQ ID NO:356, SEQ ID NO:294 and SEQ ID NO:480, were conjugated to a preparation of microbubbles as above described, according to the following methodology.

The thioacetylated peptide (200 μg, SEQ ID NO:356) was dissolved in 20 μL DMSO and then diluted in 1 mL of Phosphate Buffer Saline (PBS). This solution was mixed to the N-MPB-functionalized microbubbles dispersed in 18 mL of PBS-EDTA 10 mM, pH 7.5 and 2 mL of deacetylation solution (50 mM sodium phosphate, 25 mM EDTA, 0.5 M hydroxylamine.HCl, pH 7.5) was added. The headspace was filled with $C_4F_{10}$/Air (35/65) and the mixture was incubated for 2.5 hours at room temperature under gentle agitation (rotating wheel), in the dark. Conjugated bubbles were washed by centrifugation.

Example 36

Preparation of Ultrasound Contrast Agents Conjugated to KDR Binding Peptides Ultrasound contrast agents comprising phospholipid-stabilized microbubbles conjugated to KDR-binding polypeptides of the invention were prepared as described below.

Distilled water (30 mL) containing 6 mg of dipalmitoylphosphatidylserine (DPPS, Genzyme), 24 mg of distearoylphosphatidylcholine DSPC, Genzyme) and 3 g of mannitol was heated to 65 C in 15 minutes then cooled to room temperature. N-MPB-DPPE (1,2-Dipalmitoyl-sn-glycero-3-phosphoethanolamine-N-[4-(p-maleimidophenyl)butyramide]Na salt—Avanti Polar Lipids) was added (5% molar—1.9 mg). This derivatized phospholipid was dispersed in the aqueous phase using an ultrasonic bath (Branson 1210-3 minutes).

Perfluoroheptane (2.4 mL from Fluka) was emulsified in this aqueous phase using a high speed homogenizer (Polytron®, 10000 rpm, 1 minute).

The emulsion was washed once by centrifugation (200 g/10 min) then resuspended in 30 mL of a 10% solution of mannitol in distilled water. The washed emulsion was frozen (−45 C, 5 mutes) then freeze dried (under 0.2 mBar, for 24 hours).

Atmospheric pressure was restored by introducing a mixture of $C_4F_{10}$ and air. The lyophilizate was dissolved in distilled water (30 mL). Microbubbles were washed once by centrifugation and redispersed in 10 mL of Phosphate Buffer Saline.

Peptide Conjugation

Thioacetylated peptide (200 μg, SEQ ID NO:356) was dissolved in 20 μL DMSO and then diluted in 1 mL of Phosphate Buffer Saline (PBS). This solution was mixed to 5 mL of the N-MPB-functionalized microbubbles. 0.6 mL of deacetylation solution (50 mM sodium phosphate, 25 mM EDTA, 0.5 M hydroxylamine.HCl, pH 7.5) was added and the suspensions were stirred by inversion for 2 h 30.

Microbubbles were washed twice with a solution of maltose 5% and Pluronic F68 0.05% in distilled water, by centrifugation (200 g/10 minutes). The final volume was fixed to 5 mL.

Example 37

Preparation of Ultrasound Contrast Agents Conjugated to KDR Binding Peptides Ultrasound contrast agents comprising microballoons conjugated to KDR-binding polypeptides of the invention were prepared as described below.

Distilled water (30 mL) containing 40 mg of distearoylphosphatidylglycerol (DSPG, Genzyme) was heated to 65 C during 15 minutes then cooled to 40 C.

DPPE-PEG2000-Maleimide (3.5 mg—Avanti Polar Lipids) and tripalmitine (60 mg—Fluka) were dissolved in cyclohexane (0.6 ml) at 40 C in a ultrasound bath for 2 min.

This organic phase was emulsified in the aqueous phase using a high speed homogenizer (Polytron®, 10000 rpm, 1 minute).

Polyvinylalcohol (200 mg) dissolved in distilled water (5 mL) was added to the emulsion. The mixture was cooled to 5 C, then frozen (−45 C, 10 minutes) and finally freeze dried (under 0.2 mBar, for 24 hours).

The lyophilisate was dispersed in distilled water (15 mL). The mixture was stirred for 30 min to obtain a homogenous suspension of microballoons.

Peptide Conjugation

The thioacetylated peptide (200 μg) was dissolved in 20 μL DMSO then diluted with PBS (1 mL).

7.5 mL of the suspension of microballoons obtained as above described were centrifuged (50 rpm for 5 min). The infranatant was discarded and microballoons were redispersed in Phosphate Buffer Saline (2 mL).

The microcapsule suspension was mixed with the solution of peptide. Three hundred microliters of a hydroxylamine solution (10.4 mg in PBS 50 mM, pH: 7.5) was added to the suspension to deprotect the thiol. The suspension was stirred by inversion for two and a half hours.

The microballoons were washed twice by centrifugation (500 g/5 min) with distilled water containing 5% maltose and 0.05% Pluronic F68 and finally redispersed in 3 mL of this solution.

Example 38

Ultrasound Contrast Agents Conjugated to KDR Binding Polypeptides Bind to KDR-Expressing Cells In Vitro and In Vivo The ability of ultrasound contrast agents conjugated to peptides of the invention to bind to KDR-expressing cells in vitro was assessed using 293H cells transfected to express KDR. Additionally, the ability of ultrasound contrast agents conjugated to KDR binding polypeptides of the invention to bind to KDR-expressing tissue in vivo was assessed using two known models of angiogenesis, the rat matrigel model and the rat MatB III tumor model.

Transfection of 293H Cells on Thermanox® Coverslips 293H cells were transfected with KDR DNA as set forth in Example 5. The transfected cells were incubated with a suspension of peptide-conjugated ultrasound contrast agents or with a control peptide (a scrambled version of the conjugated peptide having no affinity for KDR).

For the incubation with the transfected cells a small plastic cap is filled with a suspension containing 1 to $3 \times 10^8$ peptide-conjugated microbubbles and the cap covered with an inverted Thermanox® coverslip as to put the transfected cells in contact with the conjugated microbubbles. After about 20 min at RT, the coverslip is lifted with tweezers, rinsed three times in PBS and examined under a microscope to assess binding of the conjugated microbubbles.

Figure 85:
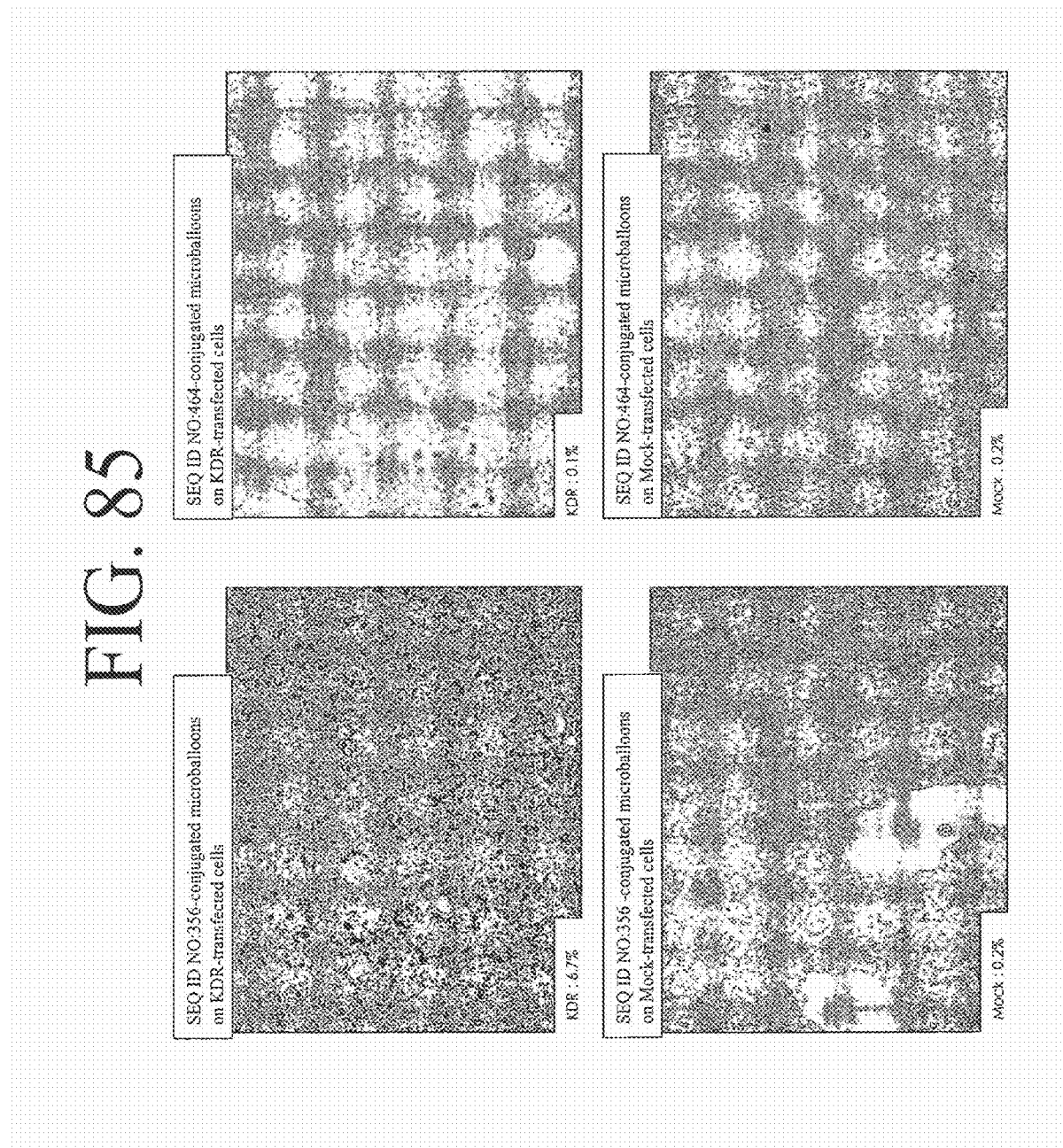
FIG. 85 shows a typical example of peptide-conjugated ultrasound contrast agents bound to KDR- or mock-transfected cells in presence of 10% human serum (magnification: 100×).

FIG. 85 indicates that microballoons conjugated to peptides of the invention bind specifically to KDR-expressing cells. Indeed, microballoons conjugated to KDR-binding peptide bound to KDR-expressing cells while they did not bind appreciably to mock transfected cells and microballoons bearing a scrambled control peptide showed no appreciable binding.

Determination of the % of Surface Covered by Microvesicles

Images were acquired with a digital camera DC300F (Leica) and the percent of surface covered by bound microbubbles or microballoons in the imaged area was determined using the software QWin (Leica Microsystem AG, Basel, Switzerland).

The following table shows the results of the binding affinity (expressed as coverage % of the imaged surface) of targeted microvesicles of the invention to KDR transfected cells, as compared to the binding of the same targeted microvesicles towards Mock-transfected cells or (only in the case of the peptide) to the binding of microvesicles targeted with a scrambled peptide to the same KDR transfected cells.

As shown in Table 21, targeted microvesicles show increased binding affinity for KDR.

TABLE 21

| | | Coverage % | | |
|---|---|---|---|---|
| | SEQ ID NO | KDR | Mock | Scrambled peptide |
| Example 35 | 356 | 14.2% | 1.4% | 2.1% |
| | 277 | 3.5% | 0.9% | n.a. |
| | 480 | 16.8% | 1.0% | n.a. |
| Example 36 | 356 | 18.3% | 0.4% | 2.2% |
| Example 37 | 356 | 6.7% | 0.2% | 0.1% |

In Vivo Animal Models

Known models of angiogenic tissue (rat matrigel model and rat Mat B III model) were used to examine the ability of the peptide conjugated ultrasound conjugates to localize to and provide an image of angiogenic tissue.

Animals: Female Fisher 344 rat (Charles River Laboratories, France) weighing 120 to 160 g were used for the MAT-BIII tumor implantation. Male OFA rats (Charles River Laboratories, France) weighing 100 to 150 g were used for Matrigel injection.

Anesthesia: Rats were anesthetized with an intramuscular injection (1 nm/kg) of Ketaminol/xylazine (Veterinaria AG/Sigma). (50/10 mg/mL) mixture before implantation of Matrigel or MatBIII cells. For imaging experiments, animals were anesthetized with the same mixture, plus subcutaneous injection of 50% urethane (1 g/kg).

Rat MATBIII tumor model: A rat mammary adenocarcinoma, designated 13762 Mat B III, was obtained from ATCC (CRL-1666) and grown in McCoy's 5a medium+10% FCS. 1% glutamine and 1% pen/strep (Invitrogen cat# 15290-018). Cells in suspension were collected and washed in growth medium, counted, centrifuged and resuspended in PBS or growth medium at $1.10^7$ cells per mL. For tumor induction: $1 \times 10^6$ cells in 0.1 mL were injected into the mammary fat pad of anesthetized female Fisher 344 rat. Tumors usually grow to a diameter of 5-8 mm within 8 days.

Rat matrigel model: Matrigel (400 µL) (ECM Sigma, St Louis, Mo.) containing human bFGF (600 ng/ml) (Chemicon: ref: GF003) was subcutaneously injected in the dorsal flank of each rat.

Matrigel solution was kept liquid at 4 C until injection. Immediately after matrigel injection, the injection site was maintained closed for a few seconds with the hand in order to avoid leaking of the matrigel. At the body temperature, matrigel becomes gelatinous. Ten days post-injection, neoangiogenesis was observed in matrigel plug of rat and imaging experiment were performed.

In vivo ultrasound imaging: Mat B III tumor or matrigel imaging was performed using an ultrasound imaging system ATL HDI 5000 apparatus equipped with a L7-4 linear probe. B-mode pulse inversion at low acoustic power (MI=0.05) was used to follow accumulation of peptide conjugated-microbubbles on the KDR receptor expressed on the endothelium of neovessels. For the control experiments, an intravenous bolus of unconjugated microbubbles or microbubbles conjugated to non-specific peptide was injected. The linear probe was fixed on the skin directly on line with the implanted tumors or matrigel plug and accumulation of targeted bubbles was followed during minutes.

In both models, a perfusion of SonoVue® was administrated before injecting the test bubble suspension. This allows for the evaluation of the vascularization status; the video intensity obtained after SonoVue® injection is taken as an internal reference.

A baseline frame was recorded and then insonation was stopped during the bubble injection. At various time points after injection (1, 2, 5, 10, 15, 20, 25, 30 minutes) insonation was reactivated and 2 frames of one second were recorded on a videotape.

Figure 81:
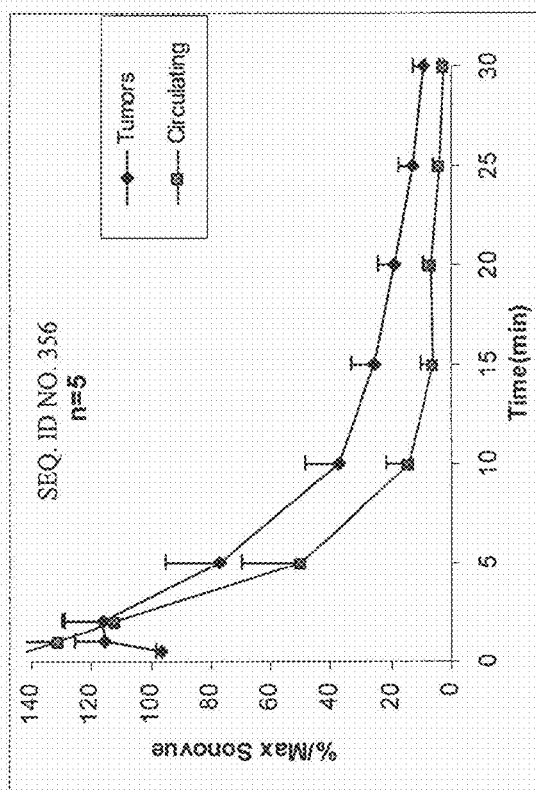
FIG. 81 shows uptake and retention of bubble contrast in the tumor up to 30 minutes post injection for suspensions of microbubbles conjugated to SEQ ID NO:356. In contrast, the same bubbles showed only transient (no more than 10 minutes) visualization/bubble contrast in the AOI situated outside the matrigel or tumor site (see FIGS. 82 and 83).
Figure 82:
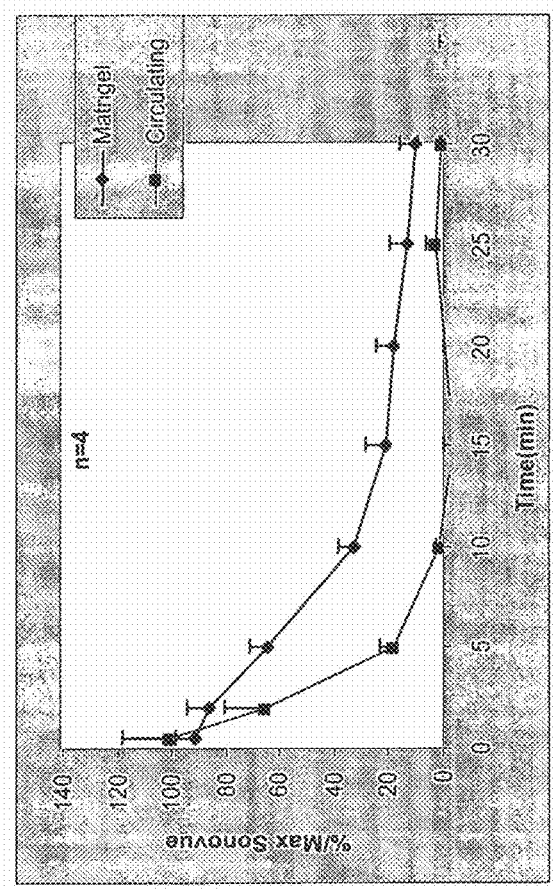
FIG. 82 shows uptake and retention of bubble contrast in the tumor up to 30 minutes post injection for suspensions of microbubbles conjugated to a SATA-modified peptide comprising SEQ ID NO:356. In contrast, the same bubbles showed only transient (no more than 10 minutes) visualization/bubble contrast in the AOI situated outside the matrigel.
Figure 83:
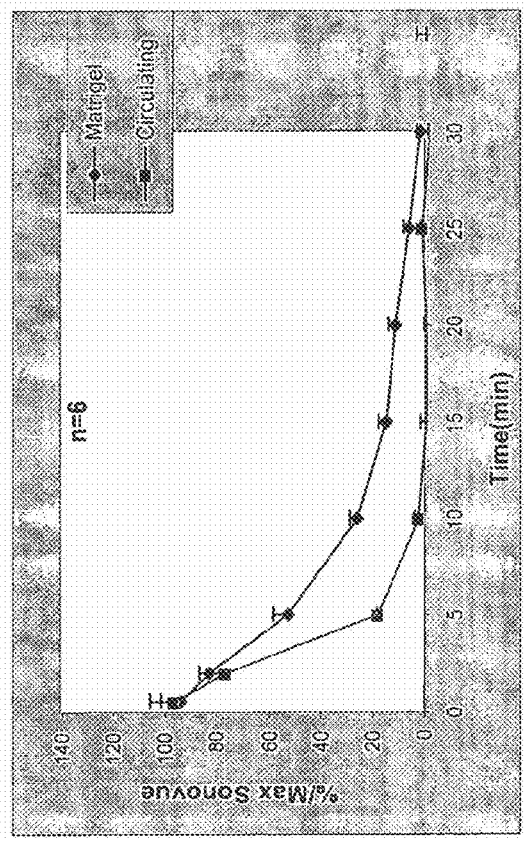
FIG. 83 shows uptake and retention of bubble contrast in the matrigel up to 30 minutes post injection for suspensions of microbubbles conjugated to a SATA-modified peptide comprising SEQ ID NO:294. In contrast, the same bubbles showed only transient (no more than 10 minutes) visualization/bubble contrast in the AOI situated outside the matrigel.

Video frames from matrigel or Mat B III tumor imaging experiments were captured and analysed with the video-capture and Image-Pro Plus 2.0 software respectively. The same rectangular Area of Interest (AOI) including the whole sectional area of the tumor or matrigel was selected on images at different time points (1, 2, 5, 10, 15, 20, 25, 30 minutes). At each time point, the sum of the video pixel inside the AOI was calculated after the subtraction of the AOI baseline. Results are expressed as the percentage of the signal obtained with SonoVue, which is taken as 100%. Similarly, a second AOI situated outside from matrigel or tumor, and representing the freely circulating contrast agent is also analysed Results The results indicate that ultrasound contrast agents bearing KDR binding moieties of the invention localize to angiogenic (and thus KDR expressing) tissue in animal models. Specifically, FIG. 81 shows uptake and retention of bubble contrast in the tumor up to 30 minutes post injection for suspensions of phospholipids stabilized microbubbles conjugated to KDR peptides of the invention prepared according to Example 35. In contrast, the same bubbles showed only transient (no more than 10 minutes) visualization/bubble contrast m the AOI situated outside the tumor site. Similarly, FIG. 82 and FIG. 83 show uptake and retention of bubble contrast in the matrigel at up to 30 minutes post injection for suspensions of phospholipids stabilized microbubbles conjugated to KDR peptides of the invention (e.g., SEQ ID NOS:374 and 294, respectively) prepared according to Example 35. In contrast, the same bubbles showed only transient (no more than 10 minutes) visualization/bubble contrast in the AOI situated outside the matrigel site.

Example 39

Enhancing the Serum Residence of KDR-Binding Peptides

Compounds that contain maleimide and other groups that can react with thiols react with thiols on serum proteins, especially serum albumin, when the compounds are injected. The adducts have serum life times similar to serum albumin, more than 14 days in humans for example.

Conjugation to Maleimide

Methods are available that allow for the direct synthesis of maleimide-labeled linear peptides encompassed by the present invention (Holmes, D. et al., 2000. *Bioconjug. Chem.*, 11:439-444).

Peptides that include disulfides can be derivatized with maleimide in one of several ways. For example, a third cysteine can be added at the carboxy terminus. The added cysteine is protected with protecting group that is orthogonal to the type of groups used for the cysteines that are to form the disulfide. The disulfide is formed by selectively deprotecting the intended cysteines and oxidizing the peptide. The final cysteine is then deprotected and the peptide reacted with a large molar excess of a bismaleimide. The resulting compound has one of the maleimides free to react with serum albumin or other thiol-containing serum proteins.

Alternatively, a cyclic peptide of the present invention is synthesized with a lysine-containing C-terminal extention, such as -GGGK (SEQ ID NO:262). Lysines of the KDR-binding motif are protected with ivDde and the C-terminal lysine is deprotected. This lysine is reacted with a maleimide-containing compound, such as N-[e-maleimidocaproyloxy] succinimide ester (pierce Biotechnology, Rockford, Ill.) or N-(a-Maleimidoacetoxy)succinimide ester (Pierce Biotechnology).

Conjugation to a Moiety that Binds Serum Albums Non-covelently

Polypeptides having a molecular weight less than 50-60 kDa are rapidly excreted. Many small molecules, such as fatty acids, bind to serum albumin. Fatty acids containing 10 to 20 carbon atoms have substantial affinity for serum albumin. Linear and branched fatty acids can be used. This binding in serum can reduce the rate of excretion. Using methods known in the art, serum-albumin-binding moieties can be conjugated to any one of the peptides herein disclosed. The serum-albumin-binding moiety can be joined to the KDR-binding peptide through a linker. The linker can be peptidic or otherwise, such as PEG. Linkers of zero to about thirty atoms are preferred. It is preferred that the linker be hydrophilic. The serum-albumin-binding moiety can be conjugated to the KDR-binding peptide at either end or though a side group of an appended amino acid. Suitable side groups include lysine and cysteine. Such compounds can also comprise chelators for radionuclides, as discussed herein. A KDR-binding peptide joined to a serum-albumin-binding moiety will bind KDR.

Conjugation to PEG

Attachment of poly(ethyleneglycol) (PEG) to proteins and peptides enhances the serum residence of these molecules. Attachment of PEG (linear or branched) to a KDR-binding peptide is expected give substantial enhancement of serum residence time. The molecular weight of the PEG should be at least 10 kDA, more preferably at least 20 kDa, and most preferably 30 kDa or more. The PEG could be attached at the N- or C-terminus. Methods of attaching PEG to peptides are well known in the art (Roberts M. et al., 2002, *Adv. Drug. Deliv. Rev.*, 54:459-476). PEG can be attached to reactive side groups such as lysine or cysteine.

Fusion to Serum Protein

Proteins comprising serum albumin (SA) and other proteins have enhanced serum residence tines. The amino-acid sequence of human SA (hSA) is shown in Table 22. Table 23 shows a fusion protein comprising: AGDWWVECRVGTGLCYRYDTGTGGGK(SEQ ID NO:286):: PGGSGGEGGSGGEGGRPGGSEGGTGG::mature hSA:: GGSGGEGGSGGEGGSGPGEGGEGSGGRP:: GDSRVCWEDSWGGEVCFRYDPGGGK(SEQ ID NO:294). The KDR-binding peptides are separated from mature hSA by linker that are rich in glycine to allow flexible spacing. One need not use all of hSA to obtain an injectable protein that wilt have an enhanced serum residence time. Chemical groups, such as maleimide and alpha bromo carboxylates, react with the unpaired cysteine (residue 34) to form stable adducts. Thus, one can attach a single chelator to hSA fusion proteins so that the adduct will bind a radionuclide. One can prepare a chelator with a maleimide group and couple that to hSA or an hSA derivative. Alternatively, hSA or an hSA derivative can be reacted with a bismaleimide and a chelator carrying a reactive thiol could be reacted with the bismaleimide-derivatized hSA.

Construction of genes that encode a given amino-acid sequence are known in the art. Expression of HSA fusions in *Saccharomyces cerevisiae* is known in the art (Sleep, D et al., 1991. *Biotechnology (NY)*, 9:183-187).

Pretargeting Radioactivity or Toxins to KDR Expressing Tumors

Conventional radioimmune cancer therapy is plagued by two problems. The generally attainable targeting ratio (ratio of administered dose localizing to tumor versus administered dose circulating in blood or ratio of administered dose localizing to tumor versus administered dose migrating to bone marrow) is low. Also, the absolute dose of radiation or therapeutic agent delivered to the tumor is insufficient in many cases to elicit a significant tumor response. Improvement in targeting ratio or absolute dose to tumor would be of great importance for cancer therapy.

The present invention provides methods of increasing active agent localization at a target cell site of a mammalian recipient. The methods include, for example, a) administering to a recipient a fusion protein comprising a targeting moiety and a member of a ligand-anti-ligand binding pair; b) thereafter administering to the recipient a clearing agent capable of directing the clearance of circulating fusion protein via hepatocyte receptors of the recipient, wherein the clearing agent incorporates a member of the ligand-anti-ligand binding pair; and c) subsequently administering to the recipient an active agent comprising a ligand/anti-ligand binding pair member.

Hexoses, particularly the hexoses galactose, glucose, mannose mannose-6-phosphate, N-acetylglucosamine, pentmannosyl phosphate, N-acetylgalactosamine, thioglycosides of galactose, and mixtures thereof are effective in causing hepatic to clearance. Binding of sugars to hepatic receptors is not, however, the only means of directing a molecule to the liver.)

Clearance of carcinoembryonic antigen (CEA) from the circulation is by binding to Kupffer cells in the liver We have shown that CEA binding to Kupffer cells occurs via a peptide sequence YPELPK representing amino acids 107-112 of the CEA sequence. This peptide sequence is located in the region between the N-terminal and the first immunoglobulin like loop domain. Using native CEA and peptides containing this sequence complexed with a heterobifunctional crosslinking agent and ligand blotting with biotinylated CEA and NCA we have shown binding to an 80 kD protein on the Kupffer cell surface. This binding protein may be important in the development of hepatic metastases. (Thomas, P. et al., 1992. *Biochem. Biophys. Res. Commun.*, 188:671-677

To use YPELPK (SEQ ID NO:498) as a clearance agent, one fuses this sequence via a linker to a moiety that binds the fusion protein (Ab). For example, if the Ab has affinity for DOTA/Re, one would make a derivative having YPELPK attached to DOTA/Re; for example, rvYPELPKpsGGGC-DOTA. 'rvYPELPKps' is a fragment of CEA that includes the YPELPK sequence identified by Thomas et al. Any convenient point on DOTA can be use for attachment. RVYPELP-KPSGGG-DOTA/cold Re (SEQ ID NO:499) would then be used as a clearing agent. The Fab corresponding to the fusion Ab would have affinity for the clearing agent of Kd<100 nM, preferably Kd<10 nM, and most preferably Kd<1 nM.

The therapeutic agent would contain DOTA/$^{185}$Re. In a preferred embodiment, the therapeutic agent would contain two or more DOTA moieties so that the Ab immobilized on the tumor would bind the bis-DOTA compound with high avidity. The two DOTA moieties would preferably be connected with a hydrophilic linker of ten to thirty units of PEG. PEG is a preferred linker because it is not degraded, promotes solubility. Ten to thirty units of PEG is not sufficient to give the bis DOTA compound a very long serum residence time. A half-life of 30 minutes to 10 hours is acceptable. The serum half life should be longer than the radioactive half life of the radionuclide used so that most of the radiation is delivered to the tumor or to the external environment.

In one embodiment, a "fusion protein" of the present invention comprises at least one KDR-binding peptide fused to the amino terminus or the carboxy terminus of either the light chain (LC) or the heavy chain (HC) of a human antibody. Optionally and preferably, two or more KDR-binding peptides are fused to the antibody. The antibody is picked to have high affinity for a small molecule that can be made radioactive or have a toxin attached, Preferably, the affinity of the Fab corresponding to the Ab has affinity for the small molecule with Kd less than 100 nM, more preferably less than 10 mM, and most preferably less than 1 nM. The small molecule could be a chelator capable of binding a useful radioactive atom, many of which are listed herein. The small molecule could be a peptide having one or more tyrosines to which radioactive iodine can be attached without greatly affecting the binding property of the peptide.

Any KDR-binding peptide (KDR-BP) of the present invention can be fined to either end of either chain of an antibody that is capable of binding a small radioactive compound. Useful embodiments include:
1) KDR-BP#1::link::LC/HC,
2) LC::link::KDR-BP#1/HC,
3) LC/KDR-BP#1::link::HC,
4) LC/HC::link:KDR-BP#1,
5) KDR-BP#1::link1::LC::link2::KDR-BP#2/HC,
6) LC/KDR-BP#1::link1::HC::link2::KDR-BP#2,
7) KDR-BP#1::link1::LC/KDR-BP#2::link2::HC,
8) KDR-BP#1::link1::LC/HC::link2::KDR-BP#2,
9) LC::link1::KDR-BP#1/KDR-BP#2::link2::HC,
10) LC::link1::KDR-BP#1/HC::link2::KDR-BP#2,
11) KDR-BP#1::link1::LC::link2::KDR-BP#2/KDR-BP#3::link3::HC,
12) KDR-BP#1::link1::LC::link2::KDR-BP#2/HC::link3::KDR-BP#3,
13) KDR-BP#3::link3::LC/KDR-BP#1::link1::HC::link2::KDR-BP#2,
14) LC::link3::KDR-BP#3/KDR-BP#1::link1::HC::link2::KDR-BP#2, and
15) KDR-BP#1::link1::LC::link2::KDR-BP#2/KDR-BP#3::link3::HC::link4::KDR-BP#4.

In cases (5)-(15), the linkers (shown as "link1", "link2", "link3" and "link4") can be the same or different or be absent. These linker if present, are preferably hydrophilic, protease resistant, non-toxic, non-immunogenic, and flexible. Preferably, the linkers do not contain glycosylation sites or sequences known to cause hepatic clearance. A length of zero to fifteen amino acids is preferred. The KDR-binding peptides (KDR-BP#1, #2, #3, and #4) could be the same or different. If the encoded amino-acid sequences are the same, it is preferred that the DNA encoding these sequences is different.

Since antibodies are dimeric, each fusion protein will present two copies of each of the fused peptides. In case (15), there will be eight KDR-BPs present and binding to KDR-displaying cells should be highly avid. It is possible that tumor penetration will be aided by moderate KDR affinity in each of the KDR-BPs rather than maximal One group of preferred embodiments have SEQ ID NO:294 as one of the KDR-BPs and SEQ ID NO:286 as the other. For example, in case (7) (KDR-BP#1::link1::LC/KDR-BP#2::link2::HC), KDR-BP#1 is SEQ ID NO:294 and KDR-BP#2 is SEQ ID NO:286 and link1 is between 10 and 20 amino acids and link2 is also between ten and twenty amino acids. A suitable sequence for link1 is GGSGGEGRPG-FGGSG (SEQ ID NO:491) and a suitable sequence for link2 is GSESGGRPEGGSGEGG (SEQ ID NO:492). Other sequences rich in Gly, Ser, Glu, Asp, Thr, Gln, Arg, and Lys are suitable. To reduce the risk of proteolysis, it is preferred to follow Arg or Lys with Pro. To avoid difficulties in production and poor solubility, it is preferred to avoid long stretches (more than twelve) of uncharged residues. Since the peptides are displayed at the ammo termini of LC and HC, the combined linker length will allow them to bind to KDR simultaneously. Additionally, in case (15)KR-BP#1::link1::.LC::link2::KDR-BP#2/KDR-BP#3::link3:HC::link4::KDR-BP#4), KDR-BP#1 and KDR-BP#2 are SEQ ID NO:294 and KDR-BP#3 and KDR-BP#4 are SEQ ID NO:29. Link1 and link3 are 10 to 20 amino acids and link2 and link4 are each 15 to 30 amino acids. Link2 and link4 are longer because they need to allow a peptide on the carboxy terminus of LC to reach a peptide on the carboxy terminus of HC.

The fusion protein is produced in eukaryotic cells so that the constant parts of the NC will be glycosylated. Preferably, the cells are mammalian cells, such as CHO cells.

The fusion proteins are injected into a patient, and time is allowed for the fusion protein to accumulate at the tumor. A clearing agent is injected so that fusion protein that has not become immobilized at the tumor will be cleared. In previous pretargeting methods, the antibody combining site has been used to target to the tumor and biotin/avidin or biotin/streptavidin has been used to attach the radioactive or toxic agent to the immobilized antibody. The biotin/avidin or streptavidin binding is essentially irreversible. Here we fuse a target-binding peptide to the antibody that is picked to bind a radioactive or toxic agent. Because the fusion protein contains 2, 4, 6, or 8 KDR-BPs, binding of the fusion protein to the tumor is very avid. A clearing agent that will cause fusion protein not immobilized at the tumor to clear can be administered between 2 and 48 hours of the injection of the fusion protein. Because the clearance agent is monomeric in the moiety that binds the antibody, complexes of clearance agent and immobilized fusion protein will not have very long life times. Within 4 to 48 hours of injecting clearance agent the immobilized antibody will have lost any clearance agent that binds there. The active agent is, preferably, dimeric in the moiety that binds the fusion protein. The active agent is injected between 2 and ~48 hours of injection of clearance agent.

TABLE 22

Amino-acid sequence of Mature HSA from GenBank entry AAN17825

(SEQ ID NO: 500)
DAHKSEVAHR FKDLGEENFK ALVLIAFAQY LQQCPFEDHV

KLVNEVTEFA KTCVADESAE NCDKSLHTLF GDKLCTVATL

RETYGEMADC CAKQEPERNE CFLQHKDDNP NLPRLVRPEV

DVMCTAFHDN EETFLKKYLY EIARRHPYFY APELLFFAKR

YKAAFTECCQ AADKAACLLP KLDELRDEGK ASSAKQRLKC

ASLQKFGERA FKAWAVARLS QRFPKAEFAE VSKLVTDLTK

VHTECCHGDL LECADDRADL AKYICENQDS ISSKLKECCE

KPLLEKSHCI AEVENDEMPA DLPSLAADFV ESKDVCKNYA

EAKDVFLGMF LYEYARRHPD YSVVLLLRLA KTYKTTLEKC

CAAADPHECY AKVFDEFKPL VEEPQNLIKQ NCELFEQLGE

YKFQNALLVR YTKKVPQVST PTLVEVSRNL GKVGSKCCKH

TABLE 22-continued

Amino-acid sequence of Mature HSA from GenBank entry AAN17825

PEAKRMPCAE DYLSVVLNQL CVLHEKTPVS DRVTKCCTES

LVNRRPCFSA LEVDETYVPK EFNAETFTFH ADICTLSEKE

RQIKKQTALV ELVKHKPKAT KEQLKAVMDD FAAFVEKCCK

ADDKETCFAE EGKKLVAASR AALGL

TABLE 23

SEQ ID NO: 286::linker1::HSA::linker2::
SEQ ID NO: 294

(SEQ ID NO: 501)
AGDWWVE<u>CRVGTGLC</u>YRYDTGTGGGK

PGGSGGEGGSGGEGGRPGGSEGGTGG

DAHKSEVAHR FKDLGEENFK ALVLIAFAQY LQQCPFEDHV

KLVNEVTEFA KTCVADESAE NCDKSLHTLF GDKLCTVATL

RETYGEMADC CAKQEPERNE CFLQHKDDNP NLPRLVRPEV

DVMCTAFHDN EETFLKKYLY EIARRHPYFY APELLFFAKR

YKAAFTECCQ AADKAACLLP KLDSLRDEGK ASSAKQRLKC

ASLQKFGERA FKAWAVARLS QRFPKAEFAE VSKLVTDLTK

VHTECCHGDL LECADDRADL AKYICENQDS ISSKLKECCE

KPLLEKSHCI AEVENDEMPA DLPSLAADFV ESKDVCKNYA

EAKDVFLGMF LYEYARRHPD YSVVLLLRLA KTYKTTLEKC

CAAADPHECY AKVFDEFKPL VEEPQNLIKQ NCELFEQLGE

YKFQNALLVR YTKKVPQVST PTLVEVSRNL GKVGSKCCKH

PEAKRMPCAE DYLSVVLNQL CVLHEKTPVS DRVTKCCTES

LVNRRPCFSA LEVDETYVPK EFNAETFTFH ADICTLSEKE

RQIKKQTALV ELVKHKPKAT KEQLKAVMDD FAAFVEKCCK

ADDKETCFAE EGKKLVAASR AALGL

GGSGGEGGSGGEGGSGPGEGGEGSGGRP

GDSRVCWEDSWGGEVCFRYDPGGGK

Example 40

Synthesis of Dimers D30 and D31

Preparation of Ac-VCWEDSWGGEVCFRYD-PGGGK{[PAO6-Glut-K(-Glut-JJ-NH(CH$_2$)$_4$—(S)—CH(Ac-AQDWYYDEILJGRGGRGG-NH)C(=O)NH$_2$]—NH$_2$}—NH$_2$: Dimer D30

Preparation of Ac-VCWEDSWGGEVCFRYDPGGGK[PnAO6-Glut-K]—NH$_2$ (Compound 3; FIG. 87A)
Ac-VCWEDSWGGEVCFRYDPGGGK[K(iV-Dde)]-NH$_2$ (1), comprising SEQ ID NO:494, is a SEQ ID NO:374 derivative; specifically Acetyl-(SEQ ID NO:374, 5-21)-GGGK[K(iV-Dde), 48 mg] was prepared by the procedures of Method 5. The compound was dissolved in DMF (0.85 mL) and treated with compound B and DIEA (7 μL) was added to maintain the basicity of the reaction mixture. The progress of the reaction was monitored by HPLC and mass spectroscopy. At the completion of the reaction (20 h), the volatiles were removed in vacuo. The residue, which consists of a compound 2 (SEQ ID NO:374, 5-21) derivative, specifically Acetyl-(SEQ ID NO:374, 5-21)-GGGK[(PnAO6-Glut-)K(iV-Dde)]-NH$_2$, was treated with 10% hydrazine in DMF (5 µL) for 10 min. HPLC analysis and mass spectroscopy indicated the completion of the reactions The mixture then was applied directly to a Waters Associates XTerra MSC18 preparative HPLC column (50 mm×19 mm i.d.) and purified by elution with a linear g ent of acetonitrile into water (both containing 0.1% TFA) to provide 11 mg of pure Compound 3.

Preparation of the Dimer D30 from Compound 3 and Ac-AQDWYYDEIL-Adoa-GRGGRGGRGGGK(Adoa-Adoa)-NH$_2$ (Compound 4 (comprising SEQ ID NO:617 with Modified Lysine Side Chains; Based on the Peptide Binding Moiety of SEQ ID NO:376)).

Disuccinimidyl glutarate (12 mg) was dissolved in DMF (500 µL), and DIEA was added (1 µL), Compound 3 in DMF was added into the DMF solution of disuccinimidyl glutarate/DIEA. The mixture was stirred for 2.5 h. HPLC and mass spectroscopy indicated the completion of the reaction. The volatiles were removed in vacuo and the residue was washed with ether (3×) to remove the unreacted bis-NHS ester. The residue was dried, re-dissolved in anhydrous DMF and treated with the Compound 4, Ac-AQDWYYDEIL-Adoa-GRGGRGGRGGGK(Adoa-Adoa)-NH$_2$, which was prepared by Method 5 and Method 8, in the presence of 2 equivalents of DIEA. The reaction was allowed to proceed for 20 h. The mixture then was applied directly to a Waters Associates MSC18 reverse phase preparative (50 mm×19 mm i.d.) HPLC column and purified by elution with a linear gradient of acetonitrile into water (both containing 0.1% TFA) to provide 2 mg of D30 (For purification and structure of D30, see below and also FIGS. 87B and C, respectively).

Synthesis of Ac-AGPTWCEDDWYYCWLFGTGGGK[Ac-VCWEDSWGGEVCFRYDPGGGK[SGS-Glut-SGS—(S)—NH(CH$_2$)$_4$—CH(Biotin-JJ-NH)—C(=O)]—NH$_2$]—NH$_2$: D31

Preparation of Monomer Compound 2 and Monomer Compound 4
See FIG. 88B.

Synthesis of Monomer Peptide 1 and Monomer Peptide 3
Monomer Peptide 1 comprises SEQ ID NO:378 with the following modification: it is an Ne22-iV-Dde-SEQ ID NO:378 peptide.

Monomer peptide 3 comprises SEQ ID NO:370, and is a derivative of SEQ ID NO:337. It is an Ne25-iV-Dde-SEQ ID NO:370 peptide.

Synthesis of the monomers 1 and 3 were cared out using the procedures of Method 5 for the ABI 433A synthesizer.

Figure 88A:
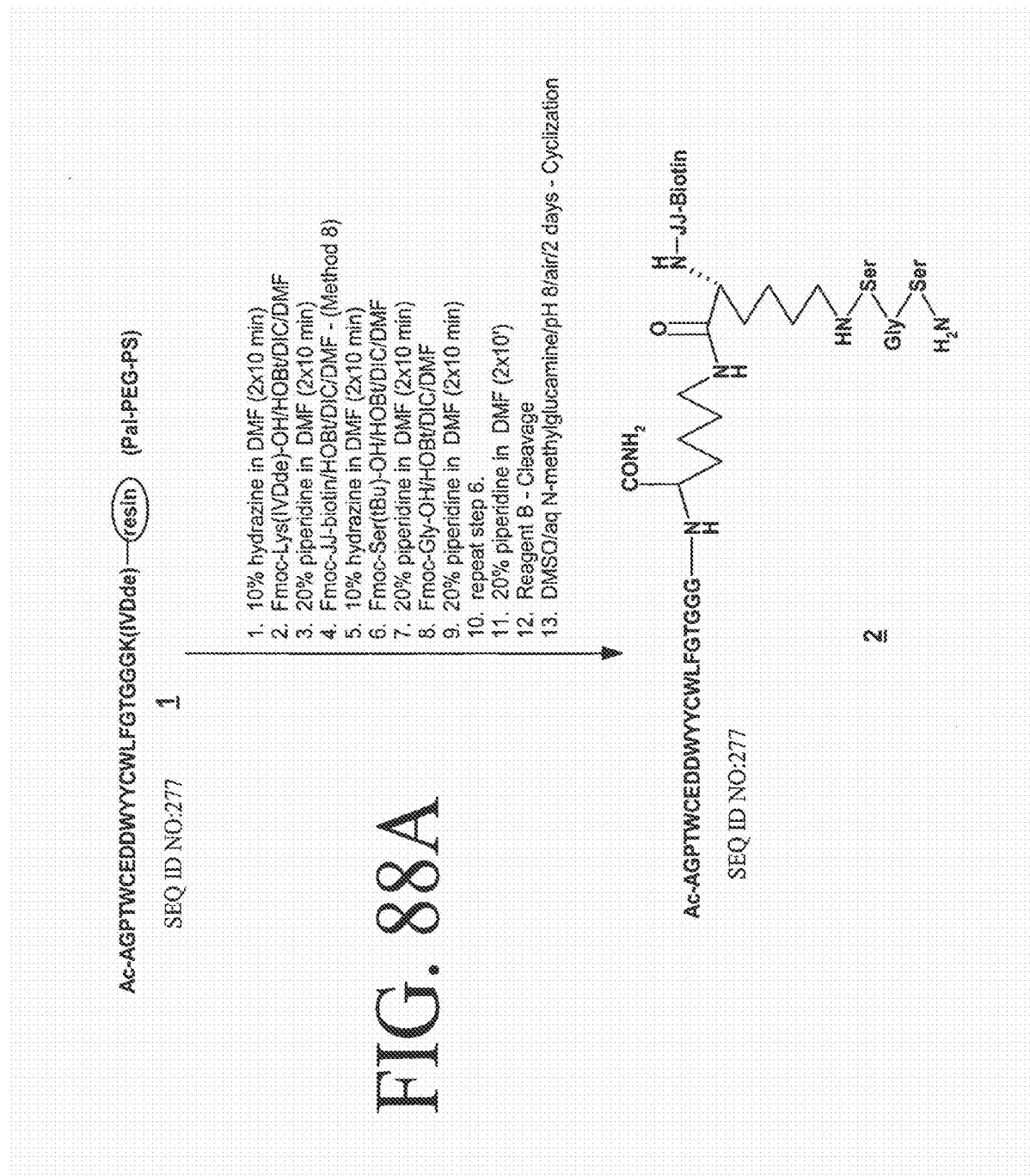
Figure 88C:
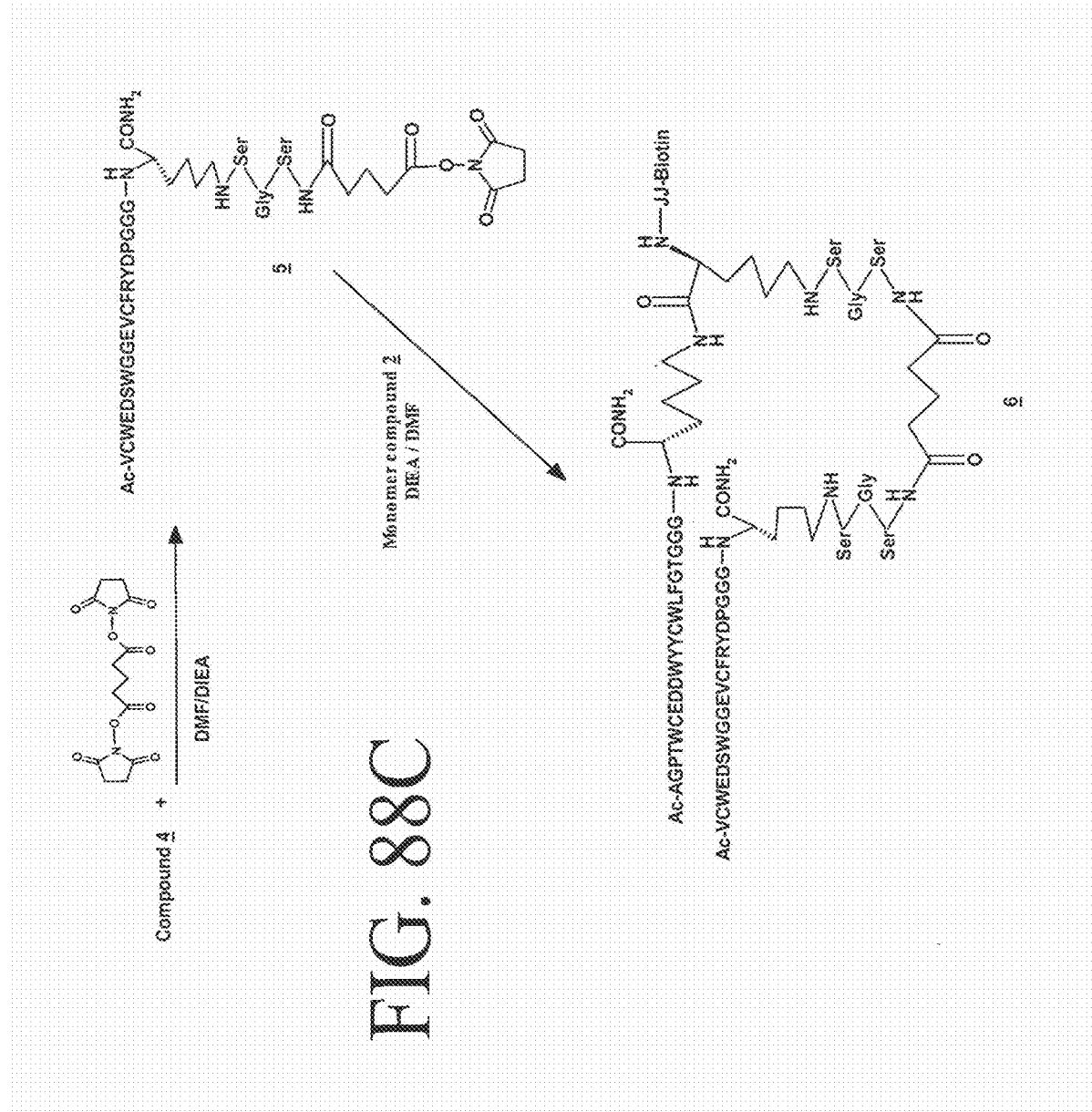

Synthesis of Monomer Peptide 2 and Monomer Peptide 4
See FIGS. 88A and 88B.

Appendage of Biotin-JJ, Lys, Gly and Ser onto Compounds 1 and 3 was done by SPPS manually using the appropriate Fmoc amino acids, Biotin-JJ and Fmoc-J (J=8-amino-3,6-dioxaoctanoic acid) according to the procedures of Methods 6, 7, 8, 9 and 10. Cleavage of the peptides from the resin, processing of the crude peptides was carried out as described in Method 1 for the synthesis of peptides. Cyclization of the cysteine moieties to form the cyclic disulfide peptides was performed by the procedures of Method 9.

Purification of the peptides was carried out using a Shimadzu LC-10A HPLC system and a YMC C-18 ODS preparative HPLC column employing a linear gradient elution of acetonitrile (0.1% TFA) into 0.1% aqueous TFA. Pure fractions were combined and lyophilized.

The dimer D31 was prepared using monomer compound 4 to generate, in situ, the activated monomer compound 5, which was then reacted with monomer compound 2 using the procedures described in Method 13, entitled: 'Preparation of Heterodimer Containing Constructs'. The crude compound D31 was purified by preparative reverse phase HPLC using a Waters-YMC C-18 ODS column to provide 10 mg of the dimer D31.

Example 41

In Vitro Competition Experiments on KDR-Transfected Cells

Figure 89:
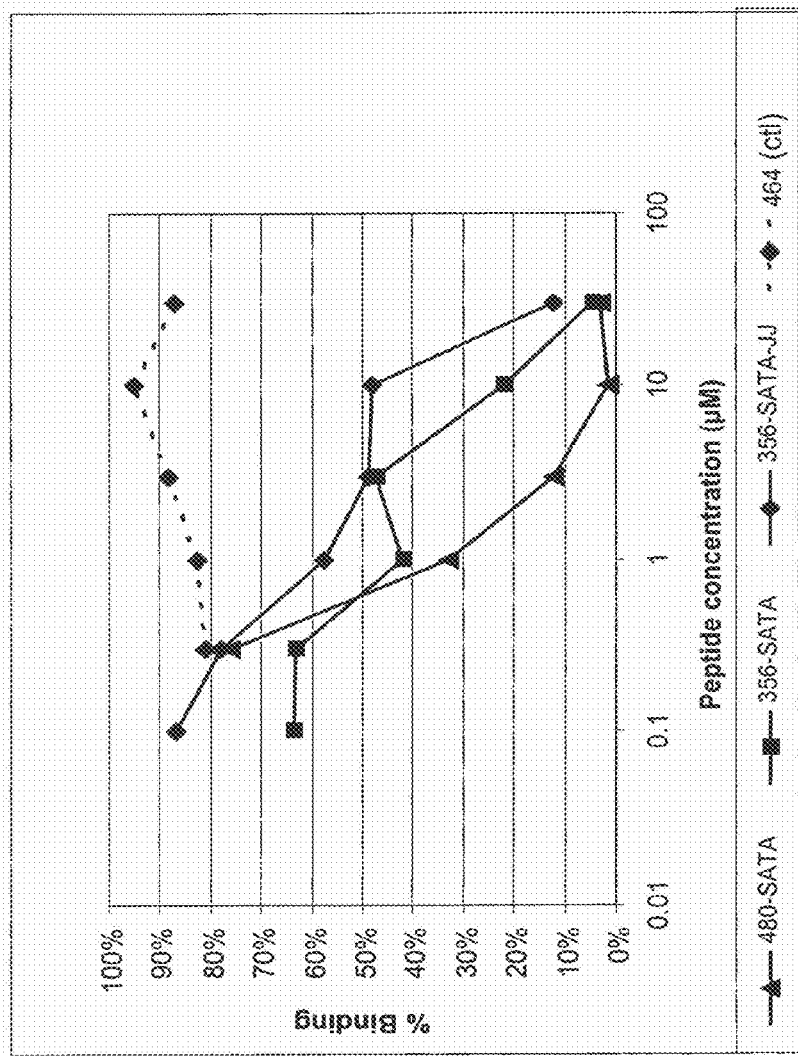
FIG. 89 is a graph that shows competition of targeted bubbles by corresponding free peptide.

The following experiment assessed the specificity of the binding of peptide-conjugated microbubbles to KDR-expressing cells.
Protocol:
293H cells were transfected with KDR cDNA. The transfected cells were incubated with a suspension of peptide-conjugated microbubbles in presence or absence of the corresponding free peptide (at 100, 30, 10, 3, 1, 0.3, 0.1 µM). Microbubbles were conjugated to a SATA-modified peptide comprising SEQ ID NO:480, a SATA-modified peptide comprising SEQ ID NO:356, or a SATA-modified peptide comprising SEQ ID NO:356 and a JJ linker. Competition was also performed using the corresponding non-binding or control free peptide as competing compound. At the end of the incubation, the transfected cells were rinsed three times in PBS and examined under a microscope. Binding of the conjugated bubbles was quantified and expressed as percent of surface covered by the targeted microbubbles.
Results:
All the KDR-conjugated microbubbles were competed off by the corresponding free KDR-specific peptide whereas the presence of control peptide had no effect. Example of curves obtained by plotting the fraction of residual binding as a function of the competitor concentration are shown in FIG. 89.

Example 42

In Vitro Competition Experiments on KDR-Transfected Cells

Figure 90:
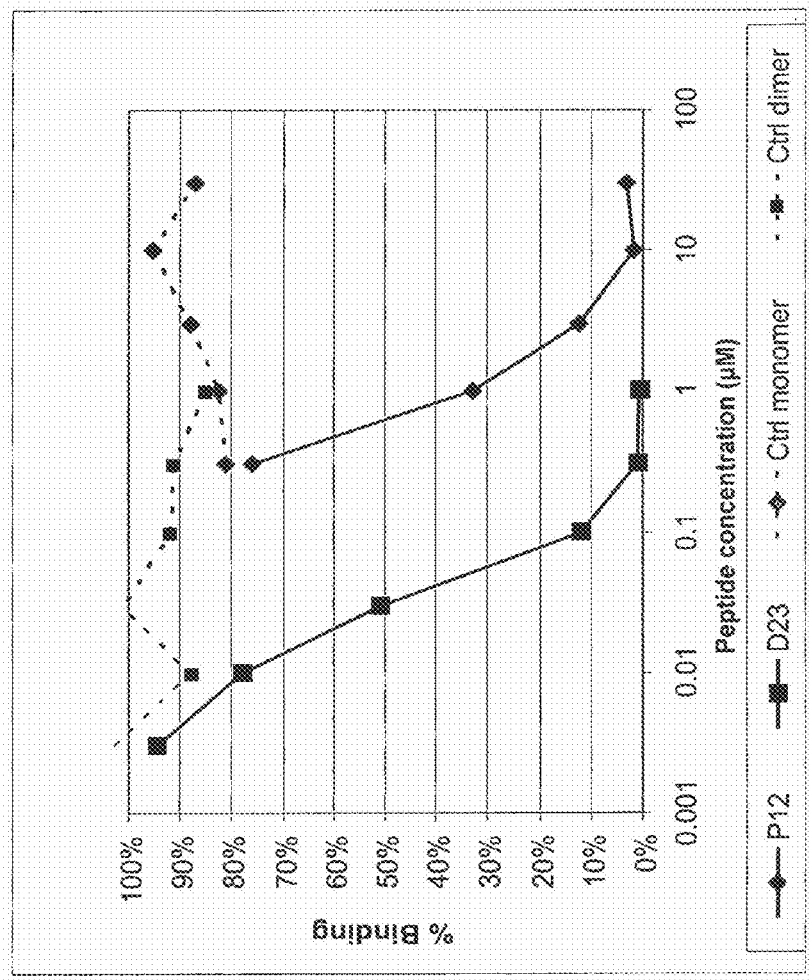
FIG. 90 is a graph that shows competition of targeted bubbles conjugate to D23 by corresponding fee peptide.

The following experiment assessed the specificity of the binding of peptide-conjugated microbubbles to KDR-expressing cells.
Protocol:
293H cells were transfected with KDR cDNA. The transfected cells were incubated with a suspension of peptide-conjugated microbubbles in presence or absence of the corresponding free peptide (between 100 µM to 3 nM). Competition was also performed using a non-binding peptide as competing compound. At the end of the incubation, the transfected cells were rinsed three times in PBS and examined under a microscope. Binding of the conjugated bubbles was quantified and expressed as percent of surface covered by the targeted microbubbles.
Results:
Microbubbles conjugated to KDR-specific dimer (D23) or monomer (SEQ ID NO:338) molecules were competed off by the corresponding free KDR-specific peptide whereas the presence of control peptide had no effect. Example of curves obtained by plotting the fraction of residual binding as a fiction of the competitor concentration are shown in FIG. 90.

In Vitro Competition Experiments on KDR-Transfected Cells

The following experiment compares the binding efficiency of monomers and dimers conjugated to microbubbles on KDR-transfected cells.

Protocol:

293H cells were transfected with KDR cDNA. The transfected cells were incubated with a suspension of microbubbles conjugated to different peptides (monomers or dimers) in presence or absence of increasing concentrations of free dimer (at 1000, 300, 100, 30, 10, 3, 1 nM). At the end of the incubation, the transfected cells were rinsed three times in PBS and examined under a microscope. Binding of the conjugated bubbles was quantified and expressed as percent of surface covered by the targeted microbubbles.

Figure 91:
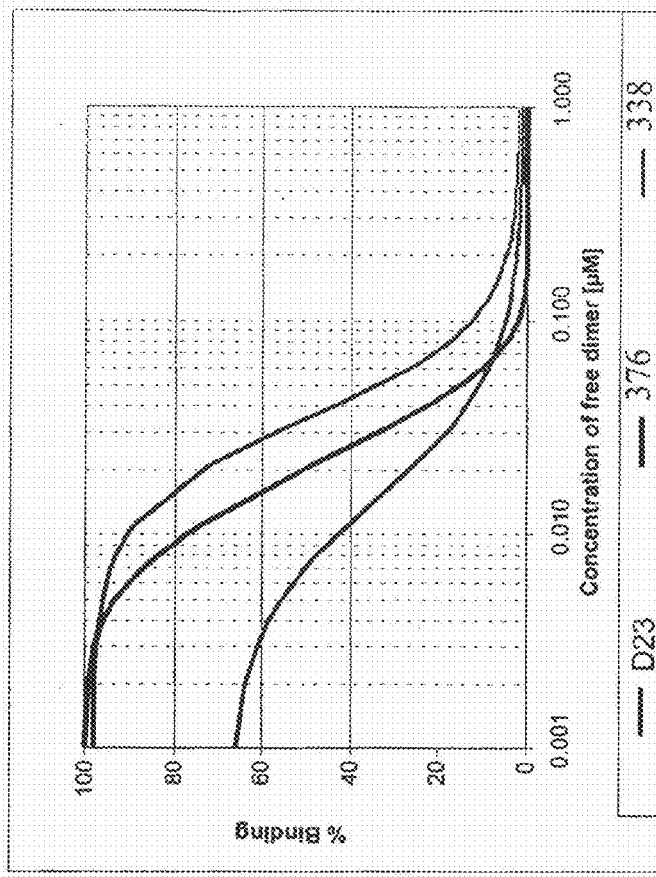
FIG. 91 is a graph that shows competition of targeted bubbles with free dimer.

Results:

Microbubbles conjugated to D23 were more resistant to competition and less easily displaced by the corresponding free dimeric peptide than KDR-specific monomer-conjugated microbubbles conjugated to SEQ ID NO:338 or SEQ ID NO:376. Representative curves obtained by plotting the fraction of residual binding as a fiction of the competitor concentration are shown in FIG. 91.

Example 43

In Vitro Binding of Heteromultimers and Dimers Compared to Multimeric Monomers

The following experiment aims at comparing the binding efficiency of mixed monomers, dimers and monomers conjugated to microbubbles in the KDR-transfected cells assay.

Protocol:

Microbubbles were conjugated to either a dimer (D23) or two different peptides monomers (SEQ ID NO:294 or SEQ ID NO:480). A fourth conjugation reaction was performed using equal quantities of each monomer (and the same total peptide load). 293H cells were transfected with KDR cDNA. The transfected cells were incubated with the same number of targeted microbubble and in presence of 50% human serum. At the end of the incubation, the transfected cells were rinsed three times in PBS and examined under a microscope. Binding of the conjugated bubbles was quantified and expressed as percent of surface covered by the targeted microbubbles.

Figure 92:
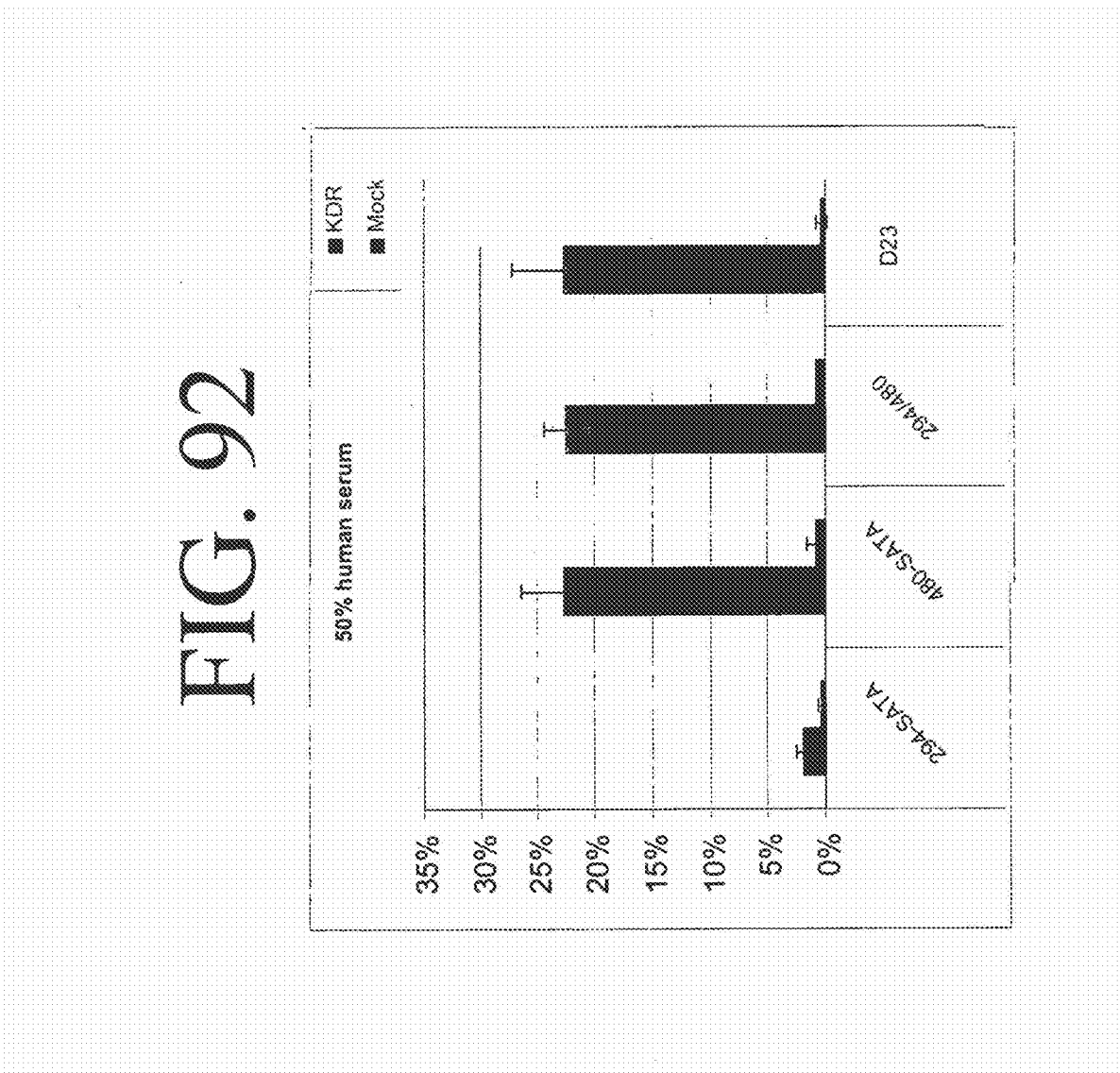
FIG. 92 is a graph showing binding values obtained with the suspensions of microbubbles conjugated to the D23, SATA-modified SEQ ID NO:480, SATA-modified SEQ ID NO:294 or SEQ ID NO:294/SEQ ID NO:480 (50/50) are equivalent (see Example 43).

Results:

As shown in FIG. 92, microbubbles conjugated with h SEQ ID NO:294 bound poorly compared with microbubbles conjugated with SEQ ID NO:480 or dimer D23. Surprisingly, microbubbles conjugated to D23 bound equivalently to those conjugated to SEQ ID NO:480 although D23 has half the Toad. Moreover, the "mixed monomer" conjugated microbubbles, which also have half the SEQ ID NO:480 load, bound as well as microbubbles conjugated with SEQ ID NO:480 or D23. These results show the increased binding capacity of heteromultimers.

Example 44

Blocking VEGF-Enhanced Peritoneal Vascular Permeability with a Heterodimeric Peptide In this example, the ability of heterodimer D10 to inhibit the enhanced vascular permeability caused by VEGF injected into the peritoneum of nude mice is demonstrated.

Protocol

Male balb/c nu/nu mice were injected intraperitoneally with 2 mL vehicle (1% bovine serum albumin in 95% saline/5% DMSO), vehicle+1.2 nM $VEGF_{165}$, or vehicle+1.2 nM $VEGF_{165}$+20 μM D10. Immediately after, the mice were injected with Evan's Blue Dye (0.5% in saline, 4 mL/kg) i.v. via their tail veins. After 60 min, mice were sacrificed by $CO_2$ asphyxiation and the peritoneal fluid was retrieved. After centrifuging the samples briefly, the absorbance at 590 nm was measured for each.

Results

Figure 93:
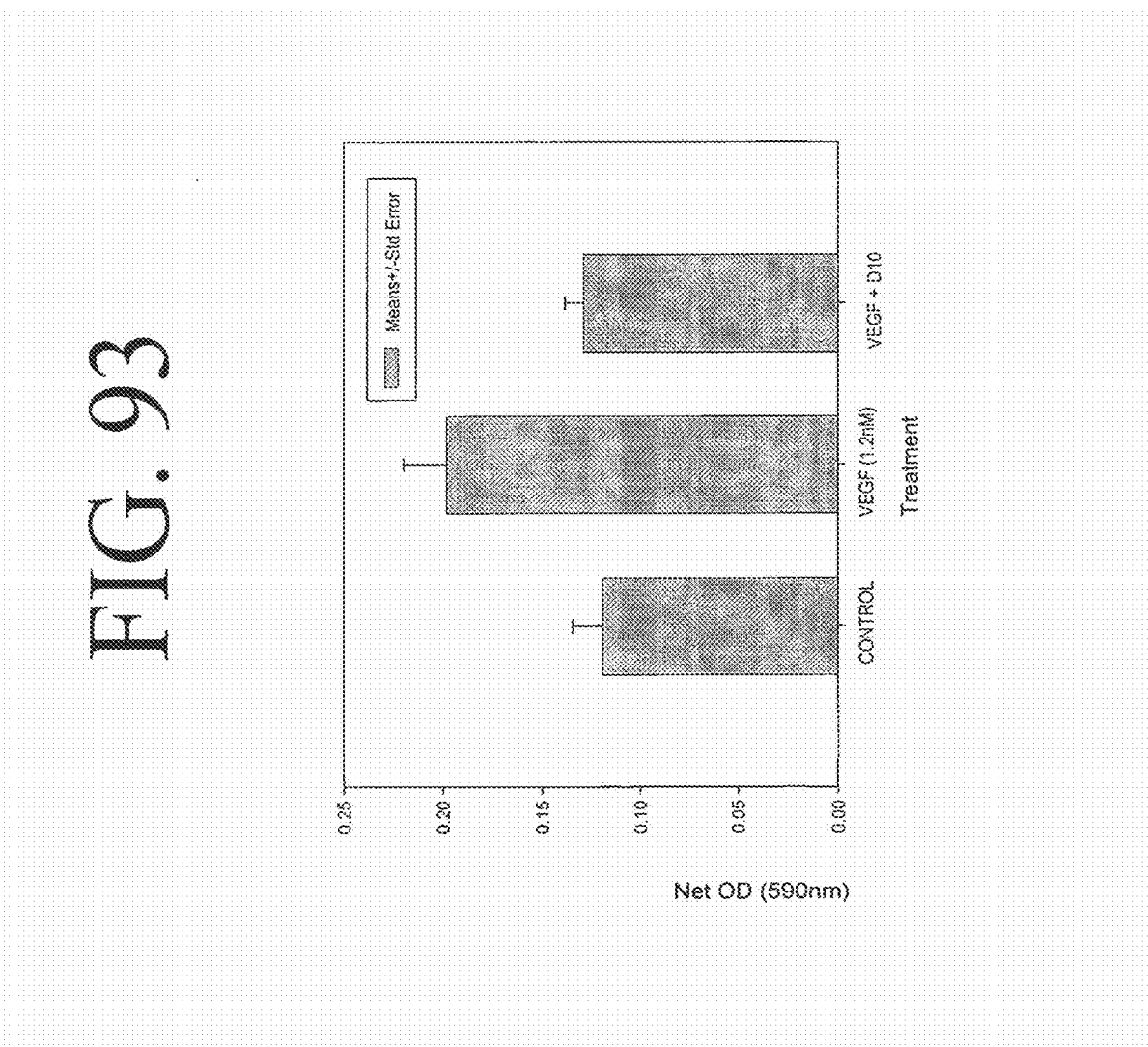
FIG. 93 is a graph showing dimer D10 blocks the increased peritoneal vascular permeability induced by VEGF injected intraperitoneally. Solutions containing the indicated additions were injected intraperitoneally, and their effect on peritoneal permeability was assessed by measuring the O.D. of the injected fluid at 590 nm after administering Evan's Blue dye i.v. as described in Example 44.

As shown in FIG. 93, VEGF, when added to the fluid injected intraperitoneally, significantly increased the dye leakage into the peritoneum, and this increase was substantially blocked by including D10 with the VEGF.

Example 45

Mouse Xenograft Tumor Model of Human Colon Cancer

This example assesses the effects of dimer D6 that has been processed into biodegradable sustained release pellets. Since D6 has a half-life on the order of 1 hour, a way of improving the residence time in sera was sought. The compound is formulated into a sustained release format so that greater therapeutic benefit to animal models is observed.

The effect of D6 on the tumor model is determined, for example, by measuring tumor size with and without treatment. Additionally, the effect of D6, engineered to have a longer residence time in sera, is compared to the effect of unmodified D6 (see Example 39).

Briefly, 140 nude mice are injected subcutaneously with the cell line, SW-480. Tumors are measured, and when tumors reach 100-200 mg, 100 ants are selected and randomized into 10 study groups of 10 animals each, The overall study is summarized in Table 24 below. The dosing schedule follows &e chart shown in Table 25. Tumor measurements are taken on each animal twice a week during the normal workweek. Measurements are made by hand-held vernier caliper. Body weights and tumor measurements are recorded twice a week. This study is based on a typical four week study from beginning of dosing and includes removal of 30 tumors.

TABLE 24

| D6 Mouse Tumor Study | |
|---|---|
| Cell line | SW-480, human colon carcinoma |
|  | $5 \times 10^6$, subcutaneous |
| Test Animal | nude mouse (CRL: NU/NU = nuBR) |
|  | female |
|  | n = 10/test group |
| Study Initiation | >6 weeks age |
|  | Tumor ~100 −/+ 50 mg |
| Control | 1. untreated |
|  | 2. Vehicle |
|  | 3. Placebo pellet |
|  | 4. Cisplatin |
| Test Article | D6 |
|  | 0.5 mg/kg/d × 21 d |
|  | 2.0 mg/kg/d × 21 d |
|  | 2.0 mg/kg/d × 21 d pellet |
| Test Article Form | 1. solution for injection (PBS, IP) |
|  | 2. sustained release pellet |
|  | (nominal 21 day, subcutaneous) |
| Primary endpoints | 1. tumor growth |
|  | 2. histopathology (necropsy) |
| Supplementary measures | 1. angiogenesis (CD-31+) |
| (representative samples) | 2. cell proliferation (PCNA) |
|  | 3. circulating D6 |
|  | 4. |

TABLE 25

| Treatment Group | n | Vehicle Administration | D6 Dose Administration | Cisplatin Dose Administration |
|---|---|---|---|---|
| 1 | 10 | — | — | — |
| 2 | 10 | PBS 1 IP inj/d, 21 d | — | — |
| 3 | 10 | — | 0.5 mg/kg/day 1 IP inj/d, 21 d | — |
| 4 | 10 | — | 2.0 mg/kg/day 1 IP inj/d, 21 d | — |
| 5 | 10 | Vehicle pellet (1), sc | — | — |
| 6 | 10 | — | 2.0 mg/kg/day pellet (1), sc | — |
| 7 | 10 | — | — | [6 mg/kg] 1 IV inj/2 days, to 5 Ttl |
| 8 | 10 | — | 2.0 mg/kg/day pellet (1), sc | [6 mg/kg] 1 IV inj/2 days to 5 Ttl |
| 9 | 10 | — | 2.0 mg/kg/day pellet (1), sc | [3 mg/kg] 1 IV/2 days, to 5 Ttl |
| 10 | 10 | — | 2.0 mg/kg/day pellet (1), sc | [1 mg/kg] 1 IV/2 days, to 5 Ttl |

Example 46

The following example describes the preparation of an ultrasound contrast agent conjugated to a KDR-binding heterodimer of the invention and the ability of the heterodimer conjugated contrast agent to localize to KDR-expressing cells in vitro and angiogenic tissue in vivo.

Preparation of Derivatized Microbubbles for Peptide Conjugation.

200 mg of DSPC (distearoylphosphatidylcholine), 275 mg of DPPG.Na (distearoylphosphatidylglycerol sodium salt) and 25 mg of N-MPH-PE were solubilized at 60° C. in 50 mL of Hexan/isopropanol (42/8). The solvent was evaporated under vacuum, and then PEG4000 (35.046 g) Was added to the lipids and the mixture was solubilized in 106.92 g of t-butyl alcohol at 60° C., in a water bath. The solution was filled in vials with 1.5 ml of solution. The samples were rapidly frozen at −45° C. and lyophilized. The air in the headspace was replaced with a mixture of $C_4F_{10}$/Air (50/50) and vials capped and crimped. The lyophilized samples were reconstituted with 10 mL saline solution (0.9%-NaCl) per vial, yielding a suspension of phospholipids stabilized microbubbles.

Peptide Conjugation

D23 was conjugated with a preparation of microbubbles as above described, according to the following methodology. The thioacetylated peptide (200 μg) was dissolved in 20 μL DMSO and then diluted in 1 ml of Phosphate Buffer Saline (PBS). This solution was mixed to the N-MPB-functionalized microbubbles dispersed in 18 mL of PBS-EDTA 10 nM, pH 7.5, and 2 mL of deacetylation solution (50 mM sodium phosphate, 25 mM EDTA, 0.5 M hydroxylamine.HCl, pH 7.5) was added. The headspace was filled with $C_4F_{10}$/Air (50/50) and the mixture was incubated for 2.5 hours at room temperature under gentle agitation (rotating wheel), in the dark. Conjugated bubbles were washed by centrifugation. Similarly, the monomer peptides making up D23 were separately conjugated to two different microbubble preparations according to the methodology described above.

In Vitro Assay on Transfected Cells

The ability of phospholipid stabilized microbubbles conjugated to peptides and heteromultimeric peptide constructs of the invention to bind to KDR-expressing cells was assessed using 293H cells transfected to express KDR.

Transfection of 293H Cells on Thermanox® Coverslips 293H cells were transfected with KDR DNA as set forth in Example 5. The transfected cells were incubated with a suspension of peptide-conjugated microbubbles prepared as described above. For the incubation with the transfected cells a small plastic cap is filled with a suspension containing 1 to 3×10⁸ peptide-conjugated microbubbles and the cap covered with an inverted Thermanox® coverslip is placed so that the transfected cells are in contact with the conjugated microbubbles. After about 20 min at room temperature, the coverslip is lifted with tweezers, rinsed three times in PBS and examined under a microscope to assess binding of the conjugated microbubbles.

Determination of the Percent of Surface Covered by Microvesicles

Images were acquired with a digital camera DC300F (Leica) and the percent of surface covered by bound microbubbles in the imaged area was determined using the software QWin (Leica Microsystem AG, Basel, Switzerland). Table 26 shows the results of the binding affinity (expressed as coverage % of the imaged surface) of targeted microvesicles of the invention to KDR transfected cells, as compared to the binding of the same targeted microvesicles to Mock-transfected cells.

TABLE 26

| Conjugated microbubbles prepared as described above | | % of covered surface | |
|---|---|---|---|
| Peptide code | Batch Id | KDR | Mock |
| SEQ ID NO: 294 Derivative | BG1979T02 | 3.5% | 0.9% |
| SEQ ID NO: 480 Derivative | BG1980T02 | 16.8% | 1.0% |
| D23 (dimer) | BG2002T02 | 22.9% | 3.3% |
| SEQ ID NO. 294/SEQ ID NO: 480 Deriv. | BG1958T02 | 12.9% | 0.8% |

Where the SEQ ID NO:294-derived sequence and the SEQ ID NO:480-derived sequence are separately attached to phospholipid stabilized microbubbles as monomers the resulting preparations achieve binding of the bubbles to KDR transfected cells in vitro to a different extent (3.5% and 16.8%). When a preparation of phospholipid stabilized microbubbles resulting from the addition of equal quantities of each of these peptide monomers (but the same total peptide load) is tested in the same system, 12.9% binding is achieved. Binding is a little mote than the average of the two but as it is achieved with two sequences that bind to different sites on the target will be more resistant to competition at one or other of the sites on the target. However, for D23, the dimer, binding is increased to 22.9% (with the same peptide load). These results indicate that heteromultimers of the invention permit increased binding and increased resistance to competition.

In Vivo Animal Models

A known model of angiogenic tissue (the rat Mat B m model) was used to examine the ability of phospholipids-stabilized microbubbles conjugated to a heteromultimer of the invention to localize to and provide images of angiogenic tissue.

Female Fisher 344 rat (Charles River Laboratories, France) weighing 120 to 160 g were used for the MATBIII tumor implantation. Male OFA rats (Charles River Laboratories, France) weighing 100 to 150 g were used for Matrigel injection.

Anesthesia

Rats were anesthetized with an intramuscular injection (1 mL/kg) of Ketaminol®/xylazine (Veterinaria AG/Sigma) (50/10 mg/ml) mixture before implantation of Matrigel or MatBIII cells. For imaging experiments, animals were anesthetized with the same mixture, plus subcutaneous injection of 50% urethane (1 g/kg).

Rat MATBIII Tumor Model

A rat mammary adenocarcinoma, designated 13762 Mat B III, was obtained from ATCC (CRL-1666) and grown in McCoy's 5a medium+10% FCS. 1% glutamine and 1% pen/strep (InVitrogen cat# 15290-018) Cells in suspension were collected and washed in growth medium, counted, centrifuged and resuspended in PBS or growth medium at $1 \times 10^7$ cells per mL. For tumor induction: $1 \times 10^6$ cells in 0.1 mL were injected into the m fat pad of anesthetized female Fisher 344 rat. Tumors usually grow to a diameter of 5-8 mm within 8 days.

In Vivo Ultrasound Imaging

Tumor imaging was performed using an ultrasound imaging system AIL HDI 5000 apparatus equipped with a L7-4 linear probe. B-mode pulse inversion at low acoustic power (MI=0.05) was Wed to follow accumulation of peptide conjugated-microbubbles on the KDR receptor expressed on the endothelium of neovessels. For the control experiments, an intravenous bolus of unconjugated microbubbles or microbubbles conjugated to non-specific peptide was injected. The linear probe was fixed on the skin directly on line with the implanted tumors and accumulation of targeted bubbles was followed during thirty minutes.

A perfusion of SonoVue® was administrated before injecting the test bubble suspension. This allows for the evaluation of the vascularization status and the video intensity obtained after SonoVue® injection is taken as an internal reference.

A baseline me was recorded and then insonation was stopped during the injection of the microbubbles. At various time points after injection (1, 2, 5, 10, 15, 20, 25, 30 minutes) insonation was reactivated and 2 frames of one second were recorded on a videotape.

Video fines from tumor imaging experiments were captured and analysed with the video-capture and Image-Pro Plus 2.0 software respectively. The same rectangular Area of Interest (AOI) including the whole sectional area of the tumor was selected on images at different time points (1, 2, 5, 10, 15, 20, 25, 30 minutes). At each time point, the sum of the video pixel inside the AOI was calculated after the subtraction of the AOI baseline. Results are expressed as the percentage of the signal obtained with SonoVue®, which is taken as 100%. Similarly, a second AOI situated outside the tumor, and representing the freely circulating contrast agent, is also analyzed.

Figure 94:
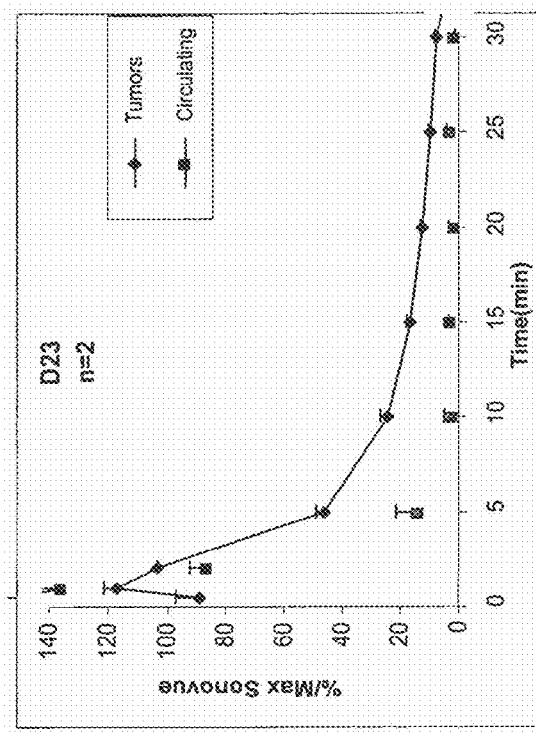
FIG. 94 is a graph showing uptake and retention of bubble contrast in the tumor up to 30 minutes post injection for suspensions of phospholipid stabilized microbubbles conjugated to a heteromultimeric construct (D23).

FIG. 94 shows uptake and retention of bubble contrast in the tumor up to 30 minutes post injection for suspensions of phospholipid stabilized microbubbles conjugated to a heteromultimeric construct of the invention prepared as described above (D23). In contrast, the same bubbles showed only transient (no more than 10 minutes) visualization/bubble contrast in the AOI situated outside the tumor site.

While this invention has been particularly shown and described with references to preferred embodiments thereof, it will be understood by those skilled in the art that various changes in form and details may be made therein without departing from the scope of the invention encompassed by the appended claims. The publications, patents and other references cited herein are incorporated by reference herein in their entirety.

---

What is claimed is:

1. An ultrasound contrast agent comprising a microvesicle conjugated to at least one polypeptide having the ability to bind to KDR or VEGF/KDR complex, wherein the polypeptide comprises an amino acid sequence selected from the group consisting of

| | |
|---|---|
| AGDSWCSTEYTYCEMIGTGGGK; | (SEQ ID NO: 263) |
| AGPKWCEEDWYYCMITGTGGGK; | (SEQ ID NO: 264) |
| AGVWECAKTFPFCHWFGTGGGK; | (SEQ ID NO: 265) |
| AGWVECWWKSGQCYEFGTGGGK; | (SEQ ID NO: 266) |
| AGWIQCNSITGHCTSGGTGGGK; | (SEQ ID NO: 268) |
| AGWIECYHPDGICYHFGTGGGK; | (SEQ ID NO: 269) |
| AGSDWCRVDWYYCWLMGTGGGK; | (SEQ ID NO: 270) |
| AGANWCEEDWYYCFITGTGGGK; | (SEQ ID NO: 271) |
| AGANWCEEDWYYCWITGTGGGK; | (SEQ ID NO: 272) |
| AGPDWCEEDWYYCWITGTGGGK; | (SEQ ID NO: 273) |
| AGSNWCEEDWYYCYITGTGGGK; | (SEQ ID NO: 274) |
| AGPDWCAADWYYCYITGTGGGK; | (SEQ ID NO: 275) |
| AGPEWCEVDWYYCWLLGTGGGK; | (SEQ ID NO: 276) |
| AGPTWCEDDWYYCWLFGTGGGK; | (SEQ ID NO: 277) |
| AGSKWCEQDWYYCWLLGTGGGK; | (SEQ ID NO: 278) |
| AGRNWCEEDWYYCFITGTGGGK; | (SEQ ID NO: 279) |
| AGVNWCEEDWYYCWITGTGGGK; | (SEQ ID NO: 280) |
| AGANWCEEDWYYCYITGTGGGK; | (SEQ ID NO: 281) |
| AGQAWVECYAETGYCWPRSWGTGGGK; | (SEQ ID NO: 282) |
| AGQAWIECYAEDGYCWPRSWGTGGGK; | (SEQ ID NO: 283) |
| AGVGWVECYQSTGFCYHSRDGTGGGK; | (SEQ ID NO: 284) |
| AGFTWVECHQATGRVCVEWTTGTGGGK; | (SEQ ID NO: 285) |
| AGDWWVECRVGTGLCYRYDTGTGGGK; | (SEQ ID NO: 286) |

-continued

| | |
|---|---|
| AGDSWVECDAQTGFCYSFLYGTGGGK; | (SEQ ID NO: 287) |
| AGERWVECRAETGFCYTWVSGTGGGK; | (SEQ ID NO: 289) |
| AGGGWVECRAETGHCQEYRLGTGGGK; | (SEQ ID NO: 290) |
| AGVAWVECYQTTGKCYTFRGGTGGGK; | (SEQ ID NO: 291) |
| AGEGWVECFANTGACFTYPRGTGGGK; | (SEQ ID NO: 292) |
| GDYPWCHELSDSVTRFCVPWDPGGGK; | (SEQ ID NO: 293) |
| GDSRVCWEDSWGGEVCFRYDPGGGK; | (SEQ ID NO: 294) |
| GDDHMCRSPDYQDHVCMYWDPGGGK; | (SEQ ID NO: 295) |
| GDPPLCYFVGTQEWHHCNPFDPGGGK; | (SEQ ID NO: 296) |
| GDDSYCMMNEKGWWNCYLYDPGGGK; | (SEQ ID NO: 297) |
| GDPAQCWESNYQGIFFCDNPDPGGGK; | (SEQ ID NO: 298) |
| GDGSWCEMRQDVGKWNCFSDDPGGGK; | (SEQ ID NO: 299) |
| GDGWACAKWPWGGEICQPSDPGGGK; | (SEQ ID NO: 300) |
| GDPDTCTMWGDSGRWYCFPADPGGGK; | (SEQ ID NO: 301) |
| GDNWKCEYTQGYDYTECVYLDPGGGK; | (SEQ ID NO: 302) |
| GDNWECGWSNMFQKEFCARPDPGGGK; | (SEQ ID NO: 303) |
| GDWWECKREEYRNTTWCAWADPGGGK; | (SEQ ID NO: 486) |
| GDSSVCFEYSWGGEVCFRYDPGGGK; | (SEQ ID NO: 487) |
| GDSRVCWEYSWGGQICLGYDPGGGK; | (SEQ ID NO: 488) |
| AQQVQYQFFLGTPRYEQWDLDKGGK; | (SEQ ID NO: 304) |
| AQEPEGYAYWEVITLYHEEDGDGGK; | (SEQ ID NO: 305) |
| AQAFPRFGGDDYWIQQYLRYTDGGK; | (SEQ ID NO: 306) |
| AQGDVYWEIIELTGATDHTPPGGK; | (SEQ ID NO: 307) |
| AQRGDYQEQYWHQQLVEQLKLLGGK; | (SEQ ID NO: 308) |
| AQRSWYLGPPYYEEWDPIPNGGK; | (SEQ ID NO: 309) |
| AQDWYYDEILSMADQLRHAFLSGGGK; | (SEQ ID NO: 310) |
| AGIDFCKGMAPWLCADMGTGGGK; | (SEQ ID NO: 311) |
| AGPWTCWLEDHLACAMLGTGGGK; | (SEQ ID NO: 312) |
| AGDWGCSLGNWYWCSTEGTGGGK; | (SEQ ID NO: 313) |
| GSDHHCYLHNGQWICYPFAPGGGK; | (SEQ ID NO: 314) |
| GSNSHCYIWDGMWLCFPDAPGGGK; | (SEQ ID NO: 315) |
| SGRLDCDKVFSGPYGKVCVSYGSGGGK; | (SEQ ID NO: 316) |
| SGRLDCDKVFSGPHGKICVNYGSGGGK; | (SEQ ID NO: 317) |
| SGRTTCHHQISGPHGKICVNYGSGGGK; | (SEQ ID NO: 318) |
| SGAHQCHHWTSGPYGEVCFNYGSGGGK; | (SEQ ID NO: 319) |
| AGMPWCVEKDHWDCWWWGTGGGK; | (SEQ ID NO: 320) |
| AGPGPCKGYMPHQCWYMGTGGGK; | (SEQ ID NO: 321) |
| AGYGPCAEMSPWLCWYPGTGGGK; | (SEQ ID NO: 322) |
| AGYGPCKNMPPWMCWHEGTGGGK; | (SEQ ID NO: 323) |
| AGGHPCKGMLPHTCWYEGTGGGK; | (SEQ ID NO: 324) |
| AQAPAWTFGTNWRSIQRVDSLTGGGGK; | (SEQ ID NO: 325) |

-continued

| | |
|---|---|
| AQEGWFRNPQEIMGFGDSWDKPGGGGGK; | (SEQ ID NO: 326) |
| AQEGWFRNPQEIMGFGDSWDKPGGGK; | (SEQ ID NO: 330) |
| AQRGDYQEQYWHQQLVEQLKLLGGGK; | (SEQ ID NO: 331) |
| AGWYWCDYYGIGCKWTGGGK; | (SEQ ID NO: 332) |
| AGWYWCDYYGIGCKWTGTGGGK; | (SEQ ID NO: 333) |
| AQWYYDWFHNQRKPPSDWIDNLGGGK; | (SEQ ID NO: 334) |
| WQPCPWESWTFCWDPGGGK; | (SEQ ID NO: 336) |
| VCWEDSWGGEVCFRYDPGGGK; | (SEQ ID NO: 337) |
| AGPTWCEDDWYYCWLFGTJK; | (SEQ ID NO: 338) |
| AQAHMPPWRPVAVDALFDWVEGGGGGK; | (SEQ ID NO: 340) |
| AQAHMPPWWPLAVDAQEDWFEGGGGGK; | (SEQ ID NO: 341) |
| AQAQMPPWWPLAVDALFDWFEGGGGGK; | (SEQ ID NO: 342) |
| AQDWYWREWMPMHAQFLADDWGGGGGK; | (SEQ ID NO: 343) |
| AQKKEDAQQWYWTDYVPSYLYRGGGGGK; | (SEQ ID NO: 344) |
| AQPVTDWTPHHPKAPDVWLFYTGGGGGK; | (SEQ ID NO: 345) |
| AQDALEAPKRDWYYDWFLNHSPGGGGGK; | (SEQ ID NO: 346) |
| KWCEEDWYYCMITGTGGGK; | (SEQ ID NO: 347) |
| AGPKWCEEDWYYCMIGGGK; | (SEQ ID NO: 348) |
| KWCEEDWYYCMIGGGK; | (SEQ ID NO: 349) |
| AQPDNWKEFYESGWKYPSLYKPLGGGGGK; | (SEQ ID NO: 350) |
| AQMPPGFSYWEQVVLHDDAQVLGGGGGK; | (SEQ ID NO: 351) |
| AQARMGDDWEEAPPHEWGWADGGGGGK; | (SEQ ID NO: 352) |
| AQPEDSEAWYWLNYRPTMFHQLGGGGGK; | (SEQ ID NO: 353) |
| AQSTNGDSFVYWEEVELVDHPGGGGGK; | (SEQ ID NO: 354) |
| AQWESDYWDQMRQQLKTAYMKVGGGGGK; | (SEQ ID NO: 355) |
| AQDWYYDEILSMADQLRHAFLSGGGGGK; | (SEQ ID NO: 356) |
| VCWEDSWGGEVCFGGGK; | (SEQ ID NO: 368) |
| GDSRVCWEDSWGGEVCFGGGK; | (SEQ ID NO: 369) |
| SRVCWEDSWGGEVCFRYGGGGK; | (SEQ ID NO: 371) |
| GDSRVCWEDSWGGEVCFRYGGGK; | (SEQ ID NO: 372) |
| GDSRVCWEDSWGGEVCFRYDP; | (SEQ ID NO: 374) |
| ERVTTCWPGEYGGVECYSVAY; | (SEQ ID NO: 504) |
| DWYYGGGK; | (SEQ ID NO: 462) |
| AEDWYYDEILGRGRGGRGG; | (SEQ ID NO: 465) |
| AGPTWEEDDWYYKWLFGTGGGK; | (SEQ ID NO: 453) |
| AGPTWKEDDWYYEWLFGTGGGK; | (SEQ ID NO: 454) |
| AGPTWDprEDDWYYDWLFGTGGGK; | (SEQ ID NO: 455) |
| AGPTWDEDDWYYDprWLFGTGGGK; | (SEQ ID NO: 456) |
| AGPTWDEDDWYYKWLFGTGGGK; and | (SEQ ID NO: 457) |
| AGPTWCEDDWYYCWLFGTGGGGK. | (SEQ ID NO: 480). | wherein J is the spacer or linker group 8-amino-3,6-dioxaoctanoyl.

2. The agent of claim 1, wherein the microvesicle is conjugated to a dimeric or multimeric compound comprising two or more polypeptides having the ability to bind KDR or VEGF/KDR complex.

3. The agent of claim 1, wherein the agent comprises two or more polypeptides and wherein the polypeptides have specificity for different epitopes on KDR.

4. The agent of claim 3, wherein the polypeptides comprise amino acid sequences that are independently selected from the group consisting of:

```
AGPKWCEEDWYYCMITGTGGGK;         (SEQ ID NO: 264)

GDSRVCWEDSWGGEVCFRYDPGGGK;      (SEQ ID NO: 294)

AQDWYYDEILSMADQLRHAFLSGGGK;     (SEQ ID NO: 310)

AGPTWCEDDWYYCWLFGTGGGK;         (SEQ ID NO: 277)

AGDWWVECRVGTGLCYRYDTGTGGGK;     (SEQ ID NO: 286)
and

VCWEDSWGGEVCFRYDPGGGK.          (SEQ ID NO: 337)
```

5. The agent of claim 1, wherein at least one of the polypeptides comprises an amino acid substitution, an amide bond substitution, a D-amino acid substitution, a glycosylated amino acid, a disulfide mimetic substitution, an amino acid translocation, a retro-inverso peptide, a peptoid, a retro-inverso peptoid, or a synthetic peptide and wherein the polypeptide maintains its ability to bind the receptor.

6. The agent of claim 1, wherein at least one of the polypeptides does not include the C terminal GGGK extension in its amino acid sequence.

7. The agent of claim 4, wherein the polypeptides comprise any of the following combinations of amino acid sequences:

```
AGPTWCEDDWYYCWLFGTGGGK          (SEQ ID NO: 277)
and

VCWEDSWGGEVCFRYDPGGGK;          (SEQ ID NO: 337)

AGPTWCEDDWYYCWLFGTGGGK          (SEQ ID NO: 277)
and

GDSRVCWEDSWGGEVCFRYDPGGGK;      (SEQ ID NO: 294)

AGPKWCEEDWYYCMITGTGGGK          (SEQ ID NO: 264)
and

GDSRVCWEDSWGGEVCFRYDPGGGK;      (SEQ ID NO: 294)
or

AQDWYYDEILSMADQLRHAFLSGGGK      (SEQ ID NO: 310)
and

VCWEDSWGGEVCFRYDPGGGK.          (SEQ ID NO: 337)
```

8. The agent of claim 1, wherein the polypeptide comprises an amino acid sequence selected from the group consisting of:

```
AGPKWCEEDWYYCMITGTGGGK;         (SEQ ID NO: 264)

AGPTWCEDDWYYCWLFGTGGGK;         (SEQ ID NO: 277)

GDSRVCWEDSWGGEVCFRYDPGGGK;      (SEQ ID NO: 294)

AQDWYYDEILSMADQLRHAFLSGGGK;     (SEQ ID NO: 310)
``` and

```
VCWEDSWGGEVCFRYDPGGGK.          (SEQ ID NO: 337)
```

9. An ultrasound contrast agent comprising a microvesicle conjugated to at least two polypeptides having the ability to bind to KDR or VEGF/KDR complex, wherein the microvesicle is conjugated to a dimer selected from the group consisting of D1, D2, D3, D5, D6, D7, D8, D9, D17, D19, D20, D22, D23, D24, D25, D26, D27, D28, and D31, wherein J is the spacer or linker *group* 8-amino-3,6-dioxaoctanoyl.

10. The agent of claim 9, wherein the dimer is selected from the group consisting of D5 and D6.

11. The agent of claim 10, wherein the dimer is D5.

12. The agent of claim 1, wherein the polypeptide is linked to the microvesicle via a linker or spacer.

13. The agent of claim 12, wherein said linker or spacer is selected from the group consisting of a substituted alkyl chain, an unsubstituted alkyl chain, a polyethylene glycol derivative, an amino acid spacer, a sugar, an aliphatic spacer, an aromatic spacer, a lipid molecule, and combinations thereof.

14. The agent of claim 1, wherein the microvesicle comprises a microvesicle-forming material selected from the group consisting of surfactants, lipids, sphingolipids, oligolipids, phospholipids, proteins, polypeptides, carbohydrates and synthetic or natural polymeric materials.

15. The agent of claim 1, wherein the microvesicle is selected from the group consisting of a microbubble, a microballoon, a microparticle and a microsphere.

16. The agent of claim 15, wherein the microbubble comprises a phospholipid.

17. The agent of claim 1, wherein the microvesicle comprises a biocompatible gas, a mixture of biocompatible gases or a gas precursor.

18. The agent of claim 17, wherein the gas or gas mixture comprises a fluorinated gas.

19. The agent of claim 17, wherein the gas or gas mixture comprises at least one gas selected from the group consisting of air; nitrogen; oxygen; carbon dioxide; argon, xenon; krypton; a low molecular weight alkane, cycloalkane, alkene or alkyne; a hyperpolarized gas, SF6, a freon and a perfluorocarbon.

20. The agent of claim 17, wherein the gas or gas mixture comprises a gas selected from the group consisting of $SF_6$, $C_3F_8$, $C_4F_8$, $C_4F_{10}$, and $C_5F_{12}$.

21. The agent of claim 1, further comprising a therapeutic agent.

22. A lyophilized residue for preparing an ultrasound contrast agent wherein said residue comprises a phospholipid and at least one polypeptide comprising an amino acid sequence selected from the group consisting of

```
                                (SEQ ID NO: 263)
AGDSWCSTEYTYCEMIGTGGGK;

(SEQ ID NO: 264)
AGPKWCEEDWYYCMITGTGGGK;

(SEQ ID NO: 265)
AGVWECAKTFPFCHWFGTGGGK;

(SEQ ID NO: 266)
AGWVECWWKSGQCYEFGTGGGK;

(SEQ ID NO: 268)
AGWIQCNSITGHCTSGGTGGGK;
```

-continued

AGWIECYHPDGICYHFGTGGGK; (SEQ ID NO: 269)

AGSDWCRVDWYYCWLMGTGGGK; (SEQ ID NO: 270)

AGANWCEEDWYYCFITGTGGGK; (SEQ ID NO: 271)

AGANWCEEDWYYCWITGTGGGK; (SEQ ID NO: 272)

AGPDWCEEDWYYCWITGTGGGK; (SEQ ID NO: 273)

AGSNWCEEDWYYCYITGTGGGK; (SEQ ID NO: 274)

AGPDWCAADWYYCYITGTGGGK; (SEQ ID NO: 275)

AGPEWCEVDWYYCWLLGTGGGK; (SEQ ID NO: 276)

AGPTWCEDDWYYCWLFGTGGGK; (SEQ ID NO: 277)

AGSKWCEQDWYYCWLLGTGGGK; (SEQ ID NO: 278)

AGRNWCEEDWYYCFITGTGGGK; (SEQ ID NO: 279)

AGVNWCEEDWYYCWITGTGGGK; (SEQ ID NO: 280)

AGANWCEEDWYYCYITGTGGGK; (SEQ ID NO: 281)

AGQAWVECYAETGYCWPRSWGTGGGK; (SEQ ID NO: 282)

AGQAWIECYAEDGYCWPRSWGTGGGK; (SEQ ID NO: 283)

AGVGWVECYQSTGFCYHSRDGTGGGK; (SEQ ID NO: 284)

AGFTWVECHQATGRCVEWTTGTGGGK; (SEQ ID NO: 285)

AGDWWVECRVGTGLCYRYDTGTGGGK; (SEQ ID NO: 286)

AGDSWVECDAQTGFCYSFLYGTGGGK; (SEQ ID NO: 287)

AGERWVECRAETGFCYTWVSGTGGGK; (SEQ ID NO: 289)

AGGGWVECRAETGHCQEYRLGTGGGK; (SEQ ID NO: 290)

AGVAWVECYQTTGKCYTFRGGTGGGK; (SEQ ID NO: 291)

AGEGWVECFANTGACFTYPRGTGGGK; (SEQ ID NO: 292)

GDYPWCHELSDSVTRFCVPWDPGGGK; (SEQ ID NO: 293)

GDSRVCWEDSWGGEVCFRYDPGGGK; (SEQ ID NO: 294)

GDDHMCRSPDYQDHVCMYWDPGGGK; (SEQ ID NO: 295)

GDPPLCYFVGTQEWHHCNPFDPGGGK; (SEQ ID NO: 296)

GDDSYCMMNEKGWWNCYLYDPGGGK; (SEQ ID NO: 297)

GDPAQCWESNYQGIFFCDNPDPGGGK; (SEQ ID NO: 298)

GDGSWCEMRQDVGKWNCFSDDPGGGK; (SEQ ID NO: 299)

GDGWACAKWPWGGEICQPSDPGGGK; (SEQ ID NO: 300)

GDPDTCTMWGDSGRWYCFPADPGGGK; (SEQ ID NO: 301)

GDNWKCEYTQGYDYTECVYLDPGGGK; (SEQ ID NO: 302)

GDNWECGWSNMFQKEFCARPDPGGGK; (SEQ ID NO: 303)

GDWWECKREEYRNTTWCAWADPGGGK; (SEQ ID NO: 486)

GDSSVCFEYSWGGEVCFRYDPGGGK; (SEQ ID NO: 487)

GDSRVCWEYSWGGQICLGYDPGGGK; (SEQ ID NO: 488)

AQQVQYQFFLGTPRYEQWDLDKGGK; (SEQ ID NO: 304)

AQEPEGYAYWEVITLYHEEDGDGGK; (SEQ ID NO: 305)

AQAFPRFGGDDYWIQQYLRYTDGGK; (SEQ ID NO: 306)

AQGDYVYWEIIELTGATDHTPPGGK; (SEQ ID NO: 307)

AQRGDYQEQYWHQQLVEQLKLLGGK; (SEQ ID NO: 308)

AQRSWYLGPPYYEEWDPIPNGGK; (SEQ ID NO: 309)

AQDWYYDEILSMADQLRHAFLSGGGK; (SEQ ID NO: 310)

AGIDFCKGMAPWLCADMGTGGGK; (SEQ ID NO: 311)

AGPWTCWLEDHLACAMLGTGGGK; (SEQ ID NO: 312)

AGDWGCSLGNWYWCSTEGTGGGK; (SEQ ID NO: 313)

GSDHHCYLHNGQWICYPFAPGGGK; (SEQ ID NO: 314)

GSNSHCYIWDGMWLCFPDAPGGGK; (SEQ ID NO: 315)

SGRLDCDKVFSGPYGKVCVSYGSGGGK; (SEQ ID NO: 316)

SGRLDCDKVFSGPHGKICVNYGSGGGK; (SEQ ID NO: 317)

SGRTTCHHQISGPHGKICVNYGSGGGK; (SEQ ID NO: 318)

SGAHQCHHWTSGPYGEVCFNYGSGGGK; (SEQ ID NO: 319)

AGMPWCVEKDHWDCWWWGTGGGK; (SEQ ID NO: 320)

AGPGPCKGYMPHQCWYMGTGGGK; (SEQ ID NO: 321)

AGYGPCAEMSPWLCWYPGTGGGK; (SEQ ID NO: 322)

AGYGPCKNMPPWMCWHEGTGGGK; (SEQ ID NO: 323)

AGGHPCKGMLPHTCWYEGTGGGK; (SEQ ID NO: 324)

AQAPAWTFGTNWRSIQRVDSLTGGGGGK; (SEQ ID NO: 325)

AQEGWFRNPQEIMGFGDSWDKPGGGGGK; (SEQ ID NO: 326)

AQEGWFRNPQEIMGFGDSWDKPGGGK; (SEQ ID NO: 330)

AQRGDYQEQYWHQQLVEQLKLLGGGK; (SEQ ID NO: 331)

AGWYWCDYYGIGCKWTGGGK; (SEQ ID NO: 332)

AGWYWCDYYGIGCKWTGTGGGK; (SEQ ID NO: 333)

AQWYYDWFHNQRKPPSDWIDNLGGGK; (SEQ ID NO: 334)

WQPCPWESWTFCWDPGGGK; (SEQ ID NO: 336)

VCWEDSWGGEVCFRYDPGGGK; (SEQ ID NO: 337)

AGPTWCEDDWYYCWLFGTJK; (SEQ ID NO: 338)

AQAHMPPWRPVAVDALFDWVEGGGGGK; (SEQ ID NO: 340)

AQAHMPPWWPLAVDAQEDWFEGGGGGK; (SEQ ID NO: 341)

AQAQMPPWWPLAVDALFDWFEGGGGGK; (SEQ ID NO: 342)

AQDWYWREWMPMHAQFLADDWGGGGGK; (SEQ ID NO: 343)

AQKKEDAQQWYWTDYVPSYLYRGGGGGK; (SEQ ID NO: 344)

AQPVTDWTPHHPKAPDVWLFYTGGGGGK; (SEQ ID NO: 345)

AQDALEAPKRDWYYDWFLNHSPGGGGGK; (SEQ ID NO: 346)

KWCEEDWYYCMITGTGGGK; (SEQ ID NO: 347)

AGPKWCEEDWYYCMIGGGK; (SEQ ID NO: 348)

KWCEEDWYYCMIGGGK; (SEQ ID NO: 349)

AQPDNWKEFYESGWKYPSLYKPLGGGGGK; (SEQ ID NO: 350)

AQMPPGFSYWEQVVLHDDAQVLGGGGGK; (SEQ ID NO: 351)

AQARMGDDWEEAPPHEWGWADGGGGGK; (SEQ ID NO: 352)

AQPEDSEAWYWLNYRPTMFHQLGGGGGK; (SEQ ID NO: 353)

AQSTNGDSFVYWEEVELVDHPGGGGGK; (SEQ ID NO: 354)

AQWESDYWDQMRQQLKTAYMKVGGGGGK; (SEQ ID NO: 355)

AQDWYYDEILSMADQLRHAFLSGGGGGK; (SEQ ID NO: 356)

VCWEDSWGGEVCFGGGK; (SEQ ID NO: 368)

GDSRVCWEDSWGGEVCFGGGK; (SEQ ID NO: 369)

SRVCWEDSWGGEVCFRYGGGGK; (SEQ ID NO: 371)

GDSRVCWEDSWGGEVCFRYGGGK; (SEQ ID NO: 372)

GDSRVCWEDSWGGEVCFRYDP; (SEQ ID NO: 374)

ERVTTCWPGEYGGVECYSVAY; (SEQ ID NO: 504)

DWYYGGGK; (SEQ ID NO: 462)

AEDWYYDEILGRGRGGRGG; (SEQ ID NO: 465)

AGPTWEEDDWYYKWLFGTGGGK; (SEQ ID NO: 453)

AGPTWKEDDWYYEWLFGTGGGK; (SEQ ID NO: 454)

AGPTWDprEDDWYYDWLFGTGGGK; (SEQ ID NO: 455)

AGPTWDEDDWYYDprWLFGTGGGK; (SEQ ID NO: 456)

AGPTWDEDDWYYKWLFGTGGGK; (SEQ ID NO: 457)
and

AGPTWCEDDWYYCWLFGTGGGGK, (SEQ ID NO: 480)

wherein J is the spacer or linker group 8-amino- 3,6dioxaoctanoyl.

23. A method of imaging at least a portion of a patient comprising administering the ultrasound contrast agent of claim 1, and imaging at least a portion of the patient using ultrasound energy.

24. A method of treating a patient comprising administering the ultrasound contrast agent of claim 21 and applying ultrasound energy to the patient.

25. A method of detecting KDR or VEGF/KDR complex in a subject comprising the steps of:
 (a) administering the ultrasound contrast agent of claim 1;
 (b) detecting the ultrasound contrast agent in the subject.

26. The method of claim 25, further comprising constructing an image.

27. The agent of claim 4, wherein at least one of the polypeptides comprises an amino acid substitution, an amide bond substitution, a D-amino acid substitution, a glycosylated amino acid, a disulfide mimetic substitution, an amino acid translocation, a retro-inverso peptide, a peptoid, a retro-inverso peptoid, or a synthetic peptide and wherein the polypeptide maintains its ability to bind the receptor.

28. The agent of claim 4, wherein at least one of the polypeptides does not include the C terminal GGGK extension in its amino acid sequence.

29. The agent of claim 4, wherein the polypeptide is linked to the microvesicle via a linker or spacer.

30. The agent of claim 29, wherein said linker or spacer is selected from the group consisting of a substituted alkyl chain, an unsubstituted alkyl chain, a polyethylene glycol derivative, an amino acid spacer, a sugar, an aliphatic spacer, an aromatic spacer, a lipid molecule, and combinations thereof.

31. The agent of claim 4, wherein the microvesicle comprises a microvesicle-forming material selected from the group consisting of surfactants, lipids, sphingolipids, oligolipids, phospholipids, proteins, polypeptides, carbohydrates and synthetic or natural polymeric materials.

32. The agent of claim 4, wherein the microvesicle is selected from the group consisting of a microbubble, a microballoon, a microparticle and a microsphere.

33. The agent of claim 10, wherein the microvesicle comprises a microvesicle-forming material selected from the group consisting of surfactants, lipids, sphingolipids, oligolipids, phospholipids, proteins, polypeptides, carbohydrates and synthetic or natural polymeric materials.

34. The agent of claim 10, wherein the microvesicle is selected from the group consisting of a microbubble, a microballoon, a microparticle and a microsphere.

35. The agent of claim 32, wherein the microbubble comprises a phospholipid.

36. The agent of claim 34, wherein the microbubble comprises a phospholipid.

37. A method of imaging at least a portion of a patient comprising administering the ultrasound contrast agent of claim 4 and imaging at least a portion of the patient using ultrasound energy.

38. A method of imaging at least a portion of a patient comprising administering the ultrasound contrast agent of claim 10 and imaging at least a portion of the patient using ultrasound energy.

39. A method of detecting KDR or VEGF/KDR complex in a subject comprising the steps of:
   (a) administering the ultrasound contrast agent of claim 4;
   (b) detecting the ultrasound contrast agent in the subject.

40. The method of claim 39, further comprising constructing an image.

41. A method of detecting KDR or VEGF/KDR complex in a subject comprising the steps of:
   (a) administering the ultrasound contrast agent of claim 9;
   (b) detecting the ultrasound contrast agent in the subject.

42. The method of claim 41, further comprising constructing an image.

* * * * *